US010004728B2

(12) United States Patent
Rancati et al.

(10) Patent No.: US 10,004,728 B2
(45) Date of Patent: Jun. 26, 2018

(54) COMPOUNDS HAVING MUSCARINIC RECEPTOR ANTAGONIST AND BETA2 ADRENERGIC RECEPTOR AGONIST ACTIVITY

(71) Applicant: CHIESI FARMACEUTICI S.p.A., Parma (IT)

(72) Inventors: Fabio Rancati, Parma (IT); Andrea Rizzi, Parma (IT); Laura Carzaniga, Parma (IT); Ian Linney, Saffron Walden (GB); Chris Knight, Saffron Walden (GB); Wolfgang Schmidt, Saffron Walden (GB)

(73) Assignee: Chiesi Farmaceutici S.p.A., Parma (IT)

( * ) Notice: Subject to any disclaimer, the term of this patent is extended or adjusted under 35 U.S.C. 154(b) by 0 days. days.

(21) Appl. No.: 15/404,897

(22) Filed: Jan. 12, 2017

(65) Prior Publication Data
US 2017/0119753 A1    May 4, 2017

Related U.S. Application Data

(62) Division of application No. 15/040,382, filed on Feb. 10, 2016, now Pat. No. 9,579,314.

(30) Foreign Application Priority Data

Feb. 12, 2015 (EP) .................................. 15154917

(51) Int. Cl.
| | | |
|---|---|---|
| *A61K 31/4709* | (2006.01) |
| *C07D 403/12* | (2006.01) |
| *C07D 401/14* | (2006.01) |
| *C07D 401/12* | (2006.01) |
| *C07D 453/02* | (2006.01) |
| *C07D 453/04* | (2006.01) |
| *A61K 9/00* | (2006.01) |
| *A61K 31/4704* | (2006.01) |
| *A61K 31/496* | (2006.01) |
| *A61K 45/06* | (2006.01) |
| *C07D 215/227* | (2006.01) |
| *C07D 409/14* | (2006.01) |
| *C07D 471/10* | (2006.01) |
| *C07D 487/04* | (2006.01) |
| *C07D 487/10* | (2006.01) |
| *C07D 498/10* | (2006.01) |
| *A61K 31/5386* | (2006.01) |

(52) U.S. Cl.
CPC ........ *A61K 31/4709* (2013.01); *A61K 9/0073* (2013.01); *A61K 31/4704* (2013.01); *A61K 31/496* (2013.01); *A61K 31/5386* (2013.01); *A61K 45/06* (2013.01); *C07D 215/227* (2013.01); *C07D 401/12* (2013.01); *C07D 401/14* (2013.01); *C07D 403/12* (2013.01); *C07D 409/14* (2013.01); *C07D 453/02* (2013.01); *C07D 453/04* (2013.01); *C07D 471/10* (2013.01); *C07D 487/04* (2013.01); *C07D 487/10* (2013.01); *C07D 498/10* (2013.01)

(58) Field of Classification Search
CPC .. C07D 453/02; C07D 453/04; C07D 401/14; C07D 403/12; C07D 401/12; C07D 409/14; C07D 215/227; C07D 487/04; C07D 487/10; C07D 471/10; C07D 498/10; A61K 31/4704; A61K 31/496; A61K 9/0073
See application file for complete search history.

(56) References Cited

U.S. PATENT DOCUMENTS

| | | | |
|---|---|---|---|
| 9,012,644 | B2 | 4/2015 | Rancati et al. |
| 2013/0045169 | A1 | 2/2013 | Rancati et al. |

FOREIGN PATENT DOCUMENTS

| | | |
|---|---|---|
| WO | 2007/017669 | 2/2007 |
| WO | 2008/104781 | 9/2008 |
| WO | 2011/048409 | 4/2011 |
| WO | 2012/168349 | 12/2012 |

OTHER PUBLICATIONS

Extended European Search Report in Application No. 15154917.7 dated Apr. 24, 2015.
International Search Report in Application No. PCT/EP2016/052812 dated Mar. 23, 2016 with Written Opinion.

*Primary Examiner* — Sudhakar Katakam
(74) *Attorney, Agent, or Firm* — Oblon, McClelland, Maier & Neustadt, L.L.P.

(57) ABSTRACT

Compounds of formula I, defined herein, act both as muscarinic receptor antagonists and beta2 adrenergic receptor agonists and are useful for treating broncho-obstructive and inflammatory diseases.

12 Claims, No Drawings

COMPOUNDS HAVING MUSCARINIC RECEPTOR ANTAGONIST AND BETA2 ADRENERGIC RECEPTOR AGONIST ACTIVITY

CROSS REFERENCES TO RELATED APPLICATIONS

This application is a division of U.S. patent application Ser. No. 15/040,382, filed on Feb. 10, 2016, and claims priority to European Patent Application No 15154917.7, filed on Feb. 12, 2015, which is incorporated herein by reference in its entirety.

BACKGROUND OF THE INVENTION

Field of the Invention

The present invention relates to compounds which act both as muscarinic receptor antagonists and beta2 adrenergic receptor agonists. The present invention also relates to processes for the preparation of such a compound, compositions which contain such a compound, certain therapeutic uses of such a compound, and combinations of such a compound with other pharmaceutical active ingredients.

Discussion of the Background

Pulmonary disorders, such as asthma and chronic obstructive pulmonary disease (COPD), are commonly treated with bronchodilators. A well-known class of bronchodilators consists of beta-2 adrenergic receptor agonists, such as salbutamol, fenoterol, formoterol and salmeterol. These compounds are generally administered by inhalation.

Another well-known class of bronchodilators consists of muscarinic receptor antagonists (anticholinergic compounds), such as ipratropium and tiotropium. These compounds are also typically administered by inhalation.

Inhaled formulations of both beta-2 agonists and muscarinic receptor antagonists are valuable agents in the treatment of asthma and COPD, with both classes of agents providing symptomatic relief due to their ability to relax constricted airways. Observations that the bronchodilator effects of the two classes of agents were additive, prompted studies with combinations of the two agents. In 1975, it was shown that beneficial effects could be achieved by combining two ingredients such as fenoterol and ipratropium bromide in a single aerosol. This prompted the development of fixed dose combinations of ipratropium bromide firstly with fenoterol (Berodual, introduced in 1980), and then with salbutamol (Combivent, introduced in 1994).

More recently the availability of both long-acting muscarinic antagonists and long-acting beta-2 agonists prompted the development of combinations of these agents. For example, WO 00/69468, which is incorporated herein by reference in its entirety, discloses medicament compositions containing a muscarinic receptor antagonist, such as tiotropium bromide, and beta-2 adrenergic receptor agonists, such as formoterol fumarate or salmeterol, and WO 2005/115467, which is incorporated herein by reference in its entirety, discloses a combination which comprises a beta-2 agonist and an antagonist of M3 muscarinic receptors which is a salt of 3(R)-(2-hydroxy-2,2-dithien-2-ylacetoxy)-1-(3-phenoxypropyl)-1-azoniabicyclo[2.2.2]octane.

An alternative approach to the development of fixed dose combinations is the identification of molecules that combine both activities of muscarinic antagonism and beta-2 agonism. In fact compounds possessing both beta-2 adrenergic receptor agonist and muscarinic receptor antagonist activity are highly desirable since such bifunctional compounds would provide bronchodilation through two independent mechanisms of action while having a single molecule pharmacokinetics.

Such kind of compounds was described in some patent applications, such as WO 2004/074246, WO 2004/074812, WO 2005/051946, WO 2006/023457, WO 2006/023460, WO 2010/123766, WO 2011/048409 and co-pending patent applications WO 2012/168349, WO 2012/168359, WO2014/086924, and WO 2014/086927, all of which are incorporated herein by reference in their entireties.

It has now been found that some particular aryl or heteroaryl hydroxyacetic ester derivatives, besides possessing both beta-2 adrenergic receptor agonist and muscarinic receptor antagonist activity, possess elevated affinity for the M3 muscarinic receptors and long lasting bronchodilating activity.

SUMMARY OF THE INVENTION

Accordingly, it is one object of the present invention to provide novel compound which act both as muscarinic receptor antagonists and beta2 adrenergic receptor agonists.

It is another object of the present invention to provide novel processes for the preparation of such a compound.

It is another object of the present invention to provide novel compositions which contain such a compound.

It is another object of the present invention to provide novel therapeutic uses of such a compound.

It is another object of the present invention to provide novel combinations of such a compound with other pharmaceutical active ingredients, for example, those currently used in the treatment of respiratory disorders, e.g. corticosteroids, P38 MAP kinase inhibitors, IKK2, HNE inhibitors, PDE4 inhibitors, leukotriene modulators, NSAIDs and mucus regulators.

These and other objects, which will become apparent during the following detailed description, have been achieved by the inventors' discovery of the compounds of formula I, defined below.

DETAILED DESCRIPTION OF THE PREFERRED EMBODIMENTS

In particular, the invention is directed to compounds of general formula

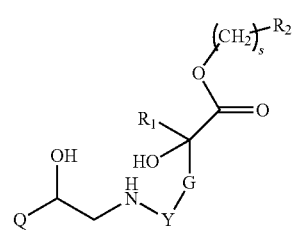

I wherein
Q is a group of formula

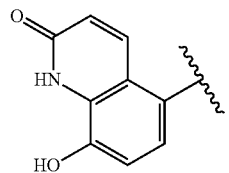 [SMILES: *c1ccc(O)c2[nH]c(=O)ccc12]

Y is selected from Y2 and Y1 which are divalent groups of formula

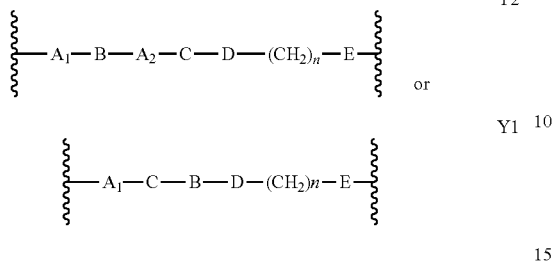

wherein

A1 and A2 are independently absent or selected from $(C_1-C_{12})$alkylene, $(C_3-C_8)$cycloalkylene and $(C_3-C_8)$heterocycloalkylene optionally substituted by one or more substituents selected from $(C_1-C_6)$alkyl, aryl$(C_1-C_6)$alkyl, and heteroaryl$(C_1-C_6)$alkyl;

B is absent or is selected from $(C_3-C_8)$cycloalkylene, $(C_3-C_8)$heterocycloalkylene, arylene or heteroarylene optionally substituted by one or more groups selected from —OH, halogens, —CN, $(C_1-C_6)$alkyl, $(C_1-C_6)$alkoxy, $(C_1-C_6)$haloalkyl, $(C_1-C_6)$haloalkoxy, and aryl$(C_1-C_6)$alkyl;

C is absent or is selected from —O—, —C(O)—, —OC(O)—, —(O)CO—, —S—, —S(O)—, —S(O)$_2$— and —N(R$_7$)—, or is one of the following groups C1-C23

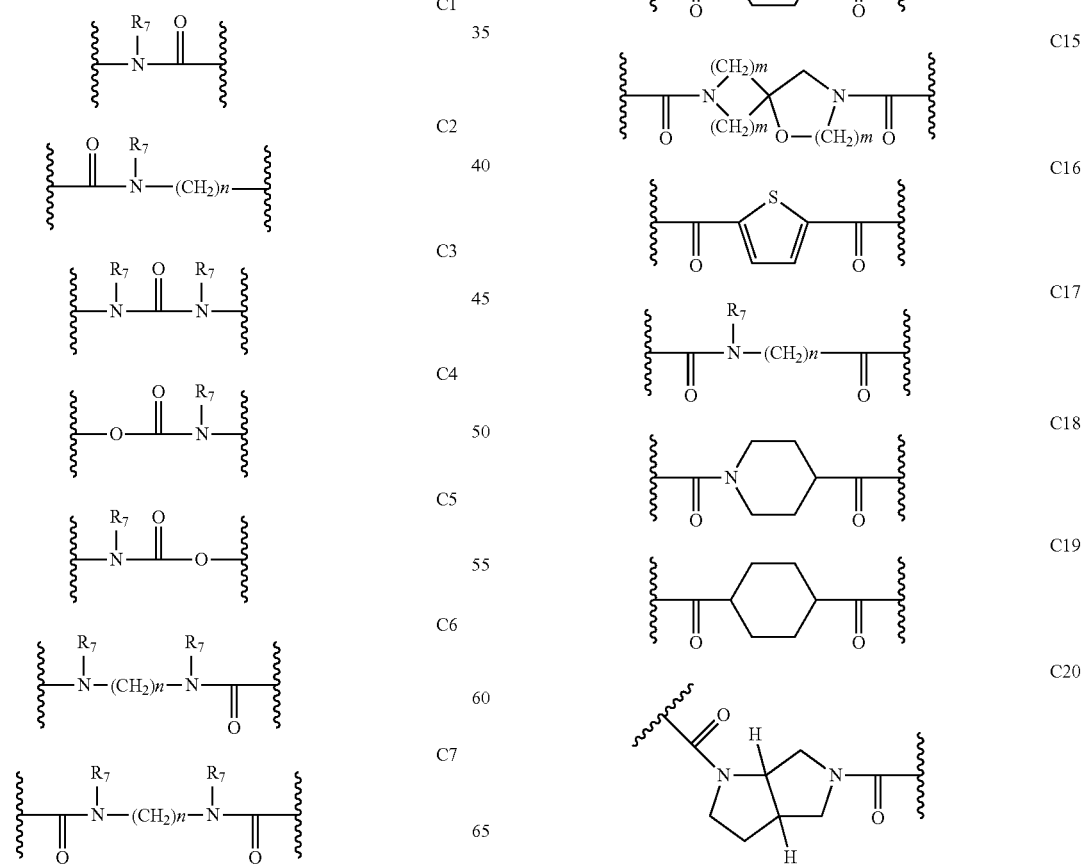

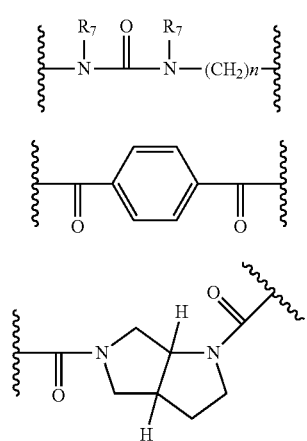

C21

C22

C23

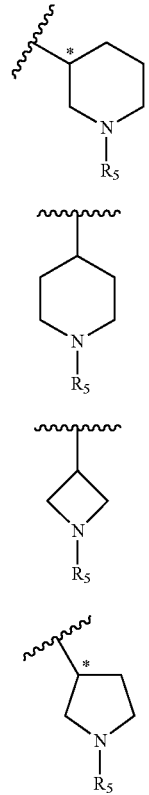

J2

J3

J4

J5 wherein $R_7$ is in each occurrence independently H or selected from linear or branched $(C_1-C_8)$alkyl, aryl$(C_1-C_6)$alkyl, arylsulfanyl, arylsulfinyl, arylsulfonyl, $(C_3-C_8)$cycloalkyl, $(C_3-C_8)$heterocycloalkyl, aryl, and heteroaryl;

D is absent or is selected from $(C_1-C_{12})$alkylene, $(C_2-C_{12})$alkenylene, $(C_2-C_6)$alkynylene, arylene, heteroarylene, $(C_3-C_8)$cycloalkylene, $(C_3-C_8)$heterocycloalkylene; said arylene, heteroarylene, $(C_3-C_8)$cycloalkylene and $(C_3-C_8)$heterocycloalkylene being optionally substituted by one or more groups selected from —OH, halogen, —CN, $(C_1-C_6)$alkyl, $(C_1-C_6)$alkoxy, $(C_1-C_6)$haloalkyl, $(C_1-C_6)$haloalkoxy and aryl$(C_1-C_6)$alkyl;

n is at each occurrence independently 0 or an integer from 1 to 3;

m is at each occurrence independently an integer from 1 to 3;

E is absent or is selected from —O—, —NR$_7$—, —NR$_7$—C(O)—, —C(O)—NR$_7$—, —OC(O)—, —C(O)—(CH$_2$)$_n$—O—; —NR$_7$—C(O)—(CH$_2$)$_n$—O—, —NR$_7$—C(O)—NR$_7$— and —S—;

G is arylene or heteroarylene, optionally substituted by one or more substituents selected from halogen atoms, —OH, oxo (=O), —SH, —NO$_2$, —CN, —CON(R$_6$)$_2$, —NH$_2$, —NHCOR$_6$, —CO$_2$R$_6$, $(C_1-C_{10})$alkylsulfanyl, $(C_1-C_{10})$alkylsulfinyl, $(C_1-C_{10})$alkylsulfonyl, $(C_1-C_{10})$alkyl, aryl, haloaryl, heteroaryl, and $(C_1-C_{10})$alkoxy;

$R_1$ is selected from $(C_3-C_8)$cycloalkyl, $(C_3-C_8)$heterocycloalkyl, aryl, heteroaryl, aryl$(C_1-C_6)$alkyl, heteroaryl$(C_1-C_6)$alkyl and $(C_3-C_8)$cycloalkyl$(C_1-C_6)$alkyl, optionally substituted by one or more group selected independently from halogen, $(C_1-C_8)$alkyl, and $(C_1-C_{10})$alkoxy;

s is 0 or an integer from 1 to 3;

$R_2$ is a nitrogen containing group which may be selected from:
  a group (a) which is —NR$_3$R$_4$ wherein R$_3$ and R$_4$ are independently hydrogen or $(C_1-C_4)$ alkyl; and
  a group (b) of formula J1, J2, J3, J4 or J5

J1

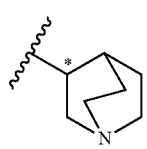

$R_5$ is a group of formula K

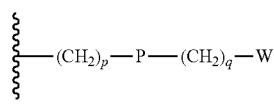

K wherein p is 0 or an integer from 1 to 4; q is 0 or an integer from 1 to 4;

P is absent or is selected from the divalent group consisting of O, S, SO, SO$_2$, CO, NR$_6$CH=CH, N(R$_6$)SO$_2$, N(R$_6$)COO, N(R$_6$)C(O), SO$_2$N(R$_6$), OC(O)N(R$_6$), and C(O)N(R$_6$);

W is selected from H, $(C_1-C_6)$alkyl, $(C_3-C_8)$cycloalkyl, aryl, and heteroaryl, optionally substituted by one or more substituents selected independently from halogen atoms, —OH, oxo (=O), —SH, —NO$_2$, —CN, —CON(R$_6$)$_2$, —NH$_2$, —NHCOR$_6$, —CO$_2$R$_6$, $(C_1-C_{10})$alkylsulfanyl, $(C_1-C_{10})$alkylsulfinyl, $(C_1-C_{10})$alkylsulfonyl, $(C_1-C_{10})$alkyl, and $(C_1-C_{10})$alkoxy;

$R_6$ is at each occurrence independently H or selected from $(C_1-C_{10})$alkyl, $(C_1-C_6)$haloalkyl, $(C_2-C_6)$alkynyl, $(C_2-C_6)$alkenyl, $(C_3-C_8)$cycloalkyl, heteroaryl and aryl optionally substituted by one or more substituents selected from halogen atoms, —OH, oxo (=O), —SH, —NO$_2$, —CN, —CONH$_2$, —COOH, $(C_1-C_{10})$alkoxycarbonyl, $(C_1-C_{10})$alkylsulfanyl, $(C_1-C_{10})$alkylsulfinyl, $(C_1-C_{10})$alkylsulfonyl, $(C_1-C_{10})$alkyl and $(C_1-C_{10})$alkoxy;

and pharmaceutically acceptable salts or solvates thereof.

The term "pharmaceutically acceptable salts", as used herein, refers to compounds according to the invention obtained by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic basic addition salts of acid residues such as carboxylic groups.

Cations of inorganic bases which can be suitably used to prepare salts within the invention comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, methane sulfonic acid, camphor sulfonic acid, acetic acid, oxalic acid, maleic acid, fumaric acid, succinic acid and citric acid.

Those skilled in the art of organic chemistry will appreciate that many organic compounds can form complexes with solvents in which they are reacted or from which they are precipitated or crystallized. These complexes are known as "solvates". Pharmaceutically acceptable solvates of compound of the invention are within the scope of the invention.

Included within the scope of the present invention are also polymorphs and crystalline forms of compounds of formula (I), or of pharmaceutically acceptable salts, or solvates thereof.

The terms "halogen," "halogens," and "halogen atoms" as used herein include fluorine, chlorine, bromine, and iodine, preferably chlorine or fluorine, referring independently to one or more of these atoms.

The expression "$(C_1-C_x)$alkyl" refers to straight or branched chain alkyl groups wherein the number of carbon atoms is from 1 to x, preferably from 1 to 6 thus referring to $(C_1-C_6)$alkyl. Examples of groups are methyl, ethyl, n-propyl, isopropyl, t-butyl, pentyl, hexyl, octyl, nonyl, decyl, undecyl, dodecyl, and the like.

In an analogous manner, the expression "$(C_1-C_x)$alkylene" herewith refers to divalent groups wherein the number of carbon atoms is from 1 to x, preferably from 1 to 6 thus referring to $(C_1-C_6)$alkylene, such as methylene, ethylene, n-propylene, isopropylene, n-butylene, t-butylene, pentylene, hexylene, octylene, nonylene, decylene, undecylene, dodecylene and the like. With alternative common name, deriving from the name of the corresponding alkanes, the above divalent groups can be referred to also as methanediyl, ethanediyl, n-propanediyl, propan1,2diyl, and the like.

The expression "$(C_1-C_6)$haloalkyl" refers to the above "$(C_1-C_6)$alkyl" group wherein one or more hydrogen atoms are replaced by one or more halogen atoms, which can be the same or different from each other.

Examples of said $(C_1-C_6)$haloalkyl groups include halogenated, poly-halogenated and fully halogenated alkyl groups wherein one or more of the hydrogen atoms are replaced by halogen atoms, e.g. trifluoromethyl group.

The expression "hydroxy$(C_1-C_6)$alkyl" likewise refers to -alkyl-OH groups.

The expressions "$(C_1-C_{10})$alkylsulfanyl," "$(C_1-C_{10})$alkylsulfinyl," or "$(C_1-C_{10})$alkylsulfonyl" refer, respectively, to alkyl-S—, alkyl-SO— or alkyl-SO$_2$— groups.

The expression "$(C_2-C_x)$alkenyl" refers to straight or branched carbon chains with one or more double bonds, wherein the number of carbon atoms is from 1 to x. Examples of said groups comprise ethenyl, propenyl, bute-nyl, pentenyl, hexenyl, heptenyl, octenyl, nonenyl, decenyl, undecenyl, dodecenyl and the like.

In an analogous manner, the expression "$(C_2-C_x)$alkenylene" refers to divalent groups, such as ethenylene, propenylene, butenylene, pentenylene, hexenylene, heptenylene, octenylene, nonenylene, decenylene, undecenylene, dodecenylene, and the like.

The expression "$(C_2-C_x)$alkynyl" refers to straight or branched carbon chains with one or more triple bonds, wherein the number of carbon atoms is from 1 to x. Examples of said groups comprise ethynyl, propynyl, butynyl, pentynyl, hexynyl, and the like.

In an analogous manner, the expression "$(C_2-C_6)$alkynylene" refers to divalent groups, such as ethynylene, propynylene, butynylene, pentynylene, hexynylene, and the like; otherwise commonly referred to as ethynediyl, propynediyl, butyndiyl and the like.

The expression "$(C_1-C_x)$alkoxy" refers to alkyl-oxy (i.e. alkoxy) groups, being the alkyl portion as above defined, wherein the number of carbon atoms is from 1 to x. Examples of said groups comprise methoxy (i.e. CH$_3$O—), ethoxy, n-propoxy, isopropoxy, n-butoxy, isobutoxy, sec-butoxy, tert-butoxy, pentoxy, hexoxy, and the like.

The expression "$(C_1-C_6)$haloalkoxy" refers to the above "$(C_1-C_6)$alkoxy" group wherein one or more hydrogen atoms are replaced by one or more halogen atoms, which can be the same or different from each other.

Examples of said $(C_1-C_6)$haloalkoxy groups include halogenated, poly-halogenated and fully halogenated alkoxy groups wherein one or more of the hydrogen atoms are replaced by halogen atoms, e.g. trifluoromethoxy group.

The expression "$(C_1-C_{10})$alkoxycarbonyl" refers to $(C_1-C_{10})$alkoxyC(O)— groups. Non limiting examples of $(C_1-C_{10})$alkoxycarbonyl may thus include methoxycarbonyl, ethoxycarbonyl, propoxycarbonyl, butoxycarbonyl, isopropoxycarbonyl, and the like.

The expression "$(C_3-C_8)$cycloalkyl" refers to mono or bi-cycloaliphatic hydrocarbon groups with 3 to 8 carbon atoms. Examples include cyclopropyl, cyclobutyl, cyclopentyl, cyclohexyl, cycloheptyl, bicyclo[2.2.1]hept-2-yl and the like.

The expression "$(C_3-C_8)$heterocycloalkyl" refers to saturated or partially saturated monocyclic $(C_3-C_8)$cycloalkyl groups, in which at least one ring carbon atom is replaced by a heteroatom or heteroaromatic group (e.g. N, NH, S or O). Examples include quinuclidinyl, pyrrolidinyl, piperidinyl, azabicyclo[3.2.1]octan-3-yl and azoniabicyclo[2.2.2]octanyl, [1.2.3.6]tetrahydropyridin-1yl and the like.

In an analogous manner, the expressions "$(C_3-C_8)$cycloalkylene" and "$(C_3-C_8)$heterocycloalkylene" herewith refer to divalent groups. The term cycloalkylene refers to saturated cycloalkane-diyl and partially saturated monocyclic groups such as cycloalkene-diyl. Examples of such $(C_3-C_8)$cycloalkylene and $(C_3-C_8)$heterocycloalkylene are divalent groups, such as, respectively, cyclopropylene, cyclobutylene, cyclopentylene, cyclohexylene, cycloheptylene, bicyclo[2.2.1]hept-2-ylene and quinuclidinylene, pyrrolidinylene, piperidinylene, azabicyclo[3.2.1]octan-3-ylene, azoniabicyclo[2.2.2]octanylene, [1.2.3.6]tetrahydropyridin-[1.4]diyl, and the like. With alternative common name, deriving from the name of the corresponding alkanes or alkenes, the above divalent groups can be referred to also as cyclopropanediyl, cyclobutanediyl, cyclopentanediyl, cyclohexanediyl, cycloheptanediyl, bicyclo[2.2.1]heptaenediyl and quinuclidinediyl, pyrrolidinediyl, piperidinediyl, azabicyclo[3.2.1]octandiyl, azoniabicyclo[2.2.2]octandiyl, [1.2.3.6]tetrahydropyridine-[1.4]diyl, and the like.

The expression "aryl" refers to mono, bi- or tricyclic ring systems having 5 to 20, preferably from 5 to 15, more preferably from 5 to 8 ring atoms, and wherein at least one ring is aromatic.

The expression "heteroaryl" refers to mono, bi- or tricyclic systems with 5 to 20 ring atoms, preferably from 5 to 15, in which at least one ring is aromatic and in which at least one carbon ring atom is a heteroatom or heteroaromatic group (e.g. N, NH, S or O).

Examples of suitable aryl or heteroaryl monocyclic systems include, for instance, thiophene (thiophenyl), benzene (phenyl), pyrrole (pyrrolyl), pyrazole (pyrazolyl), imidazole (imidazolyl), isoxazole (isoazolyl), oxazole (oxazolyl), isothiazole (isothiazolyl), thiazole (thiazolyl), pyridine (pyridinyl), imidazolidine (imidazolidinyl), furan (furanyl) radicals, and the like.

Examples of suitable aryl or heteroaryl bicyclic systems include naphthalene (naphthalenyl), biphenylene (biphenylenyl), purine (purinyl), pteridine (pteridinyl), benzotriazole (benzotriazolyl), quinoline (quinolinyl), isoquinoline (isoquinolinyl), indole (indolyl), isoindole (isoindolyl), benzothiophene (benzothiophenyl), dihydrobenzo dioxin, dihydro-indene, dihydrobenzo dioxepin, benzo oxazine radicals, and the like.

Examples of suitable aryl or heteroaryl tricyclic systems include fluorene radicals as well as benzocondensed derivatives of the aforementioned heteroaryl bicyclic systems.

In an analogous manner, the expressions "arylene" and "heteroarylene" refer to divalent groups, such a phenylene, biphenylene and thienylene. Such groups are also commonly named as "arenediyl" or "heteroarenediyl" groups. e.g. ortho-phenylene is also named benzene-1,2-diyl, para-phenylene is also named benzene-1,4-diyl, meta-phenylene is also named benzene-1,3-diyl.

The expressions "aryl($C_1$-$C_6$)alkyl", "heteroaryl($C_1$-$C_6$)alkyl" and "($C_3$-$C_8$)cycloalkyl($C_1$-$C_6$)alkyl" refer to a "($C_1$-$C_6$)alkyl" respectively substituted by one or more aryl, heteroaryl or ($C_3$-$C_8$)cycloalkyl groups, as defined above.

Examples of aryl($C_1$-$C_6$)alkyl include triphenylmethyl.

By way of analogy the expressions "arylsulfanyl," "arylsulfinyl," and "arylsulfonyl" refer, respectively, to aryl-S—, aryl-SO— or aryl-$SO_2$— groups. Preferred groups are phenyl-S—, phenyl-SO— or phenyl-$SO_2$—.

Likewise the expression "haloaryl" refers to the above "aryl" group wherein one or more hydrogen atoms are replaced by one or more halogen atoms, which can be the same or different from each other.

As used herein an oxo moiety is represented by (O) as an alternative to other common representations, e.g. (=O). Thus, in terms of general formula, the carbonyl group is herein preferably represented as —C(O)— as an alternative to the other common representations such as —CO—, —(CO)— or —C(=O)—. In general, the parenthetical group is a lateral group, not included into the chain, and parentheses are used, when deemed useful, to help disambiguating linear chemical formulas; e.g. the sulfonyl group —$SO_2$— might be also represented as —$S(O)_2$— to differentiate e.g. with respect to the sulfinic group —S(O)O—.

Whenever basic amino or quaternary ammonium groups are present in the compounds of formula I, as above said, physiological acceptable anions, selected among chloride, bromide, iodide, trifluoroacetate, formate, sulfate, phosphate, methanesulfonate, nitrate, maleate, acetate, citrate, fumarate, tartrate, oxalate, succinate, benzoate, p-toluenesulfonate, pamoate and naphthalene disulfonate may be present. Likewise, in the presence of acidic groups such as —COOH groups, corresponding physiological cation salts may be present as well, for instance including alkaline or alkaline earth metal ions.

It will be apparent to those skilled in the art that compounds of general formula I contain at least two stereogenic centers. Therefore, the present invention also includes any of the optical stereoisomers, diastereoisomers, and mixtures thereof, in any proportion.

In particular, the carbon atom (2) linked to $R_1$, —OH, G and C=O groups, and the carbon atom (1) linked to Q, —OH and the rest of the molecule, represent stereogenic centers.

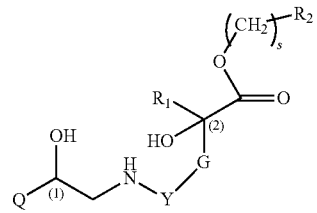

I

Thus, compounds according to the present invention, having at least two stereogenic centers, they may accordingly exist as at least four diastereoisomers. Where the compounds according to the invention possess more than two stereogenic centers, they will exist as $2^n$ diastereoisomers (wherein n here refers to the number of stereogenic centers). It is to be understood that all such isomers and mixtures thereof in any proportion are encompassed within the scope of the present invention.

In a preferred embodiment, the invention is directed to compounds of formula (I)', which are compounds of formula (I) as above defined where the absolute configuration of carbon (1) is that shown herebelow:

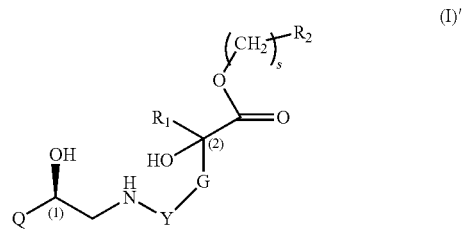

(I)'

The absolute configuration for a chiral carbon is determined via X ray and assigned on the basis of Cahn-Ingold-Prelog nomenclature based on groups' priorities.

Thus, in one preferred embodiment, for compounds of formula (I), absolute configuration at carbon (1) is (R).

As above said, compounds of formula (I) may exist as at least four diastereoisomers (Ia), (Ib), (Ic), and (Id) herebelow represented, which are comprised within the scope of the present invention; each diastereoisomer (Ia), (Ib), (Ic), and (Id) may be constituted by a mixture of corresponding epimers when a third stereogenic center is present in the molecule.

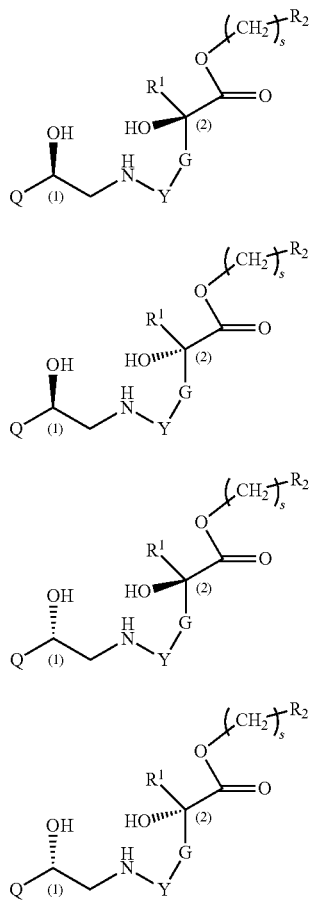

In a further preferred embodiment, the present invention is directed to compounds of formula (Ia) or (Ib), which are respectively compounds of formula (I) as above defined wherein the absolute configuration at carbon (1) is (R) and at carbon (2) is (R); or wherein the absolute configuration at carbon (1) is (R) and at carbon (2) is (S).

It is to be understood that all preferred groups or embodiments described herebelow and hereabove for compounds of formula (I) may be combined among each other and apply to compounds of formula (Ia), (Ib), (Ic), (Id), and (I)' as well mutatis mutandis.

In a first preferred embodiment the invention is directed to group of compounds of general formula I wherein $R_2$ is a group of formula J3:

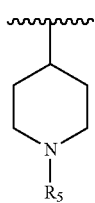

$R_5$ is a group of formula K, wherein p is 0 or 1, P is absent or is CO, q is absent or is 1 and W is H or is selected from $(C_1-C_6)$alkyl and aryl, and all the other variables are as defined above.

In a more preferred embodiment, $R_2$ is a group of formula J3, $R_5$ is methyl or benzyl, and all the other variables are as defined above.

In another preferred embodiment, G is arylene and $R_1$ is aryl, optionally substituted by one or more group independently selected from halogen, $(C_1-C_8)$alkyl and $(C_1-C_{10})$ alkoxy.

In a further preferred embodiment A1 and A2 are independently absent or selected from methylene, ethylene, propylene, butylene, pentylene, hexylene, heptylene, octylene and nonylene, G is phenylene, and $R_1$ is phenyl, optionally substituted by one or more group selected independently from halogen, $(C_1-C_8)$alkyl and $(C_1-C_{10})$alkoxy, and all the other variables are as defined above.

In this first preferred embodiment when $R_1$ is a phenyl group substituted by one or more groups independently selected from halogen, $(C_1-C_8)$alkyl and $(C_1-C_{10})$alkoxy; it is preferred that $R_1$. is substituted in para and/or meta position.

In another preferred embodiment E is —O— or —C(O)—$(CH_2)_n$—O— or —$NR_7$—C(O)—$(CH_2)_n$—O—; G is phenylene wherein E is linked to the phenyl ring G in meta position, and R1 is phenyl, optionally substituted by one or more group selected from halogen, $(C_1-C_8)$alkyl or $(C_1-C_{10})$ alkoxy groups.

Also in this other preferred embodiment, when $R_1$ is phenyl substituted by one or more group selected from halogen, $(C_1-C_8)$alkyl or $(C_1-C_{10})$alkoxy groups, it is preferred that $R_1$ is substituted in para and/or meta position.

Most preferred compounds in this other preferred embodiment are those compounds of formula (I) wherein Y is Y2;

A2 is absent and A1 is independently selected from $(C_1-C_{12})$alkylene which is methylene, ethylene, n-propylene, butylene, pentylene, hexylene, heptylene, octylene;

B is absent or is selected from $(C_3-C_8)$heterocycloalkylene which is piperidinylene, arylene which is phenylene and heteroarylene which is pyridine-diyl; B being optionally substituted by one or more groups selected independently from —OH, halogen which is fluorine, chlorine, bromine, $(C_1-C_6)$alkoxy which is methoxy, ethoxy, isopropoxy, $(C_1-C_6)$haloalkyl which is trifluoromethyl and $(C_1-C_6)$haloalkoxy which is trifluoromethoxy;

C is absent or is selected from —C(O)—, or is one of the following groups C1, C2, C7, C8, C9, C10, C12, C13, C14, C15, C16, C17, C18, C19, C20, C21, C23; wherein $R_7$ is H;

D is absent or is selected from arylene which is para-phenylene or meta-phenylene, $(C_3-C_8)$cycloalkylene which is cyclohexanediyl, $(C_3-C_8)$heterocycloalkylene which is piperidindiyl, pyrrolidindiyl, azetidindiyl;

n is at each occurrence independently 0 or an integer from 1, 2 or 3;

m is at each occurrence independently an integer from 1, 2 or 3;

E is absent or is selected from —O—, —C(O)—$(CH_2)_n$—O— which is —C(O)—$CH_2$—O—; —$NR_7$—C(O)—$(CH_2)_n$—O— which is —NH—C(O)—$CH_2$—O—;

G is arylene which is meta-phenylene;

$R_1$ is selected from thiophenyl, cyclohexyl or phenyl optionally substituted in para and/or meta position by one or more groups selected independently from fluorine, methyl, ethyl;

s is 1;

$R_2$ is J3 wherein $R_5$ is benzyl and pharmaceutically acceptable salts or solvates thereof.

A second preferred group of compounds is that of general formula I wherein $R_2$ is a nitrogen containing group selected from J1, J2, or J5

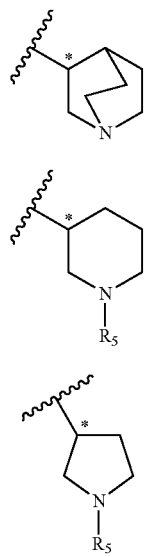

and all the other variables as defined above.

Particularly preferred compounds of formula I are those wherein

Y is a divalent groups of formula

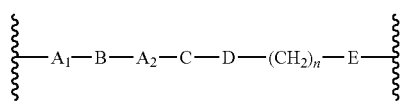

A2 is absent and A1 is independently selected from $(C_1-C_{12})$alkylene which is methylene, ethylene, n-propylene, isopropylene, butylene, pentylene, hexylene, heptylene, or octylene;

B is absent or is selected from $(C_3-C_8)$heterocycloalkylene which is piperidinylene, arylene which is phenylene, or heteroarylene which is pyridine-diyl, pyrazole-diyl; B being optionally substituted by one or more groups selected from —OH, halogen which is fluorine, chlorine, bromine, —CN, $(C_1-C_6)$alkyl which is methyl, $(C_1-C_6)$alkoxy which is methoxy, ethoxy, isopropoxy, $(C_1-C_6)$haloalkyl which is trifluoromethyl and $(C_3-C_6)$haloalkoxy which is trifluoromethoxy;

C is absent or is selected from —O—, —C(O)—, or is one of the following groups C1, C2, C4, C7, C8, C9, C10, C12, C13, C14, C15, C16, C17, C18, C19, C20, C21 C22 C23, wherein $R_7$ is in each occurrence independently H or selected from $(C_1-C_8)$alkyl which is methyl, ethyl and aryl$(C_1-C_6)$alkyl which is benzyl;

D is absent or is selected from arylene which is para-phenylene or meta-phenylene, $(C_3-C_8)$cycloalkylene which is cyclohexanediyl, $(C_3-C_8)$heterocycloalkylene which is piperidindiyl, pyrrolidindiyl, or azetidindiyl;

n is at each occurrence independently 0 or an integer from 1 to 3;

m is at each occurrence independently an integer from 1 to 3;

E is absent or is selected from —O—, —NR$_7$— which is —NH—, —NR$_7$—C(O)— which is —NH—C(O)—, —C(O)—NR$_7$— which is —C(O)—NH—, —C(O)—(CH$_2$)$_n$—O— which is —C(O)—CH$_2$—O—; —NR$_7$—C(O)—(CH$_2$)$_n$—O— which is —NH—C(O)—CH$_2$—O—;

G is arylene which is meta-phenylene or para-phenylene;

$R_1$ is selected from thiophenyl, cyclohexyl, cyclopentyl and phenyl optionally substituted by one or more group selected independently from fluorine, methyl, ethyl and methoxy;

s is 0, 1 or 2

$R_2$ is a nitrogen containing group which may be selected from:

a group (a) which is —NR$_3$R$_4$ wherein $R_3$ and $R_4$ are methyl; and a group (b) of formula J1, J2, J3, J4 or J5 wherein $R_5$ is methyl or benzyl and pharmaceutically acceptable salts or solvates thereof.

The present invention is also directed to a process for the preparation of the compounds of general formula I.

The present invention also provides pharmaceutical compositions of compounds of formula I alone or in combination with or in admixture with one or more pharmaceutically acceptable carriers and/or excipients.

The present invention also provides the use of compounds of formula I for preparing a medicament.

In a further aspect, the present invention provides the use of compounds of formula I for the prevention and/or treatment of any broncho-obstructive or inflammatory disease, preferably asthma or chronic bronchitis or chronic obstructive pulmonary disease (COPD).

In a further aspect, the present invention provides the use of compounds of formula I for the manufacture of a medicament for the prevention and/or treatment of any broncho-obstructive or inflammatory disease, preferably asthma or chronic bronchitis or chronic obstructive pulmonary disease (COPD).

The present invention further provides a method for prevention and/or treatment of any broncho-obstructive or inflammatory disease, preferably asthma or chronic bronchitis or chronic obstructive pulmonary disease (COPD), which comprises administering to a subject in need thereof a therapeutically effective amount of a compound of general formula I.

The present invention also provides pharmaceutical compositions suitable for administration by inhalation.

Inhalable preparations include inhalable powders, propellant-containing metering aerosols or propellant-free inhalable formulations.

The present invention is also directed to a device which may be a single- or multi-dose dry powder inhaler, a metered dose inhaler and a soft mist nebulizer comprising the compounds of formula I.

The present invention is also directed to a kit comprising the pharmaceutical compositions of compounds of formula I alone or in combination with or in admixture with one or more pharmaceutically acceptable carriers and/or excipients and a device which may be a single- or multi-dose dry powder inhaler, a metered dose inhaler and a soft mist nebulizer comprising the said combination or admixture.

According to specific embodiments, the present invention provides the compounds reported below:

| No. | Structure Name |
|---|---|
| 1 | (1-benzylpiperidin-4-yl)methyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate |
| 2 | (1-benzylpiperidin-4-yl)methyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-(p-tolyl)acetate |
| 3 | (1-benzylpiperidin-4-yl)methyl 2-(4-fluorophenyl)-2-hydroxy-2-(3-((5-(((R)-2-hydroxy-2-(8-hydroxy-2-oxo-1,2-dihydroquinolin-5-yl)ethyl)amino)pentyl)oxy)phenyl)acetate |
| 4 | (1-benzylpiperidin-4-yl)methyl 2-(3-fluorophenyl)-2-hydroxy-2-(3-((5-(((R)-2-hydroxy-2-(8-hydroxy-2-oxo-1,2-dihydroquinolin-5-yl)ethyl)amino)pentyl)oxy)phenyl)acetate |
| 5 | (1-benzylpiperidin-4-yl)methyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-(m-tolyl)acetate |
| 6 | (1-benzylpiperidin-4-yl)methyl 2-(2-chlorophenyl)-2-hydroxy-2-(3-((5-(((R)-2-hydroxy-2-(8-hydroxy-2-oxo-1,2-dihydroquinolin-5-yl)ethyl)amino)pentyl)oxy)phenyl)acetate |
| 7 | (1-benzylpiperidin-4-yl)methyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-(o-tolyl)acetate |
| 8 | (1-benzylpiperidin-4-yl)methyl 2-(2-ethylphenyl)-2-hydroxy-2-(3-((5-(((R)-2-hydroxy-2-(8-hydroxy-2-oxo-1,2-dihydroquinolin-5-yl)ethyl)amino)pentyl)oxy)phenyl)acetate |
| 9 | (1-benzylpiperidin-4-yl)methyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-(thiophen-2-yl)acetate |
| 10 | (1-benzylpiperidin-4-yl)methyl 2-cyclohexyl-2-hydroxy-2-(3-((5-(((R)-2-hydroxy-2-(8-hydroxy-2-oxo-1,2-dihydroquinolin-5-yl)ethyl)amino)pentyl)oxy)phenyl)acetate |
| 11 | (1-benzylpiperidin-4-yl)methyl 2-(3-ethylphenyl)-2-hydroxy-2-(3-((5-(((R)-2-hydroxy-2-(8-hydroxy-2-oxo-1,2-dihydroquinolin-5-yl)ethyl)amino)pentyl)oxy)phenyl)acetate |
| 12 | (R)-quinuclidin-3-yl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-(4-methoxyphenyl)acetate |
| 12A | (R)-quinuclidin-3-yl 2-cyclopentyl-2-hydroxy-2-(3-((5-(((R)-2-hydroxy-2-(8-hydroxy-2-oxo-1,2-dihydroquinolin-5-yl)ethyl)amino)pentyl)oxy)phenyl)acetate |
| 13 | (S)-(1-benzylpiperidin-4-yl)methyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate |
| 14 | (R)-(1-benzylpiperidin-4-yl)methyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate |
| 15 | (R)-quinuclidin-3-yl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate |
| 16 | (R)-(R)-quinuclidin-3-yl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate |
| 17 | (S)-2-(dimethylamino)ethyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate |
| 18 | (R)-2-(dimethylamino)ethyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate |
| 19 | (S)-(R)-1-methylpyrrolidin-3-yl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate |
| 20 | (R)-(R)-1-methylpyrrolidin-3-yl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate |
| 21 | (S)-1-methylpiperidin-4-yl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate |
| 22 | (R)-1-methylpiperidin-4-yl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate |
| 23 | (S)-(1-methylpiperidin-4-yl)methyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate |
| 24 | (R)-(1-methylpiperidin-4-yl)methyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate |
| 25 | (S)-(R)-1-methylpiperidin-3-yl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate |
| 26 | (S)-1-methylazetidin-3-yl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate |

-continued

| No. | Structure Name |
|---|---|
| 27 | (R)-(1-benzylpiperidin-4-yl)methyl 2-hydroxy-2-(3-((6-(((R)-2-hydroxy-2-(8-hydroxy-2-oxo-1,2-dihydroquinolin-5-yl)ethyl)amino)hexyl)oxy)phenyl)-2-phenylacetate |
| 28 | (S)-(1-benzylpiperidin-4-yl)methyl 2-hydroxy-2-(3-((7-(((R)-2-hydroxy-2-(8-hydroxy-2-oxo-1,2-dihydroquinolin-5-yl)ethyl)amino)heptyl)oxy)phenyl)-2-phenylacetate |
| 29 | (S)-(1-benzylpiperidin-4-yl)methyl 2-hydroxy-2-(3-((6-(((R)-2-hydroxy-2-(8-hydroxy-2-oxo-1,2-dihydroquinolin-5-yl)ethyl)amino)hexyl)oxy)phenyl)-2-phenylacetate |
| 30 | (S)-(1-benzylpiperidin-4-yl)methyl 2-hydroxy-2-(3-((8-(((R)-2-hydroxy-2-(8-hydroxy-2-oxo-1,2-dihydroquinolin-5-yl)ethyl)amino)octyl)oxy)phenyl)-2-phenylacetate |
| 31 | (S)-(1-benzylpiperidin-4-yl)methyl 2-hydroxy-2-(3-((1-(4-(2-(((R)-2-hydroxy-2-(8-hydroxy-2-oxo-1,2-dihydroquinolin-5-yl)ethyl)amino)ethyl)benzoyl)piperidin-4-yl)methoxy)phenyl)-2-phenylacetate |
| 32 | (S)-(1-benzylpiperidin-4-yl)methyl 2-hydroxy-2-(3-(3-(4-((((R)-2-hydroxy-2-(8-hydroxy-2-oxo-1,2-dihydroquinolin-5-yl)ethyl)amino)methyl)benzamido)propoxy)phenyl)-2-phenylacetate |
| 32A | (S)-(1-benzylpiperidin-4-yl)methyl 2-hydroxy-2-(3-(3-(4-((((R)-2-hydroxy-2-(8-hydroxy-2-oxo-1,2-dihydroquinolin-5-yl)ethyl)amino)methyl)-3-methoxybenzamido)propoxy)phenyl)-2-phenylacetate |
| 32B | (S)-(1-benzylpiperidin-4-yl)methyl 2-hydroxy-2-(3-(3-(4-((((R)-2-hydroxy-2-(8-hydroxy-2-oxo-1,2-dihydroquinolin-5-yl)ethyl)amino)methyl)-2-methoxybenzamido)propoxy)phenyl)-2-phenylacetate |
| 32C | (S)-(1-benzylpiperidin-4-yl)methyl 2-hydroxy-2-(3-(3-(6-((((R)-2-hydroxy-2-(8-hydroxy-2-oxo-1,2-dihydroquinolin-5-yl)ethyl)amino)methyl)nicotinamido)propoxy)phenyl)-2-phenylacetate |
| 32D | (S)-(1-benzylpiperidin-4-yl)methyl 2-(3-(3-(3-ethoxy-4-((((R)-2-hydroxy-2-(8-hydroxy-2-oxo-1,2-dihydroquinolin-5-yl)ethyl)amino)methyl)benzamido)propoxy)phenyl)-2-hydroxy-2-phenylacetate |
| 32E | (S)-(1-benzylpiperidin-4-yl)methyl 2-hydroxy-2-(3-(3-(4-((((R)-2-hydroxy-2-(8-hydroxy-2-oxo-1,2-dihydroquinolin-5-yl)ethyl)amino)methyl)-3-(trifluoromethoxy)benzamido)propoxy)phenyl)-2-phenylacetate |
| 32F | (S)-(1-benzylpiperidin-4-yl)methyl 2-(3-(3-(2-fluoro-4-((((R)-2-hydroxy-2-(8-hydroxy-2-oxo-1,2-dihydroquinolin-5-yl)ethyl)amino)methyl)-3-methoxybenzamido)propoxy)phenyl)-2-hydroxy-2-phenylacetate |
| 32G | (S)-(1-benzylpiperidin-4-yl)methyl 2-hydroxy-2-(3-(3-(4-((((R)-2-hydroxy-2-(8-hydroxy-2-oxo-1,2-dihydroquinolin-5-yl)ethyl)amino)methyl)-3-isopropoxybenzamido)propoxy)phenyl)-2-phenylacetate |
| 32H | (S)-(1-benzylpiperidin-4-yl)methyl 2-(3-(3-(2-chloro-4-((((R)-2-hydroxy-2-(8-hydroxy-2-oxo-1,2-dihydroquinolin-5-yl)ethyl)amino)methyl)benzamido)propoxy)phenyl)-2-hydroxy-2-phenylacetate |
| 32I | (S)-(1-benzylpiperidin-4-yl)methyl 2-(3-(3-(2-fluoro-4-((((R)-2-hydroxy-2-(8-hydroxy-2-oxo-1,2-dihydroquinolin-5-yl)ethyl)amino)methyl)-5-methoxybenzamido)propoxy)phenyl)-2-hydroxy-2-phenylacetate |
| 32J | (S)-(1-benzylpiperidin-4-yl)methyl 2-(3-(3-(2-chloro-4-((((R)-2-hydroxy-2-(8-hydroxy-2-oxo-1,2-dihydroquinolin-5-yl)ethyl)amino)methyl)-5-methoxybenzamido)propoxy)phenyl)-2-hydroxy-2-phenylacetate |
| 32K | (S)-(1-benzylpiperidin-4-yl)methyl 2-hydroxy-2-(3-(3-(5-((((R)-2-hydroxy-2-(8-hydroxy-2-oxo-1,2-dihydroquinolin-5-yl)ethyl)amino)methyl)picolinamido)propoxy)phenyl)-2-phenylacetate |
| 32L | (S)-(1-benzylpiperidin-4-yl)methyl 2-(3-(3-(2,3-difluoro-4-((((R)-2-hydroxy-2-(8-hydroxy-2-oxo-1,2-dihydroquinolin-5-yl)ethyl)amino)methyl)benzamido)propoxy)phenyl)-2-hydroxy-2-phenylacetate |
| 32M | (S)-(1-benzylpiperidin-4-yl)methyl (S)-2-hydroxy-2-(3-(3-(4-((((R)-2-hydroxy-2-(8-hydroxy-2-oxo-1,2-dihydroquinolin-5-yl)ethyl)amino)methyl)-3-(trifluoromethyl)benzamido)propoxy)phenyl)-2-phenylacetate |
| 33 | (S)-(1-benzylpiperidin-4-yl)methyl 2-hydroxy-2-(3-((4-(4-((((R)-2-hydroxy-2-(8-hydroxy-2-oxo-1,2-dihydroquinolin-5-yl)ethyl)amino)methyl)-piperidine-1-carbonyl)benzyl)oxy)phenyl)-2-phenylacetate |
| 33A | (1-benzylpiperidin-4-yl)methyl (S)-2-hydroxy-2-(3-((4-(4-(2-(((R)-2-hydroxy-2-(4-hydroxy-6-oxo-5,6-dihydronaphthalen-1-yl)ethyl)amino)ethyl)piperidine-1-carbonyl)benzyl)oxy)phenyl)-2-phenylacetate |
| 34 | (R)-(1-benzylpiperidin-4-yl)methyl 2-hydroxy-2-(3-(2-(4-(2-(((R)-2-hydroxy-2-(8-hydroxy-2-oxo-1,2-dihydroquinolin-5-yl)ethyl)amino)ethyl)benzamido)ethoxy)phenyl)-2-phenylacetate |
| 35 | (S)-(1-benzylpiperidin-4-yl)methyl 2-hydroxy-2-(3-((3-(4-((((R)-2-hydroxy-2-(8-hydroxy-2-oxo-1,2-dihydroquinolin-5-yl)ethyl)amino)methyl)-piperidine-1-carbonyl)benzyl)oxy)phenyl)-2-phenylacetate |
| 36 | (S)-(1-benzylpiperidin-4-yl)methyl 2-hydroxy-2-(3-(2-(4-((((R)-2-hydroxy-2-(8-hydroxy-2-oxo-1,2-dihydroquinolin-5-yl)ethyl)amino)methyl)piperidin-1-yl)-2-oxoethoxy)phenyl)-2-phenylacetate |

-continued

| No. | Structure Name |
|---|---|
| 36A | (1-benzylpiperidin-4-yl)methyl (S)-2-hydroxy-2-(3-(2-(4-(2-(((R)-2-hydroxy-2-(8-hydroxy-2-oxo-1,2-dihydroquinolin-5-yl)ethyl)amino)ethyl)piperidin-1-yl)-2-oxoethoxy)phenyl)-2-phenylacetate |
| 37 | (S)-(1-benzylpiperidin-4-yl)methyl 2-hydroxy-2-(3-(3-(4-(2-(((R)-2-hydroxy-2-(8-hydroxy-2-oxo-1,2-dihydroquinolin-5-yl)ethyl)amino)ethyl)benzamido)propoxy)phenyl)-2-phenylacetate |
| 38 | (S)-(1-benzylpiperidin-4-yl)methyl 2-hydroxy-2-(3-(2-(4-(2-(((R)-2-hydroxy-2-(8-hydroxy-2-oxo-1,2-dihydroquinolin-5-yl)ethyl)amino)ethyl)benzamido)ethoxy)phenyl)-2-phenylacetate |
| 39 | (1-benzylpiperidin-4-yl)methyl 2-hydroxy-2-(3-(2-(4-((((R)-2-hydroxy-2-(8-hydroxy-2-oxo-1,2-dihydroquinolin-5-yl)ethyl)amino)methyl)benzamido)ethyl)phenyl)-2-phenylacetate |
| 40 | (1-benzylpiperidin-4-yl)methyl 2-hydroxy-2-(3-(2-(4-(2-(((R)-2-hydroxy-2-(8-hydroxy-2-oxo-1,2-dihydroquinolin-5-yl)ethyl)amino)ethyl)benzamido)ethyl)phenyl)-2-phenylacetate |
| 41 | (S)-(1-benzylpiperidin-4-yl)methyl 2-hydroxy-2-(3-((1-(4-((((R)-2-hydroxy-2-(8-hydroxy-2-oxo-1,2-dihydroquinolin-5-yl)ethyl)amino)methyl)-benzoyl)azetidin-3-yl)methoxy)phenyl)-2-phenylacetate |
| 42 | (S)-(1-benzylpiperidin-4-yl)methyl 2-hydroxy-2-(3-((1-(4-(2-(((R)-2-hydroxy-2-(8-hydroxy-2-oxo-1,2-dihydroquinolin-5-yl)ethyl)amino)ethyl)benzoyl)azetidin-3-yl)methoxy)phenyl)-2-phenylacetate |
| 42A | (S)-(1-benzylpiperidin-4-yl)methyl 2-hydroxy-2-(3-(2-((4-((((R)-2-hydroxy-2-(8-hydroxy-2-oxo-1,2-dihydroquinolin-5-yl)ethyl)amino)methyl)-3-methoxyphenyl)amino)-2-oxoethoxy)phenyl)-2-phenylacetate |
| 42B | (1-benzylpiperidin-4-yl)methyl (S)-2-(3-(2-((2-fluoro-4-((((R)-2-hydroxy-2-(8-hydroxy-2-oxo-1,2-dihydroquinolin-5-yl)ethyl)amino)methyl)-5-methoxyphenyl)amino)-2-oxoethoxy)phenyl)-2-hydroxy-2-phenylacetate |
| 42C | (1-benzylpiperidin-4-yl)methyl (S)-2-hydroxy-2-(3-((4-((4-(2-(((R)-2-hydroxy-2-(8-hydroxy-2-oxo-1,2-dihydroquinolin-5-yl)ethyl)amino)ethyl)benzamido)methyl)benzyl)oxy)phenyl)-2-phenylacetate |
| 42D | (1-benzylpiperidin-4-yl)methyl (S)-2-hydroxy-2-(3-((4-((4-((((R)-2-hydroxy-2-(8-hydroxy-2-oxo-1,2-dihydroquinolin-5-yl)ethyl)amino)methyl)benzamido)methyl)benzyl)oxy)phenyl)-2-phenylacetate |
| 42E | (1-benzylpiperidin-4-yl)methyl (S)-2-hydroxy-2-(3-((4-((4-((((R)-2-hydroxy-2-(8-hydroxy-2-oxo-1,2-dihydroquinolin-5-yl)ethyl)amino)methyl)-2-methoxybenzamido)methyl)benzyl)oxy)phenyl)-2-phenylacetate |
| 42F | (1-benzylpiperidin-4-yl)methyl (S)-2-hydroxy-2-(3-((4-((4-((((R)-2-hydroxy-2-(8-hydroxy-2-oxo-1,2-dihydroquinolin-5-yl)ethyl)amino)methyl)-3-methoxybenzamido)methyl)benzyl)oxy)phenyl)-2-phenylacetate |
| 43 | (S)-(1-benzylpiperidin-4-yl)methyl 2-hydroxy-2-(3-((4-((3-(((R)-2-hydroxy-2-(8-hydroxy-2-oxo-1,2-dihydroquinolin-5-yl)ethyl)amino)propyl)carbamoyl)benzyl)oxy)phenyl)-2-phenylacetate |
| 44 | (R)-(1-benzylpiperidin-4-yl)methyl 2-hydroxy-2-(3-((4-((3-(((R)-2-hydroxy-2-(8-hydroxy-2-oxo-1,2-dihydroquinolin-5-yl)ethyl)amino)propyl)carbamoyl)benzyl)oxy)phenyl)-2-phenylacetate |
| 45 | (S)-(1-benzylpiperidin-4-yl)methyl 2-(3-((3-(benzyl(3-(((R)-2-hydroxy-2-(8-hydroxy-2-oxo-1,2-dihydroquinolin-5-yl)ethyl)amino)propyl)carbamoyl)benzyl)oxy)phenyl)-2-hydroxy-2-phenylacetate |
| 46 | (R)-quinuclidin-3-yl 2-hydroxy-2-(3-(4-((5-(((R)-2-hydroxy-2-(8-hydroxy-2-oxo-1,2-dihydroquinolin-5-yl)ethyl)amino)pentyl)oxy)benzamido)phenyl)-2-phenylacetate |
| 47 | (1-benzylpiperidin-4-yl)methyl 2-hydroxy-2-(3-((4-(((R)-2-hydroxy-2-(8-hydroxy-2-oxo-1,2-dihydroquinolin-5-yl)ethyl)amino)butyl)carbamoyl)phenyl)-2-phenylacetate |
| 48 | (R)-quinuclidin-3-yl 2-hydroxy-2-(3-((4-(((R)-2-hydroxy-2-(8-hydroxy-2-oxo-1,2-dihydroquinolin-5-yl)ethyl)amino)butyl)carbamoyl)phenyl)-2-phenylacetate |
| 49 | (R)-1-methylpyrrolidin-3-yl 2-hydroxy-2-(3-((4-(((R)-2-hydroxy-2-(8-hydroxy-2-oxo-1,2-dihydroquinolin-5-yl)ethyl)amino)butyl)carbamoyl)phenyl)-2-phenylacetate |
| 50 | (1-benzylpiperidin-4-yl)methyl 2-hydroxy-2-(3-((3-(4-((((R)-2-hydroxy-2-(8-hydroxy-2-oxo-1,2-dihydroquinolin-5-yl)ethyl)amino)methyl)benzamido)propyl)carbamoyl)phenyl)-2-phenylacetate |
| 51 | (1-benzylpiperidin-4-yl)methyl 2-hydroxy-2-(4-((5-(((R)-2-hydroxy-2-(8-hydroxy-2-oxo-1,2-dihydroquinolin-5-yl)ethyl)amino)pentyl)oxy)phenyl)-2-phenylacetate |
| 52 | (R)-quinuclidin-3-yl 2-hydroxy-2-(4-((5-(((R)-2-hydroxy-2-(8-hydroxy-2-oxo-1,2-dihydroquinolin-5-yl)ethyl)amino)pentyl)oxy)phenyl)-2-phenylacetate |
| 53 | (1-benzylpiperidin-4-yl)methyl 2-hydroxy-2-(4-((4-((4-((((R)-2-hydroxy-2-(8-hydroxy-2-oxo-1,2-dihydroquinolin-5-yl)ethyl)amino)methyl)benzamido)methyl)benzyl)oxy)phenyl)-2-phenylacetate |
| 54 | (1-benzylpiperidin-4-yl)methyl 2-hydroxy-2-(3-(((((5-(((R)-2-hydroxy-2-(8-hydroxy-2-oxo-1,2-dihydroquinolin-5-yl)ethyl)amino)pentyl)oxy)carbonyl)amino)phenyl)-2-phenylacetate |
| 55 | (R)-quinuclidin-3-yl 2-hydroxy-2-(3-(5-(((R)-2-hydroxy-2-(8-hydroxy-2-oxo-1,2-dihydroquinolin-5-yl)ethyl)amino)pentanamido)phenyl)-2-phenylacetate |

-continued

| No. | Structure Name |
|---|---|
| 56 | (1-benzylpiperidin-4-yl)methyl 2-hydroxy-2-(3-(3-(3-(4-((((R)-2-hydroxy-2-(8-hydroxy-2-oxo-1,2-dihydroquinolin-5-yl)ethyl)amino)methyl)benzamido)propyl)ureido)phenyl)-2-phenylacetate |
| 57 | (1-benzylpiperidin-4-yl)methyl (S)-2-hydroxy-2-(3-(2-((2-(4-((((R)-2-hydroxy-2-(8-hydroxy-2-oxo-1,2-dihydroquinolin-5-yl)ethyl)amino)methyl)benzamido)ethyl)amino)-2-oxoethoxy)phenyl)-2-phenylacetate |
| 58 | (1-benzylpiperidin-4-yl)methyl (S)-2-hydroxy-2-(3-(2-(4-(4-((((R)-2-hydroxy-2-(8-hydroxy-2-oxo-1,2-dihydroquinolin-5-yl)ethyl)amino)methyl)benzoyl)piperazin-1-yl)-2-oxoethoxy)phenyl)-2-phenylacetate |
| 59 | (1-benzylpiperidin-4-yl)methyl (S)-2-hydroxy-2-(3-(2-(4-(4-((((R)-2-hydroxy-2-(8-hydroxy-2-oxo-1,2-dihydroquinolin-5-yl)ethyl)amino)methyl)benzamido)piperidin-1-yl)-2-oxoethoxy)phenyl)-2-phenylacetate |
| 60 | (1-benzylpiperidin-4-yl)methyl (S)-2-hydroxy-2-(3-(2-((2-(4-((((R)-2-hydroxy-2-(8-hydroxy-2-oxo-1,2-dihydroquinolin-5-yl)ethyl)amino)methyl)benzamido)ethyl)(methyl)amino)-2-oxoethoxy)phenyl)-2-phenylacetate |
| 61 | (1-benzylpiperidin-4-yl)methyl (S)-2-hydroxy-2-(3-(2-(4-((4-((((R)-2-hydroxy-2-(8-hydroxy-2-oxo-1,2-dihydroquinolin-5-yl)ethyl)amino)methyl)benzamido)methyl)piperidin-1-yl)-2-oxoethoxy)phenyl)-2-phenylacetate |
| 62 | (1-benzylpiperidin-4-yl)methyl (S)-2-hydroxy-2-(3-(2-(((1R,4S)-4-(4-((((R)-2-hydroxy-2-(8-hydroxy-2-oxo-1,2-dihydroquinolin-5-yl)ethyl)amino)methyl)benzamido)cyclohexyl)amino)-2-oxoethoxy)phenyl)-2-phenylacetate |
| 63 | (1-benzylpiperidin-4-yl)methyl (S)-2-hydroxy-2-(3-(2-(((1R,3S)-3-(4-((((R)-2-hydroxy-2-(8-hydroxy-2-oxo-1,2-dihydroquinolin-5-yl)ethyl)amino)methyl)benzamido)cyclobutyl)amino)-2-oxoethoxy)phenyl)-2-phenylacetate |
| 64 | (1-benzylpiperidin-4-yl)methyl (S)-2-hydroxy-2-(3-(2-(9-(4-((((R)-2-hydroxy-2-(8-hydroxy-2-oxo-1,2-dihydroquinolin-5-yl)ethyl)amino)methyl)benzoyl)-3,9-diazaspiro[5.5]undecan-3-yl)-2-oxoethoxy)phenyl)-2-phenylacetate |
| 65 | (1-benzylpiperidin-4-yl)methyl (S)-2-hydroxy-2-(3-(2-((1-(4-((((R)-2-hydroxy-2-(8-hydroxy-2-oxo-1,2-dihydroquinolin-5-yl)ethyl)amino)methyl)benzoyl)piperidin-4-yl)amino)-2-oxoethoxy)phenyl)-2-phenylacetate |
| 66 | (1-benzylpiperidin-4-yl)methyl (S)-2-hydroxy-2-(3-(2-((1-(4-((((R)-2-hydroxy-2-(8-hydroxy-2-oxo-1,2-dihydroquinolin-5-yl)ethyl)amino)methyl)benzoyl)azetidin-3-yl)amino)-2-oxoethoxy)phenyl)-2-phenylacetate |
| 67 | (1-benzylpiperidin-4-yl)methyl (S)-2-hydroxy-2-(3-(2-(3-(4-((((R)-2-hydroxy-2-(8-hydroxy-2-oxo-1,2-dihydroquinolin-5-yl)ethyl)amino)methyl)benzamido)azetidin-1-yl)-2-oxoethoxy)phenyl)-2-phenylacetate |
| 68 | (1-benzylpiperidin-4-yl)methyl (S)-2-hydroxy-2-(3-(2-(((R)-1-(4-((((R)-2-hydroxy-2-(8-hydroxy-2-oxo-1,2-dihydroquinolin-5-yl)ethyl)amino)methyl)benzoyl)pyrrolidin-3-yl)amino)-2-oxoethoxy)phenyl)-2-phenylacetate |
| 69 | (1-benzylpiperidin-4-yl)methyl (S)-2-hydroxy-2-(3-(2-(((S)-1-(4-((((R)-2-hydroxy-2-(8-hydroxy-2-oxo-1,2-dihydroquinolin-5-yl)ethyl)amino)methyl)benzoyl)piperidin-3-yl)amino)-2-oxoethoxy)phenyl)-2-phenylacetate |
| 70 | (1-benzylpiperidin-4-yl)methyl (S)-2-hydroxy-2-(3-(2-(((S)-1-(4-((((R)-2-hydroxy-2-(8-hydroxy-2-oxo-1,2-dihydroquinolin-5-yl)ethyl)amino)methyl)benzoyl)pyrrolidin-3-yl)amino)-2-oxoethoxy)phenyl)-2-phenylacetate |
| 71 | (1-benzylpiperidin-4-yl)methyl (S)-2-hydroxy-2-(3-(2-(((R)-1-(4-((((R)-2-hydroxy-2-(8-hydroxy-2-oxo-1,2-dihydroquinolin-5-yl)ethyl)amino)methyl)benzoyl)piperidin-3-yl)amino)-2-oxoethoxy)phenyl)-2-phenylacetate |
| 72 | (1-benzylpiperidin-4-yl)methyl (S)-2-hydroxy-2-(3-(2-((S)-3-(4-((((R)-2-hydroxy-2-(8-hydroxy-2-oxo-1,2-dihydroquinolin-5-yl)ethyl)amino)methyl)benzamido)piperidin-1-yl)-2-oxoethoxy)phenyl)-2-phenylacetate |
| 73 | (1-benzylpiperidin-4-yl)methyl (S)-2-hydroxy-2-(3-(2-((S)-3-(4-((((R)-2-hydroxy-2-(8-hydroxy-2-oxo-1,2-dihydroquinolin-5-yl)ethyl)amino)methyl)benzamido)pyrrolidin-1-yl)-2-oxoethoxy)phenyl)-2-phenylacetate |
| 74 | (1-benzylpiperidin-4-yl)methyl (S)-2-hydroxy-2-(3-(2-((3aR,6aR)-5-(4-((((R)-2-hydroxy-2-(8-hydroxy-2-oxo-1,2-dihydroquinolin-5-yl)ethyl)amino)methyl)benzoyl)hexahydropyrrolo[3,4-b]pyrrol-1(2H)-yl)-2-oxoethoxy)phenyl)-2-phenylacetate |
| 75 | (1-benzylpiperidin-4-yl)methyl (S)-2-hydroxy-2-(3-(2-((R)-3-(4-((((R)-2-hydroxy-2-(8-hydroxy-2-oxo-1,2-dihydroquinolin-5- |

| No. | Structure Name |
|---|---|
| | yl)ethyl)amino)methyl)benzamido)piperidin-1-yl)-2-oxoethoxy)phenyl)-2-phenylacetate |
| 76 | (1-benzylpiperidin-4-yl)methyl (S)-2-hydroxy-2-(3-(2-((R)-3-(4-((((R)-2-hydroxy-2-(8-hydroxy-2-oxo-1,2-dihydroquinolin-5-yl)ethyl)amino)methyl)benzamido)pyrrolidin-1-yl)-2-oxoethoxy)phenyl)-2-phenylacetate |
| 77 | (1-benzylpiperidin-4-yl)methyl (S)-2-hydroxy-2-(3-(2-((3aS,6aS)-5-(4-((((R)-2-hydroxy-2-(8-hydroxy-2-oxo-1,2-dihydroquinolin-5-yl)ethyl)amino)methyl)benzoyl)hexahydropyrrolo[3,4-b]pyrrol-1(2H)-yl)-2-oxoethoxy)phenyl)-2-phenylacetate |
| 78 | (1-benzylpiperidin-4-yl)methyl (S)-2-hydroxy-2-(3-(2-((1-(4-((((R)-2-hydroxy-2-(8-hydroxy-2-oxo-1,2-dihydroquinolin-5-yl)ethyl)amino)methyl)-3-methoxybenzoyl)azetidin-3-yl)amino)-2-oxoethoxy)phenyl)-2-phenylacetate |
| 79 | (1-benzylpiperidin-4-yl)methyl (S)-2-hydroxy-2-(3-(2-(9-(4-((((R)-2-hydroxy-2-(8-hydroxy-2-oxo-1,2-dihydroquinolin-5-yl)ethyl)amino)methyl)-3-methoxybenzoyl)-3,9-diazaspiro[5.5]undecan-3-yl)-2-oxoethoxy)phenyl)-2-phenylacetate |
| 80 | (1-benzylpiperidin-4-yl)methyl (S)-2-hydroxy-2-(3-(2-(4-((4-((((R)-2-hydroxy-2-(8-hydroxy-2-oxo-1,2-dihydroquinolin-5-yl)ethyl)amino)methyl)-3-methoxybenzamido)methyl)piperidin-1-yl)-2-oxoethoxy)phenyl)-2-phenylacetate |
| 81 | (1-benzylpiperidin-4-yl)methyl (S)-2-hydroxy-2-(3-(2-(9-(4-((((R)-2-hydroxy-2-(8-hydroxy-2-oxo-1,2-dihydroquinolin-5-yl)ethyl)amino)methyl)-2-methoxybenzoyl)-3,9-diazaspiro[5.5]undecan-3-yl)-2-oxoethoxy)phenyl)-2-phenylacetate |
| 82 | (1-benzylpiperidin-4-yl)methyl (S)-2-hydroxy-2-(3-(2-((1-(4-((((R)-2-hydroxy-2-(8-hydroxy-2-oxo-1,2-dihydroquinolin-5-yl)ethyl)amino)methyl)-2-methoxybenzoyl)azetidin-3-yl)amino)-2-oxoethoxy)phenyl)-2-phenylacetate |
| 83 | (1-benzylpiperidin-4-yl)methyl (S)-2-(3-(2-(ethyl(2-(4-(2-(((R)-2-hydroxy-2-(8-hydroxy-2-oxo-1,2-dihydroquinolin-5-yl)ethyl)amino)ethyl)benzamido)ethyl)amino)-2-oxoethoxy)phenyl)-2-hydroxy-2-phenylacetate |
| 84 | (1-benzylpiperidin-4-yl)methyl (S)-2-hydroxy-2-(3-(2-((2-(4-(2-(((R)-2-hydroxy-2-(8-hydroxy-2-oxo-1,2-dihydroquinolin-5-yl)ethyl)amino)ethyl)benzamido)ethyl)(methyl)amino)-2-oxoethoxy)phenyl)-2-phenylacetate |
| 85 | (1-benzylpiperidin-4-yl)methyl (S)-2-hydroxy-2-(3-(2-((3-(4-(2-(((R)-2-hydroxy-2-(8-hydroxy-2-oxo-1,2-dihydroquinolin-5-yl)ethyl)amino)ethyl)benzamido)propyl)amino)-2-oxoethoxy)phenyl)-2-phenylacetate |
| 86 | (1-benzylpiperidin-4-yl)methyl (S)-2-hydroxy-2-(3-(2-(4-(4-(2-(((R)-2-hydroxy-2-(8-hydroxy-2-oxo-1,2-dihydroquinolin-5-yl)ethyl)amino)ethyl)benzoyl)piperazin-1-yl)-2-oxoethoxy)phenyl)-2-phenylacetate |
| 87 | (1-benzylpiperidin-4-yl)methyl (S)-2-(3-(2-(benzyl(2-(4-(2-(((R)-2-hydroxy-2-(8-hydroxy-2-oxo-1,2-dihydroquinolin-5-yl)ethyl)amino)ethyl)benzamido)ethyl)amino)-2-oxoethoxy)phenyl)-2-hydroxy-2-phenylacetate |
| 88 | (1-benzylpiperidin-4-yl)methyl (S)-2-hydroxy-2-(3-(2-(((1R,3S)-3-(4-(2-(((R)-2-hydroxy-2-(8-hydroxy-2-oxo-1,2-dihydroquinolin-5-yl)ethyl)amino)ethyl)benzamido)cyclobutyl)amino)-2-oxoethoxy)phenyl)-2-phenylacetate |
| 89 | (1-benzylpiperidin-4-yl)methyl (S)-2-hydroxy-2-(3-(2-(4-((4-(2-(((R)-2-hydroxy-2-(8-hydroxy-2-oxo-1,2-dihydroquinolin-5-yl)ethyl)amino)ethyl)benzamido)methyl)piperidin-1-yl)-2-oxoethoxy)phenyl)-2-phenylacetate |
| 90 | (1-benzylpiperidin-4-yl)methyl (S)-2-hydroxy-2-(3-(2-(((1R,4S)-4-(4-(2-(((R)-2-hydroxy-2-(8-hydroxy-2-oxo-1,2-dihydroquinolin-5-yl)ethyl)amino)ethyl)benzamido)cyclohexyl)amino)-2-oxoethoxy)phenyl)-2-phenylacetate |
| 91 | (1-benzylpiperidin-4-yl)methyl (S)-2-hydroxy-2-(3-(2-((1-(4-(2-(((R)-2-hydroxy-2-(8-hydroxy-2-oxo-1,2-dihydroquinolin-5-yl)ethyl)amino)ethyl)benzoyl)piperidin-4-yl)amino)-2-oxoethoxy)phenyl)-2-phenylacetate |
| 92 | (1-benzylpiperidin-4-yl)methyl (S)-2-hydroxy-2-(3-(2-(4-(4-(2-(((R)-2-hydroxy-2-(8-hydroxy-2-oxo-1,2-dihydroquinolin-5-yl)ethyl)amino)ethyl)benzamido)piperidin-1-yl)-2-oxoethoxy)phenyl)-2-phenylacetate |
| 93 | (1-benzylpiperidin-4-yl)methyl (S)-2-hydroxy-2-(3-(2-(6-(4-(2-(((R)-2-hydroxy-2-(8-hydroxy-2-oxo-1,2-dihydroquinolin-5-yl)ethyl)amino)ethyl)benzoyl)-2,6-diazaspiro[3.3]heptan-2-yl)-2-oxoethoxy)phenyl)-2-phenylacetate |
| 94 | (1-benzylpiperidin-4-yl)methyl (S)-2-hydroxy-2-(3-(2-(7-(4-(2-(((R)-2-hydroxy-2-(8-hydroxy-2-oxo-1,2-dihydroquinolin-5-yl)ethyl)amino)ethyl)benzoyl)-2,7-diazaspiro[3.5]nonan-2-yl)-2-oxoethoxy)phenyl)-2-phenylacetate |

-continued

| No. | Structure Name |
|---|---|
| 95 | (1-benzylpiperidin-4-yl)methyl (S)-2-hydroxy-2-(3-(2-(9-(4-(2-(((R)-2-hydroxy-2-(8-hydroxy-2-oxo-1,2-dihydroquinolin-5-yl)ethyl)amino)ethyl)benzoyl)-3,9-diazaspiro[5.5]undecan-3-yl)-2-oxoethoxy)phenyl)-2-phenylacetate |
| 96 | (1-benzylpiperidin-4-yl)methyl (S)-2-hydroxy-2-(3-(2-(2-(4-(2-(((R)-2-hydroxy-2-(8-hydroxy-2-oxo-1,2-dihydroquinolin-5-yl)ethyl)amino)ethyl)benzoyl)-2,7-diazaspiro[3.5]nonan-7-yl)-2-oxoethoxy)phenyl)-2-phenylacetate |
| 97 | (1-benzylpiperidin-4-yl)methyl (S)-2-hydroxy-2-(3-(2-(((1-(4-(2-(((R)-2-hydroxy-2-(8-hydroxy-2-oxo-1,2-dihydroquinolin-5-yl)ethyl)amino)ethyl)benzoyl)piperidin-4-yl)methyl)amino)-2-oxoethoxy)phenyl)-2-phenylacetate |
| 98 | (1-benzylpiperidin-4-yl)methyl (S)-2-hydroxy-2-(3-(2-(6-(4-(2-(((R)-2-hydroxy-2-(8-hydroxy-2-oxo-1,2-dihydroquinolin-5-yl)ethyl)amino)ethyl)benzoyl)-2,6-diazaspiro[3.5]nonan-2-yl)-2-oxoethoxy)phenyl)-2-phenylacetate |
| 99 | (1-benzylpiperidin-4-yl)methyl (S)-2-hydroxy-2-(3-(2-(9-(4-(2-(((R)-2-hydroxy-2-(8-hydroxy-2-oxo-1,2-dihydroquinolin-5-yl)ethyl)amino)ethyl)benzoyl)-2,9-diazaspiro[5.5]undecan-2-yl)-2-oxoethoxy)phenyl)-2-phenylacetate |
| 100 | (1-benzylpiperidin-4-yl)methyl (S)-2-hydroxy-2-(3-(2-(9-(4-(2-(((R)-2-hydroxy-2-(8-hydroxy-2-oxo-1,2-dihydroquinolin-5-yl)ethyl)amino)ethyl)benzoyl)-1-oxa-4,9-diazaspiro[5.5]undecan-4-yl)-2-oxoethoxy)phenyl)-2-phenylacetate |
| 101 | (1-benzylpiperidin-4-yl)methyl (S)-2-hydroxy-2-(3-(2-((1-(4-(2-(((R)-2-hydroxy-2-(8-hydroxy-2-oxo-1,2-dihydroquinolin-5-yl)ethyl)amino)ethyl)benzoyl)azetidin-3-yl)amino)-2-oxoethoxy)phenyl)-2-phenylacetate |
| 102 | (1-benzylpiperidin-4-yl)methyl (S)-2-hydroxy-2-(3-(2-(3-(4-(2-(((R)-2-hydroxy-2-(8-hydroxy-2-oxo-1,2-dihydroquinolin-5-yl)ethyl)amino)ethyl)benzamido)azetidin-1-yl)-2-oxoethoxy)phenyl)-2-phenylacetate |
| 103 | (1-benzylpiperidin-4-yl)methyl (S)-2-hydroxy-2-(3-(2-((2-(4-(2-(((R)-2-hydroxy-2-(8-hydroxy-2-oxo-1,2-dihydroquinolin-5-yl)ethyl)amino)ethyl)benzamido)ethyl)amino)-2-oxoethoxy)phenyl)-2-phenylacetate |
| 104 | (1-benzylpiperidin-4-yl)methyl (S)-2-hydroxy-2-(3-(2-(((R)-1-(4-(2-(((R)-2-hydroxy-2-(8-hydroxy-2-oxo-1,2-dihydroquinolin-5-yl)ethyl)amino)ethyl)benzoyl)pyrrolidin-3-yl)amino)-2-oxoethoxy)phenyl)-2-phenylacetate |
| 105 | (1-benzylpiperidin-4-yl)methyl (S)-2-hydroxy-2-(3-(2-(((R)-1-(4-(2-(((R)-2-hydroxy-2-(8-hydroxy-2-oxo-1,2-dihydroquinolin-5-yl)ethyl)amino)ethyl)benzoyl)piperidin-3-yl)amino)-2-oxoethoxy)phenyl)-2-phenylacetate |
| 106 | (1-benzylpiperidin-4-yl)methyl (S)-2-hydroxy-2-(3-(2-(((S)-1-(4-(2-(((R)-2-hydroxy-2-(8-hydroxy-2-oxo-1,2-dihydroquinolin-5-yl)ethyl)amino)ethyl)benzoyl)piperidin-3-yl)amino)-2-oxoethoxy)phenyl)-2-phenylacetate |
| 107 | (1-benzylpiperidin-4-yl)methyl (S)-2-hydroxy-2-(3-(2-(((S)-1-(4-(2-(((R)-2-hydroxy-2-(8-hydroxy-2-oxo-1,2-dihydroquinolin-5-yl)ethyl)amino)ethyl)benzoyl)pyrrolidin-3-yl)amino)-2-oxoethoxy)phenyl)-2-phenylacetate |
| 108 | (1-benzylpiperidin-4-yl)methyl (S)-2-hydroxy-2-(3-(2-((S)-3-(4-(2-(((R)-2-hydroxy-2-(8-hydroxy-2-oxo-1,2-dihydroquinolin-5-yl)ethyl)amino)ethyl)benzamido)piperidin-1-yl)-2-oxoethoxy)phenyl)-2-phenylacetate |
| 109 | (1-benzylpiperidin-4-yl)methyl (S)-2-hydroxy-2-(3-(2-((S)-3-(4-(2-(((R)-2-hydroxy-2-(8-hydroxy-2-oxo-1,2-dihydroquinolin-5-yl)ethyl)amino)ethyl)benzamido)pyrrolidin-1-yl)-2-oxoethoxy)phenyl)-2-phenylacetate |
| 110 | (1-benzylpiperidin-4-yl)methyl (S)-2-hydroxy-2-(3-(2-((R)-3-(4-(2-(((R)-2-hydroxy-2-(8-hydroxy-2-oxo-1,2-dihydroquinolin-5-yl)ethyl)amino)ethyl)benzamido)pyrrolidin-1-yl)-2-oxoethoxy)phenyl)-2-phenylacetate |
| 111 | (1-benzylpiperidin-4-yl)methyl (S)-2-hydroxy-2-(3-(2-((3aR,6aR)-1-(4-(2-(((R)-2-hydroxy-2-(8-hydroxy-2-oxo-1,2-dihydroquinolin-5-yl)ethyl)amino)ethyl)benzoyl)hexahydropyrrolo[3,4-b]pyrrol-5(1H)-yl)-2-oxoethoxy)phenyl)-2-phenylacetate |
| 112 | (1-benzylpiperidin-4-yl)methyl (S)-2-hydroxy-2-(3-(2-((3aS,6aS)-1-(4-(2-(((R)-2-hydroxy-2-(8-hydroxy-2-oxo-1,2-dihydroquinolin-5-yl)ethyl)amino)ethyl)benzoyl)hexahydropyrrolo[3,4-b]pyrrol-5(1H)-yl)-2-oxoethoxy)phenyl)-2-phenylacetate |
| 113 | (1-benzylpiperidin-4-yl)methyl (S)-2-hydroxy-2-(3-(2-((R)-3-(4-(2-(((R)-2-hydroxy-2-(8-hydroxy-2-oxo-1,2-dihydroquinolin-5-yl)ethyl)amino)ethyl)benzamido)piperidin-1-yl)-2-oxoethoxy)phenyl)-2-phenylacetate |

| No. | Structure Name |
|---|---|
| 114 | (1-benzylpiperidin-4-yl)methyl (S)-2-hydroxy-2-(3-((4-(((1R,3S)-3-(4-(2-(((R)-2-hydroxy-2-(8-hydroxy-2-oxo-1,2-dihydroquinolin-5-yl)ethyl)amino)ethyl)benzamido)cyclobutyl)carbamoyl)benzyl)oxy)phenyl)-2-phenylacetate |
| 115 | (1-benzylpiperidin-4-yl)methyl (S)-2-hydroxy-2-(3-((4-(9-(4-(2-(((R)-2-hydroxy-2-(8-hydroxy-2-oxo-1,2-dihydroquinolin-5-yl)ethyl)amino)ethyl)benzoyl)-3,9-diazaspiro[5.5]undecane-3-carbonyl)benzyl)oxy)phenyl)-2-phenylacetate |
| 116 | (1-benzylpiperidin-4-yl)methyl (S)-2-hydroxy-2-(3-((4-(6-(4-(2-(((R)-2-hydroxy-2-(8-hydroxy-2-oxo-1,2-dihydroquinolin-5-yl)ethyl)amino)ethyl)benzoyl)-2,6-diazaspiro[3.3]heptane-2-carbonyl)benzyl)oxy)phenyl)-2-phenylacetate |
| 117 | (1-benzylpiperidin-4-yl)methyl (S)-2-hydroxy-2-(3-((4-(7-(4-(2-(((R)-2-hydroxy-2-(8-hydroxy-2-oxo-1,2-dihydroquinolin-5-yl)ethyl)amino)ethyl)benzoyl)-2,7-diazaspiro[3.5]nonane-2-carbonyl)benzyl)oxy)phenyl)-2-phenylacetate |
| 118 | (1-benzylpiperidin-4-yl)methyl (S)-2-hydroxy-2-(3-((4-(4-(4-(2-(((R)-2-hydroxy-2-(8-hydroxy-2-oxo-1,2-dihydroquinolin-5-yl)ethyl)amino)ethyl)benzoyl)piperazine-1-carbonyl)benzyl)oxy)phenyl)-2-phenylacetate |
| 119 | (1-benzylpiperidin-4-yl)methyl (S)-2-hydroxy-2-(3-((4-(2-(4-(2-(((R)-2-hydroxy-2-(8-hydroxy-2-oxo-1,2-dihydroquinolin-5-yl)ethyl)amino)ethyl)benzoyl)-2,7-diazaspiro[3.5]nonane-7-carbonyl)benzyl)oxy)phenyl)-2-phenylacetate |
| 120 | (1-benzylpiperidin-4-yl)methyl (S)-2-hydroxy-2-(3-((4-(6-(4-(2-(((R)-2-hydroxy-2-(8-hydroxy-2-oxo-1,2-dihydroquinolin-5-yl)ethyl)amino)ethyl)benzoyl)-2,6-diazaspiro[3.5]nonane-2-carbonyl)benzyl)oxy)phenyl)-2-phenylacetate |
| 121 | (1-benzylpiperidin-4-yl)methyl (S)-2-hydroxy-2-(3-((4-(9-(4-(2-(((R)-2-hydroxy-2-(8-hydroxy-2-oxo-1,2-dihydroquinolin-5-yl)ethyl)amino)ethyl)benzoyl)-1-oxa-4,9-diazaspiro[5.5]undecane-4-carbonyl)benzyl)oxy)phenyl)-2-phenylacetate |
| 122 | (1-benzylpiperidin-4-yl)methyl (S)-2-hydroxy-2-(3-((4-(9-(4-(2-(((R)-2-hydroxy-2-(8-hydroxy-2-oxo-1,2-dihydroquinolin-5-yl)ethyl)amino)ethyl)benzoyl)-2,9-diazaspiro[5.5]undecane-2-carbonyl)benzyl)oxy)phenyl)-2-phenylacetate |
| 123 | (1-benzylpiperidin-4-yl)methyl (S)-2-hydroxy-2-(3-((4-(((1R,3S)-3-(4-((((R)-2-hydroxy-2-(8-hydroxy-2-oxo-1,2-dihydroquinolin-5-yl)ethyl)amino)methyl)benzamido)cyclobutyl)carbamoyl)benzyl)oxy)phenyl)-2-phenylacetate |
| 124 | (1-benzylpiperidin-4-yl)methyl (S)-2-hydroxy-2-(3-((4-(((1R,3S)-3-(4-((((R)-2-hydroxy-2-(8-hydroxy-2-oxo-1,2-dihydroquinolin-5-yl)ethyl)amino)methyl)-3-methoxybenzamido)cyclobutyl)carbamoyl)benzyl)oxy)phenyl)-2-phenylacetate |
| 125 | (1-benzylpiperidin-4-yl)methyl (S)-2-hydroxy-2-(3-((4-((2-(4-((((R)-2-hydroxy-2-(8-hydroxy-2-oxo-1,2-dihydroquinolin-5-yl)ethyl)amino)methyl)benzamido)ethyl)carbamoyl)benzyl)oxy)phenyl)-2-phenylacetate |
| 126 | (1-benzylpiperidin-4-yl)methyl (S)-2-hydroxy-2-(3-((4-((2-(4-((((R)-2-hydroxy-2-(8-hydroxy-2-oxo-1,2-dihydroquinolin-5-yl)ethyl)amino)methyl)-3-methoxybenzamido)ethyl)carbamoyl)benzyl)oxy)phenyl)-2-phenylacetate |
| 127 | (1-benzylpiperidin-4-yl)methyl (S)-2-hydroxy-2-(3-(2-(((1R,3S)-3-(3-hydroxy-4-((((R)-2-hydroxy-2-(8-hydroxy-2-oxo-1,2-dihydroquinolin-5-yl)ethyl)amino)methyl)benzamido)cyclobutyl)amino)-2-oxoethoxy)phenyl)-2-phenylacetate |
| 128 | (S)-(1-benzylpiperidin-4-yl)methyl 2-(3-(2-(((1R,3S)-3-(2-fluoro-4-((((R)-2-hydroxy-2-(8-hydroxy-2-oxo-1,2-dihydroquinolin-5-yl)ethyl)amino)methyl)benzamido)cyclobutyl)amino)-2-oxoethoxy)phenyl)-2-hydroxy-2-phenylacetate |
| 129 | (S)-(1-benzylpiperidin-4-yl)methyl 2-hydroxy-2-(3-(2-(((1R,3S)-3-(4-((((R)-2-hydroxy-2-(8-hydroxy-2-oxo-1,2-dihydroquinolin-5-yl)ethyl)amino)methyl)-3-methylbenzamido)cyclobutyl)amino)-2-oxoethoxy)phenyl)-2-phenylacetate |
| 130 | (S)-(1-benzylpiperidin-4-yl)methyl 2-hydroxy-2-(3-(2-(((1R,3S)-3-(4-((((R)-2-hydroxy-2-(8-hydroxy-2-oxo-1,2-dihydroquinolin-5-yl)ethyl)amino)methyl)-2-methoxybenzamido)cyclobutyl)amino)-2-oxoethoxy)phenyl)-2-phenylacetate |
| 131 | (S)-(1-benzylpiperidin-4-yl)methyl 2-hydroxy-2-(3-(2-(((1R,3S)-3-(4-((((R)-2-hydroxy-2-(8-hydroxy-2-oxo-1,2-dihydroquinolin-5-yl)ethyl)amino)methyl)-3-methoxybenzamido)cyclobutyl)amino)-2-oxoethoxy)phenyl)-2-phenylacetate |
| 132 | (1-benzylpiperidin-4-yl)methyl (S)-2-(3-(2-(((1R,3S)-3-(3-fluoro-4-((((R)-2-hydroxy-2-(8-hydroxy-2-oxo-1,2-dihydroquinolin-5-yl)ethyl)amino)methyl)benzamido)cyclobutyl)amino)-2-oxoethoxy)phenyl)-2-hydroxy-2-phenylacetate |
| 133 | (1-benzylpiperidin-4-yl)methyl (S)-2-(3-(2-(((1R,3S)-3-(2-chloro-4-((((R)-2-hydroxy-2-(8-hydroxy-2-oxo-1,2-dihydroquinolin-5-yl)ethyl)amino)methyl)benzamido)cyclobutyl)amino)-2-oxoethoxy)phenyl)-2-hydroxy-2-phenylacetate |
| 134 | (1-benzylpiperidin-4-yl)methyl (S)-2-(3-(2-(((1R,3S)-3-(2,3-difluoro-4-((((R)-2-hydroxy-2-(8-hydroxy-2-oxo-1,2-dihydroquinolin-5- |

| No. | Structure Name |
|---|---|
| | yl)ethyl)amino)methyl)benzamido)cyclobutyl)amino)-2-oxoethoxy)phenyl)-2-hydroxy-2-phenylacetate |
| 135 | (1-benzylpiperidin-4-yl)methyl (S)-2-(3-(2-(((1R,3S)-3-(3-chloro-4-((((R)-2-hydroxy-2-(8-hydroxy-2-oxo-1,2-dihydroquinolin-5-yl)ethyl)amino)methyl)benzamido)cyclobutyl)amino)-2-oxoethoxy)phenyl)-2-hydroxy-2-phenylacetate |
| 136 | (1-benzylpiperidin-4-yl)methyl (S)-2-(3-(2-(((1R,3S)-3-(2-bromo-4-((((R)-2-hydroxy-2-(8-hydroxy-2-oxo-1,2-dihydroquinolin-5-yl)ethyl)amino)methyl)benzamido)cyclobutyl)amino)-2-oxoethoxy)phenyl)-2-hydroxy-2-phenylacetate |
| 137 | (1-benzylpiperidin-4-yl)methyl (S)-2-(3-(2-(((1R,3S)-3-(2-chloro-4-((((R)-2-hydroxy-2-(8-hydroxy-2-oxo-1,2-dihydroquinolin-5-yl)ethyl)amino)methyl)-5-methoxybenzamido)cyclobutyl)amino)-2-oxoethoxy)phenyl)-2-hydroxy-2-phenylacetate |
| 138 | (1-benzylpiperidin-4-yl)methyl (S)-2-hydroxy-2-(3-(2-(((1R,3S)-3-(4-((((R)-2-hydroxy-2-(8-hydroxy-2-oxo-1,2-dihydroquinolin-5-yl)ethyl)amino)methyl)-3-(trifluoromethyl)benzamido)cyclobutyl)amino)-2-oxoethoxy)phenyl)-2-phenylacetate |
| 139 | (1-benzylpiperidin-4-yl)methyl (S)-2-(3-(2-(((1R,3S)-3-(2-fluoro-4-((((R)-2-hydroxy-2-(8-hydroxy-2-oxo-1,2-dihydroquinolin-5-yl)ethyl)amino)methyl)-3-methoxybenzamido)cyclobutyl)amino)-2-oxoethoxy)phenyl)-2-hydroxy-2-phenylacetate |
| 140 | (1-benzylpiperidin-4-yl)methyl (S)-2-(3-(2-(((1R,3S)-3-(3-ethoxy-4-((((R)-2-hydroxy-2-(8-hydroxy-2-oxo-1,2-dihydroquinolin-5-yl)ethyl)amino)methyl)benzamido)cyclobutyl)amino)-2-oxoethoxy)phenyl)-2-hydroxy-2-phenylacetate |
| 141 | (1-benzylpiperidin-4-yl)methyl (S)-2-hydroxy-2-(3-(2-(((1R,3S)-3-(4-((((R)-2-hydroxy-2-(8-hydroxy-2-oxo-1,2-dihydroquinolin-5-yl)ethyl)amino)methyl)-3-(trifluoromethoxy)benzamido)cyclobutyl)amino)-2-oxoethoxy)phenyl)-2-phenylacetate |
| 142 | (1-benzylpiperidin-4-yl)methyl (S)-2-(3-(2-(((1R,3S)-3-(2-fluoro-4-((((R)-2-hydroxy-2-(8-hydroxy-2-oxo-1,2-dihydroquinolin-5-yl)ethyl)amino)methyl)-5-methoxybenzamido)cyclobutyl)amino)-2-oxoethoxy)phenyl)-2-hydroxy-2-phenylacetate |
| 143 | (1-benzylpiperidin-4-yl)methyl (S)-2-hydroxy-2-(3-(2-(((1R,3S)-3-(4-((((R)-2-hydroxy-2-(8-hydroxy-2-oxo-1,2-dihydroquinolin-5-yl)ethyl)amino)methyl)-3-isopropoxybenzamido)cyclobutyl)amino)-2-oxoethoxy)phenyl)-2-phenylacetate |
| 144 | (1-benzylpiperidin-4-yl)methyl (S)-2-hydroxy-2-(3-(2-(((1R,3S)-3-(5-((((R)-2-hydroxy-2-(8-hydroxy-2-oxo-1,2-dihydroquinolin-5-yl)ethyl)amino)methyl)picolinamido)cyclobutyl)amino)-2-oxoethoxy)phenyl)-2-phenylacetate |
| 145 | (1-benzylpiperidin-4-yl)methyl (S)-2-hydroxy-2-(3-(2-(((1R,3S)-3-(6-((((R)-2-hydroxy-2-(8-hydroxy-2-oxo-1,2-dihydroquinolin-5-yl)ethyl)amino)methyl)nicotinamido)cyclobutyl)amino)-2-oxoethoxy)phenyl)-2-phenylacetate |
| 146 | (1-benzylpiperidin-4-yl)methyl (S)-2-hydroxy-2-(3-(2-(((1R,3S)-3-(2-(4-((((R)-2-hydroxy-2-(8-hydroxy-2-oxo-1,2-dihydroquinolin-5-yl)ethyl)amino)methyl)phenyl)acetamido)cyclobutyl)amino)-2-oxoethoxy)phenyl)-2-phenylacetate |
| 147 | (1-benzylpiperidin-4-yl)methyl (S)-2-hydroxy-2-(3-(2-(3-(4-((((R)-2-hydroxy-2-(8-hydroxy-2-oxo-1,2-dihydroquinolin-5-yl)ethyl)amino)methyl)piperidine-1-carbonyl)azetidin-1-yl)-2-oxoethoxy)phenyl)-2-phenylacetate |
| 148 | (1-benzylpiperidin-4-yl)methyl (S)-2-hydroxy-2-(3-(2-(4-(4-((((R)-2-hydroxy-2-(8-hydroxy-2-oxo-1,2-dihydroquinolin-5-yl)ethyl)amino)methyl)piperidine-1-carbonyl)piperidin-1-yl)-2-oxoethoxy)phenyl)-2-phenylacetate |
| 149 | (1-benzylpiperidin-4-yl)methyl (S)-2-hydroxy-2-(3-(2-(((1R,4S)-4-(4-((((R)-2-hydroxy-2-(8-hydroxy-2-oxo-1,2-dihydroquinolin-5-yl)ethyl)amino)methyl)piperidine-1-carbonyl)cyclohexyl)amino)-2-oxoethoxy)phenyl)-2-phenylacetate |
| 150 | (1-benzylpiperidin-4-yl)methyl (S)-2-hydroxy-2-(3-(2-((2-(4-((((R)-2-hydroxy-2-(8-hydroxy-2-oxo-1,2-dihydroquinolin-5-yl)ethyl)amino)methyl)piperidin-1-yl)-2-oxoethyl)amino)-2-oxoethoxy)phenyl)-2-phenylacetate |
| 151 | (1-benzylpiperidin-4-yl)methyl (S)-2-hydroxy-2-(3-((1-(1-(4-(2-(((R)-2-hydroxy-2-(8-hydroxy-2-oxo-1,2-dihydroquinolin-5-yl)ethyl)amino)ethyl)benzoyl)piperidine-4-carbonyl)piperidin-4-yl)methoxy)phenyl)-2-phenylacetate |
| 152 | (1-benzylpiperidin-4-yl)methyl (S)-2-hydroxy-2-(3-((1-((4-(2-(((R)-2-hydroxy-2-(8-hydroxy-2-oxo-1,2-dihydroquinolin-5-yl)ethyl)amino)ethyl)benzoyl)glycyl)piperidin-4-yl)methoxy)phenyl)-2-phenylacetate |
| 153 | (1-benzylpiperidin-4-yl)methyl (S)-2-hydroxy-2-(3-((1-((4-((((R)-2-hydroxy-2-(8-hydroxy-2-oxo-1,2-dihydroquinolin-5-yl)ethyl)amino)methyl)-3-methoxybenzoyl)glycyl)piperidin-4-yl)methoxy)phenyl)-2-phenylacetate |
| 154 | (1-benzylpiperidin-4-yl)methyl (S)-2-hydroxy-2-(3-((1-((4-((((R)-2-hydroxy-2-(8-hydroxy-2-oxo-1,2-dihydroquinolin-5-yl)ethyl)amino)methyl)benzoyl)glycyl)piperidin-4-yl)methoxy)phenyl)-2-phenylacetate |

| No. | Structure Name |
|---|---|
| 155 | (1-benzylpiperidin-4-yl)methyl (S)-2-hydroxy-2-(3-((1-((4-((((R)-2-hydroxy-2-(8-hydroxy-2-oxo-1,2-dihydroquinolin-5-yl)ethyl)amino)methyl)-2-methoxybenzoyl)glycyl)piperidin-4-yl)methoxy)phenyl)-2-phenylacetate |
| 156 | (1-benzylpiperidin-4-yl)methyl (S)-2-hydroxy-2-(3-((1-(5-(4-((((R)-2-hydroxy-2-(8-hydroxy-2-oxo-1,2-dihydroquinolin-5-yl)ethyl)amino)methyl)piperidine-1-carbonyl)thiophene-2-carbonyl)piperidin-4-yl)methoxy)phenyl)-2-phenylacetate |
| 157 | (1-benzylpiperidin-4-yl)methyl (S)-2-hydroxy-2-(3-((1-((1R,4S)-4-(4-((((R)-2-hydroxy-2-(8-hydroxy-2-oxo-1,2-dihydroquinolin-5-yl)ethyl)amino)methyl)piperidine-1-carbonyl)cyclohexane-1-carbonyl)piperidin-4-yl)methoxy)phenyl)-2-phenylacetate |
| 158 | 1-benzylpiperidin-4-yl (S)-2-hydroxy-2-(3-(3-(4-((((R)-2-hydroxy-2-(8-hydroxy-2-oxo-1,2-dihydroquinolin-5-yl)ethyl)amino)methyl)benzamido)propoxy)phenyl)-2-phenylacetate |
| 159 | ((R)-1-benzylpyrrolidin-3-yl)methyl (S)-2-hydroxy-2-(3-(3-(4-((((R)-2-hydroxy-2-(8-hydroxy-2-oxo-1,2-dihydroquinolin-5-yl)ethyl)amino)methyl)benzamido)propoxy)phenyl)-2-phenylacetate |
| 160 | ((S)-1-benzylpyrrolidin-3-yl)methyl (S)-2-hydroxy-2-(3-(3-(4-((((R)-2-hydroxy-2-(8-hydroxy-2-oxo-1,2-dihydroquinolin-5-yl)ethyl)amino)methyl)benzamido)propoxy)phenyl)-2-phenylacetate |
| 161 | (1-cyclobutylpiperidin-4-yl)methyl (S)-2-hydroxy-2-(3-(3-(4-((((R)-2-hydroxy-2-(8-hydroxy-2-oxo-1,2-dihydroquinolin-5-yl)ethyl)amino)methyl)benzamido)propoxy)phenyl)-2-phenylacetate |
| 162 | (1-methylpiperidin-4-yl)methyl (S)-2-hydroxy-2-(3-(3-(4-((((R)-2-hydroxy-2-(8-hydroxy-2-oxo-1,2-dihydroquinolin-5-yl)ethyl)amino)methyl)benzamido)propoxy)phenyl)-2-phenylacetate |
| 163 | (R)-1-benzylpyrrolidin-3-yl (S)-2-hydroxy-2-(3-(3-(4-((((R)-2-hydroxy-2-(8-hydroxy-2-oxo-1,2-dihydroquinolin-5-yl)ethyl)amino)methyl)benzamido)propoxy)phenyl)-2-phenylacetate |
| 164 | (S)-1-benzylpyrrolidin-3-yl (S)-2-hydroxy-2-(3-(3-(4-((((R)-2-hydroxy-2-(8-hydroxy-2-oxo-1,2-dihydroquinolin-5-yl)ethyl)amino)methyl)benzamido)propoxy)phenyl)-2-phenylacetate |
| 165 | 1-benzylazetidin-3-yl (S)-2-hydroxy-2-(3-(3-(4-((((R)-2-hydroxy-2-(8-hydroxy-2-oxo-1,2-dihydroquinolin-5-yl)ethyl)amino)methyl)benzamido)propoxy)phenyl)-2-phenylacetate |
| 166 | 1-benzylpiperidin-4-yl (S)-2-hydroxy-2-(3-((4-((3-(4-((((R)-2-hydroxy-2-(8-hydroxy-2-oxo-1,2-dihydroquinolin-5-yl)ethyl)amino)methyl)phenyl)ureido)methyl)benzyl)oxy)phenyl)-2-phenylacetate |
| 167 | 1-benzylpiperidin-4-yl (S)-2-hydroxy-2-(3-((4-((3-(4-((((R)-2-hydroxy-2-(8-hydroxy-2-oxo-1,2-dihydroquinolin-5-yl)ethyl)amino)methyl)-3-methoxyphenyl)ureido)methyl)benzyl)oxy)phenyl)-2-phenylacetate |
| 168 | 1-benzylpiperidin-4-yl (S)-2-hydroxy-2-(3-((4-((3-(4-((((R)-2-hydroxy-2-(8-hydroxy-2-oxo-1,2-dihydroquinolin-5-yl)ethyl)amino)methyl)-2-methoxyphenyl)ureido)methyl)benzyl)oxy)phenyl)-2-phenylacetate |

The compounds of the present invention can be prepared from readily available starting materials using the following general methods and procedures or by using other information readily available to those of ordinary skill in the art. Although a particular embodiment of the present invention may be shown or described herein, those skilled in the art will recognize that all embodiments or aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. While the optimum reaction conditions may vary depending on the particular reactants or solvent used, such conditions can be readily determined by one skilled in the art by routine optimisation procedures.

Compounds of general formula I may be prepared according to the following synthetic Scheme.

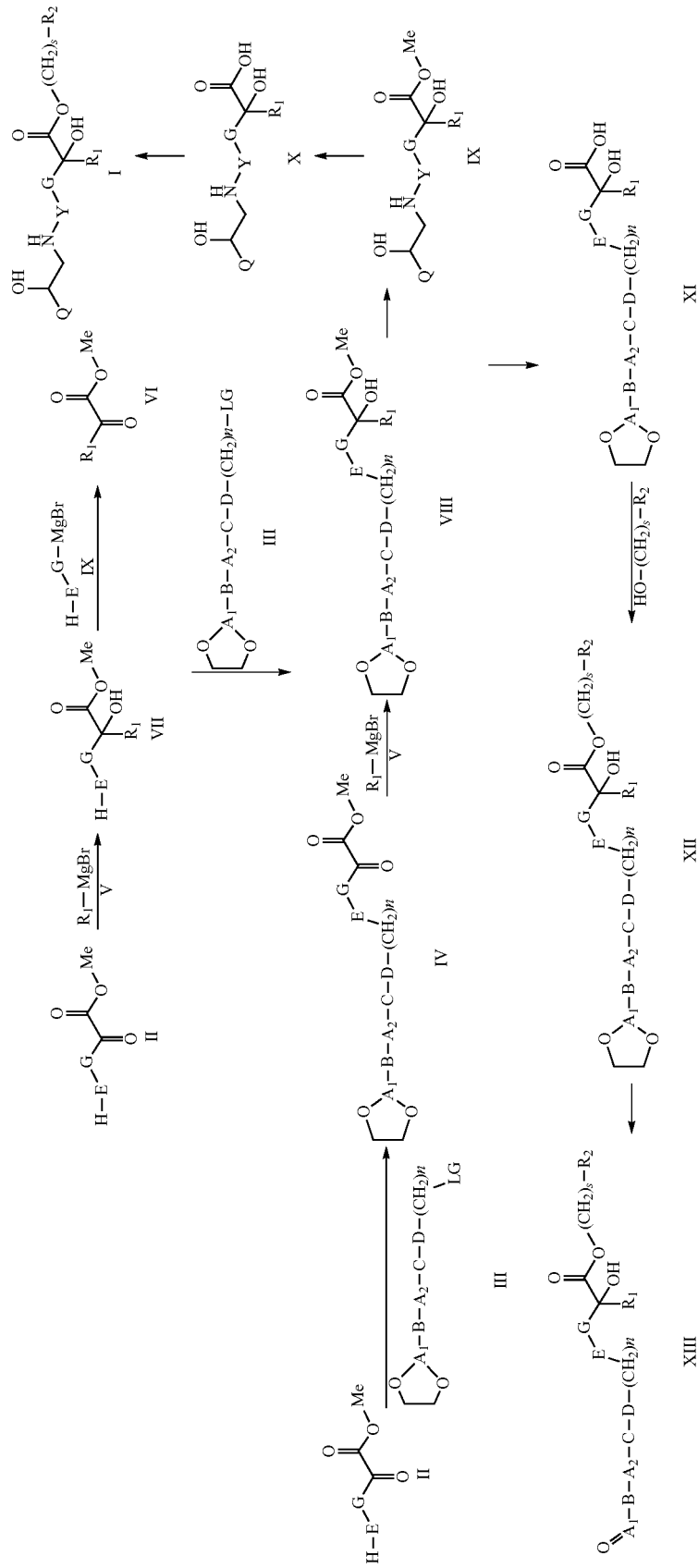

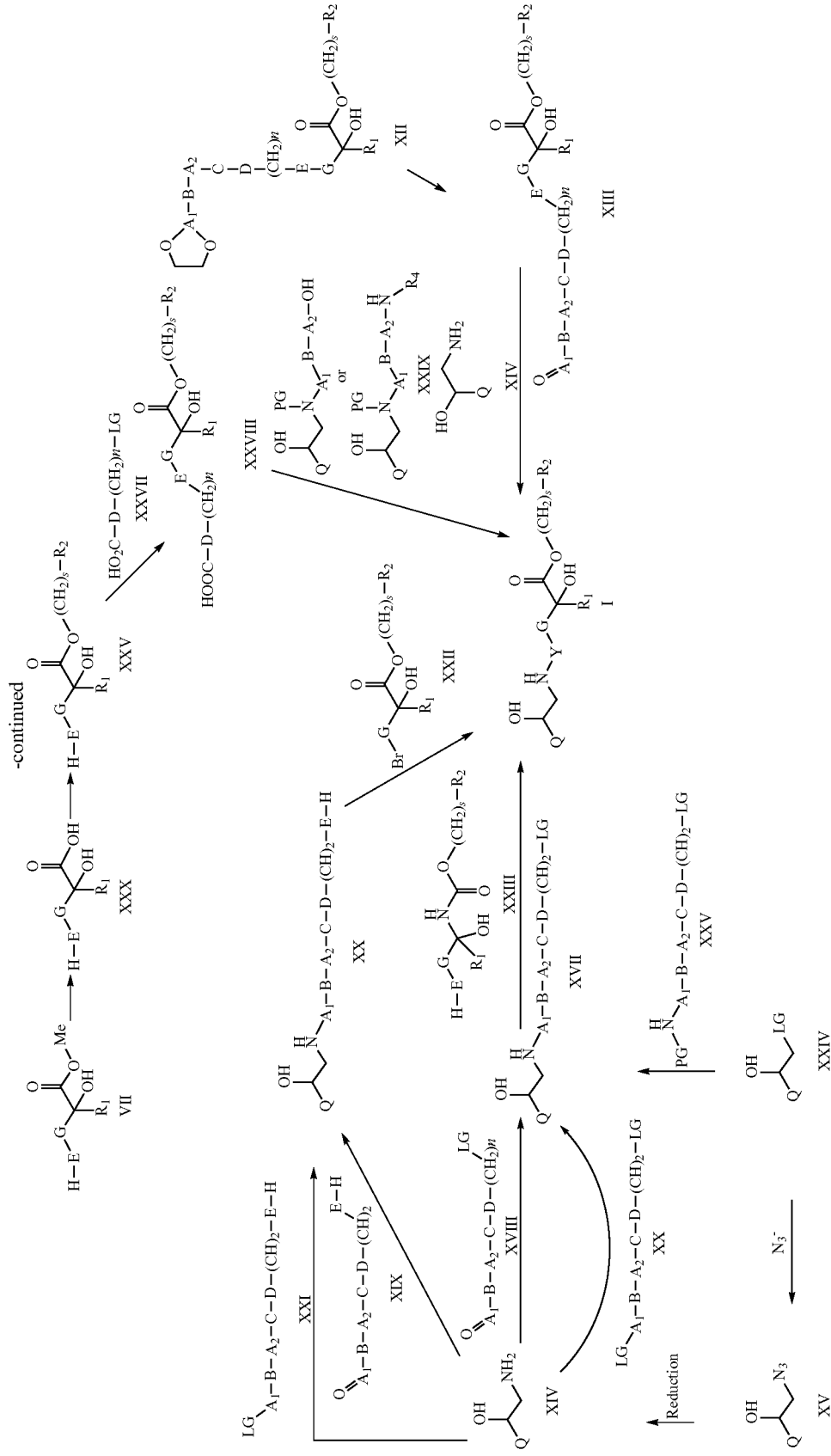

General Procedure for the Preparation of Compounds of Formula I

Compounds of general formula I are compounds in which Y is a divalent group of formula Y1 or Y2. Although groups Y1 and Y2 are different the approach to be considered for the synthesis of compounds of formula I in which Y is Y1 or Y2 is similar and mainly depends on the functional group present in the linker Y. It is evident for a person skilled in the art that the following synthesis described for Y2 can be extended with minor modification to Y1.

The compounds of general formula XII represent compounds wherein A1 is alkylene substituted with oxo, leading to an aldehyde or ketone protected as cyclic acetal. The cyclic acetal-protecting group (PG) can be removed leading to a compound of general formula XIII.

The synthesis of compounds of general formula I may require the protection of potential reactive functionalities in addition to those methods already described. In such a case, examples of compatible protecting groups (PG) and their particular methods of protection and deprotection are described in "Protecting groups in organic Synthesis" by T. W. Green and P. Wutz (Wiley-Interscience publication, 1999), which is incorporated herein by reference in its entirety. Compounds of general formula I can be prepared for example by reaction of a compound of general formula XIII with a compound of general formula XIV. This reductive amination reaction can be performed following several different protocols described in the literature and well known for those skilled in the art. For example, it can be performed in solvent such as methanol, ethanol, tetrahydrofuran (THF) or dichloromethane (DCM) using a reducing agent such as $NaBH_4$, $NaCNBH_3$ or $NaB(AcO)_3H$. It could be useful to pre-form the imine before adding the reducing agent. The reaction proceeds smoothly at room temperature (RT) over 1 to 12 hours.

The intermediate of general formula XII can be easily prepared by reaction of a compound of general formula XI with a compound of formula HO—$(CH_2)_s$—$R_2$ under the well-known condensation conditions for the preparation of esters. The reaction occurs smoothly in an aprotic polar solvent such as DCM, THF or DMF at room or higher temperature in the presence of a condensing agent such as for example EDC, DCC, HATU. Alternatively the acid XI can be converted into the corresponding chloride (e.g. with $COCl_2$ in DMC) or imidazolide (with CDI in DCM or DMF) and then treated with HO—$(CH_2)_s$—$R_2$.

Intermediate XI can be easily obtained by saponification of ester VIII using alkaline hydroxides in polar solvent, such as MeOH, EtOH, and THF mixed with water in a suitable ratio. The reaction occurs at RT, but higher temperature can speed the reaction up that can complete in a time ranging from 30 minutes to overnight.

Synthesis of compound of formula VIII can be achieved in many different ways, all depending on functional groups present in G. For example, it can be obtained by reaction of a compound of formula VII with a compound of formula III. In the case n is greater than zero and E is —O— the reaction is the well-known alkylation of phenols. The leaving group LG can be easily displaced reacting the two compounds in a polar solvent such as for example, but not limited to, ACN or DMF, for one or more hours at room or higher temperature.

The same reaction conditions can be used for the conversion of a compound of formula II into IV using a compound of formula III.

Compound of general formula VII can be obtained using the known addition of Grignard reagent (or other metal derivatives) to keto-containing compounds such as VI or II. The selection of one of the two possible reactions depends on the availability of suitable Grignard's reagent or a precursor for its generation. The conversion of VI to VII can be performed in a solvent such as $Et_2O$ or THF at a temperature below 0° C. The reaction is normally smooth and completes over a period ranging from one to overnight standing at room temperature. The same reaction conditions can be used for the reaction of a compound of formula IV with a compound of formula V to give a compound of formula VIII.

In another embodiment of the present invention, intermediate VIII can be used for the preparation of I using a different approach.

First VIII is deprotected to give an aldehyde that can be easily reacted with a compound of formula XIV under the reductive amination conditions described above for the conversion of XIII into I. The ester of formula IX obtained is then hydrolysed, under acidic or basic aqueous condition as described for the preparation of XI, to give X that can be reacted under ester formation condition with a compound of formula HO—$(CH_2)_s$—$R_2$.

It is clear to a person skilled in the art that the presence of OH and NH moiety, for example in a compound of formula X, can affect the formation of the ester I as these functional groups can compete with the OH in HO—$(CH_2)_s$—$R_2$. For this reason, it is worth considering performing such described reaction, for the conversion of X into I, using an intermediate in which the OH and NH are protected with suitable protecting group. For the purpose silyl ethers for the OH and carbamates for the NH are well known protecting groups, whose selection should not be limited to them as it often depends on the complexity of the molecule and the presence of other functional groups in Y that can be not compatible with the reaction conditions required for introduction or removal of protecting groups.

A similar consideration can be done for the moiety Q that contains a phenolic OH. In addition, in this case its reactivity can suggests its protection to avoid any competitive reaction and formation of by-products. Benzyl is a suitable protecting group. The specific sequence of reaction for the preparation of I might be different from case to case, those skilled in the art will readily recognize the appropriate sequence, that must be evaluated considering the structure of linker Y.

In another embodiment of the present invention, compounds of general formula I featuring an ester moiety in the linker Y, can be prepared by treating a compound of general formula XXVIII with a compound of general formula XXIX, wherein A2 is functionalized with OH, under the condensation reaction condition for the preparation of esters. It is possible prepare a compound of general formula I, wherein C is equal to C1, reacting a compound of general formula XXVIII with a compound XXIX wherein A2 is substituted with —$NR_7$ under the well-known reaction conditions for the preparation of amide starting from carboxylic acid and amines. Using a similar approach it is possible to synthesize a compound of formula I wherein C has one of the other meanings cited, using intermediates featuring the correct functional groups that can react together to form one of meaning of C.

Compound of formula XXVIII can be obtained by a reaction of a compound of formula XXV with a suitable intermediate whose formula depends on the structure of the linker Y. An example that must not be considered as limiting the scope of the description, is the preparation of a compound of formula I wherein E is —O— which can be easily obtained treating a compound of formula XXV with a compound of formula XXVII where LG is leaving group such as chlorine, bromine or sulfonates. The reaction of alkylation can be performed in polar solvents such as DCM, ACN or DMF at room or higher temperature in the presence of base that can catalyze the reaction.

Compound of formula XXV can be obtained from XXX via a reaction for ester formation already described for the conversion of XI into XII. Compound XXX is easily obtained from compound of formula VII by mean of a standard reaction for the hydrolysis of esters.

Compounds of general formula VII, XXX and XXV are all suitable intermediates for the preparation of single stereoisomers of compound of formula I. For example, the mixtures of isomers of these three intermediates can be separated by mean of chiral chromatographic separation. In case, for example, R2 is enantiomerically pure J1, J2 or J5, a compound of formula XXV is a mixture of diastereoisomers that can be separated by mean of a normal chromatographic separation.

The absolute configuration of the stereogenic centre present in VII is conserved unmodified within the synthetic pathway applied for the conversion of VII into the final compound of formula I.

In another embodiment of the present invention, compounds of general formula I can be prepared following a different synthetic approach in which a compound of general formula XX is reacted with a compound of formula XXII under the transition metal catalyzed cross-coupling reaction conditions, followed by reduction of the double bond —(CH)$_2$—, leading to a compound of formula I wherein n=2. Alternatively, it can be prepared by reaction of a compound of formula XVII with a compound of formula XXIII under the condition described above for the reaction of a compound of formula II with a compound of formula III.

Intermediates of formula XX and XVII can be prepared by reaction of compound of formula XIV under reductive amination conditions, described above for the reaction of compound of formula XIII with XIV, starting from compound of formula XIX and XVIII respectively. Alternatively, compounds of formula XX and XVII can be prepared by alkylation of compound XIV with compound of formula XXI and XX respectively under alkylation condition described above for the preparation of compound VIII by reaction of compound VII with compound III.

Compounds of general formula XIV can be obtained by simple reduction of the azide of formula XV. The reaction can be accomplished by mean of a catalytic hydrogenation in the presence Palladium catalyst. The reaction occurs, in polar solvent such as methanol or ethanol, under hydrogen atmosphere or under hydrogen transfer condition, using for example 1,4-cyclohexadiene or 1-methyl1,4-cyclohexadiene as source of hydrogen. The reaction proceeds at room temperature. In case it is performed under hydrogen transfer conditions higher temperature can be required. Alternatively, the conversion can be accomplished under Staudinger reaction conditions.

The azide XV can be easily prepared from XXIV by the well-known nucleophilic substitution of alkyl bromide with alkaline azide. The reaction proceeds at a temperature ranging from 50 to 80° C. and in a polar solvent such as for example DMF of NMP and can be accelerated by the presence of alkaline iodide.

In another embodiment of the present invention, compounds of general formula XVII can be prepared by reacting an intermediate of general formula XXIV with an amine of general formula XXV. This reaction is a common alkylation of amine in which the leaving group LG (normally chlorine, bromine or sulphate) is displaced by a nucleophile like the amine XXV as such or protected at the aminic moiety. Several methods to perform a reaction that normally occurs in a polar solvent at a temperature higher than room temperature are described in the literature.

It is apparent for those skilled in the art that compounds of general formula I wherein s is 0 and R2 is J1, J2, or J5 contain three stereogenic centres, as indicated below (wherein e.g. J=J2) with the symbol *. This means that the structure of formula I is characterized by different stereoisomers.

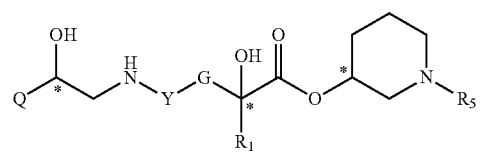

Each diastereoisomer can be obtained theoretically by chromatographic separation of the mixture obtained by reacting racemic mixtures of the required intermediates. It is clear that this approach it is not convenient and that it can be used only for the separation of mixtures containing few diastereoisomers.

In a more convenient approach, the synthesis of each single stereoisomer can be accomplished using, in the reactions described above, only enantiomerically pure intermediates.

The enantiomerically pure alcohol required for the preparation of compounds of general formula I wherein R2 is J1, J2 or J5 are commercially available.

The preparation of single enantiomerically pure compounds of general formula XXIV wherein LG is bromine are described in WO2005/092861 (cited by WO2007/107228), both of which are incorporated herein by reference in their entireties.

The present invention also provides pharmaceutical compositions of compounds of formula I in admixture with one or more pharmaceutically acceptable carriers, for example those described in Remington's Pharmaceutical Sciences Handbook, XVII Ed., Mack Pub., N.Y., U.S.A., which is incorporated herein by reference in its entirety Administration of the compounds of the present invention may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the present invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols.

Formulations for vaginal administration can be in the form of cream, gel, paste, foam, or spray formula containing, in addition to the active ingredient, such as suitable carriers, are also known.

For topical administration the pharmaceutical composition can be in the form of creams, ointments, liniments, lotions, emulsions, suspensions, gels, solutions, pastes, powders, sprays, and drops suitable for administration to the skin, eye, ear, or nose. Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the present invention, e.g. lactose or any other additive suitable for improving the respirable fraction may be added to the powdered compounds of the invention.

Inhalation aerosols containing propellant gas such as hydrofluoroalkanes may contain the compounds of the present invention either in solution or in dispersed form. The propellant-driven formulations may also contain other ingredients such as co-solvents, stabilizers and optionally other excipients.

The propellant-free inhalable formulations comprising the compounds of the present invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the present invention may be administered as the sole active agent or in combination with other pharmaceutical active ingredients including those currently used in the treatment of respiratory disorders, e.g, corticosteroids, P38 MAP kinase inhibitors, IKK2, FINE inhibitors, PDE4 inhibitors, leukotriene modulators, NSAIDs and mucus regulators.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula I can be administered for example, at a dosage of 0.001 to 1000 mg/day, preferably 0.1 to 500 mg/day.

When the compounds of formula I are administered by inhalation route, they are preferably given at a dosage of 0.001 to 500 mg/day, preferably 0.1 to 200 mg/day.

The compounds of formula I may be administered for the prevention and/or treatment of broncho-obstructive or inflammatory diseases, such as asthma, chronic bronchitis, chronic obstructive pulmonary disease (COPD), bronchial hyperreactivity, cough, emphysema or rhinitis; urological disorders such as urinary incontinence, pollakiuria, cystospasm, chronic cystitis and overactive bladder (OAB); gastrointestinal disorders such as bowel syndrome, spastic colitis, diverticulitis, peptic ulceration, gastrointestinal motility or gastric acid secretion; dry mouth; mydriasis, tachycardia; ophthalmic interventions cardiovascular disorders such as vagally induced sinus bradycardia.

Other features of the invention will become apparent in the course of the following descriptions of exemplary embodiments which are given for illustration of the invention and are not intended to be limiting thereof.

EXAMPLES

The intermediate compounds for the synthesis of final compounds of general formula (I) were obtained through the preparations herebelow described.

Preparation of Intermediates and Examples

Chemical Names of the compounds were generated with Structure To Name Enterprise 10.0 CambridgeSoft for all final compounds names or with ChemDraw Professional 15 for intermediates names.

ABBREVIATIONS $Et_2O$=diethyl ether;
$Et_3N$=triethyl amine;
DCE=1,2-dichloroethane;
TEA=tryethyl amine;
DCC=N,N'-dicyclohexylcarbodiimide;
HOBt=hydroxybenzotriazole;
HATU=(dimethylamino)-N,N-dimethyl(3H-[1,2,3]triazolo[4,5-b]pyridin-3-yloxy)methaniminium hexafluorophosphate;
EDC=1-ethyl-3-(3-dimethylaminopropyl) carbodiimide hydrochloride;
DMAP=4-dimethylaminopyridine;
DMF=dimethylformamide;
EtOAc=ethyl acetate;
RT=room temperature;
THF=tetrahydrofuran;
DCM=dichloromethane;
MeOH=methyl alcohol;
EtOH=ethylic alcohol;
LHMDS=lithium bis(trimethylsilyl)amide;
m-CPBA=meta-Chloroperoxybenzoic acid;
TFA=trifluoroacetic acid;
LC-MS=liquid chromatography/mass spectrometry;
HPLC=high pressure liquid chromatography;
MPLC=medium pressure liquid chromatography;
SFC=supercritical fluid chromatography
General Experimental Details.
NMR Characterization:
$^1$H-NMR spectra were performed on a Varian MR-400 spectrometer operating at 400 MHz (proton frequency), equipped with: a self-shielded z-gradient coil 5 mm 1H/nX broad band probehead for reverse detection, deuterium digital lock channel unit, quadrature digital detection unit with transmitter offset frequency shift.

Alternatively a Bruker instrument was used (either Bruker Avance 400 MHz or Bruker Avance III 400 MHz) operating at 400 MHz using the stated solvent at around room temperature unless otherwise stated.

In all cases, NMR data were consistent with the proposed structures. Chemical shift are reported as δ values in ppm relative to trimethyl silane (TMS) as an internal standard. Coupling constants (J values) are given in hertz (Hz) and multiplicities are reported using the following abbreviation (s=singlet, d=doublet, t=triplet, q=quartet, m=multiplet, br=broad, nd=not determined).

LC/UV/MS Analytical Methods

LC/MS retention times are estimated to be affected by an experimental error of ±0.5 min.

Methods 1-2-3-4:

LC-UV-MS instrument (Waters Acquity UPLC system) equipped with UV (PDA detector) and mass spectrometer (Acquity QDa Detector). UV acquisition range 210-400 nm. MS acquisition range 110-1200 amu.

LC-UV

Eluent A: water/ACN 95/5 (0.05% HCOOH), Eluent B: ACN/water 95/5 (0.05% HCOOH)

Flow 1 mL/min

Column Temperature: 40° C.

Gradient 1:

| Time (min) | % A | % B |
| --- | --- | --- |
| 0.00 | 99 | 1 |
| 1.50 | 0.1 | 99.9 |
| 1.90 | 0.1 | 99.9 |
| 2.00 | 99 | 1 |

Gradient 2:

| Time (min) | % A | % B |
| --- | --- | --- |
| 0.00 | 99 | 1 |
| 3.50 | 0.1 | 99.9 |
| 3.90 | 0.1 | 99.9 |
| 4.00 | 99 | 1 |

Methods:

| Method | Gradient | Column |
| --- | --- | --- |
| 1 | Gradient 1 | Acquity UPLC BEH C18 1.7 um 50 × 2.1 mm |
| 2 | Gradient 1 | Acquity UPLC CSH C18 1.7 um 50 × 2.1 mm |
| 3 | Gradient 2 | Kinetex UPLC C8 1.7 um 50 × 2.1 mm |
| 4 | Gradient 2 | Acquity UPLC CSH C18 1.7 um 50 × 2.1 mm |

MS instrument: Waters ZQ (or equivalent)
Polarity ES
Capillary (kV) 3.20
Cone (V) 25.00
Extractor (V) 3.00
RF Lens (V) 0.1
Polarity ES−
Capillary (kV) 3.40
Cone (V) 24.00
Extractor (V) 2.00
RF Lens (V) 0.2
Source Temperature (° C.) 130
Desolvation Temperature (° C.) 400
Cone Gas Flow (L/Hr) 80
Desolvation Gas Flow (L/Hr) 800
Mass range: 60 to 1200
Scan time (sec): 0.4

Method 5

LC-UV-MS instrument (Waters Acquity UPLC system) equipped with UV (PDA detector) and mass spectrometer (Waters TQS Detector). UV acquisition range 210-400 nm. MS acquisition range 100-1000 amu ESI+ and ESI−

Solvents:
A % HCOONH4 buffer 0.025M pH 3
B % ACN+0.1% HCOOH
Flow (ml/min) 0.5 mL/min
Stop time (mins) 10 min
Column Temperature 55° C.
UV acquisition range (nm): 254
Injection volume (μl): 2
Column: Kinetex 1.7 u C8 100 A 100×2.1 mm Gradient:

| Time (min) | % A | % B |
| --- | --- | --- |
| 0.00 | 99 | 1 |
| 0.5 | 99 | 1 |
| 3 | 70 | 30 |
| 6.5 | 50 | 50 |
| 7.5 | 20 | 80 |
| 8 | 20 | 80 |
| 8.1 | 99 | 1 |
| 10 | 99 | 1 |

Method 6

10 cm_Formic_ACE 3 C18 AR_HPLC_CH3CN

HPLC Setup

Solvents:—Acetonitrile (Far UV grade) with 0.1% (V/V) formic acid

Water (High purity via PureLab Ultra unit) with 0.1% formic acid

Column:—Hichrom ACE 3 C18-AR mixed mode column 100×4.6 mm

Flow Rate:—1 ml/min

Gradient:

| Time (min) | % A | % B |
| --- | --- | --- |
| 0.00 | 98 | 2 |
| 3 | 98 | 2 |
| 12 | 0 | 100 |
| 15.4 | 0 | 100 |
| 15.5 | 98 | 2 |
| 17 | 98 | 2 |

Injections 0.2-10 ul
Maximum pressure setting 400 bar.
Instrument: Agilent 1100, Binary Pump, Agilent Sampler and Agilent DAD detector
Diode array detection: (300 nm, Band Width 200 nm; Ref. 450 nm, Band Width 100 nm)

Method 7

15 cm_Formic_Ascentic_HPLC_CH3CN

HPLC Setup

Solvents:—Acetonitrile (Far UV grade) with 0.1% (V/V) formic acid

Water (High purity via PureLab Ultra unit) with 0.1% formic acid

Column:—Supelco, Ascentis® Express C18 or Hichrom Halo C18, 2.7 μm C18, 150×4.6 mm.

Flow Rate:—1 ml/min

Gradient:

| Time (min) | % A | % B |
|---|---|---|
| 0.00 | 96 | 4 |
| 3 | 96 | 4 |
| 9 | 0 | 100 |
| 13.6 | 0 | 100 |
| 13.7 | 96 | 4 |
| 15 | 96 | 4 |

Injections 0.2-10 ul
Maximum pressure setting 400 bar.
Instrument: Agilent 1100, Binary Pump, Agilent Sampler and Agilent DAD detector
Diode array detection: (300 nm, Band Width 200 nm; Ref. 450 nm, Band Width 100 nm)
Method 8
10 cm_ESCI_Formic_MeCN
HPLC Setup
Solvents:—Acetonitrile (Far UV grade) with 0.1% (V/V) formic acid
Water (High purity via PureLab Option unit) with 0.1% formic acid
Column:—Phenomenex Luna 5 u C18 (2), 100×4.6 mm. (Plus guard cartridge)
Flow Rate:—2 ml/min
Gradient:

| Time (min) | % A | % B |
|---|---|---|
| 0.00 | 95 | 5 |
| 3.5 | 5 | 95 |
| 5.5 | 5 | 95 |
| 5.6 | 95 | 5 |
| 6.5 | 95 | 5 |

Injections 2-7 ul (concentration~0.2-1 mg/ml).
UV detection via HP or Waters DAD
Start Range (nm) 210 End Range (nm) 400 Range interval (nm) 4.0
Other wavelength traces are extracted from the DAD data.
Optional ELS detection using Polymer Labs ELS-1000.
MS detection: Micromass ZQ, single quadrupole LC-MS or Quattro Micro LC-MS-MS.
Flow splitter gives approximately 300 ul/min to mass spec
Scan range for MS Data (m/z)
Start (m/z) 100
End (m/z) 650 or 1500 when required
With +ve/−ve switching
Ionization is routinely ESCI an option which gives both ESI and APCI data from a single run.
Typical ESI voltages and temperatures are:

| Source 120-150C | 3.5 KV capillary | 25 V cone |
|---|---|---|

Typical APCI voltages and temperatures are:

| Source 140-160C | 17 uA corona | 25 V cone |
|---|---|---|

Method 9. HPLC-AB
HPLC with UV-Vis or DAD detector
column: Waters Symmetry C18, 3.9×150 mm, 5.0 μm
Eluents:
(A) 0.1% formic acid-water solution
(B) 0.1% formic acid-ACN solution
injection volume: 3 μL
flow: 1.0 ml/min
Gradient:

| Time (min) | % A | % B |
|---|---|---|
| 0.00 | 95 | 5 |
| 3 | 95 | 5 |
| 9 | 83 | 17 |
| 15 | 83 | 17 |
| 25 | 20 | 80 |
| 27 | 20 | 80 |
| 28 | 95 | 5 |
| 30 | 95 | 5 |

Column compartment:
column temperature: 25° C.
time of analysis: 30 min
Detector:—wave length: 220 nm
Method 10. Chiral-HPLC
Equipment:
HPLC with UV-Vis or DAD detector
column: Chiralpak IC, 4.6 mm×250 mm×5 um
Eluents:
(A)IPA+0.1% TFA
(B)Hexane+0.1% TFA
Autosampler:
injectionvolume:3 μL
Pump:
flow: 1.0 ml/min
90% B
Column compartment:
column oven temperature: 25° C.
time of analysis: 30 min
Detector:
wave length: 220 nm
Method 11
10 cm_Formic_AQ
UPLC Setup
Solvents:—B Acetonitrile (Far UV grade) with 0.1% (V/V) formic acid
A Water (High purity via PureLab Option unit) with 0.1% formic acid
Column:—Acquity UPLC HSS C18 1.8 um 100×2.1 mm. (Plus guard cartridge)
Flow Rate:—0.5 ml/min
Gradient:

| Time (min) | % A | % B |
|---|---|---|
| 0.00 | 95 | 5 |
| 1.2 | 95 | 5 |
| 3.5 | 0 | 100 |
| 4.9 | 0 | 100 |
| 5 | 95 | 5 |
| 6 | 95 | 5 |

Injections 0.5-2 ul
UV detection via Waters DAD
Start Range (nm) 210 End Range (nm) 400 Resolution (nm) 1.2
MS detection: Waters SQD2, single quadrupole UPLC-MS
Scan range for MS Data (m/z)

Start (m/z) 100
End (m/z) 700 or 1500 when required
With +ve/−ve switching
Ionization is ESI.
ESI voltages and temperatures are:
Source 150 C 3.5 KV capillary 25 V cone
Method 12
10 cm_Bicarb_AQ
UPLC Setup
Solvents:—Acetonitrile (Far UV grade)
Water (High purity via PureLab Option unit) with 10 mM ammonium bicarbonate (ammonium hydrogen carbonate)
Column:—Acquity UPLC BEH Shield RP18 1.7 um 100×2.1 mm. (Plus guard cartridge)
Flow Rate:—0.5 ml/min
Gradient:—A: Water/Basic B: MeCN/Basic

| Time | A % | B % |
|---|---|---|
| 0.00 | 95 | 5 |
| 1.20 | 95 | 5 |
| 3.5 | 0 | 100 |
| 4.90 | 0 | 100 |
| 5.00 | 95 | 5 |
| 6.00 | 95 | 5 |

Typical Injections 0.5-2 ul (concentration ~0.2-1 mg/ml).
UV detection via Waters DAD
Start Range (nm) 210 End Range (nm) 400 Resolution (nm) 1.2
Other wavelength traces are extracted from the DAD data.
MS detection: Waters SQD2, single quadrapole UPLC-MS
Flow splitter gives approximately 300 ul/min to mass spec
Scan range for MS Data (m/z)
Start (m/z) 100
End (m/z) 700 or 1500 when required
With +ve/−ve switching
Preparative Reverse-Phase HPLC Conditions
Preparative HPLC
Waters Micromass ZQ/Sample manager 2767
Photodiode array detector 2996;
Column: XTerra Prep MS C18 Column (5 μm, 19×150 mm, Waters)
Flow rate: 20 ml/min with MS detection
UV wavelength: 254 nm.
Mobile phase: Solvent A (water:MeCN:HCOOH 95:5: 0.05); Solvent B (water:MeCN:HCOOH 5:95:0.05)
Gradient:

| Time (min) | % A | % B |
|---|---|---|
| 0.00 | 100.0 | 0.00 |
| 1.00 | 100 | 0.00 |
| 10.00 | 0.00 | 100.0 |
| 11.00 | 0.00 | 100.0 |
| 12.00 | 100.0 | 0.00 |

Where the preparation of starting materials is not described, these are commercially available, known in the literature, or readily obtainable by those skilled in the art using standard procedures.

Flash chromatography is carried out using an Isolera MPLC system (manufactured by Biotage) using pre-packed silica gel or reverse-phase cartridges (supplied by Biotage).

Many of the compounds described in the following Examples have been prepared from stereochemically pure starting materials, for example 95% ee.

The stereochemistry of the compounds in the Examples, where indicated, has been assigned on the assumption that absolute configuration at resolved stereogenic centers of staring materials is maintained throughout any subsequent reaction conditions.

In the procedures that follow, after each starting material, reference to a compound number is sometimes provided. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

Preparation of (R)-5-(2-Amino-1-hydroxyethyl)-8-hydroxyquinolin-2(1H)-one hydrochloride

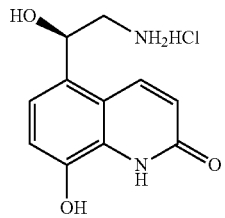

Step 1; 8-(Benzyloxy)-5-(2-bromoacetyl)quinolin-2(1H)-one

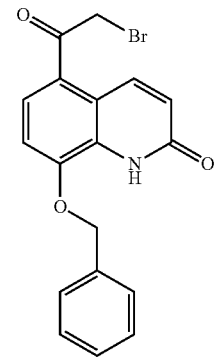 [SMILES: O=C(CBr)c1ccc(OCc2ccccc2)c2[nH]c(=O)ccc12]

A suspension of 5-acetyl-8-(benzyloxy)quinolin-2(1H)-one (19.4 g, 66.4 mmol) in anhydrous THF (240 mL) and anhydrous methanol (165 mL) was added with a solution of tetra-n-butylammonium tribromide (54.5 g, 113.0 mmol) in anhydrous THF (130 mL) drop-wise over 1.5 hours. The resulting solution was stirred at room temperature overnight before concentrating under reduced pressure without heating. The residue was re-dissolved in methanol (200 mL). Saturated aqueous ammonium chloride solution (390 mL) was added with ice-cooling. The resulting suspension was filtered and the solid washed with water and air-dried under vacuum. The solid was suspended in DCM and methanol (1:1 v/v, 100 mL) for 90 minutes. The solid was collected by filtration, washed with DCM and air-dried to afford the title compound (18.0 g, 73%).

$^1$H NMR (400 MHz, DMSO-d$_6$): δ 11.07 (s, 1H), 8.51 (d, J=10.0 Hz, 1H), 7.94-7.83 (m, 1H), 7.60 (d, J=7.5 Hz, 2H), 7.44-7.27 (m, 4H), 6.79-6.65 (m, 1H), 5.53-5.39 (s, 2H), 4.93 (s, 2H)

Step 2; (R)-8-(Benzyloxy)-5-(2-bromo-1-hydroxyethyl)quinolin-2(1H)-one

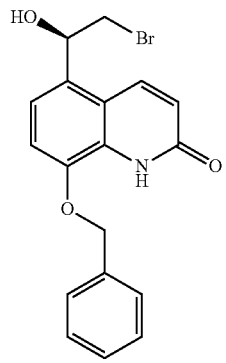 [SMILES: O=c1ccc2c([C@@H](O)CBr)ccc(OCc3ccccc3)c2[nH]1]

8-(Benzyloxy)-5-(2-bromoacetyl)quinolin-2(1H)-one (26.0 g, 69.9 mmol) and (R)-3,3-diphenyl-1-methyltetrahydro-3H-pyrrolo[1,2-c][1,3,2]oxazaborole (21.3 g, 76.8 mmol) were azeotroped with toluene (×3) then suspended in anhydrous THF (400 mL) under an atmosphere of nitrogen. The suspension was cooled to −20° C. (external temperature) and borane dimethyl sulfide complex solution (45.4 mL, 90.8 mmol, 2.0M solution in THF) was added by syringe pump over 3 hours, After complete addition the reaction mixture was stirred for one hour before quenching with methanol (25 mL). The reaction was warmed to room temperature over 20 minutes. The mixture was concentrated under reduced pressure and the residue was suspended in aqueous hydrochloric acid (500 mL, 1M solution) and stirred at room temperature for 18 hours.

After this time the solid was collected by filtration and washed with water (3×100 mL). The solid was partially dissolved in ethyl acetate and heated at reflux for 2 hours. The remaining solid was removed by hot filtration and the filtrate was evaporated to afford the title compound. The solid collected from the hot ethyl acetate was again partially dissolved in ethyl acetate and heated at reflux for 2 hours then filtered to give filtrate containing pure product. This process was repeated four more times. The combined solid was recrystallised from ethyl acetate and petroleum ether to afford the title compound (20.0 g, 76%).

$^1$H NMR (400 MHz, DMSO-d$_6$): δ 10.68 (s, 1H), 8.19 (d, J=9.9 Hz, 1H), 7.58 (d, J=7.5 Hz, 2H), 7.41-7.36 (m, 2H), 7.34-7.29 (m, 1H), 7.23-7.19 (m, 2H), 6.57 (d, J=9.8 Hz, 1H), 5.94 (d, J=4.7 Hz, 1H), 5.31 (s, 2H); 5.25-5.19 (m, 1H), 3.71-3.58 (m, 2H).

Step 3; (R)-8-(Benzyloxy)-5-(2-bromo-1-((tert-butyldimethylsilyl)oxy)ethyl)quinolin-2(1H)-one

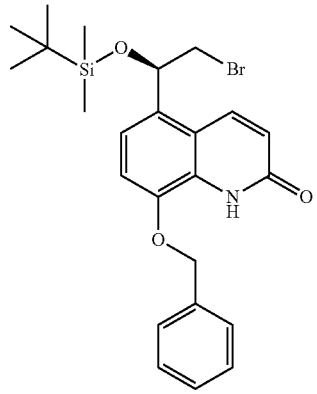 [SMILES: CC(C)(C)[Si](C)(C)O[C@@H](CBr)c1ccc(OCc2ccccc2)c2[nH]c(=O)ccc12]

2,6-Lutidine (6.9 mL, 59.5 mmol) was added to a solution of (R)-8-(benzyloxy)-5-(2-bromo-1-hydroxyethyl)quinolin-2(1H)-one (10.1 g, 27.0 mmol) in DCM (100 mL) at 0° C. The reaction mixture was stirred for 5 minutes then tert-butyldimethylsilyl trifluoromethanesulfonate (13.0 mL, 56.8 mmol) was added dropwise over 15 minutes. The mixture was stirred at 0° C. for 30 minutes, followed by room temperature overnight. After this time the reaction was quenched with saturated aqueous sodium bicarbonate solution and extracted with DCM (×3). The combined organic extracts were dried (magnesium sulfate), filtered and concentrated under reduced pressure. Iso-hexane (500 mL) was added to the crude material and the resulting solid collected by filtration. The solid was recrystallised from ethyl acetate and petroleum ether (40:60) to afford the title compound (11.3 g, 85%).

$^1$H NMR (400 MHz, CDCl$_3$): δ 9.19 (s, 1H), 8.23 (dd, J=9.9, 4.4 Hz, 1H), 7.43 (d, J=4.6 Hz, 5H), 7.17 (dd, J=8.3, 4.5 Hz, 1H), 7.03 (dd, J=8.2, 4.4 Hz, 1H), 6.71 (dd, J=9.9, 3.7 Hz, 1H), 5.18 (d, J=4.5 Hz, 3H), 3.63-3.56 (m, 1H), 3.49 (dd, J=10.4, 4.8 Hz, 1H), 0.88 (t, J=4.4 Hz, 9H), 0.14 (d, J=4.4 Hz, 3H), −0.11 (d, J=4.4 Hz, 3H).

Step 4; (R)-5-(2-Azido-1-((tert-butyldimethylsilyl)oxy)ethyl)-8-(benzyloxy)quinolin-2(1H)-one

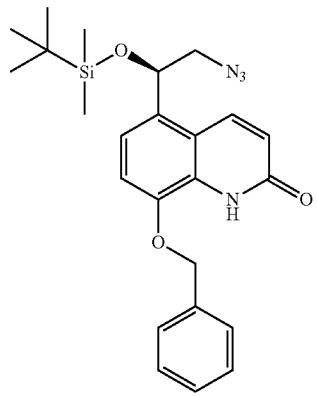 [SMILES: CC(C)(C)[Si](C)(C)O[C@@H](CN=[N+]=[N-])c1ccc(OCc2ccccc2)c2[nH]c(=O)ccc12]

(R)-8-(Benzyloxy)-5-(2-bromo-1-((tert-butyldimethylsilyl)oxy)ethyl)-quinolin-2(1H)-one (10.0 g, 20.5 mmol) was dissolved in DMF (180 mL) and water (20 mL). Sodium iodide (3.39 g, 22.6 mmol) and sodium azide (1.47 g, 22.6 mmol) were added sequentially. The reaction mixture was stirred at RT until all the solid was in solution. The solution was heated at 80° C. for 40 hours then cooled to RT and diluted with ethyl acetate (300 mL). The mixture was washed with water, brine (×2) and the organic extract was dried (magnesium sulfate), filtered and concentrated under reduced pressure. The crude residue was triturated with iso-hexane to afford the desired compound (8.16 g, 88%). Used without further purification in the next step.

$^1$H NMR (400 MHz, CDCl$_3$): δ 9.19 (s, 1H), 8.18 (d, J=9.9 Hz, 1H), 7.45-7.36 (m, 5H), 7.20 (d, J=8.3 Hz, 1H), 7.04 (d, J=8.3 Hz, 1H), 6.70 (dd, J=9.9, 2.2 Hz, 1H), 5.19-5.13 (m, 3H), 3.48 (dd, J=12.7, 8.1 Hz, 1H), 3.26 (dd, J=12.7, 3.8 Hz, 1H), 0.89 (s, 9H), 0.14 (s, 3H), −0.11 (s, 3H).

Step 5; (R)-5-(2-Amino-1-hydroxyethyl)-8-hydroxy-quinolin-2(1H)-one hydrochloride

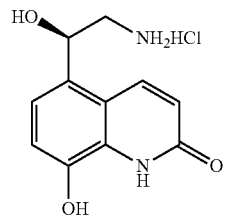

A solution of (R)-5-(2-azido-1-((tert-butyldimethylsilyl)oxy)ethyl)-8-(benzyloxy)quinolin-2(1H)-one (4.50 g, 10.0 mmol) in ethanol (50 mL) was added with 10% palladium on charcoal (4.50 g) followed by 1-methyl-1,4-cyclohexadiene (11.0 mL, 97.9 mmol). The reaction was warmed to 60° C. and then stirred at 60° C. for 2 hours. The reaction mixture was allowed to cool and filtered through a pad of celite. The filtercake was washed with further ethanol and the filtrate was evaporated under reduced pressure. The residue was evaporated from iso-propanol (×2) and dissolved in iso-propanol (30 mL). HCl-dioxane (4M, 50 mL, 200 mmol) was added and the reaction mixture stirred at room temperature for 18 hours. The resulting suspension was filtered, the filtercake washed with ether and the solid dried under vacuum in the presence of P$_2$O$_5$ to afford the title compound (1.65 g, 62%).

$^1$H NMR (400 MHz, MeOD): δ 7.71 (d, J=9.8 Hz, 1H), 6.57 (d, J=8.2 Hz, 1H), 6.31 (d, J=8.2 Hz, 1H), 6.02 (dd, J=9.8, 6.5 Hz, 1H), 4.58 (dd, J=9.6, 3.5 Hz, 1H), 2.47-2.31 (m, 2H).

General scheme for the preparation of compounds of Example 1- Scheme 1

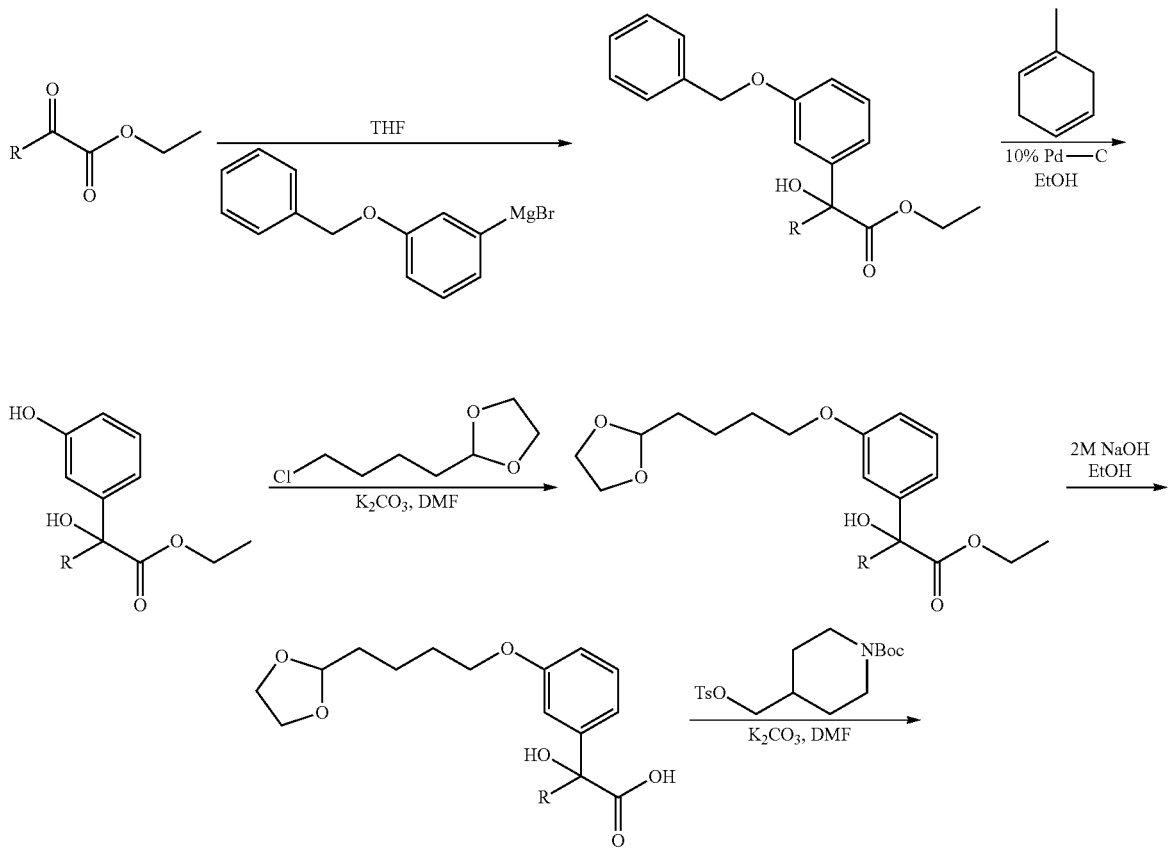

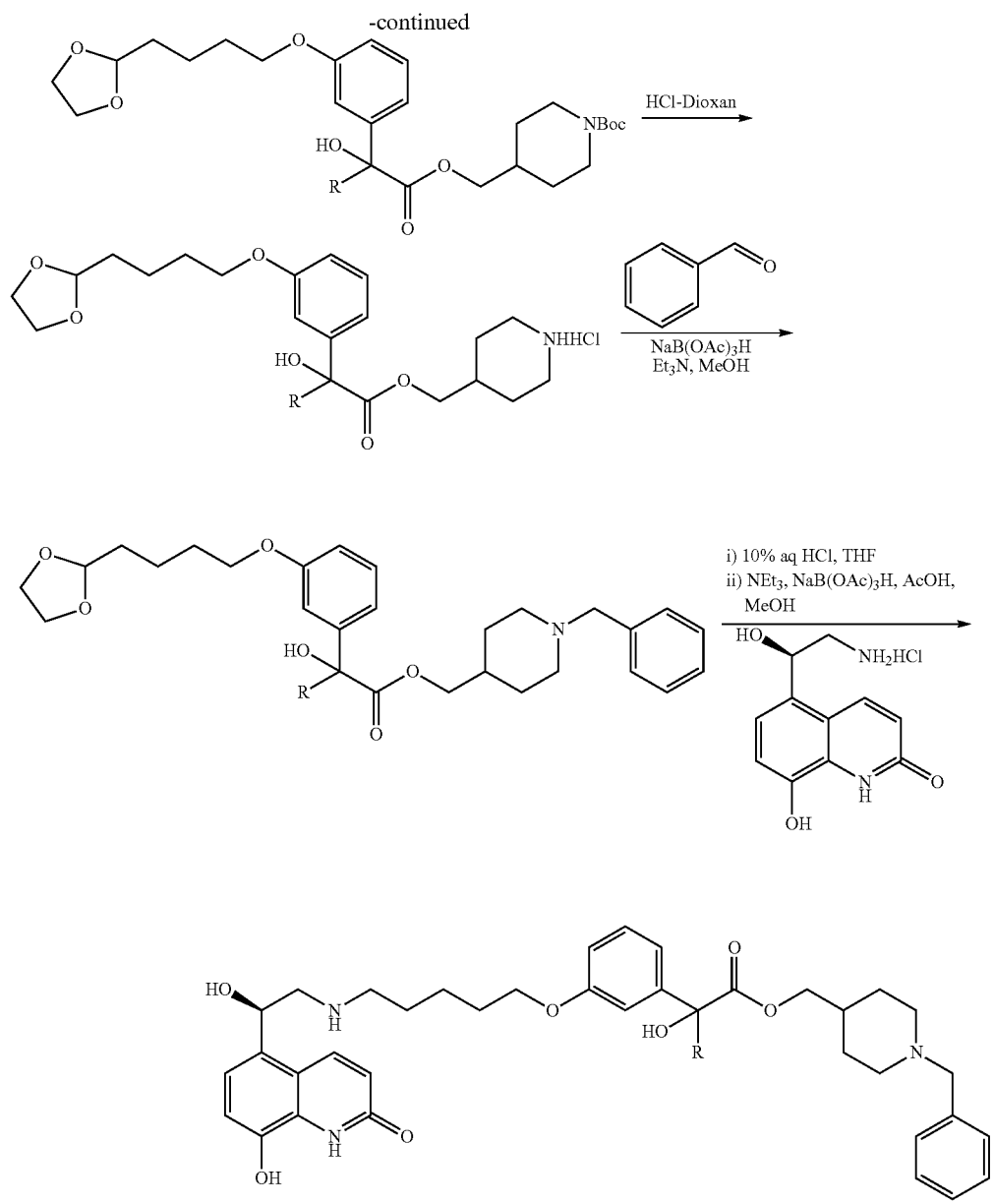
Example 1. (1-Benzylpiperidin-4-yl)methyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate (Compound 1)
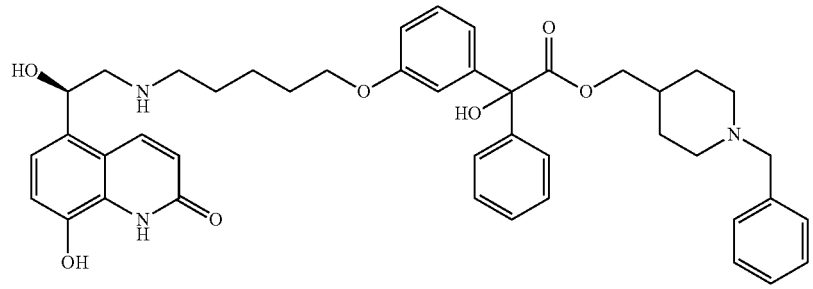 [SMILES: O=C(OCC1CCN(Cc2ccccc2)CC1)C(O)(c1ccccc1)c1cccc(OCCCCCNC[C@H](O)c2ccc(O)c3[nH]c(=O)ccc23)c1]

Step 1; Ethyl 2-(3-(benzyloxy)phenyl)-2-hydroxy-2-phenylacetate

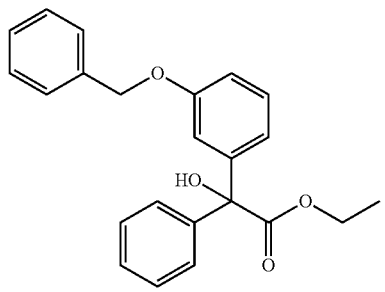 [SMILES: CCOC(=O)C(O)(c1ccccc1)c1cccc(OCc2ccccc2)c1]

A stirred solution of ethyl benzoylformate (1.78 g, 10.0 mmol) in THF (30 mL) at −78° C. was added drop-wise with a solution of 3-benzyloxyphenyl magnesium bromide (1.0M solution in THF, 11.0 mL, 11.0 mmol) over 20 minutes. The reaction mixture was allowed to warm slowly to room temperature and stirred at room temperature for 18 hours. The reaction mixture was quenched with 10% aqueous HCl and then extracted with ethyl acetate. The ethyl acetate extract was washed with brine, dried over anhydrous magnesium sulfate and the filtrate was evaporated under reduced pressure. The residue was purified by flash column chromatography (eluent—100% iso-hexane to 12:1 iso-hexane/ethyl acetate) to afford the title compound (2.23 g, 62%).

$^1$H NMR (400 MHz, CDCl$_3$); δ 7.44-7.23 (m, 11H), 7.13-7.09 (m, 1H), 7.05-7.04 (m, 1H), 6.95-6.92 (m, 1H), 5.04 (s, 2H), 4.34-4.32 (m, 2H), 4.23 (s, 1H), 1.28-1.25 (m, 3H).

Step 2; Ethyl 2-hydroxy-2-(3-hydroxyphenyl)-2-phenylacetate

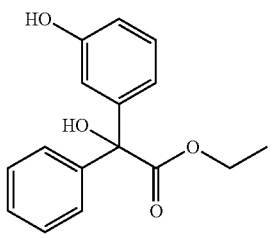 [SMILES: CCOC(=O)C(O)(c1ccccc1)c1cccc(O)c1]

10% Pd—C (2.0 g) was added to a solution of ethyl 2-(3-(benzyloxy)phenyl)-2-hydroxy-2-phenylacetate (2.22 g, 6.13 mmol) in ethanol (20 mL). After 5 minutes 1-methyl-1,4-cyclohexadiene (3.5 mL, 31.1 mmol) was added and the reaction mixture carefully heated to 70° C. [CARE—Vigorous evolution of gas]. The reaction mixture was heated at this temperature for 30 minutes and the reaction mixture was allowed to cool. The suspension was filtered and the filter-cake washed with further ethanol. The filtrate was evaporated under reduced pressure. The residue was purified by flash column chromatography (eluent—100% iso-hexane to 4:1 iso-hexane/ethyl acetate) to afford the title compound (1.20 g, 72%).

$^1$H NMR (400 MHz, CDCl$_3$); δ 7.44-7.42 (m, 2H), 7.36-7.29 (m, 3H), 7.22-7.19 (m, 1H), 7.02-6.99 (m, 1H), 6.93-6.92 (m, 1H), 6.80-6.78 (m, 1H), 4.81 (s, 1H), 4.35-4.27 (m, 2H), 4.23 (s, 1H), 1.30-1.26 (m, 3H).

Step 3; Ethyl 2-(3-(4-(1,3-dioxolan-2-yl)butoxy)phenyl)-2-hydroxy-2-phenylacetate

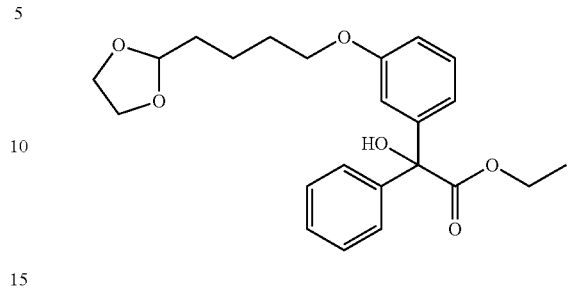

A stirred solution of ethyl 2-hydroxy-2-(3-hydroxyphenyl)-2-phenylacetate (1.19 g, 4.38 mmol) in DMF (15 mL) was added with potassium carbonate (0.907 g, 6.57 mmol). The reaction mixture was stirred at room temperature for 10 minutes and then 2-(4-chlorobutyl)-1,3-dioxolane (0.78 mL, 5.25 mmol) was added. The reaction mixture was heated at 80° C. for 42 hours. 10% Aqueous potassium hydrogen sulfate was added to the reaction mixture which was then extracted with ethyl acetate. The organic phase was washed with brine, dried over anhydrous magnesium sulfate and the filtrate was evaporated under reduced pressure. The residue was purified by flash column chromatography (eluent—100% iso-hexane to 4:1 iso-hexane/ethyl acetate) to afford the title compound (1.07 g, 61%).

$^1$H NMR (400 MHz, CDCl$_3$); δ 7.44-7.42 (m, 2H), 7.34-7.31 (m, 3H), 7.25-7.21 (m, 1H), 7.02-6.98 (m, 2H), 6.85-6.82 (m, 1H), 4.88-4.86 (m, 1H), 4.35-4.30 (m, 2H), 4.22 (s, 1H), 3.97-3.83 (m, 6H), 1.83-1.71 (m, 4H), 1.61-1.59 (m, 2H), 1.28-1.22 (m, 3H).

Step 4; 2-(3-(4-(1,3-Dioxolan-2-yl)butoxy)phenyl)-2-hydroxy-2-phenylacetic acid

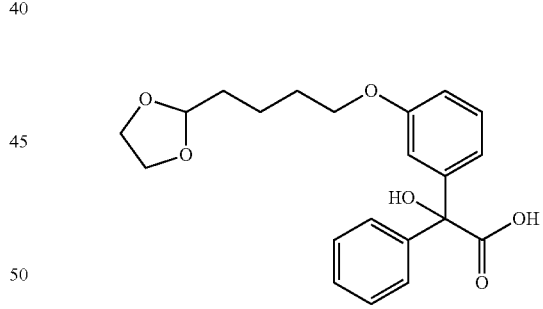

A stirred solution of ethyl 2-(3-(4-(1,3-dioxolan-2-yl)butoxy)phenyl)-2-hydroxy-2-phenylacetate (1.06 g, 2.65 mmol) in ethanol (10 mL) was added with 2M aqueous sodium hydroxide (10 mL). The reaction mixture was stirred at room temperature for 72 hours. The reaction mixture was treated with 10% aqueous potassium hydrogen sulfate and extracted with DCM (×2) and ethyl acetate. The combined organic phases were dried over anhydrous magnesium sulfate and the filtrate was evaporated under reduced pressure to afford the title compound (1.09 g, >100%).

$^1$H NMR (400 MHz, CDCl$_3$); δ 7.44-7.42 (m, 2H), 7.34-7.31 (m, 3H), 7.25-7.21 (m, 1H), 7.02-6.98 (m, 2H), 6.85-6.82 (m, 1H), 4.88-4.86 (m, 1H), 4.10-3.83 (m, 6H), 1.83-1.71 (m, 4H), 1.61-1.55 (m, 2H).

Step 5; tert-Butyl 4-(tosyloxymethyl)piperidine-1-carboxylate

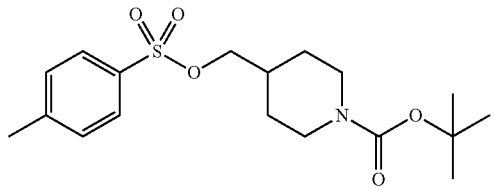 [SMILES: Cc1ccc(S(=O)(=O)OCC2CCN(C(=O)OC(C)(C)C)CC2)cc1]

A stirred solution of tert-butyl 4-(hydroxymethyl)piperidine-1-carboxylate (5.0 g, 23.2 mmol) in anhydrous pyridine (18.5 mL) at 0° C. under nitrogen was added with p-toluenesulfonyl chloride (4.87 g, 25.55 mmol) in one portion. The reaction was stirred at 0° C. for 100 minutes before warming to room temperature. After 18 hours the reaction mixture was poured into water and extracted with ethyl acetate (×3). The combined organic extracts were washed with aqueous 1M hydrochloric acid (×2), brine, dried (magnesium sulfate), filtered and evaporated under reduced pressure to yield the title compound as a yellow solid (7.87 g, 91%).

$^1$H NMR (400 MHz, CDCl$_3$): δ 7.78 (d, J=8.4 Hz, 2H), 7.35 (d, J=8.0 Hz, 2H), 4.15-4.07 (m, 2H), 3.85 (d, J=6.5 Hz, 2H), 2.68-2.60 (m, 2H), 2.46 (s, 3H), 1.88-1.78 (m, 1H), 1.66-1.59 (m, 2H), 1.44 (s, 9H), 1.16-1.04 (m, 2H).

Step 6; tert-Butyl 4-((2-(3-(4-(1,3-dioxolan-2-yl)butoxy)phenyl)-2-hydroxy-2-phenylacetoxy)methyl)piperidine-1-carboxylate

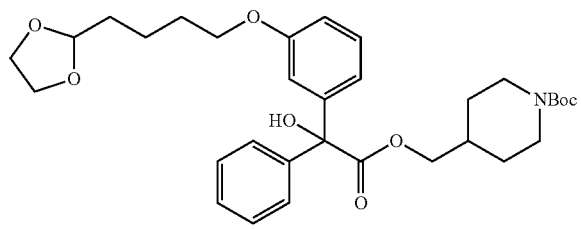 [SMILES: CC(C)(C)OC(=O)N1CCC(COC(=O)C(O)(c2ccccc2)c2cccc(OCCCCC3OCCO3)c2)CC1]

A stirred solution of 2-(3-(4-(1,3-dioxolan-2-yl)butoxy)phenyl)-2-hydroxy-2-phenylacetic acid (1.0 g, 2.69 mmol) in DMF (10 mL) was added with potassium carbonate (0.558 g, 4.04 mmol). After 10 minutes tert-butyl 4-(tosyloxymethyl)piperidine-1-carboxylate (1.29 g, 3.50 mmol) was added and the resulting mixture heated at 80° C. for 18 hours. The reaction mixture was diluted with ethyl acetate and washed with water and brine (twice). The organic phase was dried over anhydrous magnesium sulfate and the filtrate was evaporated under reduced pressure. The residue was purified by flash column chromatography (eluent—100% iso-hexane to 4:1 iso-hexane/ethyl acetate) to afford the title compound (1.42 g, 93%).

$^1$H NMR (400 MHz, CDCl$_3$); δ 7.44-7.42 (m, 2H), 7.34-7.31 (m, 3H), 7.25-7.21 (m, 1H), 7.02-6.98 (m, 2H), 6.85-6.82 (m, 1H), 4.88-4.86 (m, 1H), 4.19-3.83 (m, 11H), 2.60 (m, 2H), 1.88-1.71 (m, 4H), 1.61-1.58 (m, 3H), 1.54-1.46 (m, 11H), 1.26-1.24 (m, 2H).

Step 7; Piperidin-4-ylmethyl 2-(3-(4-(1,3-dioxolan-2-yl)butoxy)phenyl)-2-hydroxy-2-phenylacetate hydrochloride

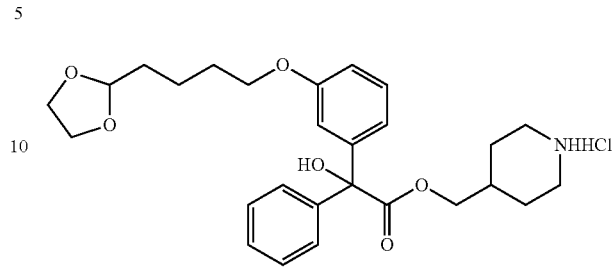

A solution of HCl in dioxane (4M, 10 mL) was added to tert-butyl 4-((2-(3-(4-(1,3-dioxolan-2-yl)butoxy)phenyl)-2-hydroxy-2-phenylacetoxy)methyl)piperidine-1-carboxylate (1.40 g, 2.46 mmol) and the mixture stirred at room temperature for 2 hours.

The solvent was evaporated under reduced pressure and the residue used directly in the next step with no purification.

Step 8; (1-Benzylpiperidin-4-yl)methyl 2-(3-(4-(1,3-dioxolan-2-yl)butoxy)phenyl)-2-hydroxy-2-phenylacetate

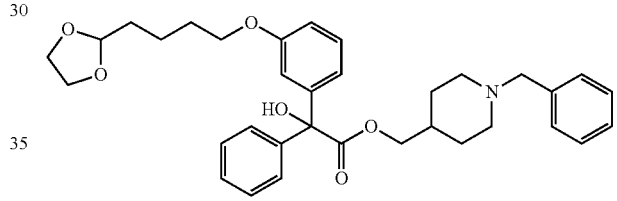

A stirred solution of piperidin-4-ylmethyl 2-(3-(4-(1,3-dioxolan-2-yl)butoxy)phenyl)-2-hydroxy-2-phenylacetate hydrochloride in acetonitrile (15 mL) was added with triethylamine (0.683 mL, 4.91 mmol). The reaction mixture was stirred at room temperature for 20 minutes. Benzaldehyde (0.325 mL, 3.20 mmol) was added and the mixture stirred for a further 30 minutes. To this mixture was added sodium triacetoxyborohydride (1.04 g, 4.91 mmol) followed by acetic acid (0.562 mL, 9.82 mmol). The resulting mixture was stirred at room temperature for 72 hours. The reaction mixture was diluted with ethyl acetate and washed with 10% aqueous potassium carbonate and brine. The organic phase was dried and the filtrate was evaporated under reduced pressure. The residue was purified by flash column chromatography (eluent—100% DCM to 25:1 DCM/methanol) to afford the title compound (0.804 g, 58%).

$^1$H NMR (400 MHz, CDCl$_3$); δ 7.42-7.38 (m, 2H), 7.35-7.19 (m, 9H), 7.00-6.94 (m, 2H), 6.83 (ddd, J=8.2, 2.5, 0.9 Hz, 1H), 5.30 (s, 2H), 4.88-4.83 (m, 1H), 4.22 (s, 1H), 4.15-4.06 (m, 2H), 4.01-3.80 (m, 6H), 3.45 (s, 2H), 2.81 (d, J=11.3 Hz, 2H), 1.92-1.66 (m, 6H), 1.70-1.46 (m, 3H), 1.28-1.13 (m, 2H).

Step 9; (Compound 1)

To a stirred solution of (1-benzylpiperidin-4-yl)methyl 2-(3-(4-(1,3-dioxolan-2-yl)butoxy)phenyl)-2-hydroxy-2-phenylacetate (0.390 g, 0.70 mmol) in THF (4 mL) was added 10% aqueous hydrochloric acid (8 mL), The resulting mixture was stirred at room temperature for 2 hours. To the mixture was added 10% aqueous potassium carbonate and then extracted with ethyl acetate (twice). The combined organic phases were dried and the filtrate was evaporated under reduced pressure. The residue was dissolved in methanol (3 mL) and added to a pre-stirred (10 minutes) mixture of (R)-5-(2-amino-1-hydroxyethyl)-8-hydroxyquinolin-2(1H)-one hydrochloride (0.193 g, 0.60 mmol, 80% purity) and triethylamine (0.167 mL, 1.20 mmol) in methanol (3 mL). This mixture was stirred at room temperature for 1 hour and then sodium triacetoxyborohydride (0.254 g, 1.20 mmol) followed by acetic acid (0.137 mL, 2.39 mmol) were added. The reaction mixture was stirred for a further 1 hour.

The reaction mixture was diluted with iso-butanol and washed with water. The aqueous phase was extracted with further iso-butanol. The combined iso-butanol extracts were evaporated under reduced pressure. The residue was purified by reverse phase preparative HPLC to afford the title compound (1).

The following compounds were prepared as described in Example 1 with the corresponding commercially available substituted ethyl benzoylformate replacing ethyl benzoylformate in Step 1. If the required substituted ethyl benzoylformate was not available it was prepared according to Scheme 2 and Procedure 1 using the appropriate Grignard reagent.

| | $R_t$ (min) | Structure | Method | NMR data (400 MHz) | Salt (2 eq unless stated) |
|---|---|---|---|---|---|
| 1 | 8.46 | 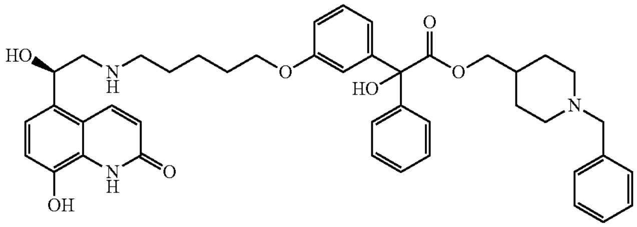 [SMILES: O=C(OCC1CCN(Cc2ccccc2)CC1)C(O)(c1ccccc1)c1cccc(OCCCCCNC[C@H](O)c2ccc(O)c3[nH]c(=O)ccc23)c1] | 6 | (DMSO-$d_6$/$D_2O$); δ 8.19 (d, J = 9.9 Hz, 1 H); 7.45 (s, 5 H); 7.30 (d, J = 7.6 Hz, 6 H); 7.22 (d, J = 8.1 Hz, 1 H); 7.16 (d, J = 8.2 Hz, 1H); 7.00 (d, J = 8.2 Hz, 1 H); 6.86-6.79 (m, 3 H); 6.60 (d, J = 9.8 Hz, 1 H); 5.31-5.24 (m, 1 H); 4.20 (s, 3 H); 4.05-3.71 (m, 4 H); 3.32-3.24 (m, 2 H); 3.07 (s, 2 H); 2.96 (s, 2 H); 2.87 (s, 2 H); 1.85 (s, 1 H); 1.76-1.61 (m, 5 H); 1.45-1.27 (m, 3 H) | TFA |
| 2 | 7.29 | 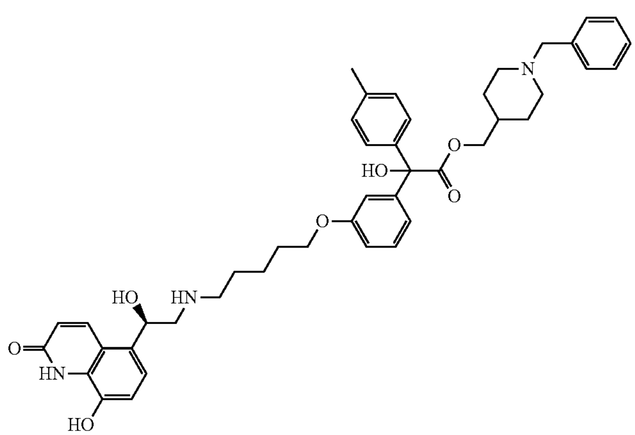 [SMILES: Cc1ccc(C(O)(C(=O)OCC2CCN(Cc3ccccc3)CC2)c2cccc(OCCCCCNC[C@H](O)c3ccc(O)c4[nH]c(=O)ccc34)c2)cc1] | 7 | (DMSO-$d_6$); δ 8.31 (s, 2H), 8.19 (d, J = 9.9 Hz, 1 H), 7.32-7.18 (m, 9H), 7.14-7.09 (m, 3H), 6.96 (d, J = 8.2 Hz, 1H), 6.88-6.83 (m, 3H), 6.53 (d, J = 9.9 Hz, 1H), 5.20 (dd, J = 4.5, 8.2 Hz, 1H), 4.01-3.96 (m, 2H), 3.89 (dd, J = 6.3, 6.3 Hz, 2H), 3.40 (s, 2H), 2.89-2.69 (m, 6H), 2.28 (s, 3H), 1.83 (dd, J = 9.5, 11.8 Hz, 2H), 1.72-1.63 (m, 2H), 1.60-1.37 (m, 7H), 1.17-1.04 (m, 2H). | Formate |
| 3 | 7.23 | 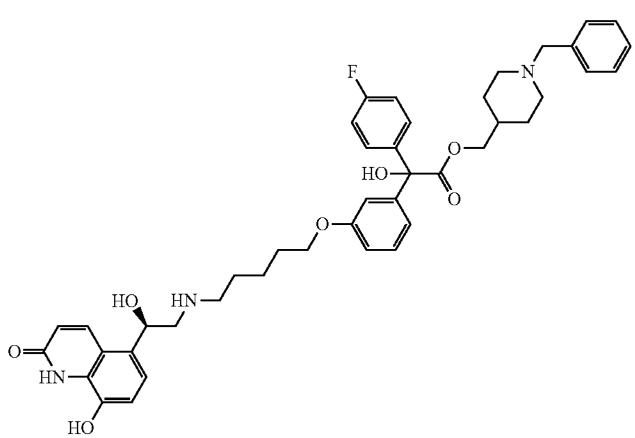 [SMILES: O=C(OCC1CCN(Cc2ccccc2)CC1)C(O)(c1ccc(F)cc1)c1cccc(OCCCCCNC[C@H](O)c2ccc(O)c3[nH]c(=O)ccc23)c1] | 7 | (DMSO-$d_6$); δ 10.54-10.49 (m, 2H), 8.60-8.59 (m, 2H), 7.48 (s, 5H), 7.38-7.33 (m, 2H), 7.25 (dd, J = 8.0, 8.0 Hz, 1H), 7.18-7.13 (m, 3H), 6.99 (d, J = 8.2 Hz, 1H), 6.90-6.85 (m, 3H), 6.58 (d, J = 9.9 Hz, 1H), 6.33-6.01 (s, 1H), 5.32 (dd, J = 2.2, 9.6 Hz, 1H), 4.31-4.20 (m, 2H), 4.01 (d, J = 6.4 Hz, 2H), 3.91 (dd, J = 6.3, 6.3 Hz, 2H), 3.34 (d, J = 14.1 Hz, 2H), 3.12-2.86 (m, 6H), 1.85-1.83 (m, 1H), 1.77 (s, 1H), 1.72-1.64 (m, 6H), 1.48-1.30 (m, 4H). | TFA |

| | R_t (min) | Structure | Method | NMR data (400 MHz) | Salt (2 eq unless stated) |
|---|---|---|---|---|---|
| 4 | 7.23 | 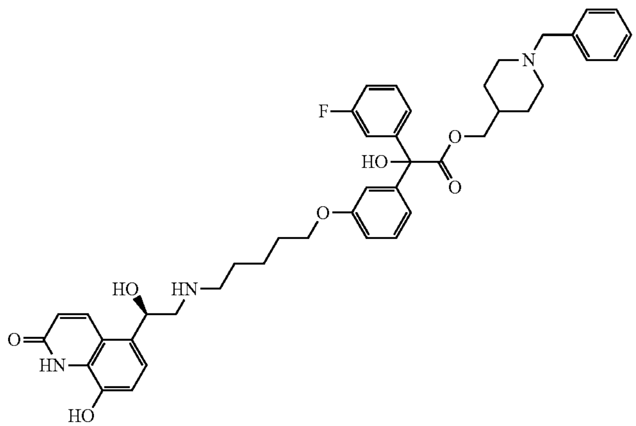 [SMILES: O=C(OCC1CCN(Cc2ccccc2)CC1)C(O)(c1cccc(F)c1)c1cccc(OCCCCCNC[C@H](O)c2ccc(O)c3[nH]c(=O)ccc23)c1] | 7 | (DMSO-d_6); δ 10.52 (s, 2H), 9.49-9.49 (m, 1H), 8.60-8.59 (m, 2H), 8.16 (d, J = 9.9 Hz, 1H), 7.48 (s, 6H), 7.42-7.35 (m, 1H), 7.26 (dd, J = 7.9, 7.9 Hz, 1H), 7.19-7.10 (m, 4H), 6.99 (d, J = 8.2 Hz, 1H), 6.91-6.86 (m, 4H), 6.58 (d, J = 9.9 Hz, 1H), 6.14-6.14 (m, 1H), 5.30 (dd, J = 2.2, 9.7 Hz, 1H), 4.31-4.21 (m, 3H), 4.02 (d, J = 6.5 Hz, 2H), 3.91 (dd, J = 6.2, 6.2 Hz, 2H), 3.34 (d, J = 11.8 Hz, 2H), 3.10-2.86 (m, 5H), 1.89-1.84 (m, 1H), 1.77-1.64 (m, 5H), 1.48-1.30 (m, 4H). | TFA |
| 5 | 7.28 | 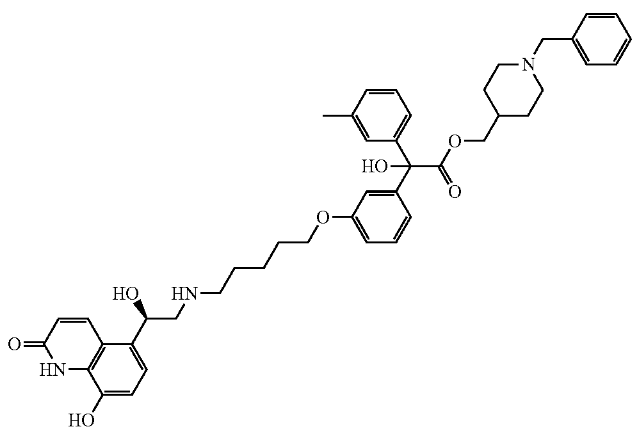 [SMILES: Cc1cccc(C(O)(C(=O)OCC2CCN(Cc3ccccc3)CC2)c2cccc(OCCCCCNC[C@H](O)c3ccc(O)c4[nH]c(=O)ccc34)c2)c1] | 7 | (DMSO-d_6); δ 10.52-10.46 (2H, m), 9.49-9.36 (1H, m), 8.57-8.56 (2H, m), 8.16 (1H, d, J = 7.3 Hz), 7.48 (5H, s), 7.26-7.19 (2H, m), 7.15 (2H, d, J = 8.2 Hz), 7.09 (2H, dd, J = 8.3, 8.3 Hz), 6.99 (1H, d, J = 8.2 Hz), 6.89-6.83 (3H, m), 6.58 (2H, dd, J = 1.9, 9.9 Hz), 6.17-6.16 (1H, m), 5.31 (1H, d, J = 8.9 Hz), 4.26 (2H, d, J = 4.9 Hz), 4.01 (2H, d, J = 6.4 Hz), 3.91 (2H, dd, J = 6.3, 6.3 Hz), 3.34 (2H, d, J = 11.5 Hz), 3.11-2.86 (6H, m), 2.27 (3H, s), 1.84 (1H, d, J = 3.1 Hz), 1.76-1.64 (6H, m), 1.48-1.34 (4H, m); | TFA |
| 6 | 8.12 | 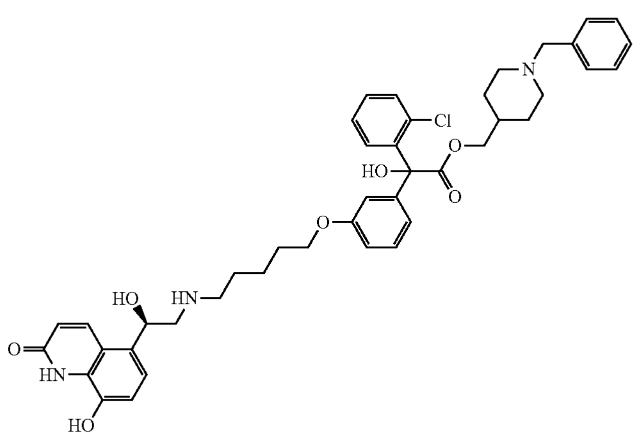 [SMILES: O=C(OCC1CCN(Cc2ccccc2)CC1)C(O)(c1cccc(OCCCCCNC[C@H](O)c2ccc(O)c3[nH]c(=O)ccc23)c1)c1ccccc1Cl] | 7 | (MeOD); δ 8.38 (d, J = 9.7 Hz, 1H), 7.54-7.47 (m, 5H), 7.44 (d, J = 7.8 Hz, 1H), 7.35-7.28 (m, 3H), 7.27 (s, 1H), 7.19-7.10 (m, 2H), 7.05 (d, J = 8.2 Hz, 1H), 6.98-6.91 (m, 2H), 6.70 (d, J = 9.9 Hz, 1H), 5.41 (t, J = 6.9 Hz, 1H), 4.29 (s, 2H), 4.12-4.02 (m, 4H), 3.50-3.44 (m, 2H), 3.25 (d, J = 6.4 Hz, 2H), 3.12 (t, J = 9.1 Hz, 2H), 2.97 (t, J = 12.2 Hz, 2H), 2.06-2.00 (m, 1H), 1.93-1.82 (m, 6H), 1.63 (t, J = 17.3 Hz, 2H), 1.57-1.42 (m, 2H). | TFA |

| R$_t$ (min) | Structure | Method | NMR data (400 MHz) | Salt (2 eq unless stated) |
|---|---|---|---|---|
| 7 8.15 | | 7 | (MeOD); δ 8.38 (d, J = 9.7 Hz, 1H), 7.53-7.48 (m, 5H), 7.32-7.19 (m, 4H), 7.13 (s, 1H), 7.07-6.99 (m, 3H), 6.93-6.86 (m, 2H), 6.70 (d, J = 9.8 Hz, 1H), 5.43-5.38 (m, 1H), 4.28 (s, 2H), 4.10 (d, J = 6.5 Hz, 2H), 4.01 (dd, J = 6.1, 6.1 Hz, 2H), 3.51-3.45 (m, 2H), 3.25 (d, J = 6.5 Hz, 2H), 3.15-3.09 (m, 2H), 2.97 (dd, J = 10.8, 13.1 Hz, 2H), 2.29-2.21 (m, 4H), 2.01-1.96 (m, 1H), 1.89-1.80 (m, 5H), 1.66-1.58 (m, 2H), 1.50-1.36 (m, 2H). | TFA |
| 8 7.36 | | 7 | (MeOD); δ 8.38 (d, J = 9.9 Hz, 1H), 7.51-7.48 (m, 5H), 7.33-7.23 (m, 4H), 7.10 (s, 1H), 7.07-7.03 (m, 2H), 6.99 (d, J = 7.8 Hz, 1H), 6.92-6.84 (m, 2H), 6.70 (d, J = 9.9 Hz, 1H), 5.41 (t, J = 8.5 Hz, 1H), 4.38-4.24 (m, 2H), 4.09 (d, J = 6.5 Hz, 2H), 4.00 (t, J = 7.0 Hz, 2H), 3.51-3.45 (m, 2H), 3.25 (d, J = 6.4 Hz, 2H), 3.16-3.08 (m, 2H), 2.96 (t, J = 12.7 Hz, 2H), 2.64-2.56 (m, 2H), 2.06-1.95 (m, 1H), 1.86-1.78 (m, 6H), 1.65-1.59 (m, 2H), 1.49-1.24 (m, 2H), 1.08 (t, J = 8.2 Hz, 3H). | TFA |
| 9 7.15 | | 7 | (DMSO-d$_6$); δ 10.49 (d, J = 10.4 Hz, 2H), 9.52-9.52 (m, 1H), 8.59-8.58 (m, 2H), 8.17 (d, J = 9.9 Hz, 1H), 7.48 (s, 6H), 7.25 (dd, J = 7.9, 7.9 Hz, 1H), 7.15 (d, J = 8.2 Hz, 1H), 7.06-7.02 (m, 2H), 7.00-6.94 (m, 4H), 6.86 (dd, J = 2.2, 8.0 Hz, 1H), 6.59 (dd, J = 1.6, 9.9 Hz, 1H), 6.17-6.17 (m, 1H), 5.30 (d, J = 9.5 Hz, 1H), 4.26 (d, J = 4.9 Hz, 2H), 4.01 (d, J = 6.4 Hz, 2H), 3.91 (dd, J = 6.2, 6.2 Hz, 2H), 3.37-3.32 (m, 2H), 3.10-2.86 (m, 6H), 1.90-1.84 (m, 1H), 1.79-1.66 (m, 6H), 1.47-1.33 (m, 4H). | TFA |

| R_f (min) | Structure | Method | NMR data (400 MHz) | Salt (2 eq unless stated) |
|---|---|---|---|---|
| 10 7.36 | | 7 | (DMSO-$d_6$, 90° C.); δ 8.15 (d, J = 9.9 Hz, 1H), 7.50-7.39 (m, 5H), 7.20 (dd, J = 7.8, 7.8 Hz, 1H), 7.12 (dd, J = 8.2, 8.2 Hz, 3H), 6.98 (d, J = 8.2 Hz, 1H), 6.80-6.76 (m, 1H), 6.54 (d, J = 9.8 Hz, 1H), 5.31 (dd, J = 4.4, 8.3 Hz, 1H), 4.20 (s, 2H), 3.95 (dd, J = 6.3, 6.3 Hz, 4H), 3.58-3.19 (m, 5H), 3.15-3.07 (m, 2H), 3.02 (dd, J = 7.7, 7.7 Hz, 2H), 2.88 (s, 1H), 2.13 (dd, J = 10.9, 10.9 Hz, 1H), 1.76-1.68 (m, 6H), 1.58 (d, J = 9.3 Hz, 2H), 1.52-1.33 (m, 6H), 1.23 (d, J = 13.1 Hz, 1H), 1.14-0.98 (m, 4H). | TFA |
| 11 7.35 | | 7 | (DMSO-$d_6$); δ 10.52 (s, 1H), 10.48 (s, 1H), 9.43 (s, 1H), 8.57 (s, 2H), 8.15 (d, J = 9.9 Hz, 1H), 7.47 (s, 4H), 7.24 (dd, J = 7.4, 7.4 Hz, 2H), 7.19-7.13 (m, 3H), 7.10 (d, J = 7.8 Hz, 1H), 6.99 (d, J = 8.2 Hz, 1H), 6.91-6.84 (m, 3H), 6.61-6.56 (m, 2H), 6.54 (s, 1H), 6.17 (d, J = 3.3 Hz, 1H), 5.30 (d, J = 9.4 Hz, 1H), 4.30-4.25 (m, 2H), 4.01 (d, J = 5.6 Hz, 1H), 3.91 (dd, J = 6.2, 6.2 Hz, 2H), 3.16-2.81 (m, 9H), 2.61-2.53 (m, 2H), 1.83 (s, 1H), 1.74-1.64 (m, 6H), 1.47-1.30 (m, 4H), 1.13 (dd, J = 7.5, 7.5 Hz, 3H). | TFA |

Scheme 2

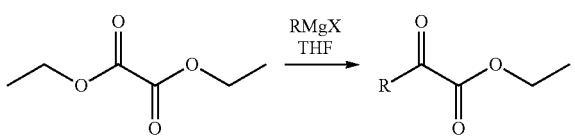

Procedure 1

Preparation of ethyl 3-methylbenzoylformate

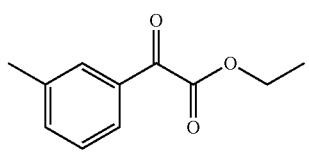

A stirred solution of diethyl oxalate (5 g, 32.2 mmol) in THF (100 mL) was cooled to −78° C. and then a solution of 3-methylphenyl magnesium bromide (0.5M in THF, 75 mL, 37.5 mmol) was added drop-wise over 25 minutes. The reaction mixture was held at −78° C. for 30 minutes and then the mixture warmed to room temperature. The reaction mixture was stirred at room temperature for 3 hours and then cooled to 0° C. 10% Aqueous hydrochloric acid was added followed by ethyl acetate. The mixture was stirred vigorously for 30 minutes and the organic phase removed. The aqueous phase was extracted with further ethyl acetate and the combined organic extracts washed with brine, and dried over anhydrous magnesium sulfate. The filtrate was evaporated under reduced pressure and the residue was purified by flash column chromatography (eluent—100% iso-hexane to 5:1 iso-hexane/ethyl acetate) to afford the title compound (3.0 g, 49%).

$^1$H NMR (400 MHz, CDCl$_3$); δ 7.81-7.79 (m, 2H), 7.48-7.46 (m, 1H), 7.45-7.37 (m, 1H), 4.44 (m, 2H), 2.42 (s, 3H), 1.42 (m, 3H).

Example 2. (R)-Quinuclidin-3-yl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-(4-methoxyphenyl)acetate (Compound 12)

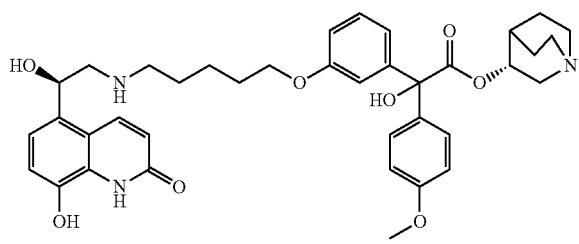 [SMILES: COc1ccc(C(O)(C(=O)O[C@H]2CN3CCC2CC3)c2cccc(OCCCCCNC[C@H](O)c3ccc(O)c4[nH]c(=O)ccc34)c2)cc1]

Step 1; 2-(3-(4-(1,3-Dioxolan-2-yl)butoxy)phenyl)-2-hydroxy-2-(4-methoxyphenyl)acetic acid

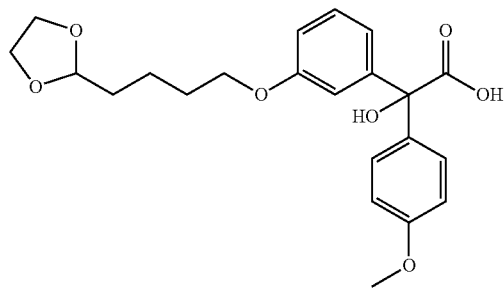 [SMILES: COc1ccc(C(O)(C(=O)O)c2cccc(OCCCCC3OCCO3)c2)cc1]

The title compound was prepared as described in Example 1 Steps 1 to 4 with ethyl 4-methoxybenzoylformate replacing ethyl benzoylformate in Step 1.

$^1$H NMR (400 MHz, DMSO-d$_6$); δ 7.34 (d, J=8.9 Hz, 2H), 7.16 (dd, J=8.2, 8.2 Hz, 1H), 6.98 (d, J=7.2 Hz, 2H), 6.82 (d, J=8.8 Hz, 2H), 6.80-6.75 (m, 1H), 4.78 (dd, J=4.7, 4.7 Hz, 1H), 3.87-3.72 (m, 9H), 1.75-1.57 (m, 4H), 1.51-1.44 (m, 2H).

Step 2; (R)-Quinuclidin-3-yl 2-(3-(4-(1,3-dioxolan-2-yl)butoxy)phenyl)-2-hydroxy-2-(4-methoxyphenyl)acetate

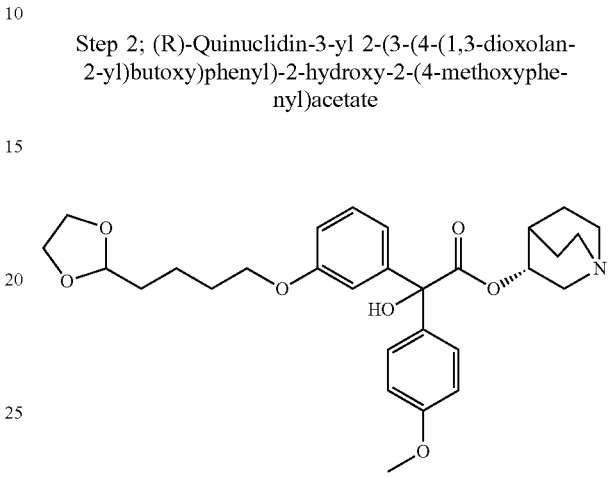

A solution of 2-(3-(4-(1,3-dioxolan-2-yl)butoxy)phenyl)-2-hydroxy-2-(4-methoxyphenyl)acetic acid (0.200 g, 0.50 mmol) in THF (20 mL) was added with carbonyldiimidazole (0.105 g, 0.65 mmol) and the reaction mixture heated under reflux for 2 hours. The reaction mixture was allowed to cool to room temperature and (R)-quinuclidinol (0.215 g, 1.69 mmol) added. The reaction mixture was heated under reflux for 72 hours. The reaction mixture was diluted with ethyl acetate and washed sequentially with 10% aqueous sodium carbonate and brine, and dried over anhydrous magnesium sulfate. The filtrate was evaporated under reduced pressure and the crude material used in the next step with no purification.

Step 3; (Compound 12)

The title compound (12) was prepared as described in Example 1 Step 9.

| N | R$_t$ (min) | Method | NMR data (400 MHz) | Salt (2 eq unless stated) |
|---|---|---|---|---|
| 12 | 6.96 | 7 | (MeOD); δ 8.53 (s, 2H), 8.38 (d, J = 9.9 Hz, 1H), 7.35-7.25 (m, 4H), 7.06-6.99 (m, 3H), 6.97-6.89 (m, 3H), 6.72-6.68 (m, 1H), 5.40 (t, J = 9.7 Hz, 1H), 5.13-5.11 (m, 1H), 4.02-3.96 (m, 2H), 3.81 (s, 3H), 3.52-3.45 (m, 1H), 3.23 (d, J = 6.4 Hz, 2H), 3.10 (t, J = 9.7 Hz, 2H), 3.06-2.99 (m, 3H), 2.88-2.73 (m, 2H), 2.19 (d, J = 1.6 Hz, 1H), 1.90-1.77 (m, 6H), 1.65-1.52 (m, 4H). | Formate |

Example 3. (R)-Quinuclidin-3-yl 2-cyclopentyl-2-hydroxy-2-(3-((5-(((R)-2-hydroxy-2-(8-hydroxy-2-oxo-1,2-dihydroquinolin-5-yl)ethyl)amino)pentyl)oxy)-phenyl)acetate (Compound 12A)

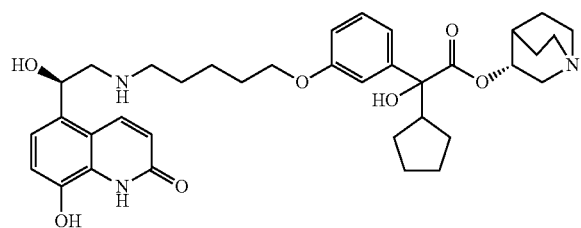 [SMILES: O=C(O[C@H]1CN2CCC1CC2)C(O)(c1cccc(OCCCCCNC[C@H](O)c2ccc(O)c3[nH]c(=O)ccc23)c1)C1CCCC1]

Step 1; Ethyl 2-(3-(benzyloxy)phenyl)-2-oxoacetate

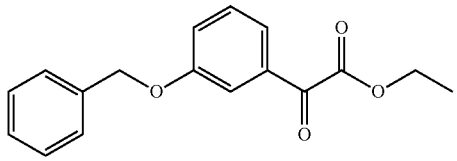 [SMILES: CCOC(=O)C(=O)c1cccc(OCc2ccccc2)c1]

The title compound was prepared as described in Procedure 1.

¹H NMR (400 MHz, DMSO-d₆); δ 7.57-7.52 (m, 3H), 7.49-7.39 (m, 5H), 7.37-7.32 (m, 1H), 5.21 (s, 2H), 4.42 (q, J=7.1 Hz, 2H), 1.33 (dd, J=7.2, 7.2 Hz, 3H).

Step 2; 2-(3-(4-(1,3-Dioxolan-2-yl)butoxy)phenyl)-2-cyclopentyl-2-hydroxyacetic acid

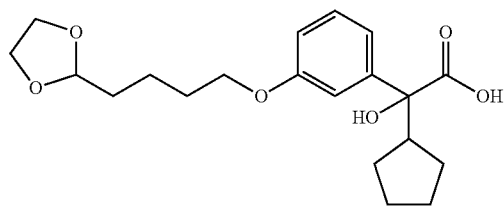 [SMILES: O=C(O)C(O)(c1cccc(OCCCCC2OCCO2)c1)C1CCCC1]

The title compound was prepared as described in Example 1 Steps 1 to 4 with ethyl 2-(3-(benzyloxy)phenyl)-2-oxoacetate and cyclopentyl magnesium bromide replacing ethyl benzoylformate and 3-benzyloxyphenyl magnesium bromide respectively in Step 1.

¹H NMR (400 MHz, DMSO-d6); δ 7.34 (d, J=8.9 Hz, 2H), 7.16 (dd, J=8.2, 8.2 Hz, 1H), 6.98 (d, J=7.2 Hz, 2H), 6.82 (d, J=8.8 Hz, 2H), 6.80-6.75 (m, 1H), 4.78 (dd, J=4.7, 4.7 Hz, 1H), 3.87-3.72 (m, 9H), 1.75-1.57 (m, 4H), 1.51-1.44 (m, 2H).

Step 3; (R)-Quinuclidin-3-yl 2-cyclopentyl-2-hydroxy-2-(3-((5-(((R)-2-hydroxy-2-(8-hydroxy-2-oxo-1,2-dihydroquinolin-5-yl)ethyl)amino)pentyl)oxy)phenyl)acetate (Compound 12A)

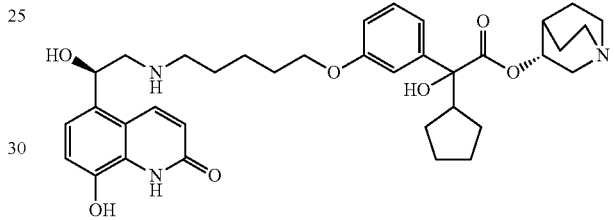

The title compound was prepared as described in Example 2 Step 2 and 3 to afford the title compound (12A).

| N | Rt (min) | Method | NMR data (400 MHz) | Salt (2 eq unless stated) |
|---|---|---|---|---|
| 12A | 7.05 | 6 | (MeOD) δ 8.39 (d, J = 9.9 Hz, 1H), 7.32-7.21 (m, 4H), 7.05 (d, J = 8.2 Hz, 1H), 6.88-6.84 (m, 1H), 6.70 (d, J = 9.9 Hz, 1H), 5.42 (t, J = 6.7 Hz, 1H), 5.14 (d, J = 10.0 Hz, 1H), 4.04 (t, J = 5.0 Hz, 2H), 3.78-3.66 (m, 1H), 3.37-3.20 (m, 6H), 3.18-3.10 (m, 2H), 3.09-2.97 (m, 1H), 2.37-2.30 (m, 1H), 2.08-1.96 (m, 2H), 1.94-1.80 (m, 6H), 1.72-1.62 (m, 8H), 1.58-1.47 (m, 1H), 1.43-1.33 (m, 2H) | TFA |

General scheme for the preparation of enantiopure intermediate 1 and 2 - scheme 3

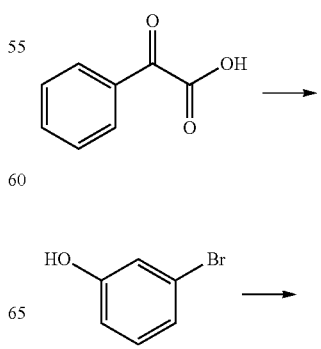

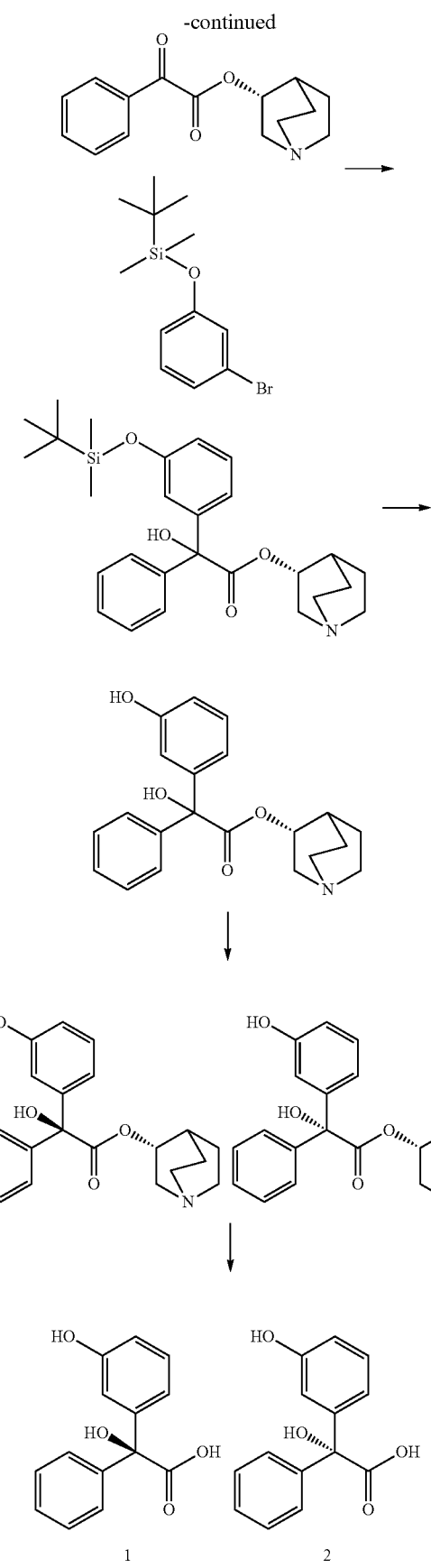

Procedure 2. Preparation of (S)-2-hydroxy-2-(3-hydroxyphenyl)-2-phenylacetic acid and (R)-2-hydroxy-2-(3-hydroxyphenyl)-2-phenylacetic acid

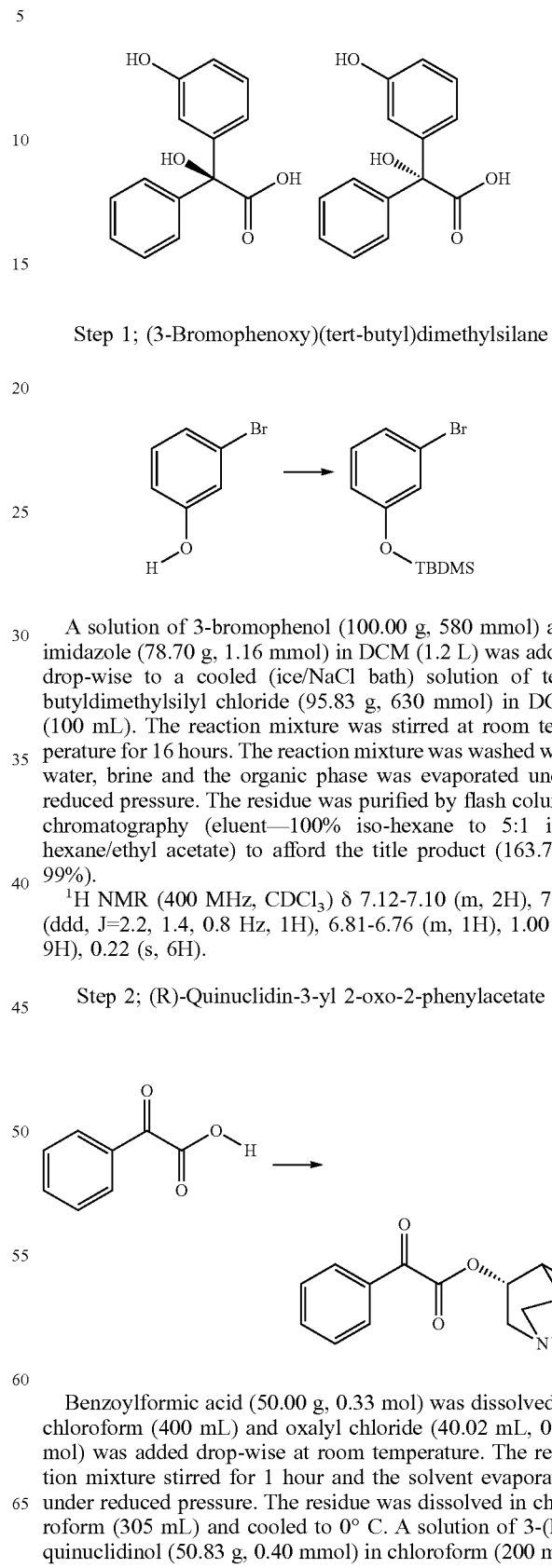

Step 1; (3-Bromophenoxy)(tert-butyl)dimethylsilane

A solution of 3-bromophenol (100.00 g, 580 mmol) and imidazole (78.70 g, 1.16 mmol) in DCM (1.2 L) was added drop-wise to a cooled (ice/NaCl bath) solution of tert-butyldimethylsilyl chloride (95.83 g, 630 mmol) in DCM (100 mL). The reaction mixture was stirred at room temperature for 16 hours. The reaction mixture was washed with water, brine and the organic phase was evaporated under reduced pressure. The residue was purified by flash column chromatography (eluent—100% iso-hexane to 5:1 iso-hexane/ethyl acetate) to afford the title product (163.7 g, 99%).

$^1$H NMR (400 MHz, CDCl$_3$) δ 7.12-7.10 (m, 2H), 7.03 (ddd, J=2.2, 1.4, 0.8 Hz, 1H), 6.81-6.76 (m, 1H), 1.00 (s, 9H), 0.22 (s, 6H).

Step 2; (R)-Quinuclidin-3-yl 2-oxo-2-phenylacetate

Benzoylformic acid (50.00 g, 0.33 mol) was dissolved in chloroform (400 mL) and oxalyl chloride (40.02 mL, 0.47 mol) was added drop-wise at room temperature. The reaction mixture stirred for 1 hour and the solvent evaporated under reduced pressure. The residue was dissolved in chloroform (305 mL) and cooled to 0° C. A solution of 3-(R)-quinuclidinol (50.83 g, 0.40 mmol) in chloroform (200 mL)

was added drop-wise. The reaction mixture was allowed warm to room temperature and stirred for 1 hour. The reaction mixture was cooled to 0° C. and quenched with 10% aqueous potassium carbonate solution. The organic layer was separated and washed with water (2×), brine (3×) and dried over anhydrous magnesium sulfate. The filtrate was evaporated under reduced pressure to afford the title compound (77.2 g, 89%).

$^1$H NMR (400 MHz, DMSO-$d_6$) δ 8.01-7.95 (m, 2H), 7.84-7.77 (m, 1H), 7.68-7.61 (m, 2H), 5.15-5.05 (m, 1H), 3.26 (dd, J=14.7, 8.2 Hz, 1H), 2.79-2.58 (m, 5H), 2.13-2.04 (m, 1H), 1.72-1.53 (m, 3H), 1.42-1.33 (m, 1H).

Step 3; (R)-Quinuclidin-3-yl 2-(3-((tert-butyldimethylsilyl)oxy)phenyl)-2-hydroxy-2-phenylacetate

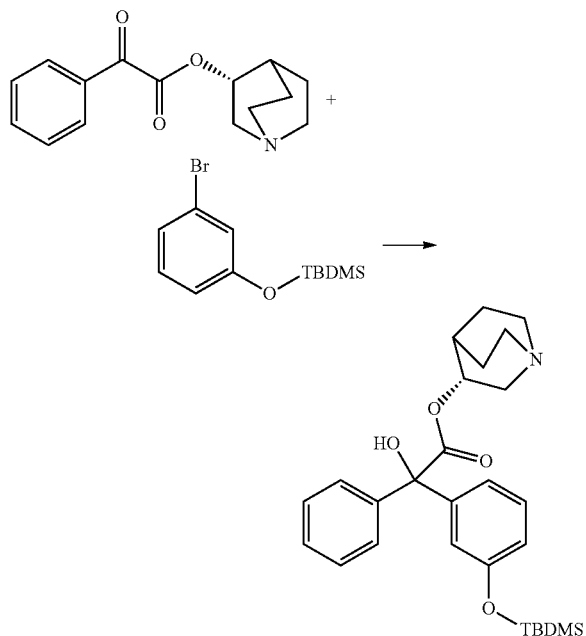

Magnesium turnings (8.58 g, 0.36 mol, 1.5 eq) and iodine (catalytic) were suspended in anhydrous THF (460 mL) under argon and a solution of (3-bromophenoxy)(tert-butyl) dimethylsilane (88.01 g, 0.306 mol, 1.2 eq) in anhydrous THF (175 mL) added drop-wise. The reaction mixture was stirred at reflux for 2 hours. The reaction mixture was cooled to room temperature and then added drop-wise via a syringe pump to a solution of (R)-quinuclidin-3-yl 2-oxo-2-phenylacetate (66.2 g, 0.26 mol, 1 eq) in anhydrous THF (660 mL) at −75° C. over 2 hours. The reaction mixture was allowed to warm to room temperature and then stirred overnight. The reaction mixture was cooled to 0° C. and quenched with saturated aqueous ammonium chloride (500 mL). The reaction mixture was extracted with ethyl acetate and the organic phase was washed with brine, dried over anhydrous magnesium sulfate and the filtrate evaporated under reduced pressure. The residue was purified by flash column chromatography (eluent—100% DCM to 20:1 DCM/methanol) to afford the title product (66.2 g, 78.5%).

$^1$H NMR (400 MHz, DMSO-$d_6$) δ 7.37-7.28 (m, 5H), 7.25-7.20 (m, 1H), 7.01-6.95 (m, 1H), 6.83-6.76 (m, 2H), 6.60 (s, 1H), 4.84-4.78 (m, 1H), 3.12-3.06 (m, 1H), 2.65-2.56 (m, 3H), 2.48-2.37 (m, 2H), 1.90-1.80 (m, 1H), 1.59-1.42 (m, 2H), 1.36-1.30 (m, 1H), 1.21-1.12 (m, 1H), 0.92-0.89 (m, 9H), 0.12 (d, J=1.0 Hz, 6H).

Step 4; (R)-Quinuclidin-3-yl 2-hydroxy-2-(3-hydroxyphenyl)-2-phenylacetate

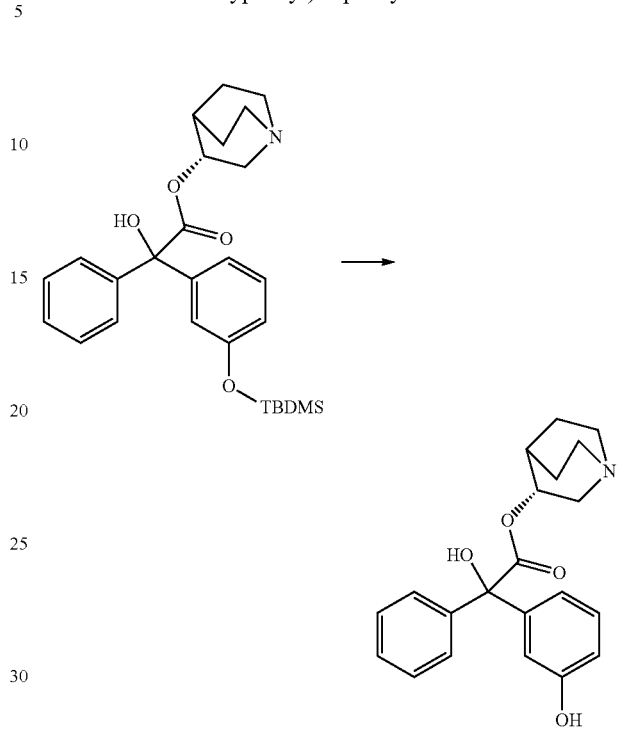

(R)-Quinuclidin-3-yl 2-(3-((tert-butyldimethylsilyl)oxy) phenyl)-2-hydroxy-2-phenylacetate (93.72 g, 200 mmol) was dissolved in THF (937 mL) and TBAF*3H2O (69.54 g, 11.5 mmol) was added and the reaction mixture was stirred at room temperature for 1 hour. THF was evaporated and the resulting crude was dissolved in ethyl acetate and washed with 0.5M hydrochloric acid (3×350 mL). The combined aqueous layers were neutralized with sodium hydrogen carbonate (to pH 8). The resulting precipitate was filtered to give 26.05 g HPLC 100% (51.9:48.1). Aqueous layer (filtrate) was washed with ethyl acetate (3×1 L) and the combined organic layers were concentrated to give desired product (38.64 g, yield 55.6, 75:25 ratio).
Method 10. Chiral-HPLC
First diastereoisomer rt 12.18 min
Second diastereoisomer rt 12.87 min Step 5; (S,R)- and (R,R)-Quinuclidin-3-yl 2-hydroxy-2-(3-hydroxyphenyl)-2-phenylacetate

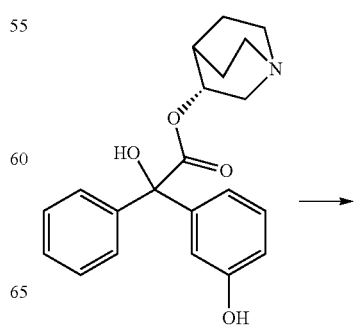

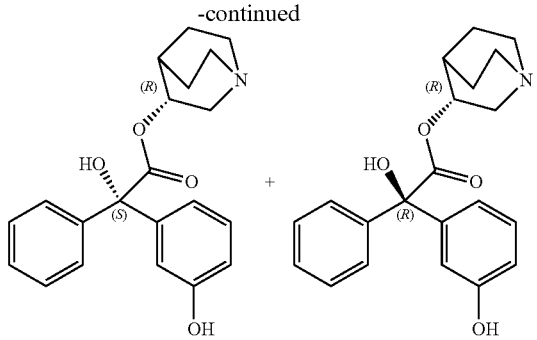

(R)-Quinuclidin-3-yl 2-(3-((tert-butyldimethylsilyl)oxy)phenyl)-2-hydroxy-2-phenylacetate (26 g, 1:1 ratio) was purified via flash column chromatography (25 g SiO₂/1 g crude, eluent: DCM; Acetone; TEA; 7:2.5:0.5) leading to i) (S)—(R)-quinuclidin-3-yl 2-hydroxy-2-(3-hydroxyphenyl)-2-phenylacetate (7.00 g, de=99.2%).

Method 9 HPLC-AB: $t_R$ 12.1 min.

ii) (R)—(R)-quinuclidin-3-yl 2-hydroxy-2-(3-hydroxyphenyl)-2-phenylacetate (1.7 g, de=95%).

Method 9 HPLC-AB: $t_R$ 12.5 min.

The absolute configuration of the unknown stereogenic center was assigned by single crystal X-ray diffraction.

Step 6; (S)-2-Hydroxy-2-(3-hydroxyphenyl)-2-phenylacetic acid

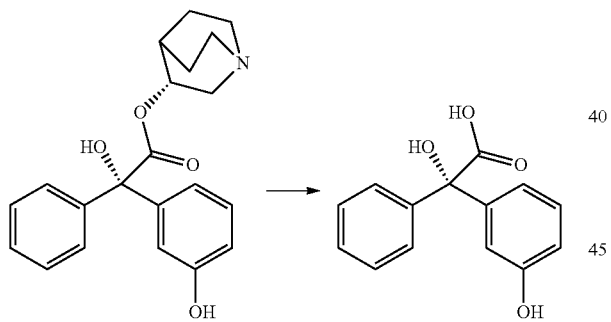

To a solution of (S)—(R)-quinuclidin-3-yl 2-hydroxy-2-(3-hydroxyphenyl)-2-phenylacetate (28.24 g, 79.91 mmol) in methanol (282.40 mL, 10 vol at 0° C., aqueous 2M sodium hydroxide (79.91 ml, 159.89 mmol) was added drop-wise. The reaction mixture was heated to reflux and stirred for 30 min. The solvent was evaporated and the reaction mixture adjusted to pH-8 with 1M hydrochloric acid and washed with ethyl acetate (2×100 mL). The aqueous layer was acidified with 1M hydrochloric acid to pH 4-5 and extracted with ethyl acetate (3×250 mL). The combined organic extracts were dried (magnesium sulfate), concentrated and then dried under vacuum for 3 day at 35° C. to give the title compound (17.58 g, 90% yield).

¹H NMR (400 MHz, DMSO-d₆) δ 13.12 (bs, 1H), 9.33 (bs, 1H), 7.41-7.25 (m, 5H), 7.14-7.07 (m, 1H), 6.84-6.78 (m, 2H), 6.69-6.64 (m, 1H).

Method 10 Chiral HPLC: $t_R$ 12.95 min

General scheme for the preparation of enantiopure intermediate 3 and 4 - scheme 4

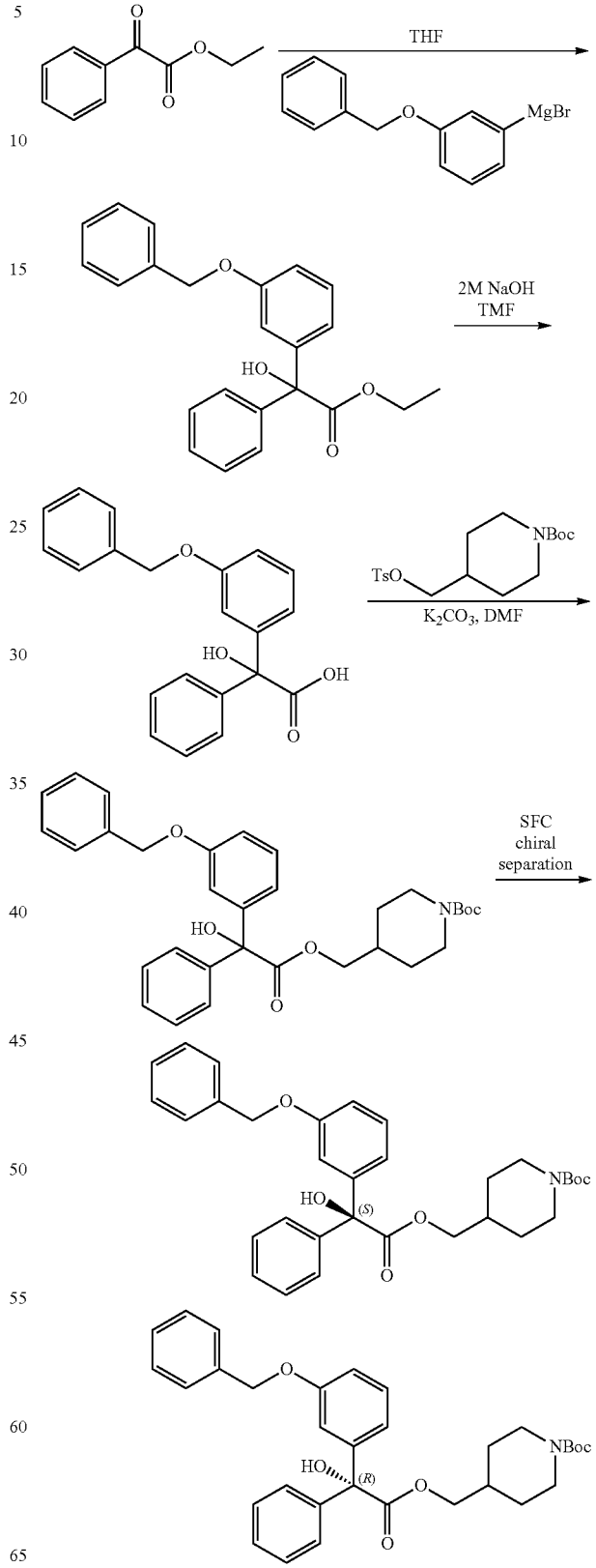

Procedure 3. Preparation of (S)-tert-butyl 4-((2-(3-(benzyloxy)phenyl)-2-hydroxy-2-phenylacetoxy)methyl)piperidine-1-carboxylate and (R)-tert-butyl 4-((2-(3-(benzyloxy)phenyl)-2-hydroxy-2-phenylacetoxy)methyl)piperidine-1-carboxylate Step 1; 2-(3-(Benzyloxy)phenyl)-2-hydroxy-2-phenylacetic acid

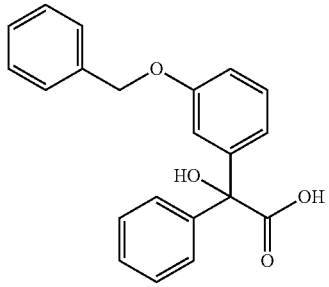 [SMILES: O=C(O)C(O)(c1ccccc1)c1cccc(OCc2ccccc2)c1]

A stirred solution of ethyl 2-(3-(benzyloxy)phenyl)-2-hydroxy-2-phenylacetate (as described in Example 1, Step 1) (20.3 g, 56.1 mmol) in THF (100 mL) was added with aqueous 2M sodium hydroxide (20 mL). The reaction mixture was stirred at room temperature for 2 hours and then the solvent removed under reduced pressure. The pH was adjusted to 1 with aqueous 1M hydrochloric acid and then extracted with ethyl acetate (×2). The combined organic extracts were washed with brine, dried over anhydrous magnesium sulfate and the filtrate evaporated under reduced pressure to afford the title product (18.4 g, 98%).

$^1$H NMR (400 MHz, DMSO-$d_6$); δ 7.45-7.23 (m, 11H), 7.02 (dd, J=2.1, 2.1 Hz, 1H), 6.98-6.93 (m, 2H), 5.05 (s, 2H), 3.34 (s, 1H).

Step 2; tert-Butyl 4-((2-(3-(benzyloxy)phenyl)-2-hydroxy-2-phenylacetoxy)methyl)piperidine-1-carboxylate

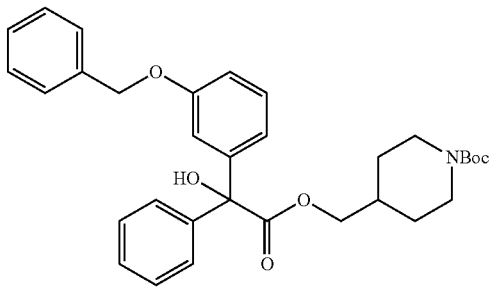 [SMILES: CC(C)(C)OC(=O)N1CCC(COC(=O)C(O)(c2ccccc2)c2cccc(OCc3ccccc3)c2)CC1]

A stirred solution of 2-(3-(benzyloxy)phenyl)-2-hydroxy-2-phenylacetic acid (10.1 g, 30.2 mmol) in DMF (100 mL) was added with potassium carbonate (5.0 g, 36.2 mmol). After 10 minutes tert-butyl 4-(tosyloxymethyl)piperidine-1-carboxylate (as described in Example 1, Step 5) (11.1 g, 30.2 mmol) was added and the resulting mixture heated at 80° C. for 18 hours. The reaction mixture was diluted with ethyl acetate and washed with water and brine (×2). The organic phase was dried over anhydrous magnesium sulfate and the filtrate was evaporated under reduced pressure. The residue was purified by flash column chromatography (eluent—100% iso-hexane to 4:1 iso-hexane/ethyl acetate) to afford the title compound (9.51 g, 59%).

$^1$H NMR (400 MHz, CDCl$_3$); δ 7.42-7.24 (m, 11H), 7.08 (dd, J=2.1, 2.1 Hz, 1H), 6.99 (d, J=7.8 Hz, 1H), 6.93 (dd, J=2.4, 8.4 Hz, 1H), 5.02 (s, 2H), 4.21 (s, 1H), 4.12-4.03 (m, 4H), 2.63-2.57 (m, 2H), 1.79-1.69 (m, 1H), 1.50-1.40 (m, 11H), 1.09-0.89 (m, 2H).

Step 3; (S)-tert-Butyl 4-((2-(3-(benzyloxy)phenyl)-2-hydroxy-2-phenylacetoxy)methyl)piperidine-1-carboxylate and (R)-tert-butyl 4-((2-(3-(benzyloxy)phenyl)-2-hydroxy-2-phenylacetoxy)methyl)piperidine-1-carboxylate

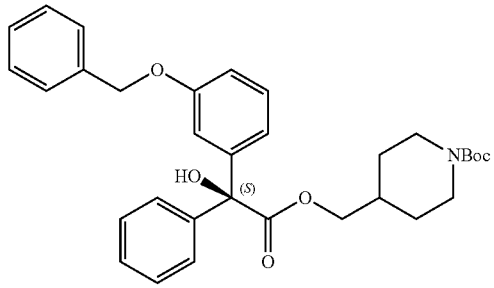

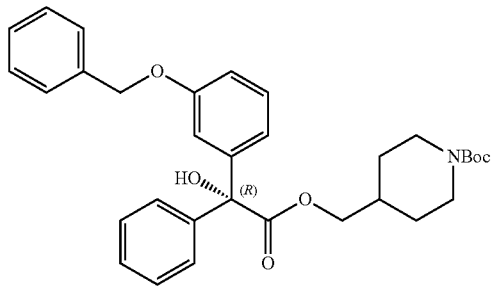

tert-Butyl 4-((2-(3-(benzyloxy)phenyl)-2-hydroxy-2-phenylacetoxy)methyl)-piperidine-1-carboxylate was separated by chiral SFC.

SFC method:

Instrument: Waters Prep 100

Column: YMC Amylose-C

Eluant; 30/70 iso-propyl alcohol/CO$_2$ at a flow rate of 100 ml/min 120 bar and 40° C.

General scheme for the preparation of enantiopure compounds of example 4 schem 5
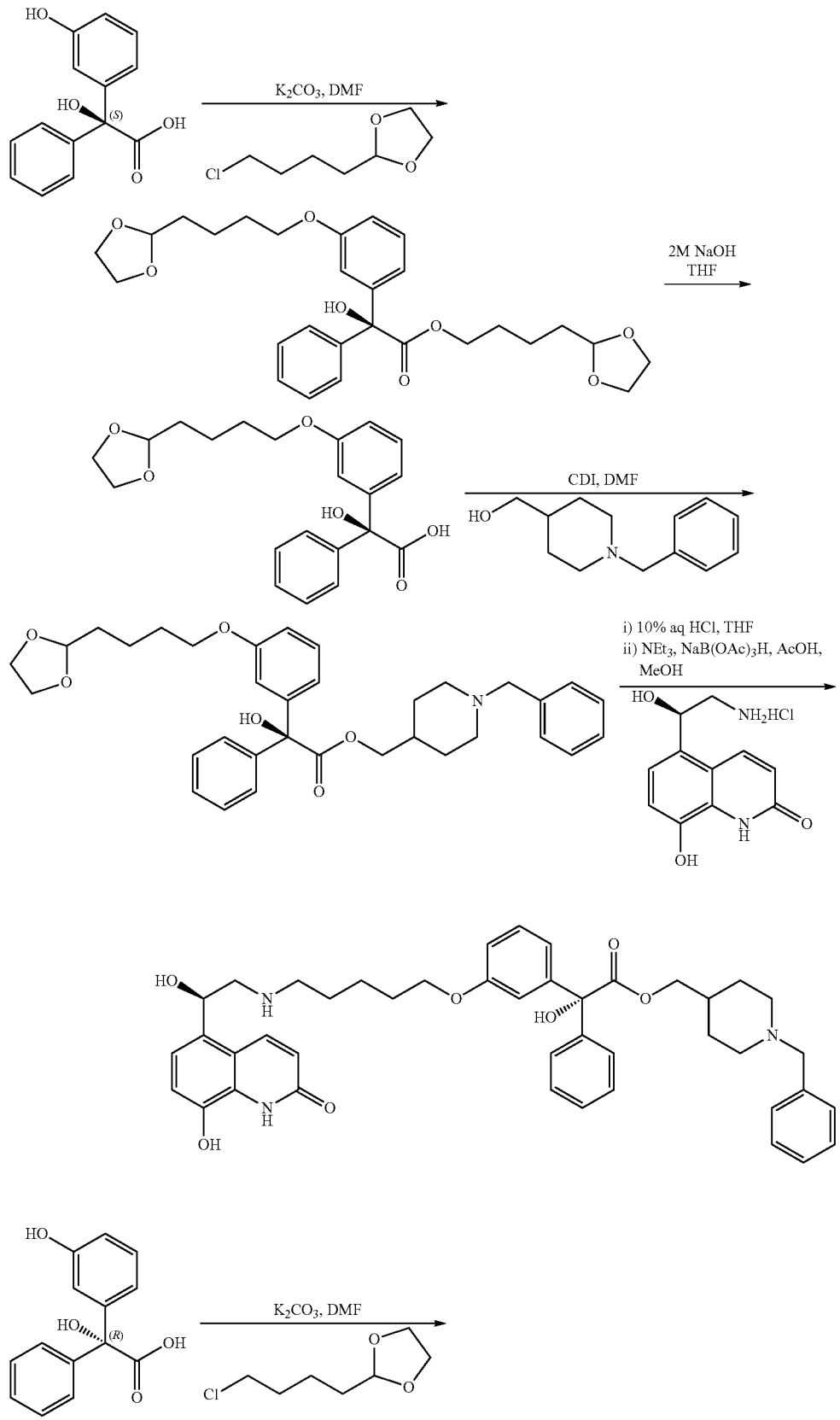

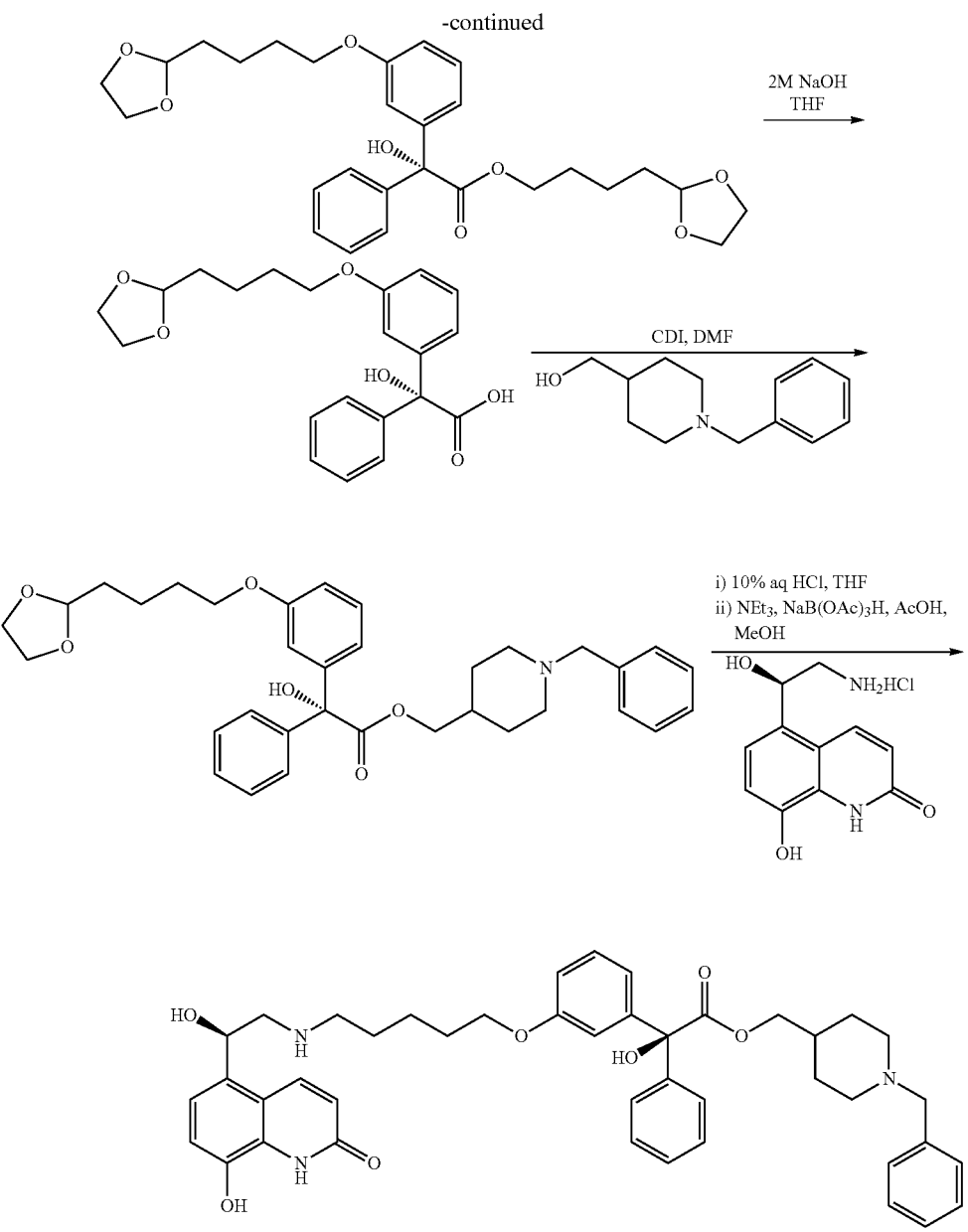
Example 4. (S)-(1-Benzylpiperidin-4-yl)methyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate (Compound 13)
Step 1; (S)-4-(1,3-Dioxolan-2-yl)butyl 2-(3-(4-(1,3-dioxolan-2-yl)butoxy)phenyl)-2-hydroxy-2-phenylacetate
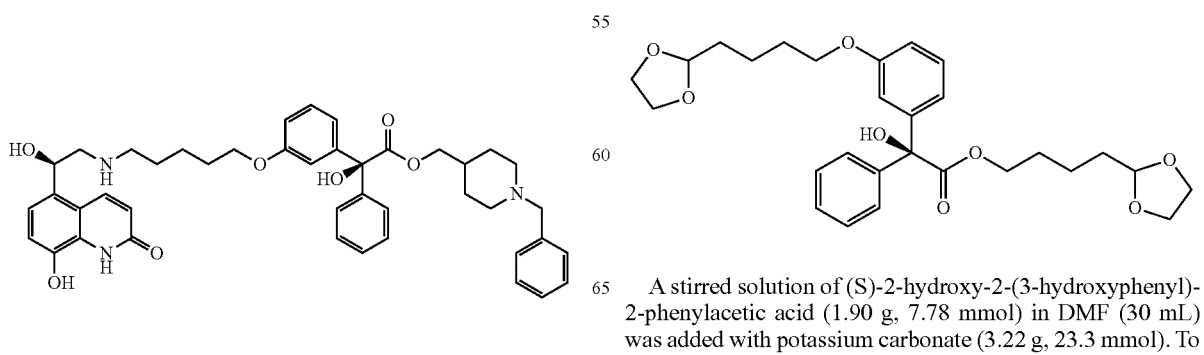
A stirred solution of (S)-2-hydroxy-2-(3-hydroxyphenyl)-2-phenylacetic acid (1.90 g, 7.78 mmol) in DMF (30 mL) was added with potassium carbonate (3.22 g, 23.3 mmol). To this mixture was added 2-(4-chlorobutyl)-1,3-dioxolane (2.89 mL, 19.45 mmol) and the reaction mixture heated at 85° C. for 72 hours. The reaction mixture was diluted with ethyl acetate and washed with water and brine (×2). The organic phase was dried over anhydrous magnesium sulfate and the filtrate was evaporated under reduced pressure. The residue was purified by flash column chromatography (eluent—100% iso-hexane to 1:1 iso-hexane/ethyl acetate) to afford the title compound (2.8 g, 72%).

$^1$H NMR (400 MHz, DMSO-d$_6$); δ 7.33 (d, J=4.1 Hz, 6H), 6.89-6.85 (m, 3H), 6.57 (s, 1H), 4.78 (dd, J=4.8, 4.8 Hz, 1H), 4.69 (dd, J=4.8, 4.8 Hz, 1H), 4.14 (dd, J=6.4, 6.4 Hz, 2H), 3.93-3.71 (m, 10H), 1.74-1.44 (m, 10H), 1.32-1.16 (m, 2H).

Step 2; (S)-2-(3-(4-(1,3-Dioxolan-2-yl)butoxy)phenyl)-2-hydroxy-2-phenylacetic acid

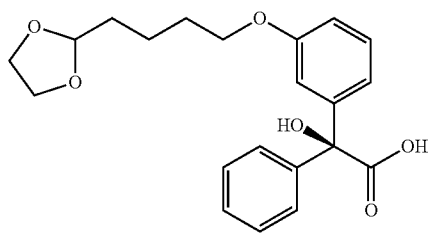 [SMILES: O=C(O)[C@](O)(c1ccccc1)c1cccc(OCCCCC2OCCO2)c1]

A stirred solution of (S)-4-(1,3-dioxolan-2-yl)butyl 2-(3-(4-(1,3-dioxolan-2-yl)butoxy)phenyl)-2-hydroxy-2-phenylacetate (2.8 g, 5.59 mmol) in THF (25 mL) was added aqueous with 2M sodium hydroxide (25 mL). The reaction mixture was stirred at room temperature for 1 hour. The organic solvent was evaporated under reduced pressure. The aqueous residue was washed with ether and the pH of the aqueous phase adjusted to 5 with aqueous 1M hydrochloric acid. The mixture was extracted with ethyl acetate and the organic phase washed with water and brine (×2). The organic phase was dried over anhydrous magnesium sulfate and the filtrate was evaporated under reduced pressure. The residue was purified by flash column chromatography (eluent—100% iso-hexane to 1:1 iso-hexane/ethyl acetate) to afford the title compound (1.46 g, 70%).

$^1$H NMR (400 MHz, DMSO-d$_6$); δ 7.45-7.25 (m, 6H), 7.01-6.96 (m, 2H), 6.91-6.88 (m, 1H), 6.40 (br s, 1H), 4.83 (dd, J=4.8, 4.8 Hz, 1H), 3.98-3.78 (m, 6H), 1.81-1.62 (m, 4H), 1.57-1.49 (m, 2H).

Step 3; (S)-(1-Benzylpiperidin-4-yl)methyl 2-(3-(4-(1,3-dioxolan-2-yl)butoxy)phenyl)-2-hydroxy-2-phenylacetate

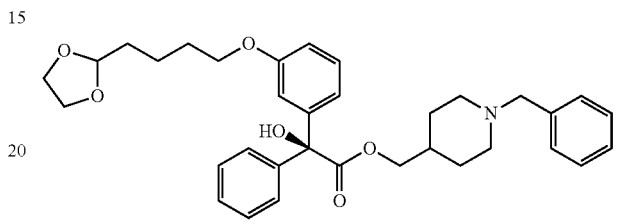

A stirred solution of (S)-2-(3-(4-(1,3-dioxolan-2-yl)butoxy)phenyl)-2-hydroxy-2-phenylacetic acid (0.119 g, 0.32 mmol) in DMF (2 mL) was added with carbonyl diimidazole (0.078 g, 0.48 mmol) and the mixture heated at 50° C. for 30 minutes. A solution of N-benzyl piperidine-4-methanol (0.098 g, 0.32 mmol) in DMF (0.5 mL) was added and the mixture heated at 50° C. for 18 hours. The reaction mixture was diluted with ethyl acetate and washed with water and brine (×2). The organic phase was dried over anhydrous magnesium sulfate and the filtrate was evaporated under reduced pressure. The residue was purified by reverse phase column chromatography to afford the title compound (0.075 g, 38%).

$^1$H NMR (400 MHz, CDCl$_3$,); δ 7.42-7.38 (m, 2H), 7.35-7.19 (m, 9H), 7.00-6.94 (m, 2H), 6.83 (ddd, J=8.2, 2.5, 0.9 Hz, 1H), 5.30 (s, 2H), 4.88-4.83 (m, 1H), 4.22 (s, 1H), 4.15-4.06 (m, 2H), 4.01-3.80 (m, 6H), 3.45 (s, 2H), 2.81 (d, J=11.3 Hz, 2H), 1.92-1.66 (m, 6H), 1.70-1.46 (m, 3H), 1.28-1.13 (m, 2H).

Step 4; (Compound 13)

The title compound (13) was prepared as described in Example 1 Step 9

| N | R$_t$ (min) | Method | NMR data (400 MHz) | Salt 2 eq unless stated |
|---|---|---|---|---|
| 113 | 2.32 | 8 | (DMSO-d6, 90° C.); δ 8.15 (d, J = 9.2 Hz, 1H), 7.48 (m, 4H), 7.35-7.31 (m, 5H), 7.24 (dd, J = 7.9, 7.9 Hz, 1H), 7.15 (d, J = 8.2 Hz, 1H), 6.99 (d, J = 8.2 Hz, 1H), 6.89-6.85 (m, 3H), 6.63-6.57 (m, 2H), 5.30 (d, J = 9.8 Hz, 1H), 4.31-4.21 (m, 3H), 4.01 (d, J = 6.4 Hz, 2H), 3.90 (dd, J = 6.2, 6.2 Hz, 2H), 3.34 (d, J = 11.3 Hz, 2H), 3.10-2.97 (m, 5H), 2.90 (d, J = 12.4 Hz, 2H), 1.85 (m, 1H), 1.71-1.65 (m, 5H), 1.47-1.30 (m, 4H). | TFA |

The following compounds were prepared as described in Example 4 with the relevant (R) or (S) stereoisomer of 2-hydroxy-2-(3-hydroxyphenyl)-2-phenylacetic acid used in Step 1 and the required commercially available amine replacing N-benzyl piperidine-4-methanol in Step 3.
| Compound number | Relevant stereoisomer | Amine | Structure |
| --- | --- | --- | --- |
| 14 | 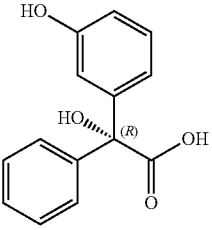 | 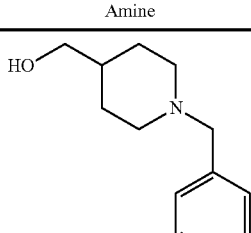 | 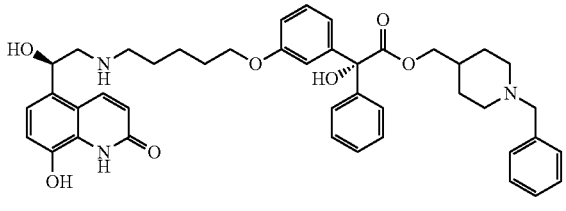 |
| 15 | 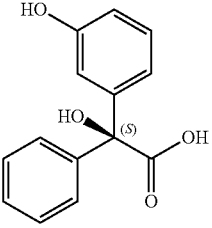 | 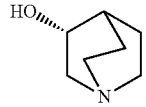 | 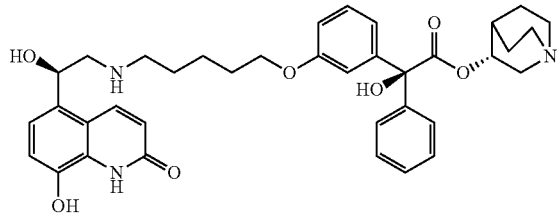 [SMILES: O=C(O[C@H]1CN2CCC1CC2)[C@](O)(c1ccccc1)c1cccc(OCCCCCNC[C@H](O)c2ccc(O)c3[nH]c(=O)ccc23)c1] |
| 16 | 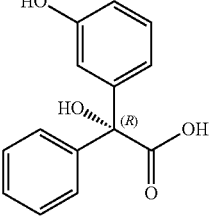 | 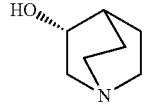 | 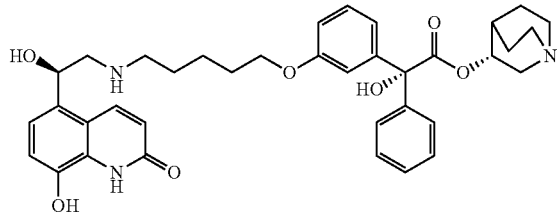 [SMILES: O=C(O[C@H]1CN2CCC1CC2)[C@@](O)(c1ccccc1)c1cccc(OCCCCCNC[C@H](O)c2ccc(O)c3[nH]c(=O)ccc23)c1] |
| 17 | 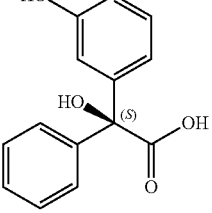 | 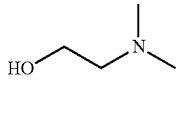 | 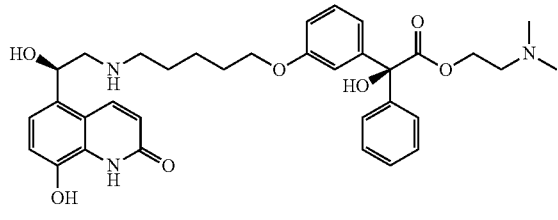 [SMILES: CN(C)CCOC(=O)[C@](O)(c1ccccc1)c1cccc(OCCCCCNC[C@H](O)c2ccc(O)c3[nH]c(=O)ccc23)c1] |
| 18 | 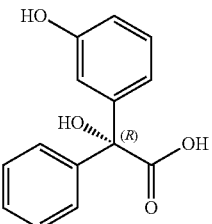 | 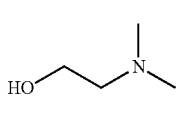 | 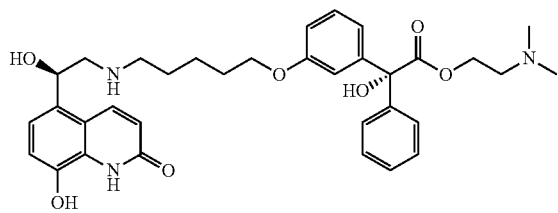 [SMILES: CN(C)CCOC(=O)[C@@](O)(c1ccccc1)c1cccc(OCCCCCNC[C@H](O)c2ccc(O)c3[nH]c(=O)ccc23)c1] |
| 19 | 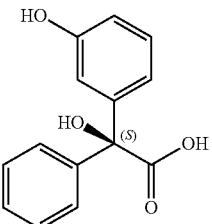 |  | 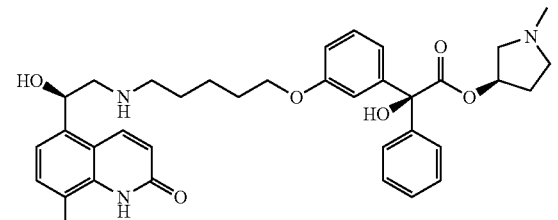 |

-continued

| Compound number | Relevant stereoisomer | Amine | Structure |
|---|---|---|---|
| 20 | 3-hydroxyphenyl phenyl (R)-hydroxyacetic acid | (R)-1-methyl-3-hydroxypyrrolidine | 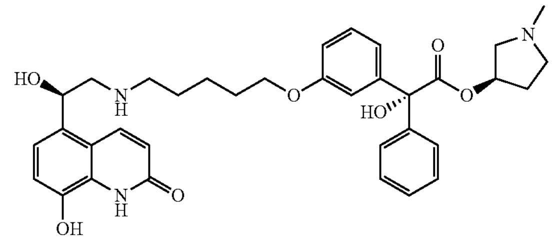 [SMILES: CN1CC[C@@H](OC(=O)[C@@](O)(c2ccccc2)c2cccc(OCCCCCNC[C@H](O)c3ccc(O)c4[nH]c(=O)ccc34)c2)C1] |
| 21 | 3-hydroxyphenyl phenyl (S)-hydroxyacetic acid | 1-methyl-4-hydroxypiperidine | 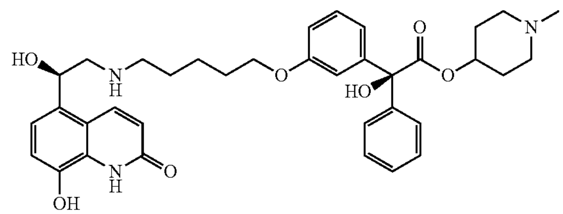 [SMILES: CN1CCC(OC(=O)[C@](O)(c2ccccc2)c2cccc(OCCCCCNC[C@H](O)c3ccc(O)c4[nH]c(=O)ccc34)c2)CC1] |
| 22 | 3-hydroxyphenyl phenyl (R)-hydroxyacetic acid | 1-methyl-4-hydroxypiperidine | 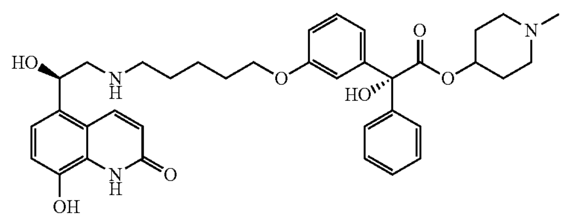 [SMILES: CN1CCC(OC(=O)[C@@](O)(c2ccccc2)c2cccc(OCCCCCNC[C@H](O)c3ccc(O)c4[nH]c(=O)ccc34)c2)CC1] |
| 23 | 3-hydroxyphenyl phenyl (S)-hydroxyacetic acid | (1-methylpiperidin-4-yl)methanol | 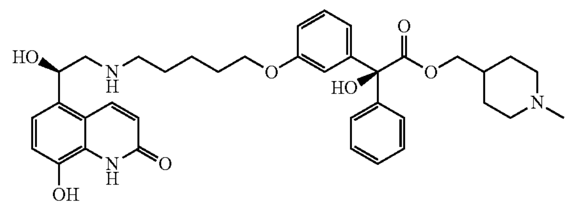 [SMILES: CN1CCC(COC(=O)[C@](O)(c2ccccc2)c2cccc(OCCCCCNC[C@H](O)c3ccc(O)c4[nH]c(=O)ccc34)c2)CC1] |
| 24 | 3-hydroxyphenyl phenyl (R)-hydroxyacetic acid | (1-methylpiperidin-4-yl)methanol | 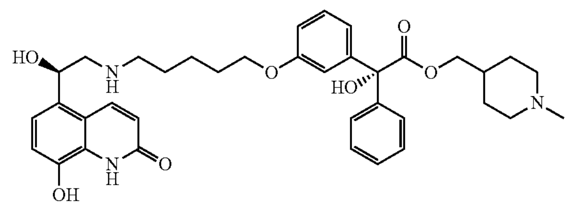 [SMILES: CN1CCC(COC(=O)[C@@](O)(c2ccccc2)c2cccc(OCCCCCNC[C@H](O)c3ccc(O)c4[nH]c(=O)ccc34)c2)CC1] |
| 25 | 3-hydroxyphenyl phenyl (S)-hydroxyacetic acid | (S)-1-methyl-3-hydroxypiperidine | 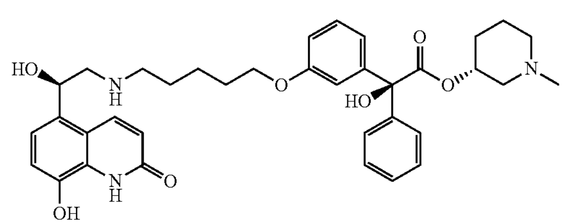 [SMILES: CN1CCC[C@@H](OC(=O)[C@](O)(c2ccccc2)c2cccc(OCCCCCNC[C@H](O)c3ccc(O)c4[nH]c(=O)ccc34)c2)C1] |

| Compound number | Relevant stereoisomer | Amine | Structure |
|---|---|---|---|
| 26 | (S)-2-hydroxy-2-(3-hydroxyphenyl)-2-phenylacetic acid | 1-methylazetidin-3-ol | (structure shown) |

| N | Rt (min) | Method | NMR data (400 MHz) | Salt (2 eq unless stated) |
|---|---|---|---|---|
| 14 | 7.19 | 7 | (DMSO-d$_6$); δ 10.54 (d, J = 15.7 Hz, 2H), 9.44 (s, 1H), 8.61-8.60 (m, 2H), 8.20 (d, J = 11.6 Hz, 1H), 7.53 (s, 5H), 7.40-7.36 (m, 6H), 7.20 (d, J = 8.3 Hz, 1H), 7.04 (d, J = 8.1 Hz, 1H), 6.95-6.90 (m, 3H), 6.69-6.62 (m, 2H), 6.21 (s, 1H), 5.37-5.34 (m, 1H), 4.37-4.26 (m, 3H), 4.06 (d, J = 6.3 Hz, 2H), 3.95 (dd, J = 6.2, 6.2 Hz, 2H), 3.38 (d, J = 10.9 Hz, 2H), 3.16-2.90 (m, 5H), 1.93-1.88 (m, 1H), 1.83-1.71 (m, 6H), 1.53-1.34 (m, 4H) | TFA |
| 15 | 6.94 | 7 | (DMSO-d$_6$); δ 10.54 (d, J = 15.9 Hz, 2H), 9.66 (s, 1H), 8.60-8.60 (m, 2H), 8.21 (d, J = 10.4 Hz, 1H), 7.41 (d, J = 4.5 Hz, 4H), 7.40-7.35 (m, 1H), 7.31 (dd, J = 8.0, 8.0 Hz, 1H), 7.20 (d, J = 8.1 Hz, 1H), 7.05-6.91 (m, 4H), 6.81 (s, 1H), 6.64 (dd, J = 1.9, 10.0 Hz, 1H), 6.20 (d, J = 2.0 Hz, 1H), 5.35 (d, J = 9.6 Hz, 1H), 5.21-5.19 (m, 1H), 3.97 (dd, J = 6.2, 6.2 Hz, 2H), 3.78-3.70 (m, 1H), 3.28-2.98 (m, 9H), 2.27 (d, J = 2.5 Hz, 1H), 1.95-1.87 (m, 2H), 1.79-1.61 (m, 6H), 1.53-1.44 (m, 4H) | TFA |
| 16 | 6.95 | 7 | (DMSO-d$_6$); δ 10.54 (d, J = 12.9 Hz, 2H), 9.74-9.71 (m, 1H), 8.61-8.60 (m, 2H), 8.21 (d, J = 9.0 Hz, 1H), 7.44-7.30 (m, 6H), 7.20 (d, J = 8.1 Hz, 1H), 7.02 (dd, J = 8.1, 14.9 Hz, 2H), 6.95-6.91 (m, 2H), 6.81 (s, 1H), 6.64 (dd, J = 1.9, 10.0 Hz, 1H), 6.22 (s, 1H), 5.35 (d, J = 9.6 Hz, 1H), 5.23-5.18 (m, 1H), 3.97 (t, J = 6.7 Hz, 2H), 3.74 (td, J = 5.2, 17.9 Hz, 1H), 3.27-2.98 (m, 9H), 2.27 (d, J = 3.0 Hz, 1H), 1.96-1.86 (m, 2H), 1.79-1.61 (m, 6H), 1.53-1.43 (m, 2H) | TFA |
| 17 | 2.14 | 8 | (DMSO-d$_6$); δ 10.50 (d, J = 18.1 Hz, 2H), 9.59 (s, 1H), 8.56-8.56 (m, 2H), 8.15 (d, J = 10.7 Hz, 1H), 7.35 (m, 6H), 7.15 (d, J = 8.3 Hz, 1H), 6.98 (d, J = 8.2 Hz, 1H), 6.94 (d, J = 8.2 Hz, 1H), 6.89-6.87 (m, 2H), 6.68 (s, 1H), 6.59 (dd, J = 2.1, 9.9 Hz, 1H), 6.17 (d, J = 3.4 Hz, 1H), 5.31-5.28 (m, 1H), 4.47 (dd, J = 5.0, 5.0 Hz, 2H), 3.97-3.88 (m, 2H), 3.14-2.98 (m, 6H), 2.69 (s, 6H), 1.74-1.64 (m, 4H), 1.48-1.40 (m, 2H). | TFA |
| 18 | 6.89 | 7 | (DMSO-d$_6$); δ 10.49 (d, J = 14.1 Hz, 2H), 9.62 (s, 1H), 8.57-8.56 (m, 2H), 8.15 (d, J = 9.9 Hz, 1H), 7.35 (d, J = 4.3 Hz, 4H), 7.33-7.23 (m, 2H), 7.15 (d, J = 8.2 Hz, 1H), 6.98 (d, J = 8.2 Hz, 1H), 6.93 (d, J = 8.0 Hz, 1H), 6.90-6.87 (m, 2H), 6.67 (s, 1H), 6.59 (dd, J = 1.8, 9.9 Hz, 1H), 6.17-6.16 (m, 1H), 5.30 (d, J = 9.4 Hz, 1H), 4.47 (dd, J = 5.1, 5.1 Hz, 2H), 3.91 (dd, J = 6.3, 6.3 Hz, 2H), 3.40 (s, 2H), 3.14-3.04 (m, 2H), 3.01-2.95 (m, 2H), 2.69 (s, 6H), 1.75-1.64 (m, 4H), 1.48-1.40 (m, 2H). | TFA |
| 19 | 6.90 | 7 | (DMSO-d$_6$); δ 10.54 (d, J = 13.9 Hz, 2H), 10.17 (s, 1H), 8.62-8.60 (m, 2H), 8.20 (d, J = 11.5 Hz, 1H), 7.41-7.28 (m, 6H), 7.20 (d, J = 10.2 Hz, 1H), 7.05-6.97 (m, 2H), 6.93 (m, 2H), 6.64 (d, J = 8.9 Hz, 2H), 6.21 (s, 1H), 5.50 (d, J = 16.6 Hz, 1H), 5.36 (d, J = 8.9 Hz, 1H), 3.97 (dd, J = 6.2, 6.2 Hz, 2H), 3.61 (m, 4H), 3.18-3.01 (m, 4H), 2.95-2.72 (m, 3H), 2.5-2.3 (m, 1H), 2.1-1.9 (m, 1H), 1.81-1.69 (m, 4H), 1.53-1.44 (m, 2H). | TFA |
| 20 | 6.90 | 7 | (DMSO-d$_6$); δ 10.49 (d, J = 13.2 Hz, 2H), 10.15 (s, 1H), 8.57 (s, 2H), 8.15 (d, J = 9.9 Hz, 1H), 7.35 (d, J = 3.3 Hz, 4H), 7.33-7.23 (m, 2H), 7.15 (d, J = 8.2 Hz, 1H), 7.00-6.92 (m, 2H), 6.88 (d, J = 7.5 Hz, 2H), 6.59 (dd, J = 1.8, 9.8 Hz, 2H), 6.17-6.17 (m, 1H), 5.44 (d, J = 22.5 Hz, 1H), 5.31 (d, J = 9.2 Hz, 1H), 3.92 (t, J = 5.4 Hz, 2H), 3.59 (m, 2H), 3.41-3.40 (m, 0.5H), 3.13-2.97 (m, 5H), 2.77 (d, J = 63.6 Hz, 4H), 2.25 (m, 0.5H), 2.09-2.08 (m, 0.5H), 1.91 (m, 0.5H), 1.74-1.64 (m, 4H), 1.48-1.40 (m, 2H). | TFA |
| 21 | 6.89 | 7 | (DMSO-d$_6$, 90° C.); δ 8.18 (d, J = 9.9 Hz, 1H), 7.42-7.24 (m, 6H), 7.15 (d, J = 8.2 Hz, 1H), 7.03-6.94 (m, 3H), 6.89 (dd, J = 2.2, 8.1 Hz, 1H), 6.56 (d, J = 9.8 Hz, 1H), 5.35 (dd, J = 4.4, 8.4 Hz, 1H), 5.09 (s, 1H), 3.95 (dd, J = 6.3, 6.3 Hz, 2H), 3.19-3.00 (m, 8H), 2.71 (s, 3H), 2.11-2.06 (m, 2H), 1.78-1.70 (m, 6H), 1.53-1.46 (m, 2H). | TFA |
| 22 | 6.90 | 7 | (DMSO-d$_6$, 90° C.); δ 8.19 (d, J = 9.9 Hz, 1H), 7.42-7.22 (m, 6H), 7.15 (d, J = 8.2 Hz, 1H), 7.02 (d, J = 8.2 Hz, 1H), 6.96 (d, J = 8.0 Hz, 2H), 6.90-6.85 (m, 1H), 6.55 (d, J = 9.9 Hz, 1H), 5.36 (dd, J = 4.5, 8.3 Hz, 1H), 5.07 (d, J = 1.9 Hz, 1H), 3.95 (dd, J = 6.3, 6.3 Hz, 2H), 3.19-3.00 (m, 8H), 2.70 (s, 3H), 2.05 (d, J = 8.9 Hz, 2H), 1.86-1.84 (m, 2H), 1.79-1.67 (m, 4H), 1.53-1.45 (m, 2H). | TFA |
| 23 | 6.96 | 7 | (DMSO-d$_6$, 90° C.); δ 8.19 (d, J = 9.9 Hz, 1H), 7.40-7.22 (m, 6H), 7.15 (d, J = 8.2 Hz, 1H), 7.02 (d, J = 8.0 Hz, 1H), 6.96-6.94 (m, 2H), 6.88-6.86 (m, 1H), 6.56 (d, J = 9.9 Hz, 1H), 6.26-6.26 (m, 1H), 5.35 (d, J = 4.5, 8.4 Hz, 1H), 4.09 (d, J = 6.5 Hz, 2H), 3.96 (dd, J = 6.4, 6.4 Hz, 2H), 3.31 (d, J = 11.0 Hz, 2H), 3.16-2.96 (m, 6H), 2.73 (s, 3H), 1.92-1.85 (m, 1H), 1.78-1.71 (m, 6H), 1.54-1.42 (m, 4H). | TFA |
| 24 | 6.97 | 7 | (DMSO-d$_6$); δ 8.30 (s, 2H), 8.19 (d, J = 9.6 Hz, 1H), 7.33-7.31 (m, 6H), 7.11 (d, J = 8.3 Hz, 1H), 6.96 (d, J = 8.2 Hz, 1H), 6.90-6.85 (m, 3H), 6.53 (d, J = 9.8 Hz, 1H), | Formate |

| N | Rt (min) | Method | NMR data (400 MHz) | Salt (2 eq unless stated) |
|---|---|---|---|---|
| | | | 5.20 (dd, J = 4.3, 8.4 Hz, 1H), 3.99 (d, J = 6.0 Hz, 2H), 3.90 (dd, J = 6.3, 6.3 Hz, 2H), 2.90-2.68 (m, 5H), 2.13 (s, 3H), 1.84-1.77 (m, 2H), 1.74-1.64 (m, 2H), 1.61-1.39 (m, 8H), 1.18-1.09 (m, 2H). | |
| 25 | 6.95 | 7 | (DMSO-$d_6$, 90° C.); δ 8.18 (d, J = 10.5 Hz, 1H), 7.43-7.31 (m, 5H), 7.25 (dd, J = 8.0, 8.0 Hz, 1H), 7.15 (d, J = 8.2 Hz, 1H), 7.03-6.94 (m, 3H), 6.87 (dd, J = 2.4, 8.3 Hz, 1H), 6.57 (d, J = 9.8 Hz, 1H), 5.33 (dd, J = 4.5, 8.5 Hz, 1H), 5.16 (m, 1H), 4.00-3.93 (m, 2H), 3.17-3.01 (m, 10H), 2.74 (s, 3H), 1.78-1.69 (m, 6H), 1.53-1.45 (m, 2H). | TFA |
| 26 | 6.87 | 7 | (DMSO-$d_6$, 90° C.); δ 8.19 (d, J = 9.9 Hz, 1H), 7.42 (dd, J = 1.5, 8.3 Hz, 2H), 7.38-7.24 (m, 4H), 7.15 (d, J = 8.2 Hz, 1H), 7.03-6.95 (m, 3H), 6.88 (dd, J = 2.3, 8.0 Hz, 1H), 6.56 (d, J = 9.9 Hz, 1H), 5.37-5.31 (m, 2H), 4.43-4.37 (m, 2H), 3.99-3.88 (m, 4H), 3.22-3.11 (m, 2H), 3.07-3.01 (m, 2H), 2.80 (s, 3H), 1.78-1.69 (m, 4H), 1.53-1.44 (m, 2H). | TFA |

The following compounds were prepared as described in Example 4 with the relevant (R) or (S) stereoisomer of 2-hydroxy-2-(3-hydroxyphenyl)-2-phenylacetic acid used in Step 1 and the appropriate alkylating agent replacing 2-(4-chlorobutyl)-1,3-dioxolane in Step 1.

| N | Relevant stereoisomer | Alkylating Agent | Structure |
|---|---|---|---|
| 27 | | | 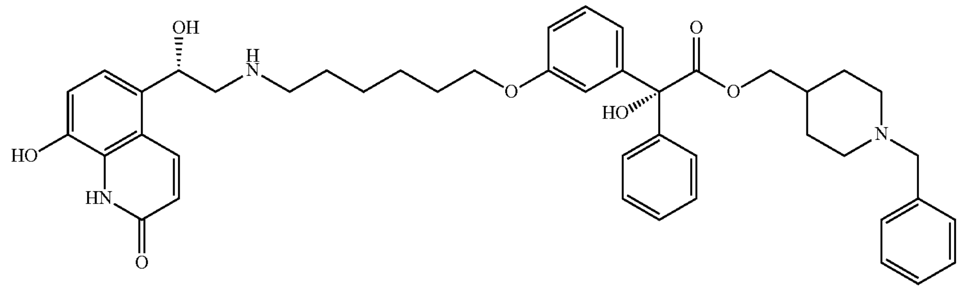 [SMILES: O=C(OCC1CCN(Cc2ccccc2)CC1)[C@@](O)(c1ccccc1)c1cccc(OCCCCCCNC[C@@H](O)c2ccc(O)c3[nH]c(=O)ccc23)c1] |
| 28 | | | 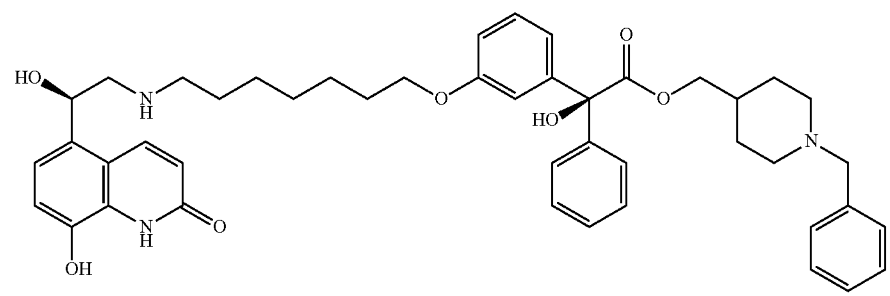 [SMILES: O=C(OCC1CCN(Cc2ccccc2)CC1)[C@](O)(c1ccccc1)c1cccc(OCCCCCCCNC[C@H](O)c2ccc(O)c3[nH]c(=O)ccc23)c1] |
| 29 | | | 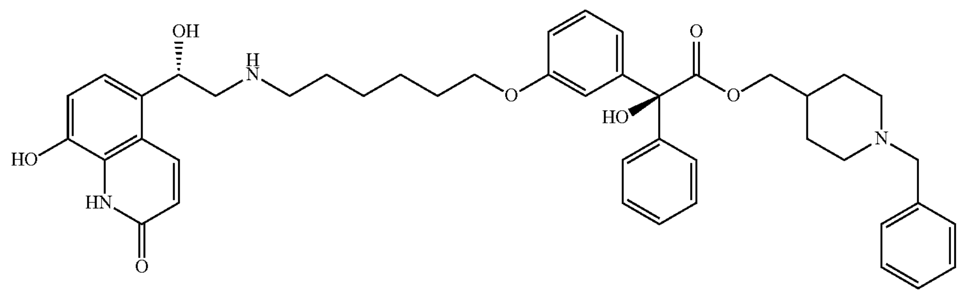 [SMILES: O=C(OCC1CCN(Cc2ccccc2)CC1)[C@](O)(c1ccccc1)c1cccc(OCCCCCCNC[C@@H](O)c2ccc(O)c3[nH]c(=O)ccc23)c1] |

| N | Relevant stereoisomer | Alkylating Agent | Structure |
|---|---|---|---|
| 30 | (structure) | (structure) | (structure) |

| N | Rt (min) | Method | NMR data (400 MHz) | Salt (2 eq unless stated) |
|---|---|---|---|---|
| 27 | 715 | 7 | (DMSO-d₆); δ 10.54 (s, 1H), 10.49 (s, 1H), 9.56 (s, 1 H), 8.61-8.61 (m, 2H), 8.16 (d, J = 9.9 Hz, 1H), 7.47 (s, 5H), 7.35-7.31 (m, 6H), 7.15 (d, J = 8.0 Hz, 1H), 7.03-6.97 (m, 1H), 6.90-6.83 (m, 3H), 6.62 (s, 1H), 6.58 (d, J = 9.9 Hz, 1H), 6.18-6.18 (m, 1H), 5.31 (d, J = 9.2 Hz, 1H), 4.25-4.21 (m, 2H), 4.01 (d, J = 6.4 Hz, 2H), 3.90 (dd, J = 6.3, 6.3 Hz, 2H), 3.08 (m, 4H), 2.97-2.88 (m, 4H), 1.75-1.61 (m, 7H), 1.36 (dd, J = 11.5, 11.5 Hz, 6H). | TFA |
| 28 | 7.34 | 77 | (DMSO-d₆); δ 10.50 (m, 2H), 9.51 (s, 1H), 8.58 (s, 2H), 8.16 (d, J = 9.9 Hz, 1H), 7.47 (s, 5H), 7.33 (s, 5H), 7.23 (dd, J = 8.0, 8.0 Hz, 1H), 7.15 (d, J = 8.2 Hz, 1H), 6.99 (d, J = 8.2 Hz, 1H), 6.90-6.85 (m, 3H), 6.64-6.57 (m, 2H), 6.18 (d, J = 2.5 Hz, 1H), 5.31 (d, J = 9.0 Hz, 1H), 4.27-4.23 (m, 2H), 4.01 (d, J = 6.3 Hz, 2H), 3.90 (dd, J = 6.4, 6.4 Hz, 2H), 2.98-2.98 (m, 10H), 1.68-1.64 (m, 5H), 1.38-1.31 (m, 8H) | TFA |
| 29 | 7.44 | 77 | (DMSO-d₆); δ 10.51 (s, 2H), 9.56 (s, 1H), 8.61 (s, 2H), 8.16 (d, J = 9.9 Hz, 1H), 7.48 (s, 5H), 7.33-722 (m, 6H), 7.15 (d, J = 8.2 Hz, 1H), 6.99 (d, J = 8.2 Hz, 1H), 6.90-6.83 (m, 3H), 6.59 (t, J = 11.1 Hz, 2H), 6.18 (s, 1H), 5.31 (d, J = 8.8 Hz, 1H), 4.28-4.21 (m, 2H), 4.01 (d, J = 6.3 Hz, 2H), 3.90 (dd, J = 6.1, 6.1 Hz, 2H), 3.14-2.85 (m, 7H), 1.75-1.62 (m, 7H), 1.40-1.34 (m, 7H). | TFA |
| 30 | 7.43 | 77 | (DMSO-d₆); δ 10.53 (d, J = 21.3 Hz, 2H), 9.79 (s, 1H), 8.76 (s, 1H), 8.61 (s, 1H), 8.19 (d, J = 12.0 Hz, 1H), 7.49-7.46 (m, 5H), 7.35-7.31 (m, 6H), 7.15 (d, J = 8.3 Hz, 1H), 7.00 (d, J = 8.2 Hz, 1H), 6.87 (d, J = 8.4 Hz, 3H), 6.62 (s, 1H), 6.57 (d, J = 9.8 Hz, 1H), 6.19 (s, 1H), 5.34 (d, J = 8.0 Hz, 1H), 4.29-4.20 (m, 2H), 4.00 (d, J = 6.4 Hz, 2H), 3.89 (dd, J = 6.4, 6.4 Hz, 2H), 3.11-2.83 (m, 7H), 1.83-1.64 (m, 8H), 1.43-1.23 (m, 10H). | TFA |

Procedure 4

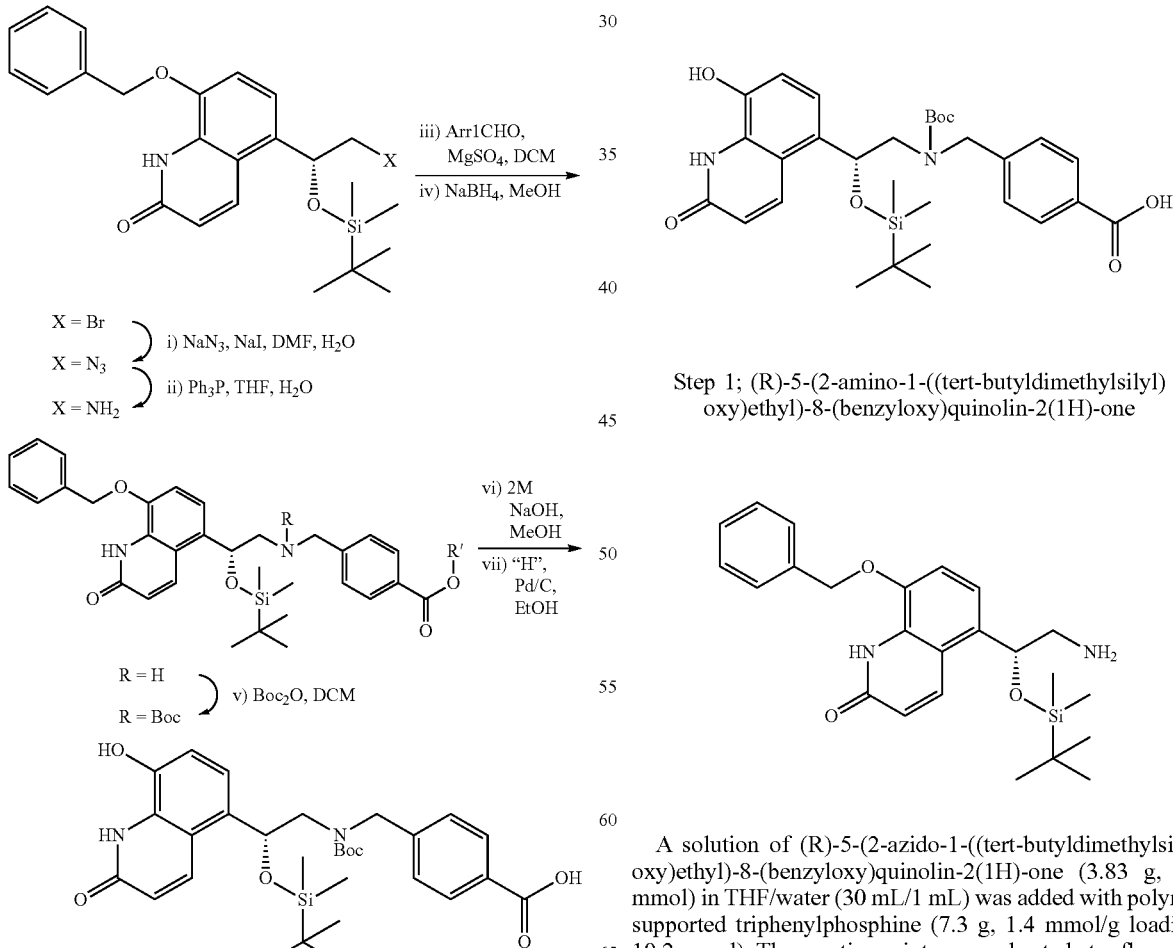

Preparation of (R)-4-(((tert-butoxycarbonyl)(2-((tert-butyldimethylsilyl)oxy)-2-(8-hydroxy-2-oxo-1,2-dihydroquinolin-5-yl)ethyl)amino)methyl)benzoic acid Step 1; (R)-5-(2-amino-1-((tert-butyldimethylsilyl)oxy)ethyl)-8-(benzyloxy)quinolin-2(1H)-one A solution of (R)-5-(2-azido-1-((tert-butyldimethylsilyl)oxy)ethyl)-8-(benzyloxy)quinolin-2(1H)-one (3.83 g, 8.5 mmol) in THF/water (30 mL/1 mL) was added with polymer supported triphenylphosphine (7.3 g, 1.4 mmol/g loading, 10.2 mmol). The reaction mixture was heated at reflux with no stirring for 18 hours. The suspension was filtered, the filter cake was washed with ethyl acetate and the filtrate was evaporated under reduced pressure to afford the title compound. The material was used directly in the next step with no purification.

Step 2; (R)-Methyl 4-(((2-(8-(benzyloxy)-2-oxo-1,2-dihydroquinolin-5-yl)-2-((tert-butyldimethylsilyl)oxy)ethyl)amino)methyl)benzoate

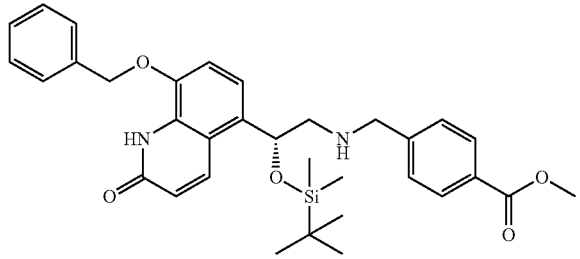 [SMILES: COC(=O)c1ccc(CNC[C@H](O[Si](C)(C)C(C)(C)C)c2ccc(OCc3ccccc3)c3[nH]c(=O)ccc23)cc1]

A stirred mixture of (R)-5-(2-amino-1-((tert-butyldimethylsilyl)oxy)ethyl)-8-(benzyloxy)quinolin-2(1H)-one (2.9 g, 6.83 mmol) and methyl 4-formylbenzoate (1.23 g, 7.49 mmol) in DCM (30 mL) was added with anhydrous magnesium sulfate and the mixture stirred at room temperature for 18 hours. The suspension was filtered through a plug of anhydrous magnesium sulfate, the filter cake was washed with further DCM and the filtrate was evaporated under reduced pressure. The residue was dissolved in methanol (30 mL) and the mixture cooled to 0° C. Sodium borohydride (0.517 g, 13.7 mmol) was added portion wise and the reaction mixture stirred at 0° C. for 30 minutes. The coolant was removed and the mixture stirred at room temperature for a further 2 hours. The mixture was quenched with 10% aqueous potassium carbonate and extracted with DCM (×2). The combined DCM extracts were washed with brine, dried over anhydrous magnesium sulfate and the filtrate was evaporated under reduced pressure. The residue was purified by flash column chromatography (eluent—100% DCM to 25:1 DCM/methanol) to afford the title compound (3.26 g, 83%).

$^1$H NMR (400 MHz, DMSO-d$_6$) δ 10.51 (s, 1H), 8.20 (d, J=9.9 Hz, 1H), 7.81 (d, J=8.3 Hz, 2H), 7.52 (d, J=7.2 Hz, 2H), 7.36-7.31 (m, 4H), 7.29-7.25 (m, 1H), 7.15 (d, J=8.3 Hz, 1H), 7.07 (d, J=8.4 Hz, 1H), 6.46 (d, J=9.9 Hz, 1H), 5.23 (s, 2H), 5.13 (dd, J=4.7, 7.2 Hz, 1H), 3.80-3.78 (m, 3H), 3.73 (s, 2H), 2.72 (dd, J=7.8, 12.0 Hz, 1H), 2.63-2.55 (m, 1H), 0.77 (s, 9H), 0.00 (s, 3H), −0.21 (s, 3H).

Step 3; (R)-Methyl 4-(((2-(8-(benzyloxy)-2-oxo-1,2-dihydroquinolin-5-yl)-2-((tert-butyldimethylsilyl)oxy)ethyl)(tert-butoxycarbonyl)amino)methyl)benzoate

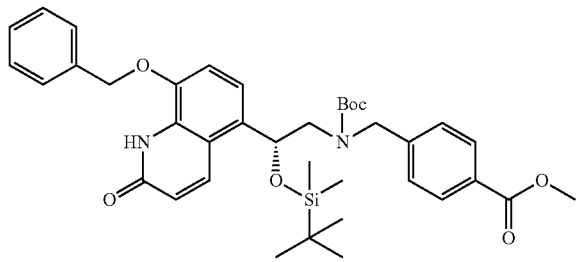 [SMILES: COC(=O)c1ccc(CN(C[C@H](O[Si](C)(C)C(C)(C)C)c2ccc(OCc3ccccc3)c3[nH]c(=O)ccc23)C(=O)OC(C)(C)C)cc1]

A stirred solution of (R)-methyl 4-(((2-(8-(benzyloxy)-2-oxo-1,2-dihydroquinolin-5-yl)-2-((tert-butyldimethylsilyl)oxy)ethyl)amino)methyl)benzoate (3.25 g, 5.67 mmol) in DCM (25 mL) was added with a solution of di-tert-butyl dicarbonate (1.49 g, 6.83 mmol) in DCM (5 mL). The reaction mixture was stirred at room temperature for 18 hours. The solvent was evaporated under reduced pressure and the residue purified by flash column chromatography (eluent—100% iso-hexane to 3:2 iso-hexane/ethyl acetate) to afford the title compound (2.84 g, 75%).

LCMS (Method 11); Rt 4.33 min; M+1 673.4

Step 4; (R)-4-(((2-(8-(Benzyloxy)-2-oxo-1,2-dihydroquinolin-5-yl)-2-((tert-butyldimethylsilyl)oxy)ethyl)(tert-butoxycarbonyl)amino)methyl)benzoic acid

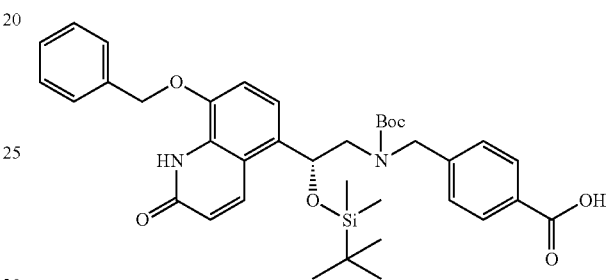

A stirred solution of (R)-methyl 4-(((2-(8-(benzyloxy)-2-oxo-1,2-dihydroquinolin-5-yl)-2-((tert-butyldimethylsilyl)oxy)ethyl)(tert-butoxycarbonyl)-amino)methyl)benzoate (2.84 g, 4.22 mmol) in methanol (10 mL) was added with aqueous 2M sodium hydroxide (10 mL). The reaction mixture was then stirred at room temperature for 18 hours. The solvent was evaporated under reduced pressure and the residue partitioned between DCM and 10% aqueous potassium hydrogen sulfate. The organic phase was removed and the aqueous phase extracted with further DCM. The combined DCM extracts were washed with brine, dried over anhydrous magnesium sulfate and the filtrate was evaporated under reduced pressure to afford the title compound (2.58 g, 93%).

LCMS (Method 11); Rt 4.05 min; M+1 659

Step 5; (R)-4-(((tert-Butoxycarbonyl)(2-((tert-butyldimethylsilyl)oxy)-2-(8-hydroxy-2-oxo-1,2-dihydroquinolin-5-yl)ethyl)amino)methyl)benzoic acid

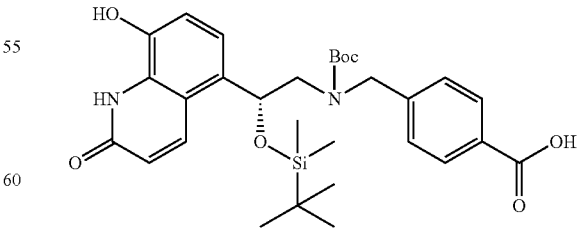

10% Palladium on carbon (2 g) was added to a stirred solution of (R)-4-(((2-(8-(benzyloxy)-2-oxo-1,2-dihydroquinolin-5-yl)-2-((tert-butyldimethylsilyl)oxy)ethyl)(tert-butoxycarbonyl)amino)methyl)benzoic acid (2.06 g, 3.12 mmol) in ethanol (25 mL) under an inert nitrogen atmosphere. 1-Methyl-1,4-cyclohexadiene (1.75 mL, 15.6 mmol) was added and the reaction mixture was carefully heated to reflux [Care—vigorous evolution of gas]. The reaction mixture was heated under reflux for 1 hour. The suspension was filtered, the filter cake washed with further ethanol and the filtrate was evaporated under reduced pressure to afford the title compound (1.66 g, 94%).

LCMS (Method 11); Rt 3.61 min; M+1 569.5.

Also prepared in the same fashion were:

(R)-4-(((tert-Butoxycarbonyl)(2-((tert-butyldimethylsilyl)oxy)-2-(8-hydroxy-2-oxo-1,2-dihydroquinolin-5-yl)ethyl)amino)methyl)-3-methoxybenzoic acid

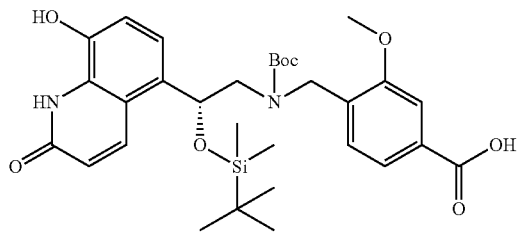 [SMILES: COc1cc(C(=O)O)ccc1CN(C[C@H](O[Si](C)(C)C(C)(C)C)c1ccc(O)c2[nH]c(=O)ccc12)C(=O)OC(C)(C)C]

Starting from methyl 4-formyl-3-methoxybenzoate
LCMS Method 11; Rt 3.75 min; ES+599.4

(R)-4-(((tert-Butoxycarbonyl)(2-((tert-butyldimethylsilyl)oxy)-2-(8-hydroxy-2-oxo-1,2-dihydroquinolin-5-yl)ethyl)amino)methyl)-2-methoxybenzoic acid

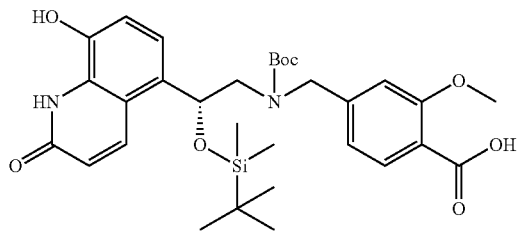 [SMILES: COc1cc(CN(C[C@H](O[Si](C)(C)C(C)(C)C)c2ccc(O)c3[nH]c(=O)ccc23)C(=O)OC(C)(C)C)ccc1C(=O)O]

Starting from methyl 4-formyl-2-methoxybenzoate
LCMS Method 11; Rt 3.61; ES+599.4

(R)-4-(((tert-Butoxycarbonyl)(2-((tert-butyldimethylsilyl)oxy)-2-(8-hydroxy-2-oxo-1,2-dihydroquinolin-5-yl)ethyl)amino)methyl)-2-fluorobenzoic acid

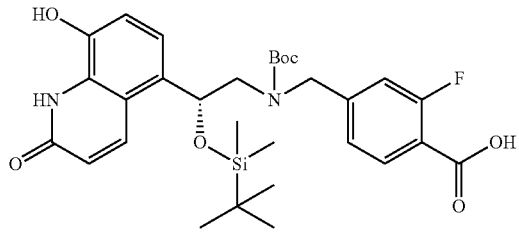 [SMILES: CC(C)(C)OC(=O)N(Cc1ccc(C(=O)O)c(F)c1)C[C@H](O[Si](C)(C)C(C)(C)C)c1ccc(O)c2[nH]c(=O)ccc12]

Starting from methyl 2-fluoro-4-formylbenzoate
LCMS Method 11; Rt 3.64; ES+587.3

(R)-4-(((tert-Butoxycarbonyl)(2-((tert-butyldimethylsilyl)oxy)-2-(8-hydroxy-2-oxo-1,2-dihydroquinolin-5-yl)ethyl)amino)methyl)-3-fluorobenzoic acid

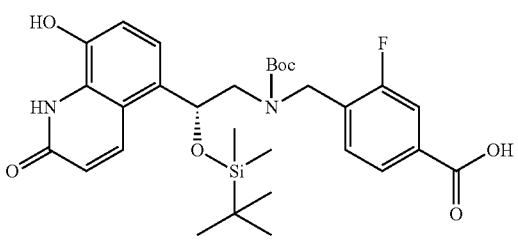 [SMILES: CC(C)(C)OC(=O)N(Cc1ccc(C(=O)O)cc1F)C[C@H](O[Si](C)(C)C(C)(C)C)c1ccc(O)c2[nH]c(=O)ccc12]

Starting from methyl 3-fluoro-4-formylbenzoate
LCMS Method 11; Rt 3.70; ES+587.4

(R)-4-(((tert-Butoxycarbonyl)(2-((tert-butyldimethylsilyl)oxy)-2-(8-hydroxy-2-oxo-1,2-dihydroquinolin-5-yl)ethyl)amino)methyl)-3-methylbenzoic acid

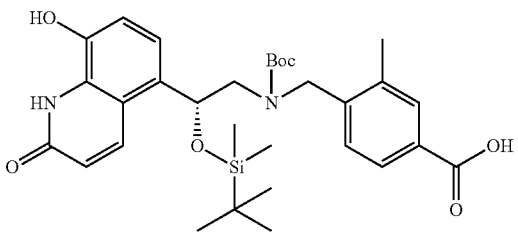 [SMILES: Cc1cc(C(=O)O)ccc1CN(C[C@H](O[Si](C)(C)C(C)(C)C)c1ccc(O)c2[nH]c(=O)ccc12)C(=O)OC(C)(C)C]

Starting from methyl 4-formyl-3-methylbenzoate
LCMS Method 11; Rt 3.70; ES+587.4

(R)-2-(4-(((tert-Butoxycarbonyl)(2-((tert-butyldimethylsilyl)oxy)-2-(8-hydroxy-2-oxo-1,2-dihydroquinolin-5-yl)ethyl)amino)methyl)phenyl)acetic acid

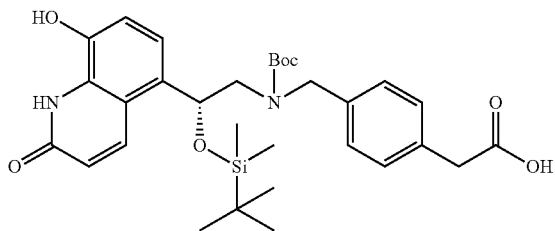 [SMILES: CC(C)(C)OC(=O)N(Cc1ccc(CC(=O)O)cc1)C[C@H](O[Si](C)(C)C(C)(C)C)c1ccc(O)c2[nH]c(=O)ccc12]

Starting from methyl 2-(4-formylphenyl)acetate.
LCMS Method 12; Rt 2.93; ES+583.4

103

(R)-4-(((tert-Butoxycarbonyl)(2-((tert-butyldimethylsilyl)oxy)-2-(8-hydroxy-2-oxo-1,2-dihydroquinolin-5-yl)ethyl)amino)methyl)-3-(trifluoromethyl)benzoic acid

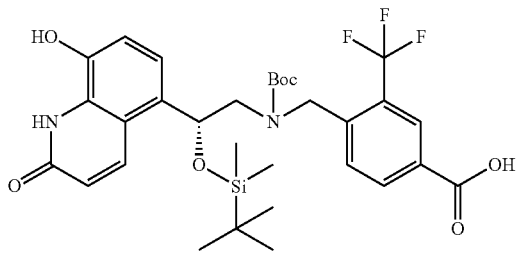 [SMILES: CC(C)(C)OC(=O)N(Cc1ccc(C(=O)O)cc1C(F)(F)F)C[C@H](O[Si](C)(C)C(C)(C)C)c1ccc(O)c2[nH]c(=O)ccc12]

Starting from methyl 3-trifluoromethyl-4-formylbenzoate
LCMS Method 11; Rt 3.79; ES$^+$637.3

Synthesis of methyl 3-trifluoromethyl-4-formylbenzoate

To a solution of 4-methyl-3-trifluoromethylbenzoic acid (1.71 g, 8.37 mmol) in DMF (20 mL) was added potassium carbonate (1.39 g, 10.1 mmol) and the reaction mixture was stirred at room temperature for five minutes. Iodomethane (0.78 mL, 12.5 mmol) was added and the reaction mixture stirred at room temperature for 18 hours. The reaction mixture was diluted with ethyl acetate and washed with water and brine (×2).

The organic phase was dried over anhydrous magnesium sulfate, filtered and the filtrate evaporated at reduced pressure to afford methyl 4-methyl-3-trifluoromethylbenzoate. The material was dissolved in carbon tetrachloride (10 mL) and treated sequentially with N-bromosuccinimide (2.74 g, 15.4 mmol) and benzoyl peroxide (catalytic) and heated at 80° C. for 18 hours. The mixture allowed to cool and diluted with water. The mixture was poured through a hydrophobic fit and the solvent evaporated at reduced pressure to afford methyl 4-(dibromomethyl)-3-trifluoromethylbenzoate. The material was dissolved in acetone/water (25 mL/5 mL) and silver nitrate (2.38 g, 14.0 mmol) added. The reaction mixture was stirred at room temperature for 72 hours. The suspension was filtered through a pad of celite and the filtrate diluted with ethyl acetate. The solution was washed with water and brine. The organic phase was dried over anhydrous magnesium sulfate, filtered and evaporated. The residue was dissolved acetone/water (25 mL/5 mL) and silver nitrate (2.38 g, 14.0 mmol) added. The reaction mixture was stirred at room temperature for 24 hours. The suspension was filtered through a pad of celite and the filtrate diluted with ethyl acetate. The solution was washed with water and brine. The organic phase was dried over anhydrous magnesium sulfate, filtered and evaporated. The residue was purified by flash column chromatography (eluent—100% i-hexane to 8:1 i-hexane/ethyl acetate) to afford the title compound (0.537 g, 33%).

$^1$H NMR (400 MHz, CDCl$_3$); δ 10.46-10.45 (m, 1H), 8.46 (s, 1H), 8.35 (d, J=8.2 Hz, 1H), 8.20 (d, J=8.2 Hz, 1H), 4.00 (s, 3H).

104

(R)-4-(((tert-Butoxycarbonyl)(2-((tert-butyldimethylsilyl)oxy)-2-(8-hydroxy-2-oxo-1,2-dihydroquinolin-5-yl)ethyl)amino)methyl)-2,3-difluorobenzoic acid

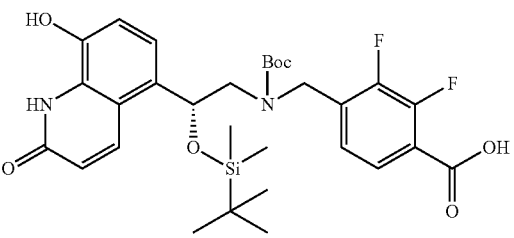 [SMILES: CC(C)(C)OC(=O)N(Cc1ccc(C(=O)O)c(F)c1F)C[C@H](O[Si](C)(C)C(C)(C)C)c1ccc(O)c2[nH]c(=O)ccc12]

Starting from methyl 2,3-difluoro-4-formylbenzoate (prepared as described for methyl 3-trifluoromethyl-4-formylbenzoate).
LCMS (10 cm_Formic_Aq); Rt 3.66; ES$^+$605/607.

(R)-4-(((tert-Butoxycarbonyl)(2-((tert-butyldimethylsilyl)oxy)-2-(8-hydroxy-2-oxo-1,2-dihydroquinolin-5-yl)ethyl)amino)methyl)-3-ethoxybenzoic acid

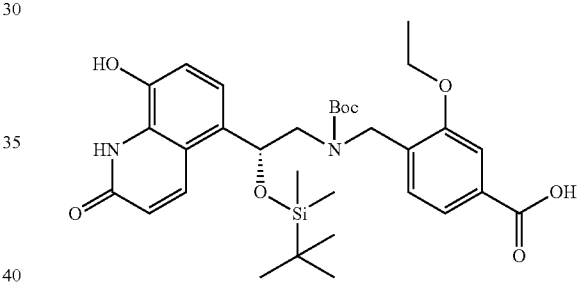

Starting from ethyl 3-ethoxy-4-formylbenzoate.
LCMS Method 11; Rt 3.76; ES$^+$613.7.

Synthesis of ethyl 3-ethoxy-4-formylbenzoate

To a solution of 4-formyl-3-hydroxybenzoic acid (1.0 g, 6.02 mmol) in DMF (20 mL) was added potassium carbonate (2.49 g, 18.1 mmol) and ethyl iodide (2.82 g, 18.1 mmol). The reaction mixture was stirred at room temperature for 72 hours. The reaction mixture was concentrated at reduced pressure and the residue partitioned between ethyl acetate and water. The organic extract was washed with brine (×2), poured through a hydrophobic frit and the solvent evaporated at reduced pressure. The residue was purified by flash column chromatography (eluent—100% i-hexane to 4:1 i-hexane/ethyl acetate) to afford the title compound (1.41 g, 100%).

$^1$H NMR (400 MHz, CDCl$_3$); δ 10.55 (s, 1H), 7.87 (d, J=8.3 Hz, 1H), 7.66 (d, J=8.3 Hz, 2H), 4.40 (q, J=7.2 Hz, 2H), 4.23 (q, J=7.0 Hz, 2H), 1.51 (dd, J=6.9, 6.9 Hz, 3H), 1.41 (dd, J=7.1, 7.1 Hz, 3H).

(R)-4-(((tert-Butoxycarbonyl)(2-((tert-butyldimethylsilyl)oxy)-2-(8-hydroxy-2-oxo-1,2-dihydroquinolin-5-yl)ethyl)amino)methyl)-3-isopropoxybenzoic acid

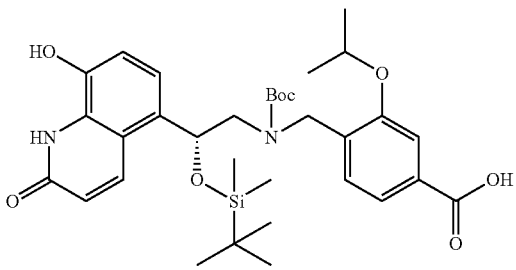 [SMILES: CC(C)Oc1cc(C(=O)O)ccc1CN(C[C@H](O[Si](C)(C)C(C)(C)C)c1ccc(O)c2[nH]c(=O)ccc12)C(=O)OC(C)(C)C]

Starting from isopropoxy 3-isopropoxy-4-formylbenzoate (prepared as ethyl 3-ethoxy-4-formylbenzoate).
LCMS Method 11; Rt 3.82; ES+627.6.

(R)-6-(((tert-Butoxycarbonyl)(2-((tert-butyldimethylsilyl)oxy)-2-(8-hydroxy-2-oxo-1,2-dihydroquinolin-5-yl)ethyl)amino)methyl)nicotinic acid

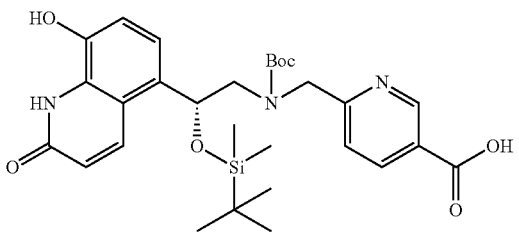

Starting from methyl 6-formylnicotinate.
LCMS Method 12; Rt 2.83; ES+570.4

(R)-4-(((tert-Butoxycarbonyl)(2-((tert-butyldimethylsilyl)oxy)-2-(8-hydroxy-2-oxo-1,2-dihydroquinolin-5-yl)ethyl)amino)methyl)-2-fluoro-5-methoxybenzoic acid

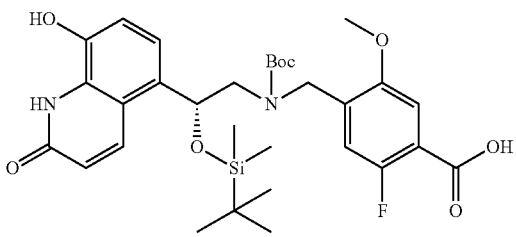 [SMILES: COc1cc(C(=O)O)c(F)cc1CN(C[C@H](O[Si](C)(C)C(C)(C)C)c1ccc(O)c2[nH]c(=O)ccc12)C(=O)OC(C)(C)C]

Starting from methyl 2-fluoro-4-formyl-5-methoxybenzoate.
LCMS Method 11; Rt 3.66; ES+617.6.

Synthesis of methyl 2-fluoro-4-formyl-5-methoxybenzoate

To a solution of methyl 2-fluoro-5-methoxy-4-methylbenzoate (0.576 g, 2.91 mmol) in carbon tetrachloride (20 mL) was added N-bromosuccinimide (0.57 g, 3.2 mmol) and benzoyl peroxide (cat). The reaction mixture was heated at 70° C. for 6 hours and then allowed to cool. The suspension was filtered and the filtrate evaporated at reduced pressure. The residue was dissolved in DCM and washed with water, 1M aqueous sodium thiosulfate and the organic phase passed through a hydrophobic frit. The filtrate was concentrated at reduced pressure and the residue purified by flash column chromatography (eluent—100% i-hexane to 4:1 i-hexane/ethyl acetate) to afford methyl 4-(bromomethyl)-2-fluoro-5-methoxybenzoate (0.591 g, 2.13 mmol). This material was dissolved in acetonitrile (20 mL) and treated with pyridine N-oxide (0.203 g, 2.13 mmol) and silver (I) oxide (0.247 g, 1.07 mmol) and the mixture stirred at room temperature for 18 hours. The suspension was filtered through a pad of celite and the filter pad washed with further acetonitrile. The filtrate was evaporated and the residue dissolved in DCM. The DCM solution was washed with water and then passed through a hydrophobic fit and the solvent was evaporated. The residue purified by flash column chromatography (eluent—100% i-hexane to 4:1 i-hexane/ethyl acetate) to afford the title compound (0.230 g, 37%).

$^1$H NMR (400 MHz, CDCl$_3$); δ 10.45-10.44 (m, 1H), 7.39-7.52 (m, 2H), 3.98 (s, 3H), 3.97 (s, 3H).

tert-Butyl (R)-(4-amino-2-methoxybenzyl)(2-((tert-butyldimethylsilyl)oxy)-2-(8-hydroxy-2-oxo-1,2-dihydroquinolin-5-yl)ethyl)carbamate

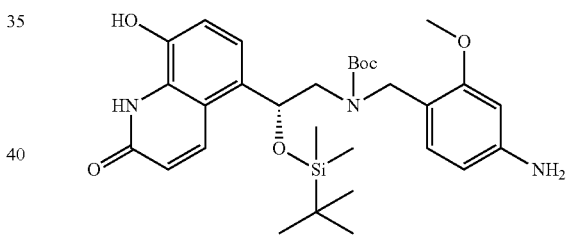

From 2-methoxy-4-nitrobenzaldehyde
LCMS Method 11; Rt 3.57 min; ES+570.4 tert-Butyl (R)-(4-amino-5-fluoro-2-methoxybenzyl)(2-((tert-butyldimethylsilyl)-oxy)-2-(8-hydroxy-2-oxo-1,2-dihydroquinolin-5-yl)ethyl)carbamate

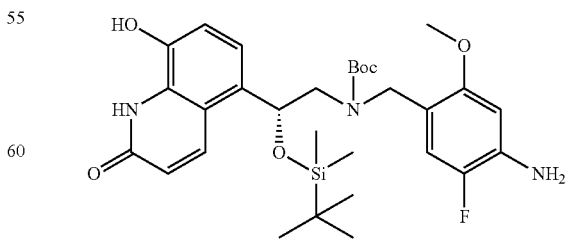

From 5-fluoro-2-methoxy-4-nitrobenzaldehyde
LCMS Method 12; Rt 3.60 min; ES+ 588.5

Procedure 4A

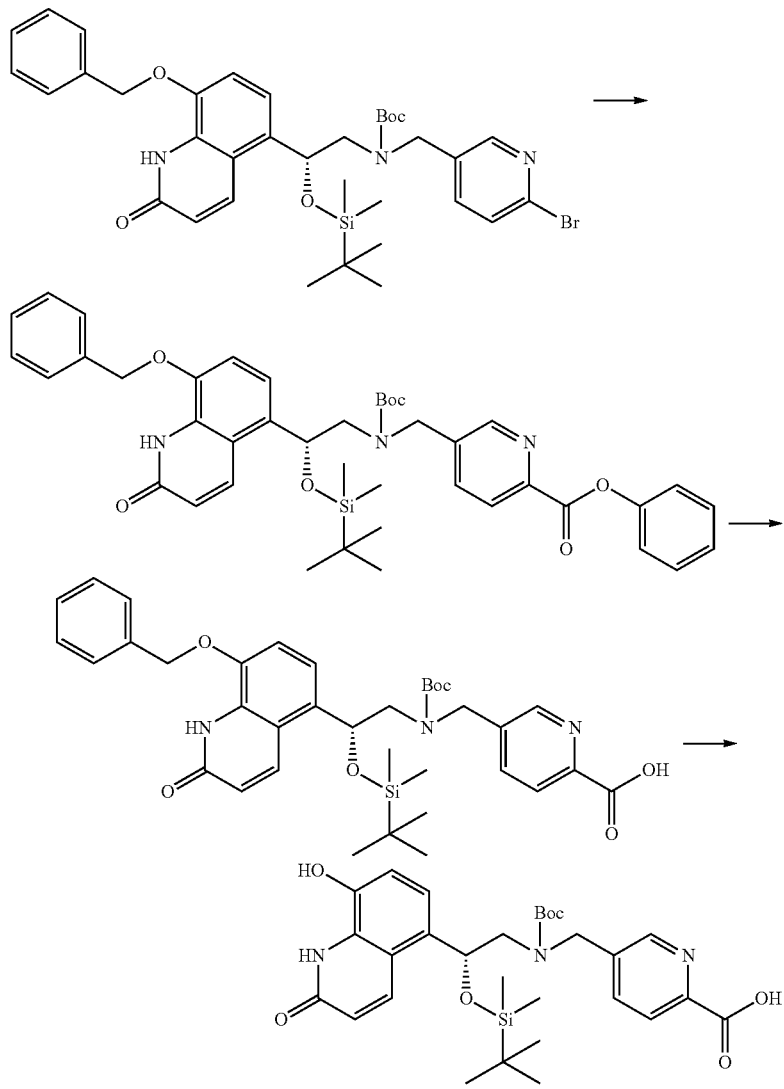

(R)-5-(((tert-Butoxycarbonyl)(2-((tert-butyldimethylsilyl)oxy)-2-(8-hydroxy-2-oxo-1,2-dihydroquinolin-5-yl)ethyl)amino)methyl)picolinic acid

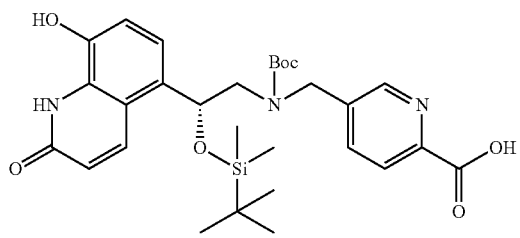

To a solution of tert-butyl (R)-(2-(8-(benzyloxy)-2-oxo-1,2-dihydroquinolin-5-yl)-2-((tert-butyldimethylsilyl)oxy)ethyl)((6-bromopyridin-3-yl)methyl)carbamate (prepared as described in Procedure 4 using 2-bromo-5-formylpyridine in Step 2) (1.47 g, 2.12 mmol) in toluene (50 mL) was added phenyl formate (1.03 g, 8.47 mmol), 4,5-bis(diphenylphosphino)-9,9-dimethylxanthene (0.294 g, 0.24 mmol), triethylamine (0.59 mL, 4.24 mmol) was added and the mixture was de-gassed for 15 minutes with nitrogen. Palladium acetate (0.057 g, 0.25 mmol) was added and the mixture was heated at 80° C. for 18 hours. Further phenyl formate (1.03 g, 8.47 mmol), 4,5-bis(diphenylphosphino)-9,9-dimethylxanthene (0.294 g, 0.24 mmol), triethylamine (0.59 mL, 4.24 mmol) and palladium acetate (0.057 g, 0.25 mmol) was added and the reaction heated at 80° C. for a further 24 hours. The reaction mixture was evaporated at reduced pressure to about ⅓ of the initial volume and then diluted with ethyl acetate. The organic phase was washed with water, brine, dried over anhydrous magnesium sulfate, filtered and the filtrate evaporated at reduced pressure. The residue was purified by flash column chromatography (eluent—100% iso-hexane to 100% ethyl acetate) to afford the major component. This material was dissolved in methanol (20 mL) and 2M aqueous sodium hydroxide added (2 mL) added. The reaction mixture was stirred at room temperature for 18 hours. The reaction mixture was concentrated and water added. The aqueous was washed with ether and then the aqueous pH adjusted to 5. The aqueous was extracted with DCM (×3), the combined DCM extracts were passed through a hydrophobic frit and evaporated at reduced pressure. The residue was dissolved in ethanol (30 mL) and 10% Pd—C (0.064 g) added followed by 1-methyl-1,4-cyclohexadiene (0.282 g, 3.00 mmol). The reaction mixture was heated to reflux and heated at reflux for three hours. The reaction mixture was filtered and the filtrate evaporated at reduced pressure to afford the title compound (0.314 g, 26%).

LCMS Method 11; Rt 3.37 min; ES$^+$570.6

Also prepared by this method:

(R)-4-(((tert-Butoxycarbonyl)(2-((tert-butyldimethylsilyl)oxy)-2-(8-hydroxy-2-oxo-1,2-dihydroquinolin-5-yl)ethyl)amino)methyl)-3-(trifluoromethoxy)benzoic acid

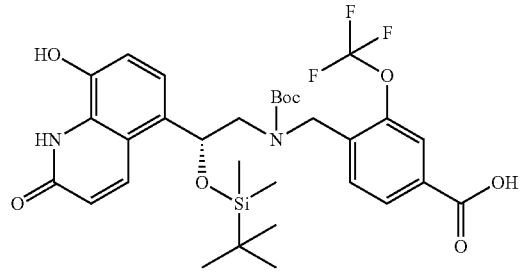 [SMILES: CC(C)(C)OC(=O)N(Cc1ccc(C(=O)O)cc1OC(F)(F)F)C[C@H](O[Si](C)(C)C(C)(C)C)c1ccc(O)c2[nH]c(=O)ccc12]

Starting from 4-bromo-2-(trifluoromethoxy)benzaldehyde.
LCMS Method 12; Rt 3.02 min; ES$^+$653.5.

(R)-4-(((tert-Butoxycarbonyl)(2-((tert-butyldimethylsilyl)oxy)-2-(8-hydroxy-2-oxo-1,2-dihydroquinolin-5-yl)ethyl)amino)methyl)-2-fluoro-3-methoxybenzoic acid

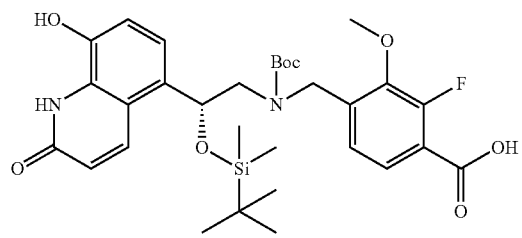 [SMILES: COc1c(CN(C[C@H](O[Si](C)(C)C(C)(C)C)c2ccc(O)c3[nH]c(=O)ccc23)C(=O)OC(C)(C)C)ccc(C(=O)O)c1F]

Starting from 4-bromo-3-fluoro-2-methoxybenzaldehyde.
LCMS Method 12; Rt 3.02 min; ES$^+$ 653.5.

Procedure 4B

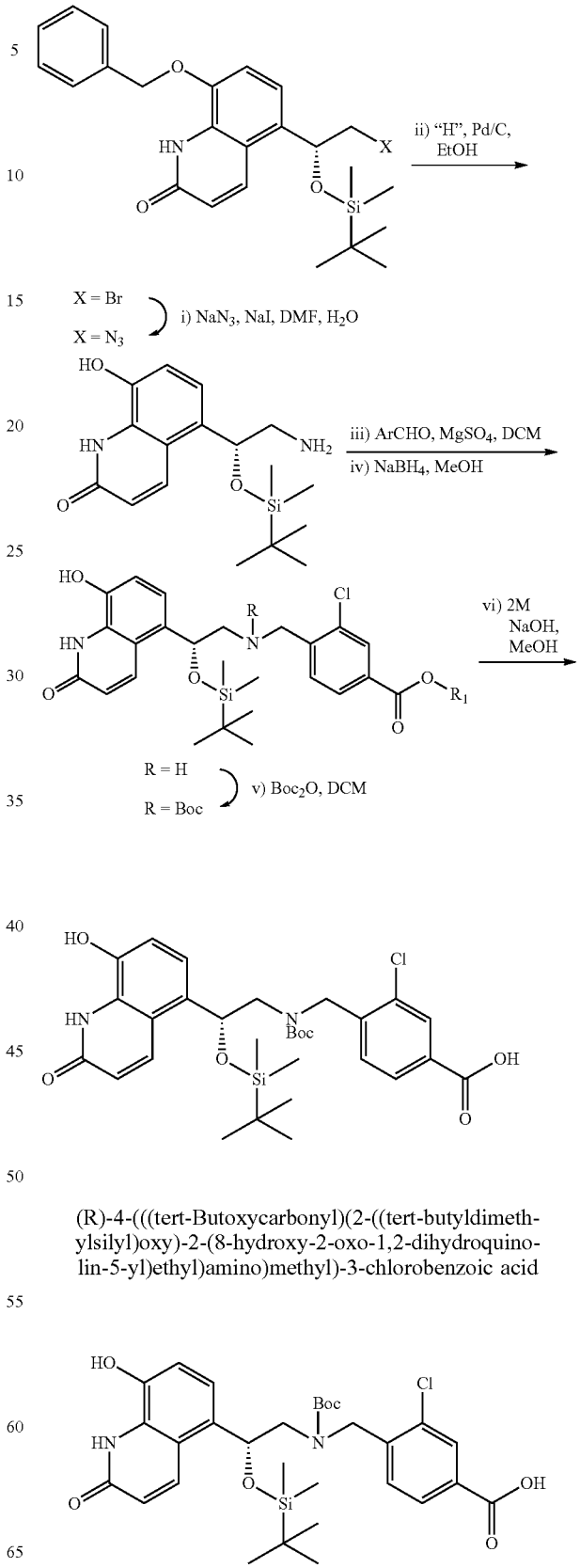

(R)-4-(((tert-Butoxycarbonyl)(2-((tert-butyldimethylsilyl)oxy)-2-(8-hydroxy-2-oxo-1,2-dihydroquinolin-5-yl)ethyl)amino)methyl)-3-chlorobenzoic acid Step 1; (R)-5-(2-Amino-1-((tert-butyldimethylsilyl)oxy)ethyl)-8-hydroxyquinolin-2(1H)-one

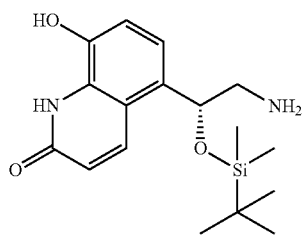 [SMILES: CC(C)(C)[Si](C)(C)O[C@@H](CN)c1ccc(O)c2[nH]c(=O)ccc12]

To a solution of (R)-5-(2-azido-1-((tert-butyldimethylsilyl)oxy)ethyl)-8-(benzyloxy)quinolin-2(1H)-one (8.5 g, 18.9 mmol) in ethanol (120 mL) was added 10% palladium on charcoal (8.5 g) followed by 1-methyl-1,4-cyclohexadiene (21 mL, 186.9 mmol) and the reaction mixture heated to 60° C. for one hour. The reaction was allowed to cool to room temperature and the suspension was filtered. The filter cake was washed with further ethanol and the filtrate evaporated at reduced pressure. The residue was triturated with i-hexane, the solid recovered by filtration and subsequently dried under vacuum to afford the title compound (5.55 g, 88%).

$^1$H NMR (400 MHz, CDCl$_3$); δ 8.22 (d, J=9.8 Hz, 1H), 7.04 (d, J=8.0 Hz, 1H), 6.91 (d, J=7.9 Hz, 1H), 6.63 (d, J=9.3 Hz, 1H), 5.03 (dd, J=4.9, 4.9 Hz, 1H), 3.04-2.93 (m, 2H), 0.92-0.85 (m, 9H), 0.20 (s, 3H), −0.18 (s, 3H).

Step 2; (R)-4-(((tert-Butoxycarbonyl)(2-((tert-butyldimethylsilyl)oxy)-2-(8-hydroxy-2-oxo-1,2-dihydroquinolin-5-yl)ethyl)amino)methyl)-3-chlorobenzoic acid

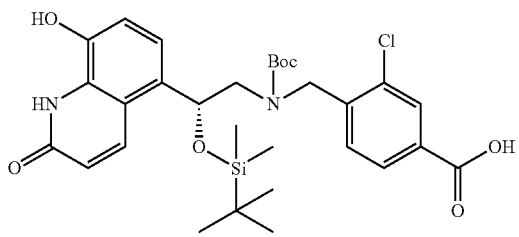

The title compound was prepared as in Preparation 4 using Step 3 and 5.

LCMS Method 11; Rt 3.76; ES$^+$603.3/605.4.

Also prepared in the same fashion were:

(R)-4-(((tert-Butoxycarbonyl)(2-((tert-butyldimethylsilyl)oxy)-2-(8-hydroxy-2-oxo-1,2-dihydroquinolin-5-yl)ethyl)amino)methyl)-2-chlorobenzoic acid

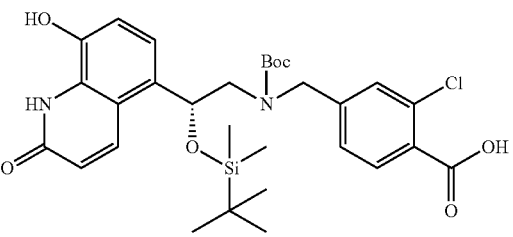

Starting from methyl 2-chloro-4-formylbenzoate
LCMS Method 11; Rt 3.70; ES$^+$603.3/605.4

(R)-4-(((tert-Butoxycarbonyl)(2-((tert-butyldimethylsilyl)oxy)-2-(8-hydroxy-2-oxo-1,2-dihydroquinolin-5-yl)ethyl)amino)methyl)-2-chloro-5-methoxybenzoic acid

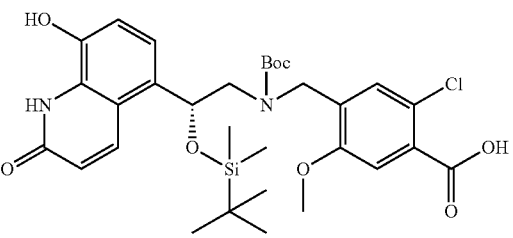 [SMILES: COc1cc(C(=O)O)c(Cl)cc1CN(C[C@H](O[Si](C)(C)C(C)(C)C)c1ccc(O)c2[nH]c(=O)ccc12)C(=O)OC(C)(C)C]

Starting from phenyl 2-chloro-4-formyl-5-methoxybenzoate
LCMS Method 11; Rt 3.88; ES$^+$633.5/635.6

Synthesis of phenyl 2-chloro-4-formyl-5-methoxybenzoate

To a stirred solution of 4-bromo-2-methoxybenzaldehyde (1.0 g, 4.56 g) in acetonitrile (15 mL) was added N-chlorosuccinimide (0.731 g, 5.48 mmol) and the reaction mixture was heated at 80° C. for 18 hours. The reaction mixture was diluted with ethyl acetate and washed with water and brine (×2). The organic phase was dried over anhydrous magnesium sulfate, filtered and the solvent evaporated at reduced pressure. The residue was dissolved in toluene (20 mL) and phenyl formate (2 mL, 18.3 mmol), 4,5-bis(diphenylphosphino)-9,9-dimethylxanthene (0.642 g, 1.11 mmol), triethylamine (1.27 mL, 9.13 mmol) was added and the mixture was de-gassed for 15 minutes with nitrogen. Palladium acetate (0.122 g, 0.54 mmol) was added and the mixture was heated at 80° C. for 18 hours. The reaction mixture was evaporated at reduced pressure to about ⅓ of the initial volume and then diluted with ethyl acetate. The organic phase was washed with water, brine, dried over anhydrous magnesium sulfate, filtered and the filtrate evaporated at reduced pressure. The residue was purified by flash column chromatography (eluent—100% iso-hexane to 100% ethyl acetate) to afford the title compound (0.554 g, 42%).

¹H NMR (400 MHz, CDCl₃); δ 10.47 (s, 1H), 7.93 (s, 1H), 7.58 (s, 1H), 7.46-7.31 (m, 5H), 4.02 (s, 3H).

Procedure 5. Preparation of (R)-4-(2-((tert-butoxycarbonyl)(2-((tert-butyldimethylsilyl)-oxy)-2-(8-hydroxy-2-oxo-1,2-dihydroquinolin-5-yl)ethyl)amino)ethyl)benzoic acid

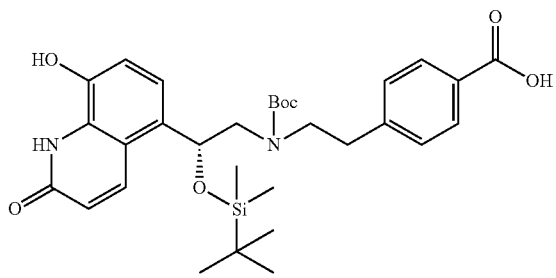 [SMILES: CC(C)(C)OC(=O)N(CCc1ccc(C(=O)O)cc1)C[C@H](O[Si](C)(C)C(C)(C)C)c1ccc(O)c2[nH]c(=O)ccc12]

Step 1; (R)-8-(Benzyloxy)-5-(1-((tert-butyldimethylsilyl)oxy)-2-((4-hydroxyphenethyl)amino)ethyl)quinolin-2(1H)-one

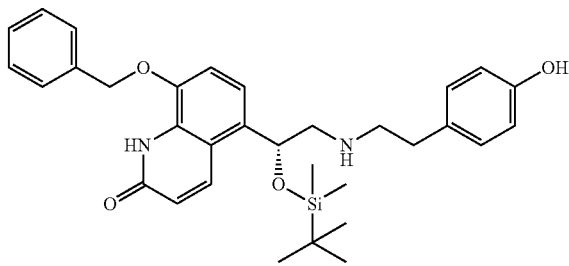 [SMILES: CC(C)(C)[Si](C)(C)O[C@@H](CNCCc1ccc(O)cc1)c1ccc(OCc2ccccc2)c2[nH]c(=O)ccc12]

A mixture of (R)-8-(benzyloxy)-5-(2-bromo-1-((tert-butyldimethylsilyl)-oxy)ethyl)quinolin-2(1H)-one (1.0 g, 2.05 mmol) in NMP (2 mL) was added with tyramine (1.41 g, 10.2 mmol). The mixture was heated at 80° C. for 18 hours. The mixture was diluted with ethyl acetate and washed sequentially with 10% aqueous potassium hydrogensulfate and brine (×2). The organic phase was dried over anhydrous magnesium sulfate and the filtrate was evaporated under reduced pressure to afford the title compound (2.58 g, 93%).

¹H NMR (400 MHz, CDCl₃); δ 9.30-9.30 (m, 1H), 8.27 (d, J=9.9 Hz, 1H), 7.46-7.38 (m, 6H), 7.08 (d, J=8.3 Hz, 1H), 6.97 (dd, J=4.8, 8.4 Hz, 3H), 6.71 (d, J=8.5 Hz, 2H), 6.65 (d, J=9.9 Hz, 1H), 5.16 (s, 2H), 5.14-5.07 (m, 1H), 2.97-2.82 (m, 3H), 2.78-2.68 (m, 3H), 1.65 (br s, 1H), 0.82 (s, 9H), 0.00 (s, 3H), −0.22 (s, 3H).

Step 2; (R)-tert-Butyl (2-(8-(benzyloxy)-2-oxo-1,2-dihydroquinolin-5-yl)-2-((tert-butyldimethylsilyl)oxy)ethyl)(4-hydroxyphenethyl)carbamate

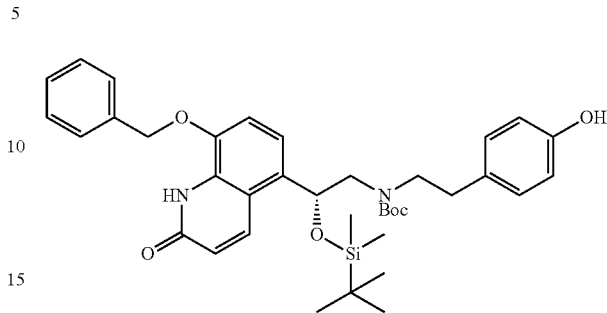

To a stirred solution of (R)-8-(benzyloxy)-5-(1-((tert-butyldimethylsilyl)oxy)-2-((4-hydroxyphenethyl)amino)ethyl)quinolin-2(1H)-one (6.0 g, 11.02 mmol) in DCM (75 mL) was added a solution of di-tert-butyldicarbonate (2.18 g, 16.5 mmol) in DCM (15 mL). The reaction mixture was stirred at room temperature for 2 hours. The solvent was evaporated under reduced pressure and the residue purified by flash column chromatography (eluent—100% iso-hexane to 3:2 iso-hexane/ethyl acetate) to afford the title compound (6.30 g, 89%).

¹H NMR (400 MHz, DMSO-d₆, 100° C.); δ 9.94-9.92 (m, 1H), 8.74 (s, 1H), 8.29 (d, J=9.9 Hz, 1H), 7.56 (d, J=7.2 Hz, 2H), 7.44-7.35 (m, 3H), 7.24 (d, J=8.3 Hz, 1H), 7.14 (d, J=8.4 Hz, 1H), 6.92 (d, J=8.4 Hz, 2H), 6.70-6.67 (m, 2H), 6.56 (d, J=9.9 Hz, 1H), 5.31 (s, 3H), 3.37-3.23 (m, 4H), 2.66-2.55 (m, 2H), 1.39 (s, 9H), 0.86 (s, 9H), 0.04 (s, 3H), −0.13 (s, 3H).

Step 3; (R)-4-(2-((2-(8-(Benzyloxy)-2-oxo-1,2-dihydroquinolin-5-yl)-2-((tert-butyldimethylsilyl)oxy)ethyl)(tert-butoxycarbonyl)amino)ethyl)phenyl trifluoromethanesulfonate

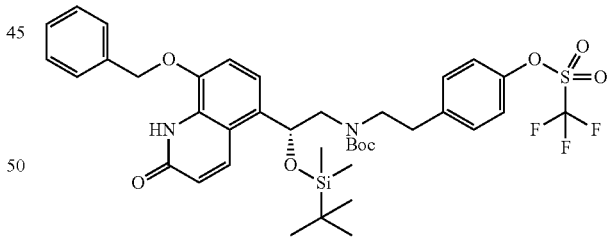

To a cooled solution of (R)-tert-butyl (2-(8-(benzyloxy)-2-oxo-1,2-dihydroquinolin-5-yl)-2-((tert-butyldimethylsilyl)oxy)ethyl)(4-hydroxyphenethyl)-carbamate (6.3 g, 9.78 mmol) in DCM (100 mL) at 0° C. was added triethylamine (2.72 mL, 19.56 mmol) followed by 2-[N,N-bis(trifluoromethanesulfonyl)amino]-5-chloropyridine (4.21 g, 10.76 mmol) and the mixture was stirred at 0° C. for 2 hours. The coolant was removed and 2M aqueous sodium hydroxide (25 mL) was added to the reaction mixture, and the mixture was stirred for 15 minutes. The organic phase was separated, dried over anhydrous magnesium sulfate, filtered and the filtrate evaporated under reduced pressure to afford the title compound (7.3 g, 96%).

¹H NMR (400 MHz, DMSO-d₆, 100° C.); δ 8.74 (s, 1H), 8.29 (d, J=9.9 Hz, 1H), 7.56 (d, J=7.2 Hz, 2H), 7.44-7.35 (m, 3H), 7.24 (d, J=8.3 Hz, 1H), 7.14 (d, J=8.4 Hz, 1H), 6.92 (d, J=8.4 Hz, 2H), 6.70-6.67 (m, 2H), 6.56 (d, J=9.9 Hz, 1H), 5.31 (s, 3H), 2.96 (s, 4H), 2.66-2.55 (m, 2H), 1.39 (s, 9H), 0.86 (s, 9H), 0.04 (s, 3H), −0.13 (s, 3H).

Step 4; (R)-Phenyl 4-(2-((2-(8-(benzyloxy)-2-oxo-1, 2-dihydroquinolin-5-yl)-2-((tert-butyldimethylsilyl) oxy)ethyl)(tert-butoxycarbonyl)amino)ethyl)benzoate

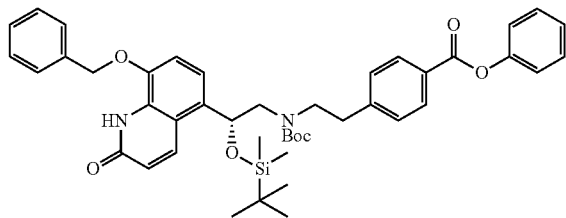 [SMILES: CC(C)(C)OC(=O)N(CCc1ccc(C(=O)Oc2ccccc2)cc1)C[C@H](O[Si](C)(C)C(C)(C)C)c1ccc(OCc2ccccc2)c2[nH]c(=O)ccc12]

To a solution of (R)-4-(2-((2-(8-(benzyloxy)-2-oxo-1,2-dihydroquinolin-5-yl)-2-((tert-butyldimethylsilyl)oxy) ethyl)(tert-butoxycarbonyl)amino)ethyl)phenyl trifluoromethanesulfonate (7.29 g, 9.4 mmol) in toluene (75 mL) was added phenyl formate (4 mL, 37.57 mmol), 4,5-bis(diphenylphosphino)-9,9-dimethylxanthene (1.3 g, 2.25 mmol), triethylamine (2.61 mL, 18.81 mmol) and the mixture was de-gassed for 15 minutes with nitrogen. Palladium acetate (0.242 g, 1.12 mmol) was added and the mixture was heated at 80° C. for 6 hours. The reaction mixture was evaporated under reduced pressure to about ⅓ of the initial volume and then diluted with ethyl acetate. The organic phase was washed with water, brine, dried over anhydrous magnesium sulfate, filtered and the filtrate evaporated under reduced pressure. The residue was purified by flash column chromatography (eluent—100% iso-hexane to 100% ethyl acetate) to afford the title compound (4.5 g, 64%).

¹H NMR (400 MHz, DMSO-d₆, 100° C.); δ 9.98-9.96 (m, 1H), 8.29 (d, J=9.9 Hz, 1H), 8.05 (d, J=8.3 Hz, 2H), 7.56 (d, J=7.2 Hz, 2H), 7.51-7.46 (m, 2H), 7.43-7.27 (m, 8H), 7.24 (s, 1H), 7.17 (d, J=8.3 Hz, 1H), 6.57 (d, J=9.9 Hz, 1H), 5.35 (d, J=1.9 Hz, 1H), 5.32 (s, 2H), 3.49-3.34 (m, 4H), 2.90-2.80 (m, 2H), 1.39 (s, 9H), 0.87 (s, 9H), 0.06 (s, 3H), −0.12 (s, 3H).

Step 5; (R)-4-(2-((2-(8-(Benzyloxy)-2-oxo-1,2-dihydroquinolin-5-yl)-2-((tert-butyldimethylsilyl)oxy) ethyl)(tert-butoxycarbonyl)amino)ethyl)benzoic acid

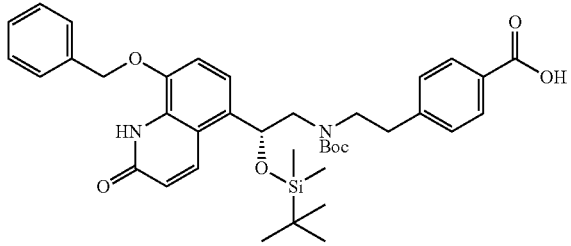 [SMILES: CC(C)(C)OC(=O)N(CCc1ccc(C(=O)O)cc1)C[C@H](O[Si](C)(C)C(C)(C)C)c1ccc(OCc2ccccc2)c2[nH]c(=O)ccc12]

To a solution of (R)-phenyl 4-(2-((2-(8-(benzyloxy)-2-oxo-1,2-dihydroquinolin-5-yl)-2-((tert-butyldimethylsilyl) oxy)ethyl)(tert-butoxycarbonyl)amino)ethyl)benzoate (4.5 g, 6.0 mmol) in THF (30 mL) was added 2M aqueous sodium hydroxide (30 mL) and the mixture was stirred at room temperature for 16 hours. The solvent was evaporated under reduced pressure to half the initial volume and then diluted with water (25 mL), The resulting mixture was acidified to pH 3 using 2M aqueous hydrochloric acid and then extracted with ethyl acetate (×3). The combined organic phases were washed sequentially with water, brine (25 ml), dried over anhydrous magnesium sulfate, filtered and the filtrate evaporated under reduced pressure to afford the title compound (4 g, 100%). Material used directly in the next step.

Step 6; (R)-4-(2-((tert-Butoxycarbonyl)(2-((tert-butyldimethylsilyl)oxy)-2-(8-hydroxy-2-oxo-1,2-dihydroquinolin-5-yl)ethyl)amino)ethyl)benzoic acid

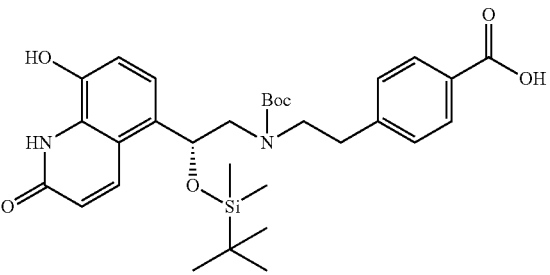 [SMILES: CC(C)(C)OC(=O)N(CCc1ccc(C(=O)O)cc1)C[C@H](O[Si](C)(C)C(C)(C)C)c1ccc(O)c2[nH]c(=O)ccc12]

To a solution of (R)-4-(2-((2-(8-(benzyloxy)-2-oxo-1,2-dihydroquinolin-5-yl)-2-((tert-butyldimethylsilyl)oxy) ethyl)(tert-butoxycarbonyl)amino)ethyl)benzoic acid (4 g, 5.95 mmol) in ethanol (100 mL) was added 10% Pd—C (2 g) and 1-methyl-1,4-cyclohexadiene (3.29 ml, 29.76 mmol) and the mixture was heated at 80° C. for 3.5 hours. The reaction mixture was filtered through celite and the celite washed with further ethanol. The filtrate was evaporated under reduced pressure to afford the title compound (3.5 g, 100%).

Procedure 6. Preparation of (R)-tert-butyl (2-((tert-butyldimethylsilyl)oxy)-2-(8-hydroxy-2-oxo-1,2-dihydroquinolin-5-yl)ethyl)(piperidin-4-ylmethyl) carbamate

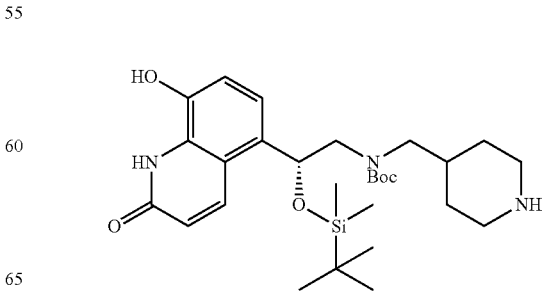

Step 1; (R)-8-(Benzyloxy)-5-(2-(((1-benzylpiperidin-4-yl)methyl)amino)-1-((tert-butyldimethylsilyl)oxy)ethyl)quinolin-2(1H)-one

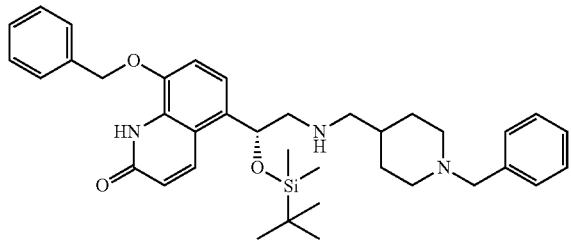 [SMILES: CC(C)(C)[Si](C)(C)O[C@@H](CNCC1CCN(Cc2ccccc2)CC1)c1ccc(OCc2ccccc2)c2[nH]c(=O)ccc12]

To a mixture of (R)-8-(benzyloxy)-5-(2-bromo-1-((tert-butyldimethylsilyl)-oxy)ethyl)quinolin-2(1H)-one (2.39 g, 4.90 mmol) in NMP (4 mL) was added (1-benzylpiperidin-4-yl)methanamine (5 g, 24.5 mmol). The mixture was heated at 80° C. for 18 hours. The mixture was diluted with ethyl acetate and washed sequentially with water (×2) and brine (×2). The organic phase was dried over anhydrous magnesium sulfate and the filtrate was evaporated. The residue was purified by flash column chromatography (eluent—100% DCM to 40:1 DCM/7M NH$_3$/MeOH) to afford the title compound (2.65 g, 88%).

$^1$H NMR (400 MHz, CDCl$_3$); δ 9.19-9.15 (m, 1H), 8.30-8.28 (s, 1H), 7.43-7.41 (m, 5H), 7.31 (d, J=4.4 Hz, 5H), 7.12 (d, J=8.3 Hz, 1H), 7.00 (d, J=8.3 Hz, 1H), 6.66 (d, J=9.9 Hz, 1H); 5.16 (s, 2H), 5.15-5.10 (m, 1H), 3.49 (s, 2H), 2.95-2.84 (m, 3H), 2.71 (dd, J=4.0, 12.2 Hz, 1H), 2.56-2.43 (m, 2H), 1.94 (dd, J=11.7, 11.7 Hz, 2H), 1.51-1.39 (m, 2H), 1.30-1.22 (m, 3H), 0.87 (s, 9H), 0.06 (s, 3H), −0.19 (s, 3H).

Step 2; (R)-tert-Butyl (2-(8-(benzyloxy)-2-oxo-1,2-dihydroquinolin-5-yl)-2-((tert-butyldimethylsilyl)oxy)ethyl)((1-benzylpiperidin-4-yl)methyl)carbamate

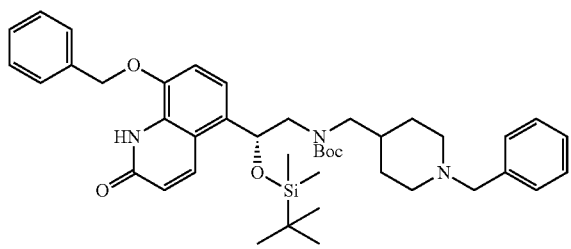 [SMILES: CC(C)(C)OC(=O)N(CC1CCN(Cc2ccccc2)CC1)C[C@H](O[Si](C)(C)C(C)(C)C)c1ccc(OCc2ccccc2)c2[nH]c(=O)ccc12]

To a stirred solution of (R)-8-(benzyloxy)-5-(2-(((1-benzylpiperidin-4-yl)methyl)amino)-1-((tert-butyldimethylsilyl)oxy)ethyl)quinolin-2(1H)-one (2.65 g, 4.33 mmol) in DCM (25 mL) was added a solution of di-tert-butyldicarbonate (1.13 g, 5.18 mmol) in DCM (5 mL). The reaction mixture was stirred at room temperature for 16 hours. The solvent was evaporated under reduced pressure and the residue purified by flash column chromatography (eluent—100% DCM to 30:1 DCM/7M NH$_3$/MeOH) to afford the title compound (2.83 g, 92%).

$^1$H NMR (400 MHz, DMSO-d$_6$, 100° C.); δ 9.96 (s, 1H), 8.30 (d, J=9.9 Hz, 1H), 7.55 (d, J=7.3 Hz, 2H), 7.42-7.21 (m, 9H), 7.14 (d, J=8.3 Hz, 1H), 6.55 (d, J=9.9 Hz, 1H), 5.40-5.33 (m, 1H), 5.30 (s, 2H), 3.44 (s, 2H), 3.38 (d, J=6.1 Hz, 2H), 3.12-2.97 (m, 2H), 2.95 (s, 2H), 2.78-2.73 (m, 2H), 2.00-1.88 (m, 2H), 1.40 (s, 10H), 1.22-1.09 (m, 2H), 0.87 (s, 9H), 0.06 (s, 3H), −0.13 (s, 3H).

Step 3; (R)-tert-Butyl (2-((tert-butyldimethylsilyl)oxy)-2-(8-hydroxy-2-oxo-1,2-dihydroquinolin-5-yl)ethyl)(piperidin-4-ylmethyl)carbamate

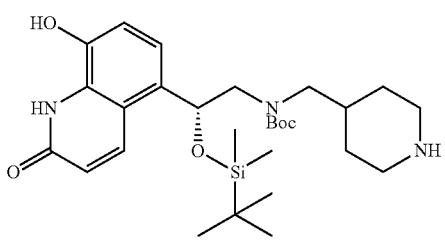 [SMILES: CC(C)(C)OC(=O)N(CC1CCNCC1)C[C@H](O[Si](C)(C)C(C)(C)C)c1ccc(O)c2[nH]c(=O)ccc12]

To a stirred solution of (R)-tert-butyl (2-(8-(benzyloxy)-2-oxo-1,2-dihydroquinolin-5-yl)-2-((tert-butyldimethylsilyl)oxy)ethyl)((1-benzylpiperidin-4-yl)methyl)carbamate (2.80 g, 4.33 mmol) in ethanol (30 mL) was added 10% Pd/C (2.8 g) and 1-methyl-1,4-cyclohexadiene (4.86 mL, 43.3 mmol). The reaction mixture was heated to reflux [care—vigorous evolution of gas] and heated under reflux for 1 hour. The suspension was filtered and the filtrate evaporated under reduced pressure to afford the title compound (2.26 g, 98%).

$^1$H NMR (400 MHz, DMSO-d$_6$, 100° C.); δ 8.26 (d, J=9.9 Hz, 1H), 7.05 (d, J=8.2 Hz, 1H), 7.01 (d, J=8.0 Hz, 1H), 6.53-6.49 (m, 1H), 5.37-5.35 (m, 1H), 3.22 (d, J=12.8 Hz, 2H), 3.08 (ddd, J=7.0, 14.3, 17.8 Hz, 2H), 2.83-2.72 (m, 2H), 1.84-1.76 (m, 1H), 1.71-1.61 (m, 2H), 1.43-1.41 (m, 14H), 0.87-0.85 (m, 9H), 0.02 (s, 3H), −0.14 (d, J=2.1 Hz, 3H).

Also Prepared by this Method (R)-tert-butyl (2-((tert-butyldimethylsilyl)oxy)-2-(8-hydroxy-2-oxo-1,2-dihydroquinolin-5-yl)ethyl)(2-(piperidin-4-yl)ethyl)carbamate

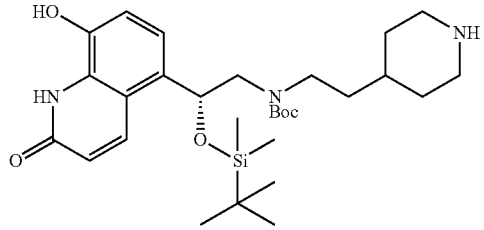 [SMILES: CC(C)(C)OC(=O)N(CCC1CCNCC1)C[C@H](O[Si](C)(C)C(C)(C)C)c1ccc(O)c2[nH]c(=O)ccc12]

$^1$H NMR (400 MHz, DMSO-d$_6$, 90° C.); δ 8.26 (d, J=9.9 Hz, 1H), 7.05 (d, J=8.2 Hz, 1H), 7.01 (d, J=8.0 Hz, 1H), 6.53-6.49 (m, 1H), 5.37-5.35 (m, 1H), 3.40-3.30 (m, 2H), 3.25-3.10 (m, 2H), 3.00-2.90 (m, 2H), 2.50-2.40 (m, 2H), 1.60-1.55 (m, 2H), 1.45 (s, 9H), 1.40-1.30 (m, 2H), 1.20-0.95 (m, 3H), 0.87-0.85 (m, 9H), 0.02 (s, 3H), −0.14 (d, J=2.1 Hz, 3H).

Procedure 7. Preparation of (S)-4-((3-(2-((1-benzylpiperidin-4-yl)methoxy)-1-hydroxy-2-oxo-1-phenylethyl)phenoxy)methyl)benzoic acid hydrochloride

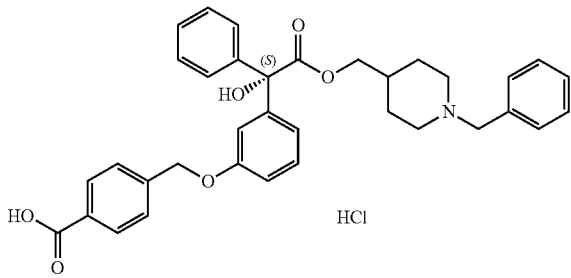

Step 1; (S)-tert-Butyl 4-((2-hydroxy-2-(3-hydroxyphenyl)-2-phenylacetoxy)methyl-)piperidine-1-carboxylate

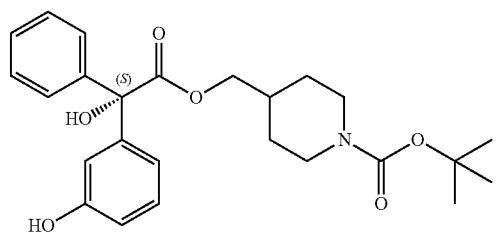

To a stirred solution of (S)-2-hydroxy-2-(3-hydroxyphenyl)-2-phenylacetic acid (10.69 g, 43.77 mmol) in DMF (30 mL) was added potassium hydrogen carbonate (8.76 g, 87.5 mmol) and the mixture stirred at room temperature for 10 minutes. A solution of tert-butyl 4-(tosyloxymethyl)piperidine-1-carboxylate (as described in Example 1, Step 5) (16.17 g, 43.77 mmol) in DMF (55 mL) was added and the reaction mixture heated at 60° C. for 27 hours. Diluted with ethyl acetate and washed with aqueous sodium hydrogen carbonate (×2), brine and dried over anhydrous magnesium sulfate. The filtrate was evaporated under reduced pressure and the residue purified by flash column chromatography (eluent—100% iso-hexane to 2:3 iso-hexane/ethyl acetate) to afford the title compound (13.42 g, 69%).

$^1$H NMR (400 MHz, DMSO-$d_6$); δ 9.35 (s, 1H), 7.33 (d, J=4.4 Hz, 4H), 7.31-7.26 (m, 1H), 7.12 (dd, J=7.8, 7.8 Hz, 1H), 6.77-6.73 (m, 2H), 6.69-6.66 (m, 1H), 6.50 (s, 1H), 4.07-3.99 (m, 2H), 3.87 (d, J=11.4 Hz, 2H), 2.68-2.63 (m, 2H), 1.76-1.67 (m, 1H), 1.48 (d, J=12.0 Hz, 2H), 1.38 (s, 9H), 1.10-0.83 (m, 2H).

Step 2; (S)-Piperidin-4-ylmethyl 2-hydroxy-2-(3-hydroxyphenyl)-2-phenylacetate hydrochloride

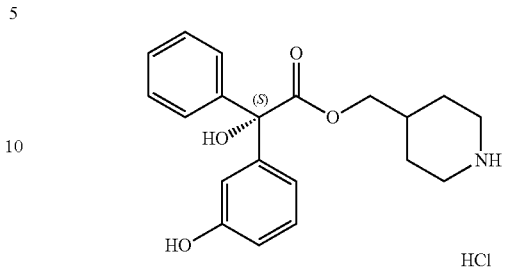

To a solution of (S)-tert-butyl 4-((2-hydroxy-2-(3-hydroxyphenyl)-2-phenylacetoxy)methyl)piperidine-1-carboxylate (7.07 g, 16.01 mmol) in 1,4-dioxane (20 mL) was added a solution of HCl-dioxane (4M, 80 mL) and the reaction mixture was stirred at room temperature for 1 hour 30 minutes. The solvent was evaporated under reduced pressure to afford the title compound (5.9 g, 97%).

$^1$H NMR (400 MHz, DMSO-$d_6$); δ 9.38 (s, 1H), 8.69-8.68 (m, 1H), 8.39 (s, 1H), 7.34 (d, J=4.0 Hz, 4H), 7.32-7.27 (m, 1H), 7.13 (dd, J=7, 8, 7.8 Hz, 1H), 6.78-6.74 (m, 2H), 6.70-6.67 (m, 1H), 6.52 (s, 1H), 4.02 (d, J=6.5 Hz, 2H), 3.21 (d, J=12.4 Hz, 2H), 2.86-2.77 (m, 2H), 1.92-1.84 (m, 1H), 1.68 (d, J=13.9 Hz, 2H), 1.35-1.25 (m, 2H).

Step 3; (S)-(1-Benzylpiperidin-4-yl)methyl 2-hydroxy-2-(3-hydroxyphenyl)-2-phenylacetate

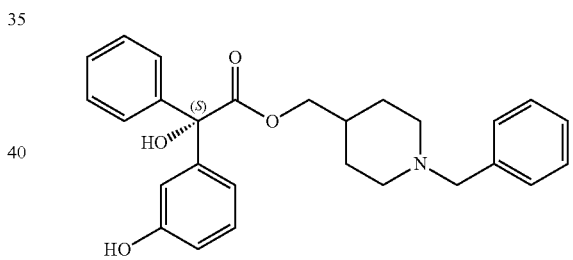

To a stirred suspension of (S)-piperidin-4-ylmethyl 2-hydroxy-2-(3-hydroxyphenyl)-2-phenylacetate hydrochloride (5.9 g, 15.61 mmol) in DCM (160 mL) was added benzaldehyde (2.38 mL, 23.4 mmol) and stirred at 30° C. for 1 hour. Sodium triacetoxyborohydride (6.62 g, 31.2 mmol) was added and the reaction mixture stirred at 30° C. for 2 hours. Further sodium triacetoxyborohydride (1.65 g, 7.8 mmol) was added and the mixture stirred at 30° C. for 18 hours. The reaction mixture was quenched with saturated aqueous sodium hydrogen carbonate and the organic phase removed. The aqueous phase was extracted with further DCM. The combined organic phases were washed with brine, dried over anhydrous magnesium sulfate, filtered and the filtrate evaporated under reduced pressure. The residue was purified by flash column chromatography (eluent—100% DCM to 9:1 DCM/methanol) to afford the title compound (13.42 g, 69%).

$^1$H NMR (400 MHz, DMSO-$d_6$); δ 9.33 (s, 1H), 7.34-7.25 (m, 9H), 7.11 (dd, J=7.8, 7.8 Hz, 1H), 6.76-6.73 (m, 2H), 6.68-6.65 (m, 1H), 6.48 (s, 1H), 5.77 (s, 1H), 3.99 (d, J=6.3 Hz, 2H), 3.40 (s, 2H), 2.72 (d, J=11.4 Hz, 2H), 1.86-1.79 (m, 2H), 1.54-1.43 (m, 3H), 1.12 (q, J=11.8 Hz, 2H).

Step 4; (S)-tert-Butyl 4-((3-(2-((1-benzylpiperidin-4-yl)methoxy)-1-hydroxy-2-oxo-1-phenylethyl)phenoxy)methyl)benzoate

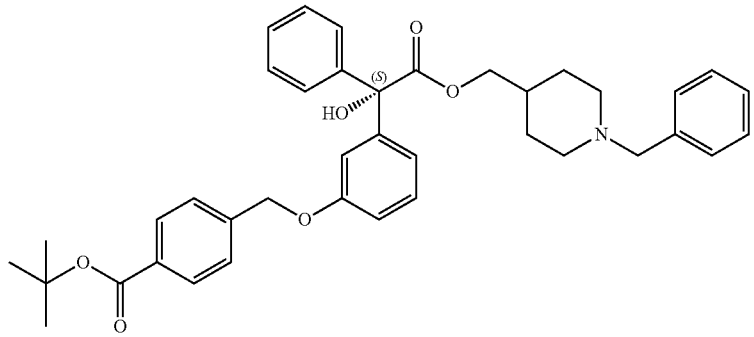

To a stirred solution of (S)-(1-benzylpiperidin-4-yl)methyl 2-hydroxy-2-(3-hydroxyphenyl)-2-phenylacetate (1.23 g, 2.84 mmol) in DMF (15 mL) was added potassium carbonate (0.785 g, 5.69 mmol) and the mixture stirred at room temperature for 5 minutes. tert-Butyl 4-(bromomethyl)benzoate (0.924 g, 6.83 mmol) was added and the reaction mixture was heated at 40° C. for 8 hours. Diluted with ethyl acetate and washed with aqueous sodium hydrogen carbonate (×2), brine and dried over anhydrous magnesium sulfate. The filtrate was evaporated under reduced pressure and the residue purified by flash column chromatography (eluent—100% DCM to 7:3 DCM/methanol) to afford the title compound (1.89 g, 100%).

$^1$H NMR (400 MHz, DMSO-$d_6$); δ 7.89 (d, J=8.4 Hz, 2H), 7.50 (d, J=8.4 Hz, 2H), 7.30-7.23 (m, 11H), 6.97-6.91 (m, 3H), 6.60 (s, 1H), 5.15 (s, 2H), 3.98 (d, J=6.3 Hz, 2H), 3.39 (s, 2H), 2.74-2.68 (m, 2H), 1.85-1.77 (m, 2H), 1.55 (s, 9H), 1.53-1.43 (m, 3H), 1.18-1.06 (m, 2H).

Step 5; (S)-4-((3-(2-((1-Benzylpiperidin-4-yl)methoxy)-1-hydroxy-2-oxo-1-phenylethyl)phenoxy)methyl)benzoic acid hydrochloride

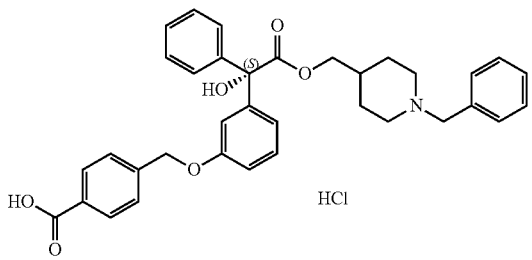

To a stirred solution of (S)-tert-butyl 4-((3-(2-((1-benzylpiperidin-4-yl)methoxy)-1-hydroxy-2-oxo-1-phenylethyl)phenoxy)methyl)benzoate (1.89 g, 3.04 mmol) in 1,4-dioxane (5 mL) was added a solution of HCl-dioxane (4M, 15 mL) and the reaction mixture stirred at room temperature for 18 hours. The solvent was evaporated under reduced pressure to afford the title compound (1.83 g, 100%).

$^1$H NMR (400 MHz, DMSO-$d_6$); δ 7.95 (d, J=8.3 Hz, 2H), 7.52 (d, J=8.3 Hz, 4H), 7.48-7.44 (m, 3H), 7.32 (dd, J=3.4, 3.4 Hz, 6H), 6.99-6.90 (m, 3H), 6.64 (s, 1H), 5.15 (s, 2H), 4.24-4.19 (m, 2H), 4.00 (d, J=6.4 Hz, 2H), 3.28 (s, 1H), 3.06 (s, 1H), 2.90-2.88 (m, 2H), 1.82 (s, 1H), 1.71 (d, J=13.2 Hz, 2H), 1.44 (d, J=11.7 Hz, 2H).

Procedure 8. Preparation of (S)-3-((3-(2-((1-benzylpiperidin-4-yl)methoxy)-1-hydroxy-2-oxo-1-phenylethyl)phenoxy)methyl)benzoic acid hydrochloride

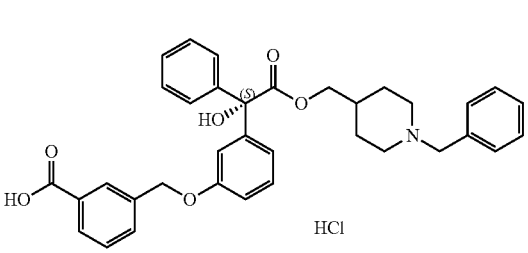

The title compound was prepared as in Procedure 7 with tert-butyl 3-(bromomethyl)benzoate replacing tert-butyl 4-(bromomethyl)benzoate in Step 4.

Procedure 9. Preparation of (S)-2-(3-(2-((1-benzylpiperidin-4-yl)methoxy)-1-hydroxy-2-oxo-1-phenylethyl)phenoxy)acetic acid hydrochloride

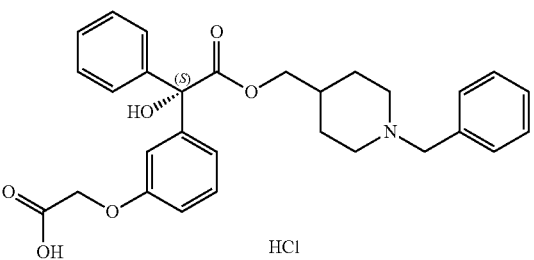

The title compound was prepared as in Procedure 7 with tert-butyl bromoacetate replacing tert-butyl 4-(bromomethyl)benzoate in Step 4.

Procedure 10. Preparation of (S)-(1-benzylpiperidin-4-yl)methyl 2-hydroxy-2-phenyl-2-(3-(piperidin-4-ylmethoxy)phenyl)acetate hydrochloride

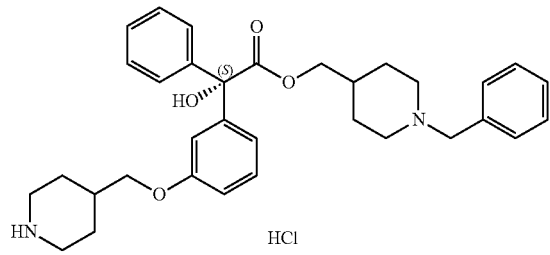

The title compound was prepared as in Procedure 7 with tert-butyl 4-(tosyloxymethyl)piperidine-1-carboxylate (as described in Example 1, Step 5) replacing tert-butyl 4-(bromomethyl)benzoate in Step 4.

Procedure 6. Preparation of (S)-(1-benzylpiperidin-4-yl)methyl 2-(3-(azetidin-3-ylmethoxy)phenyl)-2-hydroxy-2-phenylacetate 2,2,2-trifluoroacetate

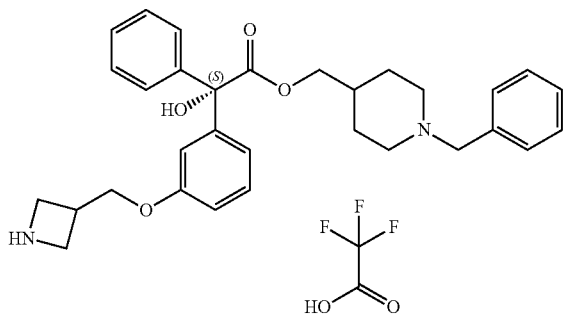

Step 1; (S)-tert-Butyl 3-((3-(2-((1-benzylpiperidin-4-yl)methoxy)-1-hydroxy-2-oxo-1-phenylethyl)phenoxy)methyl)azetidine-1-carboxylate

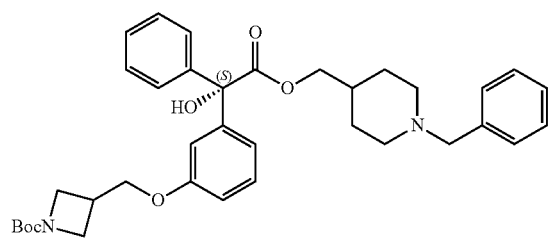

The title compound was prepared as in Procedure 7 with tert-butyl 3-(bromomethyl)azetidine-1-carboxylate replacing tert-butyl 4-(bromomethyl)benzoate in Step 4.

$^1$H NMR (400 MHz, DMSO-$d_6$); δ 7.35-7.21 (6H), 6.89 (dd, J=6.3, 6.3 Hz, 3H), 6.60 (s, 1H), 4.06-3.89 (m, 6H), 3.82 (d, J=6.8 Hz, 2H), 3.71 (d, J=7.2 Hz, 2H), 3.65-3.54 (m, 4H), 3.40 (s, 2H), 2.95-2.86 (m, 1H), 2.71 (d, J=11.8 Hz, 2H), 1.83 (dd, J=11.4, 11.4 Hz, 2H), 1.53-1.43 (m, 2H), 1.38 (s, 9H), 1.22-1.08 (m, 2H).

Step 2; (S)-(1-Benzylpiperidin-4-yl)methyl 2-(3-(azetidin-3-ylmethoxy)phenyl)-2-hydroxy-2-phenylacetate 2,2,2-trifluoroacetate

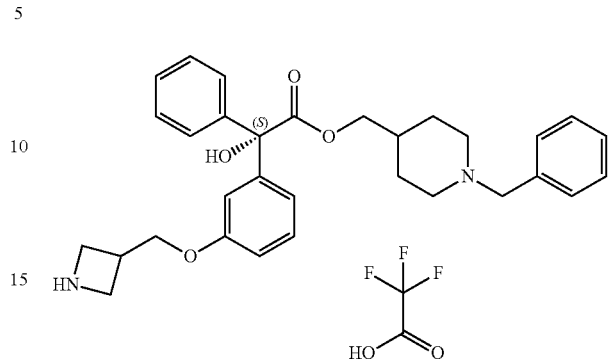

To a solution of (S)-tert-butyl 3-(3-(2-((1-benzylpiperidin-4-yl)methoxy)-1-hydroxy-2-oxo-1-phenylethyl)phenoxy)methyl)azetidine-1-carboxylate (0.388 g, 0.65 mmol) in DCM (2 mL) was added trifluoroacetic acid (2 mL). The reaction mixture was stirred at room temperature for 1 hour. The solvent was evaporated under reduced pressure and the title compound was used without further purification in subsequent steps.

Procedure 12. Preparation of (S)-(1-benzylpiperidin-4-yl)methyl 2-(3-(3-aminopropoxy)phenyl)-2-hydroxy-2-phenylacetate hydrochloride

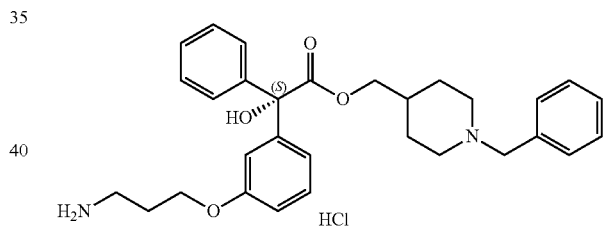

The title compound was prepared as in Procedure 7 with tert-butyl (3-bromopropyl)carbamate replacing tert-butyl 4-(bromomethyl)benzoate in Step 4.

Procedure 13. Preparation of (R)-(1-benzylpiperidin-4-yl)methyl 2-(3-(3-aminoethoxy)phenyl)-2-hydroxy-2-phenylacetate hydrochloride

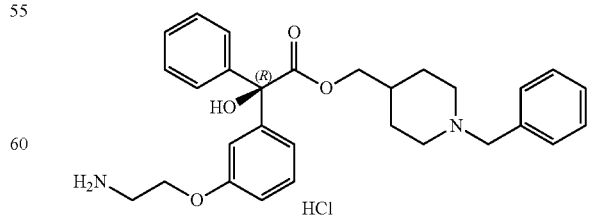

The title compound was prepared as in Procedure 7 with (R)-2-hydroxy-2-(3-hydroxyphenyl)-2-phenylacetic acid replacing (S)-2-hydroxy-2-(3-hydroxyphenyl)-2-phenylacetic acid in Step 1 and tert-butyl (2-chloroethyl)carbamate replacing tert-butyl 4-(bromomethyl)benzoate in Step 4.

Procedure 14, Preparation of (1-benzylpiperidin-4-yl)methyl 2-(3-(2-aminoethyl)phenyl)-2-hydroxy-2-phenylacetate Step 1; tert-Butyl 4-((2-hydroxy-2-(3-hydroxyphenyl)-2-phenylacetoxy)methyl)-piperidine-1-carboxylate

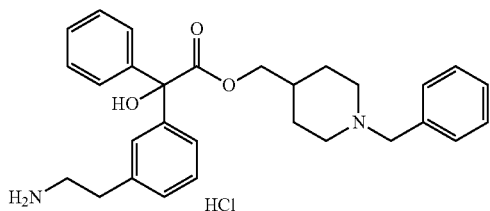 [SMILES: NCCc1cccc(C(O)(C(=O)OCC2CCN(Cc3ccccc3)CC2)c2ccccc2)c1 ; Cl]

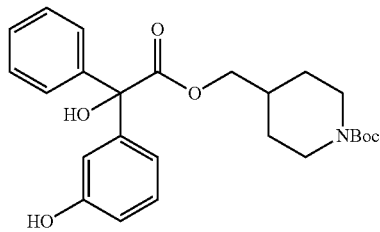 [SMILES: CC(C)(C)OC(=O)N1CCC(COC(=O)C(O)(c2ccccc2)c2cccc(O)c2)CC1]

To a stirred solution of tert-butyl 4-((2-(3-(benzyloxy)phenyl)-2-hydroxy-2-phenylacetoxy)methyl)piperidine-1-carboxylate (18.4 g, 34.6 mmol) in ethanol (300 mL) was added 10% Pd/C (4.6 g) and 1-methyl-1,4-cyclohexadiene (19.6 mL, 173.2 mmol). The reaction mixture was heated to reflux for two hours. The suspension was filtered through celite and the filtrate evaporated under reduced pressure to afford the title product (15.5 g, 100%).

$^1$H NMR (400 MHz, CDCl$_3$); δ 7.41-7.30 (m, 6H), 7.20 (dd, J=8.0, 8.0 Hz, 1H), 7.00 (s, 1H), 6.87 (s, 1H), 6.80 (dd, J=2.1, 8.0 Hz, 1H), 4.22 (s, 1H), 4.10 (d, J=5.9 Hz, 2H), 4.08-4.02 (m, 2H), 3.75-3.69 (m, 1H), 2.68-2.57 (m, 2H), 1.83-1.74 (m, 1H), 1.69-1.55 (m, 1H), 1.49 (d, J=12.7 Hz, 1H), 1.40 (s, 9H), 1.21-1.04 (m, 1H).

Step 2; tert-Butyl 4-((2-hydroxy-2-phenyl-2-(3-(((trifluoromethyl)sulfonyl)oxy)-phenyl)acetoxy)methyl)piperidine-1-carboxylate

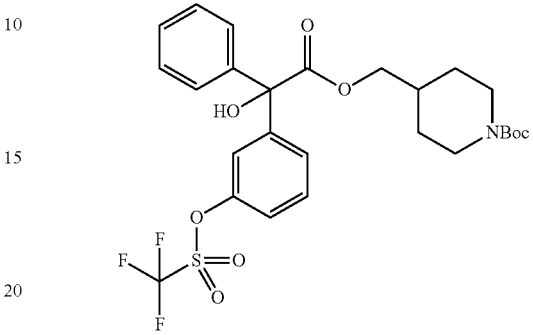

The title compound was prepared as described in Procedure 5 Step 3 with tert-butyl 4-((2-hydroxy-2-(3-hydroxyphenyl)-2-phenylacetoxy)methyl)piperidine-1-carboxylate replacing (R)-tert-Butyl (2-(8-(benzyloxy)-2-oxo-1,2-dihydroquinolin-5-yl)-2-((tert-butyldimethylsilyl)oxy)ethyl)(4-hydroxyphenethyl)carbamate. The product was used directly in the next step.

Step 3; Piperidin-4-ylmethyl 2-hydroxy-2-phenyl-2-(3-(((trifluoromethyl)sulfonyl)-oxy)phenyl)acetate hydrochloride

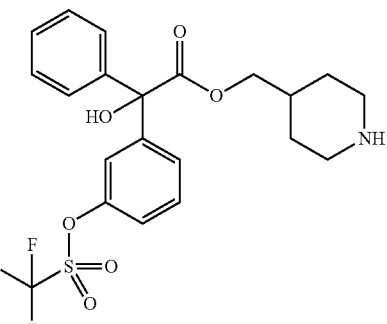

The title compound was prepared as described in Procedure 7 Step 2.

$^1$H NMR (400 MHz, DMSO-d$_6$); δ 7.57 (dd, J=8.0, 8.0 Hz, 1H), 7.49-7.46 (m, 2H), 7.41-7.31 (m, 6H), 7.05 (s, 1H), 4.06 (d, J=6.7 Hz, 2H), 3.21 (d, J=12.4 Hz, 2H), 2.85-2.75 (m, 2H), 1.93-1.85 (m, 1H), 1.69-1.60 (m, 2H), 1.36-1.25 (m, 2H).

Step 4; (1-Benzylpiperidin-4-yl)methyl 2-hydroxy-2-phenyl-2-(3-(((trifluoromethyl)sulfonyl)oxy)phenyl)acetate

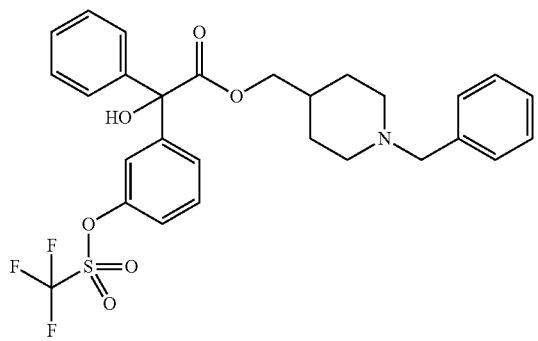 [SMILES: O=C(OCC1CCN(Cc2ccccc2)CC1)C(O)(c1ccccc1)c1cccc(OS(=O)(=O)C(F)(F)F)c1]

The title compound was prepared as described in Procedure 7 Step 3.

$^1$H NMR (400 MHz, CDCl$_3$); δ 7.52 (d, J=7.9 Hz, 1H), 7.44-7.39 (m, 2H), 7.37-7.21 (m, 11H), 4.33 (s, 1H), 4.12 (d, J=6.8 Hz, 2H), 3.49 (s, 2H), 3.46 (s, 2H), 2.82 (d, J=11.5 Hz, 2H), 1.92-1.84 (m, 2H), 1.52-1.44 (m, 1H), 1.27-1.15 (m, 2H).

Step 5; (1-Benzylpiperidin-4-yl)methyl 2-(3-(2-((tert-butoxycarbonyl)amino)-ethyl)phenyl)-2-hydroxy-2-phenylacetate

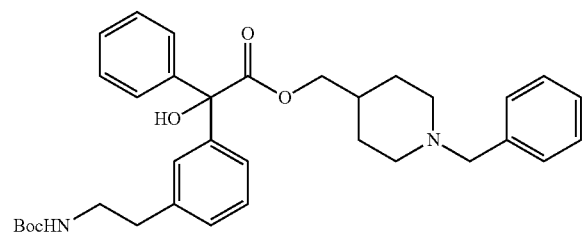 [SMILES: CC(C)(C)OC(=O)NCCc1cccc(C(O)(C(=O)OCC2CCN(Cc3ccccc3)CC2)c2ccccc2)c1]

A mixture of (1-benzylpiperidin-4-yl)methyl 2-hydroxy-2-phenyl-2-(3-(((trifluoromethyl)sulfonyl)oxy)phenyl)acetate (1.56 g, 2.77 mmol), potassium tert-butyl N-[2-(trifluoroboranuidyl)ethyl]carbamate (0.7 g, 2.79 mmol), palladium (II) acetate (0.09 g, 0.41 mmol), RuPhos (0.39 g, 0.83 mmol) and cesium carbonate (2.92 g, 8.3 mmol) in toluene/water (30 mL, 3 to 1) was thoroughly degassed with nitrogen and then heated at 95° C. for 16 hours. The reaction mixture was partitioned between DCM and brine. The organic phase passed through a hydrophobic frit and the filtrate evaporated under reduced pressure. The residue purified by flash column chromatography (eluent—100% hexane to 100% ethyl acetate) to afford the title compound (1.21 g, 78%).

Step 6: (1-Benzylpiperidin-4-yl)methyl 2-(3-(2-aminoethyl)phenyl)-2-hydroxy-2-phenylacetate hydrochloride

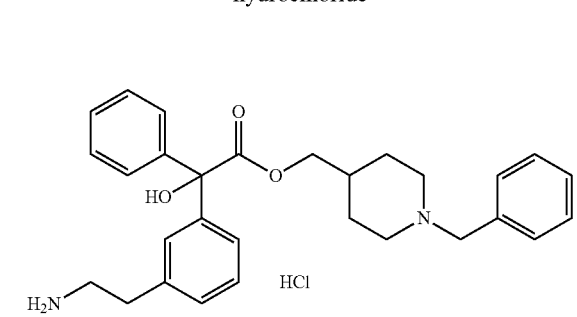

The title compound was prepared as in Procedure 7 Step 2.

Procedure 15. Preparation of 1-Benzylpiperidin-4-yl (S)-2-(3-((4-(aminomethyl)benzyl)oxy)phenyl)-2-hydroxy-2-phenylacetate dihydrochloride

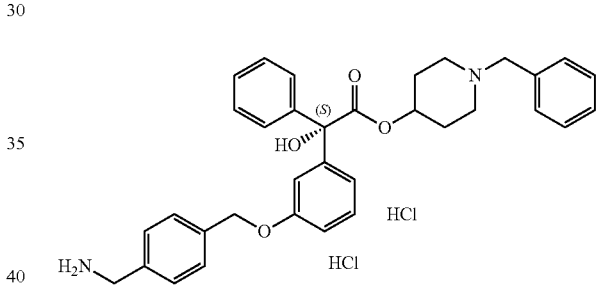

The title compound was prepared as in Procedure 6 with tert-butyl (4-(bromomethyl)benzyl)carbamate replacing tert-butyl 4-(bromomethyl)benzoate in Step 4.

Example 5. (S)-(1-Benzylpiperidin-4-yl)methyl 2-hydroxy-2-(3-((1-(4-(2-(((R)-2-hydroxy-2-(8-hydroxy-2-oxo-1,2-dihydroquinolin-5-yl)ethyl)amino)ethyl)benzoyl)piperidin-4-yl)methoxy)phenyl)-2-phenylacetate (Compound 31)

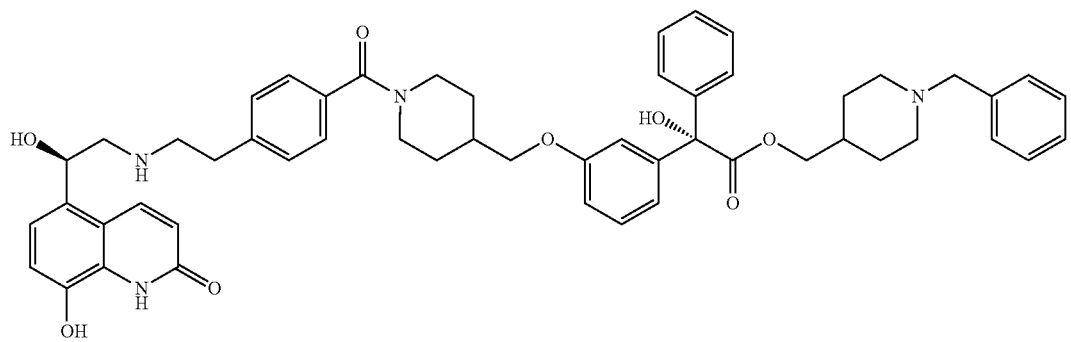 [SMILES: O=C(c1ccc(CCNC[C@H](O)c2ccc(O)c3[nH]c(=O)ccc23)cc1)N1CCC(COc2cccc([C@](O)(C(=O)OCC3CCN(Cc4ccccc4)CC3)c3ccccc3)c2)CC1]

To a stirred solution of (R)-4-(2-((tert-butoxycarbonyl)(2-((tert-butyldimethylsilyl)oxy)-2-(8-hydroxy-2-oxo-1,2-dihydroquinolin-5-yl)ethyl)amino)ethyl)benzoic acid (0.13 g, 0.23 mmol) and N,N-diisopropylethylamine (0.066 mL, 0.38 mmol) in DMF (2 mL) was added HATU (0.11 g, 0.29 mmol) and the mixture stirred at room temperature for 30 minutes, A solution of (S)-(1-benzylpiperidin-4-yl)methyl 2-hydroxy-2-phenyl-2-(3-(piperidin-4-ylmethoxy)phenyl) acetate hydrochloride (0.11 g, 0.19 mmol) in DMF (1 mL) was added and the reaction mixture stirred at room temperature for 18 hours. The reaction mixture was diluted with ethyl acetate and washed with water and brine (×2). The organic phase was dried over anhydrous magnesium sulfate and the filtrate was evaporated under reduced pressure. The residue was treated with a solution of HCl-dioxane (4M, 15 mL) and the reaction mixture stirred at room temperature for 18 hours. The solvent was evaporated under reduced pressure and the residue purified by reverse phase preparative HPLC, to afford the title compound (31).

The following compounds were prepared as described in Example 4 with the relevant acid coupled to the appropriate amine.

| N | Relevant acid | Relevant Amine | Structure |
|---|---|---|---|
| 32 | | | 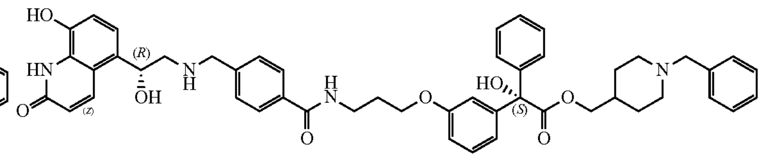 |
| 32A | | | 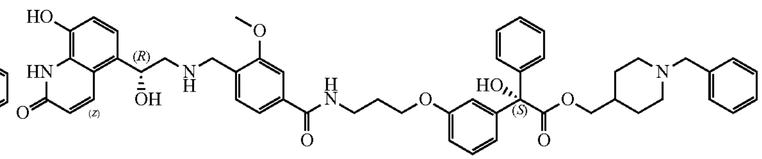 |
| 32B | | | 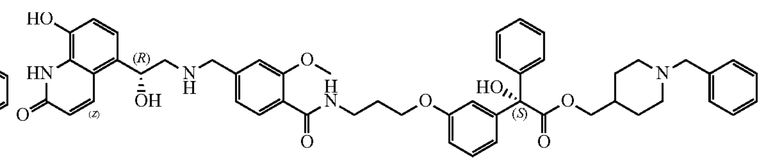 |
| 32C | | | 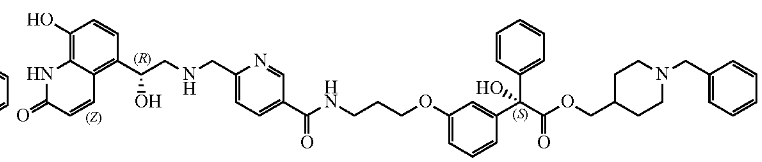 |

| N | Relevant acid | Relevant Amine | Structure |
|---|---|---|---|
| 32D | | | 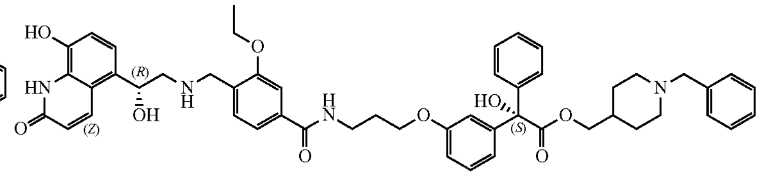 |
| 32E | | | 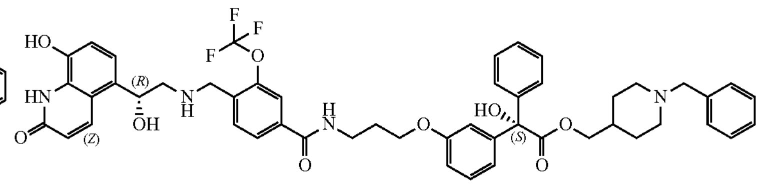 |
| 32F | | | 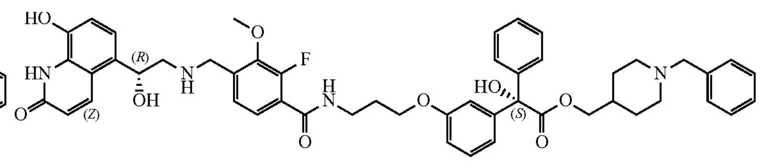 |
| 32G | | | 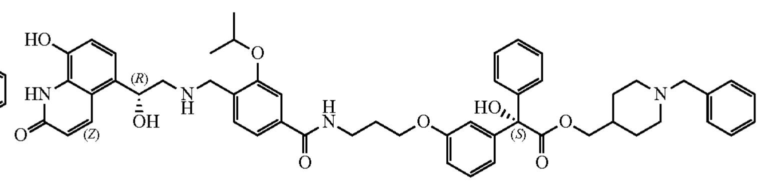 |

-continued

| N | Relevant acid | Relevant Amine | Structure |
|---|---|---|---|
| 32H | | | 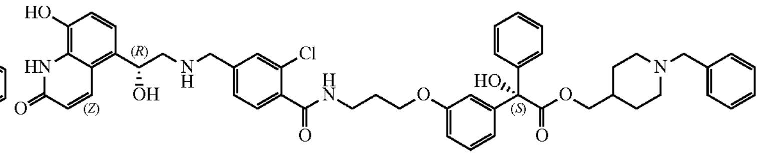 |
| 32I | | | 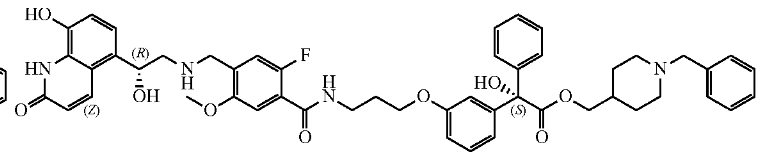 |
| 32J | | | 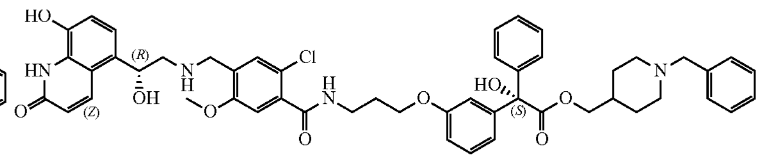 |
| 32K | | | 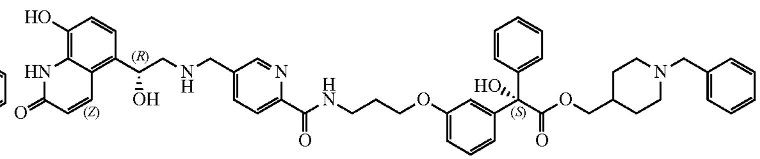 |
| 32L | | | 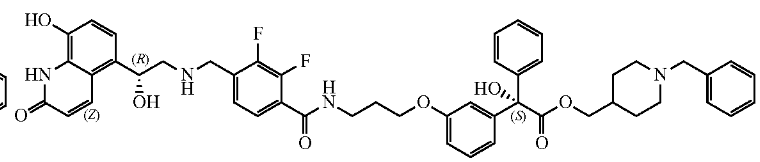 |

-continued

| N | Relevant acid | Relevant Amine | Structure |
|---|---|---|---|
| 32M | | | 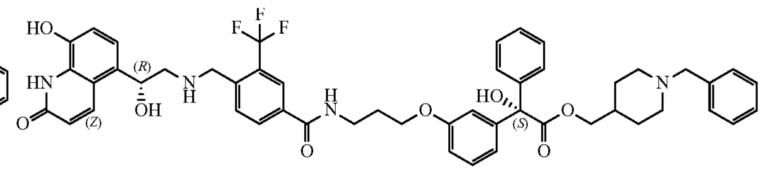 |
| 33 | | | 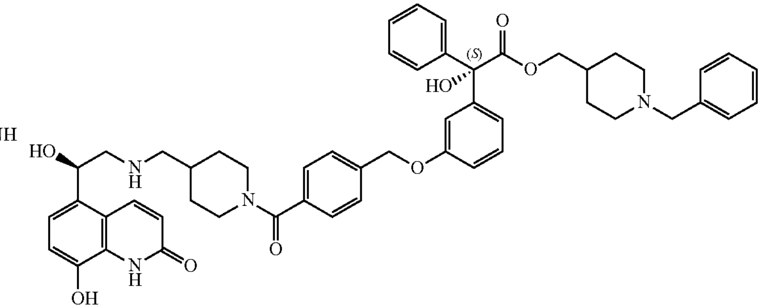 |
| 33A | | | 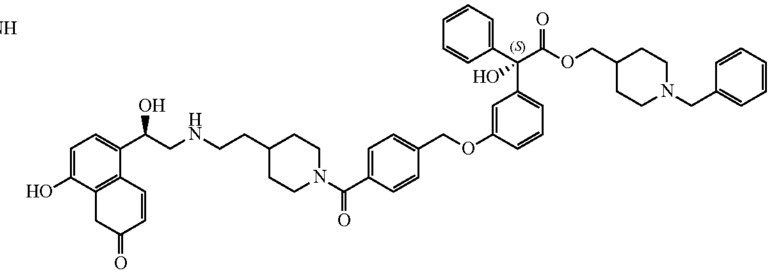 |
| 34 | | | 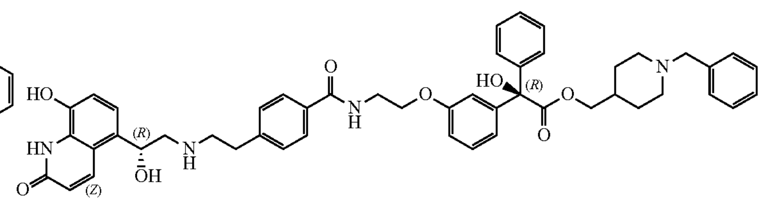 |

-continued

| N | Relevant acid | Relevant Amine | Structure |
|---|---|---|---|
| 35 | | | 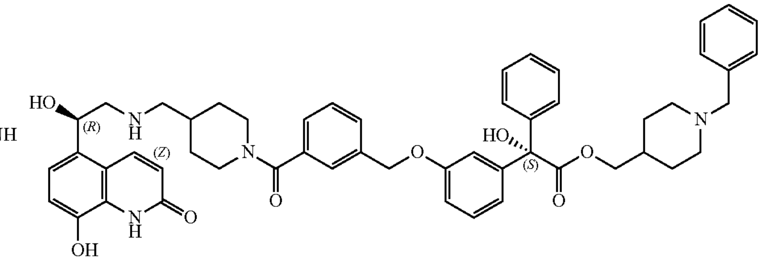 |
| 36 | | | 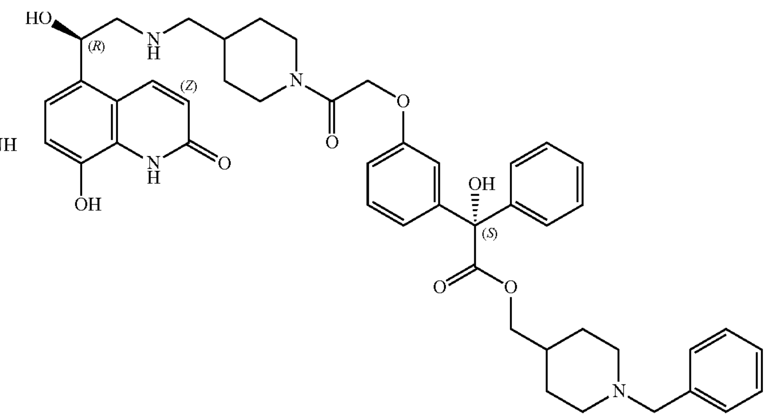 |

| N | Relevant acid | Relevant Amine | Structure |
|---|---|---|---|
| 36A | | | 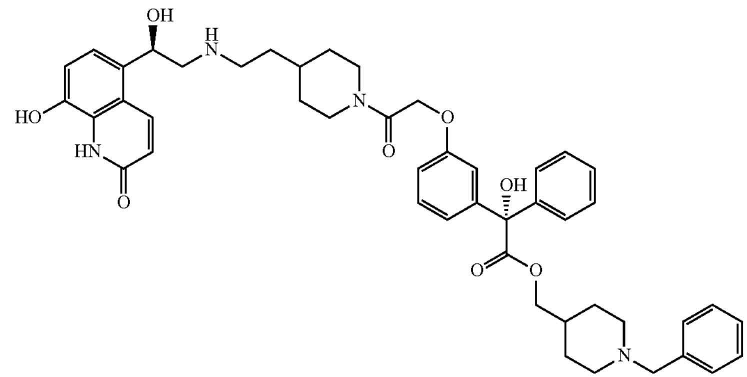 [SMILES: O=C(COc1cccc([C@](O)(C(=O)OCC2CCN(Cc3ccccc3)CC2)c2ccccc2)c1)N1CCC(CCNC[C@H](O)c2ccc(O)c3[nH]c(=O)ccc23)CC1] |
| 37 | | | 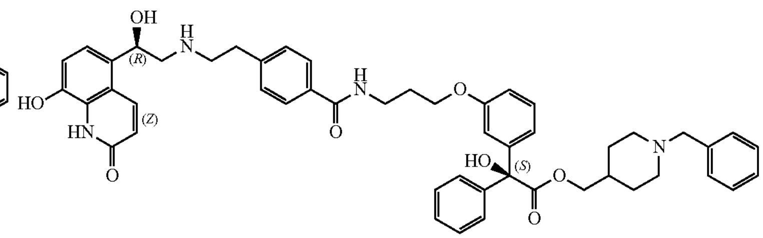 |
| 38 | | | 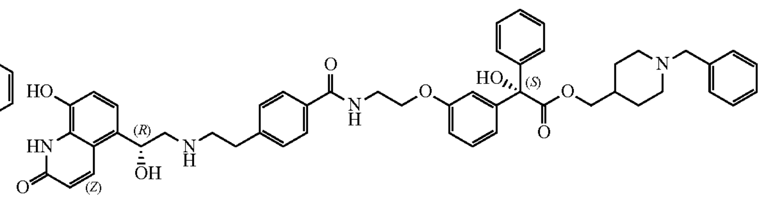 |

| N | Relevant acid | Relevant Amine | Structure |
|---|---|---|---|
| 39 | | | 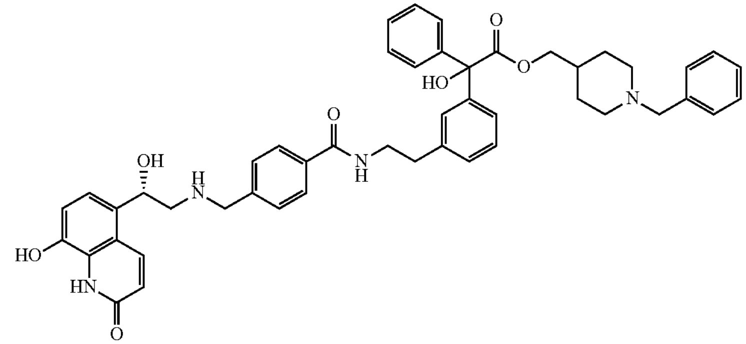 [SMILES: O=C(NCCc1cccc(C(O)(C(=O)OCC2CCN(Cc3ccccc3)CC2)c2ccccc2)c1)c1ccc(CNC[C@@H](O)c2ccc(O)c3[nH]c(=O)ccc23)cc1] |
| 40 | | | 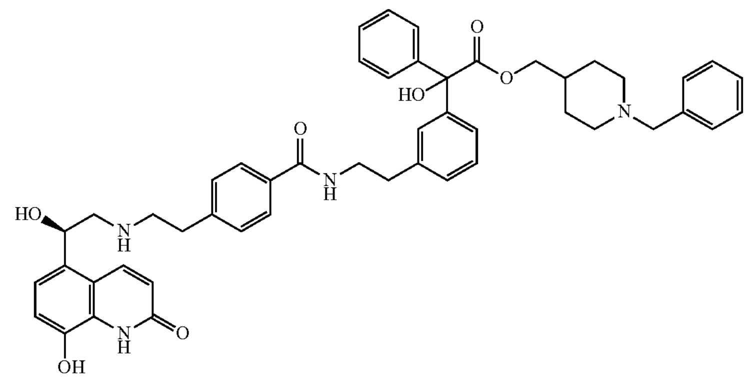 [SMILES: O=C(NCCc1cccc(C(O)(C(=O)OCC2CCN(Cc3ccccc3)CC2)c2ccccc2)c1)c1ccc(CCNC[C@H](O)c2ccc(O)c3[nH]c(=O)ccc23)cc1] |
| 41 | | | 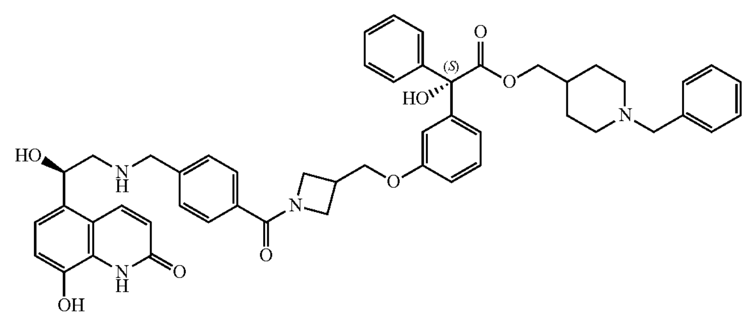 |

| N | Relevant acid | Relevant Amine | Structure |
|---|---|---|---|
| 42 | | | 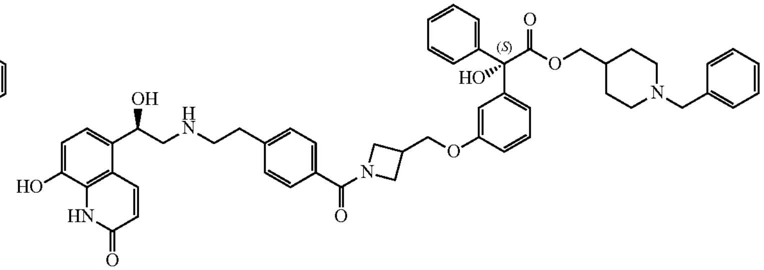 |
| 42A | | | 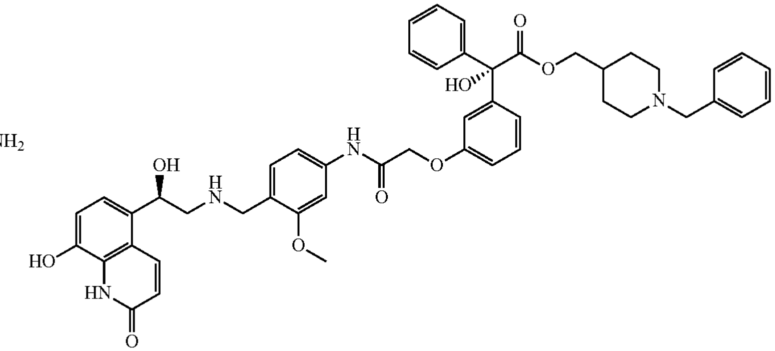 |
| 42B | | | 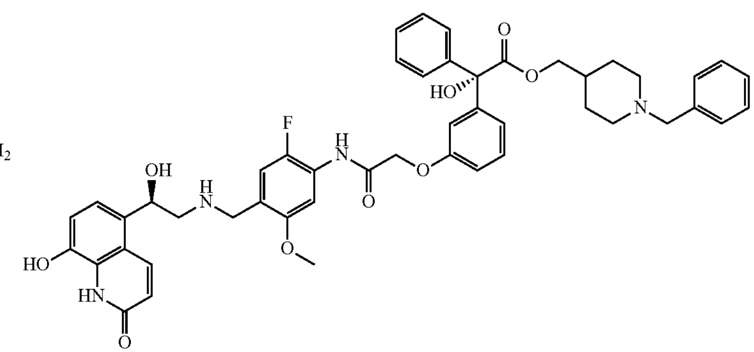 |

| N | Relevant acid | Relevant Amine | Structure |
|---|---|---|---|
| 42C | | | 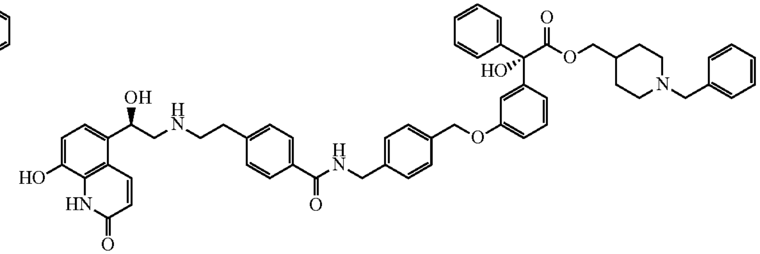 |
| 42D | | | 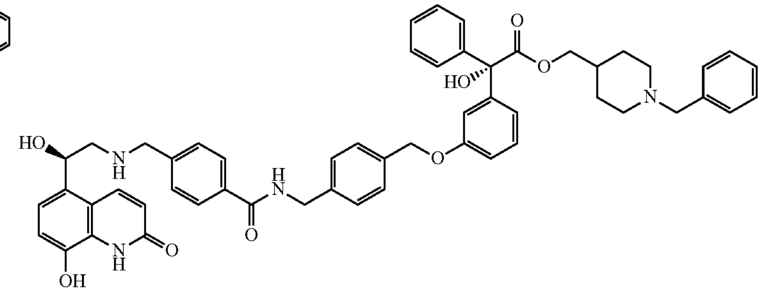 |
| 42E | | | 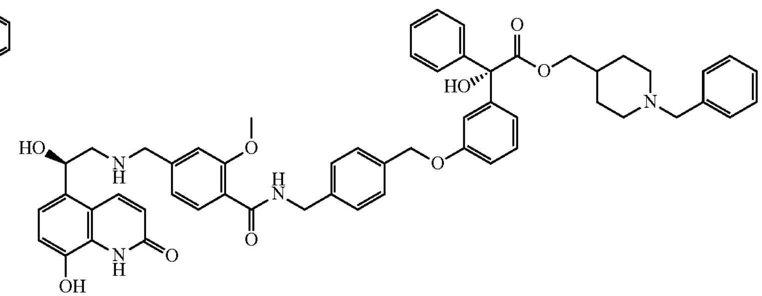 |

-continued

| N | Relevant acid | Relevant Amine | Structure |
|---|---|---|---|
| 42F | | | 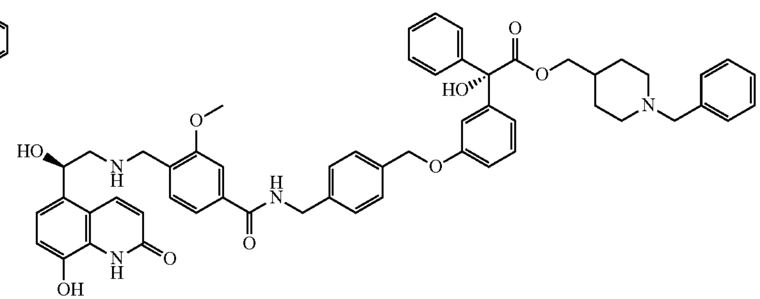 |

| N | Rt (min) | Method | NMR data (400 MHz) | Salt (2 eq unless stated) |
|---|---|---|---|---|
| 31 | 7.32 | 7 | (DMSO-d$_6$, 90° C.); δ 8.25 (s, 1H), 8.18 (d, J = 9.9 Hz, 1H), 7.33-7.22 (m, 15H), 7.08 (d, J = 8.2 Hz, 1H), 6.93 (d, J = 8.0 Hz, 1H), 6.89-6.86 (m, 3H), 6.52 (d, J = 9.9 Hz, 1H), 5.13-5.08 (m, 1H), 4.55-4.42 (m, 1H), 4.02-3.99 (m, 2H), 3.79 (d, J = 6.1 Hz, 2H), 3.67-3.55 (m, 1H), 3.39 (s, 2H), 2.95-2.85 (m, 4H), 2.84-2.76 (m, 3H), 2.75-2.67 (m, 2H), 2.04-1.95 (m, 1H), 1.87-1.67 (m, 4H), 1.53-1.42 (m, 3H), 1.24-1.07 (m, 4H). | mono Formate |
| 32 | 7.18 | 7 | (MeOD): δ 8.50 (s, 2H), 8.29 (d, J = 9.9 Hz, 1H), 7.87 (d, J = 8.4 Hz, 2H), 7.56 (d, J = 8.4 Hz, 2H), 7.40 (s, 6H), 7.39-7.32 (m, 4H), 7.28-7.23 (m, 2H), 7.03-6.96 (m, 3H), 6.90 (dd, J = 2.4, 8.2 Hz, 1H), 6.64 (d, J = 9.8 Hz, 1H), 5.36 (dd, J = 4.4, 8.8 Hz, 1H), 4.21 (s, 2H), 4.11-4.03 (m, 4H), 3.94 (s, 2H), 3.57 (dd, J = 6.9, 6.9 Hz, 2H), 3.22-3.09 (m, 4H), 2.55 (dd, J = 10.4, 12.3 Hz, 2H), 2.05 (s, 3H), 1.84-1.78 (m, 1H), 1.70 (d, J = 12.9 Hz, 2H), 1.36 (q, J = 12.5 Hz, 2H). | Formate |
| 32A | 2.47 | 11 | (MeOD); δ 8.47 (s, 2H), 8.26 (d, J = 9.9 Hz, 1H), 7.54 (s, 1H), 7.51-7.25 (m, 14H), 7.04 (d, J = 8.2 Hz, 1H), 7.00-6.96 (m, 2H), 6.91 (dd, J = 2.2, 8.0 Hz, 1H), 6.65 (d, J = 9.8 Hz, 1H), 5.46-5.38 (m, 1H), 4.34 (s, 2H), 4.13-4.04 (m, 6H), 3.97 (s, 3H), 3.59 (dd, J = 6.9, 6.9 Hz, 2H), 3.29 (d, J = 12.7 Hz, 2H), 3.22-3.18 (m, 2H), 177-2.67 (m, 2H), 2.15-2.07 (m, 2H), 1.93-1.82 (m, 1H), 1.74 (d, J = 13.6 Hz, 2H), 1.48-1.37 (m, 2H). | Formate |
| 32B | 2.51 | 11 | (MeOD); δ 8.53 (s, 1H), 8.30 (d, J = 9.9 Hz, 1H), 7.90 (d, J = 7.9 Hz, 1H), 7.41-7.23 (m, 13H), 7.14 (dd, J = 1.2, 7.9 Hz, 1H), 7.04-6.98 (m, 3H), 6.93 (dd, J = 2.0, 8.2 Hz, 1H), 6.64 (d, J = 9.9 Hz, 1H), 5.37 (dd, J = 4.8, 8.3 Hz, 1H), 4.17 (s, 2H), 4.11-4.05 (m, 4H), 3.93 (s, 2H), 3.89 (s, 3H), 3.60 (t, J = 6.7 Hz, 2H), 3.20-3.09 (m, 4H), 2.53 (dd, J = 10.2, 12.2 Hz, 2H), 2.13-2.06 (m, 2H), 1.86-1.73 (m, 1H), 1.71-1.63 (m, 2H), 1.42-1.29 (m, 2H). | mono-formate |
| 32C | 2.46 | 11 | (MeOD); δ 8.99 (d, J = 1.5 Hz, 1H), 8.50 (s, 1H), 8.36 (d, J = 9.9 Hz, 1H), 8.20 (dd, J = 2.3, 8.1 Hz, 1H), 7.54 (d, J = 8.3 Hz, 1H), 7.40-7.31 (m, 12H), 7.02 (d, J = 8.1 Hz, 1H), 6.99-6.95 (m, 2H), 6.91-6.88 (m, 1H), 6.66 (d, J = 9.9 Hz, 1H), 5.39 (dd, J = 5.2, 7.7 Hz, 1H), 4.28 (s, 2H), 4.12-4.04 (m, 4H), 3.88 (s, 2H), 3.59 (dd, J = 6.9, 6.9 Hz, 2H), 3.18-3.11 (m, 4H), 2.53-2.43 (m, 2H), 2.14-2.05 (m, 2H), 1.83-1.76 (m, 1H), 1.71-1.64 (m, 2H), 1.40-1.30 (m, 2H). | mono-formate |
| 32D | 2.53 | 11 | (MeOD); δ 8.52 (s, 1H), 8.26 (d, J = 9.9 Hz, 1H), 7.46 (s, 1H), 7.42 (s, 2H), 7.41-7.35 (m, 7H), 7.35-7.30 (m, 3H), 7.24 (dd, J = 8.3, 8.3 Hz, 2H), 7.03-6.94 (m, 3H), 6.90 (d, J = 8.6 Hz, 1H), 6.62 (d, J = 9.6 Hz, 1H), 5.33 (dd, J = 6.6, 6.6 Hz, 1H), 4.21-4.14 (m, 4H), 4.11-4.03 (m, 4H), 3.80 (s, 2H), 3.57 (dd, J = 6.8, 6.8 Hz, 2H), 3.14-3.04 (m, 4H), 2.37 (dd, J = 11.9, 11.9 Hz, 2H), 2.12-2.06 (m, 2H), 1.77-1.70 (m, 1H), 1.68-1.60 (m, 2H), 1.44 (t, J = 6.8 Hz, 3H), 1.37-1.27 (m, 2H). | mono-formate |
| 32E | 2.55 | 11 | (MeOD); δ 8.39 (s, 2H), 8.33 (d, J = 9.9 Hz, 1H), 7.85-7.81 (m, 2H), 7.69 (d, J = 8.1 Hz, 1H), 7.45 (s, 5H), 7.41-7.30 (m, 5H), 7.28-7.22 (m, 2H), 7.03-6.95 (m, 3H), 6.90 (dd, J = 2.4, 8.5 Hz, 1H), 6.63 (d, J = 9.9 Hz, 1H), 5.32 (dd, J = 4.3, 8.6 Hz, 1H), 4.16-4.10 (m, 6H), 4.05 (t, J = 6.1 Hz, 2H), 3.57 (t, J = 6.9 Hz, 2H), 3.35 (br s, 2H), 3.10-3.00 (m, 4H), 2.86-2.77 (m, 2H), 2.13-2.06 (m, 2H), 1.95-1.88 (m, 1H), 1.76 (d, J = 13.4 Hz, 2H), 1.49-1.38 (m, 2H). | formate |
| 32F | 2.51 | 11 | (MeOD); δ 8.43 (s, 2H), 8.31 (d, J = 9.6 Hz, 1H), 7.45 (s, 5H), 7.42-7.24 (m, 9H), 7.05-6.96 (m, 3H), 6.92 (dd, J = 2.5, 8.3 Hz, 1H), 6.66 (d, J = 9.9 Hz, 1H), 5.42-5.37 (m, 1H), 4.27 (s, 2H), 4.14-4.04 (m, 9H), 3.58 (dd, J = 6.8, 6.8 Hz, 2H), 3.32-3.27 (m, 2H), 3.14 (d, J = 6.8 Hz, 2H), 2.83-2.73 (m, 2H), 2.13-2.04 (m, 2H), 1.95-1.86 (m, 1H), 1.76 (d, J = 12.6 Hz, 2H), 1.48-1.38 (m, 2H). | formate |
| 32G | 2.55 | 11 | (MeOD); δ 8.36 (s, 2H), 8.14 (d, J = 9.9 Hz, 1H), 7.39 (s, 1H), 7.35-7.18 (m, 12H), 7.15-7.10 (m, 2H), 6.92-6.83 (m, 3H), 6.78 (dd, J = 2.1, 8.0 Hz, 1H), 6.52 (d, J = 9.9 Hz, 1H), 5.23 (dd, J = 4.5, 8.6 Hz, 1H), 4.71-4.64 (m, 1H), 4.12 (d, J = 2.8 Hz, 2H), 4.00-3.91 (m, 4H), 3.82 (s, 2H), 3.45 (dd, J = 6.9, 6.9 Hz, 2H), 3.09-3.02 (m, 4H), 2.43 (dd, J = 11.0, 12.0 Hz, 2H), 2.01-1.95 (m, 2H), 1.74-1.67 (m, 1H), 1.58 (d, J = 13.1 Hz, 2H), 1.28-1.23 (m, 8H). | formate |
| 32H | 2.49 | 11 | (MeOD); δ 8.46 (s, 2H), 8.32 (d, J = 9.9 Hz, 1H), 7.58 (d, J = 1.3 Hz, 1H), 7.46-7.23 (m, 14H), 7.04-6.96 (m, 3H), 6.92 (dd, J = 2.1, 8.0 Hz, 1H), 6.66 (d, J = 9.9 Hz, 1H), 5.34 (dd, J = 4.2, 9.0 Hz, 1H), 4.14-4.04 (m, 8H), 3.56 (dd, J = 6.7, 6.7 Hz, 2H), 3.28-3.22 (m, 2H), 3.06-3.01 (m, 2H), 2.75-2.65 (m, 2H), 2.09-2.05 (m, 2H), 1.91-1.83 (m, 1H), 1.77-1.71 (m, 2H), 1.45-1.35 (m, 2H). | formate |
| 32I | 2.48 | 11 | (MeOD) d 8.46 (s, 2H), 8.30 (d, J = 9.9 Hz, 1H), 7.43-7.31 (m, 12H), 7.28-7.23 (m, 2H), 7.04-6.96 (m, 3H), 6.91 (dd, J = 2.1, 8.0 Hz, 1H), 6.65 (d, J = 9.9 Hz, 1H), 5.36 (t, J = 6.6 Hz, 1H), 4.17 (s, 2H), 4.13-4.04 (m, 4H), 4.00 (s, 2H), 3.89 (s, 3H), 3.59 (dd, J = 6.7, 6.7 Hz, 2H), 3.23 (d, J = 12.1 Hz, 2H), 3.10 (d, J = 6.1 Hz, 2H), 2.67-2.58 (m, 2H), 2.10-2.05 (m, 2H), 1.90-1.82 (m, 1H), 1.72 (d, J = 12.6 Hz, 2H), 1.43-1.32 (m, 2H). | formate |
| 32J | 2.48 | 11 | (MeOD); δ 8.50 (s, 2H), 8.30 (d, J = 9.0 Hz, 1H), 7.45 (s, 1H), 7.41-7.32 (m, 12H), 7.09 (s, 1H), 7.04-6.96 (m, 3H), 6.92 (dd, J = 2.0, 8.1 Hz, 1H), 6.66 (d, J = 9.9 Hz, 1H), 5.34 (dd, J = 5.2, 8.0 Hz, 1H), 4.13-4.06 (m, 6H), 3.94 (s, 2H), 3.87 (s, 3H), 3.57 (t, J = 6.8, 6.8 Hz, 2H), 3.22-3.09 (m, 2H), 3.08-3.04 (m, 2H), 2.57 (dd, J = 11.7, 2H), 2.14-2.05 (m, 2H), 1.88-1.80 (m, 1H), 1.68 (d, J = 12.1 Hz, 2H), 1.42-1.32 (m, 2H). | formate |
| 32K | 2.47 | 11 | (MeOD); δ 8.66 (d, J = 1.5 Hz, 1H), 8.42 (s, 2H), 8.31 (d, J = 9.9 Hz, 1H), 8.10 (d, J = 8.1 Hz, 1H), 8.02 (dd, J = 2.1, 8.0 Hz, 1H), 7.44-7.37 (m, 6H), | formate |

| N | Rt (min) | Method | NMR data (400 MHz) | Salt (2 eq unless stated) |
|---|---|---|---|---|
| | | | 7.37-7.22 (m, 6H), 7.10 (dd, J = 2.0, 2.0 Hz, 1H), 7.02 (d, J = 8.3 Hz, 1H), 6.97-6.91 (m, 2H), 6.63 (d, J = 9.9 Hz, 1H), 5.34 (dd, J = 4.5, 8.3 Hz, 1H), 4.18 (s, 2H), 4.13-4.05 (m, 6H), 3.62 (t, J = 6.6, 6.6 Hz, 2H), 3.29-3.23 (m, 2H), 3.12-3.06 (m, 2H), 2.69 (dd, J = 11.5, 11.5 Hz, 2H), 2.14-2.06 (m, 2H), 1.86-1.80 (m, 1H), 1.72 (d, J = 13.6 Hz, 2H), 1.43-1.33 (m, 2H). | |
| 32L | 2.49 | 11 | (MeOD); δ 8.50 (s, 1H), 8.34 (d, J = 9.9 Hz, 1H), 7.47-7.42 (m, 2H), 7.42-7.37 (m, 6H), 7.36-7.21 (m, 6H), 7.02-6.96 (m, 3H), 6.92-6.89 (m, 1H), 6.64 (d, J = 9.9 Hz, 1H), 5.27 (dd, J = 4.0, 8.6 Hz, 1H), 4.13-4.01 (m, 6H), 3.95 (s, 2H), 3.57 (t, J = 6.8 Hz, 2H), 3.22-3.15 (m, 2H), 2.99-2.86 (m, 2H), 2.57 (dd, J = 10.0, 12.5 Hz, 2H), 2.12-2.05 (m, 2H), 1.88-1.79 (m, 1H), 1.69 (d, J = 12.4 Hz, 2H), 1.42-1.32 (m, 2H). | mono-formate |
| 32M | 2.53 | 11 | (MeOD) d 8.48 (s, 1H), 8.33 (d, J = 9.9 Hz, 1H), 8.17 (d, J = 1.3 Hz, 1H), 8.04 (dd, J = 1.4, 8.0 Hz, 1H), 7.80 (d, J = 8.1 Hz, 1H), 7.43-7.36 (m, 7H), 7.35-7.29 (m, 3H), 7.27-7.22 (m, 2H), 7.02-6.96 (m, 3H), 6.91-6.88 (m, 1H), 6.63 (d, J = 9.9 Hz, 1H), 5.27 (dd, J = 4.2, 8.5 Hz, 1H), 4.14-4.09 (m, 4H), 4.05 (t, J = 6.0 Hz, 2H), 4.01 (s, 2H), 3.58 (t, J = 6.8 Hz, 2H), 3.24 (d, J = 12.1 Hz, 2H), 3.01-2.89 (m, 2H), 2.68-2.60 (m, 2H), 2.13-2.05 (m, 2H), 1.90-1.82 (m, 1H), 1.71 (d, J = 12.9 Hz, 2H), 1.44-1.34 (m, 2H). | mono-formate |
| 33 | 7.28 | 7 | (DMSO-d$_6$, 90° C.); δ 8.23 (s, 2H), 8.19 (d, J = 10.1 Hz, 1H), 7.46 (d, J = 8.3 Hz, 2H), 7.38-7.25 (m, 13H), 7.10 (d, J = 8.2 Hz, 1H), 6.98-6.91 (m, 4H), 6.53 (d, J = 9.9 Hz, 1H), 5.19-5.43 (m, 1H), 5.09 (s, 2H), 4.53-4.40 (m, 1H), 4.00 (d, J = 6.1 Hz, 2H), 3.62-3.50 (m, 1H), 3.40 (s, 2H), 3.06-2.95 (m, 1H), 2.84 (d, J = 6.4 Hz, 2H), 2.76-2.63 (m, 4H), 1.88-1.61 (m, 5H), 1.56-1.43 (m, 3H), 1.17-1.09 (m, 4H). | Formate |
| 33A | 2.52 | 1 | (DMSO-d$_6$); δ 8.35 (s, 2H), 8.26-824 (m, 1H), 7.51 (d, J = 8.1 Hz, 2H), 7.18-7.26 (m, 15 H), 7.19-7.12 (m, 1H), 7.05-6.96 (m, 3H), 6.61-6.59 (m, 1H), 5.31 (d, J = 6.6 Hz, 1H), 5.14 (s, 2H), 4.54-4.53 (m, 1H), 4.05 (d, J = 6.3 Hz, 2H), 3.62-3.58 (m, 1H), 3.23 (s, 2H), 3.04-2.78 (m, 8H), 1.93-1.84 (m, 2H), 1.81-1.76 (m, 1H), 1.59-1.52 (m, 6H), 1.24-1.13 (m, 4H). | Formate |
| 34 | 7.39 | 7 | (DMSO-d$_6$, 90° C.); δ 8.63 (t, J = 7.2 Hz, 1H), 8.22 (s, 2H), 8.17 (d, J = 9.9 Hz, 1H), 7.80 (d, J = 8.3 Hz, 2H), 7.34-7.20 (m, 11H), 7.18-7.14 (m, 2H), 7.10 (d, J = 8.3 Hz, 1H), 6.95 (d, J = 8.2 Hz, 1H), 6.92-6.89 (m, 3H), 6.75 (d, J = 8.3 Hz, 2H), 6.53 (d, J = 9.9 Hz, 1H), 5.15 (t, J = 6.3 Hz, 1H), 4.08-3.97 (m, 4H), 3.64-3.58 (m, 2H), 3.00-2.90 (m, 2H), 2.86 (d, J = 6.5 Hz, 4H), 2.71 (d, J = 11.4 Hz, 2H), 1.84-1.78 (m, 2H), 1.53-1.44 (m, 3H), 1.16-1.06 (m, 2H). | Formate |
| 35 | 2.50 | 11 | (DMSO--d$_6$); δ 10.54-10.48 (m, 2H), 9.57-9.47 (m, 1H), 8.64-8.64 (m, 2H), 8.18 (d, J = 9.9 Hz, 1H), 7.52-7.41 (m, 8H), 7.36-7.24 (m, 6H), 7.16 (d, J = 8.2 Hz, 1H), 7.02-6.95 (m, 3H), 6.92 (d, J = 7.7 Hz, 1H), 6.73-6.63 (m, 1H), 6.59 (d, J = 9.9 Hz, 1H), 6.25-6.14 (m, 1H), 5.39-5.33 (m, 1H), 5.10 (s, 2H), 4.54-4.42 (m, 1H), 4.26 (dt, J = 6.0, 18.4 Hz, 2H), 4.00 (d, J = 6.4 Hz, 2H), 3.54-3.54 (m, 1H), 3.37-3.29 (m, 2H), 3.14-3.05 (m, 3H), 3.00-2.85 (m, 4H), 2.10-2.04 (m, 1H), 1.90-1.79 (m, 2H), 1.77-1.64 (m, 3H), 1.40-1.31 (m, 2H), 1.27-1.11 (m, 3H). | TFA |
| 36 | 2.38 | 11 | (DMSO-d$_6$, 100° C.); δ 8.24 (d, J = 9.9 Hz, 1H), 7.53-7.49 (m, 5H), 7.44-7.25 (m, 6H), 7.20 (d, J = 8.3 Hz, 1H), 7.07-7.01 (m, 3H), 6.93-6.89 (m, 1H), 6.61 (d, J = 9.9 Hz, 1H), 5.43 (dd, J = 4.7, 8.3 Hz, 1H), 4.75 (s, 2H), 4.28 (s, 2H), 4.14-4.10 (m, 3H), 3.40-3.30 (m, 2H), 3.23-3.19 (m, 2H), 3.05-2.88 (m, 6H), 2.14-2.05 (m, 1H), 2.00-1.76 (m, 6H), 1.59-1.47 (m, 2H), 1.33-1.18 (m, 2H). | TFA |
| 36A | 2.53 | 11 | (DMSO-d$_6$); δ 8.35 (s, 2H), 8.26 (d, J = 9.9 Hz, 1H), 7.39-7.28 (m, 12H), 7.18 (d, J = 8.3 Hz, 1H), 7.03 (d, J = 8.1 Hz, 1H), 6.96 (d, J = 8.3 Hz, 1H), 6.93-6.87 (m, 2H), 6.60 (d, J = 9.9 Hz, 1H), 5.31 (dd, J = 3.5, 8.8 Hz, 1H), 4.78 (d, J = 4.3 Hz, 2H), 4.32 (d, J = 12.1 Hz, 1H), 4.05 (d, J = 6.3 Hz, 2H), 3.83 (d, J = 14.1 Hz, 1H), 3.23 (s, 2H), 3.05-2.86 (m, 5H), 2.78 (d, J = 11.4 Hz, 2H), 1.93-1.85 (m, 2H), 1.69 (d, J = 12.9 Hz, 2H), 1.58-1.48 (m, 7H), 1.23-1.12 (m, 3H), 1.00-0.97 (m, 1H). | Formate |
| 37 | 2.48 | 11 | (MeOD); δ 8.37 (d, J = 9.9 Hz, 1H), 7.83 (d, J = 8.3 Hz, 2H), 7.52-7.48 (m, 6H), 7.44-7.23 (m, 9H), 7.05 (d, J = 8.2 Hz, 1H), 6.99-6.94 (m, 2H), 6.91 (dd, J = 2.3, 8.2 Hz, 1H), 6.70 (d, J = 9.9 Hz, 1H), 5.42 (dd, J = 5.5, 8.0 Hz, 1H), 4.29 (dd, J = 6.6, 24.6 Hz, 2H), 4.12-4.00 (m, 4H), 3.56 (dd, J = 6.9, 6.9 Hz, 2H), 3.50-3.35 (m, 4H), 3.31-3.28 (m, 2H), 3.20-3.10 (m, 2H), 2.97 (dd, J = 10.7, 12.7 Hz, 2H), 2.11-2.04 (m, 2H), 1.94 (dd, J = 3.1, 8.9 Hz, 1H), 1.83 (m, 2H), 1.47-1.40 (m, 2H). | TFA |
| 38 | 2.46 | 11 | (MeOD); δ 8.37 (d, J = 9.9 Hz, 1H), 7.83 (d, J = 8.3 Hz, 2H), 7.52-7.45 (m, 6H), 7.44-7.39 (m, 3H), 7.39-7.25 (m, 5H), 7.06-6.93 (m, 4H), 6.70 (d, J = 9.8 Hz, 1H), 5.42 (dd, J = 5.6, 7.9 Hz, 1H), 4.26 (s, 2H), 4.16-4.09 (m, 4H), 3.75 (dd, J = 5.7, 5.7 Hz, 2H), 3.50-3.35 (m, 5H), 3.18-3.10 (m, 2H), 2.96 (dd, J = 12.5, 12.5 Hz, 2H), 2.00-1.78 (m, 4H), 1.50-1.35 (m, 2H). | TFA |
| 39 | 2.41 | 11 | (MeOD); δ 8.28 (d, J = 9.9 Hz, 1H), 7.86 (d, J = 8.2 Hz, 1H), 7.63 (d, J = 8.4 Hz, 2H), 7.48 (s, 5H), 7.39-7.26 (m, 10H), 7.03 (d, J = 8.3 Hz, 1H), 6.65 (dd, J = 1.7, 9.9 Hz, 1H), 5.43 (dd, J = 5.8, 7.8 Hz, 1H), 4.39 (s, 2H), 4.28 (s, 2H), 4.08 (d, J = 3.5 Hz, 2H), 3.62-3.55 (m, 2H), 3.49 (d, J = 11.8 Hz, 2H), 3.27-3.23 (m, 2H), 3.01-2.89 (m, 4H), 1.95 (s, 1H), 1.82 (d, J = 14.1 Hz, 2H), 1.49-1.38 (m, 1H). | TFA |

| N | Rt (min) | Method | NMR data (400 MHz) | Salt (2 eq unless stated) |
|---|---|---|---|---|
| 40 | 2.47 | 11 | (MeOD); δ 8.37 (d, J = 9.9 Hz, 1H), 7.78 (d, J = 8.4 Hz, 2H), 7.48 (s, 5H), 7.43-7.35 (m, 5H), 7.35-7.25 (m, 7H), 7.05 (d, J = 8.2 Hz, 1H), 6.70 (d, J = 9.8 Hz, 1H), 5.43 (dd, J = 6.7, 6.7 Hz, 1H), 4.27 (s, 2H), 4.10 (dd, J = 1.5, 6.3 Hz, 2H), 3.60-3.53 (m, 2H), 3.49-3.43 (m, 2H), 3.41-3.35 (m, 2H), 3.21-3.10 (m, 3H), 3.02-2.88 (m, 5H), 1.99-1.92 (m, 1H), 1.85-1.75 (m, 2H), 1.50-1.37 (m, 2H). | TFA |
| 41 | 2.47 | 11 | (DMSO-$d_6$) δ 10.51 (s, 2H), 9.58 (s, 1H), 9.19 (d, J = 27.2 Hz, 2H), 8.10 (d, J = 9.9 Hz, 1H), 7.69 (d, J = 7.3 Hz, 2H), 7.61 (d, J = 8.3 Hz, 2H), 7.48 (s, 5H), 7.32 (s, 6H), 7.28-7.24 (m, 1H), 7.13 (d, J = 8.0 Hz, 1H), 7.01-6.96 (m, 1H), 6.93-6.88 (m, 2H), 6.57 (d, J = 9.7 Hz, 1H), 6.19 (s, 1H), 5.36 (d, J = 10.4 Hz, 1H), 4.41 (t, J = 8.6 Hz, 1H), 4.31-4.23 (m, 5H), 4.12 (d, J = 7.2 Hz, 3H), 4.01 (d, J = 6.3 Hz, 2H), 3.89-3.85 (m, 1H), 3.05-3.02 (m, 4H), 2.90-2.89 (m, 2H), 1.75 (d, J = 14.8 Hz, 3H), 1.37 (d, J = 13.3 Hz, 2H), 1.29-1.21 (m, 2H). | TFA |
| 42 | 2.46 | 11 | (MeOD) δ 8.37 (d, J = 9.9 Hz, 1H), 7.69-7.62 (m, 2H), 7.50 (dd, J = 4.0, 4.0 Hz, 6H), 7.43 (dd, J = 3.9, 8.2 Hz, 3H), 7.39-7.27 (m, 5H), 7.05 (d, J = 8.2 Hz, 1H), 7.03-6.91 (m, 3H), 6.70 (d, J = 9.8 Hz, 1H), 5.45-5.40 (m, 1H), 4.53-4.48 (m, 1H), 4.28 (s, 4H), 4.15-4.09 (m, 5H), 3.49-3.35 (m, 3H), 3.29 (d, J = 8.0 Hz, 2H), 3.17-3.09 (m, 4H), 3.01-2.94 (m, 2H), 2.13-1.72 (m, 4H), 1.50-1.38 (m, 2H). | TFA |
| 42A | 2.43 | 11 | (MeOD); δ 8.53 (s, 1H), 8.20 (d, J = 9.9 Hz, 1H), 7.52 (d, J = 1.9 Hz, 1H), 7.41-7.24 (m, 14H), 7.13 (dd, J = 2.1, 2.1 Hz, 1H), 7.09 (d, J = 7.9 Hz, 1H), 7.04-7.01 (m, 2H), 6.63 (d, J = 9.9 Hz, 1H), 5.37 (dd, J = 6.5, 6.5 Hz, 1H), 4.68 (s, 2H), 4.23 (s, 2H), 4.08 (d, J = 6.4 Hz, 2H), 3.89 (s, 3H), 3.77 (s, 2H), 3.14 (d, J = 6.5 Hz, 2H), 3.05 (d, J = 11.8 Hz, 2H), 2.39-2.31 (m, 2H), 1.79-1.71 (m, 1H), 1.61 (d, J = 12.7 Hz, 2H), 1.38-1.26 (m, 2H). | mono-Formate |
| 42B | 2.49 | 11 | (MeOD); δ 8.55 (s, 1H), 8.27 (d, J = 9.9 Hz, 1H), 7.75 (d, J = 6.4 Hz, 1H), 7.39-7.29 (m, 11H), 7.23 (d, J = 8.7 Hz, 2H), 7.13-7.09 (m, 2H), 7.05-7.00 (m, 2H), 6.63 (d, J = 9.8 Hz, 1H), 5.31 (dd, J = 5.6, 7.5 Hz, 1H), 4.73 (s, 2H), 4.10-4.05 (m, 4H), 3.83 (s, 3H), 3.68 (s, 2H), 3.07-2.96 (m, 4H), 2.24 (dd, J = 11.5, 11.5 Hz, 2H), 1.76-1.67 (m, 1H), 1.58 (d, J = 12.0 Hz, 2H), 1.34-1.27 (m, 2H). | mono-Formate |
| 42C | 2.57 | 11 | (DMSO-$d_6$, 90° C.) d 8.69 (t, J = 5.9 Hz, 1H), 8.18 (d, J = 9.9 Hz, 1H), 7.88 (d, J = 8.3 Hz, 2H), 7.46 (s, 5H), 7.38-7.24 (m, 12H), 7.16 (d, J = 8.3 Hz, 1H), 7.02 (d, J = 8.2 Hz, 2H), 6.98-6.93 (m, 2H), 6.58 (d, J = 9.9 Hz, 1H), 5.36 (dd, J = 4.4, 8.7 Hz, 1H), 5.03 (s, 2H), 4.51 (d, J = 6.0 Hz, 2H), 4.19-4.15 (m, 2H), 4.08-4.03 (m, 2H), 3.35-3.29 (m, 4H), 3.24-3.18 (m, 3H), 2.86-2.86 (m, 2H), 1.94-1.82 (m, 1H), 1.73-1.72 (m, 2H), 1.42-1.42 (m, 2H). | TFA |
| 42D | 2.64 | 11 | (DMSO-$d_6$) δ 10.53 (m, 2H), 9.45-9.40 (m, 1H), 9.17 (m, 3H), 8.13 (d, J = 9.9 Hz, 1H), 8.00 (d, J = 8.1 Hz, 2H), 7.68 (d, J = 8.3 Hz, 2H), 7.52 (m, 5H), 7.42-7.35 (m, 10H), 7.17 (d, J = 8.1 Hz, 1H), 7.04-6.93 (m, 4H), 6.67 (s, 1H), 6.63 (dd, J = 1.8, 9.9 Hz, 1H), 6.23 (d, J = 1.0 Hz, 1H), 5.39 (d, J = 8.8 Hz, 1H), 5.06 (s, 2H), 4.54 (d, J = 5.6 Hz, 2H), 4.38-4.25 (m, 4H), 4.08-4.01 (m, 2H), 3.38 (m, 2H), 3.17-3.04 (m, 2H), 2.99-2.90 (m, 2H), 1.83-1.71 (m, 3H), 1.44-1.35 (m, 2H). | TFA |
| 42E | 2.60 | 11 | (MeOD); δ 8.38 (s, 2H), 8.19 (d, J = 9.9 Hz, 1H), 7.81 (d, J = 7.9 Hz, 1H), 7.36-7.12 (m, 17H), 7.05 (d, J = 8.0 Hz, 1H), 6.93-6.83 (m, 4H), 6.54 (d, J = 9.8 Hz, 1H), 5.31-5.26 (m, 1H), 4.94 (s, 2H), 4.51 (s, 2H), 4.12 (s, 2H), 3.97 (dd, J = 1.8, 6.6 Hz, 2H), 3.91 (s, 2H), 3.88 (s, 3H), 3.14-3.02 (m, 4H), 2.54 (dd, J = 11.0, 11.0 Hz, 2H), 1.78-1.66 (m, 1H), 1.57 (d, J = 12.2 Hz, 2H), 1.31-1.19 (m, 2H). | formate |
| 42F | 2.59 | 11 | (MeOD); δ 8.51 (s, 1H), 8.28 (d, J = 9.9 Hz, 1H), 7.58 (s, 1H), 7.56-7.24 (m, 16H), 7.05-6.92 (m, 5H), 6.66 (d, J = 9.9 Hz, 1H), 5.45-5.37 (m, 1H), 5.05 (s, 2H), 4.61 (s, 2H), 4.60 (s, 1H), 4.31 (s, 2H), 4.09 (dd, J = 1.3, 6.4 Hz, 2H), 3.98 (s, 5H), 3.82 (s, 1H), 3.23-3.16 (m, 4H), 2.64-2.55 (m, 2H), 1.87-1.79 (m, 1H), 1.67 (d, J = 12.9 Hz, 2H), 1.37 (q, J = 11.9 Hz, 2H). | mono-formate |

Example 6. (S)-(1-Benzylpiperidin-4-yl)methyl 2-hydroxy-2-(3-((4-((3-(((R)-2-hydroxy-2-(8-hydroxy-2-oxo-1,2-dihydroquinolin-5-yl)ethyl)amino)propyl)carbamoyl)benzyl)oxy)phenyl)-2-phenylacetate (Compound 43)

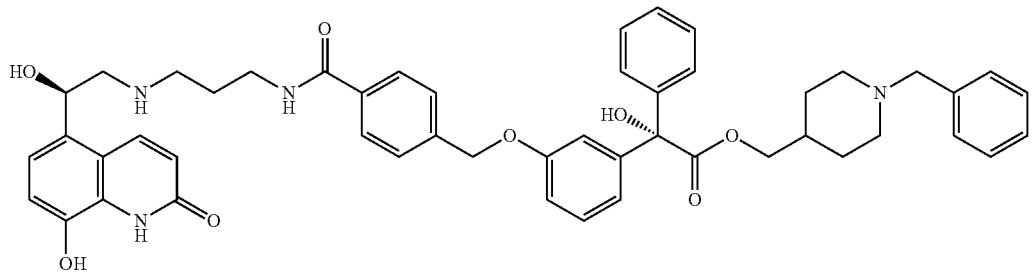 [SMILES: O=C(NCCCNC[C@H](O)c1ccc(O)c2[nH]c(=O)ccc12)c1ccc(COc2cccc([C@](O)(C(=O)OCC3CCN(Cc4ccccc4)CC3)c3ccccc3)c2)cc1]

Step 1;
4-(Chloromethyl)-N-(3,3-diethoxypropyl)benzamide

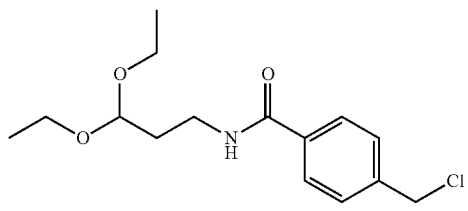 [SMILES: CCOC(CCNC(=O)c1ccc(CCl)cc1)OCC]

To a solution of 4-(chloromethyl)-benzoyl chloride (1.17 g, 6.21 mmol) in DCM (10 mL) was added a solution of 3,3-diethoxypropan-1-amine (0.914 g, 6.21 mmol) and triethylamine (1.04 mL, 7.77 mmol) in DCM (10 mL). The reaction mixture was stirred at room temperature for 3 hours. The solvent was evaporated under reduced pressure and the residue dissolved in ethyl acetate. The organic phase was washed with 1M aqueous sodium hydroxide, brine and dried over anhydrous magnesium sulfate and the filtrate was evaporated under reduced pressure to afford the title compound (1.83 g, 99%).

$^1$H NMR (400 MHz, DMSO-$d_6$); δ 8.45 (dd, J=5.5, 5.5 Hz, 1H), 7.83 (d, J=8.4 Hz, 2H), 7.52 (d, J=8.3 Hz, 2H), 4.81 (s, 2H), 4.56 (dd, J=5.5, 5.5 Hz, 1H), 3.59 (ddd, J=7.1, 9.5, 14.1 Hz, 2H), 3.45 (ddd, J=7.1, 9.5, 14.1 Hz, 2H), 3.29 (dd, J=6.0, 7.4 Hz, 2H), 1.79 (dd, J=6.4, 13.6 Hz, 2H), 1.12 (dd, J=7.0, 7.0 Hz, 6H).

Step 2; (2S)-(1-Benzylpiperidin-4-yl)methyl 2-(3-((4-((3-ethoxy-3-propoxypropyl)carbamoyl)benzyl)oxy)phenyl)-2-hydroxy-2-phenylacetate

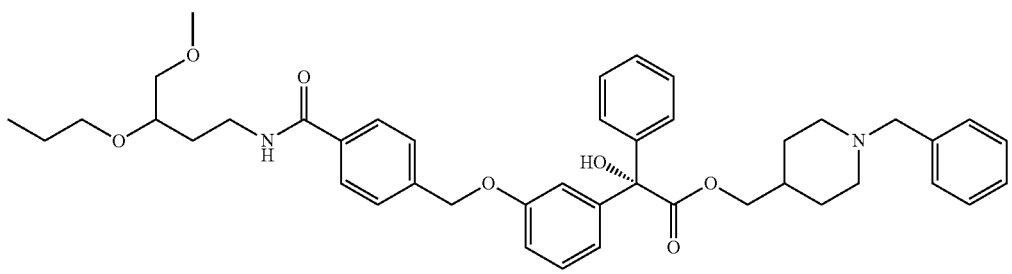 [SMILES: CCCOC(CCNC(=O)c1ccc(COc2cccc([C@](O)(C(=O)OCC3CCN(Cc4ccccc4)CC3)c3ccccc3)c2)cc1)COC]

The title compound was prepared as described in Procedure 7 Step 4 with 4-(chloromethyl)-N-(3,3-diethoxypropyl)benzamide replacing tert-butyl 4-(bromomethyl)benzoate.

$^1$H NMR (400 MHz, DMSO-$d_6$); δ 8.43 (dd, J=5.5, 5.5 Hz, 1H), 7.83 (d, J=8.4 Hz, 2H), 7.47 (d, J=8.4 Hz, 2H), 7.26-7.20 (m, 11H), 6.97-6.90 (m, 3H), 6.60 (s, 1H), 5.11 (s, 2H), 4.56 (dd, J=5.5, 5.5 Hz, 1H), 3.98 (d, J=6.3 Hz, 2H), 3.58 (ddd, J=7.1, 9.5, 14.1 Hz, 2H), 3.48-3.38 (m, 5H), 2.73-2.67 (m, 2H), 1.85-1.76 (m, 3H), 1.52-1.44 (m, 3H), 1.12 (dd, J=7.0, 7.0 Hz, 6H).

Step 3; Compound (43)

The title compound (43) was prepared as described in Example 1 Step 9.

| N | Rt (min) | Method | NMR data (400 MHz) | Salt (2 eq unless stated) |
|---|---|---|---|---|
| 43 | 7.26 | 7 | (DMSO-d$_6$, 90° C.); δ 8.37 (dd, J = 5.6, 5.6 Hz, 1H), 8.18 (d, J = 9.9 Hz, 1H), 7.85 (d, J = 8.2 Hz, 2H), 7.51-7.44 (m, 8H), 7.38-7.24 (m, 6H), 7.16 (d, J = 8.2 Hz, 1H), 7.04 (d, J = 2.0 Hz, 1H), 7.02-6.95 (m, 3H), 6.56 (d, J = 9.9 Hz, 1H), 5.34 (dd, J = 4.5, 8.5 Hz, 1H), 5.12 (s, 2H), 4.18 (s, 2H), 4.07 (s, 2H), 3.42-3.37 (m, 4H), 3.18-3.08 (m, 4H), 2.88-2.88 (m, 2H), 2.01-1.93 (m, 2H), 1.87 (s, 1H), 1.74 (d, J = 13.2 Hz, 2H), 1.42-1.42 (m, 2H). | TFA |

Example 7. (R)-(1-Benzylpiperidin-4-yl)methyl 2-hydroxy-2-(3-((4-((3-(((R)-2-hydroxy-2-(8-hydroxy-2-oxo-1,2-dihydroquinolin-5-yl)ethyl)amino)propyl)carbamoyl)benzyl)oxy)phenyl)-2-phenylacetate (Compound 44)

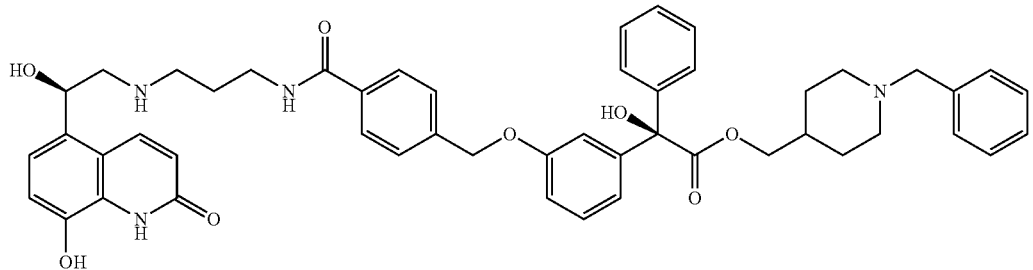 [SMILES: O=C(NCCCNC[C@H](O)c1ccc(O)c2[nH]c(=O)ccc12)c1ccc(COc2cccc([C@@](O)(C(=O)OCC3CCN(Cc4ccccc4)CC3)c3ccccc3)c2)cc1]

Step 1; 4-(Chloromethyl)-N-(3,3-diethoxypropyl)benzamide

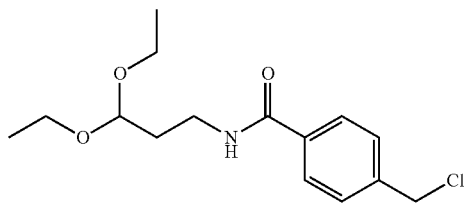 [SMILES: CCOC(CCNC(=O)c1ccc(CCl)cc1)OCC]

To a solution of 4-(chloromethyl)-benzoyl chloride (1.17 g, 6.21 mmol) in DCM (10 mL) was added a solution of 3,3-diethoxypropan-1-amine (0.914 g, 6.21 mmol) and triethylamine (1.04 mL, 7.77 mmol) in DCM (10 mL). The reaction mixture was stirred at room temperature for 3 hours. The solvent was evaporated under reduced pressure and the residue dissolved in ethyl acetate. The organic phase was washed with 1M aqueous sodium hydroxide, brine and dried over anhydrous magnesium sulfate and the filtrate was evaporated under reduced pressure to afford the title compound (1.83 g, 99%).

$^1$H NMR (400 MHz, DMSO-d$_6$); δ 8.45 (dd, J=5.5, 5.5 Hz, 1H), 7.83 (d, J=8.4 Hz, 2H), 7.52 (d, J=8.3 Hz, 2H), 4.81 (s, 2H), 4.56 (dd, J=5.5, 5.5 Hz, 1H), 3.59 (ddd, J=7.1, 9.5, 14.1 Hz, 2H), 3.45 (ddd, J=7.1, 9.5, 14.1 Hz, 2H), 3.29 (dd, J=6.0, 7.4 Hz, 2H), 1.79 (dd, J=6.4, 13.6 Hz, 2H), 1.12 (dd, J=7.0, 7.0 Hz, 6H).

Step 2; (2R)-(1-Benzylpiperidin-4-yl)methyl 2-(3-((4-((3-ethoxy-3-propoxypropyl)carbamoyl)benzyl)oxy)phenyl)-2-hydroxy-2-phenylacetate

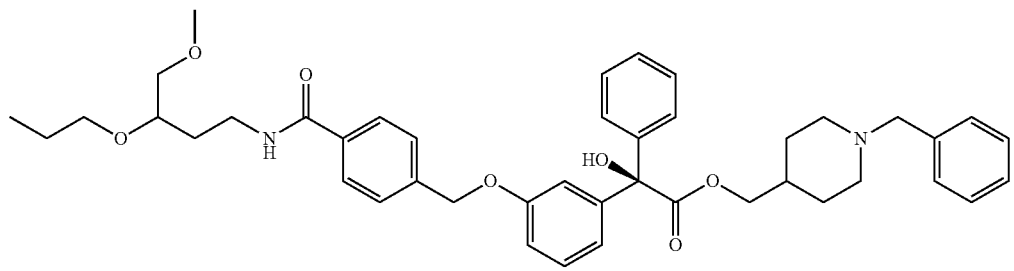 [SMILES: CCCOC(CCNC(=O)c1ccc(COc2cccc([C@@](O)(C(=O)OCC3CCN(Cc4ccccc4)CC3)c3ccccc3)c2)cc1)COC]

The title compound was prepared as described in Procedure 7 with (R)-2-hydroxy-2-(3-hydroxyphenyl)-2-phenylacetic acid replacing (S)-2-hydroxy-2-(3-hydroxyphenyl)-2-phenylacetic acid in Step 1 and 4-(chloromethyl)-N-(3,3-diethoxypropyl)benzamide replacing tert-butyl 4-(bromomethyl)benzoate in Step 4.

$^1$H NMR (400 MHz, DMSO-d$_6$); δ 8.43 (dd, J=5.5, 5.5 Hz, 1H), 7.83 (d, J=8.4 Hz, 2H), 7.47 (d, J=8.4 Hz, 2H), 7.26-7.20 (m, 11H), 6.97-6.90 (m, 3H), 6.60 (s, 1H), 5.11 (s,

2H), 4.56 (dd, J=5.5, 5.5 Hz, 1H), 3.98 (d, J=6.3 Hz, 2H), 3.58 (ddd, J=7.1, 9.5, 14.1 Hz, 2H), 3.48-3.38 (m, 5H), 2.73-2.67 (m, 2H), 1.85-1.76 (m, 3H), 1.52-1.44 (m, 3H), 1.12 (dd, J=7.0, 7.0 Hz, 6H).

Step 3; (Compound 44)

The title compound (44) was prepared as described in Example 1 Step 9.

| N | Rt (min) | Method | NMR data (400 MHz) | Salt (2 eq unless stated) |
|---|----------|--------|--------------------|----|
| 44 | 7.25 | 6 | (DMSO-d6, 90° C.); δ 8.36 (dd, J = 5.5, 5.5 Hz, 1H), 8.18 (d, J = 9.9 Hz, 1H), 7.85 (d, J = 7.7 Hz, 2H), 7.48 (m, J = 5.5 Hz, 8H), 7.38-7.24 (m, 6H), 7.16 (d, J = 8.2 Hz, 1H), 7.05 (s, 1H), 7.02-6.96 (m, 3H), 6.57 (d, J = 9.8 Hz, 1H), 5.34 (dd, J = 4.5, 8.6 Hz, 1H), 5.12 (s, 2H), 4.22 (s, 2H), 4.06 (s, 2H), 3.43-3.37 (m, 4H), 3.18-108 (m, 4H), 2.87 (s, 2H), 2.05-1.94 (m, 2H), 1.88 (s, 1H), 1.77-1.74 (m, 2H), 1.42-1.42 (m, 2H). | TFA |

Example 8. (S)-(1-Benzylpiperidin-4-yl)methyl 2-(3-((3-(benzyl(3-(((R)-2-hydroxy-2-(8-hydroxy-2-oxo-1,2-dihydroquinolin-5-yl)ethyl)amino)propyl)carbamoyl)benzyl)oxy)phenyl)-2-hydroxy-2-phenylacetate (Compound 45)

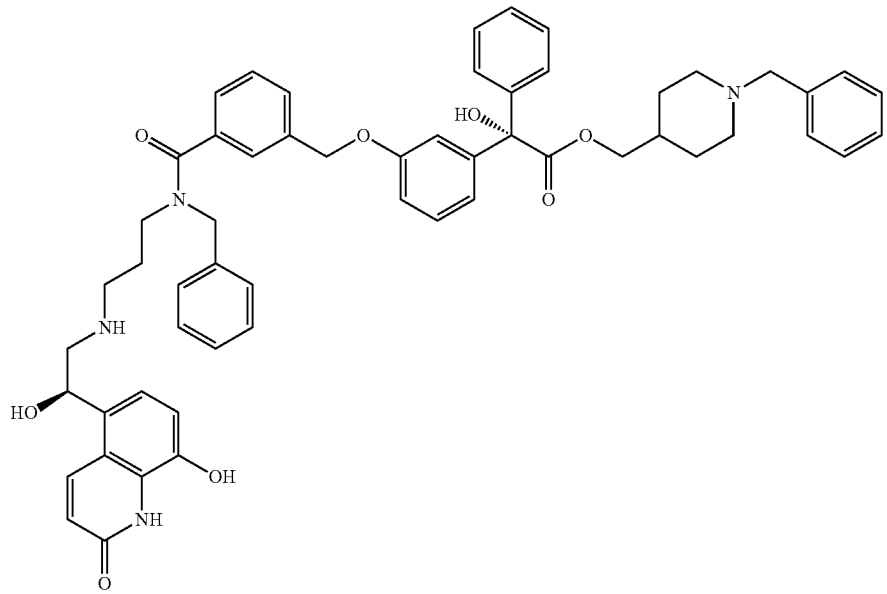 [SMILES: O=C(c1cccc(COc2cccc([C@](O)(C(=O)OCC3CCN(Cc4ccccc4)CC3)c3ccccc3)c2)c1)N(CCCNC[C@H](O)c1ccc(O)c2[nH]c(=O)ccc12)Cc1ccccc1]

Step 1; N-(2-(1,3-Dioxolan-2-yl)ethyl)-N-benzyl-3-(chloromethyl)benzamide

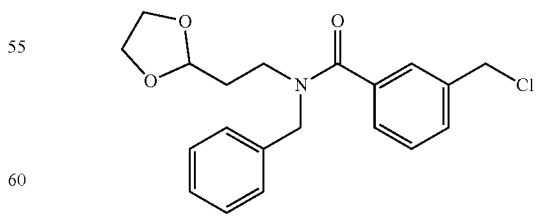

The title compound was prepared as described in Example 5 Step 1 with N-benzyl-2-(1,3-dioxolan-2-yl)ethanamine replacing 3,3-diethoxypropan-1-amine and 3-(chloromethyl)benzoyl chloride replacing 4-(chloromethyl)benzoyl chloride.

Step 2; (S)-3-(2-(1,3-Dioxolan-2-yl)ethyl)(benzyl) carbamoyl)benzyl 2-(3-((3-((2-(1,3-dioxolan-2-yl) ethyl)(benzyl)carbamoyl)benzyl)oxy)phenyl)-2-hydroxy-2-phenylacetate

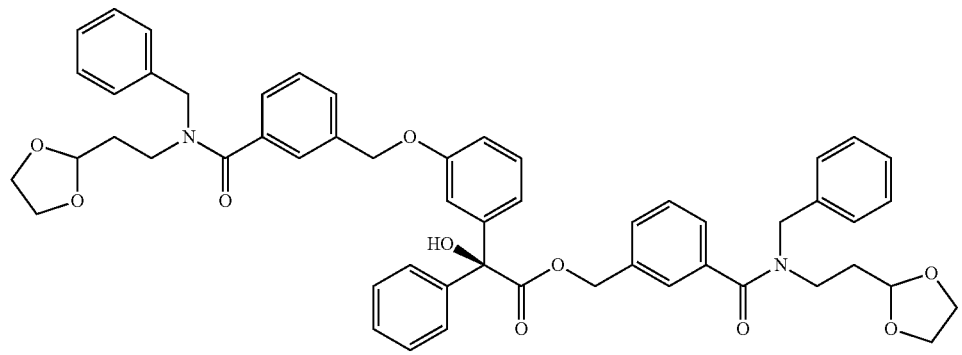 [SMILES: O=C(c1cccc(COC(=O)[C@](O)(c2ccccc2)c2cccc(OCc3cccc(C(=O)N(CCC4OCCO4)Cc4ccccc4)c3)c2)c1)N(CCC1OCCO1)Cc1ccccc1]

The title compound was prepared as described in Example 4 Step 1 with N-(2-(1,3-dioxolan-2-yl)ethyl)-N-benzyl-3-(chloromethyl)benzamide replacing 2-(4-chlorobutyl)-1,3-dioxolane.

Step 3; (Compound 45)

The title compound (45) was prepared as described in Example 4 Step 2 through Step 4.

| N | Rt (min) | Method | NMR data (400 MHz) | Salt (2 eq unless stated) |
|---|---|---|---|---|
| 45 | 7.50 | 6 | (DMSO-d6, 90° C.); δ 8.15 (d, J = 9.4 Hz, 1H), 7.45 (d, J = 8.0 Hz, 8H), 7.38-7.22 (m, 12H), 7.14 (d, J = 8.2 Hz, 1H), 7.04-6.92 (m, 4H), 6.55 (d, J = 9.9 Hz, 1H), 5.30 (dd, J = 4.8, 7.8 Hz, 1H), 5.07 (s, 2H), 4.57 (s, 2H), 4.07-4.07 (m, 2H), 3.43-3.40 (m, 2H), 3.16-108 (m, 7H), 2.99 (s, 2H), 1.96 (dd, J = 7.5, 7.5 Hz, 3H), 1.73-1.69 (m, 2H), 1.40-1.40 (m, 2H). | TFA |

Example 9. (R)-quinuclidin-3-yl 2-hydroxy-2-(3-(4-((5-(((R)-2-hydroxy-2-(8-hydroxy-2-oxo-1,2-dihydroquinolin-5-yl)ethyl)amino)pentyl)oxy)benzamido) phenyl)-2-phenylacetate diformate (Compound 46)

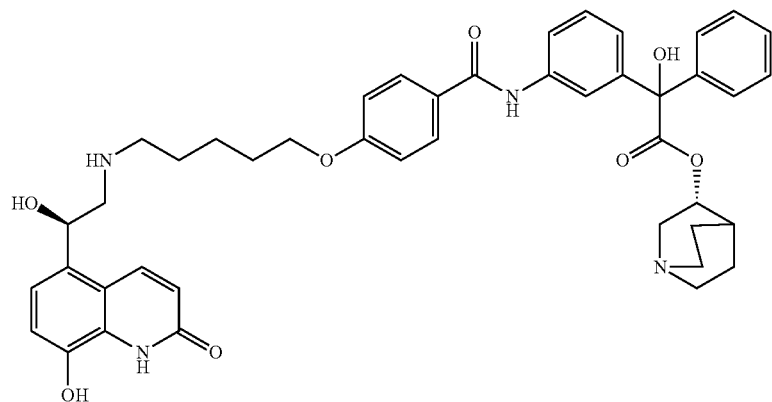 [SMILES: O=C(Nc1cccc(C(O)(C(=O)O[C@H]2CN3CCC2CC3)c2ccccc2)c1)c1ccc(OCCCCCNC[C@H](O)c2ccc(O)c3[nH]c(=O)ccc23)cc1]

Step 1; Methyl 4-(4-(1,3-dioxolan-2-yl)butoxy)benzoate

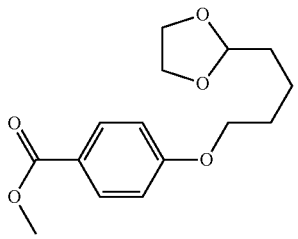 [SMILES: COC(=O)c1ccc(OCCCCC2OCCO2)cc1]

To a solution of methyl 4-hydroxybenzoate (1 g, 6.57 mmol) in DMF (0.509 ml) $K_2CO_3$ (1.045 g, 7.56 mmol) and 2-(4-bromobutyl)-1,3-dioxolane (1.649 g, 7.89 mmol) were added. The mixture was stirred at RT overnight to get to completion. The mixture was poured onto saturated $NaCl_{aq}$ (25 ml) and the aqueous phase was extracted with DCM (10 ml×3). The combined organic layers were dried over $Na_2SO_4$ and evaporated in vacuo to give a crude that was purified by flash chromatography (silica gel, eluents: 100% n-Hex to 100% AcOEt) to afford methyl 4-(4-(1,3-dioxolan-2-yl)butoxy)benzoate (1.6 g, 5.71 mmol, 87% yield).

UPLC-MS: 1.07 min, 249 [(M+H)−MeOH]+, method 2.

Step 2; 4-(4-(1,3-dioxolan-2-yl)butoxy)benzoic acid

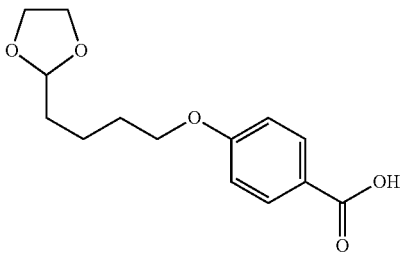 [SMILES: O=C(O)c1ccc(OCCCCC2OCCO2)cc1]

To a solution of methyl 4-(4-(1,3-dioxolan-2-yl)butoxy) benzoate (1.13 g, 4.03 mmol) in THF (24 ml, 293 mmol), LiOH 1M (1.209 ml, 1.209 mmol) was added and the mixture stirred at RT overnight. LiOH 1M (1.5 ml) was added and the mixture stirred at RT over the weekend to get to completion. $NaHCO_3$ was added till pH=6-7 and the aqueous phase extracted with AcOEt (10 ml×3). The organic phase was dried over $Na_2SO_4$ and evaporated in vacuo to give a crude that was used without further purifications for next steps.

UPLC-MS: 0.86 min, 267 [(M+H)]+, method 2.

Step 3; (R)-quinuclidin-3-yl 2-oxo-2-phenylacetate

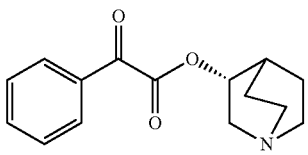 [SMILES: O=C(O[C@H]1CN2CCC1CC2)C(=O)c1ccccc1]

To a solution of 2-oxo-2-phenylacetic acid (1 g, 6.66 mmol) in DCM (25 ml, 389 mmol), oxalyl chloride (0.816 ml, 9.33 mmol) was added dropwise at RT, and the mixture stirred for 20 min. Then (R)-quinuclidin-3-ol (0.847 g, 6.66 mmol) was added and the mixture stirred at RT for 2 hrs. DCM (50 ml) was added and the organic phase washed with $NaHCO_3$ saturated solution (30 ml×3). The organic layer was evaporated in vacuo to give (R)-quinuclidin-3-yl 2-oxo-2-phenylacetate (870 mg, 3.36 mmol, 50.4% yield) as an oily crude that was used without further purifications for next steps.

UPLC-MS: 0.37 min, 260 [M+H]+, method 2.

Step 4; (R)-quinuclidin-3-yl 2-(3-((tert-butoxycarbonyl)amino)phenyl)-2-hydroxy-2-phenylacetate

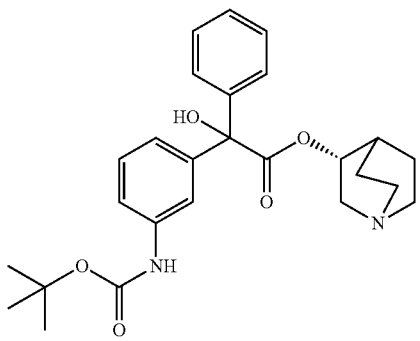 [SMILES: CC(C)(C)OC(=O)Nc1cccc(C(O)(C(=O)O[C@H]2CN3CCC2CC3)c2ccccc2)c1]

To a solution of (R)-quinuclidin-3-yl 2-oxo-2-phenylacetate (960 mg, 3.70 mmol) in THF (20 ml, 244 mmol) at −15 deg, (3-(bis(trimethylsilyl)amino)phenyl)magnesium chloride 1M in THF (3.70 ml, 3.70 mmol) was added dropwise and the mixture stirred for 15 min at 0 deg, then allowed to warm to RT and stirred for 3 hrs at RT. The reaction was quenched by addition of MeCN (2 ml) and partitioned between AcOEt (200 mL) and water (200 mL). Organic layer was washed twice with water, once with sat NaCl, dried over $Na_2SO_4$ and dried under reduced pressure to give the desylilated compound. The crude was dissolved in DCM (20 ml) and di-tert-butyl dicarbonate (1.117 ml, 4.81 mmol), DMAP (90 mg, 0.740 mmol) and N-ethyl-N-isopropylpropan-2-amine (0.838 ml, 4.81 mmol) were added and the mixture stirred at RT overnight. DCM was evaporated in vacuo to give a crude that was purified by flash chromatography (silica gel, eluents: DCM to 1/1 DCM/EtOH) to afford (R)-quinuclidin-3-yl 2-(3-((tert-butoxycarbonyl)amino)phenyl)-2-hydroxy-2-phenylacetate (580 mg, 1.282 mmol, 34.6% yield)

UPLC-MS: 0.64 min, 454 [M+H]+, method 2.

Step 5; (R)-quinuclidin-3-yl 2-(3-aminophenyl)-2-hydroxy-2-phenylacetate dihydrochloride

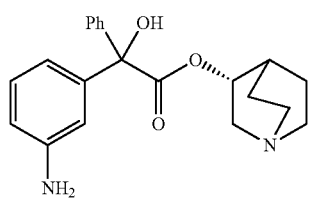 [SMILES: Nc1cccc(C(O)(C(=O)O[C@H]2CN3CCC2CC3)c2ccccc2)c1]

To a solution of (R)-quinuclidin-3-yl 2-(3-((tert-butoxycarbonyl)amino)phenyl)-2-hydroxy-2-phenylacetate (500 mg, 1.105 mmol) in acetonitrile (2 ml) HCl 4M in dioxane (1 ml, 32.9 mmol) was added and the mixture stirred at RT for 2 hrs. The solvent was evaporated in vacuo to give (R)-quinuclidin-3-yl 2-(3-aminophenyl)-2-hydroxy-2-phenylacetate dihydrochloride (493 mg, 1.160 mmol, 105% yield) that was used without further purifications for next steps.

UPLC-MS: 0.50 min, 426 [M+H]+, method 1.

Step 6; (R)-quinuclidin-3-yl 2-(3-(4-(4-(1,3-dioxolan-2-yl)butoxy)benzamido)phenyl)-2-hydroxy-2-phenylacetate Step 7; (R)-quinuclidin-3-yl 2-hydroxy-2-(3-(4-((5-oxopentyl)oxy)benzamido)phenyl)-2-phenylacetate

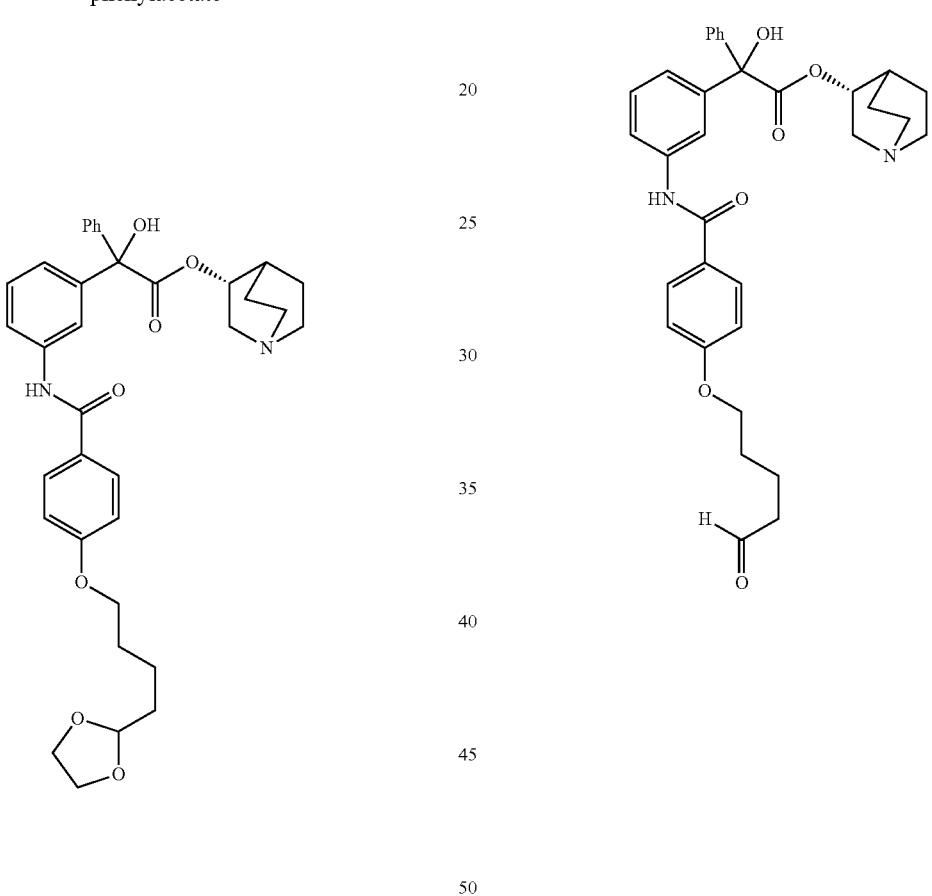

To a solution of 4-(4-(1,3-dioxolan-2-yl)butoxy)benzoic acid (324 mg, 1.215 mmol)) in DMF (5 ml), HATU (504 mg, 1.326 mmol) and DIPEA (212 µl, 1.215 mmol) were added. The mixture was stirred at RT for 30 min, then (R)-quinuclidin-3-yl 2-(3-aminophenyl)-2-hydroxy-2-phenylacetate dihydrochloride (470 mg, 1.105 mmol) in DMF (5 ml) and DIPEA (386 µl, 2.210 mmol) were added to the mixture and stirred at RT on. The mixture was purified by reverse phase chromatography (C-18 silica gel, eluents: 100% H2O/Acetonitrile 95/5+HCOOH 0.1% to 100% H2O/ACN 5/95+HCOOH 0.1%) to afford (R)-quinuclidin-3-yl 2-(3-(4-(4-(1,3-dioxolan-2-yl)butoxy)benzamido)phenyl)-2-hydroxy-2-phenylacetate (272 mg, 0.453 mmol, 41.0% yield).

UPLC-MS: 0.72 min, 601 [M+H]+, method 2.

To a solution of (R)-quinuclidin-3-yl 2-(3-(4-(4-(1,3-dioxolan-2-yl)butoxy)benzamido)phenyl)-2-hydroxy-2-phenylacetate (272 mg, 0.453 mmol) in Acetonitrile (5.723 ml) HCl 2M (5.6 ml, 11.32 mmol) was added and the mixture stirred at RT for 2 hrs. NaHCO₃ saturated solution was added till pH=8 and the aqueous phase extracted with AcOEt (50 ml×2). The organic phase was dried over Na₂SO₄ and evaporated in vacuo to give the title compound (195 mg, 0.350 mmol, 77% yield) that was used without further purifications for next steps.

UPLC-MS: 0.67 min, 557 [M+H]+, method 2.

Step 8; (R)-quinuclidin-3-yl 2-(3-(4-((5-(((R)-2-(8-(benzyloxy)-2-oxo-1,2-dihydroquinolin-5-yl)-2-((tert-butyldimethylsilyl)oxy)ethyl)amino)pentyl)oxy)-benzamido)phenyl)-2-hydroxy-2-phenylacetate

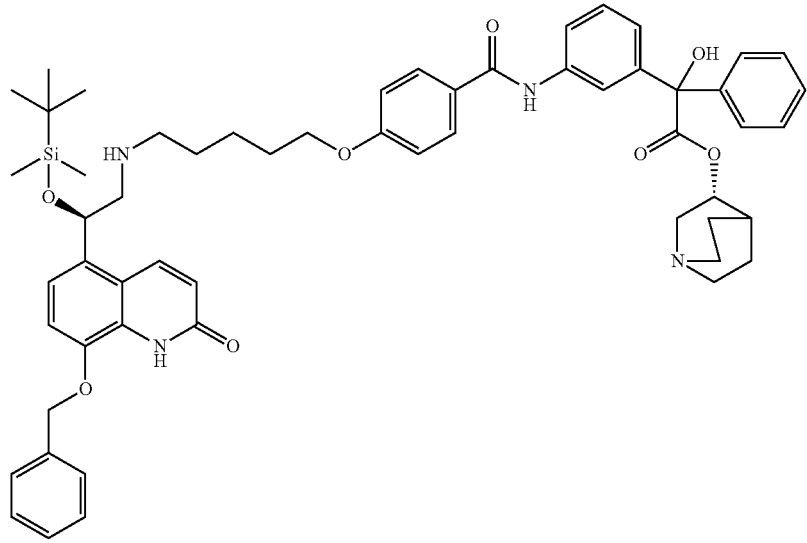 [SMILES: CC(C)(C)[Si](C)(C)O[C@@H](CNCCCCCOc1ccc(C(=O)Nc2cccc(C(O)(C(=O)O[C@H]3CN4CCC3CC4)c3ccccc3)c2)cc1)c1ccc(OCc2ccccc2)c2[nH]c(=O)ccc12]

To a solution of (R)-quinuclidin-3-yl 2-hydroxy-2-(3-(4-((5-oxopentyl)oxy)benzamido)phenyl)-2-phenylacetate (195 mg, 0.350 mmol) in 1/1 solution DCM/EtOH (4 ml) (R)-5-(2-amino-1-((tert-butyldimethylsilyl)oxy)ethyl)-8-(benzyloxy)quinolin-2(1H)-one (223 mg, 0.525 mmol) and acetic acid (0.040 ml, 0.701 mmol) were added. Then a spatula of sodium sulfate was added and the mixture stirred at RT for 15 min, sodium triacetoxyborohydride (371 mg, 1.752 mmol) was added to the mixture and stirred at RT for 2 hrs, HCl 2M (2 ml) was added, the mixture filtered and evaporated in vacuo to give a crude that was purified by reverse phase chromatography (C-18 silica gel, eluents: 100% H2O/Acetonitrile 95/5+HCOOH 0.1% to 100% H2O/ACN 5/95+HCOOH 0.1%) to afford (R)-quinuclidin-3-yl 2-(3-(4-((5-(((R)-2-(8-(benzyloxy)-2-oxo-1,2-dihydroquinolin-5-yl)-2-((tert-butyldimethylsilyl)oxy)ethyl)-amino)pentyl)oxy)benzamido)phenyl)-2-hydroxy-2-phenylacetate (150 mg, 0.155 mmol, 44.4% yield).

UPLC-MS: 1.43 min, 966 [M+H]+, method 2.

Step 9; (R)-quinuclidin-3-yl 2-(3-(4-((5-(((R)-2-((tert-butyldimethylsilyl)oxy)-2-(8-hydroxy-2-oxo-1,2-dihydroquinolin-5-yl)ethyl)amino)pentyl)oxy)benzamido)phenyl)-2-hydroxy-2-phenylacetate

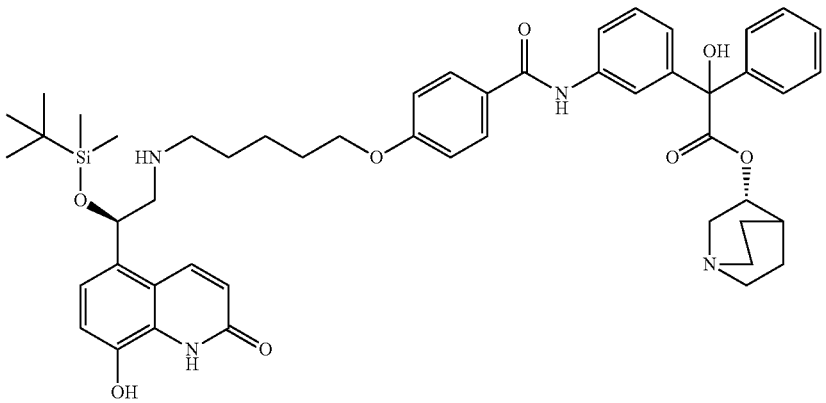 [SMILES: CC(C)(C)[Si](C)(C)O[C@@H](CNCCCCCOc1ccc(C(=O)Nc2cccc(C(O)(C(=O)O[C@H]3CN4CCC3CC4)c3ccccc3)c2)cc1)c1ccc(O)c2[nH]c(=O)ccc12]

(R)-quinuclidin-3-yl 2-(3-(4-((5-(((R)-2-(8-(benzyloxy)-2-oxo-1,2-dihydroquinolin-5-yl)-2-((tert-butyldimethylsilyl)oxy)ethyl)amino)pentyl)oxy)-benzamido)phenyl)-2-hydroxy-2-phenylacetate (150 mg, 0.155 mmol) and Pd—C 5% Enghelhart (50% water) (165 mg, 1.554 μmol) were dissolved in MeOH (5 ml) and stirred at RT under H2 atmosphere for 2 hrs. The reaction was filtered over a small pad of celite and the filtrate dried under reduced pressure to give the title compound (70 mg, 0.080 mmol, 51.5% yield).

UPLC-MS: 1.17 min, 876 [M+H]+, method 4.

Step 10 (Compound 46)

To a solution of (R)-quinuclidin-3-yl 2-(3-(4-((5-(((R)-2-((tert-butyldimethylsilyl)oxy)-2-(8-hydroxy-2-oxo-1,2-dihydroquinolin-5-yl)ethyl)amino)pentyl)oxy)benzamido)phenyl)-2-hydroxy-2-phenylacetate (70 mg, 0.080 mmol) in THF (2 ml) HCl 4M in dioxane (800 µl, 3.20 mmol) was added and the mixture stirred at RT for 6 hrs, then kept at −4 deg overnight and then stirred again at RT for 6 hrs. Et2O (20 ml) was added and removed under vacuum twice, then the residual solvent was evaporated under reduced pressure without warming to give a crude that was purified via reverse phase preparative HPLC to afford the title compound (46) (12 mg, 0.014 mmol, 17.59% yield).

mixture of 20 mL 2M $HCl_{aq}$ and 20 mL of MeCN. The reaction was stirred for 2 h at RT, then diluted with AcOEt and 1M $HCl_{aq}$, organic layer washed with saturated $NaCl_{aq}$ and dried over $Na_2SO_4$. After evaporation, the residue was purified by flash chromatography (silica gel, eluents: hexane to 6/4 AcOEt/hexane) to afford the title compound (6.8 g, 25.2 mmol, 75% yield).

UPLC-MS: 0.89 min, 253.1 [(M+H)—$H_2O$]+, method 1. a20140911_06

| N | Rt (min) | [M + H]+ | Method | NMR data (400 MHz) | Salt (2 eq unless stated) |
|---|---|---|---|---|---|
| 46 | 3.99 | 761.0 | 5 | (MeOH-$d_4$) δ 8.50 (br. s., 2 H), 8.36 (d, J = 9.87 Hz, 1 H), 7.89 (dd, J = 8.88, 7.23 Hz, 2 H), 7.64-7.16 (m, 9 H), 7.01 (dd, J = 14.63, 8.39 Hz, 3 H), 6.68 (d, J = 9.87 Hz, 1 H), 5.46-5.34 (m, 1 H), 5.16 (br. s., 1 H), 4.10 (t, J = 6.08 Hz, 2 H), 3.54-3.44 (m, 1 H), 3.26-2.73 (m, 8 H), 2.34-2.12 (m, 1 H), 2.02-1.73 (m, 5 H), 1.72-1.46 (m, 6 H) | Formate |

Example 10. (1-benzylpiperidin-4-yl)methyl 2-hydroxy-2-(3-((4-(((R)-2-hydroxy-2-(8-hydroxy-2-oxo-1,2-dihydroquinolin-5-yl)ethyl)amino)butyl)carbamoyl)phenyl)-2-phenylacetate diformate (Compound 47)

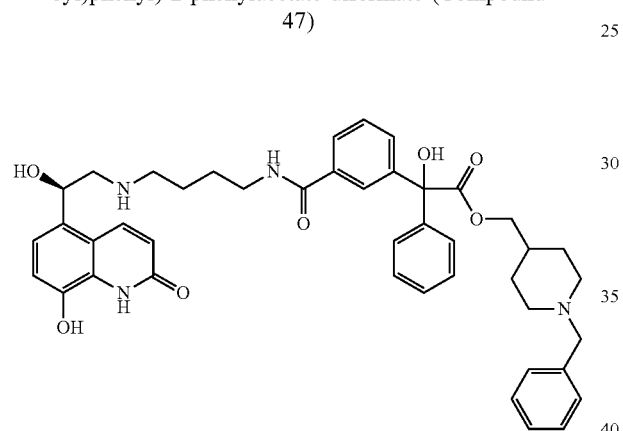

Step 1; methyl 2-(3-formylphenyl)-2-hydroxy-2-phenylacetate

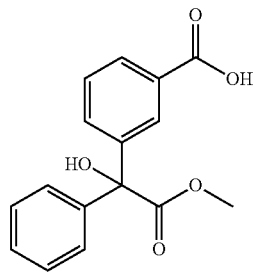 [SMILES: COC(=O)C(O)(c1ccccc1)c1cccc(C(=O)O)c1]

To a solution of methyl 2-oxo-2-phenylacetate (4.9 mL, 34.7 mmol) in 133 mL of dry THF were added dropwise, at −20° C., 40 mL of 1M (3-(diethoxymethyl)phenyl)-magnesium bromide in THF (40.0 mmol) and the mixture stirred overnight at RT. Reaction was quenched by the addition of saturated $NH4Cl_{aq}$ and extracted with EtOAc. The organic layer was washed with aqueous saturated $NaCl_{aq}$ and evaporated under reduced pressure; the residue was dissolved in a Step 2; 3-(1-hydroxy-2-methoxy-2-oxo-1-phenylethyl)benzoic acid

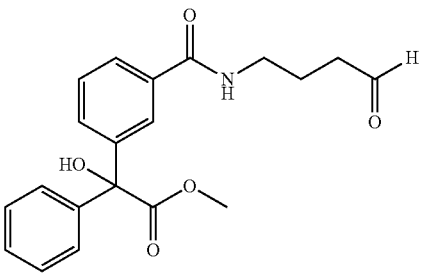 [SMILES: COC(=O)C(O)(c1ccccc1)c1cccc(C(=O)NCCCC=O)c1]

Methyl 2-(3-formylphenyl)-2-hydroxy-2-phenylacetate (3.8 g, 14.06 mmol), $K_2H_2PO_4$ (3.83 g, 28.1 mmol), 2-methyl-2-butene (14.89 ml, 141 mmol) and $NaClO_2$ (2.54 g, 28.1 mmol) were reacted in 36 mL of t-BuOH/water 1/1 from 0° C. to RT for 4 h. Reaction was quenched by the addition of 1M $HCl_{aq}$ until pH 6-7, diluted with water and extracted with AcOEt. Organic layer was dried over $Na_2SO_4$ and evaporated to dryness. The crude was submitted to flash chromatography (silica gel, eluents: 100% DCM+0.2% AcOH to 80/20 DCM/EtOH+0.2% AcOH) to afford the title compound (4.1 g). The product obtained was used in the following steps without further purifications.

UPLC-MS: 0.79 min, 269.2 [(M+H)–$H_2O$]+, method 1.

Step 3; methyl 2-hydroxy-2-(3-((4-oxobutyl)carbamoyl)phenyl)-2-phenylacetate 3-(1-hydroxy-2-methoxy-2-oxo-1-phenylethyl)benzoic acid 2 (2.6 g, 9.08 mmol) and HATU (3.45 g, 9.08 mmol) were reacted for 30 min at 0° C., then 4,4-diethoxybutan-1-amine (2.354 ml, 13.62 mmol) and DIEA (2.379 ml, 13.62 mmol) were added and the mixture stirred at RT for 2 h. Reaction was quenched by the addition of 100 mL of 1M HCl$_{aq}$ and stirred for 1 h RT, then extracted with AcOEt, organic layer dried over Na$_2$SO$_4$ and evaporated to dryness. The crude oil was purified by flash chromatography (silica gel, eluent: hexane to AcOEt) to give the title compound (2 g, 5.63 mmol, 62.0% yield). The product obtained was used in the following steps without further purifications.

UPLC-MS: 0.73 min, 356.1 [M+H]+, method 1,

Step 4; methyl 2-(3-((4-(((R)-2-(8-(benzyloxy)-2-oxo-1,2-dihydroquinolin-5-yl)-2-((tert-butyldimethylsilyl)oxy)ethyl)(tert- butoxycarbonyl)amino)butyl)carbamoyl)phenyl)-2-hydroxy-2-phenylacetate

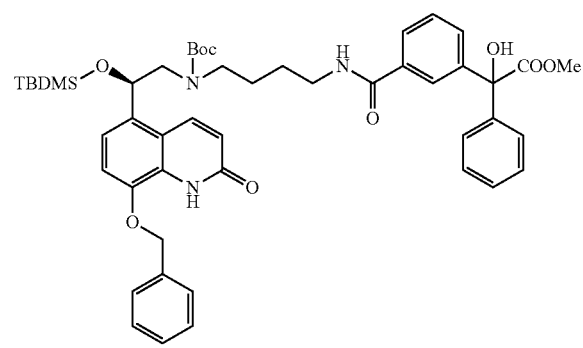

1(R)-5-(2-amino-1-((tert-butyldimethylsilyl)oxy)ethyl)-8-(benzyloxy)quinolin-2(1H)-one (2.390 g, 5.63 mmol)) and methyl 2-hydroxy-2-(3-((4-oxobutyl)carbamoyl)-phenyl)-2-phenylacetate (2 g, 5.63 mmol) were reacted for 10 min at RT in 30 mL of DCM with a spatula tip of Na$_2$SO$_4$, then 0.3 mL of AcOH and NaB(OAc)$_3$H (2.39 g, 11.30 mm) were added and the mixture stirred at RT for 2 h. The reaction was filtered, dryed to half of the initial volume and diluted with 10 mL of THF and 10 mL of saturated NaHCO$_3$ aq and added with Boc$_2$O (2.46 g, 11.30 mmol). The mixture was stirred vigorously for 0.5 h at RT, then diluted with AcOEt and washed with saturated NaHCO$_3$ $_{aq}$, saturated NaCl$_{aq}$, dried over Na$_2$SO$_4$ and evaporated to dryness. The crude was purified by flash chromatography (silica gel, DCM to AcOEt) to afford the title compound (0.9 g, 1.042 mmol, 18.51% yield).

UPLC-MS: 1.56 min, 864.5 [M+H]+, method 1.

Step 5; 2-(3-((4-(((R)-2-(8-(benzyloxy)-2-oxo-1,2-dihydroquinolin-5-yl)-2-((tert-butyldimethylsilyl)oxy)ethyl)(tert-butoxycarbonyl)amino)butyl)carbamoyl)phenyl)-2-hydroxy-2-phenylacetic acid

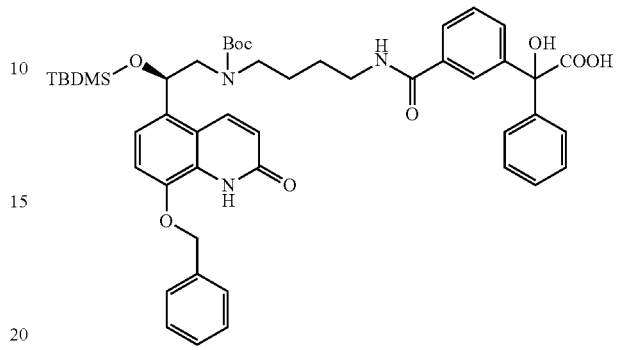

Methyl 2-(3-((4-(((R)-2-(8-(benzyloxy)-2-oxo-1,2-dihydroquinolin-5-yl)-2-((tert-butyldimethylsilyl)oxy)ethyl)(tert-butoxycarbonyl)amino)butyl)carbamoyl)phenyl)-2-hydroxy-2-phenylacetate (0.9 g, 1.042 mmol) and LiOH (0.125 g, 5.21 mmol) were reacted in 7 mL of THF/water 1/1 for 1 h at RT. The reaction was quenched by the addition of 0.1M HCl$_{aq}$ and extracted with AcOEt, organic layer washed twice with 0.1M HCl$_{aq}$, once with saturated NaCl$_{aq}$, dried over Na$_2$SO$_4$ and evaporated to dryness to give the title compound (869 mg, 1.022 mmol, 98% yield).

UPLC-MS: 1.50 min, 850.3 [M+H]+, method 1.

Step 6; benzyl 4-(hydroxymethyl)piperidine-1-carboxylate

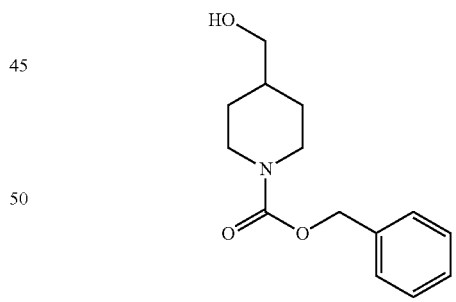

Piperidin-4-ylmethanol (5.2 g, 45.1 mmol) was dissolved in 60 mL of THF and 60 mL of saturated NaHCO$_3$ aq and then benzyl (2,5-dioxopyrrolidin-1-yl) carbonate (11.25 g, 45.1 mmol) added portionwise. The mixture was stirred for 1 h at RT, partitioned between AcOEt and water, washed twice with 1M HCl$_{aq}$ and saturated NaCl$_{aq}$. Organic layer was dried over Na$_2$SO$_4$, evaporated under reduced pressure to afford the title compound (10.77 g, 43.2 mmol, 96% yield). The product obtained was used in the following steps without further purifications.

UPLC-MS; 0.80 min, 250.2 [M+H]+, method 1.

Step 7; benzyl 4-((2-(3-((4-(((R)-2-(8-(benzyloxy)-2-oxo-1,2-dihydroquinolin-5-yl)-2-((tert-butyldimethylsilyl)oxy)ethyl)(tert-butoxycarbonyl)amino)butyl)carbamoyl)phenyl)-2-hydroxy-2-phenylacetoxy)methyl)piperidine-1-carboxylate

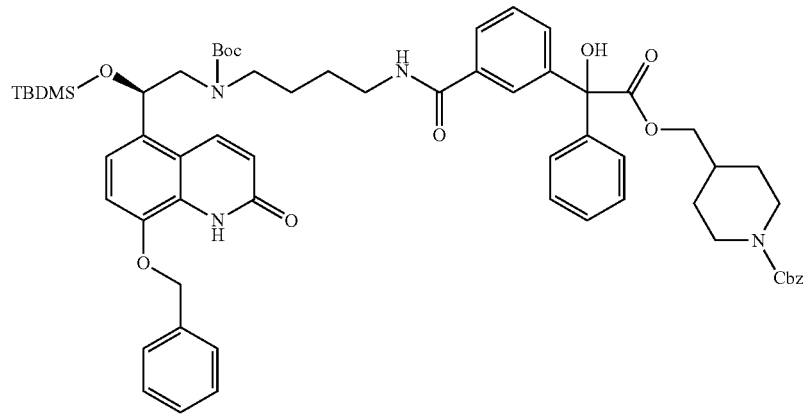

2-(3-((4-(((R)-2-(8-(benzyloxy)-2-oxo-1,2-dihydroquinolin-5-yl)-2-((tert-butyldimethylsilyl)oxy)ethyl)(tert-butoxycarbonyl)amino)butyl)carbamoyl)phenyl)-2-hydroxy-2-phenylacetic acid (400 mg, 0.471 mmol) and CDI (229 mg, 1,412 mmol) were reacted for 30 min at RT, then benzyl 4-(hydroxymethyl)piperidine-1-carboxylate (469 mg, 1.882 mmol) added and the reaction stirred for 2 h at 60° C., then RT overnight. The crude was partitioned between saturated NaHCO$_3$ $_{aq}$ and AcOEt, organic layer dried over Na$_2$SO$_4$ and evaporated to dryness. The crude was purified by flash chromatography (silica gel, eluents: DCM to AcOEt) to afford the title compound (110 mg, 0.102 mmol, 21.62% yield).

UPLC-MS: 1.68 min, 1082.6 [M+H]+, method 1.

Step 8; piperidin-4-ylmethyl 2-(3-((4-(((tert-butoxycarbonyl)((R)-2-((tert-butyldimethylsilyl)oxy)-2-(8-hydroxy-2-oxo-1,2-dihydroquinolin-5-yl)ethyl)amino)butyl)carbamoyl)phenyl)-2-hydroxy-2-phenylacetate formate

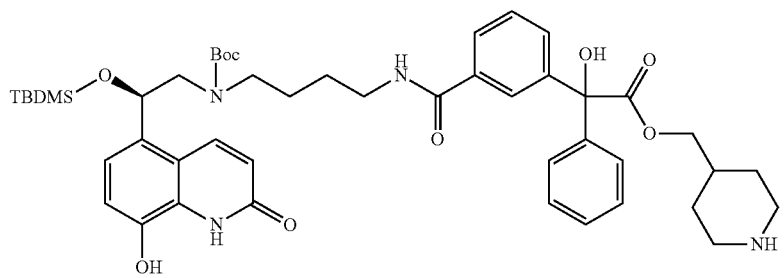

Benzyl 4-((2-(3-((4-(((R)-2-(8-(benzyloxy)-2-oxo-1,2-dihydroquinolin-5-yl)-2-((tert-butyldimethylsilyl)oxy)ethyl)(tert-butoxycarbonyl)amino)butyl)carbamoyl)phenyl)-2-hydroxy-2-phenylacetoxy)methyl)piperidine-1-carboxylate (110 mg, 0.102 mmol) was dissolved in 1 mL of MeOH, added of 7.80 μl of HCOOH, Pd—C 10% wet (10.83 mg, 5.09 mol) and hydrogenated for 3 h at RT under balloon pressure of hydrogen. Reaction mixture was filtered and reduced to dryness to give the title compound (120 mg). The product obtained was used in the following steps without further purifications.

UPLC-MS: 0.94 min, 857.6 [M+H]+, method 2.

Step 9; (1-benzylpiperidin-4-yl)methyl 2-(3-((4-((tert-butoxycarbonyl)((R)-2-((tert-butyldimethylsilyl)oxy)-2-(8-hydroxy-2-oxo-1,2-dihydroquinolin-5-yl)ethyl)amino)butyl)carbamoyl)phenyl)-2-hydroxy-2-phenylacetate

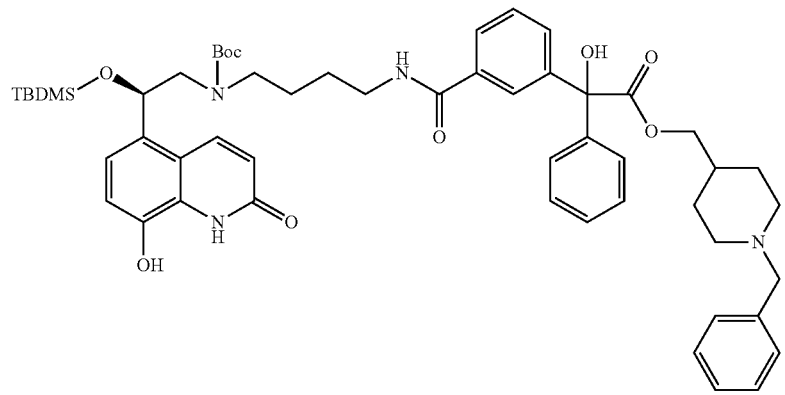

Piperidin-4-ylmethyl 2-(3-((4-((tert-butoxycarbonyl)((R)-2-((tert-butyldimethyl-silyl)oxy)-2-(8-hydroxy-2-oxo-1,2-dihydroquinolin-5-yl)ethyl)amino)butyl)carbamoyl)-phenyl)-2-hydroxy-2-phenylacetate formate (92 mg, 0.102 mmol) and benzaldehyde (13.45 µl, 0.132 mmol) were dissolved in 1 mL of DCM and stirred for 1 h at RT, then 7.58 µl of AcOH and Na(OAc)$_3$H (28.1 mg, 0.132 mmol) were and the mixture stirred overnight at RT. Further 1 eq. of aldehyde and Na(OAc)$_3$H were needed to bring reaction to completion. Reaction mixture was partitioned between AcOEt and saturated NaHCO$_3$ $_{aq}$, washed twice with saturated NaHCO$_3$ $_{aq}$ and saturated NaCl$_{aq}$, organic layer dried with Na$_2$SO$_4$ and evaporated to dryness to give the title compound (100 mg). The product obtained was used in the following steps without further purifications.

UPLC-MS: 1.04 min, 946.6 [M+H]+, method 2.

Step 10; (Compound 47)

(1-Benzylpiperidin-4-yl)methyl 2-(3-((4-((tert-butoxycarbonyl)((R)-2-((tert-butyldimethylsilyl)oxy)-2-(8-hydroxy-2-oxo-1,2-dihydroquinolin-5-yl)ethyl)amino)-butyl)carbamoyl)phenyl)-2-hydroxy-2-phenylacetate (100 mg, 0.106 mmol) was dissolved in 0.5 mL of MeCN and added with 2 mL of 5M HCl$_{aq}$. The mixture was stirred for 1 h at RT and then submitted to reversed phase flash chromatography (C18 silica gel, eluents: from 100% A to 100% B, A: water/MeCN 95/5+0.1% HCOOH, B: MeCN/water 95/5+0.1% HCOOH) to afford the title compound (47) (68 mg, 0.082 mmol, 78% yield).

Example 11. (R)-quinuclidin-3-yl 2-hydroxy-2-(3-((4-(((R)-2-hydroxy-2-(8-hydroxy-2-oxo-1,2-dihydroquinolin-5-yl)ethyl)amino)butyl)carbamoyl)phenyl)-2-phenylacetate diformate (compound 48)

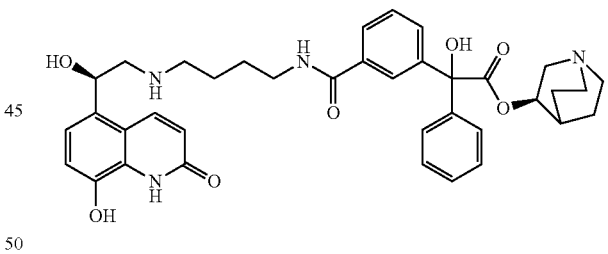

| N | Rt (min) | [M + H]+ | Method | NMR data (400 MHz) | Salt (2 eq unless stated) |
|---|---|---|---|---|---|
| 47 | 3.83 | 733.1 | 5 | (DMSO-d$_6$) δ 10.56-10.00 (bs, 1 H), 8.46 (s, 1 H), 8.13 (m, 1 H), 7.94-7.86 (m, 1 H), 7.74 (dt, J = 7.48, 1.36 Hz, 1 H), 7.50-7.117 (m, 13 H), 7.09 (d, J = 7.89 Hz, 1 H), 6.94 (d, J = 7.89 Hz, 1 H), 6.70 (br. s., 1 H), 6.52 (d, J = 9.87 Hz, 1 H), 5.15 (br. s., 1 H), 4.45-4.19 (m, 1 H), 4.00 (m, 2 H), 3.23 (m, 7 H), 2.91-2.63 (m, 6 H), 1.82 (t, J = 11.02 Hz, 2 H), 1.53 (d, J = 2.30 Hz, 5 H), 1.45 (d, J = 13.15 Hz, 2 H). | Formate |

Step 1; (R)-quinuclidin-3-yl 2-(3-((4-(((R)-2-(8-(benzyloxy)-2-oxo-1,2-dihydroquinolin-5-yl)-2-((tert-butyldimethylsilyl)oxy)ethyl)(tert-butoxycarbonyl)amino)butyl)carbamoyl)phenyl)-2-hydroxy-2-phenylacetate

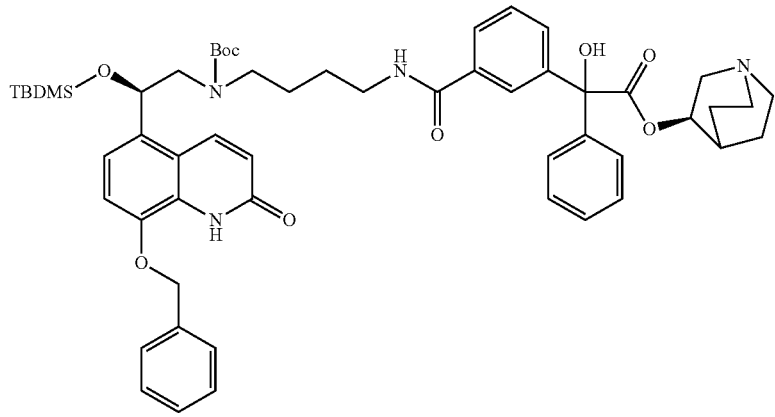

2-(3-((4-((R)-2-(8-(Benzyloxy)-2-oxo-1,2-dihydroquinolin-5-yl)-2-((tert-butyldimethylsilyl)oxy)ethyl)(tert-butoxycarbonyl)amino)butyl)carbamoyl)phenyl)-2-hydroxy-2-phenylacetic acid as described in Example 10, step 5 (150 mg, 0.176 mmol) and CDI (57.2 mg, 0.353 mmol) were reacted for 30 min at RT, then (R)-quinuclidin-3-ol (67.3 mg, 0.529 mmol) added and the reaction stirred overnight. The crude was partitioned between saturated NaHCO$_3$ $_{aq}$ and AcOEt, organic layer was washed twice with water, saturated NaCl$_{aq}$, dried over Na$_2$SO$_4$ and evaporated to dryness. The resulting crude was submitted to flash chromatography (silica gel, eluents: from 100% AcOEt to 100% AcOEt/7N NH$_3$ in MeOH 9/1) to afford the title compound (93 mg, 0.097 mmol, 54.9% yield).

UPLC-MS: 1.13 min, 959.7 [M+H]+, method 2.

Step 2; (R)-quinuclidin-3-yl 2-(3-((4-((tert-butoxycarbonyl)((R)-2-((tert-butyldimethylsilyl)oxy)-2-(8-hydroxy-2-oxo-1,2-dihydroquinolin-5-yl)ethyl)amino)butyl)carbamoyl)phenyl)-2-hydroxy-2-phenylacetate formate

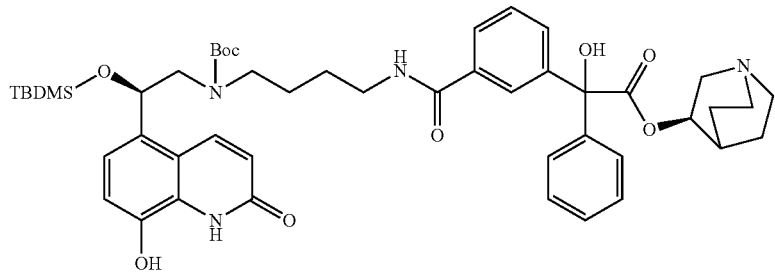

(R)-quinuclidin-3-yl 2-(3-((4-(((R)-2-(8-(benzyloxy)-2-oxo-1,2-dihydroquinolin-5-yl)-2-((tert-butyldimethylsilyl)oxy)ethyl)(tert-butoxycarbonyl)amino)butyl)carbamoyl)phenyl)-2-hydroxy-2-phenylacetate (90 mg, 0.094 mmol), Pd/C (9.98 mg, 4.69 µmol) and HCOOH (7.20 µl, 0.188 mmol) were dissolved in 0.94 mL of MeOH and hydrogenated under balloon pressure of H$_2$ for 2 h at RT until complete debenzylation. Reaction mixture was filtered on PTFE membrane and evaporated to dryness to give the title compound (95 mg). The product obtained was used in the following steps without further purifications.

UPLC-MS: 0.95 min, 869.6 [M+H]+, method 2.

Step 3; (compound 48)

The title example was made in a similar way as that of the compound of example 10, step 10 (86 mg, 0.094 mmol) to give the title compound (48) 60 mg, 0.080 mmol, 85% yield).

UPLC-MS: 3.30 min (412%)-3.32 min (56.8%), 655.1 [M+H]+, Method 5

| N | Rt (min) | [M + H]+ | Method | NMR data (400 MHz) | Salt (2 eq unless stated) |
|---|---|---|---|---|---|
| 48 | 3.31 | 655.1 | 5 | (DMSO-d6) δ ppm 10.44 (s, 2 H), 10.25 (br. s., 1 H), 9.22-8.92 (m, 1 H), 8.75-8.48 (m, 2 H), 8.32-8.16 (m, 1 H), 7.95 (dt, J = 5.59, 1.64 Hz, 1 H), 7.80 (t, J = 8.06 Hz, 1 H), 7.68-7.30 (m, 7 H), 7.15 (d, J = 8.22 Hz, 1 H), 6.99 (d, J = 8.22 Hz, 1 H), 6.95-6.80 (m, 1 H), 6.55 (d, J = 9.87 Hz, 1 H), 6.01-6.25 (m, 1 H), 5.41 (d, J = 9.87 Hz, 1 H), 5.05-5.26 (m, 1 H), 3.59-3.79 (m, 2 H), 2.78-3.33 (m, 12 H), 2.22 (br. s., 1 H), 1.32-2.00 (m, 8 H) | Formate |

Example 12. (R)-1-methylpyrrolidin-3-yl 2-hydroxy-2-(3-((4-(((R)-2-hydroxy-2-(8-hydroxy-2-oxo-1,2-dihydroquinolin-5-yl)ethyl)amino)butyl)carbamoyl)phenyl)-2-phenylacetate diformate (Compound 49)

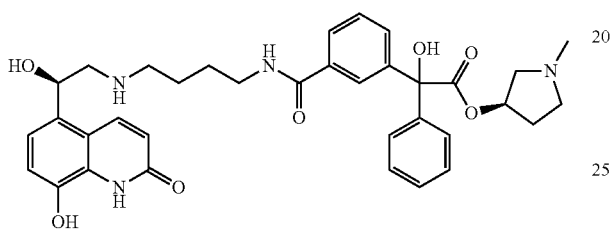

Step 1; (R)-1-methylpyrrolidin-3-yl 2-(3-((4-(((R)-2-(8-(benzyloxy)-2-oxo-1,2-dihydroquinolin-5-yl)-2-((tert-butyldimethylsilyl)oxy)ethyl)(tert-butoxycarbonyl)amino)butyl)carbamoyl)phenyl)-2-hydroxy-2-phenylacetate

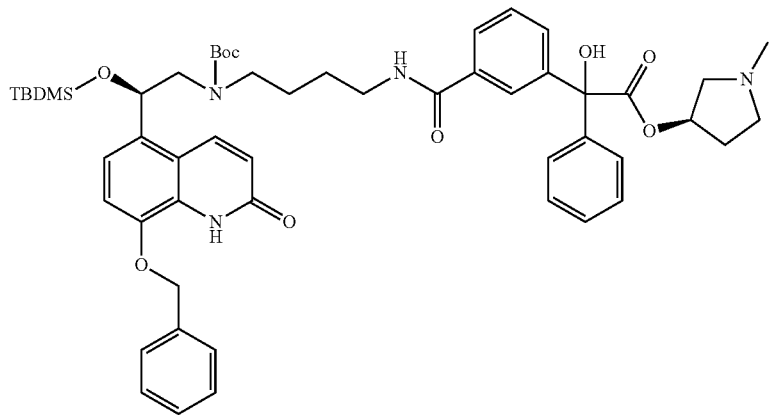

The title compound was made in similar way as that of Example 11 Step 1 from 2-(3-((4-(((R)-2-(8-(benzyloxy)-2-oxo-1,2-dihydroquinolin-5-yl)-2-((tert-butyldimethylsilyl)oxy)ethyl)(tert-butoxycarbonyl)amino)butyl)carbamoyl)phenyl)-2-hydroxy-2-phenylacetic acid (150 mg, 0.176 mmol) to give the desired product (93 mg, 0.100 mmol, 56.5% yield).

UPLC-MS: 1.12 min, 933.0 [M+H]+, method 2.

Step 2; (R)-1-methylpyrrolidin-3-yl 2-(3-((4-((tert-butoxycarbonyl)((R)-2-((tert-butyldimethylsilyl)oxy)-2-(8-hydroxy-2-oxo-1,2-dihydroquinolin-5-yl)ethyl)amino)butyl)carbamoyl)phenyl)-2-hydroxy-2-phenylacetate

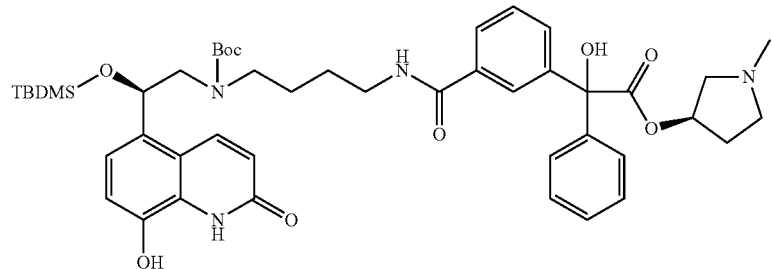

The title compound was made in similar way as that of Example 11, step 2 from (R)-1-methylpyrrolidin-3-yl 2-(3-((4-(((R)-2-(8-(benzyloxy)-2-oxo-1,2-dihydroquinolin-5-yl)-2-((tert-butyldimethylsilyl)oxy)ethyl)(tert-butoxycarbonyl)amino)butyl)carbamoyl)-phenyl)-2-hydroxy-2-phenylacetate (90 mg, 0.092 mmol), Pd—C 10% wet (9.78 mg, 4.60 μmol) and HCOOH (7.05 μl, 0.184 mmol) to give the desired product (90 mg). The product obtained was used in the following steps without further purifications.
UPLC-MS: 0.93 min, 843.7 [M+H]+, method 2.

Step 3; (Compound 49)

The title example was made in a similar way as that of the compound of example 10, step 10 from (R)-1-methylpyrrolidin-3-yl 2-(3-((4-((tert-butoxycarbonyl)((R)-2-((tert-butyldimethylsilyl)oxy)-2-(8-hydroxy-2-oxo-1,2-dihydroquinolin-5-yl)ethyl)amino)butyl)carbamoyl)phenyl)-2-hydroxy-2-phenylacetate formate (90 mg, 0.101 mmol) to give the desired compound (40 mg, 0.055 mmol, 54.8% yield).

| N | Rt (min) | [M + H]+ | Method | NMR data (400 MHz) | Salt (2 eq unless stated) |
|---|---|---|---|---|---|
| 49 | 3.08 | 629.0 | 5 | (DMSO-d$_6$) δ 10.10-10.50 (m, 1 H), 8.47 (s, 1 H), 8.21 (s, 1 H), 8.16 (d, J = 9.87 Hz, 1 H), 7.90 (q, J = 1.97 Hz, 1 H), 7.75 (dd, J = 7.73, 1.48 Hz, 1 H), 7.24-7.50 (m, 7 H), 7.09 (d, J = 8.22 Hz, 1 H), 6.94 (d, J = 7.89 Hz, 1 H), 6.68 (br. s., 1 H), 6.52 (d, J = 9.87 Hz, 1 H), 5.08-5.28 (m, 2 H), 2.88-2.80 (m, 2 H), 2.76 (d, J = 6.58 Hz, 2 H), 2.65 (dd, J = 10.69, 6.08 Hz, 1 H), 2.54 (s, 1 H), 2.47 (d, J = 10.85 Hz, 1 H), 2.25 (d, J = 7.23 Hz, 1 H), 2.18 (d, J = 3.29 Hz, 4 H), 1.64 (td, J = 6.74, 2.63 Hz, 1 H), 1.54 (br. s., 4 H) | Formate |

Example 13. (1-benzylpiperidin-4-yl)methyl 2-hydroxy-2-(3-((3-(4-((((R)-2-hydroxy-2-(8-hydroxy-2-oxo-1,2-dihydroquinolin-5-yl)ethyl)amino)methyl)benzamido)propyl)-carbamoyl)phenyl)-2-phenylacetate diformate (Compound 50)

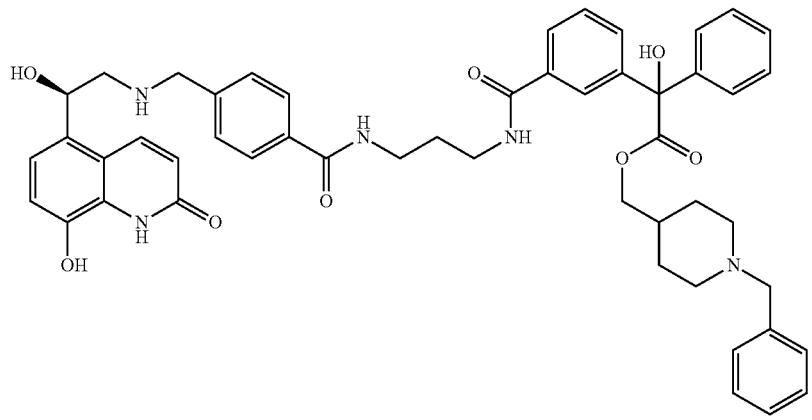 [SMILES: O=C(NCCCNC(=O)c1cccc(C(O)(C(=O)OCC2CCN(Cc3ccccc3)CC2)c2ccccc2)c1)c1ccc(CNC[C@H](O)c2ccc(O)c3[nH]c(=O)ccc23)cc1]

Step 1; Methyl 2-(3-((3-((tert-butoxycarbonyl)amino)propyl)carbamoyl)phenyl)-2-hydroxy-2-phenylacetate

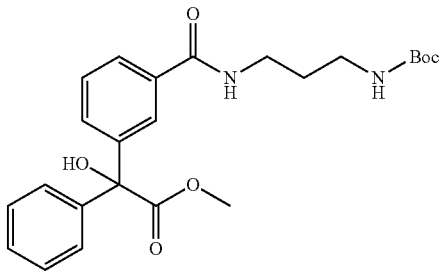 [SMILES: COC(=O)C(O)(c1ccccc1)c1cccc(C(=O)NCCCNC(=O)OC(C)(C)C)c1]

3-(1-Hydroxy-2-methoxy-2-oxo-1-phenylethyl)benzoic acid obtained as in Example 10, step 2 (500 mg, 1.747 mmol) and TBTU (561 mg, 1,747 mmol) were reacted for 5 min at RT in 5 mL DMF, then DIEA (0.305 mL, 1.747 mmol) and tert-butyl (3-aminopropyl)carbamate (335 mg, 1.921 mmol) were added and the resulting mixture stirred at RT for 30 min. Reaction was partitioned between 0.5M $HCl_{aq}$ and AcOEt, organic phase washed three times with 0.5M $HCl_{aq}$ and once with saturated $NaHCO_3$ $_{aq}$, once with saturated $NaCl_{aq}$ and dried over $Na_2SO_4$ to give the title compound (0.78 g, 1.763 mmol, quantitative yield). The product obtained was used in the following steps without further purifications.

UPLC-MS: 0.99 min, 465 [M+Na]+, method 1.

Step 2; 2-(3-((3-((tert-butoxycarbonyl)amino)propyl)carbamoyl)phenyl)-2-hydroxy-2-phenylacetic acid

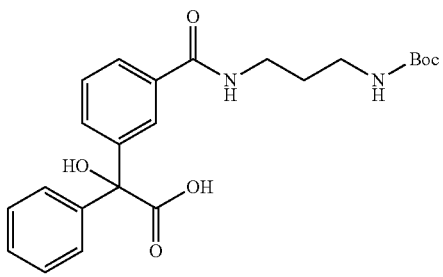 [SMILES: CC(C)(C)OC(=O)NCCCNC(=O)c1cccc(C(O)(C(=O)O)c2ccccc2)c1]

Methyl 2-(3-((3-((tert-butoxycarbonyl)amino)propyl)carbamoyl)phenyl)-2-hydroxy-2-phenylacetate (0.77 g, 1.740 mmol) and LiOH (0.208 g, 8.70 mmol) were reacted in 11 mL of THF/water 1/1 for 1 h at RT, then reaction quenched by the addition of 0.5M $HCl_{aq}$ and extracted with AcOEt. Organic phase was washed with saturated $NaCl_{aq}$, dried over $Na_2SO_4$ and evaporated to dryness to give the title compound (0.61 g, 1.424 mmol, 82% yield).

UPLC-MS: 0.86 min, 451.1 [M+Na]+, method 1.

Step 3; (1-benzylpiperidin-4-yl)methyl 2-(3-((3-((tert-butoxycarbonyl)amino)propyl)-carbamoyl)phenyl)-2-hydroxy-2-phenylacetate

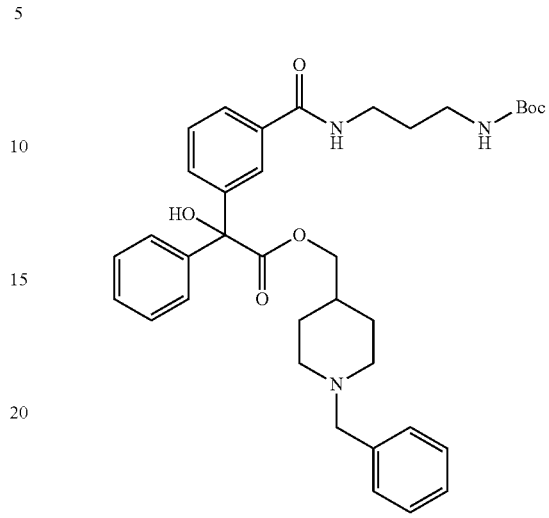

2-(3-((3-((tert-butoxycarbonyl)amino)propyl)carbamoyl)phenyl)-2-hydroxy-2-phenylacetic acid (300 mg, 0.700 mmol) and CDI (227 mg, 1.400 mmol) were reacted in 4.7 mL of DMF at RT for 5 min, then (1-benzylpiperidin-4-yl)methanol (431 mg, 2,100 mmol) added and the mixture stirred at 45.0 overnight. Reaction was partitioned between saturated $NaHCO_3$ and AcOEt, and organic phase after evaporation was submitted to flash chromatography (silica gel, eluents: from 100% AcOEt to 80/20 AcOEt/NH3 7N in MeOH) to afford the title compound (310 mg, 0.503 mmol, 71.9% yield). The product obtained was used in the following steps without further purifications.

UPLC-MS: 0.75 min, 616.2 [M+H]+, method 2.

Step 4; (1-benzylpiperidin-4-yl)methyl 2-(3-((3-aminopropyl)carbamoyl)phenyl)-2-hydroxy-2-phenylacetate

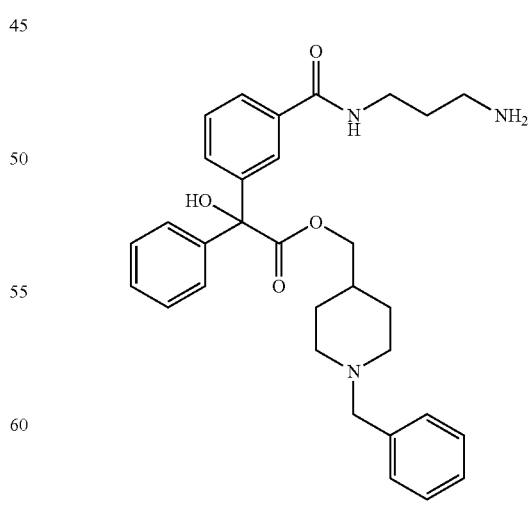

(1-Benzylpiperidin-4-yl)methyl 2-(3-((3-((tert-butoxylcarbonyl)amino)propyl)-carbamoyl)phenyl)-2-hydroxy-2-phenylacetate (310 mg, 0.503 mmol) was stirred for 1 h at RT in 4M HCl dioxane (8.00 mmol) diluted with further 2.5 mL of dioxane, then dried under reduce pressure and the residue triturated in Et₂O to give the title compound (0.22 g, 0.374 mmol, 74.2% yield) used in the next steps without further purifications.

UPLC-MS: 0.38 min, 516.1 [M+H]+, method 2.

Step 5; (1-benzylpiperidin-4-yl)methyl 2-(3-((3-(4-(((tert-butoxycarbonyl)((R)-2-((tert-butyldimethylsilyl)oxy)-2-(8-hydroxy-2-oxo-1,2-dihydroquinolin-5-yl)ethyl)amino)methyl)benzamido)propyl)carbamoyl)phenyl)-2-hydroxy-2-phenylacetate

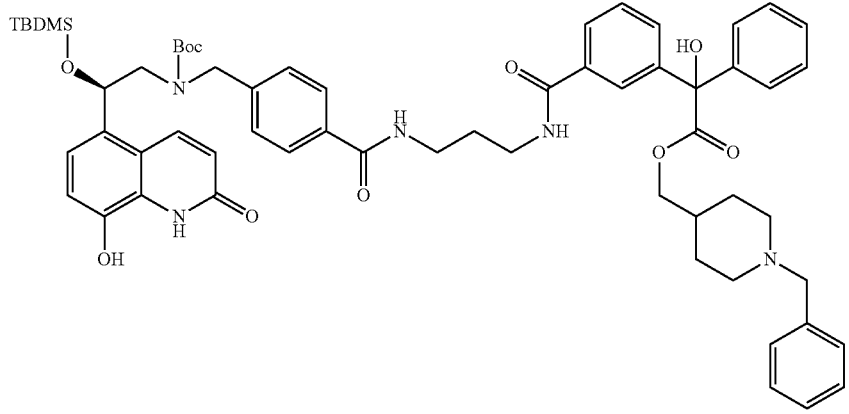

(R)-4-(((tert-butoxycarbonyl)(2-((tert-butyldimethylsilyl)oxy)-2-(8-hydroxy-2-oxo-1,2-dihydroquinolin-5-yl)ethyl)amino)methyl)benzoic acid, obtained as for Procedure 4 Steps 1-5, (63 mg, 0.111 mmol) and TBTU (35.6 mg, 0.111 mmol) was reacted for 5 min in 1.1 mL of DMF, (1-benzylpiperidin-4-yl)methyl 2-(3-((3-aminopropyl)carbamoyl)phenyl)-2-hydroxy-2-phenylacetate diformate (85 mg, 0.144 mmol) and DIEA (58.0 µl, 0.332 mmol) were added and the mixture stirred for 1 h at 60° C. Reaction was partitioned between AcOEt and saturated NaHCO₃, washed twice with water, saturated NaCl$_{aq}$, organic layer dried over Na₂SO₄ and evaporated to dryness. The resulting crude (110 mg, 0.103 mmol, 93% yield) was used in the next step without further purifications.

UPLC-MS: 1.06 min, 1066.2 [M+H]+, method 2.

Step 6; (Compound 50)

The title example was made in a similar way as that of the compound of example 10, step 10, from (1-benzylpiperidin-4-yl)methyl 2-(3-((3-(4-(((tert-butoxycarbonyl)((R)-2-((tert-butyldimethylsilyl)oxy)-2-(8-hydroxy-2-oxo-1,2-dihydroquinolin-5-yl)ethyl)-amino)methyl)benzamido)propyl)carbamoyl)phenyl)-2-hydroxy-2-phenylacetate (108 mg, 0.101 mmol) to give the title compound (50) (22 mg, 0.023 mmol, 23.01% yield).

| N | Rt (min) | [M + H]+ | Method | NMR data (400 MHz) | Salt (2 eq unless stated) |
|---|---|---|---|---|---|
| 50 | 3.91 | 852.1 | 5 | (DMSO-d6) δ ppm 10.54-9.76 (bs, 2 H), 8.66-8.38 (m, 2 H), 8.23-8.05 (m, 2 H), 7.90 (s, 1 H), 7.80 (d, J = 7.94 Hz, 3 H), 7.52-7.14 (m, 15 H), 7.07 (d, J = 8.38 Hz, 1 H), 6.91 (d, J = 8.38 Hz, 1 H), 6.73 (s, 1 H), 6.48 (d, J = 9.70 Hz, 1 H), 5.70-5.35 (m, 1 H), 5.53-4.94 (m, 1 H), 4.23-4.45 (m, 1 H), 4.00 (d, J = 6.62 Hz, 2 H), 3.88 (br. s., 2 H), 3.38 (m, 8 H), 2.72 (br. s., 4 H), 1.75 (s, 4 H), 1.64-1.43 (m, 3 H) | Formate |

Example 14. (1-benzylpiperidin-4-yl)methyl 2-hydroxy-2-(4-((5-(((R)-2-hydroxy-2-(8-hydroxy-2-oxo-1,2-dihydroquinolin-5-yl)ethyl)amino)pentyl)oxy)phenyl)-2-phenylacetate diformate (Compound 51)

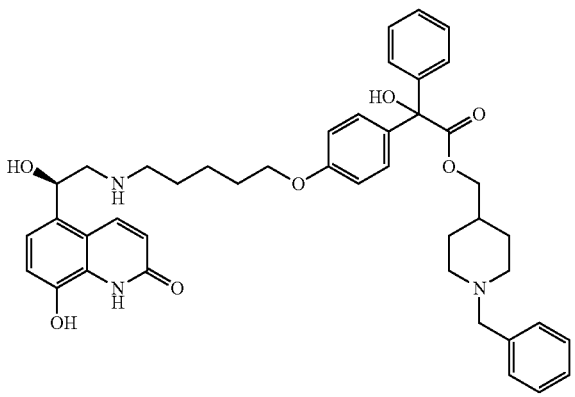 [SMILES: O=C(OCC1CCN(Cc2ccccc2)CC1)C(O)(c1ccccc1)c1ccc(OCCCCCNC[C@H](O)c2ccc(O)c3[nH]c(=O)ccc23)cc1]

Step 1; methyl 2-(4-(benzyloxy)phenyl)-2-hydroxy-2-phenylacetate

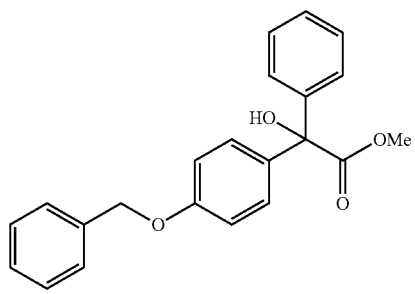 [SMILES: COC(=O)C(O)(c1ccccc1)c1ccc(OCc2ccccc2)cc1]

To a solution of methyl 2-oxo-2-phenylacetate (12.83 ml, 91 mmol) in 350 mL of THF, 100 mL of a solution 1M (4-(benzyloxy)phenyl)magnesium bromide (100 mmol) in THF was added dropwise at 0° C. over 30 min and stirred overnight at RT. Reaction was partitioned between AcOEt and saturated NaCl$_{aq}$, organic layer dried over Na$_2$SO$_4$ and evaporated to dryness. The residue was crystallised in Et$_2$O to afford the title compound (15 g, 43.1 mmol, 47.4% yield).
UPLC-MS: 1.24 min, 331.2 [(M+H)−H2O]+, method 1.

Step 2; methyl 2-hydroxy-2-(4-hydroxyphenyl)-2-phenylacetate

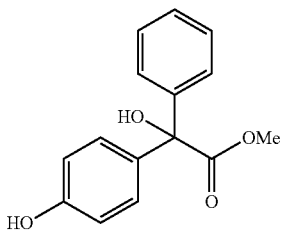 [SMILES: COC(=O)C(O)(c1ccccc1)c1ccc(O)cc1]

Methyl 2-(4-(benzyloxy)phenyl)-2-hydroxy-2-phenylacetate (5 g, 14.35 mmol) was dissolved in 100 mL of a mixture ethanol/AcOEt 6/4, added with Pd—C 5% wet (3.05 g, 0.718 mmol) and stirred under 25 psi of hydrogen for 2 h at RT. Reaction mixture was filtered on PTFE membrane and evaporated to dryness to give the crude, that was recrystallized in iPr$_2$O to afford the title compound (2.95 g, 11.43 mmol, 79.6% yield).
UPLC-MS: 0.76 min, 241.1 [(M+H)−H2O]+, method 1, Step 3; methyl 2-(4-(4-(1,3-dioxolan-2-yl)butoxy)phenyl)-2-hydroxy-2-phenylacetate (343-28-1)

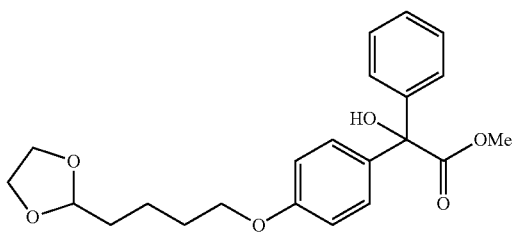 [SMILES: COC(=O)C(O)(c1ccccc1)c1ccc(OCCCCC2OCCO2)cc1]

Methyl 2-hydroxy-2-(4-hydroxyphenyl)-2-phenylacetate (1 g, 3.87 mmol) and 2-(4-bromobutyl)-1,3-dioxolane (0.616 ml, 4.07 mmol) were reacted in 15.5 mL of at 80° C. for 8 h and RT overnight. Reaction mixture was partitioned between water and AcOEt, washed twice with water and once with saturated NaCl$_{aq}$. Organic layer was dried over Na$_2$SO$_4$ and evaporate to dryness to give the title compound (1.54 g, 3.99 mmol, 103% yield). The product obtained was used in the following steps without further purifications.
UPLC-MS: 1.12 min, 369.3 [(M+H)−H2O]+, method 1.

Step 4; methyl 2-hydroxy-2-(4-((5-oxopentyl)oxy)phenyl)-2-phenylacetate

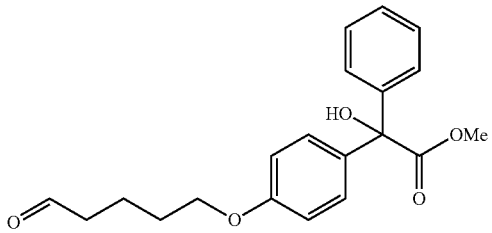 [SMILES: COC(=O)C(O)(c1ccccc1)c1ccc(OCCCCC=O)cc1]

Methyl 2-(4-(4-(1,3-dioxolan-2-yl)butoxy)phenyl)-2-hydroxy-2-phenylacetate (1.50 g, 3.88 mmol) was dissolved in 19.4 mL of a mixture ACN/1M HCl$_{aq}$ and stirred for 6 h at RT. Reaction was partitioned in AcOEt and washed three times with water and once with saturated NaCl$_{aq}$. Organic layer was dried over Na$_2$SO$_4$ and evaporated to dryness to give the title compound (1.12 g, 3.27 mmol, 84% yield). The product obtained was used in the following steps without further purifications.
UPLC-MS: 1.04 min, 325.2 [(M+H)−H2O]+, method 1.

Step 5; methyl 2-(4-((5-(((R)-2-(8-(benzyloxy)-2-oxo-1,2-dihydroquinolin-5-yl)-2-((tert-butyldimethylsilyl)oxy)ethyl)(tert-butoxycarbonyl)amino)pentyl)oxy)phenyl)-2-hydroxy-2-phenylacetate

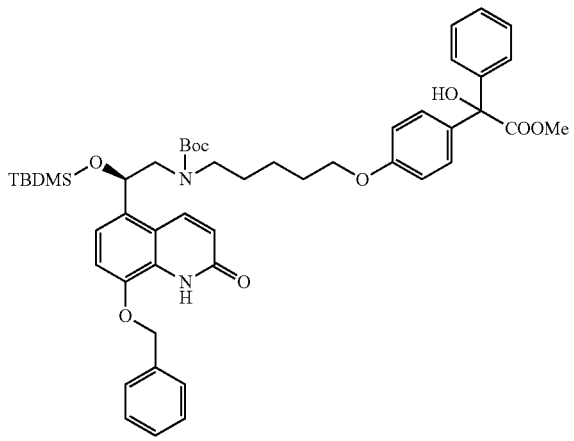

(R)-5-(2-amino-1-((tert-butyldimethylsilyl)oxy)ethyl)-8-(benzyloxy)quinolin-2(1H)-one (1.637 g, 3.86 mmol) and methyl 2-hydroxy-2-(4-((5-oxopentyl)oxy)phenyl)-2-phenylacetate (1.10 g, 3.21 mmol) were reacted for 1 h at RT in 16 mL of DCM with a spatula tip of Na$_2$SO$_4$, then AcOH (0.184 ml, 3.21 mmol) and Na(OAc)$_3$H (1.362 g, 6.43 mmol) were added in sequence and the mixture stirred for 3 h at RT. The reaction was cooled to 0° C. before addition of TEA (0.448 ml, 3.21 mmol) and di-tert-butyl dicarbonate (0.746 ml, 3.21 mmol), then the reaction was stirred for further 2 h at RT. The mixture was partitioned between AcOEt and washed three times with 0.2M HCl$_{aq}$, twice with water and once with saturated NaCl$_{aq}$. Organic layer was dried over Na$_2$SO$_4$ and evaporated to dryness to give a crude that after purification by flash chromatography (silica gel—eluents: hexane to hexane/THF) afforded the title compound (1.33 g, 1.563 mmol, 48.6% yield).

UPLC-MS: 1.78 min, 873.7 [M+Na]+, method 2.

Step 6; 2-(4-((5-(((R)-2-(8-(benzyloxy)-2-oxo-1,2-dihydroquinolin-5-yl)-2-((tert-butyldimethylsilyl)oxy)ethyl)(tert-butoxycarbonyl)amino)pentyl)oxy)phenyl)-2-hydroxy-2-phenylacetic acid

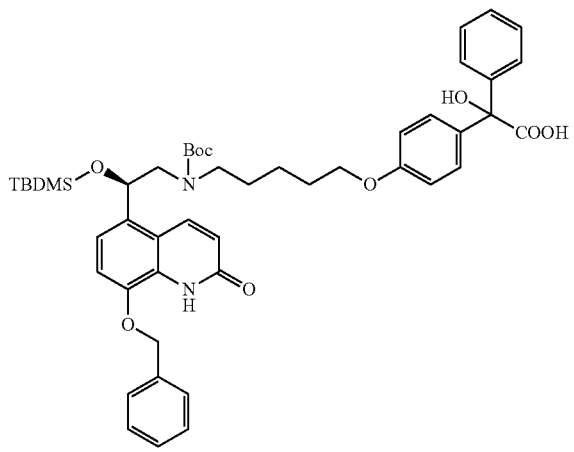

The title compound was made in a similar way as that of the Example 10, step 5 from methyl 2-(4-((5-(((R)-2-(8-(benzyloxy)-2-oxo-1,2-dihydroquinolin-5-yl)-2-((tert-butyldimethylsilyl)oxy)ethyl)(tert-butoxycarbonyl)amino)pentyl)oxy)phenyl)-2-hydroxy-2-phenylacetate (1.33 g, 1.563 mmol) and LiOH (0.187 g, 7.81 mmol) to give the desired product (1.1 g, 1.314 mmol, 84% yield).

UPLC-MS: 1.68 min, 838.2 [M+H]+, method 1.20141106_16

Step 7; benzyl 4-((2-(4-((5-(((R)-2-(8-(benzyloxy)-2-oxo-1,2-dihydroquinolin-5-yl)-2-((tert-butyldimethylsilyl)oxy)ethyl)(tert-butoxycarbonyl)amino)pentyl)oxy)phenyl)-2-hydroxy-2-phenylacetoxy)methyl)piperidine-1-carboxylate

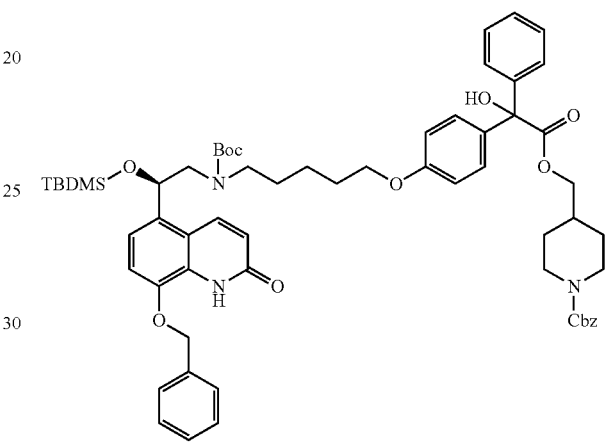

The title compound was made in a similar way as that of the compound of Example 10, step 7 from 2-(4-((5-(((R)-2-(8-(benzyloxy)-2-oxo-1,2-dihydroquinolin-5-yl)-2-((tert-butyldimethylsilyl)oxy)ethyl)(tert-butoxycarbonyl)amino)pentyl)oxy)phenyl)-2-hydroxy-2-phenylacetic acid (200 mg, 0.239 mmol) to give the desired product (98 mg, 0.092 mmol, 38.4% yield).

UPLC-MS: 3.25 min, 1068.5 [M+H]+, method 3.

Step 8; piperidin-4-ylmethyl 2-(4-((5-((tert-butoxycarbonyl)((R)-2-((tert-butyldimethylsilyl)oxy)-2-(8-hydroxy-2-oxo-1,2-dihydroquinolin-5-yl)ethyl)amino)pentyl)oxy)phenyl)-2-hydroxy-2-phenylacetate

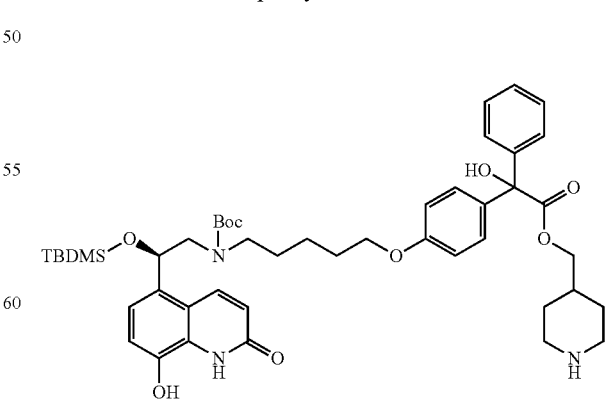

The title compound was made in a similar way as that of the Example 10, step 8 from benzyl 4-((2-(4-((5-(((R)-2-(8-(benzyloxy)-2-oxo-1,2-dihydroquinolin-5-yl)-2-((tert-butyldimethylsilyl)oxy)ethyl)(tert-butoxycarbonyl)amino)pentyl)oxy)phenyl)-2-hydroxy-2-phenylacetoxy)methyl)piperidine-1-carboxylate (98 mg, 0.092 mmol), Pd—C 10% wet (9.76 mg, 4.59 μmol), and HCOOH (7.04 μl, 0.183 mmol) to give the desired product (73 mg, 0.082 mmol, 89% yield). The product obtained was used in the following steps without further purifications.

UPLC-MS; 1.08 min, 844.7 [M+H]+, method 2.

Step 9; (1-benzylpiperidin-4-yl)methyl 2-(4-((5-((tert-butoxycarbonyl)((R)-2-((tert-butyldimethylsilyl)oxy)-2-(8-hydroxy-2-oxo-1,2-dihydroquinolin-5-yl)ethyl)amino)pentyl)oxy)phenyl)-2-hydroxy-2-phenylacetate

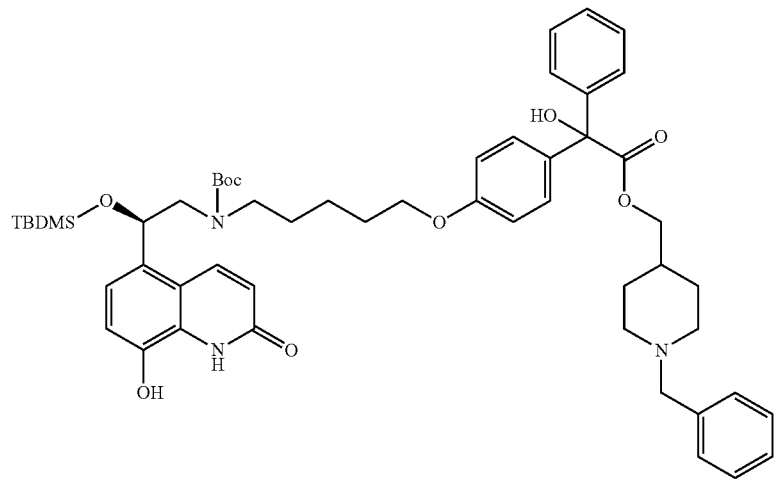

The title compound was made in a similar way as that of the Example 10, step 9 from (1-benzylpiperidin-4-yl)methyl 2-(4-((5-((tert-butoxycarbonyl)((R)-2-((tert-butyldimethylsilyl)oxy)-2-(8-hydroxy-2-oxo-1,2-dihydroquinolin-5-yl)ethyl)amino)-pentyl)oxy)phenyl)-2-hydroxy-2-phenylacetate (73 mg, 0.082 mmol), benzaldehyde (26.1 mg, 0.246 mmol), AcOH (9.39 μl, 0.164 mmol) and NaB(OAc)$_3$H (52.1 mg, 0.246 mmol) to give the desired product (77 mg). The product obtained was used in the following steps without further purifications.

UPLC-MS: 1.17 min, 934.7 [M+H]+, method 2.

Step 10; (Compound 51)

The title example was made in a similar way as that of the example 10, step 10 from (1-benzylpiperidin-4-yl)methyl 2-(4-((5-((tert-butoxycarbonyl)((R)-2-((tert-butyldimethylsilyl)oxy)-2-(8-hydroxy-2-oxo-1,2-dihydroquinolin-5-yl)ethyl)amino)-pentyl)oxy)phenyl)-2-hydroxy-2-phenylacetate (77 mg, 0.082 mmol) to give the title product (51) (28 mg, 0.037 mmol, 44.4% yield).

| N | Rt (min) | [M + H]+ | Method | NMR data (400 MHz) | Salt (2 eq unless stated) |
|---|---|---|---|---|---|
| 51 | 4.15 | 720 | 5 | (DMSO-d6) δ ppm 10.51-10.21 (bs, 1 H), 8.27-8.10 (m, 2 H), 7.40-7.18 (m, 12 H), 7.11 (d, J = 8.22 Hz, 1 H), 6.95 (d, J = 8.22 Hz, 1 H), 6.90-6.82 (m, 2 H), 6.54 (d, J = 9.87 Hz, 1 H), 6.42 (br. s., 1 H), 5.19 (br. s., 1 H), 4.02-3.90 (m, 4 H), 3.41-3.35 (m, 2 H), 2.68-2.96 (m, 6 H), 1.91-1.39 (m, 10 H), 1.15-1.07 (m, 2 H) | Formate |

Example 15. (R)-quinuclidin-3-yl 2-hydroxy-2-(4-((5-(((R)-2-hydroxy-2-(8-hydroxy-2-oxo-1,2-dihydroquinolin-5-yl)ethyl)amino)pentyl)oxy)phenyl)-2-phenylacetate diformate (Compound 52)

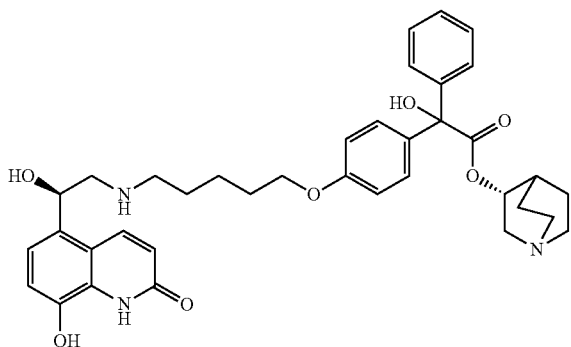 [SMILES: O=C(O[C@H]1CN2CCC1CC2)C(O)(c1ccccc1)c1ccc(OCCCCCNC[C@H](O)c2ccc(O)c3[nH]c(=O)ccc23)cc1]

Step 1; (R)-quinuclidin-3-yl 2-(4-((5-(((R)-2-(8-(benzyloxy)-2-oxo-1,2-dihydroquinolin-5-yl)-2-((tert-butyldimethylsilyl)oxy)ethyl)(tert-butoxycarbonyl)amino)-pentyl)oxy)phenyl)-2-hydroxy-2-phenylacetate

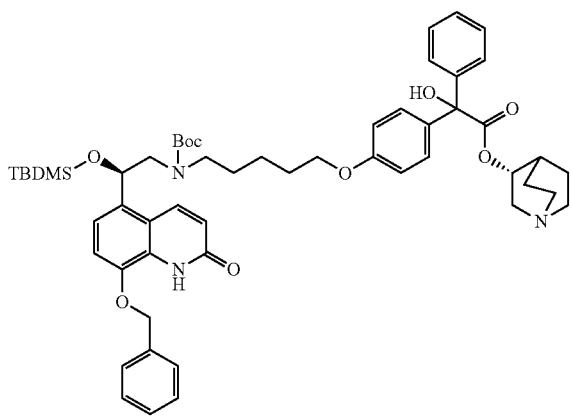

The title compound was made in a similar way as that of the Example 14, step 7 to give the desired product (138 mg, 0.146 mmol, 81% yield).
UPLC-MS: 1.27 min, 946.7 [M+H]+, method 2.

Step 2; (R)-quinuclidin-3-yl 2-(4-((5-((tert-butoxycarbonyl)((R)-2-((tert-butyldimethyl-silyl)oxy)-2-(8-hydroxy-2-oxo-1,2-dihydroquinolin-5-yl)ethyl)amino)pentyl)oxy)phenyl)-2-hydroxy-2-phenylacetate

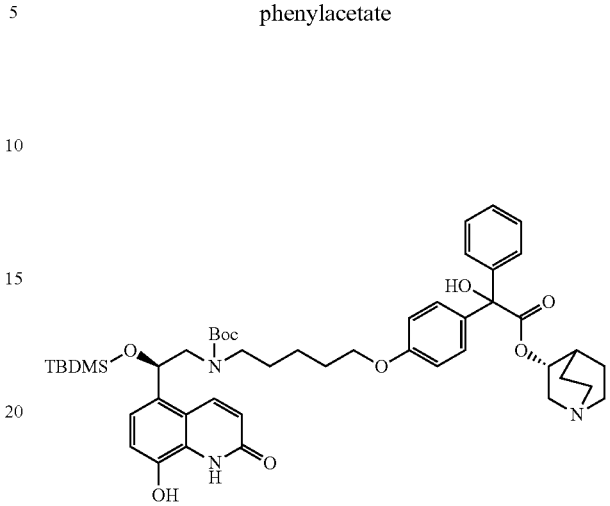

The title compound was made in a similar way as that of the Example 14, step 8 from (R)-quinuclidin-3-yl 2-(4-((5-(((R)-2-(8-(benzyloxy)-2-oxo-1,2-dihydroquinolin-5-yl)-2-((tert-butyldimethylsilyl)oxy)ethyl)(tert-butoxycarbonyl)amino)pentyl)oxy)phenyl)-2-hydroxy-2-phenylacetate (138 mg, 0.146 mmol), Pd—C 10% wet (15.52 mg, 7.29 μmol) and HCOOH (11.19 μl, 0.292 mmol) to give the desired product (150 mg). The product obtained was used in the following step without further purifications.
UPLC-MS: 1.09 min, 856.7 [M+H]+, method 2.

Step 3; (compound 52)

The title example was made in a similar way as that of the compound of example 10, step 10, from (R)-quinuclidin-3-yl 2-(4-((5-((tert-butoxycarbonyl)((R)-2-((tert-butyldimethylsilyl)oxy)-2-(8-hydroxy-2-oxo-1,2-dihydroquinolin-5-yl)ethyl)amino)pentyl)oxy)phenyl)-2-hydroxy-2-phenylacetate formate (132 mg, 0.146 mmol) to give the title product (52) (68 mg, 0.099 mmol, 67.6% yield).

| N | Rt (min) | [M + H]+ | Method | NMR data (400 MHz) | Salt (2 eq unless stated) |
|---|----------|----------|--------|--------------------|---------------------------|
| 52 | 3.64 | 642.0 | 5 | (DMSO-d6) δ ppm 10.59-10.24 (bs, 1 H), 8.19 (d, J = 10.19 Hz, 1 H), 8.15 (s, 1 H), 7.38-7.27 (m, 5 H), 7.25 (d, J = 8.88 Hz, 2 H), 7.14 (d, J = 8.22 Hz, 1 H), 6.98 (d, J = 8.22 Hz, 1 H), 6.92-6.83 (m, 2 H), 6.56 (d, J = 9.87 Hz, 1 H), 6.45 (br. s., 1 H), 5.32 (dd, J = 9.87, 2.63 Hz, 1 H), 4.92-4.71 (m, 1 H), 4.44-4.21 (m, 1 H), 4.05-3.89 (m, 2 H), 3.18 (dd, J = 13.98, 8.39 Hz, 2 H), 3.10-2.88 (m, 5 H), 2.77-2.58 (m, 3 H), 1.92 (br. s., 1 H), 1.76-1.34 (m, 8 H) | Formate |

Example 16. (1-benzylpiperidin-4-yl)methyl 2-hydroxy-2-(4-((4-((4-((((R)-2-hydroxy-2-(8-hydroxy-2-oxo-1,2-dihydroquinolin-5-yl)ethyl)amino)methyl)benzamido)methyl)-benzyl)oxy)phenyl)-2-phenylacetate diformate (Compound 53)

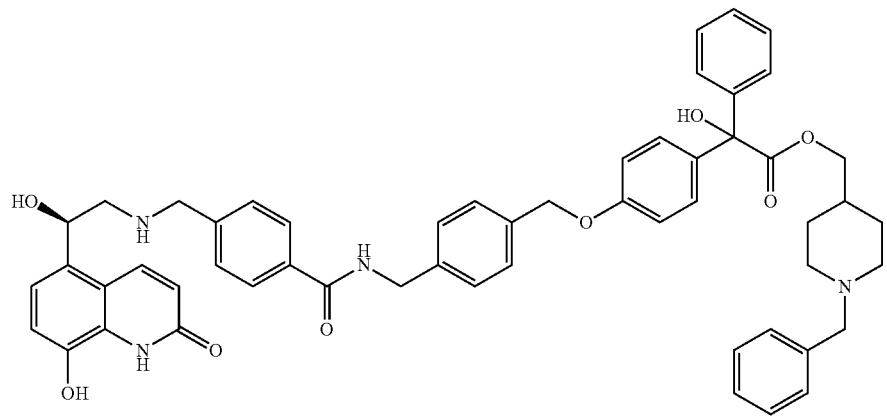 [SMILES: O=C(NCc1ccc(COc2ccc(C(O)(C(=O)OCC3CCN(Cc4ccccc4)CC3)c3ccccc3)cc2)cc1)c1ccc(CNC[C@H](O)c2ccc(O)c3[nH]c(=O)ccc23)cc1]

Step 1; methyl 2-(4-((4-(((tert-butoxycarbonyl)amino)methyl)benzyl)oxy)phenyl)-2-hydroxy-2-phenylacetate

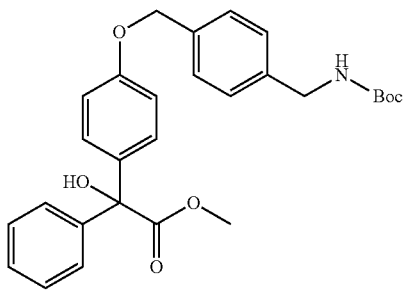 [SMILES: COC(=O)C(O)(c1ccccc1)c1ccc(OCc2ccc(CNC(=O)OC(C)(C)C)cc2)cc1]

Methyl 2-hydroxy-2-(4-hydroxyphenyl)-2-phenylacetate obtained as in Example 14, step 2 (0.5 g, 1.936 mmol), tert-butyl 4-(bromomethyl)benzylcarbamate (0.581 g, 1.936 mmol) and K$_2$CO$_3$ (0.268 g, 1.936 mmol) were reacted in 9.7 mL DMF at 80° C. for 3 h. Reaction was partitioned between water and AcOEt, washed three times with water and saturated NaCl$_{aq}$, dried over Na$_2$SO$_4$ and evaporated to dryness. The residue was purified by flash column chromatography (silica gel; eluents: hexane to 50/50 hexane/AcOEt) to afford the title compound (1.42 g, 93%).

UPLC-MS: 1.30 min, 460.0 [(M+H)–H2O]+, method 2.

Step 2; 2-(4-((4-(((tert-butoxycarbonyl)amino)methyl)benzyl)oxy)phenyl)-2-hydroxy-2-phenylacetic acid

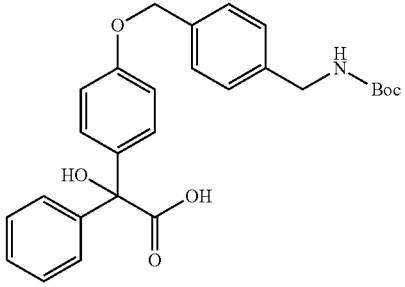 [SMILES: CC(C)(C)OC(=O)NCc1ccc(COc2ccc(C(O)(C(=O)O)c3ccccc3)cc2)cc1]

The title compound was made in a similar way as that of the example 10, step 5 from methyl 2-(4-((4-(((tert-butoxycarbonyl)amino)methyl)benzyl)oxy)phenyl)-2-hydroxy-2-phenylacetate (0.65 g, 1.361 mmol) and LiOH (0.163 g, 6.81 mmol) to give the desired product (673 mg, 1.452 mmol, 107% yield).

UPLC-MS: 2.28 min, 446.0 [(M+H)–H2O]+, method 4.

Step 3; 2 (1-benzylpiperidin-4-yl)methyl 2-(4-((4-(((tert-butoxycarbonyl)amino)methyl)-benzyl)oxy)phenyl)-2-hydroxy-2-phenylacetate Step 4; (1-benzylpiperidin-4-yl)methyl 2-(4-((4-(aminomethyl)benzyl)oxy)phenyl)-2-hydroxy-2-phenylacetate bis hydrochloride

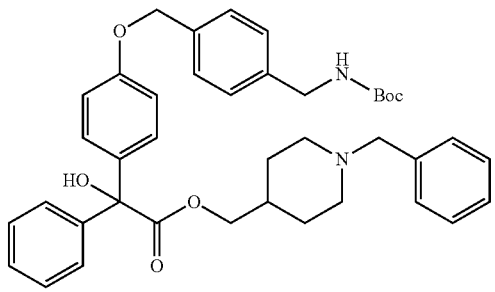 [SMILES: CC(C)(C)OC(=O)NCc1ccc(COc2ccc(C(O)(C(=O)OCC3CCN(Cc4ccccc4)CC3)c3ccccc3)cc2)cc1]

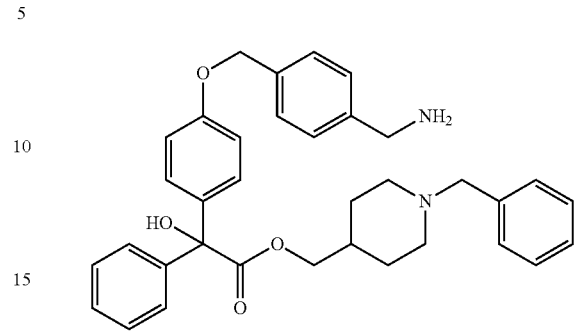

The title compound was made in a similar way as that of the Example 10, step 10 from 2 (1-benzylpiperidin-4-yl)methyl 2-(4-((4-(((tert-butoxycarbonyl)amino)methyl)-benzyl)oxy)phenyl)-2-hydroxy-2-phenylacetate (520 mg, 0.799 mmol) to give the title compound (357 mg, 0.572 mmol, 71.6% yield).

UPLC-MS: 0.49 min, 551.1 [M+H]+, method 2.

Step 5; (1-benzylpiperidin-4-yl)methyl 2-(4-((4-(((tert-butoxycarbonyl)((R)-2-((tert-butyldimethylsilyl)oxy)-2-(8-hydroxy-2-oxo-1,2-dihydroquinolin-5-yl)ethyl)amino)-methyl)benzamido)methyl)benzyl)oxy)phenyl)-2-hydroxy-2-phenylacetate The title intermediate was made in a similar way as that of the compound of Example 10, step 7 from 2-(4-((4-(((tert-butoxycarbonyl)amino)methyl)benzyl)oxy)-phenyl)-2-hydroxy-2-phenylacetic acid (630 mg, 1.359 mmol), CDI (661 mg, 4.08 mmol) and (1-benzylpiperidin-4-yl)methanol (1116 mg, 5.44 mmol) to give the desired product (520 mg, 0.799 mmol, 58.8% yield).

UPLC-MS: 0.92 min, 651.1 [M+H]+, method 2.

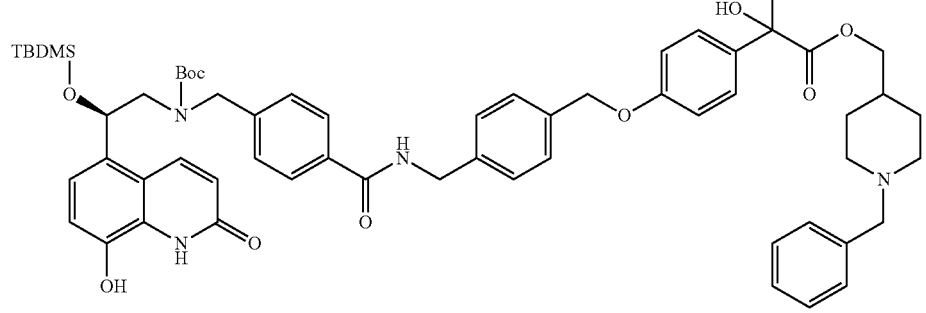

(R)-4-(((tert-butoxycarbonyl)(2-((tert-butyldimethylsilyl)oxy)-2-(8-hydroxy-2-oxo-1,2-dihydroquinolin-5-yl)ethyl)amino)methyl)benzoic acid, obtained as described in Procedure 4, steps 1-5, (50 mg, 0.264 mmol), (1-benzylpiperidin-4-yl)methyl 2-(4-((4-(aminomethyl)benzyl)oxy)phenyl)-2-hydroxy-2-phenylacetate bis hydrochloride (164 mg, 0.264 mmol), 1H-benzo[d][1,2,3]triazol-1-ol (46.3 mg, 0.343 mmol), DMAP (4 mg, 0.033 mmol) and DIEA (0.138 ml, 0.791 mmol) were stirred for 5 min in 3 mL of DMF, then EDC (65.7 mg, 0.343 mmol) added and the mixture stirred overnight at RT. Reaction mixture was partitioned between saturated NaHCO$_3$ $_{aq}$ and AcOEt, organic layer washed three times with water and saturated NaCl$_{aq}$, dried over Na$_2$SO$_4$ and evaporated to dryness to give the crude (292 mg). The crude obtained was used in the following step without further purifications.

UPLC-MS: 1.14 min, 1102.1 [M+H]+, method 2.

Step 6; (Compound 53)

The title example was made in a similar way as that of the example 10, step 10 from 1-benzylpiperidin-4-yl)methyl 2-(4-((4-(((tert-butoxycarbonyl)((R)-2-((tert-butyldimethylsilyl)oxy)-2-(8-hydroxy-2-oxo-1,2-dihydroquinolin-5-yl)ethyl)amino)-methyl)benzamido)methyl)benzyl)oxy)phenyl)-2-hydroxy-2-phenylacetate (290 mg, 0.263 mmol) to give the title product (53) (62 mg, 0.063 mmol, 24.05% yield).

| N | $R_t$ (min) | [M + H]+ | Method | NMR data (400 MHz) | Salt 2 eq unless stated |
|---|---|---|---|---|---|
| 53 | 4.72 | 887.0 | 5 | (DMSO-d6) d ppm 10.33 (br. s., 1 H), 9.00 (t, J = 5.95 Hz, 1 H), 8.22-8.01 (m, 2 H), 7.85 (d, J = 7.94 Hz, 2 H), 7.49-6.83 (m, 22 H), 6.60-6.34 (m, 2 H), 5.20-4.97 (m, 3 H), 4.47 (d, J = 5.73 Hz, 2 H), 4.34 (br. s., 1 H), 3.97 (d, J = 6.17 Hz, 2 H), 3.89 (s, 2 H), 3.59-3.37 (m, 5 H), 2.84-2.59 (m, 4 H), 1.84 (t, J = 11.03 Hz, 2 H), 1.58-1.35 (m, 3 H), 1.19-0.97 (m, 4 H) | Formate |

Example 17. (1-benzylpiperidin-4-yl)methyl 2-hydroxy-2-(3-((((5-(((R)-2-hydroxy-2-(8-hydroxy-2-oxo-1,2-dihydroquinolin-5-yl)ethyl)amino)pentyl)oxy)carbonyl)amino)-phenyl)-2-phenylacetate bis hydrochloride (Compound 54)

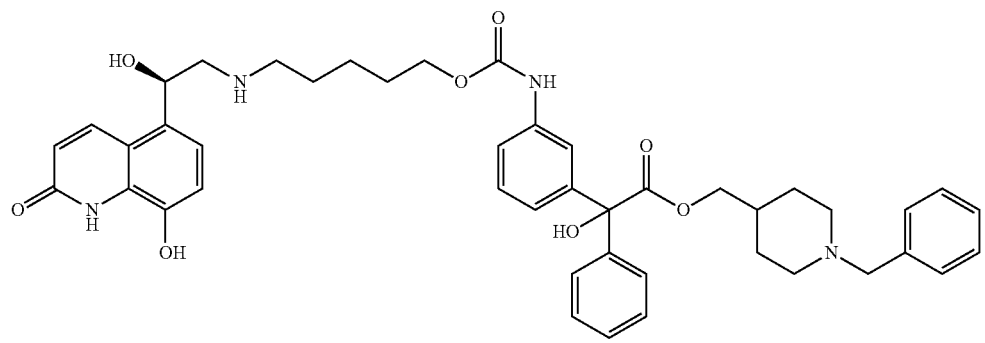 [SMILES: O=C(Nc1cccc(C(O)(C(=O)OCC2CCN(Cc3ccccc3)CC2)c2ccccc2)c1)OCCCCCNC[C@H](O)c1ccc(O)c2[nH]c(=O)ccc12]

Step 1; Methyl 2-(3-aminophenyl)-2-hydroxy-2-phenylacetate

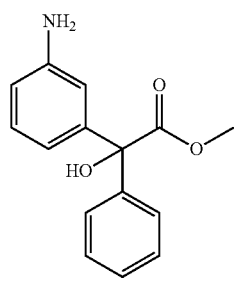 [SMILES: COC(=O)C(O)(c1ccccc1)c1cccc(N)c1]

Methyl 2-oxo-2-phenylacetate 16.4 mmol, 4.22 g), was dissolved (in DMF (5 ml, 21.32 mmol) and the solution was cooled down to −15 C.°, then (3-(bis(trimethylsilyl)-amino)phenyl)magnesium chloride (21.32 ml, 21.32 mmol) was added dropwise and the mixture left to reach rt. Methyl 2-oxo-2-phenylacetate (3.5 g, 21.32 mmol) was dissolved in DMF dry (10 ml) under argon and the solution was cooled down to −20 C.°, then (3-(bis(trimethylsilyl)amino)phenyl)magnesium chloride 1.0M in THF (21.32 ml, 21.32 mmol) was added dropwise and the mixture left to reach rt and stirred for further 1.5 h. The reaction was quenched by the addition of Acetonitrile (20 ml) and partitioned between AcOEt (80 ml) and water (80 ml). Organic layer was washed twice with water, once with sat NaCl, dried over $Na_2SO_4$ and dried under reduced pressure. The crude was purified by flash chromatography on silica gel (eluent—from 95/5 Hexane/AcOEt to 100% AcOEt) to afford the title compound (3.73 g, 14.50 mmol, 68% yield).

UPLC-MS: 0.89 min, 258.1 [(M+H)]+, method 4.

Step 2; (R)-tert-butyl (2-(8-(benzyloxy)-2-oxo-1,2-dihydroquinolin-5-yl)-2-((tert-butyldimethylsilyl)oxy)ethyl)(5-hydroxypentyl)carbamate

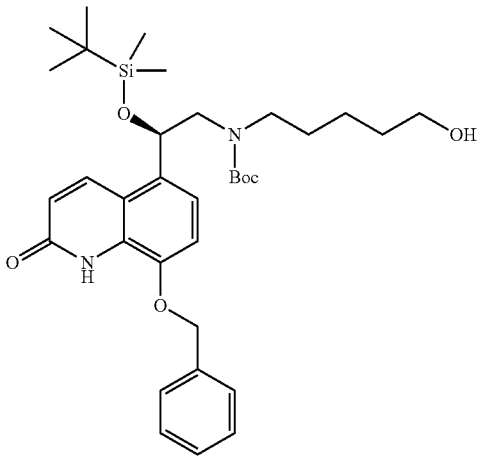 [SMILES: CC(C)(C)OC(=O)N(CCCCCO)C[C@H](O[Si](C)(C)C(C)(C)C)c1ccc(OCc2ccccc2)c2[nH]c(=O)ccc12]

(R)-8-(benzyloxy)-5-(2-bromo-1-((tert-butyldimethylsilyl)oxy)ethyl)quinolin-2(1H)-one (500 mg, 1.024 mmol) and 5-aminopentan-1-ol (106 mg, 1.024 mmol) were dissolved in NMP (3 ml) and the solution was stirred under nitrogen at 85° C. overnight. The reaction mixture was partitioned between AcOEt and water, the organic phase washed twice with water and the organic layers were dried over Na2SO4 and evaporated under reduced pressure to give a crude that was dissolved in 1/1 THF and NaHCO3 sat. sol. (6 ml), ditertbutyldicarbonate (67.1 mg, 0.308 mmol) was added and the mixture heated at rt for 1 h. The reaction mixture was partitioned between AcOEt (20 ml) and water and the organic phase washed twice with water, once with HCl 0.5M (20 ml) and once with brine. Organic layers were dried over Na$_2$SO$_4$ and dried under reduced pressure. The crude was purified by flash chromatography on silica gel (eluent—from 100% Hexane to 20%/80% Hexane/Ethyl acetate 80%.) to give the title compound (76 mg, 0.124 mmol, 12.16% yield).

UPLC-MS: 2.86 min, 611 [(M+H)]+, method 4.

Step 3; methyl 2-(3-(((R)-10-(8-(benzyloxy)-2-oxo-1,2-dihydroquinolin-5-yl)-8-(tert-butoxycarbonyl)-12,12,13,13-tetramethyl-2,11-dioxa-8-aza-12-silatetradecan-1-oyl)amino)phenyl)-2-hydroxy-2-phenylacetate

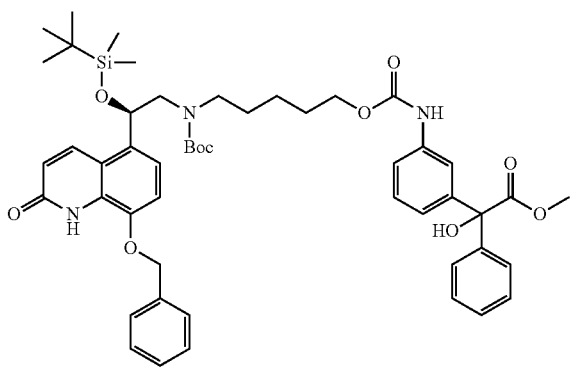 [SMILES: COC(=O)C(O)(c1ccccc1)c1cccc(NC(=O)OCCCCCN(C[C@H](O[Si](C)(C)C(C)(C)C)c2ccc(OCc3ccccc3)c3[nH]c(=O)ccc23)C(=O)OC(C)(C)C)c1]

Methyl 2-(3-aminophenyl)-2-hydroxy-2-phenylacetate (1 g, 3.89 mmol) was dissolved in Acetonitrile (12 ml) and trichloromethyl carbonochloridate (1.922 g, 9.72 mmol) was added. The solution was stirred at rt for 7 hours then it was evaporated under vacuum, added with 1 ml of DCM and evaporated again. The residue was dissolved in DCM (5 ml), added with (R)-tert-butyl (2-(8-(benzyloxy)-2-oxo-1,2-dihydroquinolin-5-yl)-2-((tert-butyldimethylsilyl)oxy)ethyl)(5-hydroxypentyl)carbamate (2.374 g, 3.89 mmol), and the reaction was stirred at rt for 6 hours. The solvent was evaporated and the residue purified by flash chromatography on silica gel (eluent—Hexane/Ethyl acetate from 0 to 90%) to afford the title compound (344 mg, 9.9%).

UPLC-MS: 1.64 min, 895.4 [(M+H)]+, method 2.

Step 4; 2-(3-(((R)-10-(8-(benzyloxy)-2-oxo-1,2-dihydroquinolin-5-yl)-8-(tert-butoxycarbonyl)-12,12,13,13-tetramethyl-2,11-dioxa-8-aza-12-silatetradecan-1-oyl)amino)phenyl)-2-hydroxy-2-phenylacetic acid

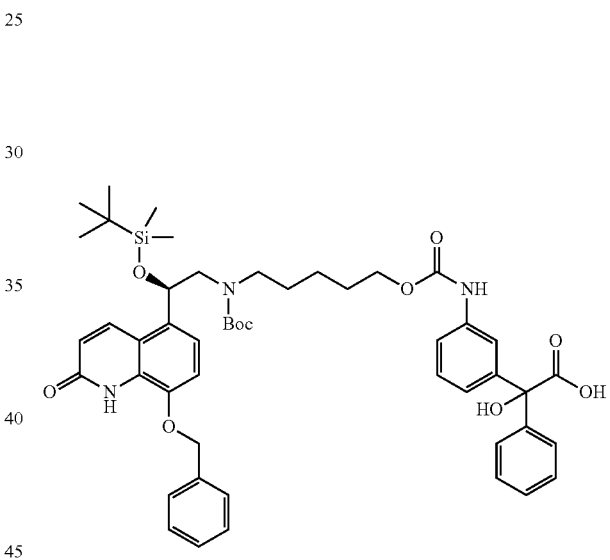

Methyl 2-(3-(((R)-10-(8-(benzyloxy)-2-oxo-1,2-dihydroquinolin-5-yl)-8-(tert-butoxycarbonyl)-12,12,13,13-tetramethyl-2,11-dioxa-8-aza-12-silatetradecan-1-oyl)amino)phenyl)-2-hydroxy-2-phenylacetate (143 mg, 0.160 mmol) was dissolved in DMF (0.7 ml) and LiOH 1N (0.320 ml, 0.320 mmol) was dropped inside; the mixture was stirred at rt for 2 h. The pH of mixture was adjust with a 1N HCl aq solution till pH=5. Reaction mixture was partitioned between AcOEt (5 ml) and water and the organic phase washed twice with water then with brine. Finally the organic solution was dried over sodium sulphate, evaporated under vacuum to afford the title compound (120 mg, 85%), that was used as such for the next steps.

UPLC-MS: 1.59 min, 880.2 [(M+H)]+, method 2.

Step 5; (1-benzylpiperidin-4-yl)methyl 2-(3-(((R)-8-(tert-butoxycarbonyl)-10-(8-hydroxy-2-oxo-1,2-dihydroquinolin-5-yl)-12,12,13,13-tetramethyl-2,11-dioxa-8-aza-12-silatetradecan-1-oyl)amino)phenyl)-2-hydroxy-2-phenylacetate

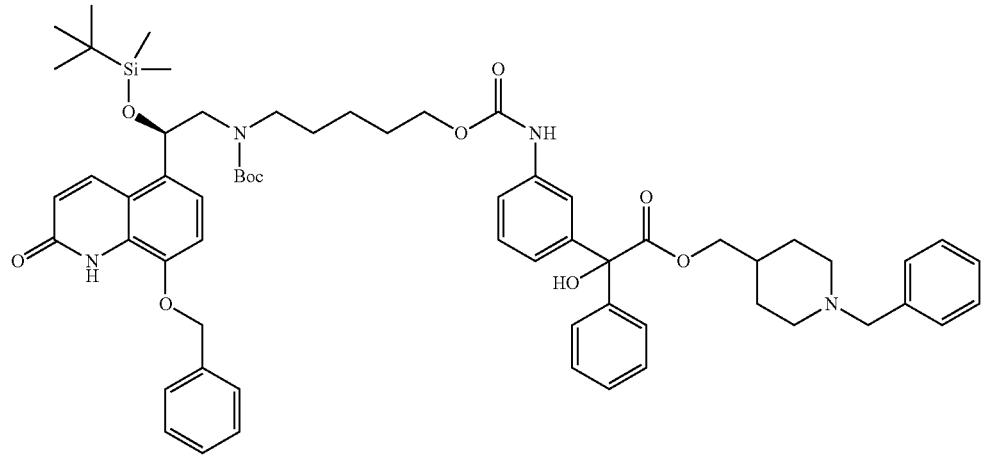 [SMILES: CC(C)(C)OC(=O)N(CCCCCOC(=O)Nc1cccc(C(O)(C(=O)OCC2CCN(Cc3ccccc3)CC2)c2ccccc2)c1)C[C@H](O[Si](C)(C)C(C)(C)C)c1ccc(OCc2ccccc2)c2[nH]c(=O)ccc12]

2-(3-(((R)-10-(8-(benzyloxy)-2-oxo-1,2-dihydroquinolin-5-yl)-8-(tert-butoxy-carbonyl)-12,12,13,13-tetramethyl-2,11-dioxa-8-aza-12-silatetradecan-1-oyl)amino)-phenyl)-2-hydroxy-2-phenylacetic acid (120 mg, 0.136 mmol) was dissolved in DMF (1.5 ml, 0.136 mmol) and di(1H-imidazol-1-yl)methanone, CDI (33.2 mg, 0.205 mmol) was added and the mixture was stirred at rt for 1 h. Finally, (1-benzylpiperidin-4-yl)methanol (33.6 mg, 0.164 mmol) was added and the reaction was left to stir at rt for 3 h. Reaction mixture was partitioned between AcOEt (20 ml) and water; the organic phase was washed twice with water, HCl 0.5M (20 ml) and brine. Finally the solution was dried over sodium sulphate and evaporated under vacuum. The residue was submitted to flash chromatography on silica gel (eluent—from 100% AcOEt to 80/20 AcOEt/(NH$_3$ 7N in MeOH) to afford the title compound (75 mg, 0.070 mmol, 51.5% yield) as yellowish foam.

UPLC-MS: 2.51 min, 1066.6 [(M+H)]+, method 4.

Step 6; (1-benzylpiperidin-4-yl)methyl 2-(3-(((R)-8-(tert-butoxycarbonyl)-10-(8-hydroxy-2-oxo-1,2-dihydroquinolin-5-yl)-12,12,13,13-tetramethyl-2,11-dioxa-8-aza-12-silatetradecan-1-oyl)amino)phenyl)-2-hydroxy-2-phenylacetate

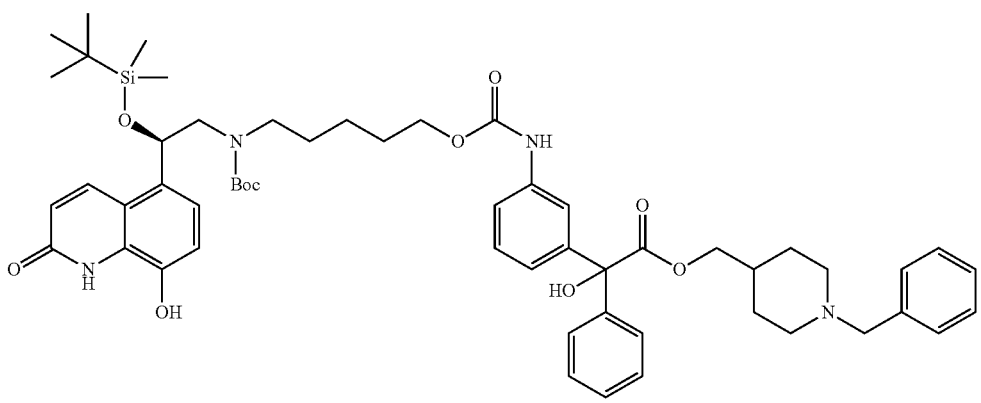 [SMILES: CC(C)(C)OC(=O)N(CCCCCOC(=O)Nc1cccc(C(O)(C(=O)OCC2CCN(Cc3ccccc3)CC2)c2ccccc2)c1)C[C@H](O[Si](C)(C)C(C)(C)C)c1ccc(O)c2[nH]c(=O)ccc12]

(1-benzylpiperidin-4-yl)methyl 2-(3-(((R)-10-(8-(benzyloxy)-2-oxo-1,2-dihydroquinolin-5-yl)-8-(tert-butoxycarbonyl)-12,12,13,13-tetramethyl-2,11-dioxa-8-aza-12-silatetradecan-1-oyl)amino)phenyl)-2-hydroxy-2-phenylacetate (150 mg, 0.281 mmol) was dissolved in methanol (2 ml, 0.281 mmol) under nitrogen then the suspension was added with Pd/BaSO$_4$ (40 mg, 0.281 mmol) and hydrogenated for 2 h at rt under balloon pressure of hydrogen. Reaction mixture was filtered and dried to give the crude title compound (75 mg, 0.153 mmol, 54.6% yield) as a yellowish oil, used as is in the next step without further purification.

UPLC-MS: 2.59 min, 977.53 [(M+H)]+, method 4.

Step 7; (Compound 54)

(1-benzylpiperidin-4-yl)methyl 2-(3-(((R)-8-(tert-butoxy-carbonyl)-10-(8-hydroxy-2-oxo-1,2-dihydroquinolin-5-yl)-12,12,13,13-tetramethyl-2,11-dioxa-8-aza-12-silatetradecan-1-oyl)amino)phenyl)-2-hydroxy-2-phenylacetate (30 mg, 0.031 mmol) was dissolved in HCl 37% (0.5 ml) and the solution was stirred at room temperature for 5 min. with complete disappearing of starting material in UPLC. Evaporation of solvent was performed using V10 Biotage. The residue was triturated in acetone and filtrate on a cartridge to afford the title compound (54) (11 mg, 47%).

| N | $R_t$ (min) | [M + H]+ | Method | NMR data (400 MHz) | Salt 2 eq unless stated |
|---|---|---|---|---|---|
| 54 | 4.19 | 763.1 | 5 | (DMSO-d6) δ ppm 10.44 (br. s., 2 H), 9.58 (s, 1 H), 9.16 (br. s., 1 H), 8.66 (br. s., 1 H), 8.26 (d, J = 9.87 Hz, 1 H), 7.69-6.82 (m, 15 H), 6.55 (d, J = 9.87 Hz, 1 H), 6.26-5.95 (m, 1 H), 5.44 (dd, J = 10.03, 2.14 Hz, 1 H), 4.22 (d, J = 4.93 Hz, 2 H), 4.06-3.87 (m, 4 H), 3.28 (d, J = 11.84 Hz, 2 H), 3.12-2.73 (m, 6 H), 1.86-1.25 (m, 10 H) | HCl |

Example 18. (R)-quinuclidin-3-yl 2-hydroxy-2-(3-(5-(((R)-2-hydroxy-2-(8-hydroxy-2-oxo-1,2-dihydroquinolin-5-yl)ethyl)amino)pentanamido)phenyl)-2-phenylacetate bis hydrochloride (Compound 55)

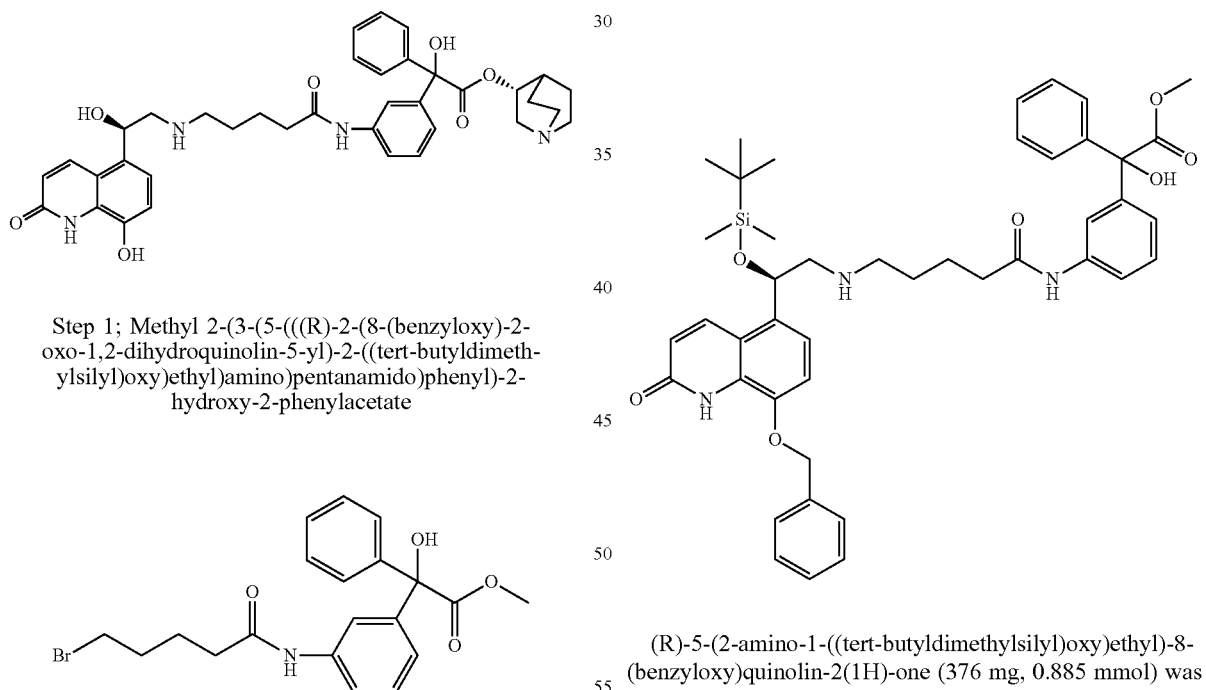

Step 1; Methyl 2-(3-(5-(((R)-2-(8-(benzyloxy)-2-oxo-1,2-dihydroquinolin-5-yl)-2-((tert-butyldimethylsilyl)oxy)ethyl)amino)pentanamido)phenyl)-2-hydroxy-2-phenylacetate Methyl 2-(3-aminophenyl)-2-hydroxy-2-phenylacetate (500 mg, 1.943 mmol) obtained as in Example 17, step 1, was dissolved in DCM (2 ml) and 5-bromopentanoyl chloride (504 mg, 2.53 mmol) was added and the reaction was stirred at rt for 2 hours. The mixture was diluted with DCM (2 ml) and the organic phase was washed with NaHCO₃ saturated solution, then with 1M HCl and the twice with brine. The solution was dried over sodium sulphate and evaporated under vacuum to give the title compound as a pale brown oil (490 mg, 60%).

UPLC-MS: 1.82 min, 404.01 [(M+H)−H2O]+, method 4.

Step 2; Methyl 2-(3-(5-(((R)-2-(8-(benzyloxy)-2-oxo-1,2-dihydroquinolin-5-yl)-2-((tert-butyldimethylsilyl)oxy)ethyl)amino)pentanamido)phenyl)-2-hydroxy-2-phenylacetate (R)-5-(2-amino-1-((tert-butyldimethylsilyl)oxy)ethyl)-8-(benzyloxy)quinolin-2(1H)-one (376 mg, 0.885 mmol) was dissolved in DMF dry (2 ml). 4-aminobutan-1-ol (0.082 ml, 0.884 mmol) was added and the solution stirred under nitrogen at 95° C. for 4 hrs. Reaction mixture was partitioned between AcOEt and water and the organic phase washed twice with water. The organic layer was dried over Na₂SO₄ and evaporated under reduced pressure to give an pale yellow oil. The residue was purified by reversed phase flash column chromatography (eluent—from 100% A to 100% B in 15CV; A: water/MeCN 95/5+0.01% HCOOH; B: water/MeCN 5/95+0.01% HCOOH) to afford the title compound (464 mg, 0.607 mmol, 82% yield).

UPLC-MS: 2.13 min, 764.01 [(M+H)+], method 4.

Step 3; Methyl 2-(3-(5-(((R)-2-(8-(benzyloxy)-2-oxo-1,2-dihydroquinolin-5-yl)-2-((tert-butyldimethylsilyl)oxy)ethyl)(tert-butoxycarbonyl)amino)pentanamido)phenyl)-2-hydroxy-2-phenylacetate

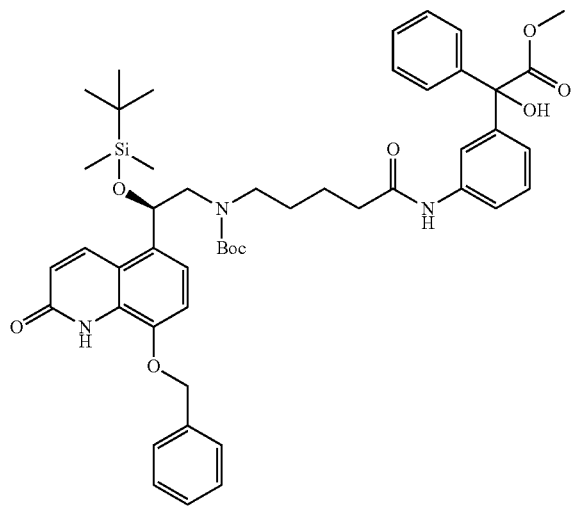 [SMILES: COC(=O)C(O)(c1ccccc1)c1cccc(NC(=O)CCCCN(C[C@H](O[Si](C)(C)C(C)(C)C)c2ccc(OCc3ccccc3)c3[nH]c(=O)ccc23)C(=O)OC(C)(C)C)c1]

Methyl 2-(3-(5-(((R)-2-(8-(benzyloxy)-2-oxo-1,2-dihydroquinolin-5-yl)-2-((tert-butyldimethylsilyl)oxy)ethyl)amino)pentanamido)phenyl)-2-hydroxy-2-phenylacetate (170 mg, 0.223 mmol) was dissolved in THF (1 ml), the di-tert-butyl dicarbonate (72.8 mg, 0.334 mmol) and NaHCO3 saturated solution (1 ml, 4.45 mmol) were added and the mixture was stirred at rt for 1 h. Reaction mixture was partitioned between AcOEt (20 ml) and water and the organic phase washed twice with water, HCl 0.5M (20 ml) and brine. Finally the organic solution was dried over sodium sulphate, evaporated under vacuum to give the title compound in quantitative yield (192 mg). No purification was needed.
UPLC-MS: 1.57 min, 864.37 [(M+H)]+, method 2.

Step 4; 2-(3-(5-(((R)-2-(8-(benzyloxy)-2-oxo-1,2-dihydroquinolin-5-yl)-2-((tert-butyldimethylsilyl)oxy)ethyl)(tert-butoxycarbonyl)amino)pentanamido)phenyl)-2-hydroxy-2-phenylacetic acid

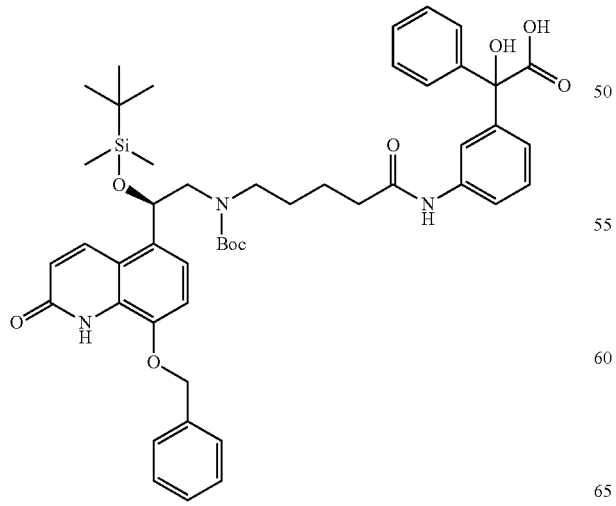

Methyl 2-(3-(5-(((R)-2-(8-(benzyloxy)-2-oxo-1,2-dihydroquinolin-5-yl)-2-((tert-butyldimethylsilyl)oxy)ethyl)(tert-butoxycarbonyl)amino)pentanamido)phenyl)-2-hydroxy-2-phenylacetate (170 mg, 0.197 mmol) was dissolved in DMF (1 ml) and LiOH 1N (0.393 ml, 0.393 mmol) was added and the mixture was stirred at rt for 1 h. The pH of mixture was adjust with a 1N HCl aq solution till pH=5. Reaction mixture was partitioned between AcOEt (5 ml) and water and the organic phase washed twice with water then with brine. Finally the organic solution was dried over sodium sulphate, evaporated under vacuum to afford the title compound (170 mg, 90%). No purification was needed.
UPLC-MS: 1.50 min, 850.01 [(M+H)]+, method 2.

Step 5; (R)-quinuclidin-3-yl 2-(3-(5-(((R)-2-(8-(benzyloxy)-2-oxo-1,2-dihydroquinolin-5-yl)-2-((tert-butyldimethylsilyl)oxy)ethyl)(tert-butoxycarbonyl)amino)pentanamido)-phenyl)-2-hydroxy-2-phenylacetate

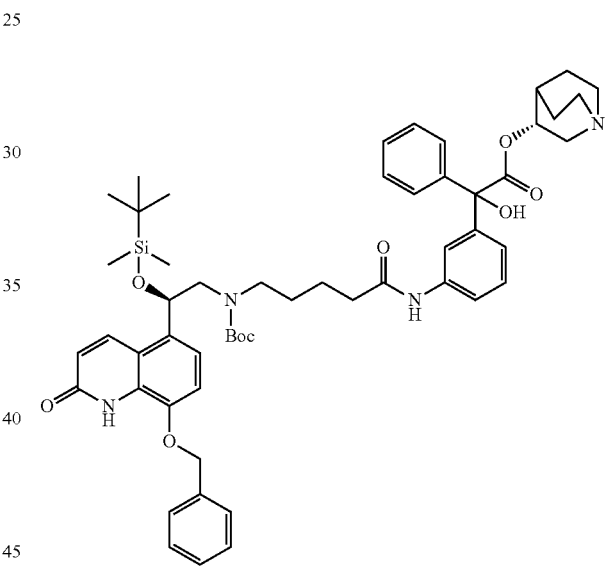

2-(3-(5-(((R)-2-(8-(benzyloxy)-2-oxo-1,2-dihydroquinolin-5-yl)-2-((tert-butyldimethylsilyl)oxy)ethyl)(tert-butoxycarbonyl)amino)pentanamido)phenyl)-2-hydroxy-2-phenylacetic acid (170 mg, 0.20 mmol) was dissolved in DMF (1.3 ml) and di(1H-imidazol-1-yl)methanone, CDI (48.6 mg, 0.30 mmol) was added and the mixture was stirred at rt for 1 h. Finally (R)-quinuclidin-3-ol (30.5 mg, 0.240 mmol) was added and the reaction was left to stir at rt for 3 h. Reaction mixture was partitioned between AcOEt (20 ml) and water; the organic phase was washed twice with water, HCl 0.5M (20 ml) and brine. Finally the solution was dried over sodium sulphate and evaporated under vacuum. The residue was purified by flash column chromatography (eluent—100% AcOEt to 80/20 AcOEt/NH3 7N in MeOH) to afford the title compound (105 mg, 54.7%).
UPLC-MS: 1.30 min, 959.52 [(M+H)]+, method 2.

Step 6; (R)-quinuclidin-3-yl 2-(3-(5-((tert-butoxy-carbonyl)((R)-2-((tert-butyldimethyl-silyl)oxy)-2-(8-hydroxy-2-oxo-1,2-dihydroquinolin-5-yl)ethyl)amino)pentanamido)-phenyl)-2-hydroxy-2-phenylacetate (1-benzylpiperidin-4-yl)methyl 2-(3-(((R)-10-(8-(benzyloxy)-2-oxo-1,2-dihydroquinolin-5-yl)-8-(tert-butoxycarbonyl)-12,12,13,13-tetramethyl-2,11-dioxa-8-aza-12-silatetradecan-1-oyl)amino)phenyl)-2-hydroxy-2-phenylacetate (102 mg, 0.106 mmol) was dissolved in Methanol (1.5 ml) under nitrogen then the suspension was added with Pd/BaSO4 (40 mg, 0.281 mmol) and hydrogenated for 2 h at rt under balloon pressure of hydrogen. Reaction mixture was filtered and dried to give the crude (1-benzylpiperidin-4-yl)methyl 2-(3-(((R)-8-(tert-butoxycarbonyl)-10-(8-hydroxy-2-oxo-1,2-dihydroquinolin-5-yl)-12,12,13,13-tetramethyl-2,11-dioxa-8-aza-12-silatetradecan-1-oyl)amino)phenyl)-2-hydroxy-2-phenylacetate (75 mg, 0.086 mmol, 81.1% yield) as a yellowish oil, used as is in the next step without further purification.

UPLC-MS: 2.29 min, 435.1 [(M+H)/2]+, method 4.

Step 7; (Compound 55)

(R)-quinuclidin-3-yl 2-(3-(5-((tert-butoxycarbonyl)((R)-2-((tert-butyldimethyl-silyl)oxy)-2-(8-hydroxy-2-oxo-1,2-dihydroquinolin-5-yl)ethyl)amino)pentanamido)-phenyl)-2-hydroxy-2-phenylacetate (45 mg, 0.052 mmol) was dissolved in HCl 35% (0.7 ml) and stirred at rt for 5 min. with complete disappearing of starting material in UPLC. Evaporation of solvent was performed using V10 Biotage. The residue was triturated in acetone and filtrate on a cartridge to afford the title compound (55) (34 mg, 88%).

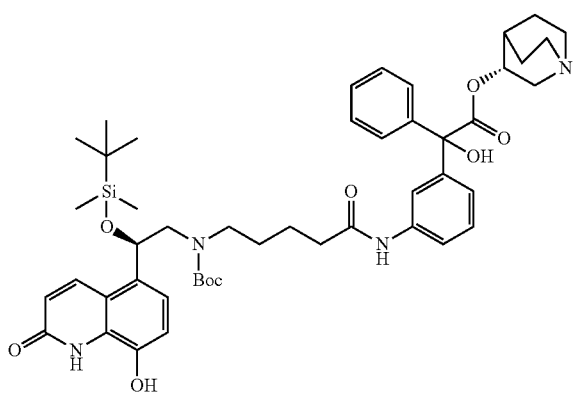 [SMILES: CC(C)(C)OC(=O)N(CCCCC(=O)Nc1cccc(C(O)(C(=O)O[C@H]2CN3CCC2CC3)c2ccccc2)c1)C[C@H](O[Si](C)(C)C(C)(C)C)c1ccc(O)c2[nH]c(=O)ccc12]

| N | R$_t$ (min) | [M + H]+ | Method | NMR data (400 MHz) | Salt 2 eq unless stated |
|---|---|---|---|---|---|
| 55 | 3.38/3.41 | 655.1 | 5 | 1H NMR (400 MHz, DMSO-d6) δ ppm 10.60-10.37 (3 s, 3 H each), 9.94-5.17 (m, 21 H), 5.21-5.08 (m, 1 H), 3.75-1.75 (m, 17 H); | HCl |

Example 19. (1-benzylpiperidin-4-yl)methyl 2-hydroxy-2-(3-(3-(3-(4-((((R)-2-hydroxy-2-(8-hydroxy-2-oxo-1,2-dihydroquinolin-5-yl)ethyl)amino)methyl)benzamido)-propyl)ureido)phenyl)-2-phenylacetate diformate (Compound 56)

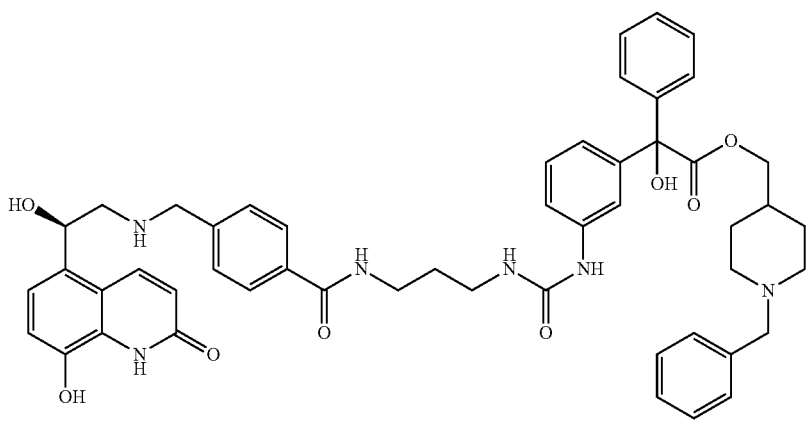 [SMILES: O=C(NCCCNC(=O)c1ccc(CNC[C@H](O)c2ccc(O)c3[nH]c(=O)ccc23)cc1)Nc1cccc(C(O)(C(=O)OCC2CCN(Cc3ccccc3)CC2)c2ccccc2)c1]

Step 1; methyl 2-(3-(3-(3-((tert-butoxycarbonyl)amino)propyl)ureido)phenyl)-2-hydroxy-2-phenylacetate

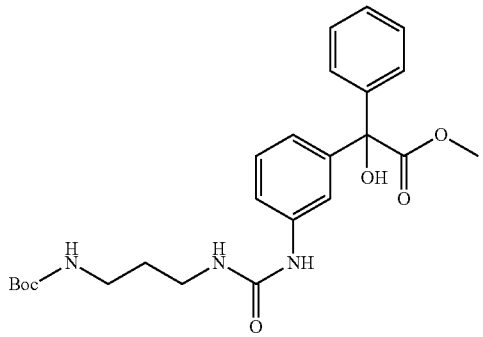 [SMILES: COC(=O)C(O)(c1ccccc1)c1cccc(NC(=O)NCCCNC(=O)OC(C)(C)C)c1]

Methyl 2-(3-aminophenyl)-2-hydroxy-2-phenylacetate (500 mg, 1.943 mmol) obtained as in Example 17, step 1, was dissolved in acetonitrile (1.5 ml, 1.943 mmol) and trichloromethyl carbonochloridate (961 mg, 4.86 mmol) was added. The solution was stirred at rt for 7 hours then it was evaporated under vacuum, added with 1 ml of DCM and evaporated again. The residue was dissolved in DCM (3 ml) and added with tert-butyl (3-aminopropyl)carbamate (Aldrich, 339 mg, 1.943 mmol). The reaction was stirred at rt 1 hour, just after a few minutes abundant precipitation of salt. The solvent was filtered and the filtrate was evaporated to give a pale yellow oil of title compound (800 mg, 1.749 mmol, 90%). No further purification was needed.

UPLC-MS: 1.15 min, 457.1 ([M+H]+), method 2.

Step 2; 2-(3-(3-(3-((tert-butoxycarbonyl)amino)propyl)ureido)phenyl)-2-hydroxy-2-phenylacetic acid

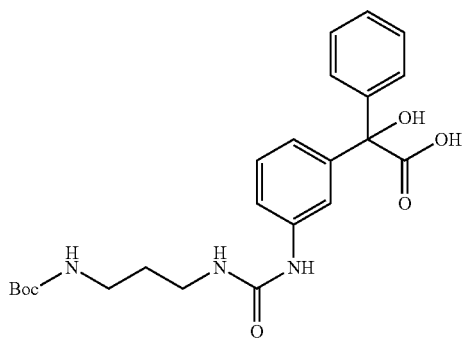 [SMILES: CC(C)(C)OC(=O)NCCCNC(=O)Nc1cccc(C(O)(C(=O)O)c2ccccc2)c1]

Methyl 2-(3-(3-(3-((tert-butoxycarbonyl)amino)propyl)ureido)phenyl)-2-hydroxy-2-phenylacetate (200 mg, 0.437 mmol) and LiOH (52.3 mg, 2.186 mmol) were dissolved in tetrahydrofuran (Volume: 1.5)/Water (Volume: 1.5) for 2 h at rt, then the mixture partitioned between AcOEt and HCl 0.2M. Organic layer was washed with sat NaCl aq, dried over Na2SO4 dry and evaporated under reduced pressure to give 2-(3-(3-(3-((tert-butoxycarbonyl)amino)propyl)ureido)phenyl)-2-hydroxy-2-phenylacetic acid (174 mg, 0.393 mmol, 90% yield) as a white foam. No further purification was needed.

UPLC-MS: 0.93 min, 444.1 [M+H]+, method 2.

Step 3; (1-benzylpiperidin-4-yl)methyl 2-(3-(3-(3-aminopropyl)ureido)phenyl)-2-hydroxy-2-phenylacetate

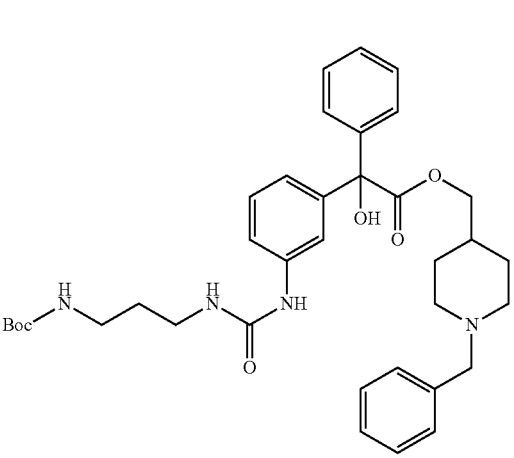 [SMILES: CC(C)(C)OC(=O)NCCCNC(=O)Nc1cccc(C(O)(C(=O)OCC2CCN(Cc3ccccc3)CC2)c2ccccc2)c1]

2-(3-(3-(3-((tert-butoxycarbonyl)amino)propyl)ureido)phenyl)-2-hydroxy-2-phenylacetic acid (200 mg, 0.451 mmol) were reacted with di(1H-imidazol-1-yl)methanone (146 mg, 0.902 mmol) for 30 min. at rt, then (1-benzylpiperidin-4-yl)methanol (278 mg, 1.353 mmol) was added and the reaction stirred for 2 h at 60° C., then at rt overnight. The crude was partitioned between sat NaHCO3 and AcOEt. Organic layer was dried over Na2SO4 and dried under reduced pressure. The crude was purified over silica gel by flash chromatography (silica gel, eluents: from 100% AcOEt to 80/20 AcOEt/NH3 7N in MeOH) to afford the title compound (138 mg, 0.219 mmol, 48.5% yield)

UPLC-MS: 1.29 min, 630.55 [M+H]+, method 4.

Step 4; (1-benzylpiperidin-4-yl)methyl 2-(3-(3-(3-aminopropyl)ureido)phenyl)-2-hydroxy-2-phenylacetate bis hydrochloride

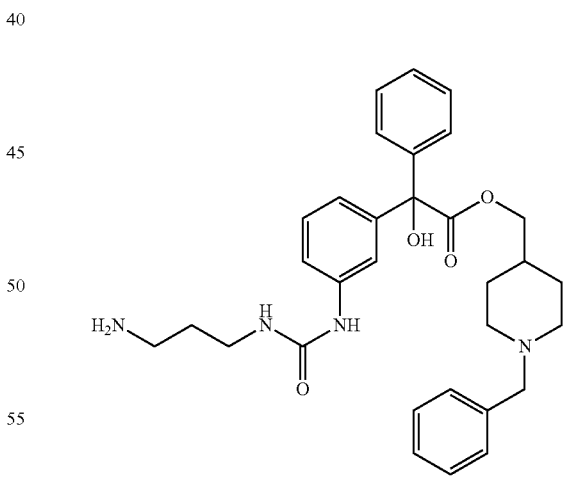

(1-benzylpiperidin-4-yl)methyl 2-(3-(3-(3-((tert-butoxycarbonyl)amino)propyl)-ureido)phenyl)-2-hydroxy-2-phenylacetate (138 mg, 0.219 mmol) was stirred for 1 h at rt in Dioxane/HCl 4N (1.5 ml) diluted with further 1.5 mL of dioxane; then the mixture was dried under reduce pressure and the residue triturated in Et2O to give (1-benzylpiperidin-4-yl)methyl 2-(3-((3-aminopropyl)carbamoyl)phenyl)-2-hydroxy-2-phenylacetate, 2HCl (0.22 g, 0.374 mmol, 74.2% yield) and (1-benzylpiperidin-4-yl)methyl 2-(3-((3-aminopropyl)carbamoyl)phenyl)-2-hydroxy-2-phenylacetate (0.090 g, 0.170 mmol, 77.6% yield) both as white solid used in the next steps without further purifications.

UPLC-MS: 0.51 min, 530.86 [M+H]+, method 4.

Step 5; (1-benzylpiperidin-4-yl)methyl 2-(3-(3-(3-(4-(((tert-butoxycarbonyl)((R)-2-((tert-butyldimethylsilyl)oxy)-2-(8-hydroxy-2-oxo-1,2-dihydroquinolin-5-yl)ethyl)amino)-methyl)benzamido)propyl)ureido)phenyl)-2-hydroxy-2-phenylacetate

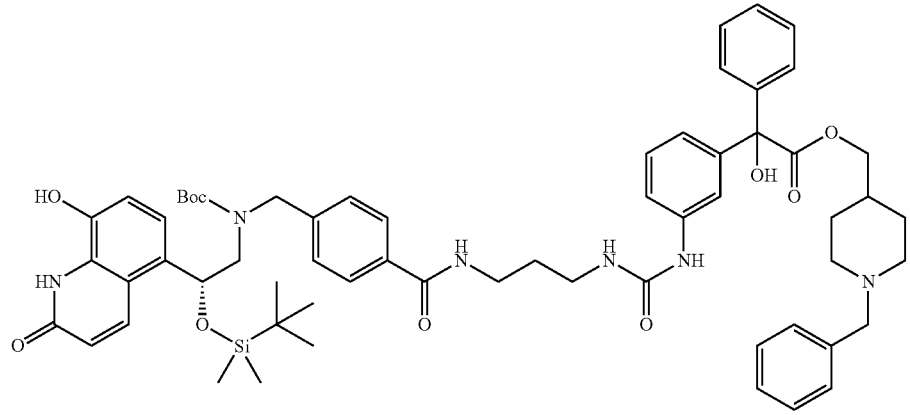 [SMILES: CC(C)(C)OC(=O)N(Cc1ccc(C(=O)NCCCNC(=O)Nc2cccc(C(O)(C(=O)OCC3CCN(Cc4ccccc4)CC3)c3ccccc3)c2)cc1)C[C@H](O[Si](C)(C)C(C)(C)C)c1ccc(O)c2[nH]c(=O)ccc12]

(R)-4-(((tert-butoxycarbonyl)(2-((tert-butyldimethylsilyl)oxy)-2-(8-hydroxy-2-oxo-1,2-dihydroquinolin-5-yl)ethyl)amino)methyl)benzoic acid, obtained as described in Procedure 4, steps 1-5 (65.2 mg, 0.115 mmol) and TBTU (36.6 mg, 0.115 mmol) were reacted for 5 min in 1.1 mL of DMF, then (1-benzylpiperidin-4-yl)methyl 2-(3-(3-(3-aminopropyl)ureido)phenyl)-2-hydroxy-2-phenylacetate (90 mg, 0.149 mmol) and DIEA (58.0 μl, 0.332 mmol) were added and the mixture stirred for 1 h at 60° C. Reaction was partitioned between AcOEt and saturated NaHCO₃, organic layer was washed twice with water, saturated NaCl aq, then dried over Na₂SO₄ and evaporated to dryness. The orange resulting oil (43.4 mg, 0.040 mmol, 35% yield) was used in the next step without further purifications.

UPLC-MS: 1.14 min, 1081.24 [M+H]+, method 2.

Step 6; (Compound 56)

(1-benzylpiperidin-4-yl)methyl 2-(3-(3-(3-(4-(((tert-butoxycarbonyl)((R)-2-((tert-butyldimethylsilyl)oxy)-2-(8-hydroxy-2-oxo-1,2-dihydroquinolin-5-yl)ethyl)amino)-methyl)benzamido)propyl)ureido)phenyl)-2-hydroxy-2-phenylacetate (50 mg, 0.046 mmol) was dissolved in acetonitrile (1 ml) and HCl 5N (1 ml) were added. The mixture was stirred at rt for 15 min. then submitted to reverse phase flash chromatography (C18 silica gel, eluents: from 100% A to 100% B, A: water/MeCN 95/5+0.1% HCOOH, B: MeCN/water 95/5+0.1% HCOOH) to afford the title compound (56) (17 mg, 0.020 mmol, 43.5% yield).

| N | $R_t$ (min) | [M + H]+ | Method | NMR data (400 MHz) | Salt 2 eq unless stated |
|---|---|---|---|---|---|
| 56 | 3.94 | 867.0 | 5 | ¹H NMR (400 MHz, DMSO-d6) δ ppm 10.45-10.11 (m, 2 H), 8.60-6.12 (m, 36 H), 3.78-0.82 (m, 18 H) | Formate |

Example 20

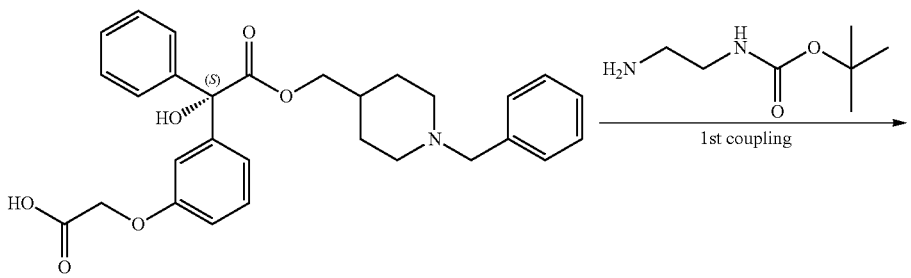

-continued
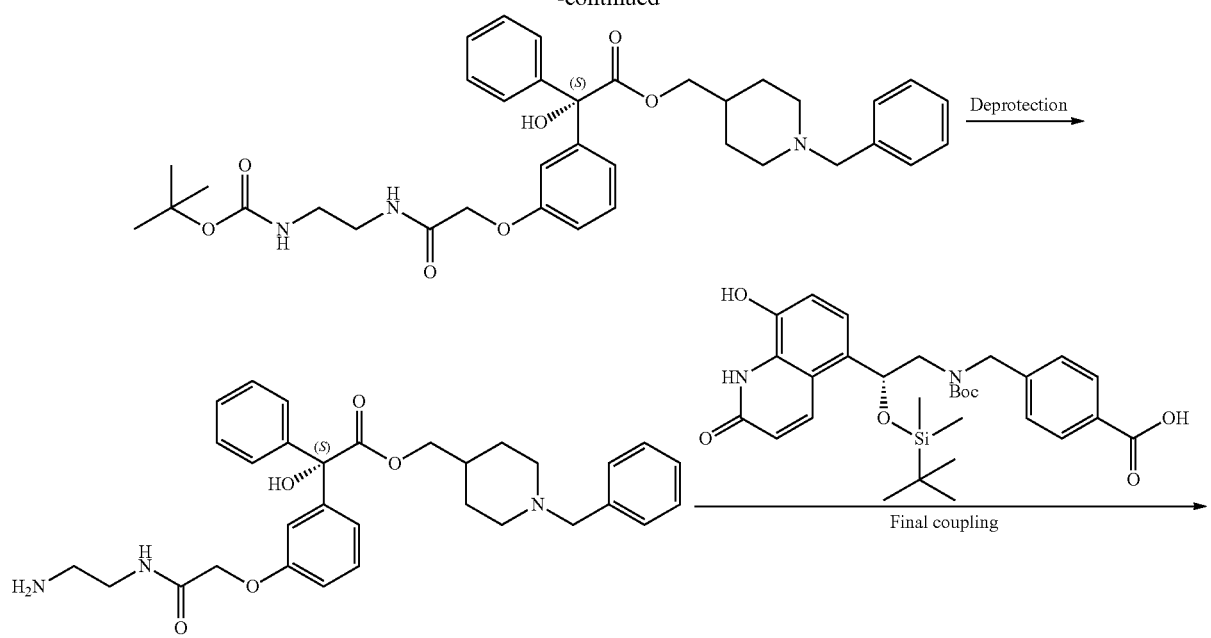
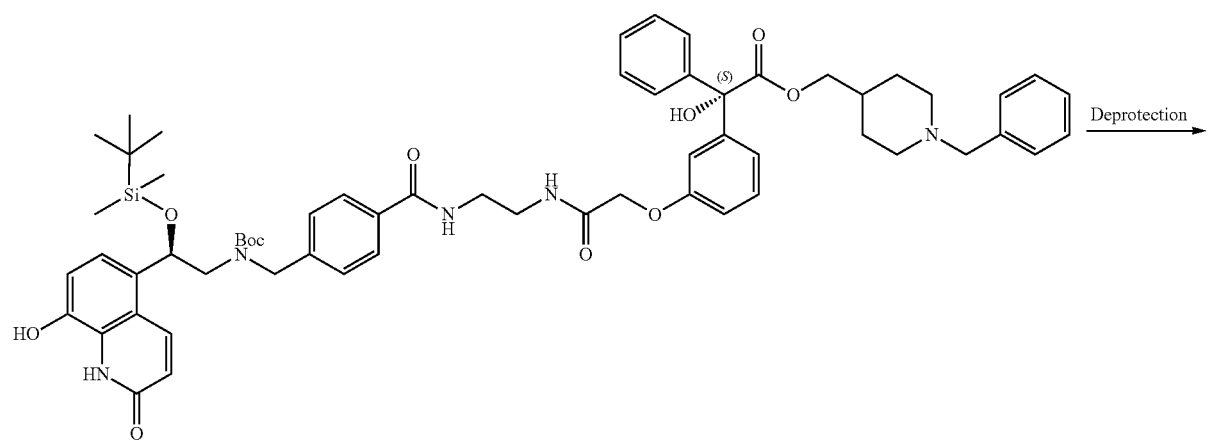
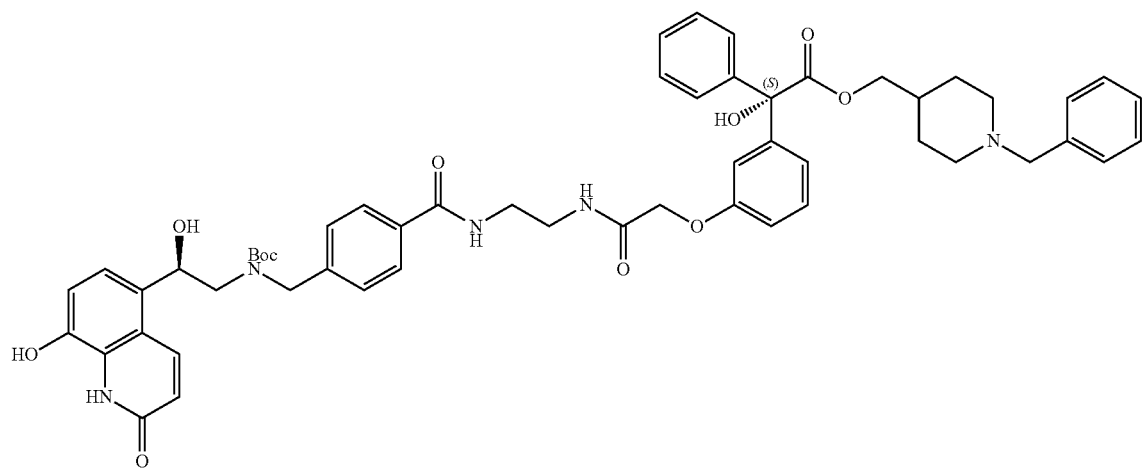

(1-Benzylpiperidin-4-yl)methyl (S)-2-hydroxy-2-(3-
(2-((2-(4-((((R)-2-hydroxy-2-(8-hydroxy-2-oxo-1,2-
dihydroquinolin-5-yl)ethyl)amino)methyl)ben-
zamido)ethyl)amino)-2-oxoethoxy)phenyl)-2-
phenylacetate (Compound 57)

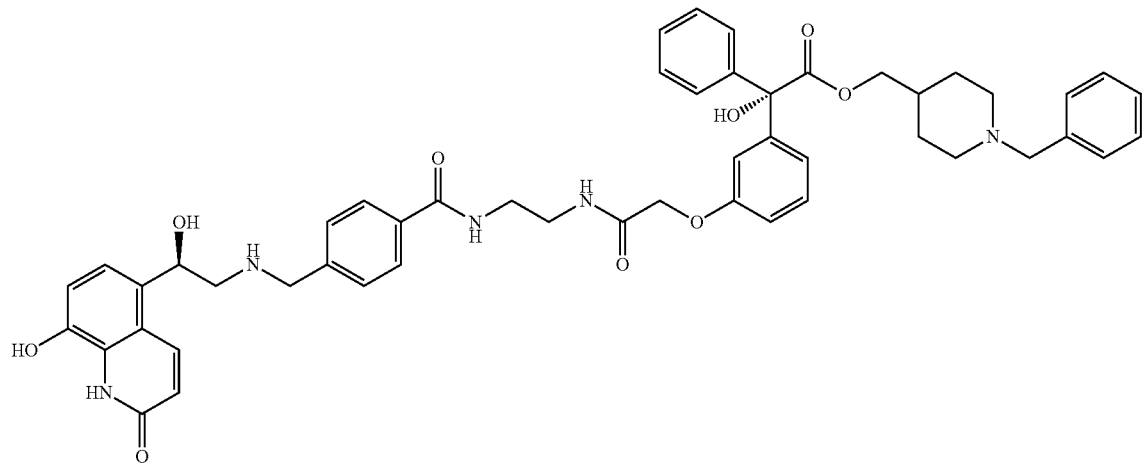 [SMILES: O=C(COc1cccc([C@](O)(C(=O)OCC2CCN(Cc3ccccc3)CC2)c2ccccc2)c1)NCCNC(=O)c1ccc(CNC[C@H](O)c2ccc(O)c3[nH]c(=O)ccc23)cc1]

Step 1; (1-Benzylpiperidin-4-yl)methyl (S)-2-(3-(2-
((2-(((tert-butoxycarbonyl)-amino)ethyl)amino)-2-
oxoethoxy)phenyl)-2-hydroxy-2-phenylacetate

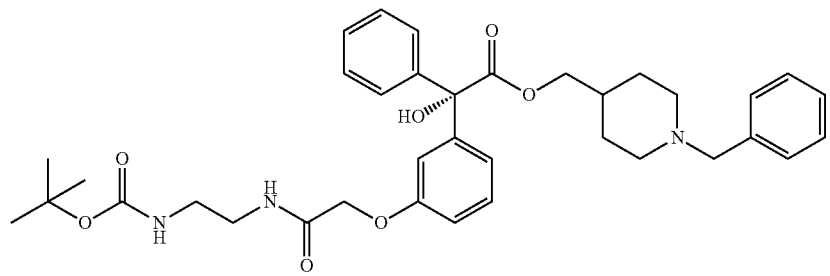 [SMILES: CC(C)(C)OC(=O)NCCNC(=O)COc1cccc([C@](O)(C(=O)OCC2CCN(Cc3ccccc3)CC2)c2ccccc2)c1]

To a stirred solution of (S)-2-(3-(2-((1-benzylpiperidin-4-yl)methoxy)-1-hydroxy-2-oxo-1-phenylethyl)phenoxy) acetic acid hydrochloride (0.20 g, 0.38 mmol) in DMF (1.9 mL) was added DIPEA (0.132 mL, 0.76 mmol) and HATU (0.173 g, 0.46 mmol) and the mixture stirred at room temperature for 30 minutes. To this mixture was added a solution of N-(tert-butoxycarbonyl)ethylenediamine HCl (0.061 g, 0.38 mmol) and DIPEA (0.13 mL, 0.76 mmol) in DMF (1.9 mL). The reaction mixture diluted with ethyl acetate and washed with 2M aqueous sodium hydroxide and brine. The organic phase was dried over magnesium sulfate, filtered and the filtrate evaporated at reduced pressure to afford the title compound (0.265 g, >100%).

$^1$H NMR (400 MHz, CDCl$_3$); δ 7.39 (dd, J=1.9, 7.7 Hz, 2H), 7.34-7.17 (m, 10H), 7.07-7.04 (m, 2H), 6.87 (dd, J=2.0, 7.9 Hz, 1H), 5.07 (s, 1H), 4.42 (s, 2H), 4.14-4.07 (m, 4H), 3.48 (s, 2H), 3.42-3.38 (m, 3H), 3.29-3.22 (m, 2H), 2.97 (s, 2H), 2.85-2.81 (m, 2H), 1.96-1.88 (m, 2H), 1.67-1.56 (m, 1H), 1.40 (s, 9H).

Step 2; (1-Benzylpiperidin-4-yl)methyl (S)-2-hydroxy-2-(3-(2-((2-(4-((((R)-2-hydroxy-2-(8-hydroxy-2-oxo-1,2-dihydroquinolin-5-yl)ethyl)amino)methyl)benzamido)ethyl)-amino)-2-oxoethoxy)phenyl)-2-phenylacetate (Compound 57)

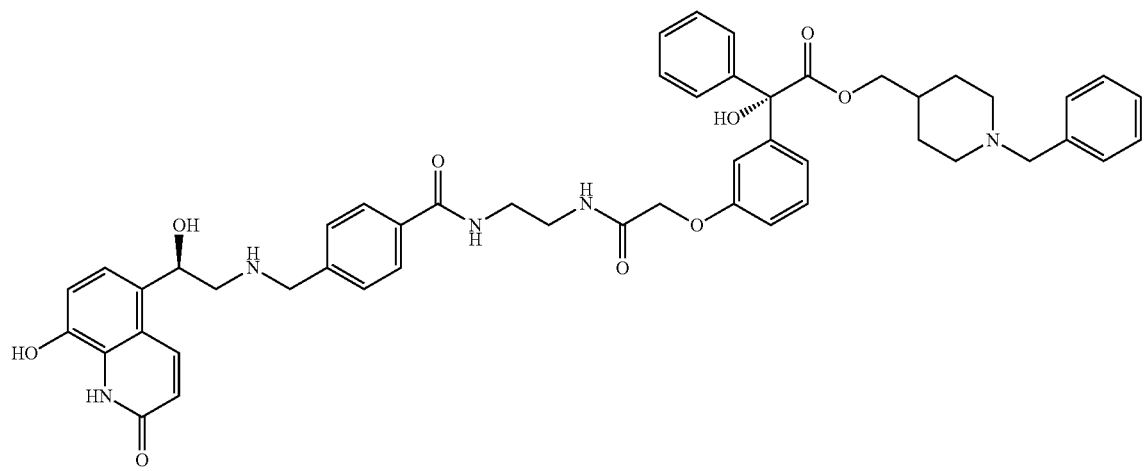 [SMILES: O=C(COc1cccc([C@](O)(C(=O)OCC2CCN(Cc3ccccc3)CC2)c2ccccc2)c1)NCCNC(=O)c1ccc(CNC[C@H](O)c2ccc(O)c3[nH]c(=O)ccc23)cc1]

To a stirred solution of (1-benzylpiperidin-4-yl)methyl (S)-2-(3-(2-((2-((tert-butoxycarbonyl)amino)ethyl)amino)-2-oxoethoxy)phenyl)-2-hydroxy-2-phenylacetate (0.265 g, 0.42 mmol) was added a solution of HCl in dioxan (4M, 15 mL) and the mixture stirred at room temperature for 1 hour. The solvent evaporated under reduced pressure. The residue was dissolved in DMF (3 ml) and added to a pre-stirred (15 minutes) mixture of (R)-4-(((tert-butoxycarbonyl)(2-((tert-butyldimethylsilyl)oxy)-2-(8-hydroxy-2-oxo-1,2-dihydroquinolin-5-yl)ethyl)amino)methyl)benzoic acid (0.20 g, 0.35 mmol), DIPEA (0.214 mL, 1.23 mmol) and HATU (0.16 g, 0.42 mmol) in DMF (2 mL). The reaction mixture was stirred at room temperature for 18 hours. The reaction mixture dissolved in ethyl acetate and washed with saturated aqueous sodium carbonate and brine. The organic phase was dried with magnesium sulfate, filtered and the filtrate evaporated at reduced pressure. The residue was dissolved in dioxan (1 mL) and a solution of HCl—dioxan (2 mL) added. The reaction mixture was stirred at room temperature for 1 hour. The solvent was evaporated at reduced pressure and the residue purified by reverse preparative HPLC.

$^1$H NMR (400 MHz, DMSO-d$_6$); δ 10.50 (s, 2H), 9.44 (s, 1H), 9.16 (s, 2H), 8.61 (dd, J=5.3, 5.3 Hz, 1H), 8.30 (dd, J=5, 4, 5.4 Hz, 1H), 8.08 (d, J=9.9 Hz, 1H), 7.88 (d, J=8.3 Hz, 2H), 7.61 (d, J=8.4 Hz, 2H), 7.47 (s, 5H), 7.33 (d, J=4.5 Hz, 3H), 7.32-7.23 (m, 3H), 7.12 (d, J=8.3 Hz, 1H), 7.00-6.93 (m, 2H), 6.89 (dd, J=2.3, 8.0 Hz, 2H), 6.67 (s, 1H), 6.57 (d, J=9.9 Hz, 1H), 6.19 (s, 1H), 5.36-5.32 (m, 1H), 4.43 (s, 2H), 4.30-4.23 (m, 4H), 4.01 (d, J=5.0 Hz, 2H), 3.36-3.28 (m, 5H), 3.09-3.08 (m, 2H), 3.04-2.94 (m, 1H), 2.93-2.88 (m, 2H), 1.78-1.66 (m, 3H), 1.40-1.31 (m, 2H).

The following compounds were prepared in a similar fashion using the appropriate amine:

| N | Appropriate amine | Structure |
|---|---|---|
| 58 | tert-butyl piperazine-1-carboxylate | (structure shown) |

-continued
| N | Appropriate amine | Structure |
|---|---|---|
| 59 | 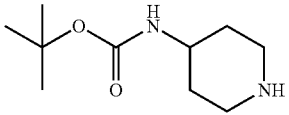 | 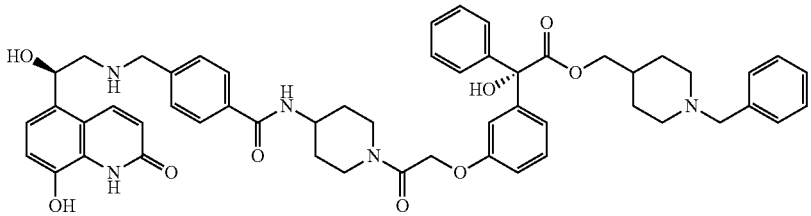 [SMILES: O=C(NC1CCN(C(=O)COc2cccc([C@](O)(C(=O)OCC3CCN(Cc4ccccc4)CC3)c3ccccc3)c2)CC1)c1ccc(CNC[C@H](O)c2ccc(O)c3[nH]c(=O)ccc23)cc1] |
| 60 | 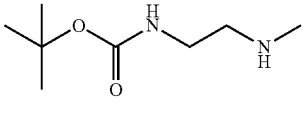 | 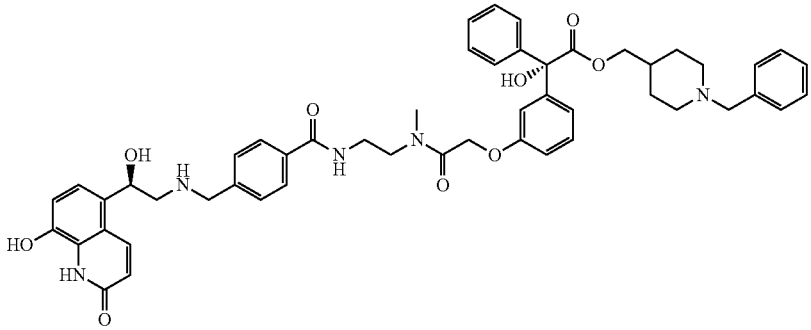 [SMILES: CN(CCNC(=O)c1ccc(CNC[C@H](O)c2ccc(O)c3[nH]c(=O)ccc23)cc1)C(=O)COc1cccc([C@](O)(C(=O)OCC2CCN(Cc3ccccc3)CC2)c2ccccc2)c1] |
| 61 | 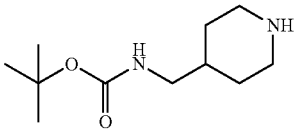 | 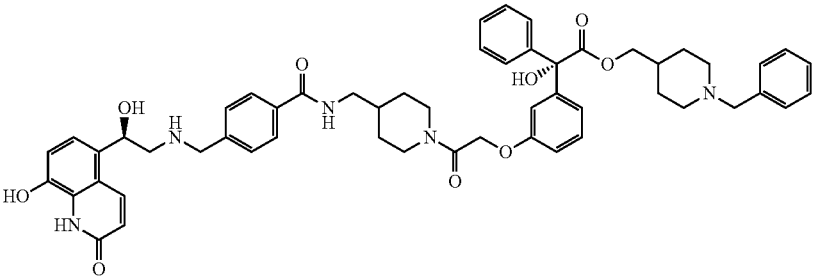 [SMILES: O=C(NCC1CCN(C(=O)COc2cccc([C@](O)(C(=O)OCC3CCN(Cc4ccccc4)CC3)c3ccccc3)c2)CC1)c1ccc(CNC[C@H](O)c2ccc(O)c3[nH]c(=O)ccc23)cc1] |
| 62 | 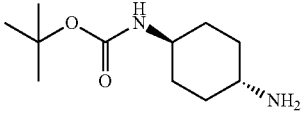 | 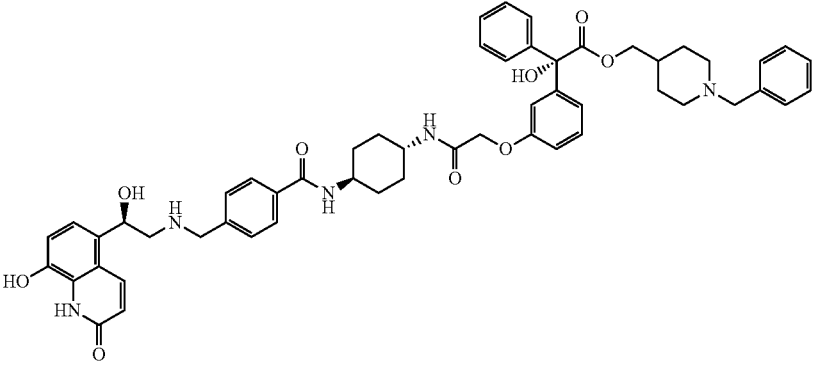 [SMILES: O=C(COc1cccc([C@](O)(C(=O)OCC2CCN(Cc3ccccc3)CC2)c2ccccc2)c1)N[C@H]1CC[C@H](NC(=O)c2ccc(CNC[C@H](O)c3ccc(O)c4[nH]c(=O)ccc34)cc2)CC1] |
| 63 | 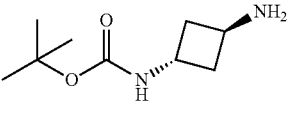 | 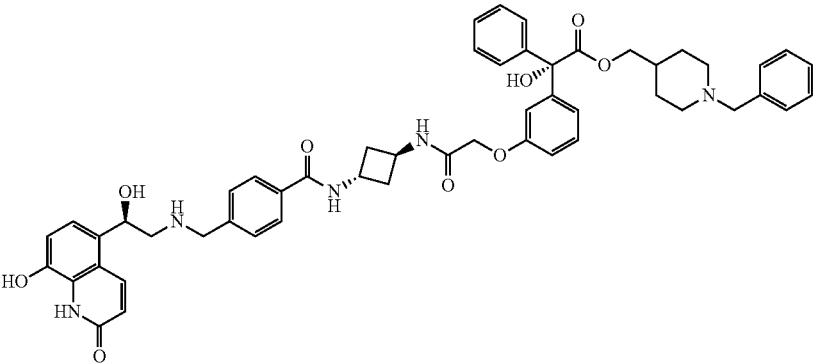 [SMILES: O=C(COc1cccc([C@](O)(C(=O)OCC2CCN(Cc3ccccc3)CC2)c2ccccc2)c1)N[C@H]1C[C@H](NC(=O)c2ccc(CNC[C@H](O)c3ccc(O)c4[nH]c(=O)ccc34)cc2)C1] |

| N | Appropriate amine | Structure |
|---|---|---|
| 64 | 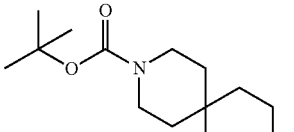 | 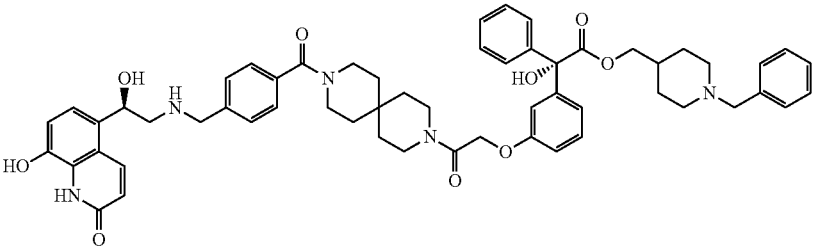 [SMILES: O=C(COc1cccc([C@](O)(C(=O)OCC2CCN(Cc3ccccc3)CC2)c2ccccc2)c1)N1CCC2(CC1)CCN(C(=O)c1ccc(CNC[C@H](O)c3ccc(O)c4[nH]c(=O)ccc34)cc1)CC2] |
| 65 | 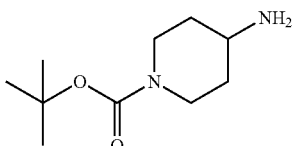 | 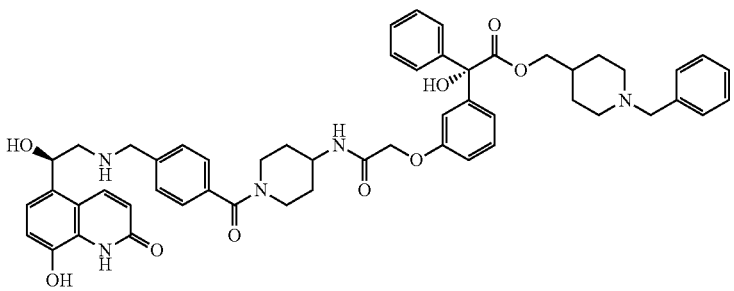 [SMILES: O=C(COc1cccc([C@](O)(C(=O)OCC2CCN(Cc3ccccc3)CC2)c2ccccc2)c1)NC1CCN(C(=O)c2ccc(CNC[C@H](O)c3ccc(O)c4[nH]c(=O)ccc34)cc2)CC1] |
| 66 | 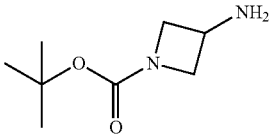 | 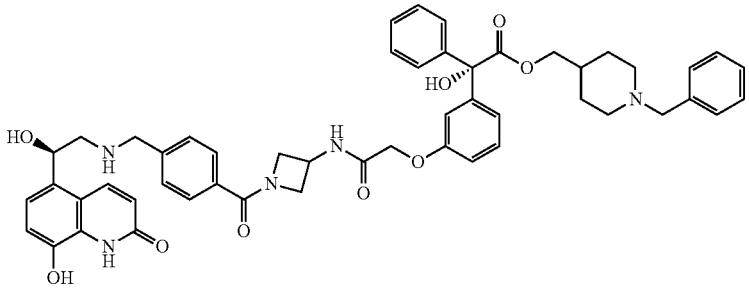 [SMILES: O=C(COc1cccc([C@](O)(C(=O)OCC2CCN(Cc3ccccc3)CC2)c2ccccc2)c1)NC1CN(C(=O)c2ccc(CNC[C@H](O)c3ccc(O)c4[nH]c(=O)ccc34)cc2)C1] |
| 67 | 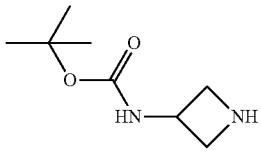 | 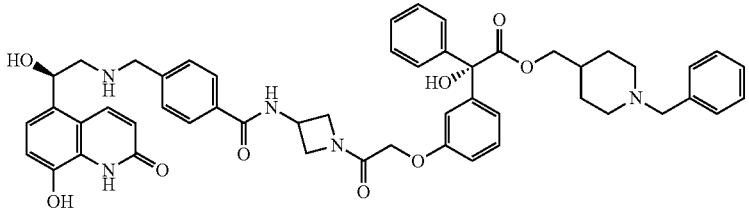 [SMILES: O=C(NC1CN(C(=O)COc2cccc([C@](O)(C(=O)OCC3CCN(Cc4ccccc4)CC3)c3ccccc3)c2)C1)c1ccc(CNC[C@H](O)c2ccc(O)c3[nH]c(=O)ccc23)cc1] |
| 68 | 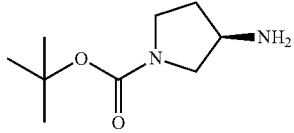 | 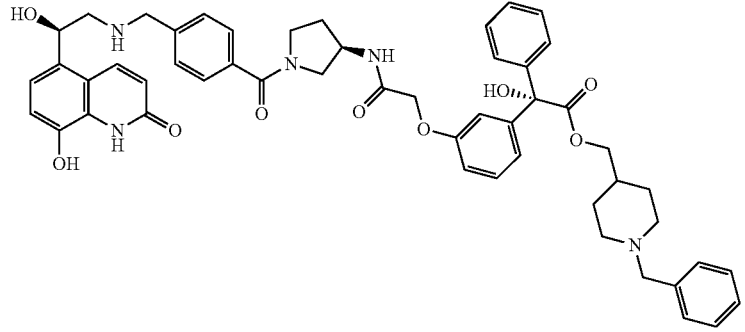 [SMILES: O=C(COc1cccc([C@](O)(C(=O)OCC2CCN(Cc3ccccc3)CC2)c2ccccc2)c1)N[C@@H]1CCN(C(=O)c2ccc(CNC[C@H](O)c3ccc(O)c4[nH]c(=O)ccc34)cc2)C1] |

-continued
| N | Appropriate amine | Structure |
|---|---|---|
| 69 | 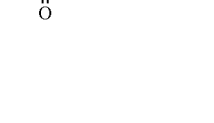 | 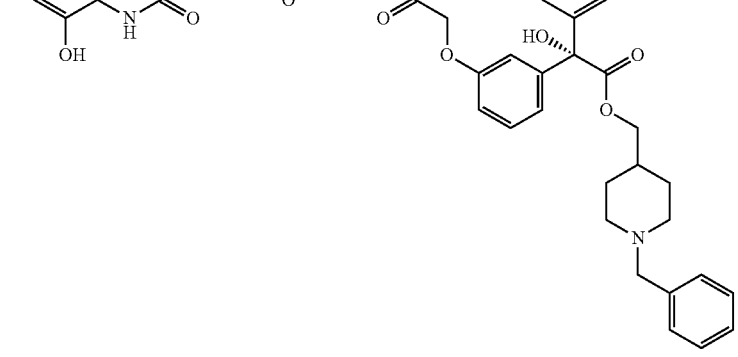 |
| 70 | 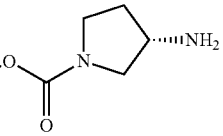 | 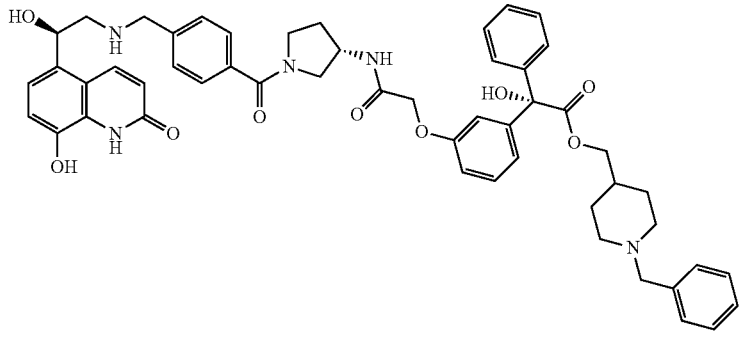 [SMILES: O=C(COc1cccc([C@](O)(C(=O)OCC2CCN(Cc3ccccc3)CC2)c2ccccc2)c1)N[C@H]1CCN(C(=O)c2ccc(CNC[C@H](O)c3ccc(O)c4[nH]c(=O)ccc34)cc2)C1] |
| 71 | 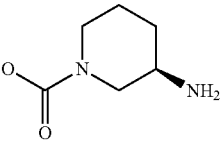 | 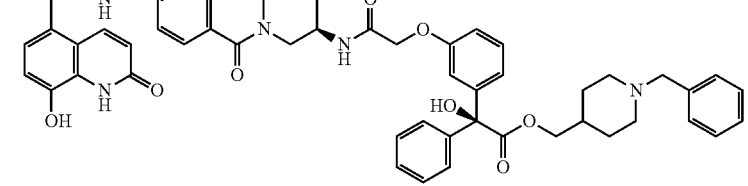 |
| 72 | 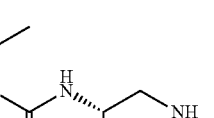 | 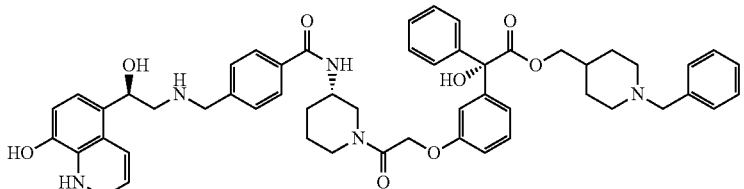 |
| 73 |  | 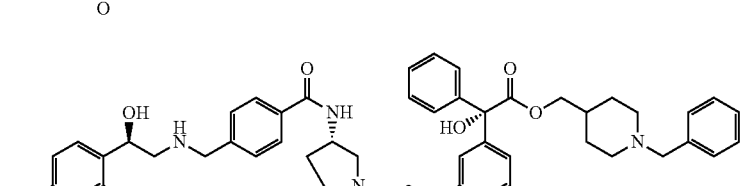 |

| N | Appropriate amine | Structure |
|---|---|---|
| 74 | | 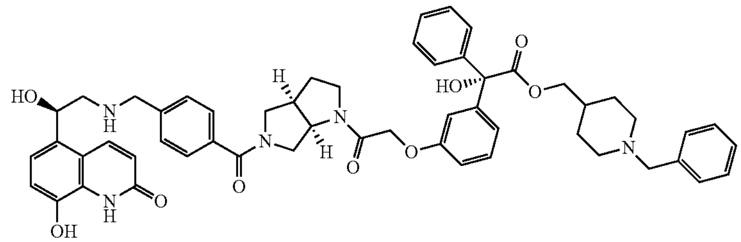 [SMILES: O=C(c1ccc(CNC[C@H](O)c2ccc(O)c3[nH]c(=O)ccc23)cc1)N1C[C@H]2CCN(C(=O)COc3cccc([C@](O)(C(=O)OCC4CCN(Cc5ccccc5)CC4)c4ccccc4)c3)[C@H]2C1] |
| 75 | | 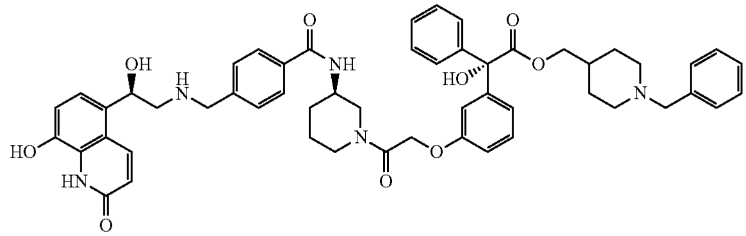 [SMILES: O=C(N[C@@H]1CCCN(C(=O)COc2cccc([C@](O)(C(=O)OCC3CCN(Cc4ccccc4)CC3)c3ccccc3)c2)C1)c1ccc(CNC[C@H](O)c2ccc(O)c3[nH]c(=O)ccc23)cc1] |
| 76 | | 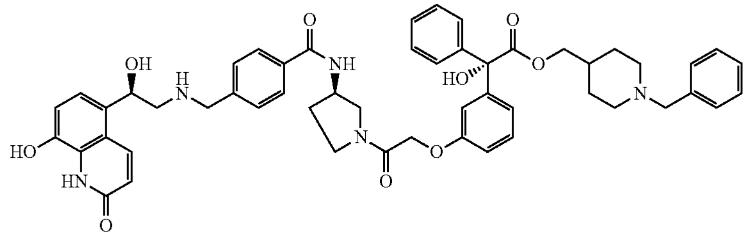 [SMILES: O=C(N[C@@H]1CCN(C(=O)COc2cccc([C@](O)(C(=O)OCC3CCN(Cc4ccccc4)CC3)c3ccccc3)c2)C1)c1ccc(CNC[C@H](O)c2ccc(O)c3[nH]c(=O)ccc23)cc1] |
| 77 | | 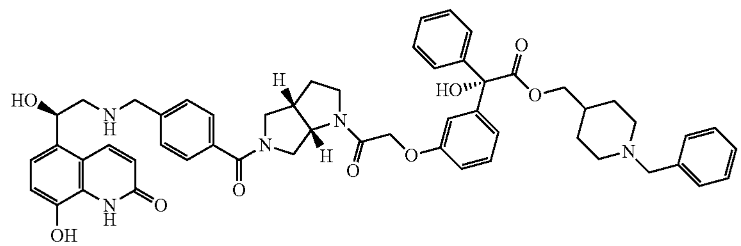 [SMILES: O=C(c1ccc(CNC[C@H](O)c2ccc(O)c3[nH]c(=O)ccc23)cc1)N1C[C@@H]2CCN(C(=O)COc3cccc([C@](O)(C(=O)OCC4CCN(Cc5ccccc5)CC4)c4ccccc4)c3)[C@@H]2C1] |

| N | Rt (min) | Method | NMR data (400 MHz) | (Salt 2 eq unless stated) |
|---|---|---|---|---|
| 57 | 2.38 | 11 | (DMSO-d$_6$); δ 10.50 (s, 2H), 9.44 (s, 1H), 9.16 (s, 2H), 8.61 (dd, J = 5.3, 5.3 Hz, 1H), 8.30 (dd, J = 5.4, 5.4 Hz, 1H), 8.08 (d, J = 9.9 Hz, 1H), 7.88 (d, J = 8.3 Hz, 2H), 7.61 (d, J = 8.4 Hz, 2H), 7.47 (s, 5H), 7.33 (d, J = 4.5 Hz, 3H), 7.32-7.23 (m, 3H), 7.12 (d, J = 8.3 Hz, 1H), 7.00-6.93 (m, 2H), 6.89 (dd, J = 2.3, 8.0 Hz, 2H), 6.67 (s, 1H), 6.57 (d, J = 9.9 Hz, 1H), 6.19 (s, 1H), 5.36-5.32 (m, 1H), 4.43 (s, 2H), 4.30-4.23 (m, 4H), 4.01 (d, J = 5.0 Hz, 2H), 3.36-3.28 (m, 5H), 3.09-3.08 (m, 2H), 3.04-2.94 (m, 1H), 2.93-2.88 (m, 2H), 1.78-1.66 (m, 3H), 1.40-1.31 (m, 2H). | TFA |
| 58 | 2.43 | 11 | (DMSO-d$_6$); δ 10.52 (s, 2H), 9.40 (s, 1H), 9.12-9.12 (m, 2H), 8.07 (d, J = 9.9 Hz, 1H), 7.62 (d, J = 8.3 Hz, 2H), 7.51 (d, J = 8.3 Hz, 2H), 7.47 (s, 6H), 7.33 (d, J = 4.4 Hz, 4H), 7.31-7.21 (m, 2H), 7.15-7.11 (m, 1H), 6.98 (d, J = 8.2 Hz, 1H), 6.93-6.88 (m, 3H), 6.58 (d, J = 9.7 Hz, 1H), 6.20 (s, 1H), 5.35 (dd, J = 2.1, 9.9 Hz, 1H), 4.82 (s, 2H), 4.29-4.21 (m, 6H), 4.04-3.97 (m, 5H), 3.34 (d, J = 12.1 Hz, 4H), 3.12-2.98 (m, 3H), 2.92-2.88 (m, 2H), 1.77-1.67 (m, 3H), 1.41-1.33 (m, 2H). | TFA |
| 59 | 2.45 | 11 | (DMSO-d$_6$); δ 8.24 (d, J = 7.7 Hz, 1H), 8.12 (d, J = 9.9 Hz, 1H), 7.79 (d, J = 8.3 Hz, 2H), 7.38 (d, J = 8.3 Hz, 2H), 7.32 (d, J = 4.4 Hz, 4H), 7.30-7.21 (m, 7H), 7.06 (d, J = 8.2 Hz, 1H), 6.91 (d, J = 7.8 Hz, 3H), 6.85 (dd, J = 1.9, 7.3 Hz, 1H), 6.61 (s, 1H), 6.46 (d, J = 9.9 Hz, 1H), 5.36 (s, 1H), 5.06 (dd, J = 4.1, 7.8 Hz, 1H), 4.80-4.71 (m, 2H), 4.28 (d, J = 12.5 Hz, 2H), 4.04 (dd, J = 3.2, 7.2 Hz, 1H), 4.00 (d, J = 6.3 Hz, 2H), 3.85-3.81 (m, 1H), 3.79 (s, 2H), 3.13 (dd, J = 11.7, 11.7 Hz, 1H), 2.76-2.59 (m, 5H), 1.86-1.77 (m, 4H), 1.54-1.44 (m, 6H), 1.15-1.06 (m, 2H). | Free Base |
| 60 | 2.39 | 11 | (DMSO-d$_6$); δ 10.33 (s, 1H), 8.65 and 8.46 (s, 1H), 8.12 (dd, J = 4.6, 10.0 Hz, 1H), 7.77 (dd, J = 8.3, 10.3 Hz, 2H), 7.40 (dd, J = 5.7, 7.8 Hz, 2H), 7.34-7.23 (m, 9H), 7.14 (dd, J = 8.0, 8.0 Hz, 1H), 7.05 (dd, J = 8.4, 8.4 Hz, 2H), 6.92-6.78 (m, 3H), | Free Base |

| N | Rt (min) | Method | NMR data (400 MHz) | (Salt 2 eq unless stated) |
|---|---|---|---|---|
| | | | 6.68-6.57 (m, 1H), 6.47 (d, J = 9.8 Hz, 1H), 5.41 (s, 1H), 5.10-5.06 (m, 1H), 4.74 (d, J = 12.4 Hz, 2H), 4.01-3.96 (m, 2H), 3.81 (s, 2H), 3.46 (s, 2H), 3.38 (s, 3H), 3.00 (s, 2H), 2.85 (s, 2H), 2.74-2.66 (m, 5H), 1.85-1.79 (m, 2H), 1.51-1.44 (m, 2H), 1.15-1.06 (m, 2H). | |
| 61 | 2.50 | 11 | (DMSO-d$_6$); δ 10.51 (s, 1H), 10.49 (s, 1H), 9.40 (s, 1H), 9.15 (s, 2H), 8.58 (dd, J = 5.7, 5.7 Hz, 1H), 8.07 (d, J = 7.9 Hz, 1H), 7.91 (d, J = 8.0 Hz, 2H), 7.62 (d, J = 8.4 Hz, 2H), 7.46 (s, 5H), 7.34-7.32 (m, 3H), 7.32-7.29 (m, 1H), 7.23 (dd, J = 8.0, 8.0 Hz, 1H), 7.12 (d, J = 8.2 Hz, 1H), 6.97 (d, J = 8.2 Hz, 1H), 6.90 (d, J = 7.9 Hz, 1H), 6.86 (s, 1H), 6.83 (d, J = 8.3 Hz, 1H), 6.63 (s, 1H), 6.58-6.53 (m, 2H), 6.19 (d, J = 2.5 Hz, 1H), 5.37-5.36 (m, 1H), 4.75 (d, J = 3.5 Hz, 2H), 4.29-4.28 (m, 6H), 4.02 (d, J = 6.1 Hz, 2H), 3.83-3.83 (m, 1H), 3.15-3.14 (m, 5H), 3.02 (s, 4H), 1.82-1.81 (m, 1H), 1.71 (s, 6H), 1.35-1.35 (m, 3H). | TFA |
| 62 | 2.50 | 11 | (DMSO-d$_6$); δ 10.51 (s, 1H), 10.47 (s, 1H), 9.38 (s, 1H), 9.13 (s, 2H), 8.29 (d, J = 7.8 Hz, 1H), 8.07 (d, J = 10.1 Hz, 1H), 7.96 (d, J = 8.0 Hz, 1H), 7.89 (d, J = 8.3 Hz, 2H), 7.60 (d, J = 8.4 Hz, 2H), 7.48 (s, 5H), 7.34-7.32 (m, 4H), 7.12 (d, J = 8.3 Hz, 1H), 7.00-6.93 (m, 3H), 6.88 (dd, J = 2.4, 8.2 Hz, 1H), 6.66 (s, 1H), 6.57 (dd, J = 2.1, 9.9 Hz, 1H), 6.19-6.19 (m, 1H), 5.33 (d, J = 10.0 Hz, 1H), 4.41 (s, 2H), 4.31-4.21 (m, 4H), 4.04-3.97 (m, 2H), 3.75-3.74 (m, 1H), 3.61-3.61 (m, 1H), 3.33 (d, J = 11.8 Hz, 2H), 3.09-3.08 (m, 2H), 3.01-2.87 (m, 3H), 1.88-1.67 (m, 6H), 1.43-1.34 (m, 6H). | TFA |
| 63 | 2.43 | 11 | (DMSO-d$_6$); δ 10.51 (s, 1H), 10.47 (s, 1H), 9.38 (s, 1H), 9.13 (s, 2H), 8.79 (d, J = 7.0 Hz, 1H), 8.51 (d, J = 7.4 Hz, 1H), 8.08 (d, J = 10.0 Hz, 1H), 7.93 (d, J = 8.4 Hz, 2H), 7.62 (d, J = 8.3 Hz, 2H), 7.48 (s, 5H), 7.35-7.26 (m, 6H), 7.12 (d, J = 8.3 Hz, 1H), 7.02-6.93 (m, 3H), 6.89 (dd, J = 2.6, 7.9 Hz, 1H), 6.67-6.66 (m, 1H), 6.58 (d, J = 9.3 Hz, 1H), 6.19-6.19 (m, 1H), 5.36-5.34 (m, 1H), 4.43 (s, 4H), 4.31-4.21 (m, 5H), 4.03 (d, J = 6.5 Hz, 2H), 3.34 (d, J = 11.5 Hz, 2H), 3.11-2.87 (m, 3H), 2.35 (dd, J = 6.9, 6.9 Hz, 4H), 1.77-1.67 (m, 4H), 1.40-1.31 (m, 2H). | TFA |
| 64 | 2.46 | 11 | (DMSO-d$_6$); δ 10.60 (s, 1H), 10.50 (s, 1H), 9.40 (s, 1H), 9.10 (s, 2H), 8.06 (d, J = 10.4 Hz, 1H), 7.60 (d, J = 8.2 Hz, 2H), 7.48 (s, 5H), 7.45 (d, J = 8.2 Hz, 2H), 7.36-7.27 (m, 5H), 7.23 (t, J = 7.9 Hz, 1H), 7.13 (d, J = 8.3 Hz, 1H), 6.98 (d, J = 8.2 Hz, 1H), 6.91-6.87 (m, 2H), 6.86-6.81 (m, 1H), 6.64 (s, 1H), 6.59-6.55 (m, 1H), 6.15 (s, 1H), 5.35-5.33 (m, 1H), 4.76 (s, 2H), 4.32-4.22 (m, 4H), 4.04-3.97 (m, 2H), 3.62 (s, 2H), 3.44-3.26 (m, 8H), 3.10-3.02 (m, 3H), 2.95-2.86 (m, 2H), 1.76-1.66 (m, 2H), 1.50 (s, 4H), 1.42-1.33 (m, 6H). | TFA |
| 65 | 2.43 | 11 | (DMSO-d$_6$); δ 10.55 (s, 1H), 10.45 (s, 1H), 9.40 (s, 1H), 8.75 (s, 2H), 8.08 (d, J = 9.9 Hz, 1H), 8.04 (d, J = 7.4 Hz, 1H), 7.61 (d, J = 8.2 Hz, 2H), 7.47 (s, 5H), 7.44 (d, J = 7.4 Hz, 2H), 7.32 (d, J = 4.4 Hz, 4H), 7.30-7.23 (m, 2H), 7.13 (d, J = 8.3 Hz, 1H), 7.00-6.92 (m, 3H), 6.87 (dd, J = 2.3, 8.1 Hz, 1H), 6.65 (s, 1H), 6.58 (d, J = 9.9 Hz, 1H), 6.15 (s, 1H), 5.35-5.33 (m, 1H), 4.42 (s, 2H), 4.32-4.20 (m, 4H), 4.03-3.97 (m, 2H), 3.93-3.88 (m, 1H), 3.48-3.48 (m, 2H), 3.34 (d, J = 11.9 Hz, 2H), 3.11-3.02 (m, 4H), 2.94-2.86 (m, 3H), 1.85-1.84 (m, 1H), 1.76-1.66 (m, 4H), 1.39-1.30 (m, 4H). | TFA |
| 66 | 2.39 | 11 | (MeOD); δ 8.29 (d, J = 9.8 Hz, 1H), 7.75 (d, J = 7.9 Hz, 2H), 7.63 (d, J = 6.9 Hz, 2H), 7.53-7.48 (m, 4H), 7.39 (d, J = 7.2 Hz, 2H), 7.34-7.27 (m, 6H), 7.09 (s, 1H), 7.04 (d, J = 8.3 Hz, 2H), 6.98 (dd, J = 2.2, 8.0 Hz, 1H), 6.66 (d, J = 9.3 Hz, 1H), 5.43 (dd, J = 6.7, 6.7 Hz, 1H), 4.76-4.69 (m, 1H), 4.60 (dd, J = 7.9, 7.9 Hz, 1H), 4.52 (s, 2H), 4.46 (dd, J = 9.1, 9.1 Hz, 1H), 4.28 (s, 3H), 4.12 (d, J = 6.4 Hz, 3H), 3.51-3.45 (m, 2H), 3.27 (d, J = 6.7 Hz, 2H), 3.01-2.91 (m, 2H), 2.68 (s, 3H), 1.83 (d, J = 14.1 Hz, 2H), 1.42 (d, J = 12.9 Hz, 2H). | TFA |
| 67 | 2.42 | 11 | (MeOD); δ 8.52 (s, 2H), 8.29 (d, J = 9.9 Hz, 1H), 7.91 (d, J = 8.0 Hz, 2H), 7.56 (d, J = 8.3 Hz, 2H), 7.42-7.38 (m, 6H), 7.37-7.23 (m, 6H), 7.09-7.05 (m, 1H), 7.03-6.97 (m, 2H), 6.93 (dd, J = 2.5, 8.2 Hz, 1H), 6.63 (d, J = 9.8 Hz, 1H), 5.35 (dd, J = 4.3, 8.8 Hz, 1H), 4.84-4.76 (m, 1H), 4.70-4.59 (m, 3H), 4.41-4.27 (m, 2H), 4.18-4.10 (m, 5H), 3.94 (d, J = 2.3 Hz, 2H), 3.22-3.04 (m, 4H), 2.56 (dd, J = 12.4, 12.4 Hz, 2H), 1.85-1.79 (m, 1H), 1.71-1.64 (m, 2H), 1.43-1.30 (m, 2H). | Formate |
| 68 | 2.38 | 11 | (DMSO-d$_6$, 100° C.) δ 8.12 (d, J = 9.8 Hz, 1H), 7.99 (d, J = 6.3 Hz, 2H), 7.58 (q, J = 8.6 Hz, 4H), 7.50-7.47 (m, 5H), 7.41-7.24 (m, 6H), 7.14 (d, J = 8.3 Hz, 1H), 7.04-7.00 (m, 3H), 6.90 (dd, J = 2.2, 8.0 Hz, 1H), 6.56 (d, J = 9.9 Hz, 1H), 5.39 (dd, J = 4.6, 8.3 Hz, 1H), 4.44 (s, 2H), 4.34-4.30 (m, 3H), 4.26 (s, 2H), 4.13-4.06 (m, 2H), 3.76-3.70 (m, 2H), 3.37-3.29 (m, 4H), 3.23-3.15 (m, 2H), 2.95-2.91 (m, 2H), 2.19-2.10 (m, 1H), 1.97-1.87 (m, 2H), 1.80-1.76 (m, 2H), 1.49-1.49 (m, 2H). | TFA |
| 69 | 2.46 | 11 | (DMSO-d$_6$, 100° C.) δ 8.19-8.15 (m, 3H), 7.57 (d, J = 7.5 Hz, 1H), 7.40-7.23 (m, 15H), 7.10 (d, J = 8.3 Hz, 1H), 7.06-7.00 (m, 2H), 6.96 (d, J = 8.2 Hz, 1H), 6.90 (dd, J = 2.3, 8.0 Hz, 1H), 6.47 (d, J = 9.9 Hz, 1H), 5.09 (dd, J = 4.6, 7.7 Hz, 1H), 4.41 (d, J = 2.8 Hz, 2H), 4.05 (d, J = 6.3 Hz, 2H), 3.92 (d, J = 14.0 Hz, 1H), 3.81 (s, 2H), 3.72 (d, J = 13.4 Hz, 1H), 3.44 (s, 2H), 3.13-3.02 (m, 4H), 2.88-2.67 (m, 4H), 1.97-1.86 (m, 3H), 1.71-1.49 (m, 6H), 1.28-1.13 (m, 2H). | Formate |
| 70 | 2.42 | 11 | (DMSO-d$_6$, 100° C.) δ 8.19-8.15 (m, 3H), 7.92 (d, J = 6.4 Hz, 1H), 7.45-7.23 (m, 15H), 7.09 (d, J = 8.0 Hz, 1H), 7.04-7.00 (m, 2H), 6.96 (d, J = 8.0 Hz, 1H), 6.90 (dd, J = 2.4, 8.1 Hz, 1H), 6.47 (d, J = 9.9 Hz, 1H), 5.08 (dd, J = 4.7, 7.6 Hz, 1H), 4.43 (s, 2H), 4.40-4.30 (m, 1H), 4.05 (d, J = 6.4 Hz, 2H), 3.82 (s, 2H), 3.70 (d, J = 6.7, 11.4 Hz, 1H), 3.62-3.47 (m, 2H), 3.45 (s, 2H), 3.36 (dd, J = 5.3, 11.5 Hz, 1H), 2.88-2.71 (m, 4H), 2.20-2.07 (m, 1H), 1.98-1.85 (m, 3H), 1.62-1.49 (m, 3H), 1.28-1.13 (m, 2H). | Formate |
| 71 | 2.41 | 11 | (DMSO-d$_6$, 100° C.) δ 8.11 (d, J = 9.9 Hz, 1H), 7.66 (d, J = 7.7 Hz, 1H), 7.60 (d, J = 8.2 Hz, 2H), 7.46 (d, J = 8.5 Hz, 7H), 7.41-7.24 (m, 6H), 7.14 (d, J = 8.2 Hz, 1H), | TFA |

| N | Rt (min) | Method | NMR data (400 MHz) | (Salt 2 eq unless stated) |
|---|---|---|---|---|
|  |  |  | 7.06-7.00 (m, 3H), 6.90 (dd, J = 2.3, 8.2 Hz, 1H), 6.56 (d, J = 9.9 Hz, 1H), 5.38 (dd, J = 4.7, 8.2 Hz, 1H), 4.42 (s, 2H), 4.31 (d, J = 2.4 Hz, 2H), 4.23 (s, 2H), 4.10 (d, J = 5.6 Hz, 2H), 4.00-3.95 (m, 1H), 3.85-3.74 (m, 2H), 3.50-3.25 (m, 2H), 3.23-2.98 (m, 5H), 2.57-2.53 (m, 1H), 1.92-1.87 (m, 2H), 1.81-1.71 (m, 3H), 1.66-1.47 (m, 4H). |  |
| 72 | 2.43 | 11 | (DMSO-$d_6$, 100° C.) δ 8.19-8.12 (m, 2H), 7.86 (d, J = 6.5 Hz, 1H), 7.78 (d, J = 8.0 Hz, 2H), 7.39 (d, J = 7.9 Hz, 4H), 7.35-7.20 (m, 8H), 7.09 (d, J = 8.2 Hz, 1H), 7.01-6.94 (m, 3H), 6.90-6.86 (m, 1H), 6.48 (d, J = 9.8 Hz, 1H), 5.11 (dd, J = 4.6, 7.5 Hz, 1H), 4.72 (s, 2H), 4.04 (d, J = 6.4 Hz, 3H), 3.85 (br s, 4H), 3.46 (s, 2H), 2.89-2.71 (m, 5H), 2.54-2.40 (m, 1H), 2.06-1.92 (m, 3H), 1.81-1.77 (m, 1H), 1.69-1.57 (m, 2H), 1.52-1.50 (m, 3H), 1.24-1.14 (m, 2H). | mono-Formate |
| 73 | 2.45 | 11 | (DMSO-$d_6$, 100° C.) δ 8.17 (d, J = 7.9 Hz, 3H), 7.79 (d, J = 8.3 Hz, 2H), 7.41-7.36 (m, 4H), 7.35-7.21 (m, 9H), 7.09 (d, J = 8.2 Hz, 1H), 7.00-6.94 (m, 3H), 6.89 (dd, J = 1.9, 8.2 Hz, 1H), 6.47 (d, J = 9.9 Hz, 1H), 5.08 (dd, J = 4.9, 7.7 Hz, 1H), 4.64 (s, 2H), 4.54-4.45 (m, 1H), 4.05 (d, J = 6.3 Hz, 3H), 3.85-3.21 (m, 3H), 3.65-3.59 (m, 1H), 3.46-3.43 (m, 3H), 2.87-2.67 (m, 4H), 2.56-2.47 (m, 1H under the DMSO), 2.17-2.17 (m, 1H), 2.06-2.00 (m, 1H), 1.98-1.90 (m, 2H), 1.62-1.49 (m, 3H), 1.25-1.13 (m, 2H). | mono-Formate |
| 74 | 2.40 | 11 | (DMSO-$d_6$, 100° C.) δ 8.17 (d, J = 9.9 Hz, 1H), 8.15 (s, 1H), 7.40-7.20 (m, 15H), 7.10 (d, J = 8.3 Hz, 1H), 7.01-6.94 (m, 3H), 6.87-6.84 (m, 1H), 6.47 (d, J = 9.9 Hz, 1H), 5.09 (dd, J = 4.6, 7.7 Hz, 1H), 4.63 (s, 2H), 4.43-4.34 (m, 1H), 4.05 (d, J = 6.3 Hz, 2H), 3.81 (s, 2H), 3.76-3.49 (m, 4H), 3.45-3.39 (m, 3H), 2.88-2.68 (m, 5H), 2.57-2.51 (m, 1H), 2.06-1.99 (m, 1H), 1.97-1.90 (m, 2H), 1.78-1.77 (m, 1H), 1.62-1.49 (m, 3H), 1.28-1.13 (m, 2H). | mono-Formate |
| 75 | 2.43 | 11 | (DMSO-$d_6$, 100° C.) δ 8.21 (s, 1H), 8.17 (d, J = 9.9 Hz, 1H), 7.86 (d, J = 6.3 Hz, 1H), 7.77 (d, J = 8.3 Hz, 2H), 7.41-720 (m, 13H), 7.09 (d, J = 8.2 Hz, 1H), 7.00-6.94 (m, 3H), 6.91-6.87 (m, 1H), 6.47 (d, J = 9.9 Hz, 1H), 5.08 (dd, J = 4.7, 7.6 Hz, 1H), 4.73 (s, 2H), 4.05 (d, J = 6.4 Hz, 3H), 3.87-3.78 (m, 4H), 3.44 (s, 2H), 2.87-2.67 (m, 6H), 2.57-2.46 (m, 1H), 2.11-1.89 (m, 3H), 1.82-1.56 (m, 3H), 1.56-1.49 (m, 2H), 1.24-1.13 (m, 2H). | mono-Formate |
| 76 | 2.40 | 11 | (DMSO-$d_6$, 100° C.) δ 8.19-8.14 (m, 3H), 7.82 (d, J = 8.3 Hz, 2H), 7.46-7.38 (m, 4H), 7.35-7.23 (m, 9H), 7.10 (d, J = 8.2 Hz, 1H), 7.00-6.95 (m, 3H), 6.90 (dd, J = 2.0, 8.2 Hz, 1H), 6.49 (d, J = 9.9 Hz, 1H), 6.07 (s, 1H), 5.16 (dd, J = 4.6, 7.8 Hz, 1H), 4.64 (s, 2H), 4.54-4.44 (m, 1H), 4.06 (d, J = 6.3 Hz, 2H), 3.93 (s, 2H), 3.74-3.60 (m, 2H), 3.51 (s, 2H), 3.46-3.39 (m, 1H), 2.90-2.77 (m, 4H), 2.57-2.47 (m, 1H), 2.25-2.12 (m, 1H), 2.04-1.97 (m, 3H), 1.65-1.51 (m, 3H), 1.28-1.16 (m, 2H). | mono-Formate |
| 77 | 2.40 | 11 | (DMSO-$d_6$, 100° C.) δ 8.19-8.15 (m, 2H), 7.40-7.20 (m, 15H), 7.10 (d, J = 8.3 Hz, 1H), 7.00-6.94 (m, 3H), 6.85 (dd, J = 1.9, 8.0 Hz, 1H), 6.47 (d, J = 9.9 Hz, 1H), 5.09 (dd, J = 4.6, 7.7 Hz, 1H), 4.63 (s, 2H), 4.44-4.37 (m, 1H), 4.05 (d, J = 6.3 Hz, 2H), 3.82 (s, 2H), 3.79-3.73 (m, 1H), 3.72-3.49 (m, 3H), 3.45-3.42 (m, 3H), 2.95-2.71 (m, 5H), 2.57-2.50 (m, 1H), 2.08-2.01 (m, 1H), 2.03-1.89 (m, 2H), 1.80-1.74 (m, 1H), 1.62-1.49 (m, 3H), 1.24-1.14 (m, 2H). | mono-Formate |

The following compounds were prepared using the appropriate amine and protected acid in the final coupling step.

| N | Appropriate amine | protected acid | Structure |
|---|---|---|---|
| 78 | | | 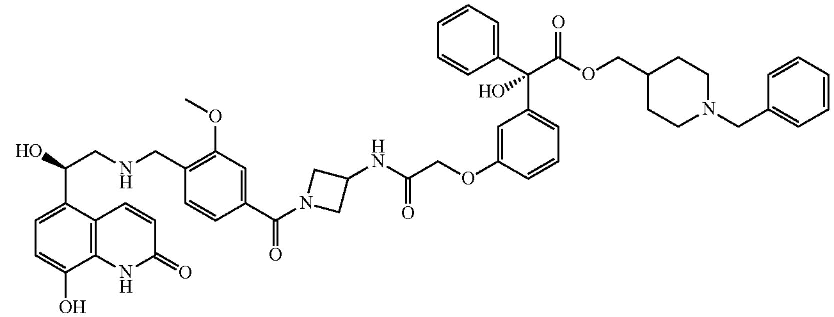 [SMILES: COc1cc(C(=O)N2CC(NC(=O)COc3cccc([C@](O)(C(=O)OCC4CCN(Cc5ccccc5)CC4)c4ccccc4)c3)C2)ccc1CNC[C@H](O)c1ccc(O)c2[nH]c(=O)ccc12] |
| 79 | | | 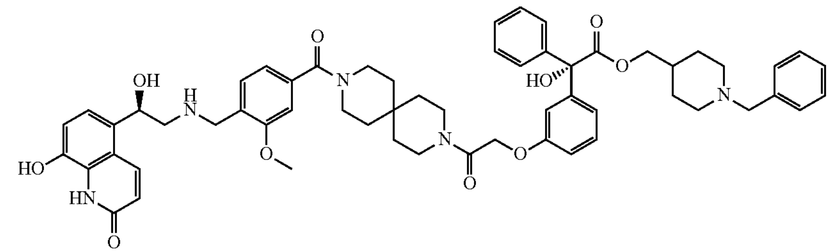 [SMILES: COc1cc(C(=O)N2CCC3(CCN(C(=O)COc4cccc([C@](O)(C(=O)OCC5CCN(Cc6ccccc6)CC5)c5ccccc5)c4)CC3)CC2)ccc1CNC[C@H](O)c1ccc(O)c2[nH]c(=O)ccc12] |
| 80 | | | 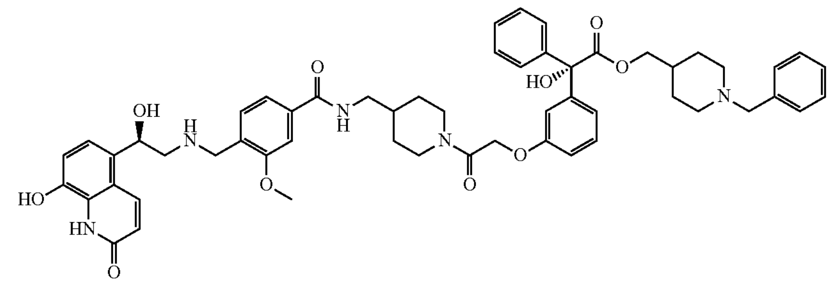 [SMILES: COc1cc(C(=O)NCC2CCN(C(=O)COc3cccc([C@](O)(C(=O)OCC4CCN(Cc5ccccc5)CC4)c4ccccc4)c3)CC2)ccc1CNC[C@H](O)c1ccc(O)c2[nH]c(=O)ccc12] |

| N | Appropriate amine | protected acid | Structure |
|---|---|---|---|
| 81 | | | 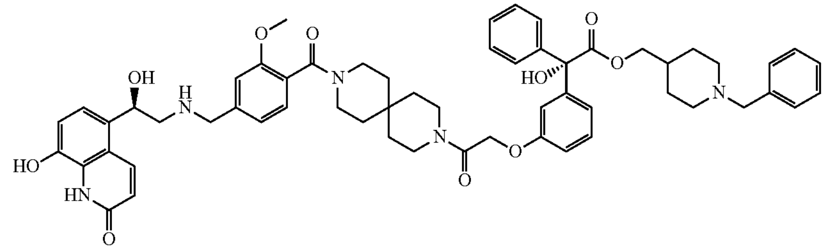 [SMILES: COc1cc(CNC[C@H](O)c2ccc(O)c3[nH]c(=O)ccc23)ccc1C(=O)N1CCC2(CCN(C(=O)COc3cccc([C@](O)(C(=O)OCC4CCN(Cc5ccccc5)CC4)c4ccccc4)c3)CC2)CC1] |
| 82 | | | 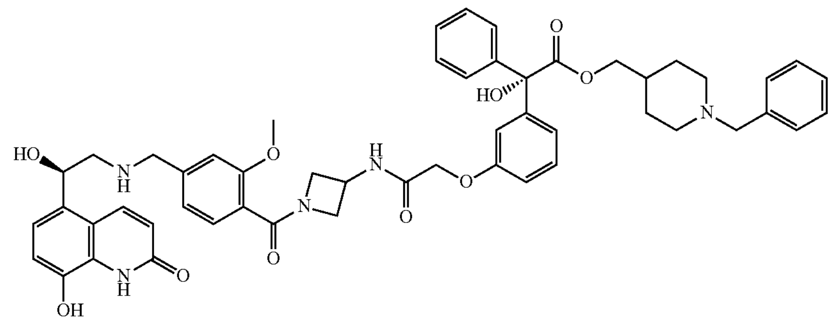 [SMILES: COc1cc(CNC[C@H](O)c2ccc(O)c3[nH]c(=O)ccc23)ccc1C(=O)N1CC(NC(=O)COc2cccc([C@](O)(C(=O)OCC3CCN(Cc4ccccc4)CC3)c3ccccc3)c2)C1] |

| N | Rt (min) | Method | NMR data (400 MHz) | Salt (2 eq unless stated) |
|---|---|---|---|---|
| 78 | 2.39 | 11 | (MeOD); δ 8.46 (s, 2H), 8.26 (dd, J = 4.0, 9.9 Hz, 1H), 7.48 (d, J = 7.8 Hz, 1H), 7.44 (s, 5H), 7.41-7.37 (m, 2H), 7.36-7.24 (m, 7H), 7.09-7.02 (m, 3H), 6.99-6.95 (m, 1H), 6.64 (d, J = 9.6 Hz, 1H), 5.44-5.38 (m, 1H), 4.77-4.68 (m, 1H), 4.62 (t, J = 8.6 Hz, 1H), 4.52 (s, 2H), 4.50-4.42 (m, 1H), 4.33-4.26 (m, 3H), 4.18-4.10 (m, 3H), 4.07 (s, 2H), 3.95 (s, 3H), 3.27 (d, J = 12.4 Hz, 2H), 3.19 (d, J = 8.6 Hz, 2H), 2.72 (ddd, J = 12.6, 12.6, 2.5 Hz, 2H), 1.94-1.82 (m, 1H), 1.74 (d, J = 12.9 Hz, 2H), 1.47-1.36 (m, 2H). | Formate |
| 79 | 2.47 | 11 | (MeOD); δ 8.55 (s, 1H), 8.28 (d, J = 9.9 Hz, 1H), 7.45-7.23 (m, 13H), 7.08 (d, J = 1.3 Hz, 1H), 7.06-6.99 (m, 4H), 6.93 (dq, J = 0.7, 3.6 Hz, 1H), 6.65 (d, J = 9.9 Hz, 1H), 5.34 (dd, J = 5.2, 8.0 Hz, 1H), 4.77 (s, 2H), 4.18 (s, 2H), 4.10 (d, J = 6.3 Hz, 2H), 3.91 (s, 3H), 3.77 (s, 4H), 3.61-3.50 (m, 4H), 3.42 (s, 2H), 3.10-3.02 (m, 4H), 2.33 (dd, J = 10.2, 11.7 Hz, 2H), 1.80-1.69 (m, 1H), 1.63 (d, J = 15.7 Hz, 6H), 1.57-1.47 (m, 4H), 1.38-1.24 (m, 2H). | mono-formate |
| 80 | 2.44 | 11 | (DMSO-$d_6$); δ 10.32 (s, 2H), 9.23-9.19 (m, 1H), 8.72-8.67 (m, 2H), 8.45 (dd, J = 5.7, 5.7 Hz, 1H), 7.89 (d, J = 11.9 Hz, 1H), 7.35 (d, J = 2.8 Hz, 3H), 7.30 (s, 6H), 7.16 (d, J = 4.3 Hz, 7H), 6.97 (d, J = 8.3 Hz, 1H), 6.81 (d, J = 8.1 Hz, 1H), 6.75-6.69 (m, 2H), 6.65 (dd, J = 2.4, 8.2 Hz, 1H), 6.40 (d, J = 9.9 Hz, 1H), 5.18 (dd, J = 4.5, 7.6 Hz, 1H), 4.59 (d, J = 3.3 Hz, 2H), 4.12-4.03 (m, 6H), 3.87-3.79 (m, 4H), 3.67-3.63 (m, 1H), 3.16 (d, J = 11.4 Hz, 2H), 3.06-2.98 (m, 2H), 2.92-2.68 (m, 5H), 1.67-1.64 (m, 2H), 1.61-1.48 (m, 5H), 1.24-1.13 (m, 2H), 1.03-0.97 (m, 1H), 0.84 (dd, J = 6.8, 12.1 Hz, 1H). | TFA |
| 81 | 2.49 | 11 | (MeOD); δ 8.54 (s, 1H), 8.32 (d, J = 9.9 Hz, 1H), 7.45-7.26 (m, 13H), 7.23 (d, J = 4.5 Hz, 1H), 7.16-7.10 (m, 1H), 7.07-7.02 (m, 2H), 7.00 (s, 1H), 6.94 (dd, J = 2.3, 8.2 Hz, 1H), 6.66 (d, J = 9.8 Hz, 1H), 5.38 (dd, J = 4.6, 8.4 Hz, 1H), 4.78 (s, 2H), 4.19 (s, 2H), 4.12 (dd, J = 2.6, 6.2 Hz, 2H), 3.96 (s, 2H), 3.90 (s, 3H), 3.81-3.74 (m, 2H), 3.58-3.52 (m, 4H), 3.28-3.08 (m, 6H), 2.57 (dd, J = 11.4, 11.4 Hz, 2H), 1.87-1.79 (m, 1H), 1.70-1.31 (m, 12H). | mono-formate |
| 82 | 2.41 | 11 | (MeOD); δ 8.50 (s, 2H), 8.33 (d, J = 9.8 Hz, 1H), 7.44 (s, 5H), 7.41-7.25 (m, 9H), 7.14 (d, J = 7.4 Hz, 1H), 7.10-7.02 (m, 3H), 6.97 (dd, J = 2.4, 8.2 Hz, 1H), 6.67 (d, J = 9.7 Hz, 1H), 5.41 (dd, J = 6.2, 6.2 Hz, 1H), 4.73-4.65 (m, 1H), 4.53 (s, 2H), 4.46-4.39 (m, 1H), 4.24 (s, 2H), 4.23-4.18 (m, 1H), 4.13 (d, J = 6.2 Hz, 2H), 4.11-4.07 (m, 1H), 4.05 (s, 2H), 4.00-3.95 (m, 1H), 3.93 (s, 3H), 3.26 (d, J = 12.2 Hz, 2H), 3.16 (d, J = 6.3 Hz, 2H), 2.69 (dd, J = 11.6, 11.6 Hz, 2H), 1.89-1.85 (m, 1H), 1.75 (d, J = 12.8 Hz, 2H), 1.48-1.30 (m, 2H). | formate |

The following compounds were prepared as described in Example 20 with (R)-4-(2-((tert-butoxycarbonyl)(2-((tert-butyldimethylsilyl)oxy)-2-(8-hydroxy-2-oxo-1,2-dihydroquinolin-5-yl)ethyl)amino)ethyl)benzoic acid (prepared in Procedure 5) replacing (R)-4-(((tert-butoxycarbonyl)(2-((tert-butyldimethylsilyl)oxy)-2-(8-hydroxy-2-oxo-1,2-dihydroquinolin-5-yl)ethyl)amino)methyl)benzoic acid and the use of the appropriate amine replacing N-(tert-butoxycarbonyl)ethylenediamine HCl in Step 1.

| N | Appropriate amine | Structure |
|---|---|---|
| 83 | 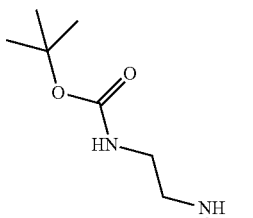 | 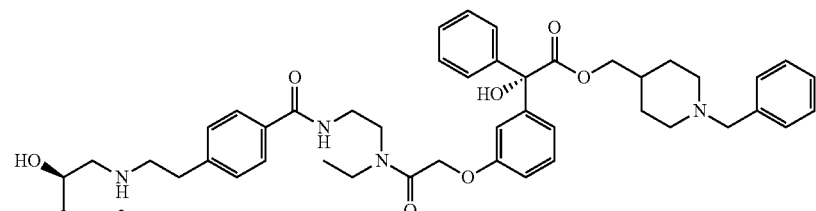 |
| 84 | 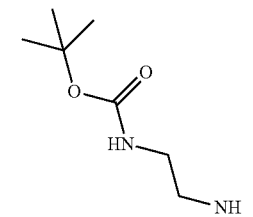 | 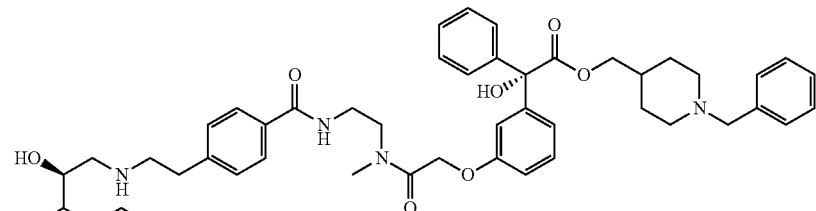 |

-continued

| N | Appropriate amine | Structure |
|---|---|---|
| 85 | | 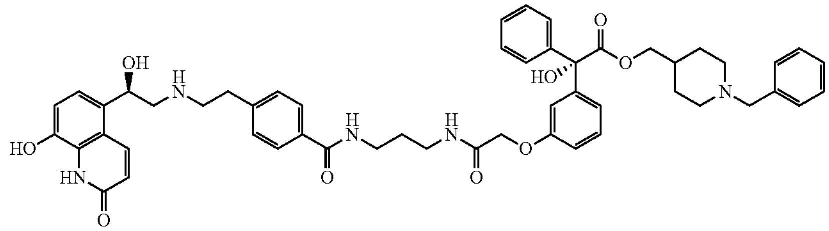 [SMILES: O=C(COc1cccc([C@](O)(C(=O)OCC2CCN(Cc3ccccc3)CC2)c2ccccc2)c1)NCCCNC(=O)c1ccc(CCNC[C@H](O)c2ccc(O)c3[nH]c(=O)ccc23)cc1] |
| 86 | | 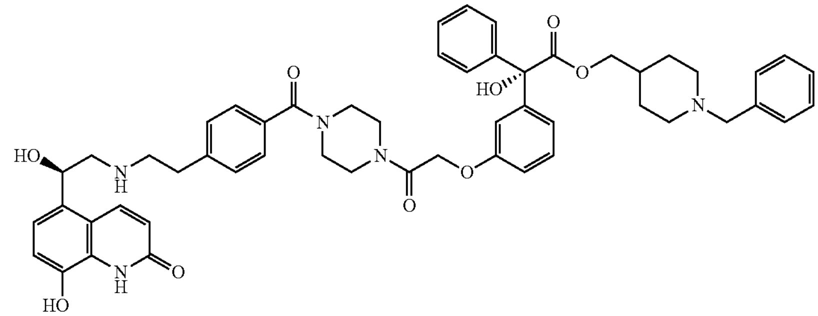 [SMILES: O=C(COc1cccc([C@](O)(C(=O)OCC2CCN(Cc3ccccc3)CC2)c2ccccc2)c1)N1CCN(C(=O)c2ccc(CCNC[C@H](O)c3ccc(O)c4[nH]c(=O)ccc34)cc2)CC1] |
| 87 | | 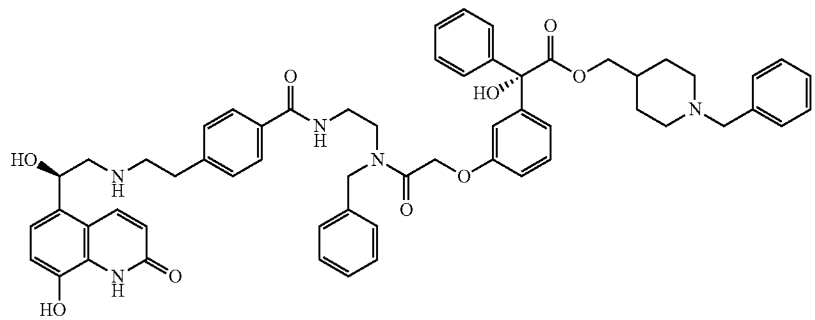 [SMILES: O=C(NCCN(Cc1ccccc1)C(=O)COc1cccc([C@](O)(C(=O)OCC2CCN(Cc3ccccc3)CC2)c2ccccc2)c1)c1ccc(CCNC[C@H](O)c2ccc(O)c3[nH]c(=O)ccc23)cc1] |
| 88 | | 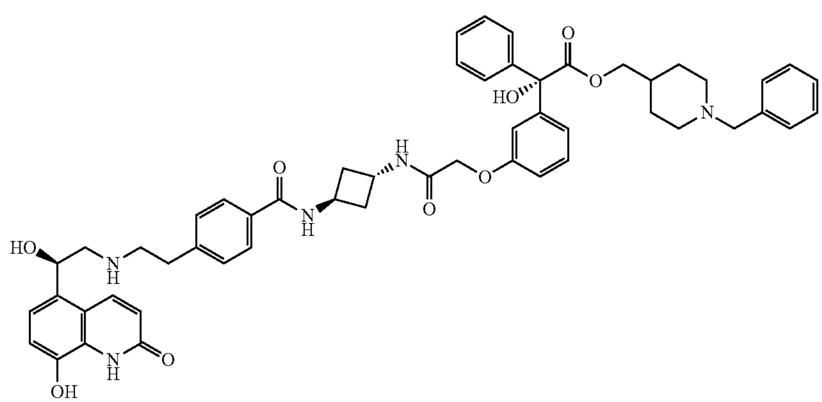 [SMILES: O=C(COc1cccc([C@](O)(C(=O)OCC2CCN(Cc3ccccc3)CC2)c2ccccc2)c1)N[C@H]1C[C@H](NC(=O)c2ccc(CCNC[C@H](O)c3ccc(O)c4[nH]c(=O)ccc34)cc2)C1] |

-continued
| N | Appropriate amine | Structure |
|---|---|---|
| 89 | 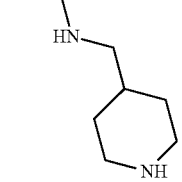 | 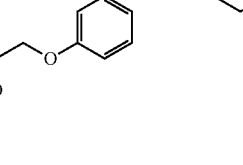 |
| 90 | 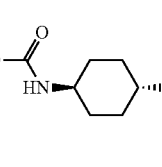 | 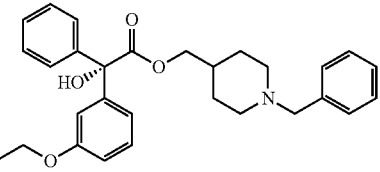 |
| 91 | 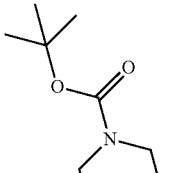 | 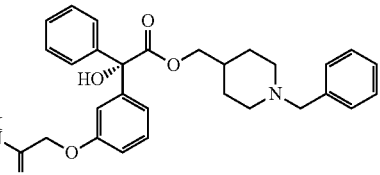 |
| 92 | 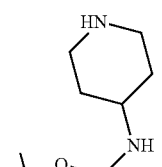 | 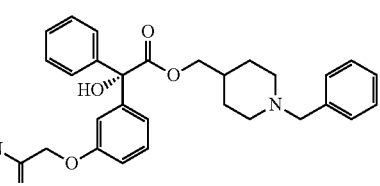 |
| 93 | 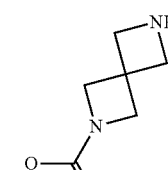 | 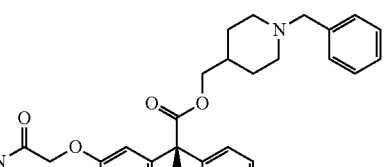 |

-continued
| N | Appropriate amine | Structure |
|---|---|---|
| 94 | 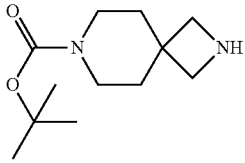 [SMILES: CC(C)(C)OC(=O)N1CCC2(CC1)CNC2] | 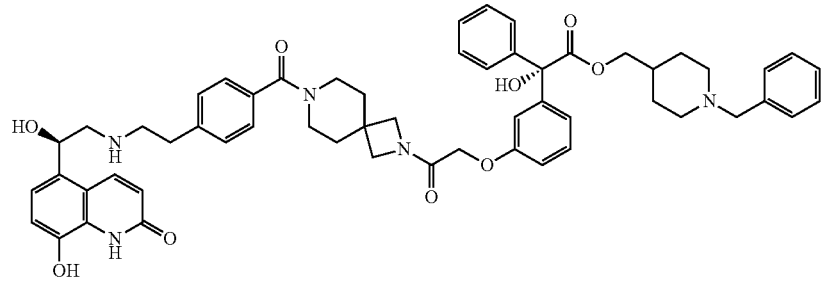 [SMILES: O=C(COc1cccc([C@](O)(C(=O)OCC2CCN(Cc3ccccc3)CC2)c2ccccc2)c1)N1CC2(CCN(C(=O)c3ccc(CCNC[C@H](O)c4ccc(O)c5[nH]c(=O)ccc45)cc3)CC2)C1] |
| 95 | 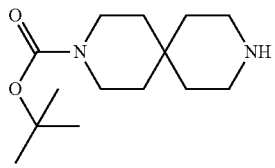 [SMILES: CC(C)(C)OC(=O)N1CCC2(CCNCC2)CC1] | 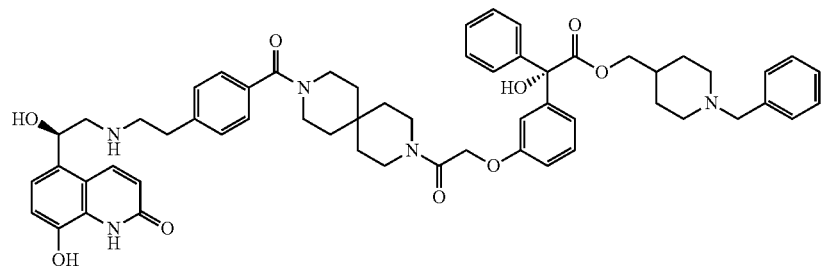 [SMILES: O=C(COc1cccc([C@](O)(C(=O)OCC2CCN(Cc3ccccc3)CC2)c2ccccc2)c1)N1CCC2(CC1)CCN(C(=O)c1ccc(CCNC[C@H](O)c3ccc(O)c4[nH]c(=O)ccc34)cc1)CC2] |
| 96 | 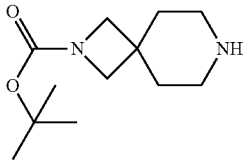 [SMILES: CC(C)(C)OC(=O)N1CC2(CCNCC2)C1] | 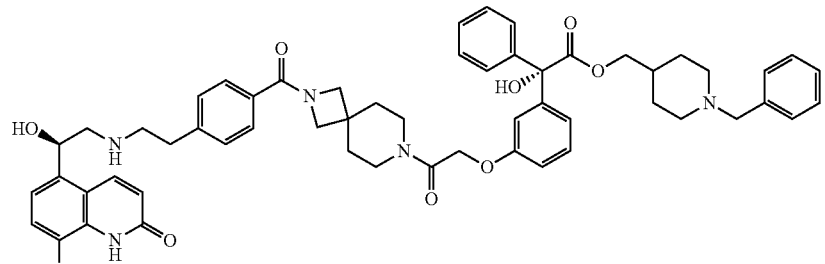 |
| 97 | 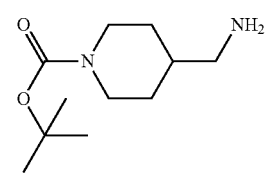 | 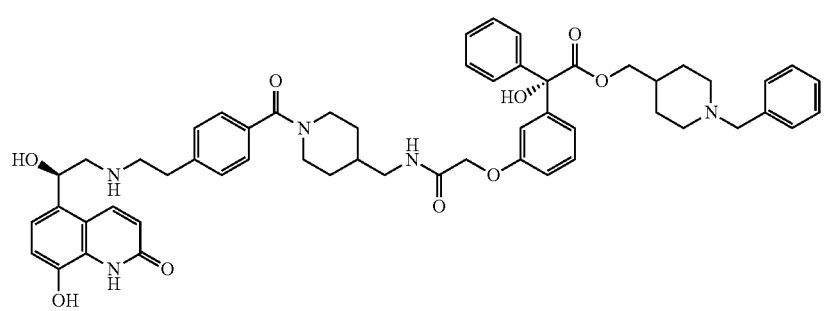 [SMILES: O=C(COc1cccc([C@](O)(C(=O)OCC2CCN(Cc3ccccc3)CC2)c2ccccc2)c1)NCC1CCN(C(=O)c2ccc(CCNC[C@H](O)c3ccc(O)c4[nH]c(=O)ccc34)cc2)CC1] |
| 98 | 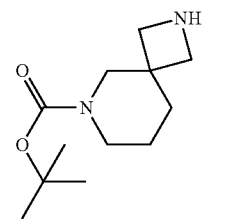 [SMILES: CC(C)(C)OC(=O)N1CCCC2(CNC2)C1] | 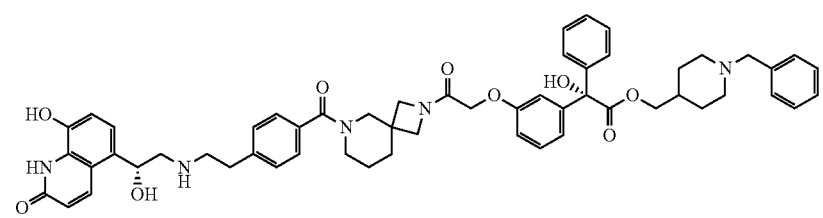 [SMILES: O=C(COc1cccc([C@](O)(C(=O)OCC2CCN(Cc3ccccc3)CC2)c2ccccc2)c1)N1CC2(CCCN(C(=O)c3ccc(CCNC[C@H](O)c4ccc(O)c5[nH]c(=O)ccc45)cc3)C2)C1] |
| 99 | 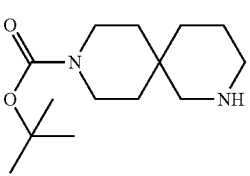 [SMILES: CC(C)(C)OC(=O)N1CCC2(CCCNC2)CC1] | 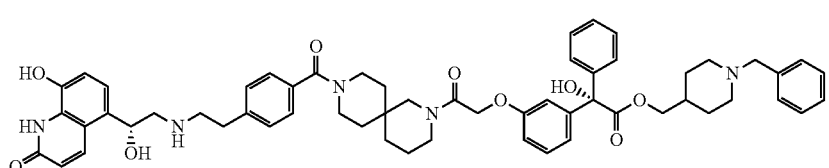 |

| N | Appropriate amine | Structure |
|---|---|---|
| 100 | | 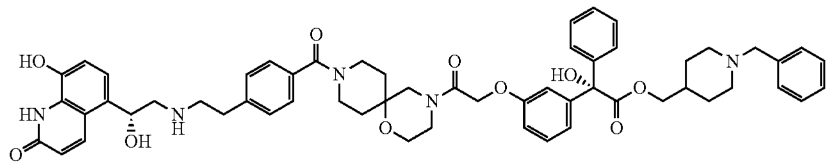 [SMILES: O=C(COc1cccc([C@](O)(C(=O)OCC2CCN(Cc3ccccc3)CC2)c2ccccc2)c1)N1CCOC2(CCN(C(=O)c3ccc(CCNC[C@H](O)c4ccc(O)c5[nH]c(=O)ccc45)cc3)CC2)C1] |
| 101 | | 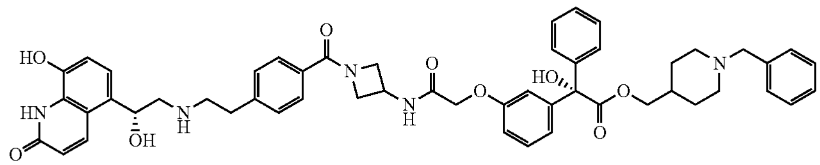 [SMILES: O=C(COc1cccc([C@](O)(C(=O)OCC2CCN(Cc3ccccc3)CC2)c2ccccc2)c1)NC1CN(C(=O)c2ccc(CCNC[C@H](O)c3ccc(O)c4[nH]c(=O)ccc34)cc2)C1] |
| 102 | | 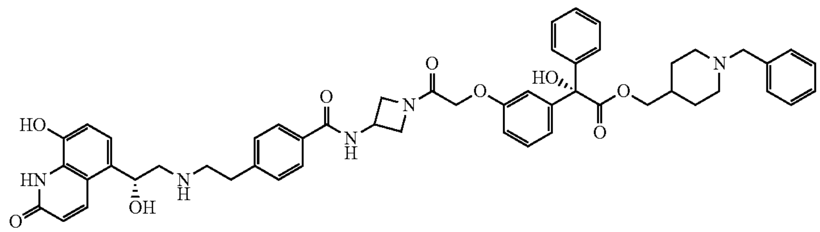 [SMILES: O=C(NC1CN(C(=O)COc2cccc([C@](O)(C(=O)OCC3CCN(Cc4ccccc4)CC3)c3ccccc3)c2)C1)c1ccc(CCNC[C@H](O)c2ccc(O)c3[nH]c(=O)ccc23)cc1] |
| 103 | | 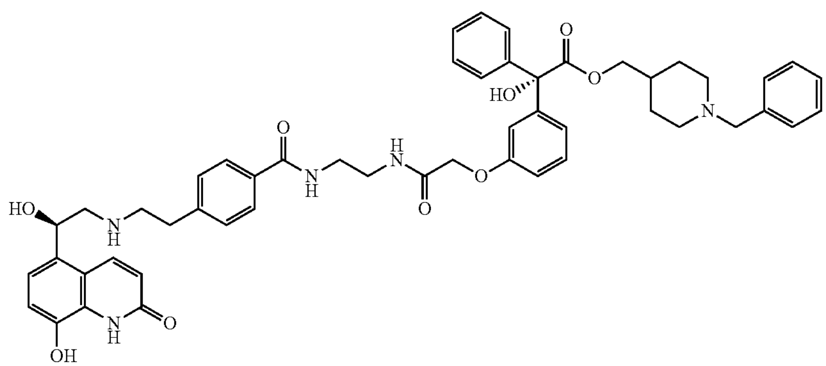 [SMILES: O=C(COc1cccc([C@](O)(C(=O)OCC2CCN(Cc3ccccc3)CC2)c2ccccc2)c1)NCCNC(=O)c1ccc(CCNC[C@H](O)c2ccc(O)c3[nH]c(=O)ccc23)cc1] |
| 104 | | 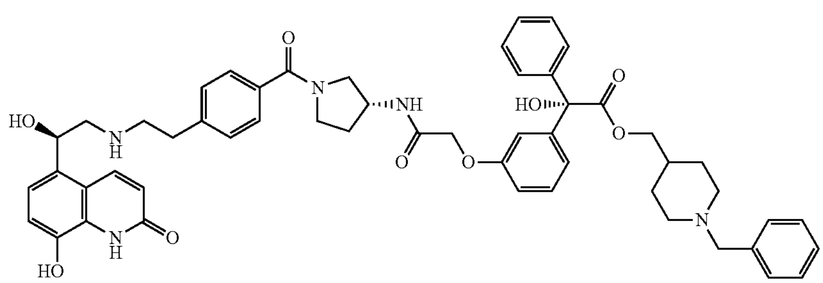 [SMILES: O=C(COc1cccc([C@](O)(C(=O)OCC2CCN(Cc3ccccc3)CC2)c2ccccc2)c1)N[C@@H]1CCN(C(=O)c2ccc(CCNC[C@H](O)c3ccc(O)c4[nH]c(=O)ccc34)cc2)C1] |
| 105 | | 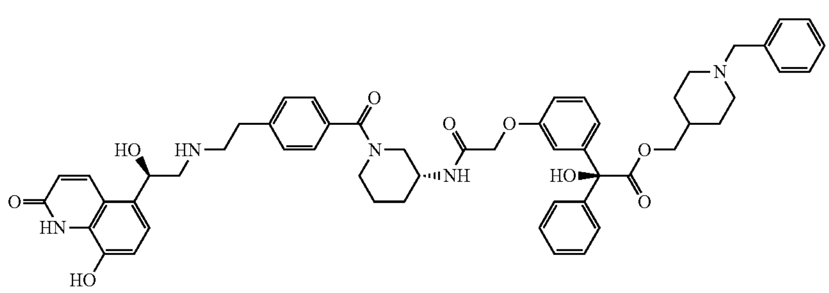 [SMILES: O=C(COc1cccc([C@](O)(C(=O)OCC2CCN(Cc3ccccc3)CC2)c2ccccc2)c1)N[C@@H]1CCCN(C(=O)c2ccc(CCNC[C@H](O)c3ccc(O)c4[nH]c(=O)ccc34)cc2)C1] |

-continued

| N | Appropriate amine | Structure |
|---|---|---|
| 106 | | 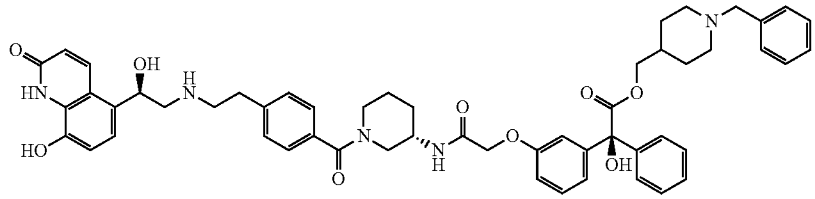 [SMILES: O=C(COc1cccc([C@](O)(C(=O)OCC2CCN(Cc3ccccc3)CC2)c2ccccc2)c1)N[C@H]1CCCN(C(=O)c2ccc(CCNC[C@H](O)c3ccc(O)c4[nH]c(=O)ccc34)cc2)C1] |
| 107 | | 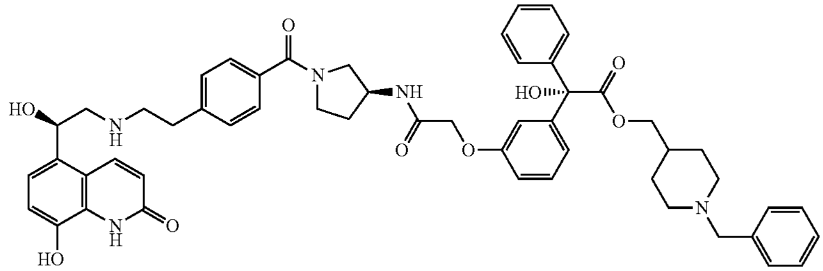 [SMILES: O=C(COc1cccc([C@](O)(C(=O)OCC2CCN(Cc3ccccc3)CC2)c2ccccc2)c1)N[C@H]1CCN(C(=O)c2ccc(CCNC[C@H](O)c3ccc(O)c4[nH]c(=O)ccc34)cc2)C1] |
| 108 | | 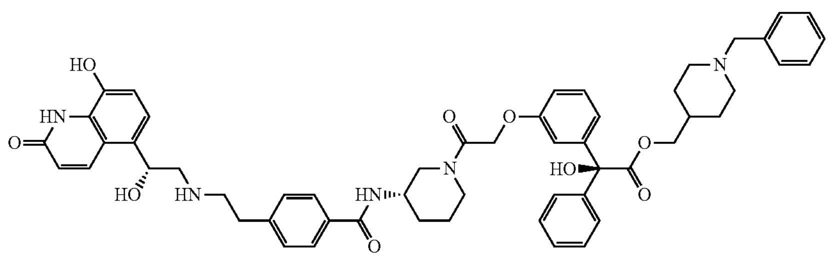 [SMILES: O=C(N[C@H]1CCCN(C(=O)COc2cccc([C@](O)(C(=O)OCC3CCN(Cc4ccccc4)CC3)c3ccccc3)c2)C1)c1ccc(CCNC[C@H](O)c2ccc(O)c3[nH]c(=O)ccc23)cc1] |
| 109 | | 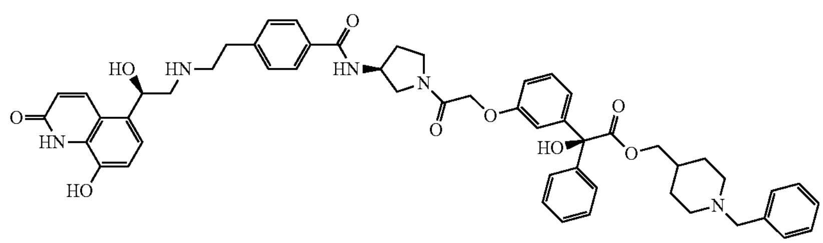 [SMILES: O=C(N[C@H]1CCN(C(=O)COc2cccc([C@](O)(C(=O)OCC3CCN(Cc4ccccc4)CC3)c3ccccc3)c2)C1)c1ccc(CCNC[C@H](O)c2ccc(O)c3[nH]c(=O)ccc23)cc1] |
| 110 | | 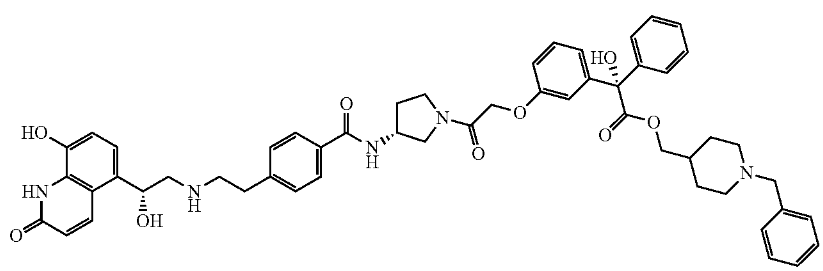 [SMILES: O=C(N[C@@H]1CCN(C(=O)COc2cccc([C@](O)(C(=O)OCC3CCN(Cc4ccccc4)CC3)c3ccccc3)c2)C1)c1ccc(CCNC[C@H](O)c2ccc(O)c3[nH]c(=O)ccc23)cc1] |
| 111 | | 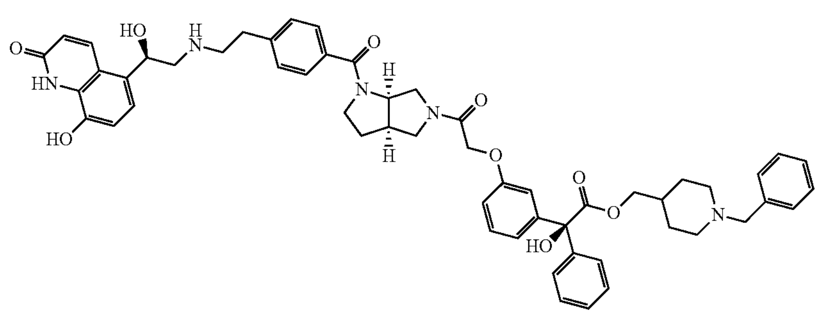 [SMILES: O=C(COc1cccc([C@](O)(C(=O)OCC2CCN(Cc3ccccc3)CC2)c2ccccc2)c1)N1C[C@H]2CCN(C(=O)c3ccc(CCNC[C@H](O)c4ccc(O)c5[nH]c(=O)ccc45)cc3)[C@H]2C1] |

-continued

| N | Appropriate amine | Structure |
|---|---|---|
| 112 | | 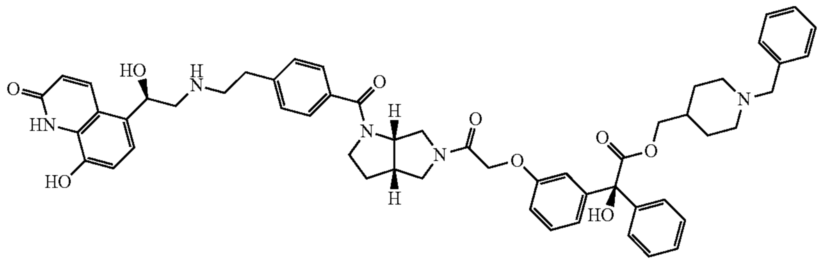 [SMILES: O=C(COc1cccc([C@](O)(C(=O)OCC2CCN(Cc3ccccc3)CC2)c2ccccc2)c1)N1C[C@@H]2CCN(C(=O)c3ccc(CCNC[C@H](O)c4ccc(O)c5[nH]c(=O)ccc45)cc3)[C@@H]2C1] |
| 113 | | 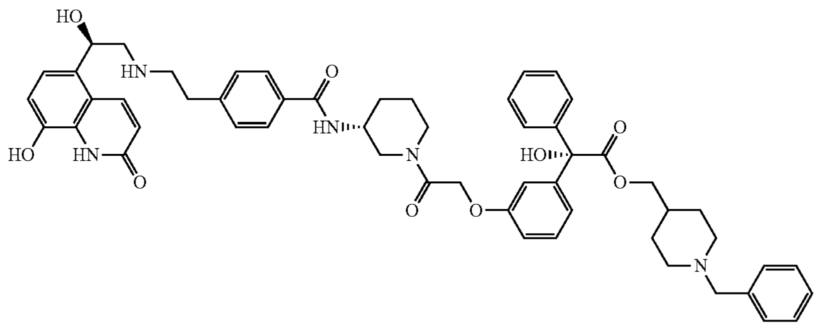 [SMILES: O=C(N[C@@H]1CCCN(C(=O)COc2cccc([C@](O)(C(=O)OCC3CCN(Cc4ccccc4)CC3)c3ccccc3)c2)C1)c1ccc(CCNC[C@H](O)c2ccc(O)c3[nH]c(=O)ccc23)cc1] |

| N | Rt (min) | Method | NMR data (400 MHz) | Salt (2 eq unless stated) |
|---|---|---|---|---|
| 83 | 2.45 | 11 | (MeOD); δ 8.38 (d, J = 9.9 Hz, 1H), 7.82 (d, J = 8.3 Hz, 1H), 7.75 (d, J = 8.3 Hz, 1H), 7.48 (s, 5H), 7.43-7.29 (m, 9H), 7.23-7.15 (m, 1H), 7.04 (dd, J = 8.3, 8.3 Hz, 2H), 6.93 (dd, J = 2.2, 2.2 Hz, 1H), 6.89-6.81 (m, 1H), 6.70 (d, J = 9.9 Hz, 1H), 5.42 (dd, J = 6.7, 6.7 Hz, 1H), 4.80 (ddd, J = 12.7, 12.7, 12.7 Hz, 2H), 4.28 (t, J = 9.7 Hz, 2H), 4.13-4.06 (m, 2H), 3.59-3.43 (m, 7H), 3.37-3.35 (m, 2H), 3.29 (d, J = 5.8 Hz, 2H), 3.16-3.08 (m, 3H), 3.01-2.92 (m, 2H), 1.96-1.95 (m, 1H), 1.81-1.76 (m, 2H), 1.42-1.30 (m, 2H), 1.25-1.12 (m, 3H). | TFA |
| 84 | 2.40 | 11 | (MeOD); δ 8.37 (d, J = 9.9 Hz, 1H), 7.81 (d, J = 8.3 Hz, 1H), 7.74 (d, J = 8.2 Hz, 1H), 7.51-7.46 (m, 6H), 7.41-7.29 (m, 8H), 7.15 (q, J = 7.9 Hz, 1H), 7.05 (d, J = 8.3 Hz, 1H), 7.00 (d, J = 8.2 Hz, 1H), 6.93-6.91 (m, 1H), 6.82 (ddd, J = 5.7, 10.6, 17.0 Hz, 1H), 6.70 (d, J = 9.8 Hz, 1H), 5.45-5.40 (m, 1H), 4.84-4.76 (m, 2H), 4.26 (d, J = 8.0 Hz, 2H), 4.11-4.05 (m, 2H), 3.61-3.35 (m, 7H), 3.29 (d, J = 7.5 Hz, 2H), 3.12 (s, 3H), 3.08 (d, J = 7.8 Hz, 1H), 3.00 (s, 1H), 2.99-2.92 (m, 2H), 1.95-1.89 (m, 1H), 1.80-1.69 (m, 3H), 1.43-1.30 (m, 2H). | TFA |
| 85 | 2.43 | 11 | (MeOD); δ 8.37 (d, J = 9.9 Hz, 1H), 7.84 (d, J = 8.4 Hz, 2H), 7.52-7.48 (m, 6H), 7.40 (dd, J = 8.6, 8.6 Hz, 4H), 7.35-7.28 (m, 6H), 7.07-7.04 (m, 3H), 6.98 (dd, J = 2.1, 8.8 Hz, 1H), 6.70 (d, J = 9.8 Hz, 1H), 5.45-5.40 (m, 1H), 4.51 (s, 2H), 4.27 (s, 2H), 4.11 (d, J = 6.3 Hz, 2H), 3.49-3.35 (m, 6H), 3.32-3.28 (m, 3H), 3.19-3.10 (m, 3H), 2.97 (dd, J = 10.9, 12.7 Hz, 2H), 2.01-1.93 (m, 1H), 1.84-1.77 (m, 4H), 1.47-1.37 (m, 2H). | TFA |
| 86 | 2.43 | 11 | (MeOD); δ 8.38 (1H, d, J = 9.9 Hz), 7.53-7.49 (6H, m), 7.46 (4H, d, J = 4.3 Hz), 7.41-7.26 (6H, m), 7.06 (2H, d, J = 8.2 Hz), 6.97 (1H, s), 6.94 (1H, d, J = 7.2 Hz), 6.71 (1H, d, J = 9.9 Hz), 5.43 (1H, dd, J = 5.6, 7.8 Hz), 4.84 (2H, s), 4.28 (2H, s), 4.17-4.08 (1H, m), 3.69 (6H, m), 3.51-3.37 (4H, m), 3.30 (2H, s), 3.20-3.11 (3H, m), 3.01-2.93 (2H, m), 1.98-1.92 (1H, m), 1.84-1.77 (4H, m), 1.47-1.33 (2H, m) | TFA |
| 87 | 2.57 | 11 | (MeOD); δ 8.37 (dd, J = 2.1, 9.9 Hz, 1H), 7.81 (d, J = 8.4 Hz, 1H), 7.75 (d, J = 8.2 Hz, 1H), 7.42-7.23 (m, 16H), 7.22-7.14 (m, 1H), 7.07-6.95 (m, 4H), 6.87 (dd, J = 1.9, 7.3 Hz, 1H), 6.79 (dd, J = 2.3, 8.1 Hz, 1H), 6.70 (d, J = 9.8 Hz, 1H), 5.42 (dd, J = 6.3, 6.3 Hz, 1H), 5.02-4.97 (m, 1H), 4.81 (t, J = 4.4 Hz, 1H), 4.70 (d, J = 5.9 Hz, 2H), 4.26 (s, 2H), 4.19 (s, 2H), 3.63-3.49 (m, 5H), 3.16-3.10 (m, 2H), 2.93-2.93 (m, 3H), 1.79 (dt, J = 15.4, 39.6 Hz, 5H), 1.31 (s, 3H). | TFA |
| 88 | 2.45 | 11 | (MeOD); δ 8.37 (d, J = 9.9 Hz, 1H), 7.86 (d, J = 8.4 Hz, 2H), 7.53-7.48 (m, 5H), 7.43 (d, J = 8.4 Hz, 2H), 7.41-7.29 (m, 7H), 7.10-7.04 (m, 3H), 6.98 (dd, J = 2.0, 8.2 Hz, 1H), 6.71 (d, J = 9.8 Hz, 1H), 5.42 (dd, J = 5.3, 8.2 Hz, 1H), 4.60-4.43 (m, 5H), 4.28 (s, 2H), 4.13 (d, J = 6.4 Hz, 2H), 3.50-3.41 (m, 4H), 3.20-3.11 (m, 3H), 3.01-2.95 (m, 2H), 2.54-2.42 (m, 4H), 2.05-1.75 (m, 3H), 1.50-1.32 (m, 2H). | TFA |
| 89 | 2.46 | 11 | (MeOD); δ 8.54 (d, J = 1.9 Hz, 1H), 8.37 (d, J = 9.9 Hz, 1H), 7.84 (d, J = 8.3 Hz, 2H), 7.53-7.48 (m, 5H), 7.43 (d, J = 8.3 Hz, 2H), 7.41-7.29 (m, 6H), 7.29-7.24 (m, 1H), 7.05 (d, J = 8.2 Hz, 2H), 6.95-6.89 (m, 2H), 6.70 (d, J = 9.9 Hz, 1H), 5.42 (dd, J = 5.8, 7.8 Hz, 1H), 4.83-4.72 (m, 2H), 4.42 (s, 2H), 4.27 (s, 2H), 4.18-4.10 (m, 2H), 3.94 (d, J = 12.8 Hz, 1H), 3.49-3.35 (m, 7H), 3.20-3.07 (m, 4H), 2.97 (dd, J = 12.5, 12.5 Hz, 2H), 2.67 (s, 1H), 1.95 (d, J = 3.0 Hz, 2H), 1.78 (dd, J = 13.9, 15.6 Hz, 4H), 1.45-1.31 (m, 2H), 1.25-1.11 (m, 2H). | TFA |

| N | Rt (min) | Method | NMR data (400 MHz) | Salt (2 eq unless stated) |
|---|---|---|---|---|
| 90 | 2.51 | 11 | (MeOD); δ 8.37 (d, J = 9.9 Hz, 1H), 7.83 (d, J = 8.3 Hz, 2H), 7.53-7.48 (m, 6H), 7.44-7.28 (m, 8H), 7.09-7.04 (m, 3H), 6.96 (dd, J = 2.3, 8.3 Hz, 1H), 6.71 (d, J = 9.9 Hz, 1H), 5.42 (dd, J = 5.3, 8.2 Hz, 1H), 4.48 (s, 2H), 4.29 (s, 2H), 4.13 (d, J = 6.3 Hz, 2H), 3.90-3.72 (m, 2H), 3.38 (d, J = 6.3 Hz, 5H), 3.30 (s, 1H), 3.16-3.10 (m, 3H), 3.01-2.94 (m, 2H), 2.01 (s, 2H), 1.95-1.81 (m, 5H), 1.52-1.41 (m, 5H). | TFA |
| 91 | 2.46 | 11 | (MeOD); δ 8.38 (d, J = 9.9 Hz, 1H), 7.53-7.48 (m, 5H), 7.43 (s, 4H), 7.40-7.27 (m, 6H), 7.09-7.03 (m, 3H), 6.96 (dd, J = 2.3, 8.1 Hz, 1H), 6.71 (d, J = 9.8 Hz, 1H), 5.42 (dd, J = 5.3, 8.1 Hz, 1H), 4.58-4.44 (m, 2H), 4.35-4.27 (m, 3H), 4.28 (s, 2H), 4.12 (d, J = 6.3 Hz, 2H), 4.05-3.98 (m, 1H), 3.73-3.68 (m, 1H), 3.51-3.40 (m, 2H), 3.24-3.09 (m, 3H), 3.06-2.93 (m, 3H), 2.06-1.67 (m, 6H), 1.61-1.36 (m, 5H). | TFA |
| 92 | 2.44 | 11 | (MeOD); δ 8.37 (d, J = 9.9 Hz, 1H), 7.85 (d, J = 6.8 Hz, 2H), 7.53-7.49 (m, 4H), 7.45-7.25 (m 11H), 7.08-6.91 (m, 3H), 6.70 (d, J = 9.8 Hz, 1H), 5.42 (dd, J = 5.6, 8.0 Hz, 1H), 4.85-4.77 (m, 2H), 4.52-4.43 (m, 1H), 4.28 (s, 2H), 4.19-4.08 (m, 2H), 4.01-3.97 (m, 1H), 3.50-3.35 (m, 6H), 3.30-3.08 (m, 4H), 3.04-2.83 (m, 3H), 2.08-1.95 (m, 3H), 1.79 (s, 4H), 1.65-1.50 (m, 2H), 1.42-1.31 (m, 2H). | TFA |
| 93 | 2.53 | 11 | (MeOD); δ 8.38 (d, J = 9.9 Hz, 1H), 7.66 (d, J = 8.3 Hz, 2H), 7.51-7.50 (m, 5H), 7.43 (d, J = 8.2 Hz, 2H), 7.41-7.35 (m, 6H), 7.33-7.26 (m, 1H), 7.09-7.03 (m, 2H), 6.97-6.89 (m, 2H), 6.70 (d, J = 9.9 Hz, 1H), 5.43 (dd, J = 5.8, 7.6 Hz, 1H), 4.54-4.41 (m, 4H), 4.30 (d, J = 14.1 Hz, 4H), 4.19-4.10 (m, 4H), 3.47-3.35 (m, 4H), 3.29 (d, J = 7.3 Hz, 2H), 3.20-3.10 (m, 3H), 3.01-2.88 (m, 2H), 1.95 (d, J = 3.8 Hz, 1H), 1.80-1.78 (m, 2H), 1.49-1.29 (m, 3H) | TFA |
| 94 | 2.54 | 11 | (MeOD); δ 8.37 (d, J = 9.9 Hz, 1H), 7.69 (d, J = 8.3 Hz, 2H), 7.53-7.48 (m, 5H), 7.44 (d, J = 8.2 Hz, 4H), 7.40-7.25 (m, 5H), 7.05 (d, J = 8.2 Hz, 2H), 6.94-6.90 (m, 2H), 6.71 (d, J = 9.8 Hz, 1H), 5.42 (dd, J = 5.1, 8.3 Hz, 1H), 4.79 (dd, J = 4.1, 4.1 Hz, 2H), 4.28 (s, 2H), 4.14-4.10 (m, 4H), 3.95 (s, 2H), 3.59-337 (m, 6H), 3.17-3.10 (m, 3H), 3.02-2.94 (m, 2H), 1.96 (s, 1H), 1.85-1.74 (m, 9H), 1.46-1.35 (m, 2H). | TFA |
| 95 | 2.60 | 11 | (MeOD); δ 8.38 (d, J = 9.9 Hz, 1H), 7.53-7.47 (m, 6H), 7.43 (s, 4H), 7.41-7.25 (m, 6H), 7.05 (d, J = 8.2 Hz, 2H), 6.97-6.90 (m, 2H), 6.71 (d, J = 9.8 Hz, 1H), 5.42 (dd, J = 5.1, 8.3 Hz, 1H), 4.79-4.77 (m, 2H), 4.28 (s, 2H), 4.16-4.09 (m, 2H), 3.77-3.77 (m, 2H), 3.57-3.36 (m, 10H), 3.30 (d, J = 5.3 Hz, 2H), 3.19-3.10 (m, 3H), 3.01-2.94 (m, 2H), 1.96-1.92 (m, 1H), 1.79 (dd, J = 12.9, 12.9 Hz, 2H), 1.70-1.47 (m, 7H), 1.44-1.31 (m, 2H). | TFA |
| 96 | 2.53 | 11 | (MeOD); δ 8.38 (dd, J = 5.6, 8.4 Hz, 1H), 7.54-7.48 (m, 6H), 7.43 (s, 4H), 7.40-7.27 (m, 6H), 7.06 (dd, J = 7.7, 7.7 Hz, 2H), 6.96 (s, 1H), 6.92 (dd, J = 2.3, 8.0 Hz, 1H), 6.71 (d, J = 9.9 Hz, 1H), 5.42 (dd, J = 5.0, 8.4 Hz, 1H), 4.62 (s, 2H), 4.28 (s, 2H), 4.13 (d, J = 6.1 Hz, 2H), 4.09-4.01 (m, 2H), 3.75 (s, 3H), 3.51-3.35 (m, 5H), 3.30 (d, J = 5.0 Hz, 2H), 3.16-3.10 (m, 3H), 3.02-2.94 (m, 2H), 2.01-1.96 (m, 1H), 1.80-1.80 (m, 7H), 1.47-1.42 (m, 2H). | TFA |
| 97 | 2.49 | 11 | (MeOD); δ 8.38 (d, J = 9.9 Hz, 1H), 7.53-7.49 (m, 5H), 7.48 (s, 1H), 7.42-7.29 (m, 10H), 7.05 (d, J = 8.2 Hz, 3H), 6.96 (dd, J = 2.0, 8.2 Hz, 1H), 6.70 (d, J = 9.8 Hz, 1H), 5.42 (dd, J = 5.3, 8.3 Hz, 1H), 4.65-4.50 (m, 3H), 4.28 (s, 2H), 4.12 (d, J = 6.3 Hz, 2H), 3.75-3.62 (m, 1H), 3.51-3.38 (m, 5H), 3.18-3.08 (m, 5H), 3.02-2.94 (m, 4H), 2.01-1.94 (m, 1H), 1.85-1.77 (m, 4H), 1.60 (s, 1H), 1.48-1.29 (m, 2H), 1.16-1.16 (m, 2H). | TFA |
| 98 | 2.47 | 11 | (DMSO-d6) δ 8.17 (d, J = 9.9 Hz, 1H), 7.32-7.22 (m, 16H), 7.05 (d, J = 8.3 Hz, 1H), 6.94-6.87 (m, 3H), 6.84-6.84 (m, 1H), 6.49 (d, J = 9.9 Hz, 1H), 5.01 (dd, J = 4.5, 7.8 Hz, 1H), 4.58-4.47 (m, 2H), 4.03-3.97 (m, 2H), 3.85-3.83 (m, 2H), 3.60-3.52 (m, 2H), 3.30 (m, 3H), 2.84-2.67 (m, 8H), 1.87-1.72 (m, 5H), 1.53-1.40 (m, 6H), 1.16-1.05 (m, 3H) | Free Base |
| 99 | 2.50 | 11 | (MeOD); δ 8.52 (s, 2H), 8.37 (d, J = 9.9 Hz, 1H), 7.39 (s, 9H), 7.37-7.22 (m, 6H), 7.04-6.93 (m, 5H), 6.69 (d, J = 9.9 Hz, 1H), 5.38 (dd, J = 4.3, 9.0 Hz, 1H), 4.89-4.74 (m, 2H), 4.05 (d, J = 5.9 Hz, 2H), 3.86-3.83 (m, 2H), 161-3.04 (m, 19H), 2.39 (s, 1H), 1.60-1.56 (m, 6H), 1.43-1.42 (m, 1H), 1.35-1.29 (m, 4H). | Formate |
| 100 | 2.44 | 11 | (DMSO-d6, 100° C.) δ 8.18 (1H, d, J = 9.9 Hz), 7.47 (5H, s), 7.39-7.22 (10H, m), 7.16 (1H, d, J = 8.2 Hz), 7.04-6.97 (3H, m), 6.89 (1H, dd, J = 2.1, 7.8 Hz), 6.58 (1H, d, J = 9.8 Hz), 5.36 (1H, dd, J = 4.9, 8.3 Hz), 4.74 (2H, s), 4.21 (3H, m), 4.06 (3H, m), 3.67 (5H, dd, J = 5.0, 5.0 Hz), 3.48 (2H, dd, J = 4.8, 4.8 Hz), 3.41-3.19 (8H, m), 3.10-3.04 (2H, m), 2.98-2.77 (2H, m), 2.56-2.54 (1H, m), 1.89 (1H, s), 1.78-1.74 (3H, m), 1.57-1.40 (3H, m); | TFA |
| 101 | 2.42 | 11 | (MeOD); δ 8.47 (s, 2H), 8.37 (d, J = 9.9 Hz, 1H), 7.87 (d, J = 7.9 Hz, 2H), 7.45-7.28 (m, 14H), 7.07-7.03 (m, 2H), 7.01-6.91 (m, 2H), 6.70 (d, J = 9.8 Hz, 1H), 5.41 (dd, J = 5.5, 8.0 Hz, 1H), 4.84-4.76 (m, 1H), 4.69-4.63 (m, 1H), 4.62 (s, 2H), 4.41-4.27 (m, 2H), 4.14-4.07 (m, 6H), 3.29-3.23 (m, 4H), 3.16-3.08 (m, 3H), 2.78-2.67 (m, 2H), 1.94-1.85 (m, 1H), 1.76-1.72 (m, 2H), 1.45-1.34 (m, 2H) | Formate |
| 102 | 2.43 | 11 | (MeOD); δ 8.47 (s, 2H), 8.37 (d, J = 9.9 Hz, 1H), 7.87 (d, J = 7.9 Hz, 2H), 7.45-7.28 (m, 14H), 7.07-7.03 (m, 2H), 7.01-6.91 (m, 2H), 6.70 (d, J = 9.8 Hz, 1H), 5.41 (dd, J = 5.5, 8.0 Hz, 1H), 4.84-4.76 (m, 1H), 4.69-4.63 (m, 1H), 4.62 (s, 2H), 4.41-4.27 (m, 2H), 4.14-4.07 (m, 6H), 3.29-3.23 (m, 4H), 3.16-3.08 (m, 3H), 2.78-2.67 (m, 2H), 1.94-1.85 (m, 1H), 1.76-1.72 (m, 2H), 1.45-1.34 (m, 2H) | Formate |
| 103 | 2.41 | 11 | (MeOD); δ 8.41 (d, J = 9.9 Hz, 1H), 7.78 (d, J = 8.3 Hz, 2H), 7.50 (s, 5H), 7.42-7.24 (m, 9H), 7.06 (d, J = 8.3 Hz, 3H), 6.97-6.93 (m, 2H), 6.72 (d, J = 9.8 Hz, 1H), 5.45 (dd, J = 6.8, 6.8 Hz, 1H), 4.50 (s, 2H), 4.28 (s, 2H), 4.10 (d, J = 6.4 Hz, 2H), 3.54-3.37 (m, 9H), 3.21-3.10 (m, 3H), 3.02-2.93 (m, 2H), 2.01-1.93 (m, 1H), 1.84-1.74 (m, 2H), 1.49-1.37 (m, 2H). | TFA |
| 104 | 2.39 | 11 | (DMSO, 100° C.); δ 8.21 (d, J = 9.9 Hz, 1H), 8.17 (s, 1H), 7.92-7.92 (m, 1H), 7.39-7.24 (m, 15H), 7.08 (d, J = 8.2 Hz, 1H), 7.04-7.00 (m, 2H), 6.95 (d, J = 8.2 Hz, 1H), 6.90 (dd, J = 2.4, 8.0 Hz, 1H), 6.49 (d, J = 9.9 Hz, 1H), 5.04 (dd, J = 5.0, 7.5 Hz, 1H), 4.43 (s, | mono Formate |

| N | Rt (min) | Method | NMR data (400 MHz) | Salt (2 eq unless stated) |
|---|---|---|---|---|
| | | | 2H), 4.37 (br s, 1H), 4.05 (d, J = 6.3 Hz, 2H), 3.71 (dd, J = 6.7, 11.4 Hz, 1H), 3.60-3.49 (m, 2H), 3.44 (s, 2H), 3.36 (dd, J = 5.3, 11.4 Hz, 2H), 2.91-2.72 (m, 6H), 2.17-2.07 (m, 1H), 1.97-1.86 (m, 3H), 1.62-1.48 (m, 3H), 1.28-1.13 (m, 2H). | |
| 105 | 2.44 | 11 | (DMSO-d₆, 100° C.); δ 8.21 (d, J = 9.9 Hz, 1H), 8.16 (s, 2H), 7.57 (d, J = 8.4 Hz, 1H), 7.40-7.21 (m, 15H), 7.10-7.04 (m, 2H), 7.01 (d, J = 8.0 Hz, 1H), 6.95 (d, J = 8.2 Hz, 1H), 6.91 (dd, J = 2.3, 8.2 Hz, 1H), 6.49 (d, J = 9.9 Hz, 1H), 5.06-5.02 (m, 1H), 4.41 (s, 2H), 4.04 (d, J = 6.3 Hz, 2H), 3.93-3.69 (m, 4H), 3.43 (s, 2H), 3.13-3.04 (m, 4H), 2.91-2.68 (m, 7H), 1.98-1.90 (m, 2H), 1.69-1.48 (m, 4H), 1.24-1.13 (m, 2H). | Formate |
| 106 | 2.47 | 11 | (DMSO-d₆, 100° C.); δ 8.21 (d, J = 9.9 Hz, 1H), 8.17 (s, 1H), 7.57 (d, J = 7.4 Hz, 1H), 7.41-7.37 (m, 2H), 7.32-7.22 (m, 12H), 7.10-7.00 (m, 3H), 6.95 (d, J = 8.0 Hz, 1H), 6.90 (dd, J = 2.3, 8.2 Hz, 1H), 6.50 (d, J = 9.9 Hz, 1H), 5.04 (dd, J = 4.9, 7.4 Hz, 1H), 4.41 (d, J = 2.5 Hz, 2H), 4.05 (d, J = 6.3 Hz, 2H), 3.92 (d, J = 12.5 Hz, 1H), 3.85-3.77 (m, 1H), 3.72 (d, J = 11.8 Hz, 1H), 3.44 (s, 2H), 3.13-3.02 (m, 2H), 2.91-2.72 (m, 8H), 2.57-2.47 (m, 1H), 1.97-1.85 (m, 3H), 1.72-1.48 (m, 6H), 1.28-1.13 (m, 2H). | mono Formate |
| 107 | 240 | 11 | (DMSO-d₆, 100° C.); δ 8.20 (d, J = 9.9 Hz, 1H), 7.97 (d, J = 6.1 Hz, 1H), 7.51-7.47 (m, 6H), 7.41-7.24 (m, 9H), 7.17 (d, J = 8.3 Hz, 1H), 7.04-7.00 (m, 3H), 6.90 (dd, J = 2.1, 8.2 Hz, 1H), 6.58 (d, J = 9.8 Hz, 1H), 5.38 (dd, J = 4.8, 8.3 Hz, 1H), 4.43 (s, 2H), 4.33 (dd, J = 6.3, 12.4 Hz, 1H), 4.23 (s, 2H), 4.10 (d, J = 5.3 Hz, 2H), 3.72 (dd, J = 6.8, 11.4 Hz, 1H), 3.61-3.48 (m, 4H), 3.14-3.05 (m, 6H), 2.99-2.95 (m, 2H), 2.57-2.55 (m, 1H), 2.17-2.05 (m, 1H), 1.94-1.85 (m, 2H), 1.79-1.75 (m, 2H), 1.45-1.44 (m, 2H). | TFA |
| 108 | 2.44 | 11 | (DMSO-d₆, 100° C.); δ 8.21-8.19 (m, 2H), 7.85-7.80 (m, 1H), 7.75 (d, J = 8.2 Hz, 2H), 7.41-7.38 (m, 2H), 7.33-7.22 (m, 11H), 7.08 (d, J = 8.2 Hz, 1H), 7.00-6.94 (m, 3H), 6.90-6.87 (m, 1H), 6.49 (d, J = 9.9 Hz, 1H), 5.03 (dd, J = 5.0, 7.5 Hz, 1H), 4.73 (s, 2H), 4.06-4.03 (m, 3H), 3.88-3.87 (m, 2H), 3.74-3.68 (m, 1H), 3.44 (s, 2H), 3.13-2.97 (m, 1H), 2.93-2.71 (m, 8H), 2.57-2.47 (m, 1H), 2.05-1.89 (m, 3H), 1.82-1.76 (m, 1H), 1.72-1.46 (m, 4H), 1.24-1.13 (m, 2H). | mono-formate |
| 109 | 2.41 | 11 | (DMSO, 100° C.); δ 8.21-8.17 (m, 3H), 8.12 (s, 1H), 7.76 (d, J = 8.2 Hz, 2H), 7.39 (dd, J = 1.4, 8.3 Hz, 2H), 7.35-7.22 (m, 11H), 7.08 (d, J = 8.2 Hz, 1H), 7.00-6.94 (m, 3H), 6.89 (dd, J = 1.9, 8.2 Hz, 1H), 6.49 (d, J = 9.9 Hz, 1H), 5.03 (dd, J = 5.0, 7.5 Hz, 1H), 4.64 (s, 2H), 4.53 (s, 1H), 4.05 (d, J = 6.3 Hz, 2H), 3.88-3.58 (m, 2H), 3.43 (s, 2H), 2.91-2.71 (m, 9H), 2.56-2.45 (m, 1H), 2.17 (br s, 1H), 2.05 (br s, 1H), 1.98-1.90 (m, 2H), 1.63-1.49 (m, 3H), 1.28-1.13 (m, 2H). | formate |
| 110 | 2.43 | 11 | (DMSO-d₆, 100° C.); δ 8.20 (d, J = 9.9 Hz, 1H), 8.16-8.11 (m, 2H), 7.77 (d, J = 8.3 Hz, 2H), 7.39 (dd, J = 1.4, 8.3 Hz, 2H), 7.35-7.21 (m, 11H), 7.09 (d, J = 8.3 Hz, 1H), 7.00-6.95 (m, 3H), 6.89 (dd, J = 2.0, 8.2 Hz, 1H), 6.50 (d, J = 9.9 Hz, 1H), 6.10 (s, 1H), 5.09 (dd, J = 4.9, 7.5 Hz, 1H), 4.64 (s, 2H), 4.54-4.45 (m, 1H), 4.05 (d, J = 6.3 Hz, 2H), 3.72-3.59 (m, 2H), 3.47-3.40 (m, 3H), 3.00-2.73 (m, 8H), 2.57-2.47 (m, 1H), 2.17 (br s, 1H), 2.04-1.91 (m, 3H), 1.63-1.55 (m, 1H), 1.52 (d, J = 13.2 Hz, 2H), 1.25-1.14 (m, 2H). | mono-formate |
| 111 | 2.41 | 11 | (DMSO-d₆); δ 8.21 (d, J = 9.8 Hz, 1H), 8.16 (s, 2H), 7.40-7.20 (m, 15H), 7.08 (d, J = 8.4 Hz, 1H), 7.00-6.94 (m, 3H), 6.85 (dd, J = 1.9, 8.0 Hz, 1H), 6.50 (d, J = 9.0 Hz, 1H), 5.04 (dd, J = 5.0, 7.4 Hz, 1H), 4.63 (s, 2H), 4.43-4.37 (m, 1H), 4.04 (d, J = 6.4 Hz, 2H), 3.79-3.73 (m, 1H), 3.72-3.49 (m, 4H), 3.46-3.39 (m, 3H), 2.95-2.73 (m, 8H), 2.57-2.47 (m, 1H), 2.06-2.00 (m, 1H), 1.97-1.89 (m, 2H), 1.81-1.76 (m, 1H), 1.62-1.49 (m, 3H), 1.28-1.13 (m, 2H). | formate |
| 112 | 2.42 | 11 | (DMSO-d₆, 100° C.); δ 8.21 (d, J = 9.9 Hz, 1H), 8.16 (s, 1H), 7.41-7.20 (m, 15H), 7.08 (d, J = 8.4 Hz, 1H), 7.00-6.94 (m, 3H), 6.87-6.84 (m, 1H), 6.50 (d, J = 9.9 Hz, 1H), 5.04 (dd, J = 5.0, 7.4 Hz, 1H), 4.63 (s, 2H), 4.44-4.36 (m, 1H), 4.05 (d, J = 6.3 Hz, 2H), 3.81-3.75 (m, 1H), 3.72-3.49 (m, 4H), 3.46-3.40 (m, 3H), 2.94-2.72 (m, 8H), 2.58-2.50 (m, 1H), 2.08-2.01 (m, 1H), 1.97-1.89 (m, 2H), 1.80-137 (m, 1H), 1.62-1.49 (m, 3H), 1.28-1.13 (m, 2H). | mono-formate |
| 113 | 2.45 | 11 | (DMSO-d₆, 100° C.); δ 8.22-8.18 (m, 2H), 7.84 (d, J = 5.4 Hz, 1H), 7.74 (d, J = 8.2 Hz, 2H), 7.39 (dd, J = 1.3, 8.3 Hz, 2H), 7.33-7.22 (m, 11H), 7.08 (d, J = 8.2 Hz, 1H), 7.01-6.94 (m, 3H), 6.91-6.87 (m, 1H), 6.49 (d, J = 9.9 Hz, 1H), 5.03 (dd, J = 5.0, 7.5 Hz, 1H), 4.73 (s, 2H), 4.05 (d, J = 6.4 Hz, 3H), 3.91-3.84 (m, 2H), 3.43 (s, 2H), 3.10-3.00 (m, 2H), 2.91-2.68 (m, 7H), 2.57-2.46 (m, 1H), 2.00-1.89 (m, 3H), 1.83-1.49 (m, 6H), 1.24-1.13 (m, 2H). | mono-formate |

Example 21, (1-Benzylpiperidin-4-yl)methyl (S)-2-hydroxy-2-(3-((4-(((1R,3S)-3-(4-(2-(((R)-2-hydroxy-2-(8-hydroxy-2-oxo-1,2-dihydroquinolin-5-yl)ethyl)amino)-ethyl)benzamido)cyclobutyl)carbamoyl)benzyl)oxy)phenyl)-2-phenylacetate (Compound 114)

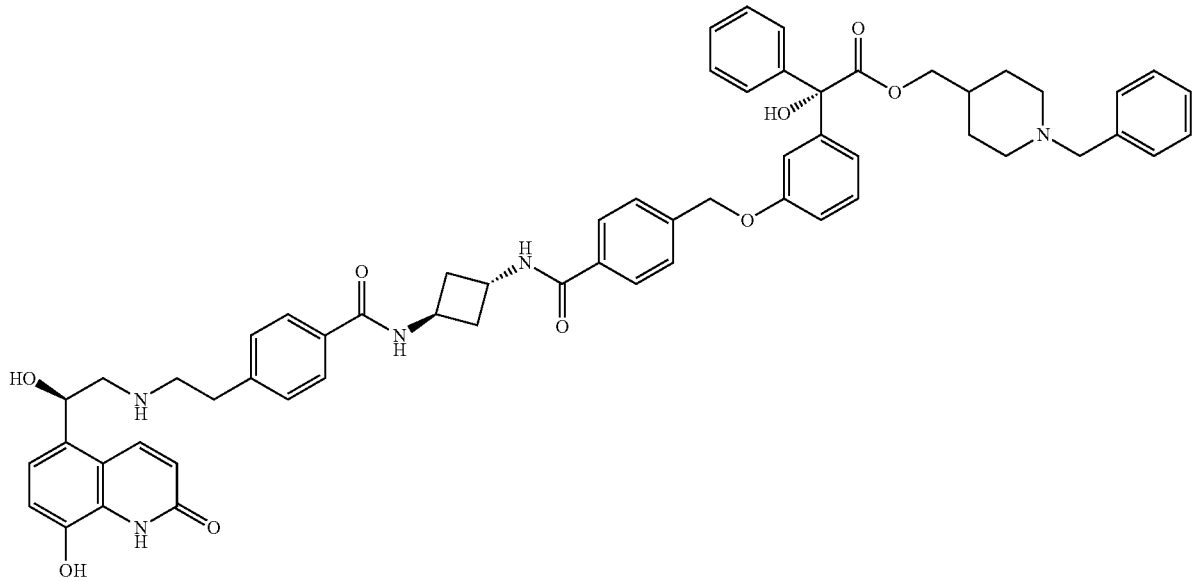 [SMILES: O=C(N[C@H]1C[C@H](NC(=O)c2ccc(COc3cccc([C@](O)(C(=O)OCC4CCN(Cc5ccccc5)CC4)c4ccccc4)c3)cc2)C1)c1ccc(CCNC[C@H](O)c2ccc(O)c3[nH]c(=O)ccc23)cc1]

Step 1; (1-Benzylpiperidin-4-yl)methyl (S)-2-(3-((4-(((1r,3S)-3-((tert-butoxycarbonyl)amino)cyclobutyl)carbamoyl)benzyl)oxy)phenyl)-2-hydroxy-2-phenylacetate

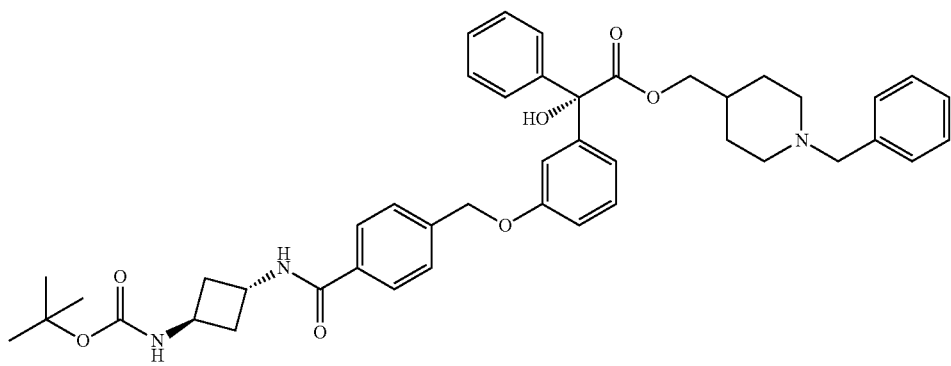 [SMILES: CC(C)(C)OC(=O)N[C@H]1C[C@H](NC(=O)c2ccc(COc3cccc([C@](O)(C(=O)OCC4CCN(Cc5ccccc5)CC4)c4ccccc4)c3)cc2)C1]

To a stirred solution of (S)-4-((3-(2-((1-benzylpiperidin-4-yl)methoxy)-1-hydroxy-2-oxo-1-phenylethyl)phenoxy)methyl)benzoic acid hydrochloride (0.20 g, 0.33 mmol) in DMF (1.9 mL) was added DIPEA (0.132 mL, 0.76 mmol) and HATU (0.173 g, 0.46 mmol) and the mixture stirred at room temperature for 30 minutes. To this mixture was added a solution of tert-butyl trans-(3-aminocyclobutyl)carbamate hydrochloride (0.068 g, 0.38 mmol) and DIPEA (0.13 mL, 0.76 mmol) in DMF (1.9 mL). The reaction mixture diluted with ethyl acetate and washed with 2M aqueous sodium hydroxide and brine. The organic phase was dried over magnesium sulfate, filtered and the filtrate evaporated at reduced pressure to afford the title compound (0.247 g, >100%).

$^1$H NMR (400 MHz, DMSO-$d_6$); δ 8.67 (d, J=6.9 Hz, 1H), 7.86 (d, J=8.3 Hz, 2H), 7.47 (d, J=8.3 Hz, 2H), 7.33-7.24 (m, 12H), 6.96 (d, J=5.9 Hz, 2H), 6.92 (dd, J=8.1, 8.1 Hz, 1H), 6.60 (s, 1H), 5.12 (s, 2H), 4.41-4.39 (m, 1H), 4.15-4.06 (m, 1H), 4.01-3.97 (m, 2H), 3.39 (s, 2H), 2.34-2.22 (m, 5H), 1.82 (dd, J=11.0, 11.0 Hz, 2H), 1.46 (d, J=12.9 Hz, 3H), 1.39 (s, 9H), 1.37 (s, 1H), 1.17-1.05 (m, 2H).

Step 2; (1-Benzylpiperidin-4-yl)methyl (S)-2-hydroxy-2-(3-((4-(((1R,3S)-3-(4-(2-(((R)-2-hydroxy-2-(8-hydroxy-2-oxo-1,2-dihydroquinolin-5-yl)ethyl)amino)ethyl)benzamido)-cyclobutyl)carbamoyl)benzyl)oxy)phenyl)-2-phenylacetate (Compound 114)

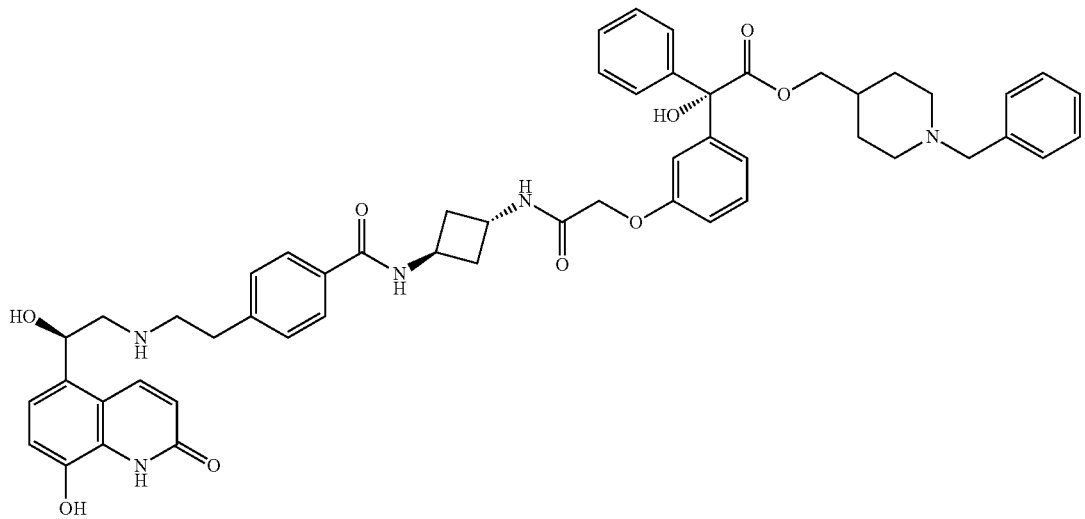 [SMILES: O=C(COc1cccc([C@](O)(C(=O)OCC2CCN(Cc3ccccc3)CC2)c2ccccc2)c1)N[C@H]1C[C@H](NC(=O)c2ccc(CCNC[C@H](O)c3ccc(O)c4[nH]c(=O)ccc34)cc2)C1]

To a stirred solution of (1-benzylpiperidin-4-yl)methyl (S)-2-(3-((4-(((1r,3S)-3-((tert-butoxycarbonyl)amino)cyclobutyl)carbamoyl)benzyl)oxy)phenyl)-2-hydroxy-2-phenylacetate (0.247 g, 0.34 mmol) was added a solution of HCl in dioxan (4M, 15 mL) and the mixture stirred at room temperature for 1 hour. The solvent evaporated under reduced pressure. The residue was dissolved in DMF (3 ml) and added to a pre-stirred (15 minutes) mixture of (R)-4-(2-((tert-butoxycarbonyl)(2-((tert-butyldimethylsilyl)oxy)-2-(8-hydroxy-2-oxo-1,2-dihydroquinolin-5-yl)ethyl)amino)ethyl)benzoic acid (0.196 g, 0.35 mmol), DIPEA (0.214 mL, 1.23 mmol) and HATU (0.16 g, 0.42 mmol) in DMF (2 mL). The reaction mixture was stirred at room temperature for 18 hours. The reaction mixture dissolved in ethyl acetate and washed with saturated aqueous sodium carbonate and brine. The organic phase was dried with magnesium sulfate, filtered and the filtrate evaporated at reduced pressure. The residue was dissolved in dioxan (1 mL) and a solution of HCl-dioxan (2 mL) added. The reaction mixture was stirred at room temperature for 1 hour. The solvent was evaporated at reduced pressure and the residue purified by reverse preparative HPLC.

$^1$H NMR (400 MHz, DMSO-$d_6$); δ 8.81 (d, J=7.1 Hz, 1H), 8.74 (d, J=7.1 Hz, 1H), 8.28 (s, 1H), 8.22 (d, J=9.5 Hz, 1H), 7.94 (d, J=8.3 Hz, 2H), 7.87 (d, J=8.3 Hz, 2H), 7.54 (d, J=8.3 Hz, 2H), 7.37-7.28 (m, 13H), 7.13 (d, J=8.1 Hz, 1H), 7.02-6.95 (m, 4H), 6.57 (d, J=9.9 Hz, 1H), 5.18 (s, 2H), 5.14 (dd, J=5.2, 7.5 Hz, 1H), 4.66-4.57 (m, 2H), 4.04 (d, J=6.3 Hz, 2H), 3.44 (s, 2H), 2.97-2.83 (m, 6H), 2.77 (d, J=11.1 Hz, 2H), 2.49 (t, J=7.1 Hz, 4H), 1.88 (dd, J=9.9, 11.6 Hz, 2H), 1.57-1.47 (m, 3H), 1.21-1.12 (m, 2H).

The following compounds were prepared in a similar fashion using the appropriate amine:

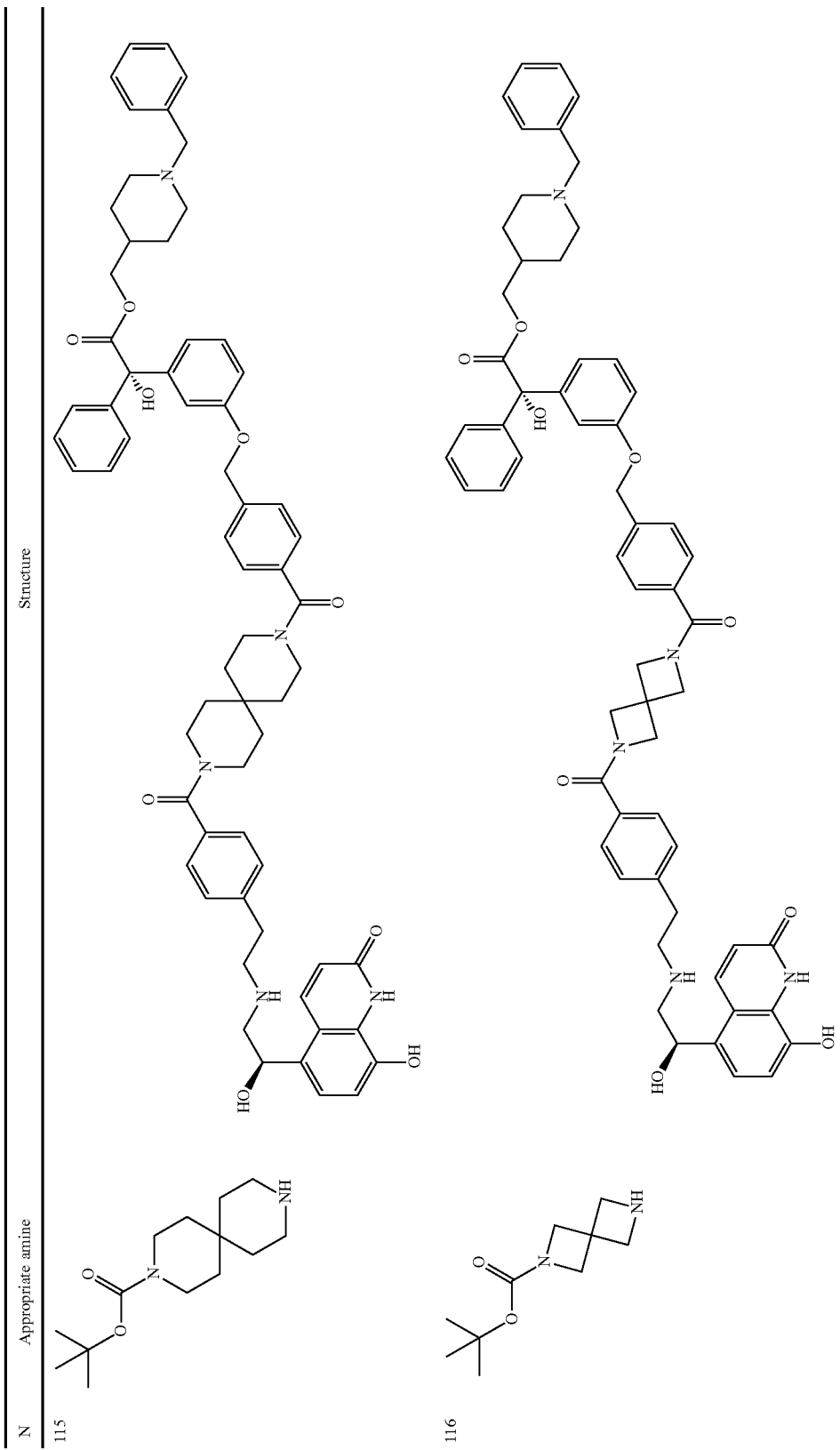

| N | Appropriate amine | Structure |
|---|---|---|
| 117 | 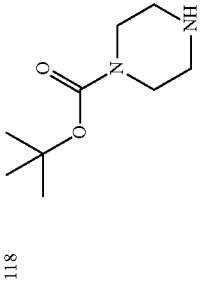 | 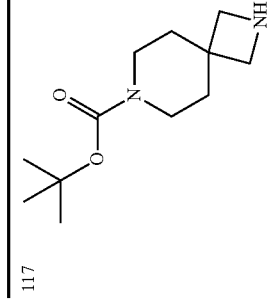 |
| 118 | 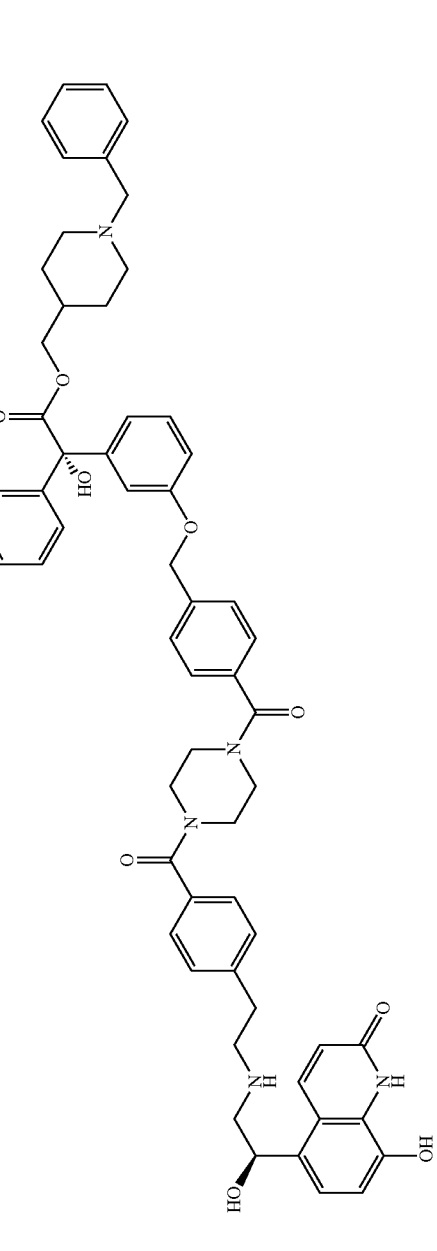 | 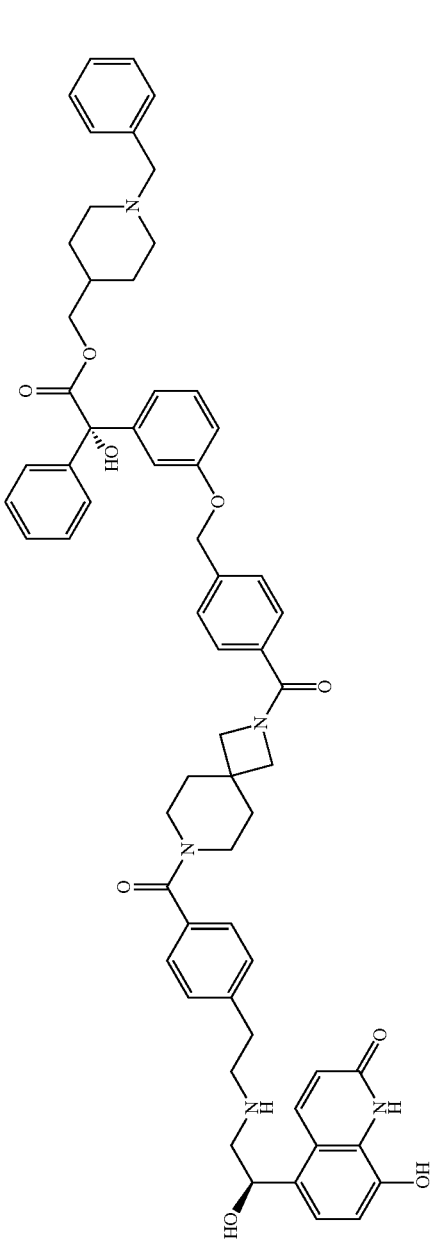 |

| N | Appropriate amine | Structure |
|---|---|---|
| 119 |  | 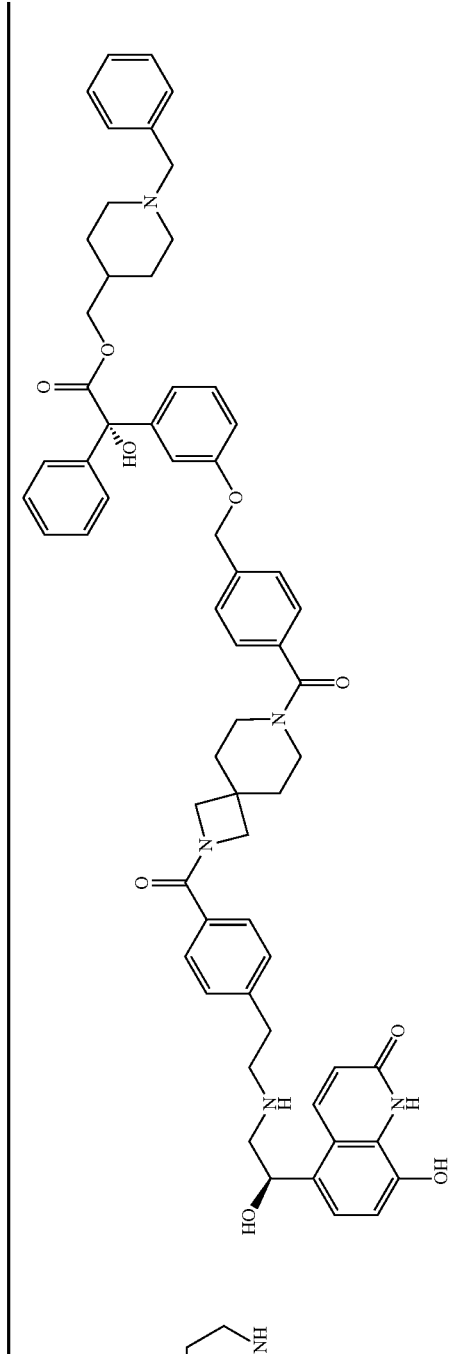 |
| 120 |  | 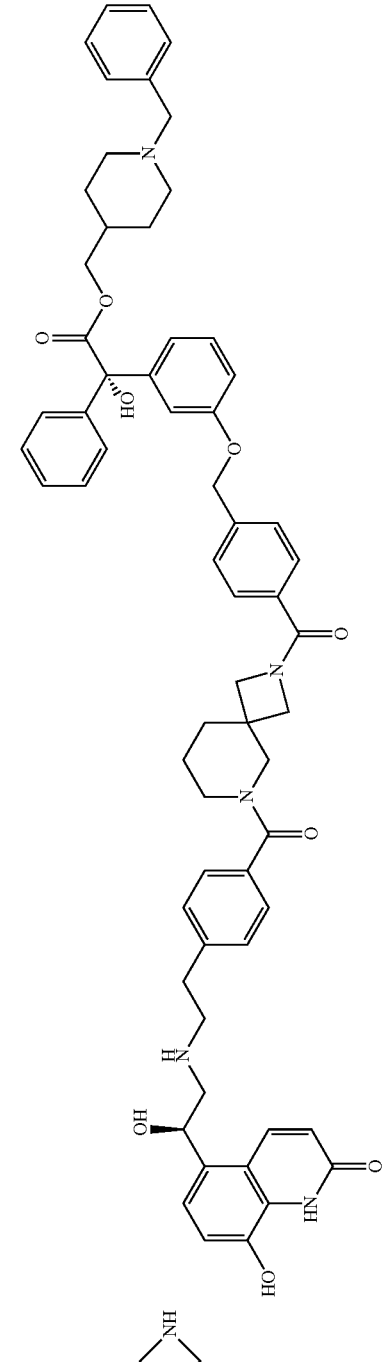 |

| N | Appropriate amine | Structure |
|---|---|---|
| 121 | (structure) | (structure) |
| 122 | (structure) | (structure) |

| N | Rt (min) | Method | NMR data (400 MHz) | Salt (2 eq unless stated) |
|---|---|---|---|---|
| 114 | 2.57 | 11 | (DMSO-d$_6$); δ 8.81 (d, J = 7.1 Hz, 1H), 8.74 (d, J = 7.1 Hz, 1H), 8.28 (s, 1H), 8.22 (d, J = 9.5 Hz, 1H), 7.94 (d, J = 8.3 Hz, 2H), 7.87 (d, J = 8.3 Hz, 2H), 7.54 (d, J = 8.3 Hz, 2H), 7.37-7.28 (m, 13H), 7.13 (d, J = 8.1 Hz, 1H), 7.02-6.95 (m, 4H), 6.57 (d, J = 9.9 Hz, 1H), 5.18 (s, 2H), 5.14 (dd, J = 5.2, 7.5 Hz, 1H), 4.66-4.57 (m, 2H), 4.04 (d, J = 6.3 Hz, 2H), 3.44 (s, 2H), 2.97-2.83 (m, 6H), 2.77 (d, J = 11.1 Hz, 2H), 2.49 (t, J = 7.1 Hz, 4H), 1.88 (dd, J = 9.9, 11.6 Hz, 2H), 1.57-1.47 (m, 3H), 1.21-1.12 (m, 2H). | TFA |
| 115 | 2.58 | 11 | (DMSO-d$_6$); δ 8.23 (s, 1H), 8.18 (d, J = 9.9 Hz, 1H), 7.46 (d, J = 8.2 Hz, 2H), 7.37 (d, J = 8.2 Hz, 2H), 7.33-7.25 (m, 15H), 7.08 (d, J = 8.3 Hz, 1H), 6.98-6.91 (m, 4H), 6.52 (d, J = 9.8 Hz, 1H), 5.12 (d, J = 5.9 Hz, 1H), 5.09 (s, 2H), 4.00 (d, J = 6.3 Hz, 2H), 3.60 (s, 2H), 3.39 (s, 2H), 3.29 (s, 6H), 2.97-2.87 (m, 2H), 2.83-2.77 (m, 4H), 2.72 (d, J = 11.3 Hz, 2H), 1.87-1.79 (m, 2H), 1.53-1.45 (m, 10H), 1.17-1.08 (m, 2H). | Formate |
| 116 | 2.57 | 11 | (DMSO-d$_6$, 90° C.); δ 8.18 (d, J = 9.9 Hz, 1H), 7.65-7.59 (m, 3H), 7.48 (d, J = 7.2 Hz, 5H), 7.39-7.24 (m, 8H), 7.16 (d, J = 8.3 Hz, 1H), 7.04-6.95 (m, 3H), 6.58 (d, J = 9.9 Hz, 1H), 5.36 (dd, J = 4.5, 8.5 Hz, 1H), 5.12 (s, 2H), 4.35-4.33 (m, 8H), 4.22 (s, 2H), 4.06 (s, 2H), 3.34-3.29 (m, 4H), 3.21-3.17 (m, 4H), 3.10-3.04 (m, 5H), 1.97-1.71 (m, 4H), 1.42-1.42 (m, 2H). | TFA |
| 117 | 2.57 | 11 | (DMSO-d$_6$); δ 8.23 (s, 1H), 8.18 (d, J = 9.9 Hz, 1H), 7.65 (d, J = 8.3 Hz, 2H), 7.48 (d, J = 8.3 Hz, 2H), 7.32-7.24 (m, 15H), 7.08 (d, J = 8.3 Hz, 1H), 6.98-6.90 (m, 4H), 6.61 (s, 1H), 6.52 (d, J = 9.9 Hz, 1H), 5.12-5.08 (m, 3H), 4.06 (s, 2H), 3.99 (d, J = 6.3 Hz, 2H), 3.81 (s, 2H), 3.48 (m, 1H), 3.39 (s, 2H), 3.28 (m, 3H), 2.94-2.85 (m, 2H), 2.83-2.77 (m, 4H), 2.72 (d, J = 11.4 Hz, 2H), 1.87-1.72 (m, 6H), 1.53-1.45 (m, 3H), 1.16-1.07 (m, 2H). | mono-Formate |
| 118 | 2.55 | 11 | (DMSO-d$_6$); δ 10.55 (s, 1H), 10.45 (s, 1H), 9.40 (s, 1H), 8.75 (s, 2H), 8.16 (d, J = 9.9 Hz, 1H), 7.52-7.41 (m, 11H), 7.36-7.25 (m, 8H), 7.17 (d, J = 8.3 Hz, 1H), 7.01-6.95 (m, 3H), 6.92 (d, J = 7.9 Hz, 1H), 6.65 (s, 1H), 6.60 (d, J = 9.9 Hz, 1H), 6.15 (s, 1H), 5.34 (d, J = 8.0 Hz, 1H), 5.10 (s, 2H), 4.25 (dt, J = 6.3, 18.9 Hz, 2H), 4.00 (d, J = 6.5 Hz, 2H), 3.63-3.26 (m, 10H), 3.18-2.99 (m, 5H), 2.94-2.85 (m, 2H), 1.84-1.83 (m, 1H), 1.75-1.66 (m, 3H), 1.35 (q, J = 11.9 Hz, 2H). | TFA |
| 119 | 2.55 | 11 | (DMSO-d$_6$) δ 10.55 (s, 1H), 10.45 (s, 1H), 9.40 (s, 1H), 8.75 (s, 2H), 8.16 (d, J = 9.9 Hz, 1H), 7.63 (d, J = 8.3 Hz, 2H), 7.48 (m, 7H), 7.40-7.24 (m, 10H), 7.16 (d, J = 8.3 Hz, 1H), 7.01-6.96 (m, 3H), 6.92 (d, J = 8.2 Hz, 1H), 6.65 (s, 1H), 6.60 (dd, J = 2.0, 9.8 Hz, 1H), 6.15 (s, 1H), 5.33 (d, J = 8.4 Hz, 1H), 5.09 (s, 2H), 4.26 (dt, J = 5.5, 18.7 Hz, 2H), 4.04-3.97 (m, 4H), 3.81 (s, 2H), 3.56-3.56 (m, 2H), 3.34-3.24 (m, 5H), 3.18-2.97 (m, 5H), 2.89 (m, 2H), 1.75-1.66 (m, 7H), 1.36 (dd, J = 12.3, 12.3 Hz, 2H). | TFA |
| 120 | 2.57 | 11 | (DMSO-d$_6$); δ 10.49 (m, 2H), 9.50 (s, 1H), 8.70 (m, 2H), 8.18 (d, J = 9.7 Hz, 1H), 7.64-7.64 (m, 2H), 7.52-7.46 (m, 7H), 7.36-7.31 (m, 10H), 7.16 (d, J = 8.3 Hz, 1H), 7.01-6.96 (m, 3H), 6.92 (d, J = 7.5 Hz, 1H), 6.60 (s, 1H), 6.59 (d, J = 9.8 Hz, 1H), 6.20 (s, 1H), 5.35 (d, J = 9.4 Hz, 1H), 5.11 (s, 2H), 4.30-4.19 (m, 2H), 4.02-3.96 (m, 2H), 3.84-3.51 (m, 6H), 3.34-3.00 (m, 10H), 2.90-2.85 (m, 2H), 1.83-1.82 (m, 3H), 1.74 (m, 2H), 1.48-1.32 (m, 4H). | TFA |
| 121 | 2.56 | 11 | (DMSO-d$_6$); δ 10.51-10.46 (m, 2H), 9.40 (s, 1 H), 8.76-8.76 (m, 2H), 8.17 (d, J = 9.9 Hz, 1H), 7.51-7.47 (m, 7H), 7.35-7.31 (m, 12H), 7.17 (d, J = 8.3 Hz, 1H), 7.01-6.95 (m, 3H), 6.92 (d, J = 8.0 Hz, 1H), 6.65 (s, 1H), 6.60 (d, J = 9.8 Hz, 1H), 6.21-6.20 (m, 1H), 5.34 (d, J = 8.0 Hz, 1H), 5.10 (s, 2H), 4.32-4.19 (m, 2H), 4.10-4.10 (m, 1H), 4.03-3.96 (m, 2H), 3.63-3.62 (m, 5H), 3.34 (d, J = 12.0 Hz, 4H), 3.18-2.99 (m, 6H), 2.90-2.89 (m, 4H), 1.75-1.66 (m, 7H), 1.39-1.33 (m, 2H). | TFA |
| 122 | 2.63 | 11 | (DMSO-d$_6$) δ 10.52-10.46 (m, 2H), 9.40 (s, 1H), 8.75 (s, 2H), 8.16 (d, J = 9.9 Hz, 1H), 7.50-7.46 (m, 7H), 7.38-7.24 (m, 12H), 7.16 (d, J = 8.3 Hz, 1H), 7.01-6.94 (m, 3H), 6.91 (d, J = 7.7 Hz, 1H), 6.65 (s, 1 H), 6.60 (dd, J = 1.8, 9.9 Hz, 1H), 6.20 (m, 1H), 5.33 (d, J = 8.5 Hz, 1H), 5.09 (s, 2H), 4.25 (dt, J = 5.7, 18.7 Hz, 2H), 4.02-3.96 (m, 2H), 3.36-3.26 (m, 9H), 3.18 (s, 2H), 3.10-3.08 (m, 2H), 3.01 (d, J = 7.9 Hz, 3H), 2.94-2.85 (m, 2H), 1.83 (s, 1H), 1.75-1.65 (m, 2H), 1.50 (m, 6H), 1.34 (m, 4H). | TFA |

The following compounds were prepared as described in Example 20 with the appropriate acid replacing (R)-4-(((tert-butoxycarbonyl)(2-((tert-butyldimethylsilyl)oxy)-2-(8-hydroxy-2-oxo-1,2-dihydroquinolin-5-yl)ethyl)amino)methyl)benzoic acid and the use of the appropriate amine replacing tert-butyl trans-(3-aminocyclobutyl)carbamate hydrochloride in Step 1.

| N | Appropriate amine | Appropriate acid |
|---|---|---|
| 123 | 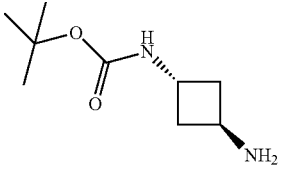 | 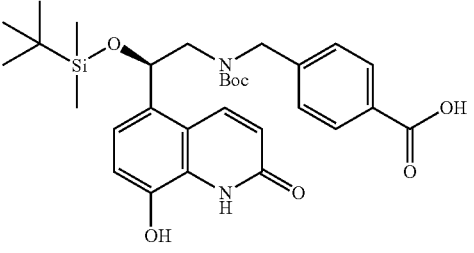 [SMILES: CC(C)(C)OC(=O)N(Cc1ccc(C(=O)O)cc1)C[C@H](O[Si](C)(C)C(C)(C)C)c1ccc(O)c2[nH]c(=O)ccc12] |
| 124 | 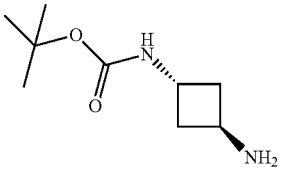 | 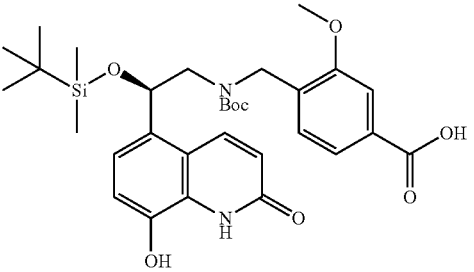 [SMILES: COc1cc(C(=O)O)ccc1CN(C[C@H](O[Si](C)(C)C(C)(C)C)c1ccc(O)c2[nH]c(=O)ccc12)C(=O)OC(C)(C)C] |
| 125 | 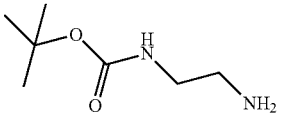 | 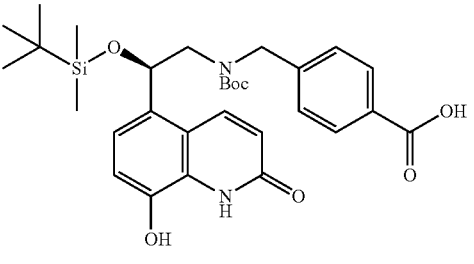 [SMILES: CC(C)(C)OC(=O)N(Cc1ccc(C(=O)O)cc1)C[C@H](O[Si](C)(C)C(C)(C)C)c1ccc(O)c2[nH]c(=O)ccc12] |
| 126 | 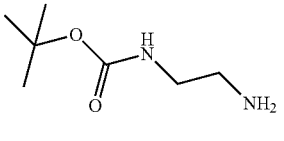 | 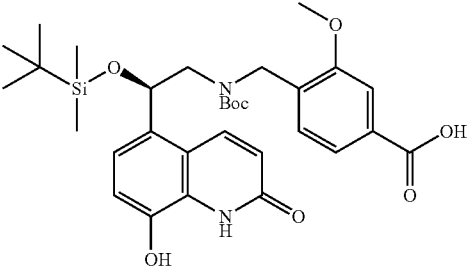 [SMILES: COc1cc(C(=O)O)ccc1CN(C[C@H](O[Si](C)(C)C(C)(C)C)c1ccc(O)c2[nH]c(=O)ccc12)C(=O)OC(C)(C)C] |

| N | Appropriate amine | Appropriate acid |
|---|---|---|
123
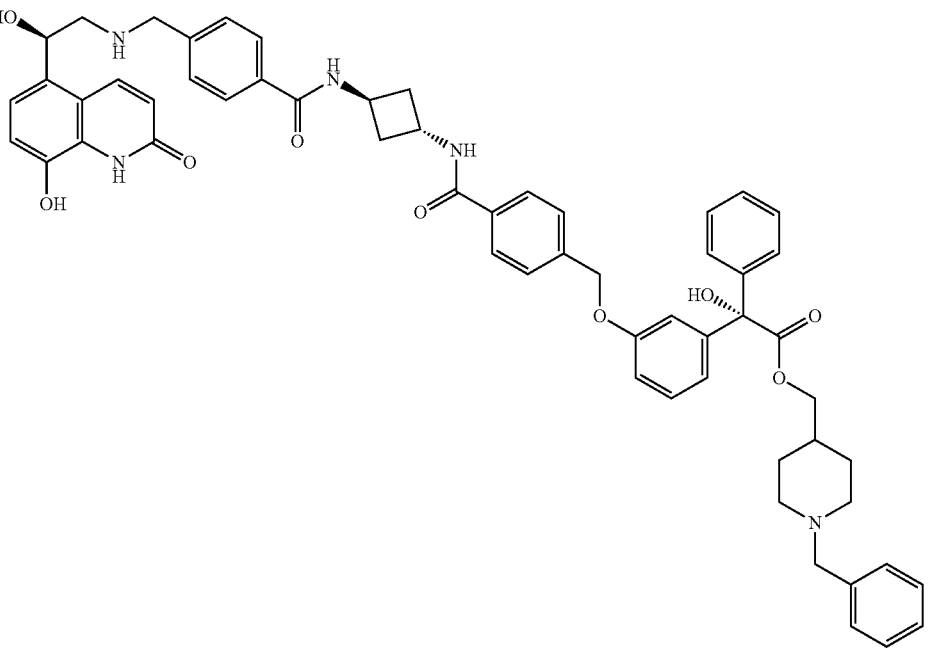
124
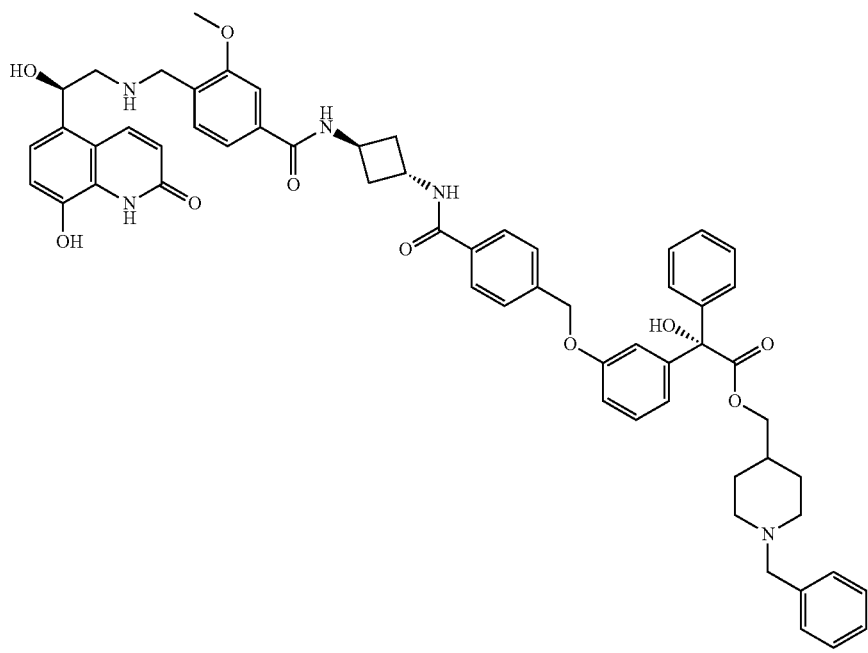 [SMILES: COc1cc(C(=O)N[C@H]2C[C@H](NC(=O)c3ccc(COc4cccc([C@](O)(C(=O)OCC5CCN(Cc6ccccc6)CC5)c5ccccc5)c4)cc3)C2)ccc1CNC[C@H](O)c1ccc(O)c2[nH]c(=O)ccc12]

| N | Appropriate amine | Appropriate acid |
|---|---|---|
| 125 | (structure) | |
| 126 | (structure) | |

| N | Rt (min) | Method | NMR data (400 MHz) | Salt (2 eq unless stated) |
|---|---|---|---|---|
| 123 | 2.55 | 11 | (MeOD); δ 8.49 (s, 2H), 8.33 (d, J = 9.9 Hz, 1H), 7.95 (d, J = 8.4 Hz, 2H), 7.87 (d, J = 8.3 Hz, 2H), 7.63 (d, J = 8.3 Hz, 2H), 7.51 (d, J = 8.4 Hz, 2H), 7.45 (s, 5H), 7.41-7.26 (m, 7H), 7.06-6.97 (m, 4H), 6.68 (d, J = 9.9 Hz, 1H), 5.42 (dd, J = 5.5, 7.7 Hz, 1H), 5.15 (s, 2H), 4.70-4.61 (m, 2H), 4.31 (s, 2H), 4.11-4.06 (m, 4H), 3.29-3.18 (m, 4H), 2.75-2.65 (m, 2H), 2.60 (t, J = 6.9 Hz, 4H), 1.90-1.80 (m, 1H), 1.71 (d, J = 13.1 Hz, 2H), 1.45-1.33 (m, 2H). | formate |
| 124 | 2.55 | 11 | (MeOD); δ 8.50 (s, 2H), 8.29 (d, J = 9.9 Hz, 1H), 7.87 (d, J = 8.3 Hz, 2H), 7.59-7.50 (m, 5H), 7.44 (s, 5H), 7.41-7.26 (m, 7H), 7.07-6.98 (m, 4H), 6.67 (d, J = 9.8 Hz, 1H), 5.43 (dd, J = 5.6, 7.7 Hz, 1H), 5.15 (s, 2H), 4.69-4.62 (m, 2H), 4.36 (s, 2H), | formate |

| N | Rt (min) | Method | NMR data (400 MHz) | Salt (2 eq unless stated) |
|---|---|---|---|---|
| 125 | 2.35 | 11 | 4.10 (d, J = 6.2 Hz, 2H), 4.05 (s, 2H), 4.02 (s, 3H), 3.28-3.19 (m, 4H), 2.69-2.58 (m, 6H), 1.89-1.81 (m, 1H), 1.70 (d, J = 13.1 Hz, 2H), 1.38 (q, J = 12.4 Hz, 2H). (MeOD); δ 8.53 (s, 1H), 8.29 (d, J = 10.0 Hz, 1H), 7.88 (d, J = 8.3 Hz, 2H), 7.82 (d, J = 8.4 Hz, 2H), 7.55 (d, J = 8.3 Hz, 2H), 7.47 (d, J = 8.3 Hz, 2H), 7.42-7.24 (m, 12H), 7.04-6.96 (m, 4H), 6.64 (d, J = 9.8 Hz, 1H), 5.36 (dd, J = 4.6, 8.7 Hz, 1H), 5.12 (s, 2H), 4.19 (s, 2H), 4.06 (d, J = 6.5 Hz, 2H), 3.90 (s, 2H), 3.66 (s, 4H), 3.17-3.09 (m, 4H), 2.49 (dd, J = 10.3, 12.2 Hz, 2H), 1.83-1.71 (m, 1H), 1.68-1.61 (m, 2H), 1.39-1.27 (m, 2H). | mono-formate |
| 126 | 2.54 | 11 | (MeOD); δ 8.53 (s, 2H), 8.24 (d, J = 9.9 Hz, 1H), 7.83 (d, J = 8.3 Hz, 2H), 7.50-7.44 (m, 5H), 7.41-7.23 (m, 12H), 7.04-6.95 (m, 4H), 6.63 (d, J = 9.8 Hz, 1H), 5.37 (dd, J = 6.6, 6.6 Hz, 1H), 5.12 (s, 2H), 4.23 (s, 2H), 4.06 (d, J = 6.5 Hz, 2H), 3.92 (s, 3H), 3.86 (s, 2H), 3.67 (s, 4H), 3.15-3.07 (m, 4H), 2.44 (dd, J = 10.2, 12.5 Hz, 2H), 1.81-1.72 (m, 1H), 1.62 (d, J = 12.0 Hz, 2H), 1.37-1.27 (m, 2H). | formate |
Example 22
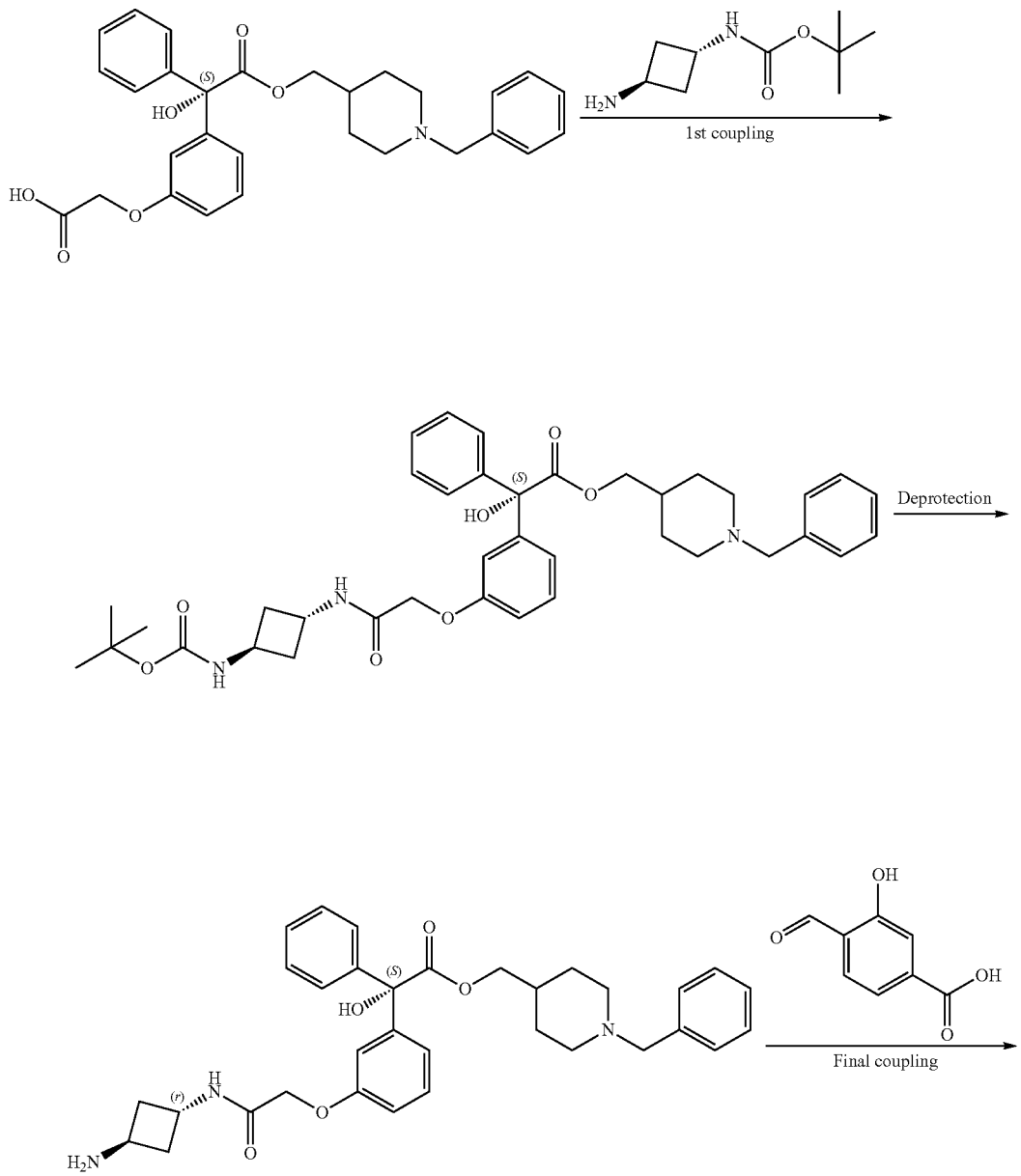

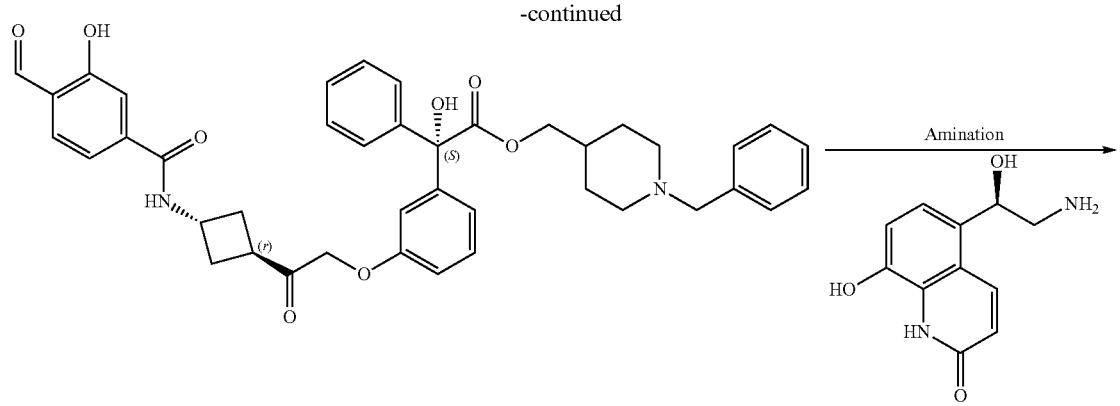
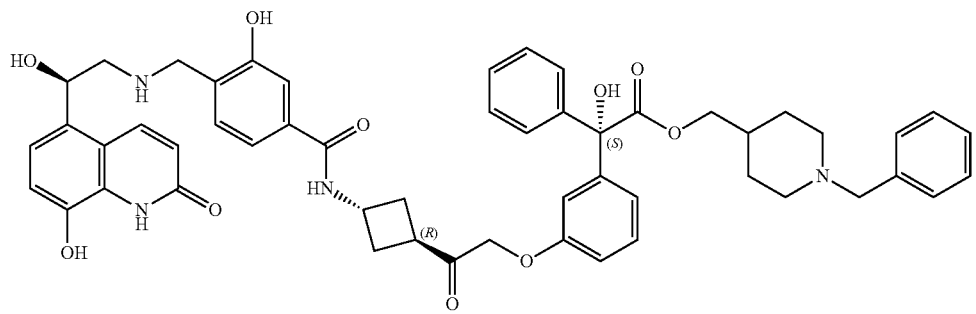
(1-Benzylpiperidin-4-yl)methyl (S)-2-hydroxy-2-(3-(2-(((1R,3S)-3-(3-hydroxy-4-((((R)-2-hydroxy-2-(8-hydroxy-2-oxo-1,2-dihydroquinolin-5-yl)ethyl)amino)methyl)-benzamido)cyclobutyl)amino)-2-oxoethoxy)phenyl)-2-phenylacetate (Compound 127)
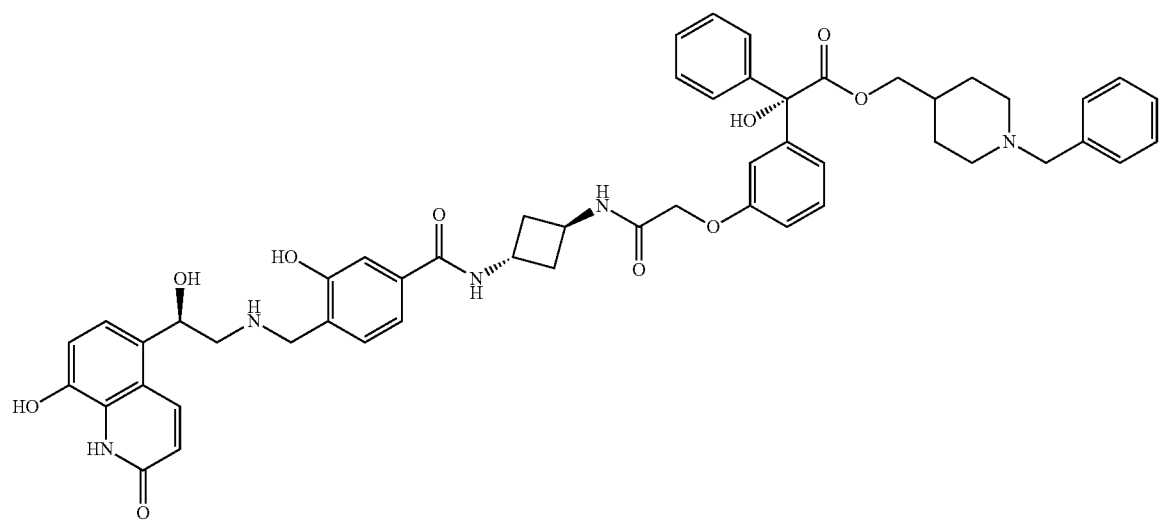 [SMILES: O=C(COc1cccc([C@](O)(C(=O)OCC2CCN(Cc3ccccc3)CC2)c2ccccc2)c1)N[C@H]1C[C@H](NC(=O)c2ccc(CNC[C@H](O)c3ccc(O)c4[nH]c(=O)ccc34)c(O)c2)C1]

Step 1; (1-Benzylpiperidin-4-yl)methyl (S)-2-(3-(2-(((1r,3S)-3-aminocyclobutyl)amino)-2-oxoethoxy)phenyl)-2-hydroxy-2-phenylacetate dihydrochloride

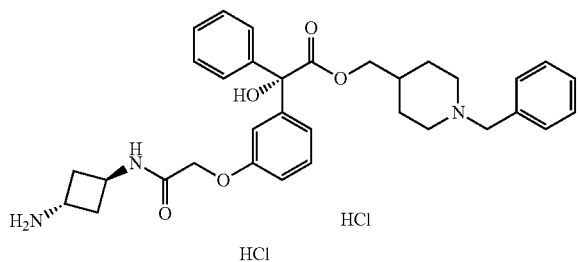 [SMILES: N[C@H]1C[C@H](NC(=O)COc2cccc([C@](O)(C(=O)OCC3CCN(Cc4ccccc4)CC3)c3ccccc3)c2)C1 ; Cl ; Cl]

The title compound was prepared as described in Example 20 Step 1 and 2.

Step 2; (1-Benzylpiperidin-4-yl)methyl (S)-2-hydroxy-2-(3-(2-(((1R,3S)-3-(3-hydroxy-4-((((R)-2-hydroxy-2-(8-hydroxy-2-oxo-1,2-dihydroquinolin-5-yl)ethyl)amino)methyl)-benzamido)cyclobutyl)amino)-2-oxoethoxy)phenyl)-2-phenylacetate (Compound 127)

To a solution of 4-formyl-3-hydroxybenzaldehyde (0.103 g, 0.62 mmol) and DIPEA (0.24 mL, 1.4 mmol) in DMF (2 mL) was added HATU (0.255 g, 0.67 mmol) followed by a solution of (1-benzylpiperidin-4-yl)methyl (S)-2-(3-(2-(((1r,3S)-3-aminocyclobutyl)amino)-2-oxoethoxy)phenyl)-2-hydroxy-2-phenylacetate dihydrochloride (0.177 g, 0.28 mmol) in DMF (3 mL) and the reaction stirred at room temperature for 18 hours. The reaction mixture was dissolved in ethyl acetate and washed with saturated aqueous sodium hydrogenbicarbonate (×2) and brine. The organic phase was dried over anhydrous magnesium sulfate, filtered and the filtrate evaporated at reduced pressure. The residue was dissolved in methanol (4 mL) and triethylamine (0.056 mL, 0.4 mmol) and (R)-5-(2-amino-1-hydroxyethyl)-8-hydroxyquinolin-2(1H)-one hydrochloride (0.061 g, 0.19 mmol) added. The reaction mixture was stirred at room temperature for 1.5 hours then sodium triacetoxyborohydride (0.136 g, 0.64 mmol) and acetic acid (0.034 mL) added. The reaction mixture was stirred for a further 2 hours. The reaction mixture was diluted with iso-butanol and washed with water. The aqueous phase was extracted with further iso-butanol. The combined iso-butanol extracts were evaporated under reduced pressure. The residue was purified by reverse phase preparative HPLC to afford the title compound.

The following compounds were prepared by this method or using the method described in Example 20 (using the required protected acid in the final coupling step).

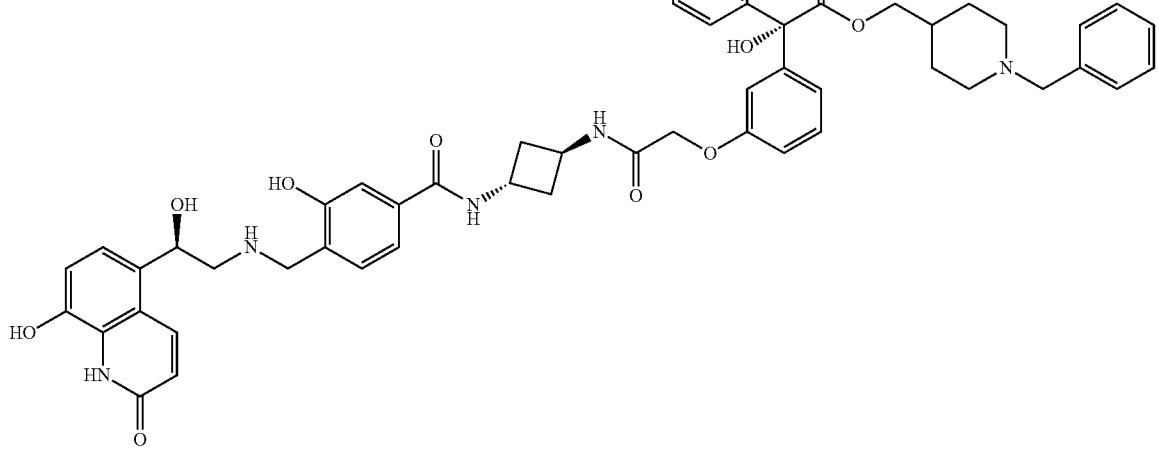

| N | Preparation method as in | Structure |
|---|---|---|
| 128 | Example 22 | 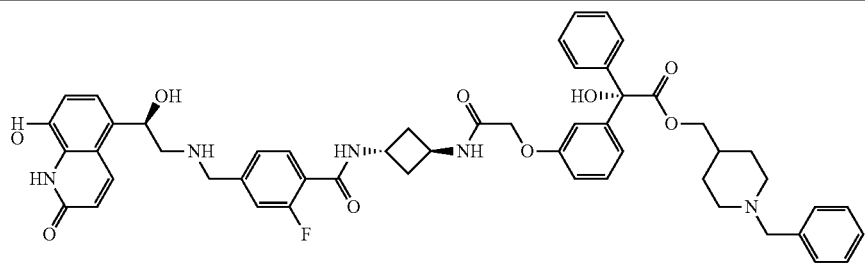 |
| 129 | Example 22 | 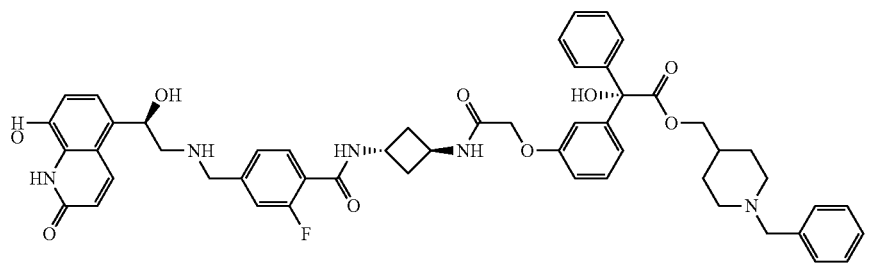 [SMILES: O=C(COc1cccc([C@](O)(C(=O)OCC2CCN(Cc3ccccc3)CC2)c2ccccc2)c1)N[C@H]1C[C@H](NC(=O)c2ccc(CNC[C@H](O)c3ccc(O)c4[nH]c(=O)ccc34)cc2F)C1] |
| 130 | Examaple 22 | 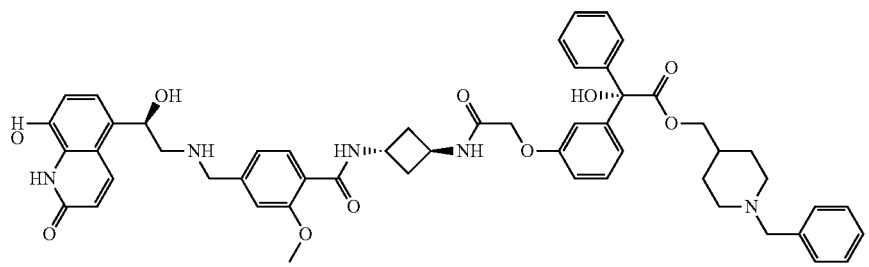 [SMILES: COc1cc(CNC[C@H](O)c2ccc(O)c3[nH]c(=O)ccc23)ccc1C(=O)N[C@H]1C[C@H](NC(=O)COc2cccc([C@](O)(C(=O)OCC3CCN(Cc4ccccc4)CC3)c3ccccc3)c2)C1] |
| 131 | Example 22 | 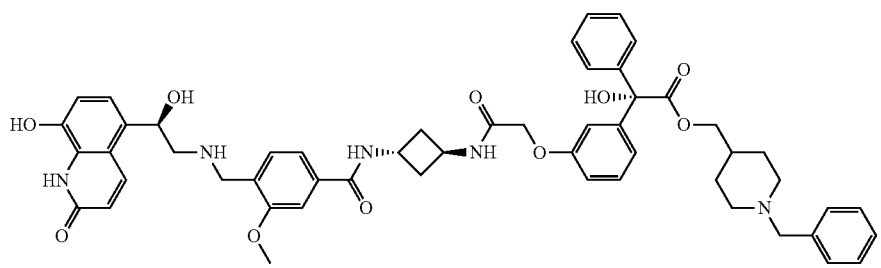 [SMILES: COc1cc(C(=O)N[C@H]2C[C@H](NC(=O)COc3cccc([C@](O)(C(=O)OCC4CCN(Cc5ccccc5)CC4)c4ccccc4)c3)C2)ccc1CNC[C@H](O)c1ccc(O)c2[nH]c(=O)ccc12] |
| 132 | Example 22 | 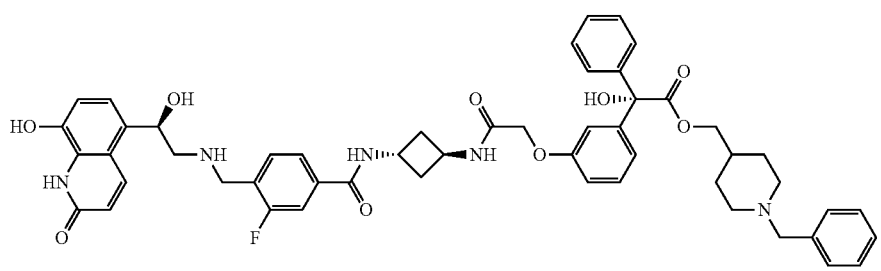 |
| 133 | Example 22 | 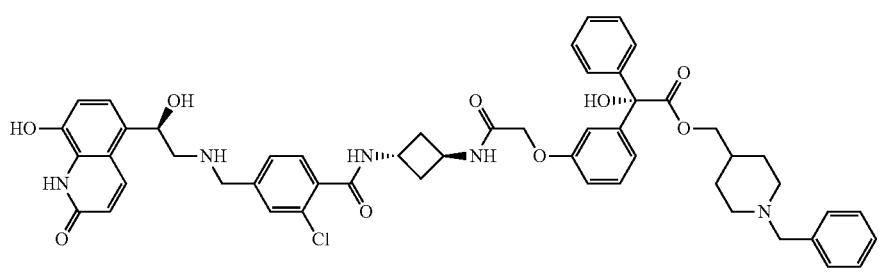 |

| N | Preparation method as in | Structure |
|---|---|---|
| 134 | Example 22 | 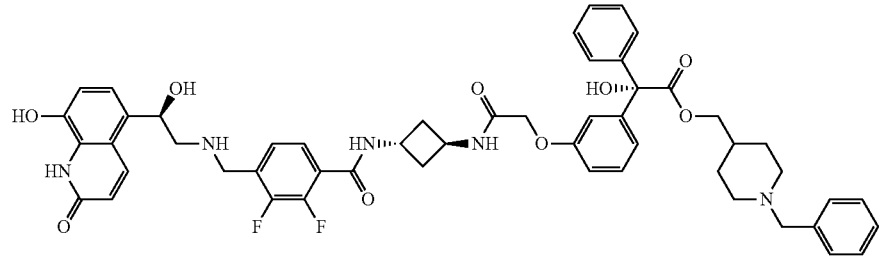 [SMILES: O=C(COc1cccc([C@](O)(C(=O)OCC2CCN(Cc3ccccc3)CC2)c2ccccc2)c1)N[C@H]1C[C@H](NC(=O)c2ccc(CNC[C@H](O)c3ccc(O)c4[nH]c(=O)ccc34)c(F)c2F)C1] |
| 135 | Example 22 | 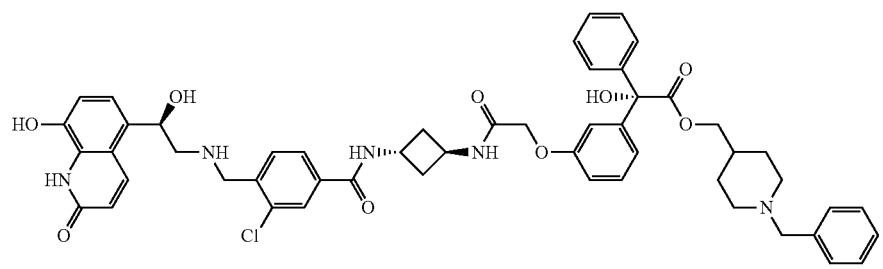 [SMILES: O=C(COc1cccc([C@](O)(C(=O)OCC2CCN(Cc3ccccc3)CC2)c2ccccc2)c1)N[C@H]1C[C@H](NC(=O)c2ccc(CNC[C@H](O)c3ccc(O)c4[nH]c(=O)ccc34)c(Cl)c2)C1] |
| 136 | Example 22 | 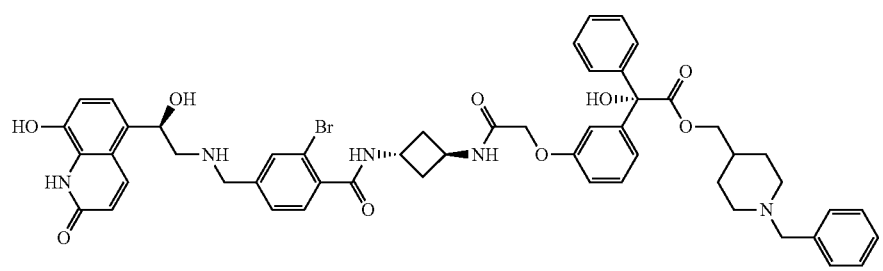 |
| 137 | Example 22 | 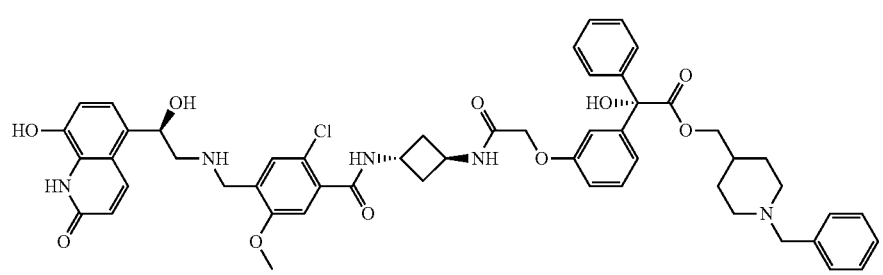 [SMILES: COc1cc(C(=O)N[C@H]2C[C@H](NC(=O)COc3cccc([C@](O)(C(=O)OCC4CCN(Cc5ccccc5)CC4)c4ccccc4)c3)C2)c(Cl)cc1CNC[C@H](O)c1ccc(O)c2[nH]c(=O)ccc12] |
| 138 | Example 20 | 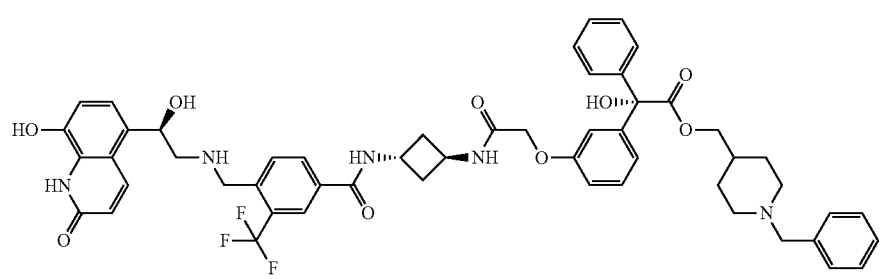 [SMILES: O=C(COc1cccc([C@](O)(C(=O)OCC2CCN(Cc3ccccc3)CC2)c2ccccc2)c1)N[C@H]1C[C@H](NC(=O)c2ccc(CNC[C@H](O)c3ccc(O)c4[nH]c(=O)ccc34)c(C(F)(F)F)c2)C1] |

| N | Preparation method as in | Structure |
|---|---|---|
| 139 | Example 20 | 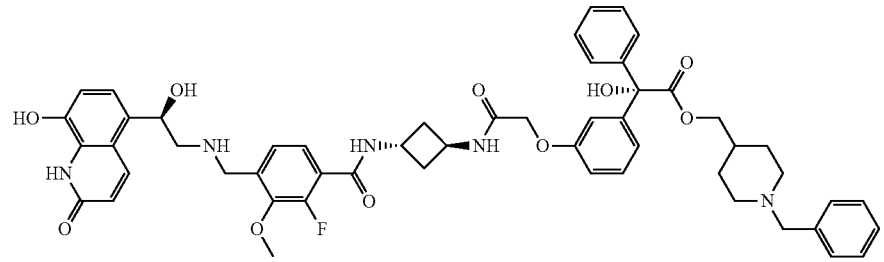 [SMILES: COc1c(CNC[C@H](O)c2ccc(O)c3[nH]c(=O)ccc23)ccc(C(=O)N[C@H]2C[C@H](NC(=O)COc3cccc([C@](O)(C(=O)OCC4CCN(Cc5ccccc5)CC4)c4ccccc4)c3)C2)c1F] |
| 140 | Example 20 | 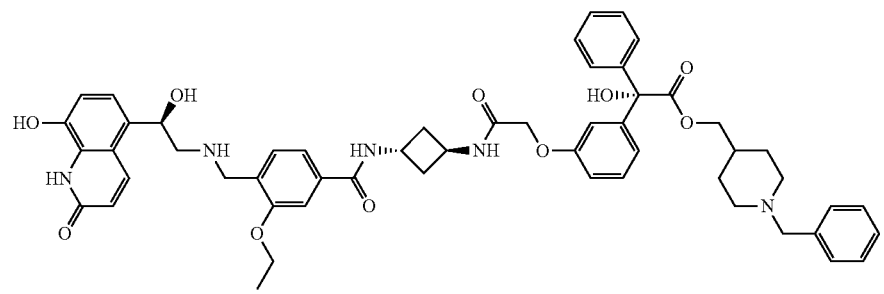 [SMILES: CCOc1cc(C(=O)N[C@H]2C[C@H](NC(=O)COc3cccc([C@](O)(C(=O)OCC4CCN(Cc5ccccc5)CC4)c4ccccc4)c3)C2)ccc1CNC[C@H](O)c1ccc(O)c2[nH]c(=O)ccc12] |
| 141 | Example 20 | 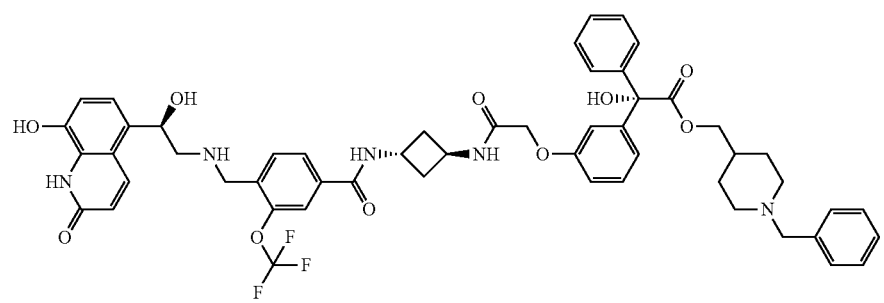 [SMILES: O=C(COc1cccc([C@](O)(C(=O)OCC2CCN(Cc3ccccc3)CC2)c2ccccc2)c1)N[C@H]1C[C@H](NC(=O)c2ccc(CNC[C@H](O)c3ccc(O)c4[nH]c(=O)ccc34)c(OC(F)(F)F)c2)C1] |
| 142 | Example 20 | 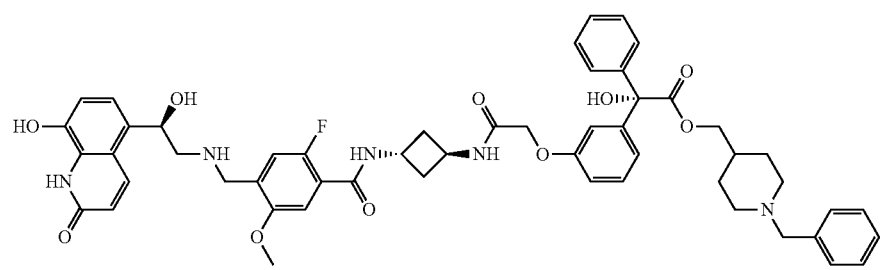 [SMILES: COc1cc(C(=O)N[C@H]2C[C@H](NC(=O)COc3cccc([C@](O)(C(=O)OCC4CCN(Cc5ccccc5)CC4)c4ccccc4)c3)C2)c(F)cc1CNC[C@H](O)c1ccc(O)c2[nH]c(=O)ccc12] |
| 143 | Example 20 | 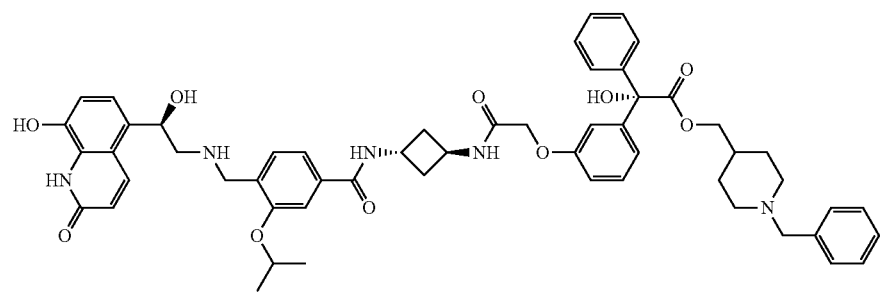 |

-continued

| N | Preparation method as in | Structure |
|---|---|---|
| 144 | Example 20 | 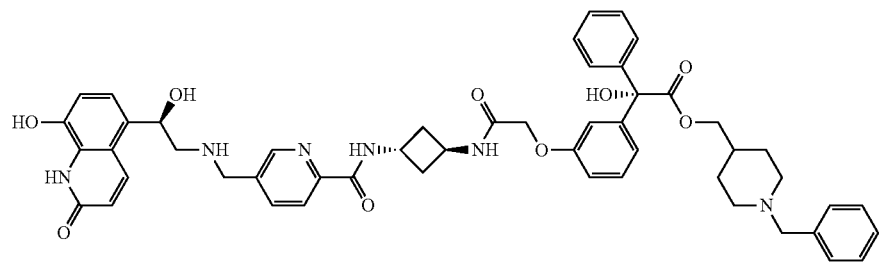 |
| 145 | Example 20 | 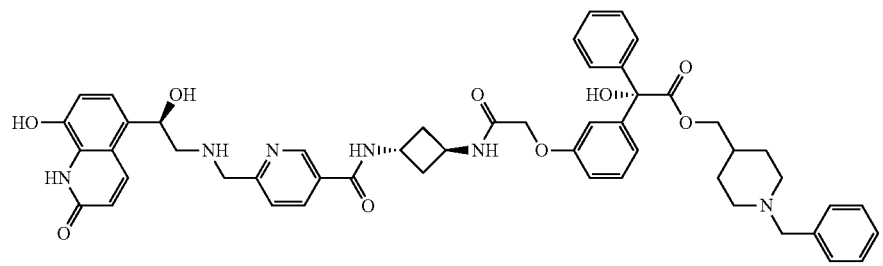 |
| 146 | Example 20 | 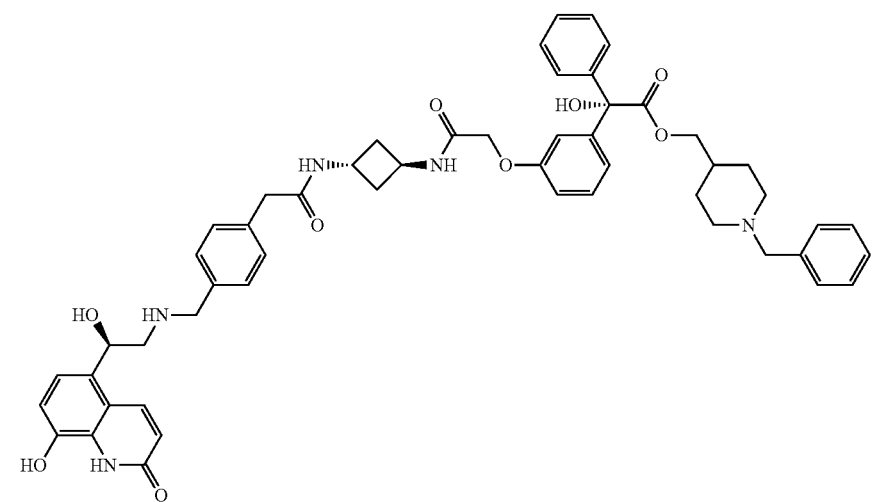 [SMILES: O=C(COc1cccc([C@](O)(C(=O)OCC2CCN(Cc3ccccc3)CC2)c2ccccc2)c1)N[C@H]1C[C@H](NC(=O)Cc2ccc(CNC[C@H](O)c3ccc(O)c4[nH]c(=O)ccc34)cc2)C1] |

| N | Rt (min) | Method | NMR data (400 MHz) | Salt (2 eq unless stated) |
|---|---|---|---|---|
| 127 | 2.45 | 11 | (DMSO-$d_6$); δ 10.53-10.46 (m, 3H), 9.35 (s, 1H), 8.88 (s, 1H), 8.78 (s, 1H), 8.73 (d, J = 6.7 Hz, 1H), 8.49 (d, J = 7.4 Hz, 1H), 8.07 (d, J = 9.3 Hz, 1H), 7.49 (m, 6H), 7.38-7.32 (m, 8H), 7.12 (t, J = 7.2 Hz, 1H), 7.01-6.92 (m, 3H), 6.88 (dd, J = 2.3, 8.2 Hz, 1H), 6.67 (s, 1H), 6.56 (dd, J = 2.0, 9.9 Hz, 1H), 6.19 (d, J = 3.8 Hz, 1H), 5.37-5.33 (m, 1H), 4.43 (m, 4H), 4.30-4.24 (m, 4H), 4.02 (d, J = 6.3 Hz, 2H), 3.04 (m, 4H), 2.92-2.86 (m, 2H), 2.33 (dd, J = 6.8, 6.8 Hz, 4H), 1.75 (m, 3H), 1.35 (m, 2H). | TFA |
| 128 | 2.43 | 11 | (DMSO-$d_6$); δ 10.50 (m, 2H), 9.34 (s, 1H), 9.17 (s, 2H), 8.77 (d, J = 7.3 Hz, 1H), 8.50 (d, J = 7.4 Hz, 1H), 8.10 (d, J = 9.6 Hz, 1H), 7.64 (dd, J = 7.7, 7.7 Hz, 1H), 7.49 (s, 6H), 7.42 (d, J = 8.0 Hz, 1H), 7.34 (m, 6H), 7.14-7.10 (m, 1H), 7.01-6.93 (m, 3H), 6.88 (dd, J = 2.4, 8.0 Hz, 1H), 6.66 (s, 1H), 6.60 (dd, J = 2.1, 9.9 Hz, 1H), 6.21 (d, J = 2.6 Hz, 1H), 5.35 (d, J = 9.5 Hz, 1H), 4.42 (s, 4H), 4.31-4.21 (m, 4H), 4.04-3.97 (m, 2H), 3.35 (d, J = 12.3 Hz, 2H), 3.09-2.87 (m, 4H), 2.37-2.29 (m, 4H), 1.77-1.66 (m, 3H), 1.41-1.30 (m, 2H). | TFA |
| 129 | 2.43 | 11 | (DMSO-$d_6$); δ 10.50 (m, 2H), 9.42 (s, 1H), 9.08 (s, 2H), 8.76 (d, J = 7.2 Hz, 1H), 8.51 (d, J = 7.3 Hz, 1H), 8.15 (d, J = 8.2 Hz, 1H), 7.76 (d, J = 7.3 Hz, 2H), 7.58 (d, J = 8.5 Hz, 1H), 7.48 (m, 5H), 7.35-7.26 (m, 6H), 7.16 (d, J = 8.3 Hz, 1H), 7.02-6.97 (m, 2H), 6.94 (d, J = 8.5 Hz, 1H), 6.89 (dd, J = 2.3, 8.0 Hz, 1H), 6.67 (s, 1H), 6.59 (dd, J = 2.1, 9.9 Hz, 1H), 6.22-6.20 (m, 1H), 5.41 (d, J = 9.8 Hz, 1H), 4.43 (m, 4H), 4.35-4.21 (m, 4H), 4.03 (d, J = 5.4 Hz, 2H), 3.35 (d, J = 12.2 Hz, 2H), 3.18-3.13 (m, 2H), 2.95-2.86 (m, 2H), 2.43 (s, 3H), 2.34 (dd, J = 6.8, 6.8 Hz, 4H), 1.86-1.84 (m, 1H), 1.76-1.67 (m, 2H), 1.36 (q, J = 12.0 Hz, 2H). | TFA |

| N | Rt (min) | Method | NMR data (400 MHz) | Salt (2 eq unless stated) |
|---|---|---|---|---|
| 130 | 2.43 | 11 | (DMSO-d$_6$); δ 10.53-10.47 (m, 2H), 9.39 (s, 1H), 9.16 (s, 2H), 8.50 (d, J = 7.4 Hz, 1H), 8.42 (d, J = 7.0 Hz, 1H), 8.08 (d, J = 9.9 Hz, 1H), 7.65 (d, J = 7.8 Hz, 1H), 7.48 (m, 5H), 7.37-7.24 (m, 7H), 7.16-7.11 (m, 2H), 7.02-6.93 (m, 3H), 6.89 (dd, J = 8.0 Hz, 1H), 6.66 (s, 1H), 6.58 (dd, J = 2.0, 9.9 Hz, 1H), 6.22-6.22 (m, 1H), 5.36 (d, J = 9.0 Hz, 1H), 4.49-4.44 (m, 1H), 4.43 (s, 2H), 4.37 (dd, J = 6.7, 13.4 Hz, 1H), 4.25 (t, J = 4.7 Hz, 4H), 4.01 (d, J = 5.4 Hz, 2H), 3.89 (s, 3H), 3.34 (d, J = 9.4 Hz, 2H), 3.11-2.86 (m, 4H), 2.32 (dd, J = 6.8, 6.8 Hz, 4H), 1.85-1.84 (m, 1H), 1.77-1.67 (m, 2H), 1.40-1.31 (m, 2H). | TFA |
| 131 | 2.47 | 11 | (DMSO-d$_6$); δ 10.48 (m, 2H), 9.37 (s, 1H), 8.87-8.86 (m, 2H), 8.79 (d, J = 6.9 Hz, 1H), 8.52 (d, J = 7.3 Hz, 1H), 8.08 (d, J = 8.4 Hz, 1H), 7.53 (m, 1H), 7.48 (m, 6H), 7.35-7.26 (m, 6H), 7.13 (dd, J = 8.2, 8.2 Hz, 1H), 7.02-6.93 (m, 3H), 6.89 (dd, J = 2.4, 8.0 Hz, 1H), 6.58 (dd, J = 1.8, 9.9 Hz, 1H), 6.20 (s, 1H), 5.38-5.33 (m, 1H), 4.44 (m, 4H), 4.30-4.21 (m, 4H), 4.03 (d, J = 7.0 Hz, 2H), 3.97 (s, 3H), 3.33 (d, J = 11.3 Hz, 2H), 3.07 (m, 2H), 2.95-2.87 (m, 2H), 2.36 (dd, J = 7.2, 7.2 Hz, 4H), 1.86-1.85 (m, 1H), 1.77-1.67 (m, 2H), 1.41-1.30 (m, 2H). | TFA |
| 132 | 2.46 | 11 | (DMSO-d$_6$); δ 10.52-10.46 (m, 2H), 9.37 (s, 1H), 9.18 (s, 2H), 8.88 (d, J = 6.9 Hz, 1H), 8.51 (d, J = 7.4 Hz, 1H), 8.14 (d, J = 11.8 Hz, 1H), 7.81-7.71 (m, 3H), 7.48 (m, 6H), 7.34 (m, 6H), 7.15 (d, J = 8.2 Hz, 1H), 7.02-6.93 (m, 3H), 6.89 (dd, J = 2.4, 8.0 Hz, 1H), 6.59 (dd, J = 1.7, 9.9 Hz, 1H), 6.22 (s, 1H), 5.38-5.36 (m, 4H), 4.43 (m, 4H), 4.36-4.21 (m, 4H), 4.05-3.97 (m, 2H), 3.35 (d, J = 11.8 Hz, 2H), 3.18-3.09 (m, 2H), 2.95-2.86 (m, 2H), 2.35 (dd, J = 6.8, 6.8 Hz, 4H), 1.85-1.84 (m, 1H), 1.77-1.67 (m, 2H), 1.40-1.30 (m, 2H). | TFA |
| 133 | 2.46 | 11 | (MeOD); δ 8.51 (s, 2H), 8.34 (d, J = 9.9 Hz, 1H), 7.55 (s, 1H), 7.47 (d, J = 7.9 Hz, 1H), 7.42-7.40 (m, 7H), 739-7.29 (m, 4H), 7.24 (d, J = 8.4 Hz, 1H), 7.09-7.06 (m, 2H), 7.03-6.96 (m, 2H), 6.67 (d, J = 9.9 Hz, 1H), 5.31 (dd, J = 3.9, 8.9 Hz, 1H), 4.53-4.45 (m, 4H), 4.13 (d, J = 6.4 Hz, 2H), 4.03 (s, 2H), 3.92 (s, 2H), 3.35-3.33 (m, 2H), 3.17 (d, J = 11.9 Hz, 2H), 3.03-2.91 (m, 2H), 2.53-2.43 (m, 5H), 1.88-1.80 (m, 1H), 1.69 (dd, J = 1.8, 13.6 Hz, 2H), 1.43-1.30 (m, 2H) | Formate |
| 134 | 2.44 | 11 | (DMSO-d$_6$); δ 10.55 (d, J = 8.8 Hz, 2H), 9.45-9.41 (m, 1H), 9.33-9.30 (m, 2H), 8.99 (d, J = 7.1 Hz, 1H), 8.55 (d, J = 7.6 Hz, 1H), 8.20 (d, J = 9.8 Hz, 1H), 7.58-7.50 (m, 6H), 7.43-7.37 (m, 4H), 7.37-7.30 (m, 2H), 7.21 (d, J = 8.3 Hz, 1H), 7.08-7.02 (m, 2H), 7.00 (d, J = 7.8 Hz, 1H), 6.95 (dd, J = 2.4, 8.2 Hz, 1H), 6.71 (s, 1H), 6.66 (dd, J = 1.8, 9.9 Hz, 1H), 6.58 (s, 1H), 6.30-6.27 (m, 1H), 5.42 (d, J = 8.8 Hz, 1H), 4.51-4.42 (m, 7H), 4.38-4.27 (m, 2H), 4.08 (d, J = 6.3 Hz, 2H), 3.24-3.11 (m, 3H), 3.01-2.92 (m, 2H), 2.46-2.33 (m, 4H), 1.93-1.72 (m, 3H), 1.47-1.35 (m, 2H) | TFA |
| 135 | 2.64 | 11 | (DMSO-d$_6$); δ 10.22 (s, 1H), 8.73 (d, J = 7.1 Hz, 1H), 8.41 (d, J = 7.3 Hz, 1H), 8.10 (d, J = 8.6 Hz, 2H), 7.85 (d, J = 1.8 Hz, 1H), 7.73 (dd, J = 1.6, 8.0 Hz, 1H), 7.51 (d, J = 7.8 Hz, 1H), 7.28-7.16 (m, 10H), 7.00 (d, J = 8.3 Hz, 1H), 6.94 (dd, J = 2.1, 2.1 Hz, 1H), 6.89-6.80 (m, 3H), 6.55 (s, 1H), 6.42 (d, J = 9.9 Hz, 1H), 5.34 (s, 1H), 5.01 (dd, J = 4.7, 7.7 Hz, 1H), 4.35 (s, 4H), 3.94 (d, J = 6.3 Hz, 2H), 3.80 (s, 2H), 3.33 (s, 2H), 2.72-2.59 (m, 3H), 2.27 (dd, J = 6.8, 6.8 Hz, 4H), 1.81-1.73 (m, 2H), 1.50-1.36 (m, 3H), 1.11-1.00 (m, 2H). | mono-formate |
| 136 | 2.51 | 11 | (DMSO-d$_6$); δ 10.51 (d, J = 12.8 Hz, 2H), 9.35 (s, 1H), 9.15 (s, 2H), 8.87 (d, J = 6.8 Hz, 1H), 8.49 (d, J = 7.6 Hz, 1H), 8.11 (d, J = 11.2 Hz, 1H), 7.88 (d, J = 1.3 Hz, 1H), 7.58 (dd, J = 1.1, 8.0 Hz, 1H), 7.52-7.47 (m, 5H), 7.38-7.24 (m, 6H), 7.16-7.11 (m, 2H), 7.03-6.98 (m, 3H), 6.95 (d, J = 8.1 Hz, 1H), 6.90 (dd, J = 2.4, 8.5 Hz, 1H), 6.62 (dd, J = 5.7, 5.7 Hz, 1H), 6.23 (s, 1H), 5.36 (d, J = 7.6 Hz, 1H), 4.47-4.36 (m, 4H), 4.32-4.22 (m, 3H), 4.03 (d, J = 7.1 Hz, 2H), 336 (d, J = 12.8 Hz, 2H), 3.13-2.88 (m, 5H), 2.38-2.29 (m, 4H), 1.90-1.82 (m, 1H), 1.78-1.66 (m, 2H), 1.41-1.33 (m, 2H). | TFA |
| 137 | 2.45 | 11 | (DMSO-d$_6$); δ 10.52-10.50 (m, 2H), 9.39 (s, 1H), 8.93 (s, 2H), 8.87 (d, J = 6.8 Hz, 1H), 8.50 (d, J = 7.4 Hz, 1H), 8.12 (d, J = 9.9 Hz, 1H), 7.61 (s, 1H), 7.49-7.48 (m, 5H), 7.38-7.25 (m, 6H), 7.15 (dd, J = 4.1, 4.1 Hz, 2H), 7.02-6.94 (m, 3H), 6.89 (dd, J = 2.4, 7.9 Hz, 1H), 6.69 (s, 1H), 6.61 (d, J = 9.9 Hz, 1H), 6.22 (s, 1H), 5.37 (dd, J = 3.5, 8.9 Hz, 1H), 4.46-4.36 (m, 4H), 4.32-4.22 (m, 4H), 4.03 (d, J = 6.4 Hz, 2H), 3.88 (s, 3H), 3.34 (d, J = 11.5 Hz, 2H), 3.07-3.07 (m, 2H), 2.96-2.87 (m, 2H), 2.39-2.30 (m, 4H), 1.77-1.67 (m, 3H), 1.41-1.31 (m, 2H). | TFA |
| 138 | 2.48 | 11 | (DMSO-d$_6$); δ 10.26-10.21 (s, 1H), 8.87 (d, J = 7.1 Hz, 1H), 8.43 (d, J = 7.3 Hz, 1H), 8.12-8.08 (m, 3H), 8.05 (d, J = 8.1 Hz, 1H), 7.79 (d, J = 8.1 Hz, 1H), 7.29-7.17 (m, 11H), 7.01 (d, J = 8.3 Hz, 1H), 6.95 (dd, J = 2.0, 2.0 Hz, 1H), 6.90-6.81 (m, 3H), 6.56 (s, 1H), 6.42 (d, J = 9.9 Hz, 1H), 5.40 (s, 1H), 5.02 (dd, J = 4.7, 7.7 Hz, 1H), 4.46-4.37 (m, 2H), 4.36 (s, 2H), 3.97-3.87 (m, 4H), 3.45 (s, 2H), 2.72-2.60 (m, 4H), 2.29 (t, J = 6.8, 6.8 Hz, 4H), 1.83-1.73 (t, 2H), 1.49-1.37 (m, 3H), 1.12-1.00 (m, 2H). | formate |
| 139 | 2.43 | 11 | (DMSO-d$_6$); δ 10.51 (s, 2H), 9.40 (s, 1H), 9.04-9.04 (m, 2H), 8.83 (d, J = 6.9 Hz, 1H), 8.51 (d, J = 7.4 Hz, 1H), 8.13 (d, J = 9.8 Hz, 1H), 7.49-7.48 (m, 5H), 7.42-7.24 (m, 8H), 7.15 (d, J = 8.3 Hz, 1H), 7.02-6.93 (m, 3H), 6.89 (dd, J = 2.4, 8.1 Hz, 1H), 6.67 (s, 1H), 6.60 (d, J = 9.9 Hz, 1H), 6.23 (s, 1H), 5.38 (dd, J = 3.0, 9.3 Hz, 1H), 4.48-4.38 (m, 4H), 4.36-4.26 (m, 4H), 4.04 (d, J = 5.2 Hz, 2H), 3.96 (d, J = 2.0 Hz, 3H), 3.34 (d, J = 11.5 Hz, 2H), 3.15-3.05 (m, 2H), 2.96-2.87 (m, 2H), 2.38-2.29 (m, 4H), 1.84-1.66 (m, 3H), 1.41-1.31 (m, 2H). | TFA |
| 140 | 2.46 | 11 | (MeOD); δ 8.54 (s, 1H), 8.29 (d, J = 9.9 Hz, 1H), 7.49 (d, J = 6.7 Hz, 2H), 7.46-7.31 (m, 12H), 7.24 (d, J = 8.3 Hz, 1H), 7.11-7.07 (m, 2H), 7.04-6.98 (m, 2H), 6.64 (d, J = 9.9 Hz, 1H), 5.36-5.31 (m, 1H), 4.59-4.48 (m, 4H), 4.23-4.17 (m, 4H), 4.12 (d, J = 6.9 Hz, 2H), 3.79 (s, 2H), 3.13-3.04 (m, 4H), 2.53-2.46 (m, 4H), 2.36 (dd, | mono-formate |

| N | Rt (min) | Method | NMR data (400 MHz) | Salt (2 eq unless stated) |
|---|---|---|---|---|
| | | | J = 11.6, 11.6 Hz, 2H), 1.82-1.74 (m, 1H), 1.67-1.64 (m, 2H), 1.46 (dd, J = 7.0, 7.0 Hz, 3H), 1.39-1.29 (m, 2H). | |
| 141 | 2.49 | 11 | (MeOD); δ 8.50 (s, 1H), 8.34 (d, J = 9.9 Hz, 1H), 7.87 (dd, J = 1.6, 7.9 Hz, 1H), 7.83-7.82 (m, 1H), 7.67 (d, J = 8.0 Hz, 1H), 7.45-7.40 (m, 7H), 7.39-7.30 (m, 4H), 7.24 (d, J = 8.2 Hz, 1H), 7.10-7.08 (m, 2H), 7.03-6.98 (m, 2H), 6.64 (d, J = 9.8 Hz, 1H), 5.28 (dd, J = 4.3, 8.4 Hz, 1H), 4.60-4.45 (m, 4H), 4.14 (d, J = 6.3 Hz, 2H), 4.04 (s, 2H), 3.97 (s, 2H), 3.21 (d, J = 12.6 Hz, 2H), 3.00-2.88 (m, 2H), 2.64-2.57 (m, 2H), 2.53-2.44 (m, 4H), 1.91-1.83 (m, 1H), 1.74-1.70 (m, 2H), 1.44-1.33 (m, 2H). | mono-formate |
| 142 | 2.47 | 11 | (MeOD); δ 8.49 (s, 2H), 8.32 (d, J = 9.9 Hz, 1H), 7.45-7.40 (m, 7H), 7.39-7.25 (m, 7H), 7.10-7.07 (m, 2H), 7.04 (d, J = 8.2 Hz, 1H), 7.01-6.97 (m, 1H), 6.68 (d, J = 9.9 Hz, 1H), 5.40-5.35 (m, 1H), 4.60-4.45 (m, 4H), 4.18 (s, 2H), 4.15 (d, J = 6.2 Hz, 2H), 4.02 (s, 2H), 3.93 (s, 3H), 3.24 (d, J = 12.0 Hz, 2H), 3.12 (d, J = 6.1 Hz, 2H), 2.65 (dd, J = 11.5, 13.1 Hz, 2H), 2.48 (dd, J = 6.9, 6.9 Hz, 4H), 1.89-1.84 (m, 1H), 1.73 (d, J = 12.0 Hz, 2H), 1.47-1.33 (m, 2H) | formate |
| 143 | 2.52 | 11 | (MeOD); δ 8.50 (s, 2H), 8.29 (d, J = 9.9 Hz, 1H), 7.54 (s, 1H), 7.51-7.47 (m, 2H), 7.44-7.40 (m, 7H), 7.39-7.30 (m, 4H)), 7.26 (d, J = 8.3 Hz, 1H), 7.11-7.07 (m, 2H), 7.04 (d, J = 7.9 Hz, 1H), 7.01-6.97 (m, 1H), 6.66 (d, J = 9.9 Hz, 1H), 5.37 (dd, J = 4.6, 8.7 Hz, 1H), 4.87-4.82 (m, 1H), 4.61-4.46 (m, 4H), 4.26 (d, J = 2.8 Hz, 2H), 4.14 (d, J = 6.4 Hz, 2H), 3.96 (s, 2H), 3.24-3.17 (m, 4H), 2.61-2.46 (m, 6H), 1.90-1.83 (m, 1H), 1.76-1.70 (m, 2H), 1.45-1.32 (m, 8H). | formate |
| 144 | 2.46 | 11 | (MeOD); δ 8.71 (d, J = 1.5 Hz, 1H), 8.45 (s, 2H), 8.35 (d, J = 9.9 Hz, 1H), 8.10 (d, J = 8.0 Hz, 1H), 8.03 (dd, J = 2.0, 8.2 Hz, 1H), 7.48-7.41 (m, 7H), 7.39-7.31 (m, 4H), 7.27 (d, J = 7.6 Hz, 1H), 7.11-7.07 (m, 2H), 7.05-6.98 (m, 2H), 6.66 (d, J = 9.9 Hz, 1H), 5.35 (dd, J = 4.3, 8.7 Hz, 1H), 4.65-4.57 (m, 1H), 4.51 (s, 2H), 4.50-4.43 (m, 1H), 4.18-4.13 (m, 4H), 4.11 (s, 2H), 3.34-3.27 (m, 2H), 3.11-3.06 (m, 2H), 2.80-2.74 (m, 2H), 2.59-2.45 (m, 4H), 1.94-1.88 (m, 1H), 1.76 (d, J = 14.2 Hz, 2H), 1.49-1.36 (m, 2H). | formate |
| 145 | 2.44 | 11 | (MeOD); δ 9.12 (d, J = 1.8 Hz, 1H), 9.02 (d, J = 5.5 Hz, 1H), 8.56 (d, J = 7.6 Hz, 1H), 8.39 (d, J = 9.9 Hz, 1H), 8.31 (dd, J = 2.2, 8.2 Hz, 1H), 7.59 (d, J = 8.3 Hz, 1H), 7.52-7.51 (m, 5H), 7.43-7.32 (m, 7H), 7.11-7.05 (m, 3H), 7.00 (dd, J = 2.1, 7.2 Hz, 1H), 6.71 (d, J = 9.8 Hz, 1H), 5.55 (dd, J = 5.2, 8.2 Hz, 1H), 4.63-4.48 (m, 6H), 4.29 (s, 2H), 4.14 (d, J = 6.3 Hz, 2H), 3.52-3.42 (m, 2H), 3.41-3.36 (m, 2H), 2.99 (dd, J = 10.6, 13.2 Hz, 2H), 2.50 (dd, J = 6.8, 6.8 Hz, 4H), 2.02-1.96 (m, 1H), 1.84 (d, J = 14.7 Hz, 2H), 1.49-1.39 (m, 2H) | TFA |
| 146 | 2.49 | 11 | (MeOD); δ 8.52 (s, 1H), 8.26 (d, J = 9.9 Hz, 1H), 7.47-7.43 (m, 2H), 7.42-7.38 (m, 9H), 7.37-7.25 (m, 5H), 7.09-7.06 (m, 2H), 7.03 (d, J = 8.2 Hz, 1H), 6.99-6.96 (m, 1H), 6.66 (d, J = 9.9 Hz, 1H), 5.37 (dd, J = 4.7, 8.7 Hz, 1H), 4.49-4.41 (m, 3H), 4.34-4.25 (m, 1H), 4.22 (s, 2H), 4.12 (d, J = 6.4 Hz, 2H), 3.90 (s, 2H), 3.56 (s, 2H), 3.18-3.13 (m, 4H), 2.50 (dd, J = 11.5, 11.5 Hz, 2H), 2.42-2.27 (m, 4H), 1.86-1.78 (m, 1H), 1.68 (d, J = 12.2 Hz, 2H), 1.42-1.30 (m, 2H) | mono-formate |

Example 23

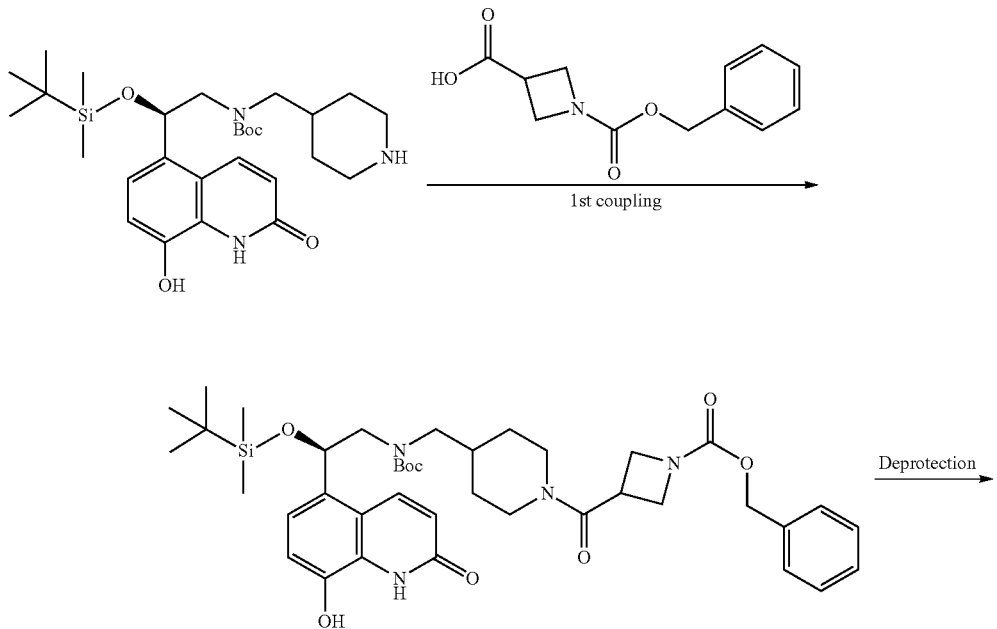

-continued
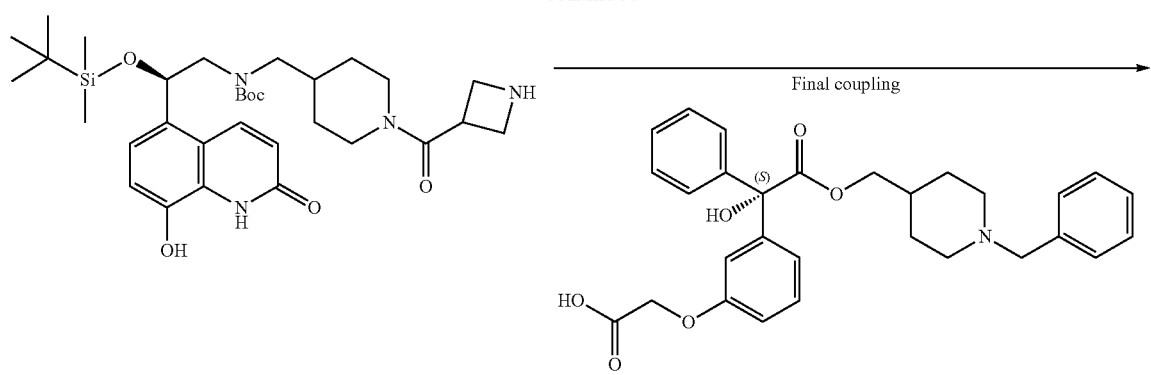
Final coupling →
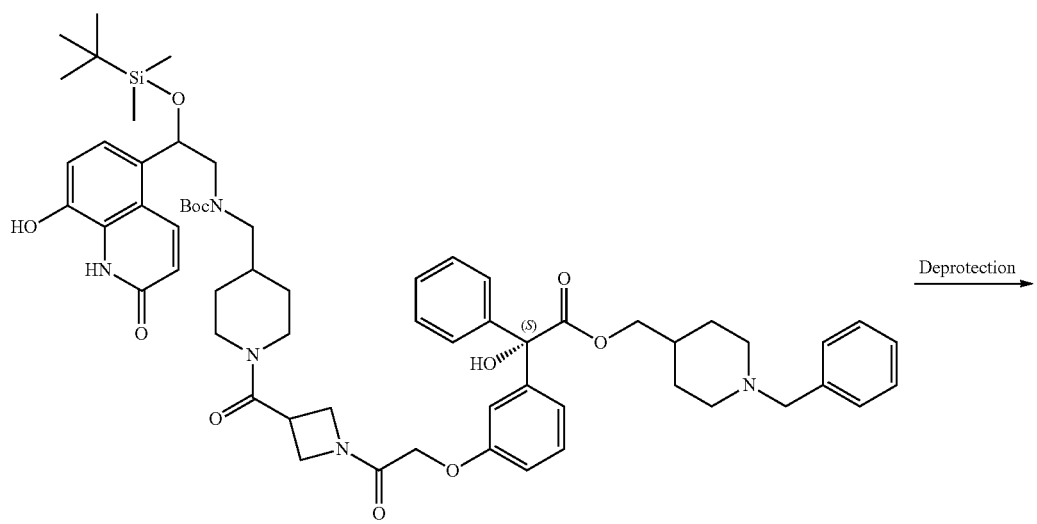
Deprotection →
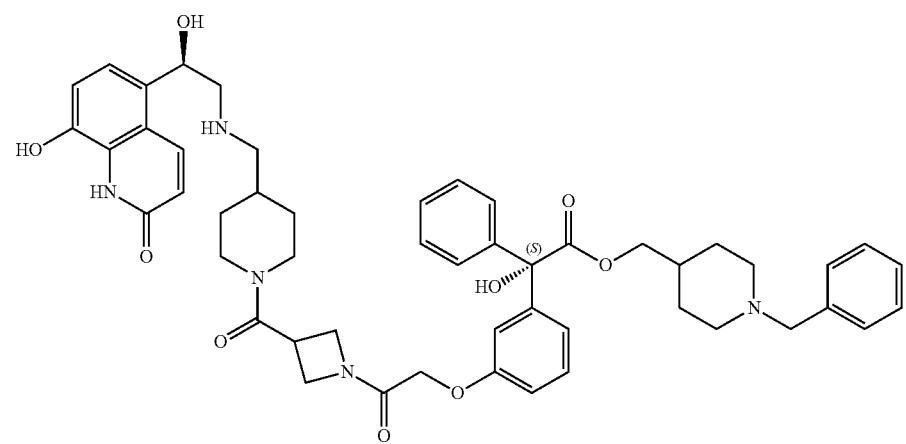

(1-Benzylpiperidin-4-yl)methyl (S)-2-hydroxy-2-(3-(2-(3-(4-((((R)-2-hydroxy-2-(8-hydroxy-2-oxo-1,2-dihydroquinolin-5-yl)ethyl)amino)methyl)piperidine-1-carbonyl)azetidin-1-yl)-2-oxoethoxy)phenyl)-2-phenylacetate (Compound 147)

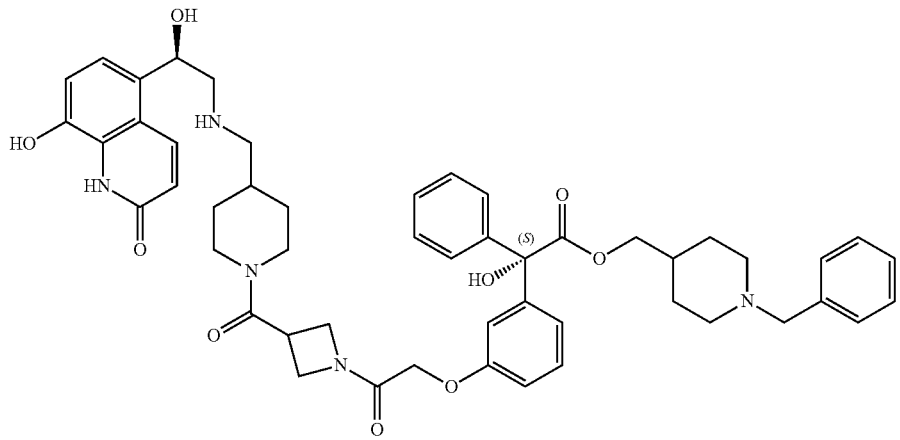

Step 1; Benzyl (R)-3-(4-(((tert-butoxycarbonyl)(2-((tert-butyldimethylsilyl)oxy)-2-(8-hydroxy-2-oxo-1,2-dihydroquinolin-5-yl)ethyl)amino)methyl)piperidine-1-carbonyl)azetidine-1-carboxylate Step 2; tert-Butyl (R)-((1-(azetidine-3-carbonyl)piperidin-4-yl)methyl)(2-((tert-butyldimethylsilyl)oxy)-2-(8-hydroxy-2-oxo-1,2-dihydroquinolin-5-yl)ethyl)carbamate

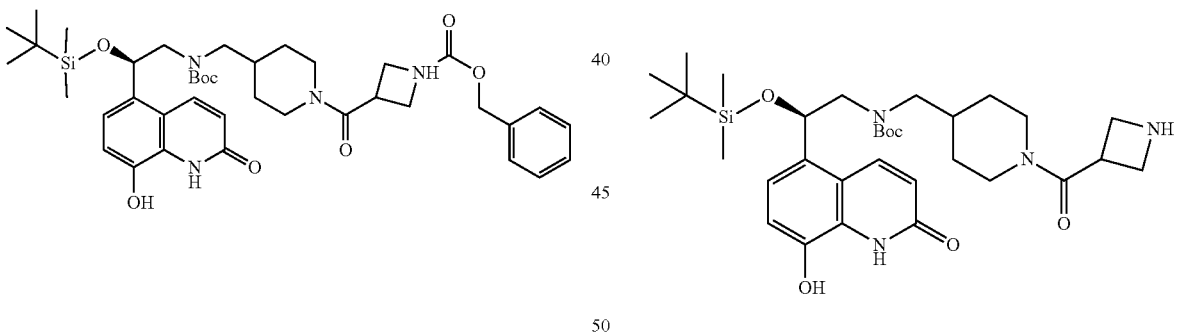

To a solution of 1-((benzyloxy)carbonyl)azetidine-3-carboxylic acid (0.306 g, 1.3 mmol) and DIPEA (0.266 mL, 1.3 mmol) in DMF (10 mL) was added HATU (0.494 g, 0.494 g, 1.3 mmol) and the reaction mixture stirred at room temperature for 30 minutes. (R)-Tert-butyl (2-((tert-butyldimethylsilyl)oxy)-2-(8-hydroxy-2-oxo-1,2-dihydroquinolin-5-yl)ethyl)(piperidin-4-ylmethyl)carbamate (0.531 g, 1.0 mmol) was added and the mixture stirred for a further 18 hours. The mixture was diluted with ethyl acetate and washed with water, 10% aqueous potassium carbonate and brine (×2). The organic phase was dried over anhydrous magnesium sulfate, filtered and the filtrate evaporated at reduced pressure to afford the title compound (0.759 g, 100%).

LCMS Method 11; Rt 3.80 min; ES$^+$749.6.

To a solution of benzyl (R)-3-(4-(((tert-butoxycarbonyl)(2-((tert-butyldimethyl-silyl)oxy)-2-(8-hydroxy-2-oxo-1,2-dihydroquinolin-5-yl)ethyl)amino)methyl)piperidine-1-carbonyl)azetidine-1-carboxylate (0.759 g, 1.0 mmol) in ethanol (10 mL) was added 10% palladium on carbon (0.8 g) and 1-methyl-1,4-cyclohexadiene (0.562 mL). The reaction mixture was heated to reflux and heated at reflux for one hour. The suspension was filtered and the filtrate evaporated at reduced pressure to afford the title compound (0.516 g, 84%).

LCMS Method 11; Rt 3.02 min; ES$^+$615.

Step 3; (1-Benzylpiperidin-4-yl)methyl (S)-2-hydroxy-2-(3-(2-(3-(4-((((R)-2-hydroxy-2-(8-hydroxy-2-oxo-1,2-dihydroquinolin-5-yl)ethyl)amino)methyl)piperidine-1-carbonyl)azetidin-1-yl)-2-oxoethoxy)phenyl)-2-phenylacetate (Compound 147)

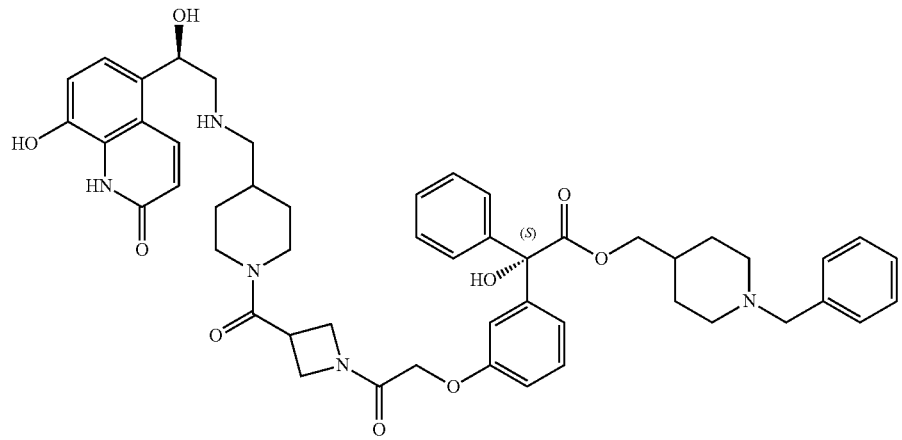

To a stirred solution of tert-butyl (R)-((1-(azetidine-3-carbonyl)piperidin-4-yl)methyl)(2-((tert-butyldimethylsilyl)oxy)-2-(8-hydroxy-2-oxo-1,2-dihydroquinolin-5-yl)ethyl)carbamate (0250 g, 0.41 mmol) and (S)-2-(3-(2-((1-benzylpiperidin-4-yl)methoxy)-1-hydroxy-2-oxo-1-phenylethyl)phenoxy)acetic acid hydrochloride (0.235 g, 0.45 mmol) in DMF (3 mL) was added EDC (0.11 g, 0.57 mmol), HOBt (0.078 g, 0.58 mmol) and 4-DMAP (catalytic). The reaction mixture was stirred at room temperature for 72 hours. The reaction mixture was diluted with ethyl acetate and washed with water, 10% aqueous potassium carbonate and brine (×2). The organic phase was dried over anhydrous magnesium sulfate, filtered and the filtrate evaporated at reduced pressure. The residue was dissolved in MeCN (2 mL) and a solution of HCl-dioxan (4 mL) added. The reaction mixture was stirred at room temperature for 1 hour. The solvent was evaporated at reduced pressure and the residue purified by reverse preparative HPLC.

The following compounds were prepared by this method:

| N | Structure |
|---|-----------|
| 147 | 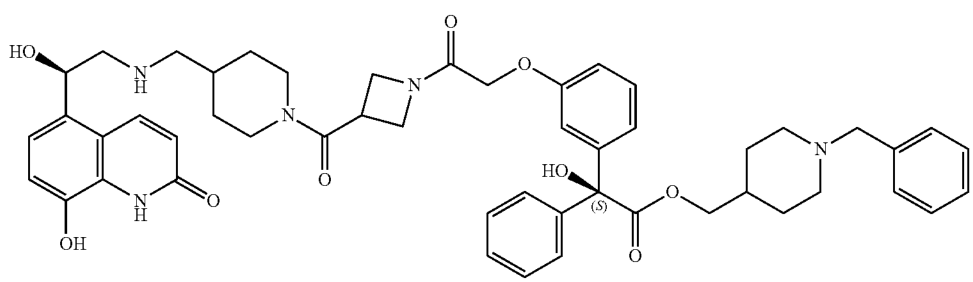 |
| 148 | 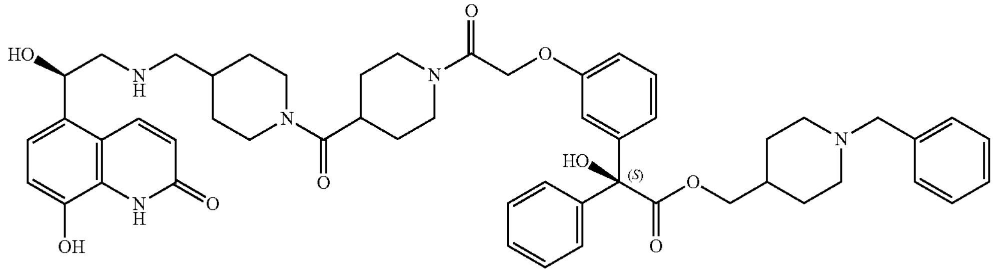 |

-continued

| N | Structure |
|---|---|
| 149 | 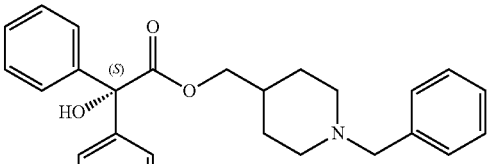 |
| 150 | 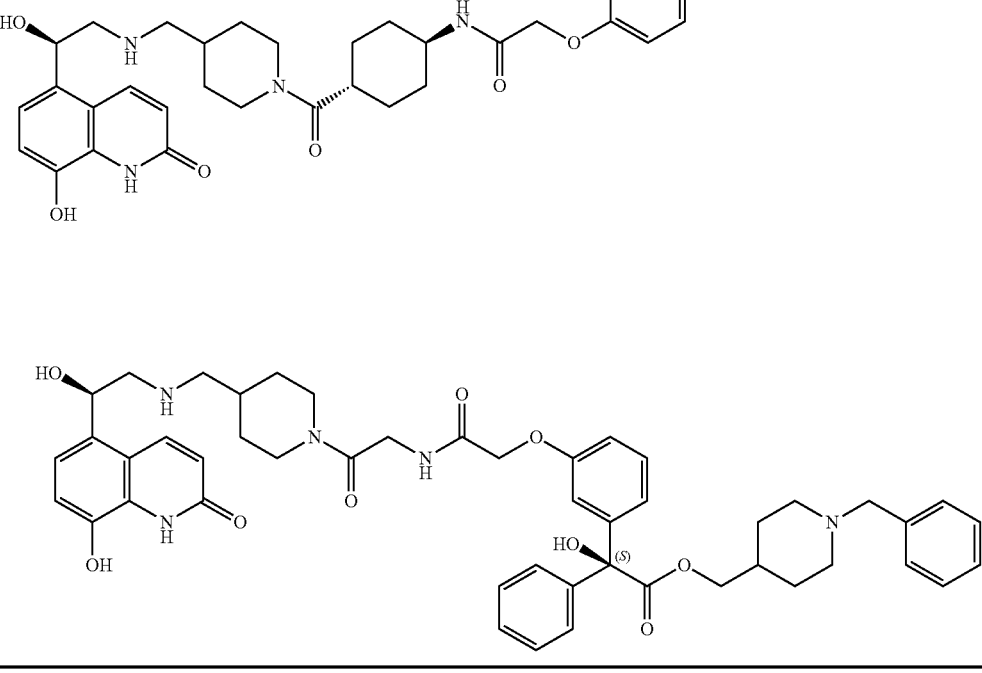 |

| N | Rt (min) | Method | NMR data (400 MHz) | Salt (2 eq unless stated) |
|---|---|---|---|---|
| 147 | 2.40 | 11 | (MeOD); δ 8.43-8.38 (m, 1H), 7.54-7.48 (m, 6H), 7.41-7.28 (m, 6H), 7.10-7.05 (m, 2H), 7.00-6.98 (m, 1H), 6.93 (dd, J = 2.3, 8.1 Hz, 1H), 6.73-6.68 (m, 1H), 5.46 (dd, J = 5.6, 8.0 Hz, 1H), 4.61 (d, J = 4.1 Hz, 3H), 4.53-4.40 (m, 2H), 4.29 (s, 2H), 4.26-4.16 (m, 1H), 4.14 (d, J = 6.0 Hz, 3H), 3.89-3.80 (m, 1H), 3.72 (d, J = 14.6 Hz, 1H), 3.52-3.45 (m, 2H), 3.29 (d, J = 7.2 Hz, 2H), 3.19-2.95 (m, 6H), 2.76 (dd, J = 12.7, 12.7 Hz, 1H), 2.13-2.09 (m, 1H), 2.02-1.72 (m, 4H), 1.42 (dd, J = 12.9, 12.9 Hz, 2H), 1.32-1.24 (m, 2H). | TFA |
| 148 | 2.40 | 11 | (MeOD); δ 8.40 (d, J = 9.9 Hz, 1H), 7.54-7.47 (m, 6H), 7.42-7.25 (m, 6H), 7.06 (d, J = 8.2 Hz, 2H), 6.99 (s, 1H), 6.92 (dd, J = 2.1, 8.3 Hz, 1H), 6.71 (d, J = 9.9 Hz, 1H), 5.46 (t, J = 7.3 Hz, 1H), 4.83-4.72 (m, 3H), 4.61 (d, J = 14.6 Hz, 1H), 4.49-4.33 (m, 1H), 4.28 (s, 2H), 4.20-4.10 (m, 3H), 3.98 (d, J = 15.6 Hz, 1H), 3.51-3.42 (m, 2H), 3.30-3.15 (m, 5H), 3.10-2.94 (m, 5H), 2.82 (t, J = 11.9 Hz, 1H), 2.70 (t, J = 11.9 Hz, 1H), 2.14-2.10 (m, 1H), 1.98-1.93 (m, 2H), 1.84-1.78 (m, 4H), 1.70-1.55 (m, 1H), 1.46-1.20 (m, 4H). | TFA |
| 149 | 2.43 | 11 | (MeOD) d 8.41 (d, J = 9.8 Hz, 1H), 7.95 (d, J = 6.6 Hz, 1H), 7.51 (s, 5H), 7.40-7.27 (m, 6H), 7.11-7.05 (m, 2H), 7.01 (s, 1H), 6.96 (dd, J = 2.1, 8.0 Hz, 1H), 6.71 (d, J = 9.9 Hz, 1H), 5.45 (t, J = 6.4 Hz, 1H), 4.61 (d, J = 13.6 Hz, 1H), 4.47 (s, 2H), 4.28 (s, 2H), 4.17-4.08 (m, 3H), 3.72-3.67 (m, 1H), 3.50-3.43 (m, 2H), 3.28 (d, J = 7.3 Hz, 2H), 3.21-3.13 (m, 2H), 3.10-2.93 (m, 5H), 2.71-2.62 (m, 2H), 2.13-2.09 (m, 1H), 1.97-1.91 (m, 4H), 1.86-1.76 (m, 4H), 1.64-1.47 (m, 2H), 1.43-1.19 (m, 6H). | TFA |
| 150 | 2.42 | 11 | (MeOD); δ 8.40 (d, J = 9.9 Hz, 1H), 7.53-7.48 (m, 5H), 7.42-7.29 (m, 7H), 7.11-7.04 (m, 3H), 7.00 (dd, J = 2.3, 8.1 Hz, 1H), 6.71 (d, J = 9.8 Hz, 1H), 5.45 (dd, J = 6.0, 7.8 Hz, 1H), 4.59-4.53 (m, 3H), 4.28 (s, 2H), 4.25-4.09 (m, 4H), 3.96 (d, J = 13.2 Hz, 1H), 3.51-3.45 (m, 2H), 3.28 (d, J = 7.8 Hz, 2H), 3.21-3.14 (m, 2H), 3.09-2.94 (m, 4H), 2.74 (t, J = 13.2 Hz, 1H), 2.15-2.08 (m, 1H), 1.99-1.80 (m, 5H), 1.47-1.20 (m, 3H). | TFA |

303
Example 24
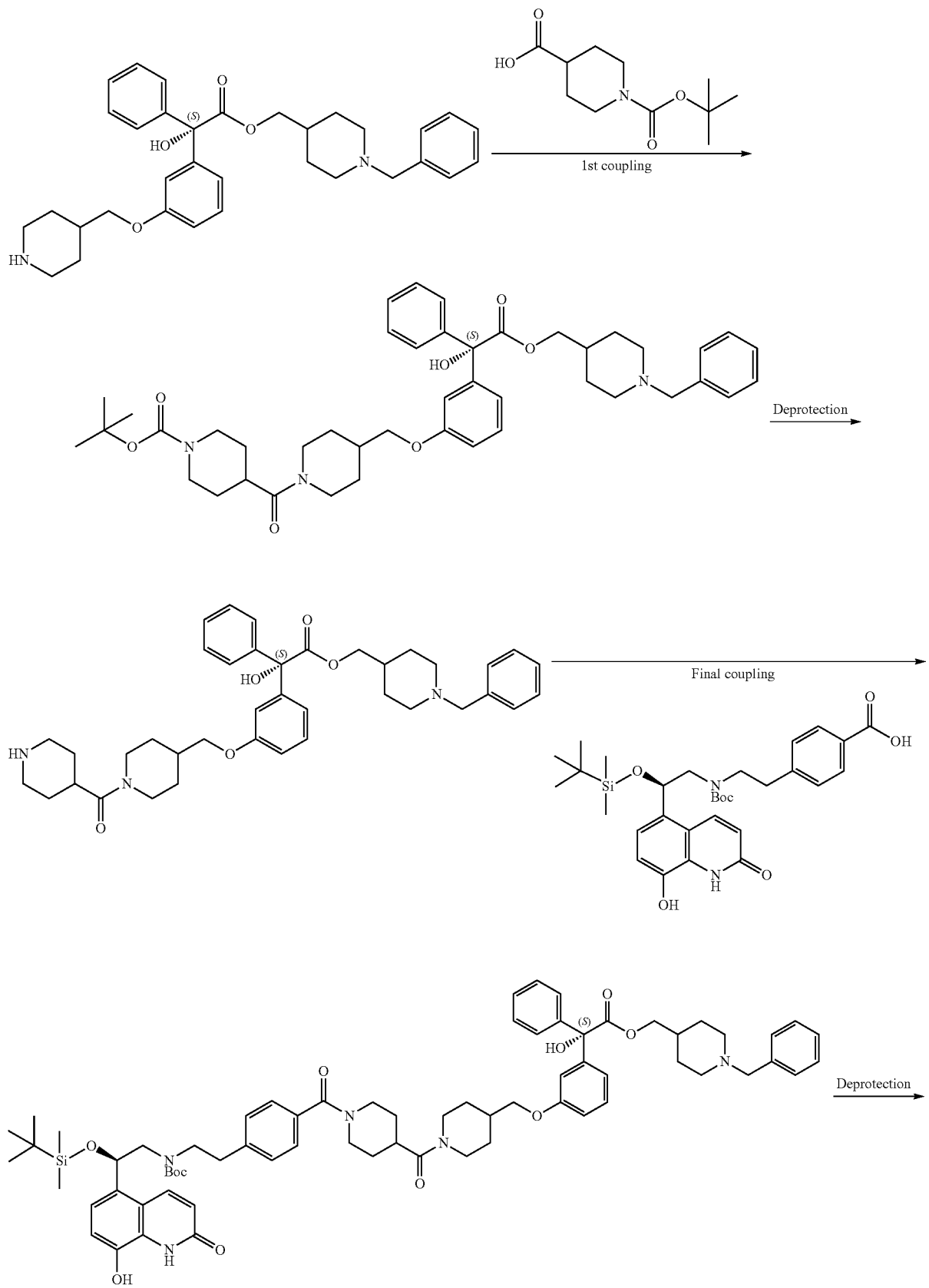

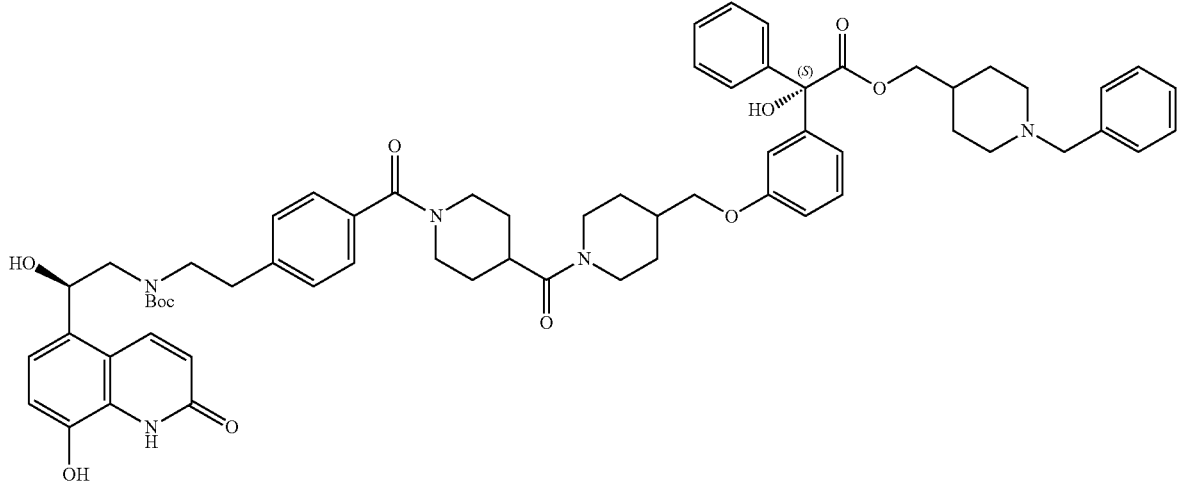

(1-Benzylpiperidin-4-yl)methyl (S)-2-hydroxy-2-(3-((1-(1-(4-(2-(((R)-2-hydroxy-2-(8-hydroxy-2-oxo-1,2-dihydroquinolin-5-yl)ethyl)amino)ethyl)benzoyl)piperidine-4-carbonyl)piperidin-4-yl)methoxy)phenyl)-2-phenylacetate (Compound 151)

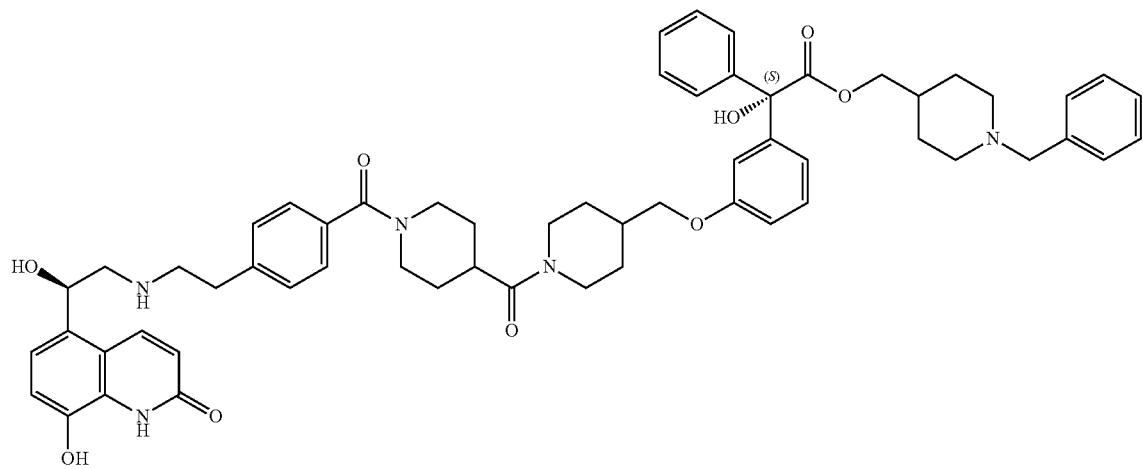

The title compound was prepared using a similar route to that described in Example 22 using previously described compounds (see Procedures section). An acidic deprotection step (as described in Example 20 Step 2) was utilized prior to the final coupling step.

The following compounds were prepared by this method;

| N | Structure |
|---|---|
| 152 | 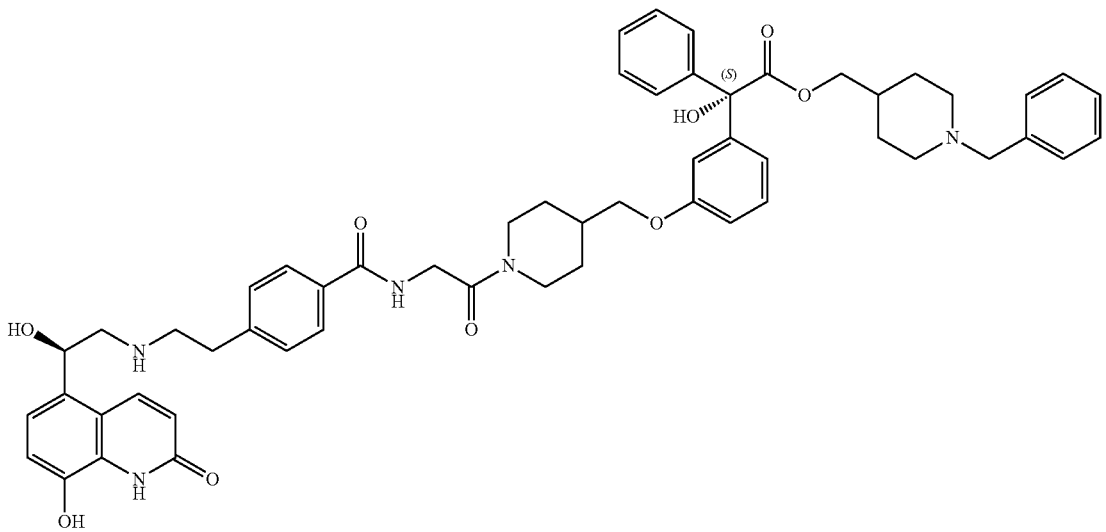 |
| 153 | 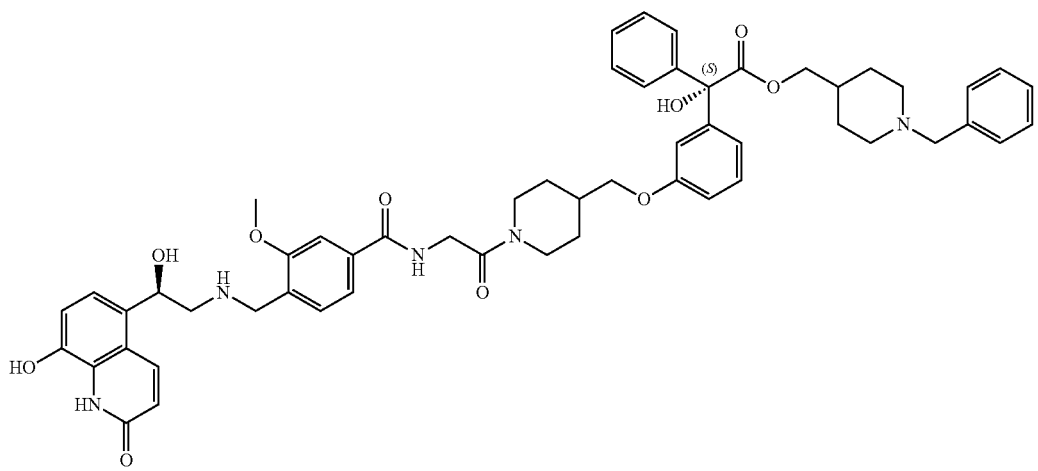 |
| 154 | 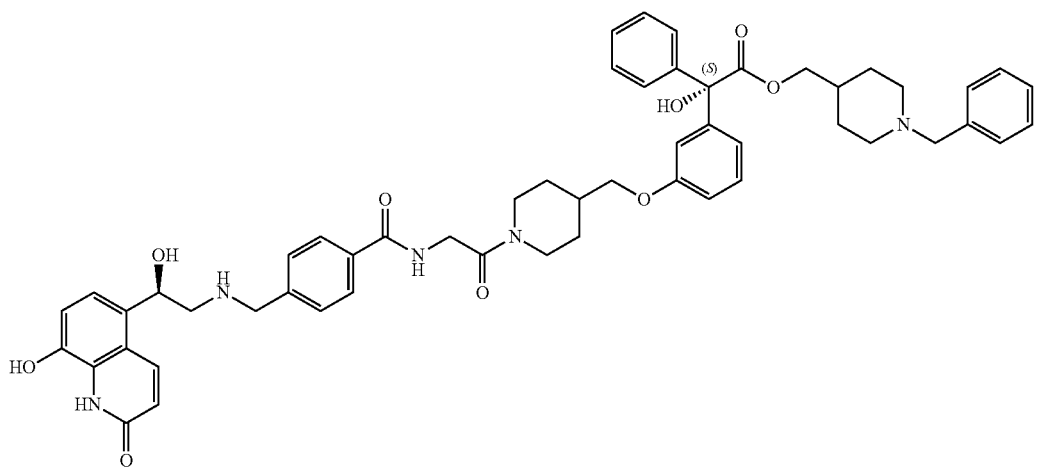 |

| N | Structure |
|---|---|
| 155 | 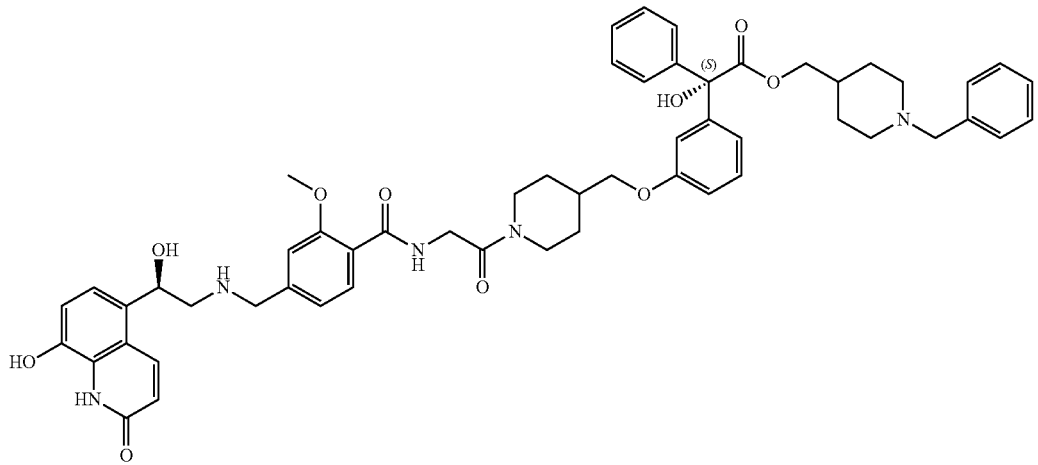 |

| N | Rt (min) | Method | NMR data (400 MHz) | Salt (2 eq unless stated) |
|---|---|---|---|---|
| 151 | 2.55 | 11 | (DMSO-d₆, 90° C.); δ 8.20 (d, J = 9.9 Hz, 1H), 7.49-7.43 (m, 5H), 7.35 (dd, J = 7.6, 7.6 Hz, 9H), 7.27-7.21 (m, 1H), 7.16 (d, J = 8.3 Hz, 1H), 7.02 (d, J = 8.2 Hz, 1H), 6.96-6.92 (m, 2H), 6.89-6.86 (m, 1H), 6.57 (d, J = 9.9 Hz, 1H), 5.38 (dd, J = 4.3, 8.6 Hz, 1H), 4.19-4.19 (m, 4H), 4.11-3.97 (m, 3H), 3.82 (d, J = 6.3 Hz, 2H), 3.31 (t, J = 8.2 Hz, 2H), 3.28-3.08 (m, 9H), 3.01-2.75 (m, 5H), 2.02-1.97 (m, 1H), 1.81-1.53 (m, 11H), 1.28-1.18 (m, 2H). | TFA |
| 152 | 2.53 | 11 | (MeOD); δ 8.50 (s, 1H), 8.37 (d, J = 9.9 Hz, 1H), 7.88 (d, J = 8.3 Hz, 2H), 7.44-7.33 (m, 12H), 7.32-7.24 (m, 2H), 7.04 (d, J = 8.2 Hz, 1H), 7.03-6.98 (m, 2H), 6.90 (dd, J = 2.1, 7.9 Hz, 1H), 6.70 (d, J = 9.8 Hz, 1H), 5.39 (dd, J = 4.8, 8.7 Hz, 1H), 4.57 (d, J = 12.2 Hz, 1H), 4.29 (dd, J = 15.6, 38.7 Hz, 2H), 4.12 (d, J = 6.7 Hz, 2H), 4.01 (d, J = 13.4 Hz, 1H), 3.92 (s, 2H), 3.84 (d, J = 6.0 Hz, 2H), 3.28-3.07 (m, 9H), 2.79-2.67 (m, 1H), 2.52-2.52 (m, 2H), 2.12-2.06 (m, 1H), 1.95-1.79 (m, 3H), 1.70 (d, J = 13.6 Hz, 2H), 1.48-1.28 (m, 4H). | mono-formate |
| 153 | 2.53 | 11 | ¹H NMR (400 MHz, MeOD) d 8.40 (s, 2H), 8.14 (d, J = 9.9 Hz, 1H), 7.41 (s, 1H), 7.39-7.35 (m, 1H), 7.32-7.19 (m, 11H), 7.14-7.08 (m, 2H), 6.89-6.82 (m, 3H), 6.77-6.74 (m, 1H), 6.51 (d, J = 9.9 Hz, 1H), 5.20 (dd, J = 5.3, 7.8 Hz, 1H), 4.43 (d, J = 12.8 Hz, 1H), 4.24-4.08 (m, 2H), 4.04 (s, 2H), 3.98-3.85 (m, 3H), 3.81 (s, 3H), 3.70 (d, J = 6.0 Hz, 2H), 3.58 (s, 2H), 3.03-2.84 (m, 5H), 2.66-2.53 (m, 1H), 2.13 (dd, J = 11.5, 11.5 Hz, 2H), 1.96-1.91 (m, 1H), 1.83-1.70 (m, 2H), 1.63-1.54 (m, 1H), 1.48 (d, J = 13.3 Hz, 2H), 1.36-1.24 (m, 1H), 1.17 (q, J = 12.5 Hz, 3H). | formate |
| 154 | 2.50 | 11 | (MeOD); δ 8.48 (s, 2H), 8.32 (d, J = 9.9 Hz, 1H), 7.97 (d, J = 8.3 Hz, 2H), 7.62 (d, J = 8.3 Hz, 2H), 7.45 (s, 5H), 7.43-7.34 (m, 5H), 7.27 (dd, J = 7.8, 7.8 Hz, 2H), 7.04 (d, J = 8.2 Hz, 1H), 6.99 (d, J = 2.3 Hz, 2H), 6.91 (dd, J = 1.9, 8.2 Hz, 1H), 6.67 (d, J = 9.8 Hz, 1H), 5.44-5.39 (m, 1H), 4.61-4.60 (m, 1H), 4.35-4.27 (m, 4H), 4.16-4.08 (m, 4H), 4.02 (d, J = 13.7 Hz, 1H), 3.85 (d, J = 6.0 Hz, 2H), 3.28 (d, J = 12.3 Hz, 2H), 3.20 (d, J = 7.4 Hz, 3H), 2.79-2.68 (m, 4H), 2.11-2.06 (m, 1H), 1.96-1.86 (m, 2H), 1.76 (d, J = 13.2 Hz, 2H), 1.51-1.39 (m, 3H), 1.37-1.26 (m, 1H). | formate |
| 155 | 2.52 | 11 | (DMSO-d₆); d 10.50 (s, 2H), 9.44-9.44 (m, 1H), 9.20-9.20 (m, 2H), 8.74 (dd, J = 4.3, 4.3 Hz, 1H), 8.10 (d, J = 9.9 Hz, 1H), 7.98 (d, J = 7.9 Hz, 1H), 7.48 (s, 5H), 7.42 (s, 1H), 7.34 (d, J = 3.8 Hz, 4H), 7.32-7.21 (m, 3H), 7.14 (d, J = 8.3 Hz, 1H), 6.99 (d, J = 8.2 Hz, 1H), 6.89 (d, J = 7.8 Hz, 3H), 6.64 (s, 1H), 6.58 (d, J = 9.9 Hz, 1H), 6.34-6.12 (m, 1H), 5.39-5.35 (m, 1H), 4.44 (d, J = 12.5 Hz, 1H), 4.31-4.19 (m, 4H), 4.02 (d, J = 6.4 Hz, 2H), 3.86-3.77 (m, 4H), 3.34 (d, J = 11.8 Hz, 2H), 3.11-3.01 (m, 4H), 2.96-2.87 (m, 2H), 2.70-2.64 (m, 1H), 2.03-2.00 (m, 1H), 1.82-1.67 (m, 6H), 1.42-1.24 (m, 3H), 1.20-1.11 (m, 1H). | TFA |

311
Example 25
312
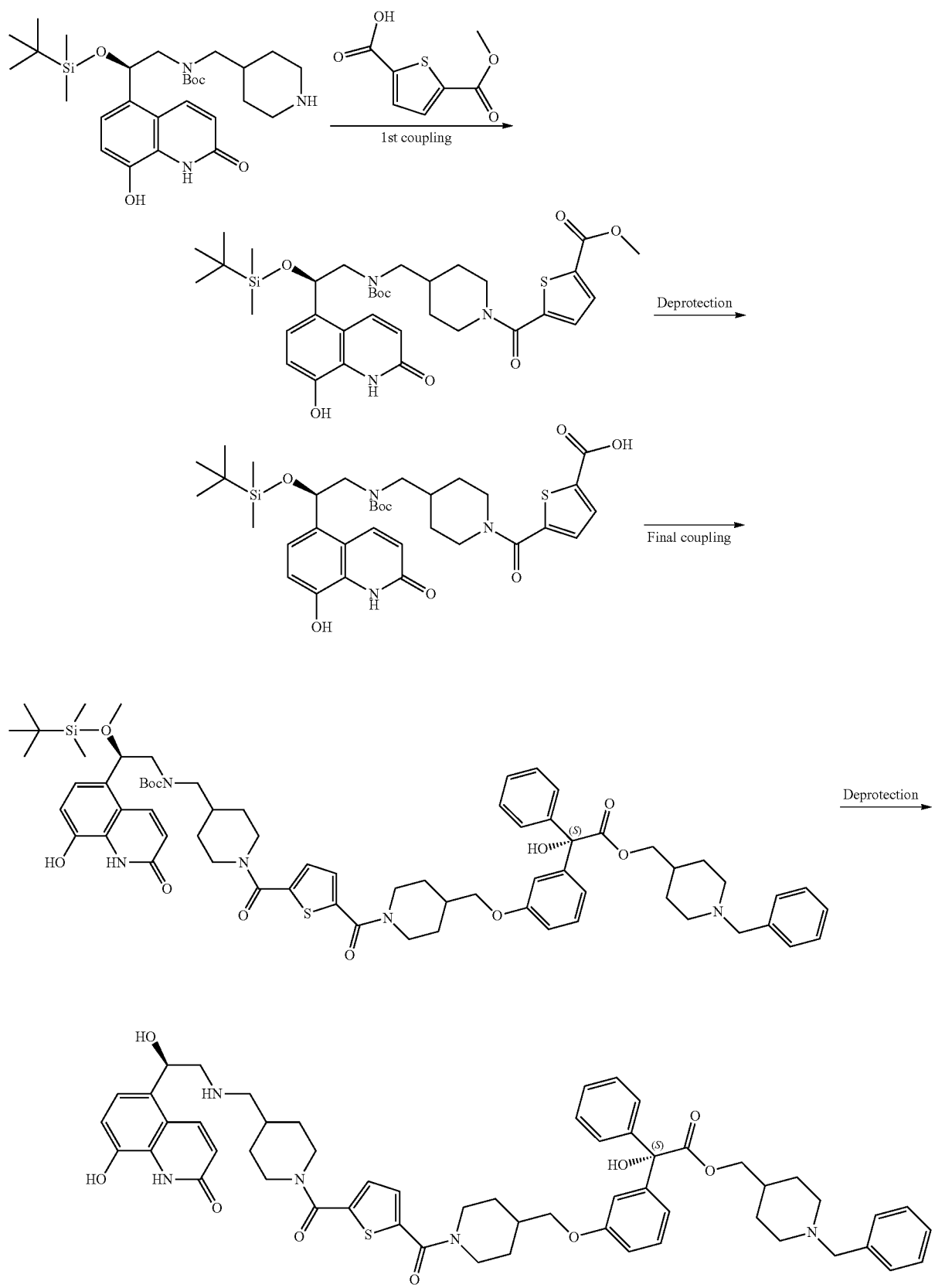

(1-Benzylpiperidin-4-yl)methyl (S)-2-hydroxy-2-(3-((1-(5-(4-((((R)-2-hydroxy-2-(8-hydroxy-2-oxo-1,2-dihydroquinolin-5-yl)ethyl)amino)methyl)piperidine-1-carbonyl)thiophene-2-carbonyl)piperidin-4-yl)methoxy)phenyl)-2-phenylacetate (Compound 156)

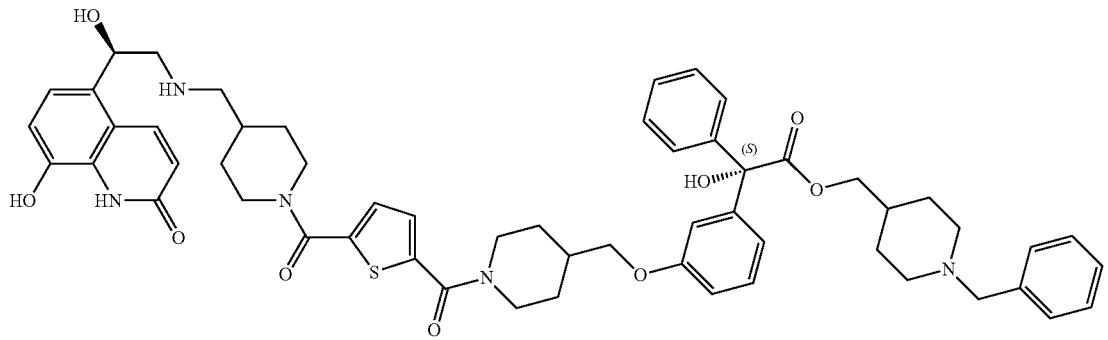

The title compound was prepared using a similar route to that described in Example 23 using previously described compounds (see Procedures section). A base promoted deprotection step (as described in Example 1 Step 4) was utilized prior to the final coupling step.

The following compounds were prepared by this method:

| N | Structure |
|---|---|
| 157 | 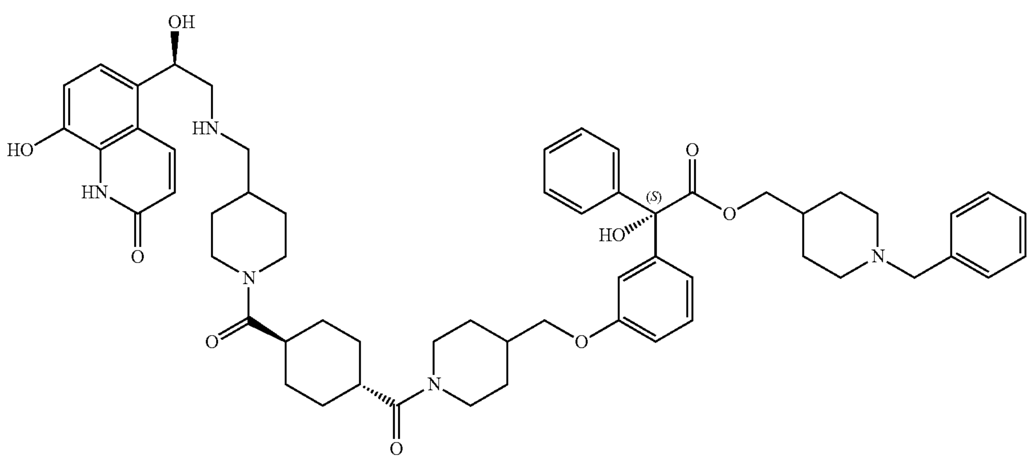 |

| N | Rt (min) | Method | NMR data (400 MHz) | Salt (2 eq unless stated) |
|---|---|---|---|---|
| 156 | 2.53 | 11 | (MeOD); δ 8.53 (s, 1H), 8.41 (d, J = 9.9 Hz, 1H), 7.40-7.25 (m, 14H), 7.05 (d, J = 8.2 Hz, 1H), 6.99-6.97 (m, 2H), 6.90 (dd, J = 2.1, 8.0 Hz, 1H), 6.70 (d, J = 9.8 Hz, 1H), 5.42 (dd, J = 5.0, 8.5 Hz, 1H), 4.44 (s, 4H), 4.11 (dd, J = 2.8, 6.4 Hz, 2H), 3.87-3.81 (m, 4H), 3.23-3.05 (m, 7H), 3.00 (d, J = 6.9 Hz, 3H), 2.39 (t, J = 12.9 Hz, 2H), 2.15-2.09 (m, 2H), 1.98-1.88 (m, 4H), 1.80-1.74 (m, 1H), 1.67 (d, J = 12.8 Hz, 2H), 1.45-1.29 (m, 6H). | mono-formate |
| 157 | 2.55 | 11 | (DMSO-d$_6$, 100° C.); δ 8.20 (d, J = 9.9 Hz, 1H), 7.48-7.46 (m, 5H), 7.41-7.21 (m, 6H), 7.16 (d, J = 8.3 Hz, 1H), 7.02 (d, J = 8.2 Hz, 1H), 6.97-6.93 (m, 2H), 6.89-6.86 (m, 1H), 6.58 (d, J = 9.9 Hz, 1H), 5.38 (dd, J = 4.8, 8.2 Hz, 1H), 4.26-4.06 (m, 8H), 3.83 (d, J = 6.3 Hz, 2H), 3.20-3.14 (m, 2H), 3.01-2.98 (m, 2H), 2.93-2.76 (m, 7H), 2.61-2.60 (m, 2H), 2.10-1.99 (m, 2H), 1.80-1.69 (m, 12H), 1.62-1.48 (m, 6H), 1.29-1.11 (m, 4H). | TFA |

Example 26
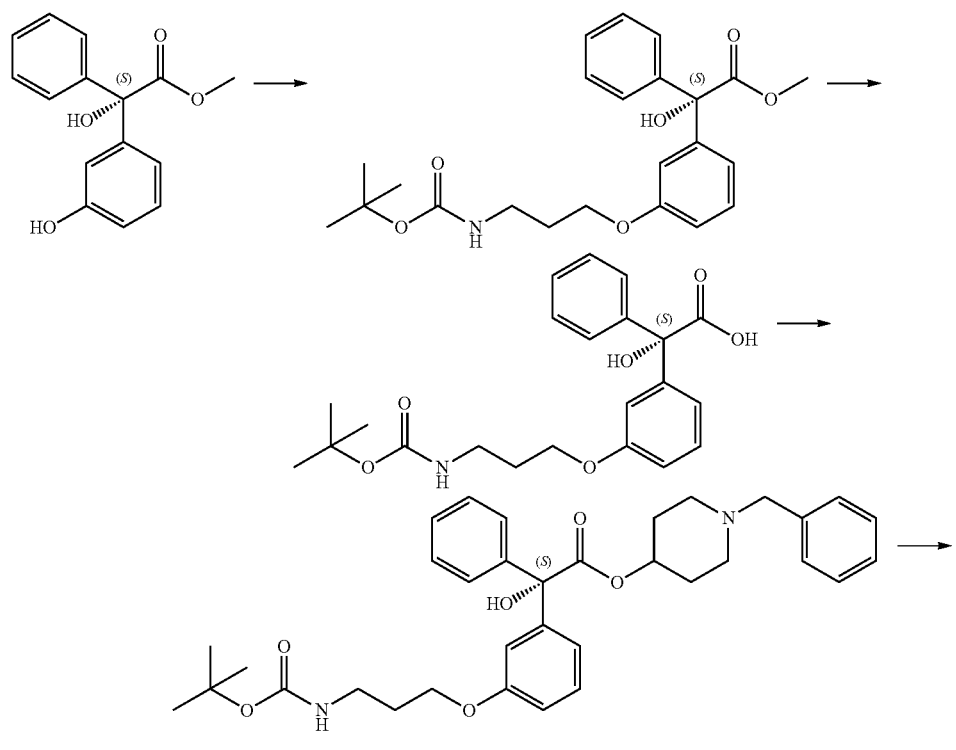
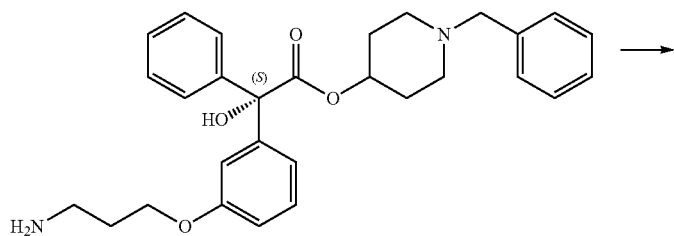
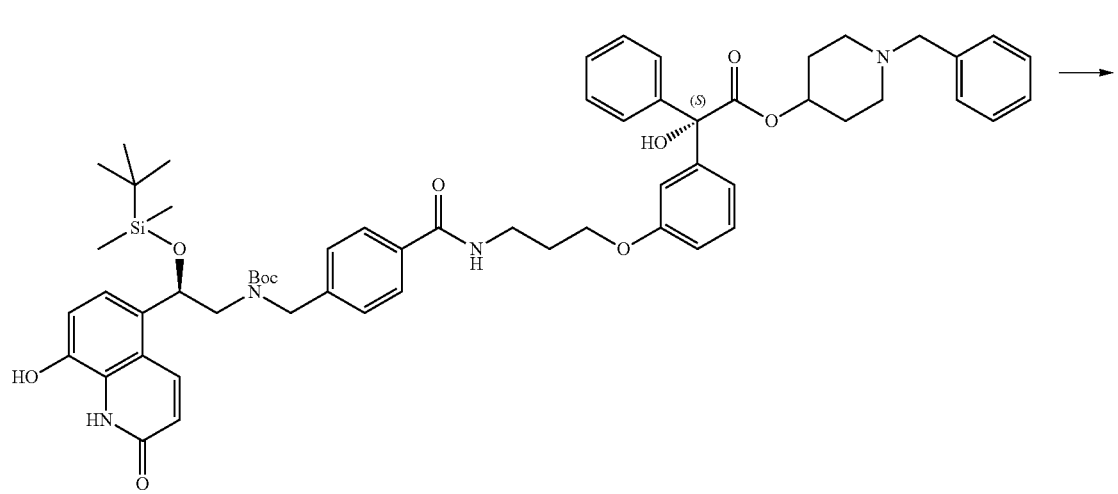

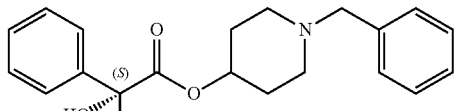
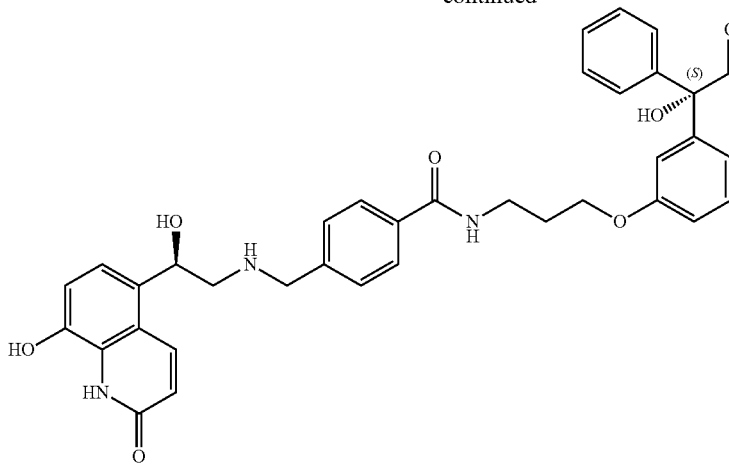

1-Benzylpiperidin-4-yl (S)-2-hydroxy-2-(3-(3-(4-((((R)-2-hydroxy-2-(8-hydroxy-2-oxo-1,2-dihydroquinolin-5-yl)ethyl)amino)methyl)benzamido)propoxy)phenyl)-2-phenylacetate (Compound 158)

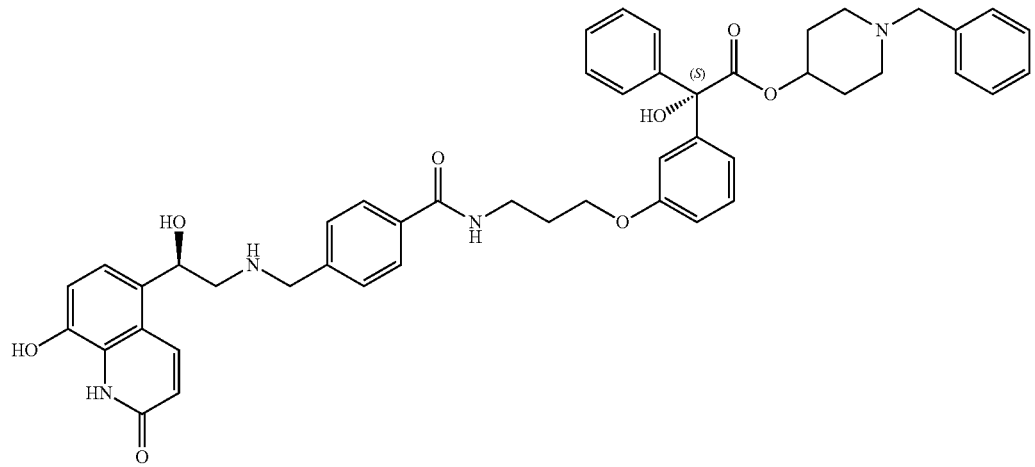

Step 1; Methyl (S)-2-(3-(3-((tert-butoxycarbonyl)amino)propoxy)phenyl)-2-hydroxy-2-phenylacetate

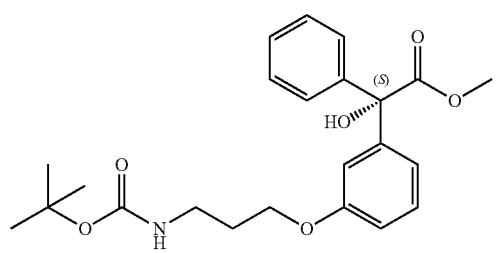

To a stirred solution of methyl (S)-2-hydroxy-2-(3-hydroxyphenyl)-2-phenylacetic acid (3.0 g, 11.62 mmol) in DMF (11 mL) was added potassium carbonate (3.21 g, 23.23 mmol) followed by a solution of tert-butyl (3-bromopropyl) carbamate (3.46 g, 14.52 mmol) in DMF (11 mL). The reaction mixture was heated at 60° C. for 18 hours. The reaction mixture was dissolved in ethyl acetate and washed with aqueous 1M sodium hydroxide (×2), water and brine. The organic phase was dried over anhydrous magnesium sulfate, filtered and the filtrate evaporated at reduced pressure. The residue was purified by flash column chromatography (eluent 100% i-hexane to 60% ethyl acetate/i-hexane) to afford the title compound (4.71 g, 98%).

$^1$H NMR (400 MHz, DMSO-$d_6$); δ 7.38-7.27 (m, 6H), 6.95-6.88 (m, 4H), 6.70 (s, 1H), 3.96 (dd, J=6.3, 6.3 Hz, 2H), 3.77 (s, 3H), 3.11 (q, J=6.5 Hz, 2H), 1.90-1.81 (m, 2H), 1.42 (s, 9H).

Step 2; (S)-2-(3-(3-((tert-Butoxycarbonyl)amino) propoxy)phenyl)-2-hydroxy-2-phenylacetic acid

Step 3; 1-Benzylpiperidin-4-yl (S)-2-(3-(3-aminopropoxy)phenyl)-2-hydroxy-2-phenylacetate dihydrochloride

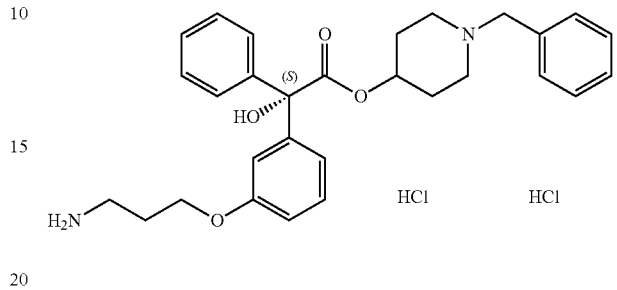

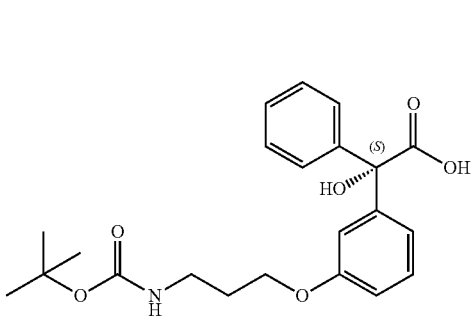

To a stirred solution of methyl (S)-2-(3-(3-((tert-butoxycarbonyl)amino)propoxy)-phenyl)-2-hydroxy-2-phenylacetate (4.71 g, 11.34 mmol) in THF/methanol (57 mL/57 mL) was added aqueous 2M sodium hydroxide (57 mL). The reaction mixture was stirred at room temperature for 18 hours. The solvent was concentrated under reduced pressure to ⅓ volume. The solution was washed with ether and the pH adjusted to pH2 and the solution was extracted with ethyl acetate. The organic phase was dried over anhydrous magnesium sulfate, filtered and the filtrate evaporated at reduced pressure to afford the title compound (4.1 g, 90%).

$^1$H NMR (400 MHz, DMSO-$d_6$); δ 7.45-7.41 (m, 2H), 7.39-7.26 (m, 4H), 7.01-6.96 (m, 2H), 6.94-6.87 (m, 2H), 6.37 (br s), 3.96 (dd, J=6.3, 6.3 Hz, 2H), 3.14-3.07 (m, 2H), 1.89-1.81 (m, 2H), 1.42 (s, 9H).

Carbonyldiimidazole (0.242 g, 1.50 mmol) was added to a solution of (S)-2-(3-(3-((tert-butoxycarbonyl)amino) propoxy)phenyl)-2-hydroxy-2-phenylacetic acid (0.20 g, 0.5 mmol) in DMF (2 mL) and the mixture stirred at room temperature for 15 mins. 1-Benzylpiperidin-4-ol (0.381 g, 1.99 mmol) in DMF (0.5 mL) was added and the reaction mixture heated at 60° C. for 18 hours. The reaction mixture was diluted with ethyl acetate and washed with saturated aqueous sodium carbonate (×2) and brine. The organic phase was dried over anhydrous magnesium sulfate, filtered and the filtrate evaporated at reduced pressure. The residue was purified by flash column chromatography (eluent 100% DCM to 5% MeOH/DCM) to afford major product. This material was dissolved in dioxane (1 mL) and a solution of 4M HCl in dioxane (2 mL) added. The reaction mixture stirred at room temperature for 1.5 hours. The solvent was evaporated at reduced pressure to afford the title compound (0.157 g, 57%).

LCMS Method 11; Rt 2.35; ES$^+$475.

Step 4; 1-Benzylpiperidin-4-yl (S)-2-hydroxy-2-(3-(3-(4-((((R)-2-hydroxy-2-(8-hydroxy-2-oxo-1,2-dihydroquinolin-5-yl)ethyl)amino)methyl)benzamido)propoxy)phenyl)-2-phenylacetate (Compound 158)

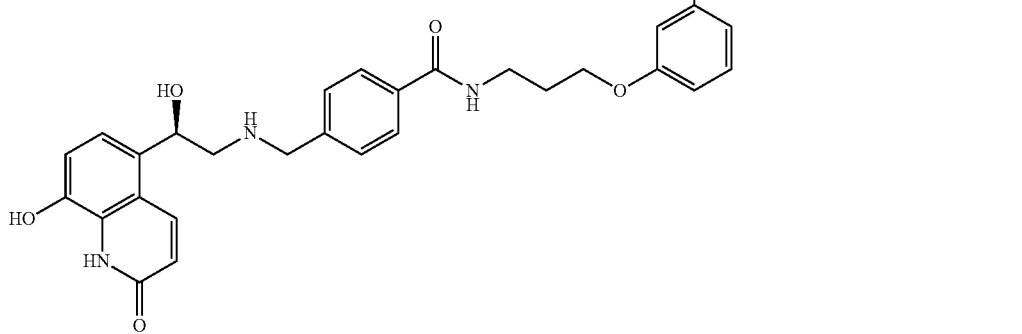

The title compound was prepared as described in Example 5.
The following compounds were prepared according to Example 26:
| N | Structure |
|---|---|
| 159 | 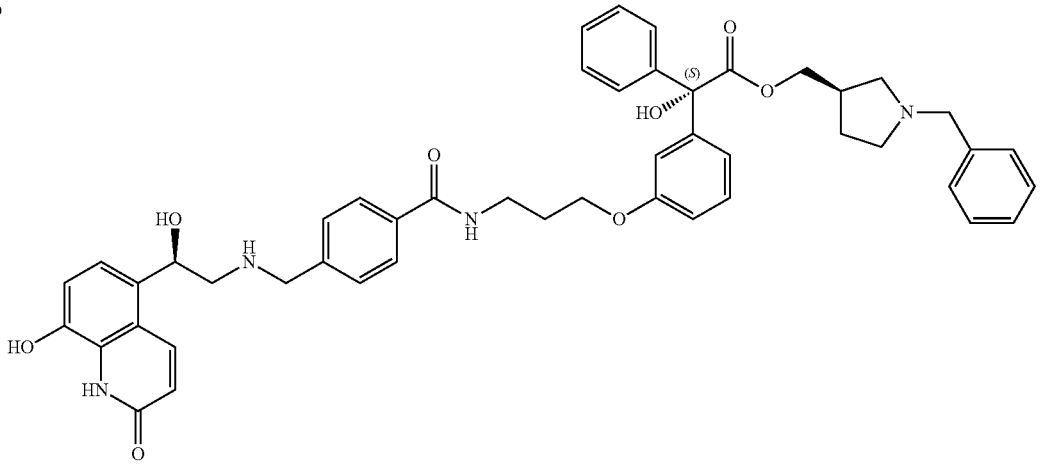 |
| 160 | 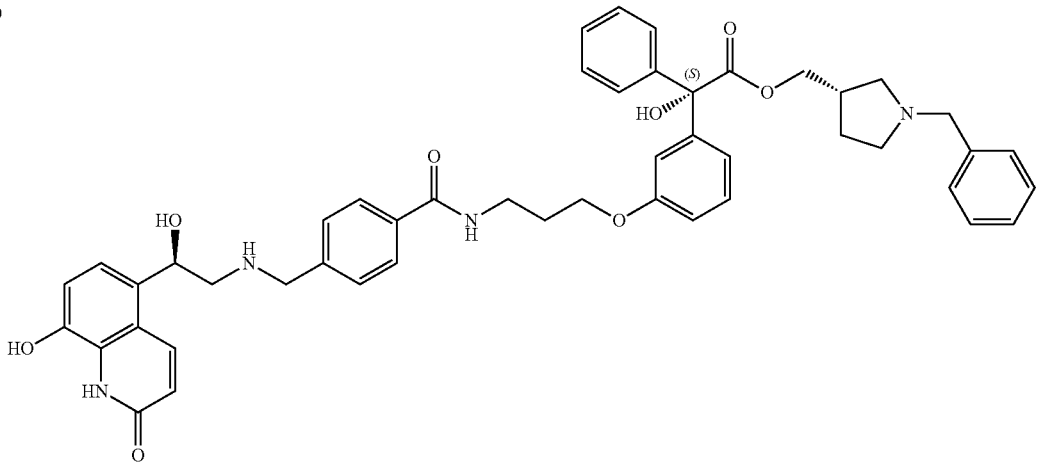 |
| 161 | 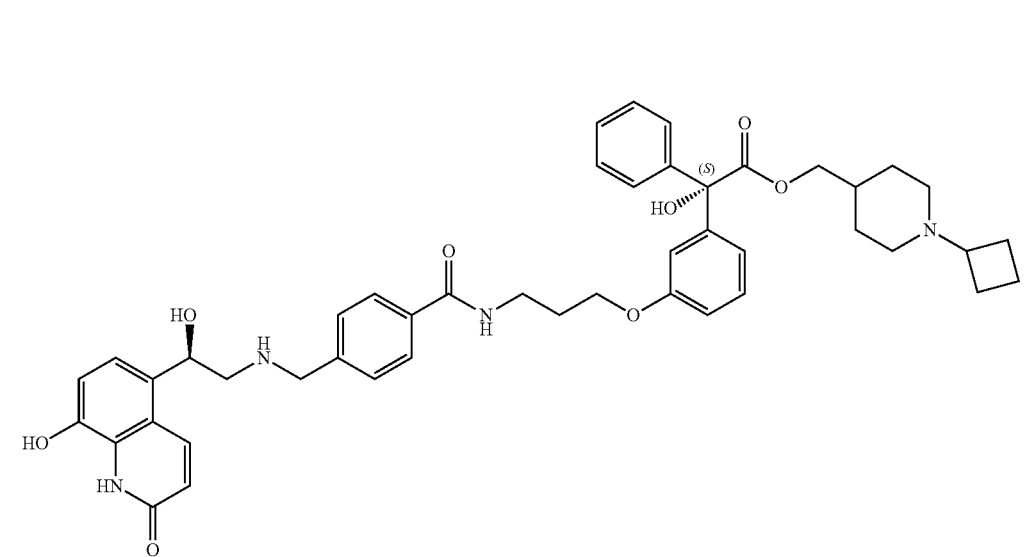 |

-continued
| N | Structure |
|---|---|
| 162 | 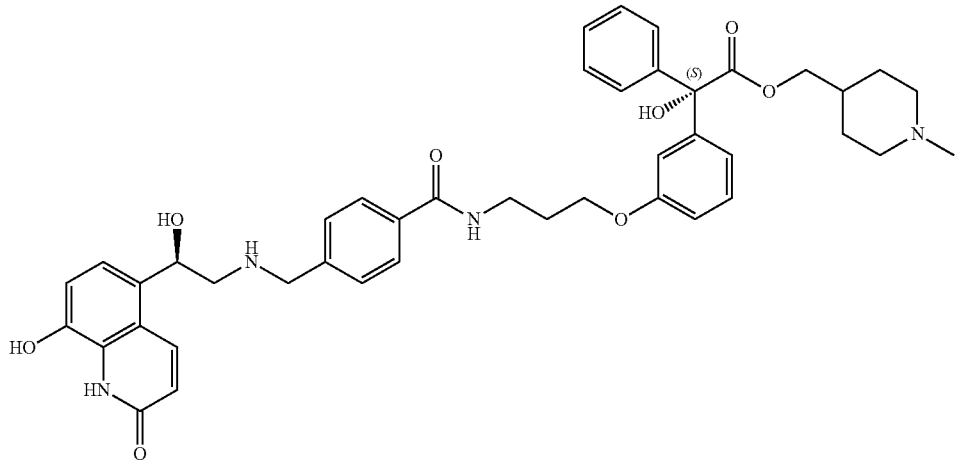 |
| 163 | 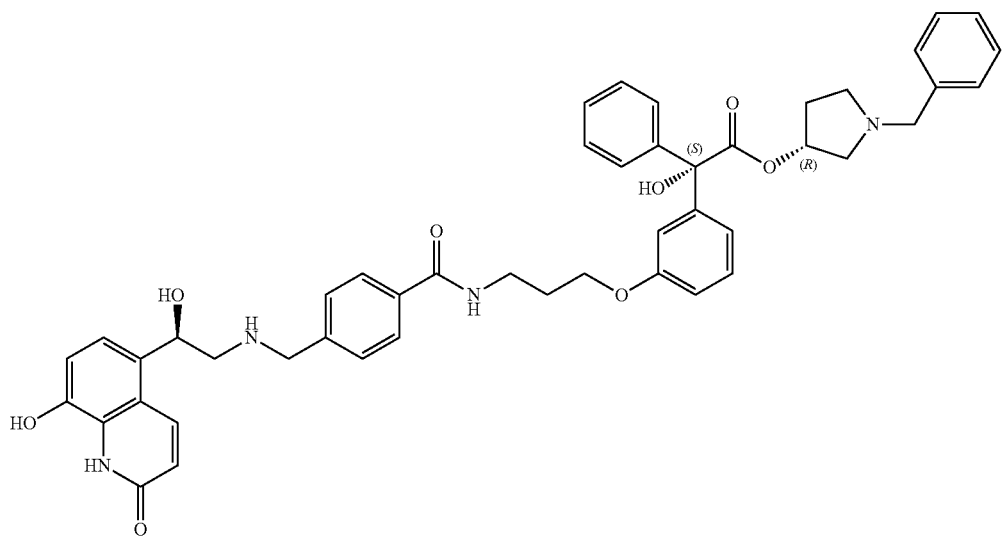 |
| 164 | 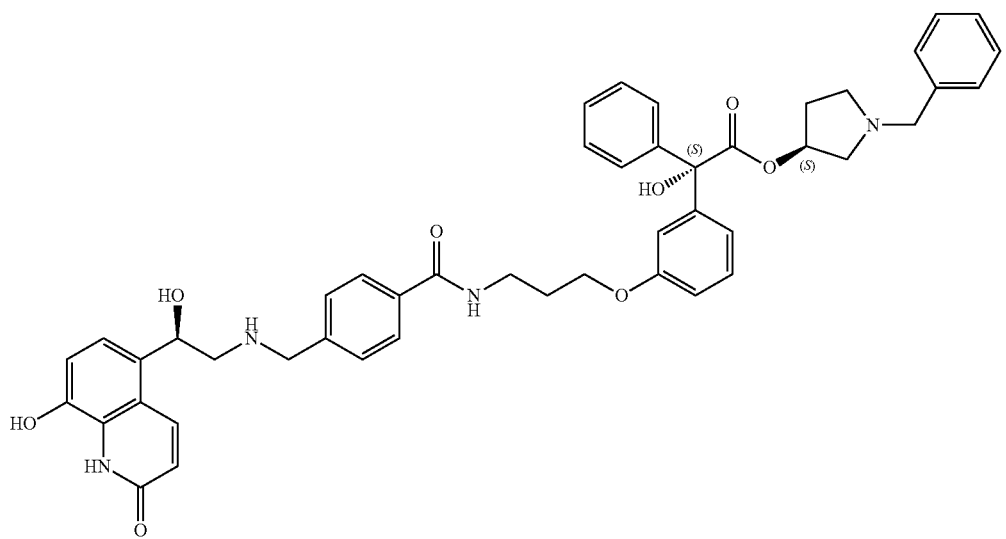 |

| N | Structure |
|---|---|
| 165 | 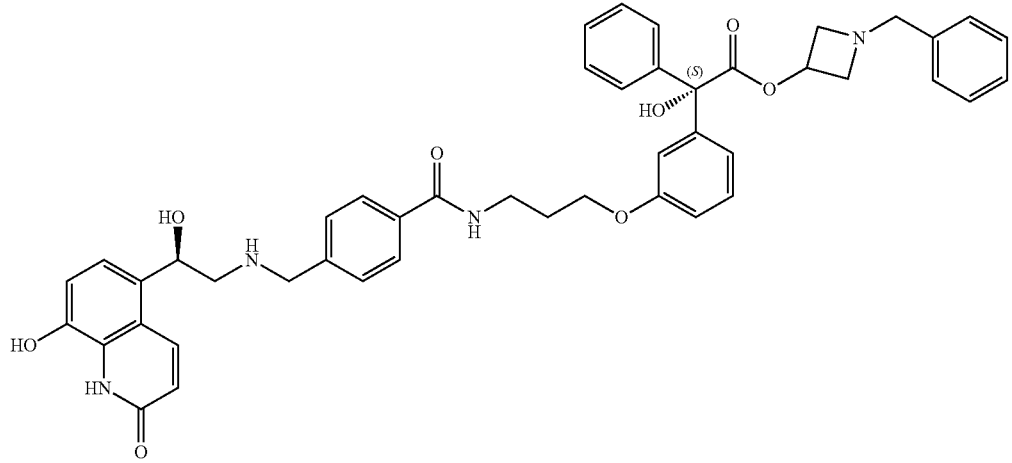 |

| N | Rt (min) | Method | NMR data (400 MHz) | Salt (2 eq unless stated) |
|---|---|---|---|---|
| 158 | 2.42 | 11 | (MeOD); δ 8.44 (s, 2H), 8.30 (d, J = 9.9 Hz, 1H), 7.89 (d, J = 8.2 Hz, 2H), 7.60 (d, J = 8.2 Hz, 2H), 7.45-7.34 (m, 10H), 7.29 (dd, J = 8.1, 8.1 Hz, 2H), 7.05-6.93 (m, 4H), 6.66 (d, J = 9.8 Hz, 1H), 5.42 (t, J = 6.6 Hz, 1H), 5.12-5.04 (m, 1H), 4.33 (s, 2H), 4.09 (t, J = 6.0 Hz, 2H), 3.82 (s, 2H), 3.59 (t, J = 6.8 Hz, 2H), 3.21 (d, J = 6.7 Hz, 2H), 2.85-2.76 (m, 2H), 2.62-2.62 (m, 2H), 2.16-2.07 (m, 2H), 2.01-1.96 (m, 2H), 1.90-1.82 (m, 2H). | formate |
| 159 | 2.44 | 11 | (DMSO-d$_6$); δ 10.54 (m, 2H), 9.96-9.96 (m, 1H), 9.18 (s, 2H), 8.66 (dd, J = 5.4, 5.4 Hz, 1H), 8.13 (d, J = 8.9 Hz, 1H), 7.95 (d, J = 8.1 Hz, 2H), 7.66 (d, J = 8.1 Hz, 2H), 7.52 (d, J = 5.3 Hz, 6H), 7.41-7.38 (m, 2H), 7.36 (s, 3H), 7.33-7.25 (m, 1H), 7.18 (d, J = 8.3 Hz, 1H), 7.03 (d, J = 8.1 Hz, 1H), 6.97-6.91 (m, 3H), 6.63 (d, J = 9.9 Hz, 1H), 6.25 (s, 1H), 5.39 (d, J = 7.8 Hz, 1H), 4.43-4.15 (m, 6H), 4.07-4.02 (m, 3H), 3.47-3.47 (m, 4H), 3.17-3.02 (m, 3H), 2.88-2.73 (m, 1H), 2.19-2.19 (m, 1H), 2.06-1.98 (m, 2H), 1.84-1.76 (m, 1H). | TFA |
| 160 | 2.44 | 11 | (DMSO-d$_6$); δ 10.54 (m, 2H), 10.01 (s, 1H), 9.18 (s, 2H), 8.66 (dd, J = 5.6, 5.6 Hz, 1H), 8.13 (d, J = 9.9 Hz, 1H), 7.95 (d, J = 8.1 Hz, 2H), 7.66 (d, J = 8.3 Hz, 2H), 7.52 (m, 5H), 7.40-7.34 (m, 5H), 7.30 (dd, J = 8.0, 8.0 Hz, 1H), 7.18 (d, J = 8.1 Hz, 1H), 7.03 (d, J = 8.1 Hz, 1H), 6.98-6.90 (m, 3H), 6.78-6.71 (m, 1H), 6.63 (d, J = 9.9 Hz, 1H), 6.24 (s, 1H), 5.40 (d, J = 9.3 Hz, 1H), 4.41-4.15 (m, 7H), 4.08-4.01 (m, 2H), 3.48 (dd, J = 6.9, 11.1 Hz, 4H), 3.17-3.05 (m, 4H), 2.87-2.77 (m, 1H), 2.06-1.98 (m, 2H), 1.83-1.74 (m, 1H). | TFA |
| 161 | 2.41 | 11 | (DMSO-d$_6$); δ 8.54-8.47 (m, 1H), 8.20 (s, 2H), 8.13 (dd, J = 3.1, 9.2 Hz, 1H), 7.79 (d, J = 8.3 Hz, 2H), 7.41 (d, J = 8.3 Hz, 2H), 7.33 (d, J = 4.4 Hz, 4H), 7.32-7.22 (m, 2H), 7.07 (d, J = 8.2 Hz, 1H), 6.94-6.87 (m, 4H), 6.48 (d, J = 9.8 Hz, 1H), 5.10 (dd, J = 4.3, 8.0 Hz, 1H), 3.99 (dd, J = 4.0, 5.9 Hz, 4H), 3.84 (s, 2H), 3.40 (td, J = 7.6, 19.3 Hz, 2H), 2.77-2.61 (m, 5H), 1.99-1.88 (m, 4H), 1.77-1.47 (m, 9H), 1.14-1.05 (m, 2H). | formate |
| 162 | 2.46 | 11 | (DMSO-d$_6$); δ 8.50 (t, J = 7.1 Hz, 1H), 8.22 (s, 2H), 8.13 (d, J = 9.9 Hz, 1H), 7.79 (d, J = 8.2 Hz, 2H), 7.41 (d, J = 8.3 Hz, 2H), 7.33 (d, J = 4.4 Hz, 4H), 7.32-7.22 (m, 2H), 7.07 (d, J = 8.2 Hz, 1H), 6.94-6.87 (m, 4H), 6.48 (d, J = 9.9 Hz, 1H), 5.10 (dd, J = 4.3, 8.0 Hz, 1H), 4.02-3.96 (m, 4H), 3.83 (s, 2H), 3.44-3.37 (m, 2H), 2.79-2.64 (m, 4H), 2.17 (s, 3H), 1.99-1.87 (m, 4H), 1.53-1.45 (m, 3H), 1.21-1.10 (m, 2H). | formate |
| 163 | 2.41 | 11 | (MeOD); δ 8.43 (s, 2H), 8.30 (d, J = 9.8 Hz, 1H), 7.90 (d, J = 8.3 Hz, 2H), 7.61 (d, J = 8.3 Hz, 2H), 7.43 (dd, J = 1.7, 8.0 Hz, 2H), 7.38-7.24 (m, 10H), 7.05-6.99 (m, 3H), 6.92 (dd, J = 2.0, 8.2 Hz, 1H), 6.66 (d, J = 9.9 Hz, 1H), 5.46-5.39 (m, 2H), 4.34 (s, 2H), 4.06 (dd, J = 6.0, 6.0 Hz, 2H), 3.90-3.77 (m, 2H), 3.58 (dd, J = 6.8, 6.8 Hz, 2H), 3.22 (d, J = 6.7 Hz, 2H), 3.15 (dd, J = 5.5, 12.4 Hz, 1H), 3.01-2.82 (m, 3H), 2.38-2.28 (m, 1H), 2.10 (ddd, J = 8.2, 8.2, 8.2 Hz, 2H), 2.00-1.93 (m, 1H). | formate |
| 164 | 2.41 | 11 | (MeOD); δ 8.43 (s, 2H), 8.30 (d, J = 9.8 Hz, 1H), 7.90 (d, J = 8.2 Hz, 2H), 7.61 (d, J = 8.2 Hz, 2H), 7.44-7.24 (m, 12H), 7.05-7.00 (m, 3H), 6.92 (dd, J = 2.3, 8.3 Hz, 1H), 6.66 (d, J = 9.8 Hz, 1H), 5.41 (q, J = 6.5 Hz, 2H), 4.33 (s, 2H), 4.06 (dd, J = 6.0, 6.0 Hz, 2H), 3.81 (q, J = 12.5 Hz, 2H), 3.58 (dd, J = 6.8, 6.8 Hz, 2H), 3.22 (d, J = 6.7 Hz, 2H), 3.13 (dd, J = 5.7, 12.5 Hz, 1H), 2.97-2.88 (m, 2H), 2.88-2.79 (m, 1H), 2.38-2.27 (m, 1H), 2.14-2.06 (m, 2H), 1.98-1.91 (m, 1H). | formate |

| N | Rt (min) | Method | NMR data (400 MHz) | Salt (2 eq unless stated) |
|---|---|---|---|---|
| 165 | 2.41 | 11 | (MeOD); δ 8.46 (s, 2H), 8.31 (d, J = 9.9 Hz, 1H), 7.89 (d, J = 8.3 Hz, 2H), 7.60 (d, J = 8.3 Hz, 2H), 7.44-7.41 (m, 2H), 7.38-7.24 (m, 10H), 7.05-6.99 (m, 3H), 6.93 (dd, J = 2.1, 8.2 Hz, 1H), 6.66 (d, J = 9.8 Hz, 1H), 5.41 (dd, J = 5.7, 7.7 Hz, 1H), 5.25-5.18 (m, 1H), 4.31 (s, 2H), 4.08 (t, J = 6.0 Hz, 2H), 3.85 (dd, J = 6.8, 9.7 Hz, 2H), 3.77 (s, 2H), 3.59 (t, J = 6.8 Hz, 2H), 3.35-3.30 (m, 2H), 3.23-3.19 (m, 2H), 2.15-2.07 (m, 2H). | formate |

Example 27. 1-Benzylpiperidin-4-yl(S)-2-hydroxy-2-(3-((4-((3-(4-((((R)-2-hydroxy-2-(8-hydroxy-2-oxo-1,2-dihydroquinolin-5-yl)ethyl)amino)methyl)phenyl)ureido)-methyl)benzyl)oxy)phenyl)-2-phenylacetate (Compound 166)

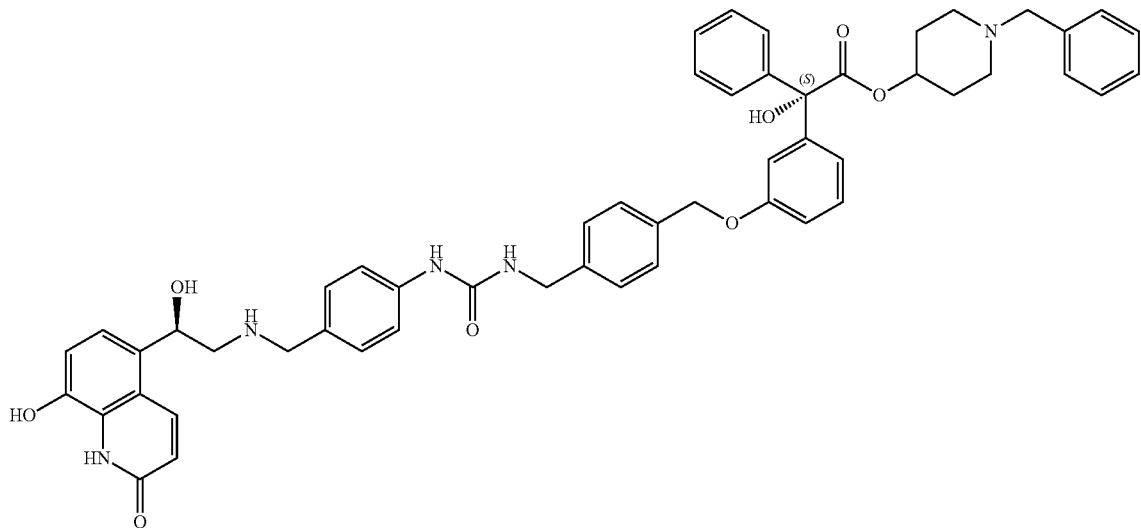

To a suspension of (R)-4-(((tert-butoxycarbonyl)(2-((tert-butyldimethylsilyl)oxy)-2-(8-hydroxy-2-oxo-1,2-dihydroquinolin-5-yl)ethyl)amino)methyl)benzoic acid (0.337 g, 0.59 mmol) in toluene (5 mL) was added triethylamine (0.108 mL, 0.77 mmol) and diphenyl phosphoraylazide (0.153 mL, 0.71 mmol). The reaction mixture was heated at 90° C. for 3.5 hours. A solution of 1-benzylpiperidin-4-yl (S)-2-(3-((4-(aminomethyl)-benzyl)oxy)phenyl)-2-hydroxy-2-phenylacetate dihydrochloride (0.37 g, 0.59 mmol) and triethylamine (0.165 mL, 1.19 mmol) in DMF (2 mL) was added and the reaction mixture heated at 90° C. for 18 hours. The reaction mixture was diluted with ethyl acetate and washed with saturated aqueous sodium hydrogen carbonate and brine. The organic phase was dried over anhydrous magnesium sulfate, filtered and the filtrate evaporated at reduced pressure. The residue was dissolved in MeCN (1 mL) and a solution of HCl-dioxan (4 mL) added. The reaction mixture was stirred at room temperature for 1 hour. The solvent was evaporated at reduced pressure and the residue purified by reverse preparative HPLC.

The following compounds were prepared by this method:

| N | Structure |
|---|---|
| 167 | *(structure)* |
| 168 | *(structure)* |

| N | Rt (min) | Method | NMR data (400 MHz) | Salt (2 eq unless stated) |
|---|---|---|---|---|
| 166 | 2.60 | 11 | (MeOD); δ 8.57 (s, 1H), 8.26 (d, J = 9.8 Hz, 1H), 7.47 (d, J = 8.5 Hz, 2H), 7.39-7.32 (m, 16H), 7.29-7.23 (m, 2H), 7.04-6.94 (m, 4H), 6.65 (d, J = 9.8 Hz, 1H), 5.34 (dd, J = 4.3, 9.0 Hz, 1H), 5.05 (s, 2H), 4.42 (s, 2H), 4.11 (s, 2H), 4.10-4.03 (m, 2H), 3.64 (s, 2H), 3.16-3.06 (m, 2H), 2.95 (d, J = 11.8 Hz, 2H), 2.17 (dd, J = 9.9, 12.2 Hz, 2H), 1.71-1.65 (m, 1H), 1.57 (d, J = 13.2 Hz, 2H), 1.33-1.18 (m, 2H). | TFA |
| 167 | 2.57 | 11 | (MeOD); δ 8.57 (s, 1H), 8.22 (d, J = 9.9 Hz, 1H), 7.40-7.18 (m, 18H), 7.03-6.95 (m, 4H), 6.86 (dd, J = 1.9, 8.1 Hz, 1H), 6.64 (d, J = 9.9 Hz, 1H), 5.32 (dd, J = 5.0, 8.4 Hz, 1H), 5.05 (s, 2H), 4.43 (s, 2H), 4.09 (s, 2H), 4.06 (dd, J = 3.5, 6.5 Hz, 2H), 3.85 (s, 3H), 3.53 (s, 2H), 3.09-3.05 (m, 2H), 2.91-2.86 (m, 2H), 2.08-1.99 (m, 2H), 1.65-1.62 (m, 1H), 1.54 (d, J = 13.2 Hz, 2H), 1.32-1.19 (m, 2H). | mono-formate |
| 168 | 2.58 | 11 | (MeOD); δ 8.57 (s, 1H), 8.25 (d, J = 9.9 Hz, 1H), 8.08 (d, J = 8.3 Hz, 1H), 7.37-7.24 (m, 18H), 7.08-6.94 (m, 4H), 6.64 (d, J = 9.9 Hz, 1H), 5.32 (dd, J = 4.4, 8.7 Hz, 1H), 5.05 (s, 2H), 4.93 (d, J = 2.1 Hz, 1H), 4.42 (s, 2H), 4.09-4.04 (m, 4H), 3.91 (s, 3H), 3.60 (s, 2H), 3.11-3.05 (m, 2H), 2.95-2.88 (m, 2H), 2.11 (t, J = 11.4 Hz, 1H), 1.71-1.60 (m, 1H), 1.59-1.53 (m, 2H), 1.24 (ddd, J = 6.3, 12.3, 18.3 Hz, 2H). | mono-formate |

Biological Characterization.

Example 28. M3 Receptor Radioligand Binding Assay

Human M3 receptor membranes (15 ug/well) from Perkin Elmer were incubated with 0.52 nM Scopolamine Methyl Chloride, (N-methyl-3H) with or without test compounds, or a saturating concentration of Atropine (5 μM) for the determination of non-specific binding. The assay was carried out in 96-well polypropylene plates in a volume of 250 ul. The assay buffer used was 50 mM Tris-HCl, 154 mM NaCl (pH 7.4). The final assay concentration of DMSO was 0.5% (v/v). The plates were sealed and incubated for 2 h at room temperature on an orbital shaker (slow speed). Membranes were harvested onto 96-well unifilter GF/C filter plates pre-treated with 0.5% polyethyleneimine (v/v), using a filter manifold, washed four times with 200 ul of assay buffer. The plates were dried before addition of 50 μl of microscint-0, sealed then read in a Trilux Microbeta scintillation counter. IC50 values are determined from competition curves using a non-linear curve fitting program. Ki values were calculated from 1050 values by the Cheng and Prusoff equation.

The M3 Ki values of the compounds according to the invention are less than 50 nM, most of them even less than 10 nM. The preferred compounds according to the invention have Ki value less than 4 nM or even less than 3 nM for the enantiomeric mixture and at least for one of the enantiomeric pure form (S or R) on the stereogenic center (2).

Example 29. β2 Adrenoceptor Radioligand Binding Assay

Human $β_2$ adrenoceptor membranes (7.5 ug/well) from Perkin Elmer were incubated with 0.3 nM 125-I Cyanopindolol with or without test compounds, or a saturating concentration of s-propranolol (2 μM) for the determination of non-specific binding. The assay was carried out in 96-well polypropylene plates in a volume of 200 ul. The assay buffer used was 25 mM HEPES, 0.5% BSA (w/v), 1 mM EDTA, 0.02% ascorbic acid (v/v), (pH 7.4). The final assay concentration of DMSO was 0.5% (v/v). The plates were sealed and incubated for 1 h at room temperature on an orbital shaker (slow speed). Membranes were harvested onto 96-well unifilter GF/C filter plates pre-treated with 0.5% polyethyleneimine (v/v), using a filter manifold, washed six times with 200 ul of wash buffer containing 10 mM HEPES and 500 mM NaCl. The plates were dried before addition of 50 μl of microscint-0, sealed then read in a Trilux Microbeta scintillation counter. 1050 values are determined from competition curves using a non-linear curve fitting program. Ki values were calculated from 1050 values by the Cheng and Prusoff equation.

The β2 Ki values of the compounds according to the invention are less than 50 nM, most of them even less than 10 nM.

In the following table the compounds tested are classified in terms of binding affinity according to the following ranges:

| No | M3 | B2 |
|---|---|---|
| 1 | ++ | +++ |
| 2 | ++ | ++ |
| 3 | ++ | +++ |
| 4 | ++ | +++ |
| 5 | ++ | ++ |
| 6 | + | +++ |
| 7 | + | ++ |
| 8 | + | ++ |
| 9 | ++ | +++ |
| 10 | ++ | ++ |
| 11 | +++ | +++ |
| 12 | + | + |
| 12A | ++ | +++ |
| 13 | +++ | +++ |
| 14 | + | +++ |
| 15 | +++ | +++ |
| 16 | + | ++ |
| 17 | + | ++ |
| 18 | + | +++ |
| 19 | ++ | +++ |
| 20 | + | +++ |
| 21 | ++ | +++ |
| 22 | + | +++ |
| 23 | ++ | ++ |
| 24 | + | +++ |
| 25 | ++ | +++ |
| 26 | ++ | +++ |
| 27 | + | ++ |
| 28 | ++ | ++ |
| 29 | + | +++ |
| 30 | ++ | ++ |
| 31 | +++ | +++ |
| 32 | ++ | +++ |
| 32A | ++ | +++ |
| 32B | +++ | +++ |
| 32C | ++ | +++ |
| 32D | ++ | +++ |
| 32E | ++ | ++ |
| 32F | ++ | +++ |
| 32G | ++ | ++ |
| 32H | ++ | +++ |
| 32I | +++ | +++ |
| 32J | ++ | +++ |
| 32K | ++ | +++ |
| 32L | ++ | + |
| 32M | ++ | + |
| 33 | +++ | +++ |
| 33A | ++ | +++ |
| 34 | + | ++ |
| 35 | +++ | +++ |
| 36 | +++ | +++ |
| 36A | ++ | ++ |
| 37 | +++ | +++ |
| 38 | +++ | +++ |
| 39 | ++ | +++ |
| 40 | ++ | ++ |
| 41 | ++ | ++ |
| 42 | +++ | +++ |
| 42A | +++ | ++ |
| 42B | +++ | +++ |
| 42B | ++ | +++ |
| 42C | ++ | +++ |
| 42D | ++ | +++ |
| 42E | ++ | +++ |
| 42F | ++ | +++ |
| 43 | +++ | +++ |
| 44 | ++ | +++ |
| 45 | ++ | ++ |
| 46 | ++ | +++ |
| 47 | ++ | +++ |
| 48 | + | +++ |
| 49 | ++ | +++ |
| 50 | ++ | + |
| 51 | ++ | +++ |
| 52 | ++ | +++ |
| 53 | + | + |
| 54 | ++ | +++ |
| 55 | ++ | + |
| 56 | + | + |
| 57 | ++ | ++ |
| 58 | ++ | ++ |
| 59 | ++ | ++ |
| 60 | ++ | ++ |

| | | |
|---|---|---|
| 61 | ++ | +++ |
| 62 | +++ | +++ |
| 63 | +++ | +++ |
| 64 | +++ | ++ |
| 65 | +++ | ++ |
| 66 | ++ | +++ |
| 67 | +++ | +++ |
| 68 | ++ | ++ |
| 69 | ++ | ++ |
| 70 | ++ | ++ |
| 71 | ++ | + |
| 72 | ++ | + |
| 73 | ++ | +++ |
| 74 | ++ | ++ |
| 75 | ++ | + |
| 76 | ++ | ++ |
| 77 | ++ | ++ |
| 78 | +++ | +++ |
| 79 | +++ | +++ |
| 80 | ++ | +++ |
| 81 | ++ | ++ |
| 82 | ++ | ++ |
| 83 | + | ++ |
| 84 | + | ++ |
| 85 | ++ | +++ |
| 86 | ++ | +++ |
| 87 | ++ | ++ |
| 88 | +++ | ++ |
| 89 | ++ | +++ |
| 90 | ++ | ++ |
| 91 | ++ | +++ |
| 92 | +++ | +++ |
| 93 | ++ | +++ |
| 94 | +++ | +++ |
| 95 | +++ | +++ |
| 96 | +++ | +++ |
| 97 | ++ | +++ |
| 98 | ++ | ++ |
| 99 | ++ | ++ |
| 100 | +++ | ++ |
| 101 | +++ | +++ |
| 102 | +++ | +++ |
| 103 | +++ | ++ |
| 104 | +++ | ++ |
| 105 | ++ | ++ |
| 106 | ++ | ++ |
| 107 | ++ | +++ |
| 108 | ++ | ++ |
| 109 | ++ | ++ |
| 110 | ++ | ++ |
| 111 | ++ | ++ |
| 112 | ++ | +++ |
| 113 | ++ | ++ |
| 114 | ++ | ++ |
| 115 | ++ | ++ |
| 116 | ++ | +++ |
| 117 | ++ | +++ |
| 118 | +++ | ++ |
| 119 | +++ | ++ |
| 120 | +++ | +++ |
| 121 | +++ | +++ |
| 122 | ++ | + |
| 123 | ++ | ++ |
| 124 | ++ | ++ |
| 125 | ++ | ++ |
| 126 | ++ | ++ |
| 127 | +++ | +++ |
| 128 | ++ | +++ |
| 129 | ++ | +++ |
| 130 | ++ | ++ |
| 131 | ++ | +++ |
| 132 | ++ | +++ |
| 133 | +++ | +++ |
| 134 | ++ | +++ |
| 135 | ++ | +++ |
| 136 | ++ | +++ |
| 137 | ++ | +++ |
| 138 | ++ | ++ |
| 139 | ++ | +++ |
| 140 | ++ | ++ |
| 141 | ++ | ++ |
| 142 | ++ | +++ |
| 143 | ++ | ++ |
| 144 | ++ | +++ |
| 145 | ++ | ++ |
| 146 | ++ | + |
| 147 | ++ | +++ |
| 148 | ++ | +++ |
| 149 | +++ | ++ |
| 150 | +++ | +++ |
| 151 | +++ | +++ |
| 152 | +++ | ++ |
| 153 | +++ | +++ |
| 154 | +++ | +++ |
| 155 | ++ | +++ |
| 156 | +++ | +++ |
| 157 | ++ | + |
| 158 | ++ | +++ |
| 159 | ++ | +++ |
| 160 | ++ | +++ |
| 161 | ++ | +++ |
| 162 | ++ | +++ |
| 163 | ++ | +++ |
| 164 | ++ | ++ |
| 165 | ++ | +++ |
| 166 | ++ | ++ |
| 167 | ++ | ++ |
| 168 | ++ | ++ |

+++: IC50 < 0.3 nM
++: IC50 in the range 0.3 to 3 nM
+: IC50 > 3 nM

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for the treatment of a broncho-obstructive disease, comprising administering to a subject in need thereof an effective amount of a compound of formula I

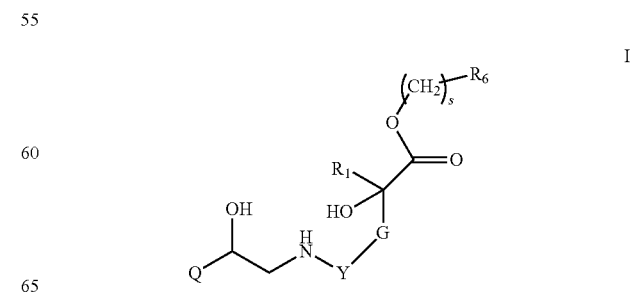

wherein:

Q is a group of formula

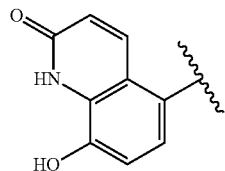 [SMILES: *c1ccc(O)c2[nH]c(=O)ccc12]

Y is Y2 or Y1 which are divalent groups of formula

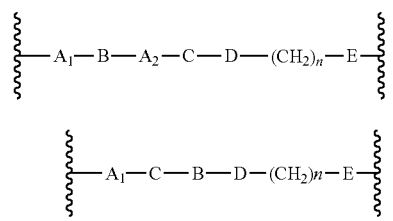

wherein

A1 and A2 are independently absent or selected from the group consisting of $(C_1-C_{12})$alkylene, $(C_3-C_8)$cycloalkylene, and $(C_3-C_8)$heterocycloalkylene, each of which are optionally substituted by one or more substituents selected from the group consisting of $(C_1-C_6)$alkyl, aryl$(C_1-C_6)$alkyl, and heteroaryl$(C_1-C_6)$alkyl;

B is absent or is selected from the group consisting of $(C_3-C_8)$cycloalkylene, $(C_3-C_8)$heterocycloalkylene, arylene, and heteroarylene, each of which is optionally substituted by one or more groups selected from the group consisting of —OH, halogen, —CN, $(C_1-C_6)$alkyl, $(C_1-C_6)$alkoxy, $(C_1-C_6)$haloalkyl, $(C_1-C_6)$haloalkoxy, and aryl$(C_1-C_6)$alkyl;

C is absent or is selected from the group consisting of —O—, —C(O)—, —OC(O)—, —(O)CO—, —S—, —S(O)—, —S(O)$_2$—, and —N(R$_7$)—, or is one of the following groups C1-C23

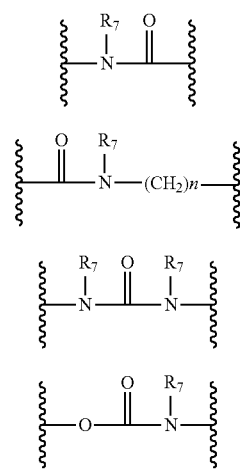

C1

C2

C3

C4

-continued

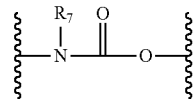 C5

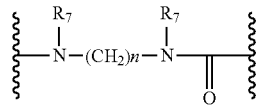 C6

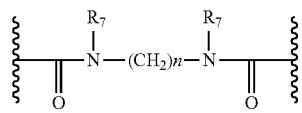 C7

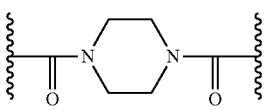 C8

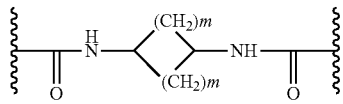 C9

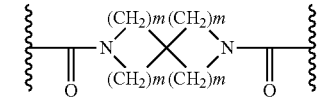 C10

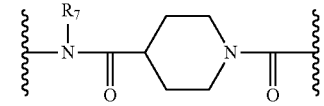 C11

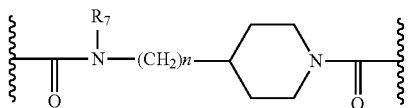 C12

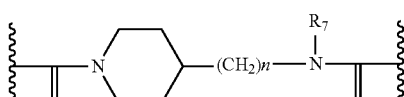 C13

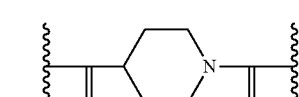 C14

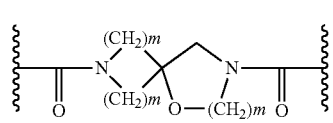 C15

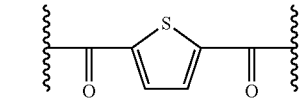 C16

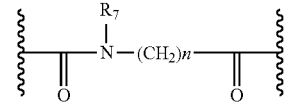 C17

-continued

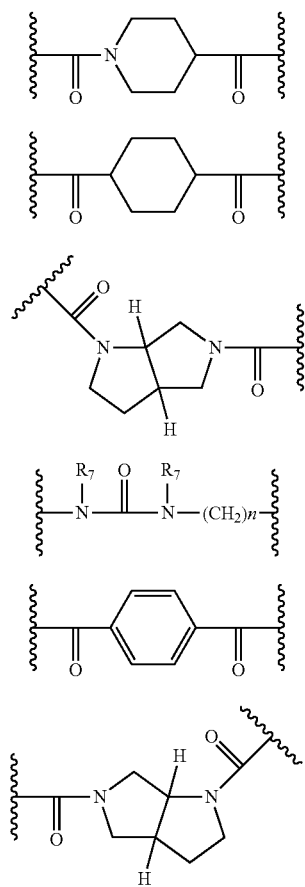

wherein R₇ is in each occurrence independently H or selected from the group consisting of linear or branched $(C_1-C_8)$alkyl, aryl$(C_1-C_6)$alkyl, arylsulfanyl, arylsulfinyl, arylsulfonyl, $(C_3-C_8)$cycloalkyl, $(C_3-C_8)$heterocycloalkyl, aryl, and heteroaryl;

D is absent or is selected from the group consisting of $(C_1-C_{12})$alkylene, $(C_2-C_{12})$alkenylene, $(C_2-C_6)$alkynylene, arylene, heteroarylene, $(C_3-C_8)$cycloalkylene, $(C_3-C_8)$heterocycloalkylene; wherein said arylene, heteroarylene, $(C_3-C_8)$cycloalkylene, and $(C_3-C_8)$heterocycloalkylene is optionally substituted by one or more groups selected from the group consisting of —OH, halogen, —CN, $(C_1-C_6)$alkyl, $(C_1-C_6)$alkoxy, $(C_1-C_6)$haloalkyl, $(C_1-C_6)$haloalkoxy, and aryl$(C_1-C_6)$alkyl;

n is at each occurrence independently 0 or an integer from 1 to 3;

m is at each occurrence independently an integer from 1 to 3;

E is absent or is selected from the group consisting of —O—, —NR₇—, —NR₇—C(O)—, —C(O)—NR₇—, —OC(O)—, —C(O)—(CH₂)ₙ—O—; —NR₇—C(O)—(CH₂)ₙ—O—, —NR₇—C(O)—NR₇—, and —S—;

G is arylene or heteroarylene, each of which is optionally substituted by one or more substituents selected from the group consisting of halogen, —OH, oxo (=O), —SH, —NO₂, —CN, —CON(R₆)₂, —NH₂, —NH-COR₆, —CO₂R₆, $(C_1-C_{10})$alkylsulfanyl, $(C_1-C_{10})$alkylsulfinyl, $(C_1-C_{10})$alkylsulfonyl, $(C_1-C_{10})$alkyl, aryl, haloaryl, heteroaryl, and $(C_1-C_{10})$alkoxy;

R₁ is selected from the group consisting of $(C_3-C_8)$cycloalkyl, $(C_3-C_8)$heterocycloalkyl, aryl, heteroaryl, aryl$(C_1-C_6)$alkyl, heteroaryl$(C_1-C_6)$alkyl, and $(C_3-C_8)$cycloalkyl$(C_1-C_6)$alkyl, each of which is optionally substituted by one or more groups selected independently from the group consisting of halogen, $(C_1-C_8)$alkyl, and $(C_1-C_{10})$alkoxy;

s is 0 or an integer from 1 to 3;

R₂ is a nitrogen containing group which is:
  a group (a) which is —NR₃R₄ wherein R₃ and R₄ are independently hydrogen or $(C_1-C_4)$ alkyl; or
  a group (b) of formula J1, J2, J3, J4 or J5

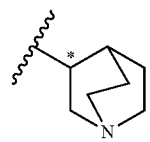

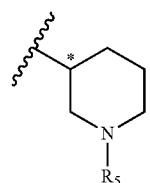

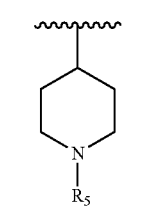

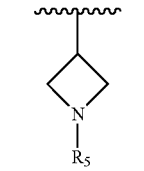

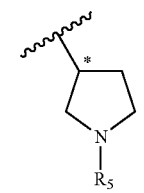

R₅ is a group of formula K

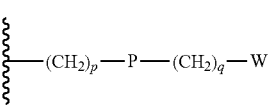

wherein p is 0 or an integer from 1 to 4; q is 0 or an integer from 1 to 4;

P is absent or is a divalent moiety selected from the group consisting of O, S, SO, SO₂, CO, NR₆CH=CH, N(R₆)SO₂, N(R₆)COO, N(R₆)C(O), SO₂N(R₆), OC(O)N(R₆), and C(O)N(R₆);

W is H or is selected from the group consisting of (C$_1$-C$_6$)alkyl, (C$_3$-C$_8$)cycloalkyl, aryl, and heteroaryl, each of which is optionally substituted by one or more substituents selected independently from the group consisting of halogen, —OH, oxo (=O), —SH, —NO$_2$, —CN, —CON(R$_6$)$_2$, —NH$_2$, —NHCOR$_6$, —CO$_2$R$_6$, (C$_1$-C$_{10}$)alkylsulfanyl, (C$_1$-C$_{10}$)alkylsulfinyl, (C$_1$-C$_{10}$)alkylsulfonyl, (C$_1$-C$_{10}$)alkyl, and (C$_1$-C$_{10}$)alkoxy;

R$_6$ is at each occurrence independently H or selected from the group consisting of (C$_1$-C$_{10}$)alkyl, (C$_1$-C$_6$)haloalkyl, (C$_2$-C$_6$)alkynyl, (C$_2$-C$_6$)alkenyl, (C$_3$-C$_8$)cycloalkyl, heteroaryl, and aryl, each of which is optionally substituted by one or more substituents selected from the group consisting of halogen, —OH, oxo (=O), —SH, —NO$_2$, —CN, —CONH$_2$, —COOH, (C$_1$-C$_{10}$)alkoxycarbonyl, (C$_1$-C$_{10}$)alkylsulfanyl, (C$_1$-C$_{10}$)alkylsulfinyl, (C$_1$-C$_{10}$)alkylsulfonyl, (C$_1$-C$_{10}$)alkyl, and (C$_1$-C$_{10}$)alkoxy;

or a pharmaceutically acceptable salt thereof.

2. A method according to claim 1, wherein R$_2$ is a group of formula J3:

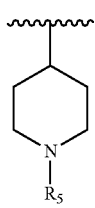

and R$_5$ is a group of formula K, wherein p is 0 or 1, P is absent or is CO, q is absent or is 1, and W is H, (C$_1$-C$_6$)alkyl, or aryl.

3. A method according to claim 2, wherein R$_5$ is methyl or benzyl.

4. A method according to claim 1, wherein G is arylene and R$_1$ is aryl, optionally substituted by one or more group independently selected from the group consisting of halogen, (C$_1$-C$_8$)alkyl, and (C$_1$-C$_{10}$)alkoxy.

5. A method according to claim 4, wherein A1 and A2 are independently absent or selected from the group consisting of methylene, ethylene, propylene, butylene, pentylene, hexylene, heptylene, octylene, and nonylene, G is phenylene, and R$_1$ is phenyl, optionally substituted by one or more group independently selected from the group consisting of halogen, (C$_1$-C$_8$)alkyl, and (C$_1$-C$_{10}$)alkoxy.

6. A method according to claim 1, wherein E is —O—, —C(O)—(CH$_2$)$_n$—O—, or —NR$_7$—C(O)—(CH$_2$)$_n$—O—; G is phenylene, wherein E is linked to the phenyl ring G in the meta position, and R$_1$ is phenyl, optionally substituted by one or more groups selected from the group consisting of halogen, (C$_1$-C$_8$)alkyl, and (C$_1$-C$_{10}$)alkoxy.

7. A method according to claim 1, wherein R$_2$ is J1, J2, or J5

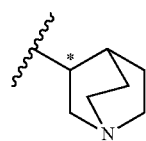

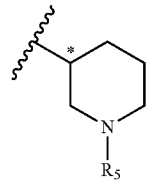

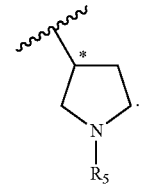

8. A method according to claim 2, wherein the absolute configuration of carbon (1) is that shown hereinbelow:

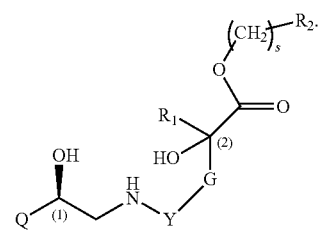

9. A method according to claim 1, wherein Y is a divalent group of formula Y2:

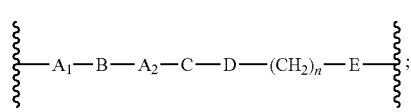

A2 is absent and A1 is independently selected from the group consisting of methylene, ethylene, n-propylene, isopropylene, butylene, pentylene, hexylene, and octylene;

B is absent or is selected from the group consisting of piperidinylene, phenylene, pyridine-diyl, and pyrazole-diyl; wherein B is optionally substituted by one or more groups selected from the group consisting of —OH, fluorine, chlorine, bromine, —CN, methyl, methoxy, ethoxy, isopropoxy, trifluoromethyl, and trifluoromethoxy;

C is absent or is —O— or —C(O)—, or is one of the groups C1, C2, C4, C7, C8, C9, C10, C12, C13, C14, C15, C16, C17, C18, C19, C20, C21 C22 C23, wherein R$_7$ is in each occurrence independently H, methyl, ethyl, or benzyl;

D is absent or is para-phenylene, meta-phenylene, cyclohexanediyl, piperidindiyl, pyrrolidindiyl or azetidindiyl;

n is at each occurrence independently 0 or an integer from 1 to 3;

m is at each occurrence independently an integer from 1 to 3;

E is absent or is —O—, —NH—, —NH—C(O)—, —C(O)—NH—, —C(O)—CH$_2$—O—, or —NH—C(O)—CH$_2$—O—;

G is meta-phenylene or para-phenylene;

R₁ is thiophenyl, cyclohexyl, cyclopentyl, or phenyl, each of which is optionally substituted by one or more groups selected independently from the group consisting of fluorine, methyl, ethyl, and methoxy;

s is 0, 1, or 2

R₂ is:
   a group (a) which is —NR₃R₄ wherein R₃ and R₄ are methyl; or
   a group (b) of formula J1, J2, J3, J4 or J5 wherein R₅ is methyl or benzyl.

10. A method according to claim 1, comprising administering a compound which is selected from the group consisting of:

(1-benzylpiperidin-4-yl)methyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate;

(1-benzylpiperidin-4-yl)methyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-(p-tolyl)acetate;

(1-benzylpiperidin-4-yl)methyl 2-(4-fluorophenyl)-2-hydroxy-2-(3-((5-(((R)-2-hydroxy-2-(8-hydroxy-2-oxo-1,2-dihydroquinolin-5-yl)ethyl)amino)pentyl)oxy)phenyl)-acetate;

(1-benzylpiperidin-4-yl)methyl 2-(3-fluorophenyl)-2-hydroxy-2-(3-((5-(((R)-2-hydroxy-2-(8-hydroxy-2-oxo-1,2-dihydroquinolin-5-yl)ethyl)amino)pentyl)oxy)phenyl)-acetate;

(1-benzylpiperidin-4-yl)methyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-(m-tolyl)acetate;

(1-benzylpiperidin-4-yl)methyl 2-(2-chlorophenyl)-2-hydroxy-2-(3-((5-(((R)-2-hydroxy-2-(8-hydroxy-2-oxo-1,2-dihydroquinolin-5-yl)ethyl)amino)pentyl)oxy)-phenyl)acetate;

(1-benzylpiperidin-4-yl)methyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-(o-tolyl)acetate;

(1-benzylpiperidin-4-yl)methyl 2-(2-ethylphenyl)-2-hydroxy-2-(3-((5-(((R)-2-hydroxy-2-(8-hydroxy-2-oxo-1,2-dihydroquinolin-5-yl)ethyl)amino)pentyl)oxy)phenyl)-acetate;

(1-benzylpiperidin-4-yl)methyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-(thiophen-2-yl)acetate;

(1-benzylpiperidin-4-yl)methyl 2-cyclohexyl-2-hydroxy-2-(3-((5-(((R)-2-hydroxy-2-(8-hydroxy-2-oxo-1,2-dihydroquinolin-5-yl)ethyl)amino)pentyl)oxy)phenyl)-acetate;

(1-benzylpiperidin-4-yl)methyl 2-(3-ethylphenyl)-2-hydroxy-2-(3-((5-(((R)-2-hydroxy-2-(8-hydroxy-2-oxo-1,2-dihydroquinolin-5-yl)ethyl)amino)pentyl)oxy)phenyl)-acetate;

(R)-quinuclidin-3-yl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-(4-methoxyphenyl)acetate;

(R)-quinuclidin-3-yl 2-cyclopentyl-2-hydroxy-2-(3-((5-(((R)-2-hydroxy-2-(8-hydroxy-2-oxo-1,2-dihydroquinolin-5-yl)ethyl)amino)pentyl)oxy)phenyl)acetate;

(S)-(1-benzylpiperidin-4-yl)methyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate;

(R)-(1-benzylpiperidin-4-yl)methyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate;

(R)-quinuclidin-3-yl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate;

(R)—(R)-quinuclidin-3-yl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate;

(S)-2-(dimethylamino)ethyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate;

(R)-2-(dimethylamino)ethyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate;

(S)—(R)-1-methylpyrrolidin-3-yl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate;

(R)—(R)-1-methylpyrrolidin-3-yl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate;

(S)-1-methylpiperidin-4-yl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate;

(R)-1-methylpiperidin-4-yl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate;

(S)-(1-methylpiperidin-4-yl)methyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate;

(R)-(1-methylpiperidin-4-yl)methyl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate;

(S)—(R)-1-methylpiperidin-3-yl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate;

(S)-1-methylazetidin-3-yl 2-hydroxy-2-(3-((5-(((R)-2-hydroxy-2-(8-hydroxy-2-oxo-1,2-dihydroquinolin-5-yl)ethyl)amino)pentyl)oxy)phenyl)-2-phenylacetate;

(R)-(1-benzylpiperidin-4-yl)methyl 2-hydroxy-2-(3-((6-(((R)-2-hydroxy-2-(8-hydroxy-2-oxo-1,2-dihydroquinolin-5-yl)ethyl)amino)hexyl)oxy)phenyl)-2-phenylacetate;

(S)-(1-benzylpiperidin-4-yl)methyl 2-hydroxy-2-(3-((7-(((R)-2-hydroxy-2-(8-hydroxy-2-oxo-1,2-dihydroquinolin-5-yl)ethyl)amino)heptyl)oxy)phenyl)-2-phenylacetate;

(S)-(1-benzylpiperidin-4-yl)methyl 2-hydroxy-2-(3-((6-(((R)-2-hydroxy-2-(8-hydroxy-2-oxo-1,2-dihydroquinolin-5-yl)ethyl)amino)hexyl)oxy)phenyl)-2-phenylacetate;

(S)-(1-benzylpiperidin-4-yl)methyl 2-hydroxy-2-(3-((8-(((R)-2-hydroxy-2-(8-hydroxy-2-oxo-1,2-dihydroquinolin-5-yl)ethyl)amino)octyl)oxy)phenyl)-2-phenylacetate;

(S)-(1-benzylpiperidin-4-yl)methyl 2-hydroxy-2-(3-((1-(4-(2-(((R)-2-hydroxy-2-(8-hydroxy-2-oxo-1,2-dihydroquinolin-5-yl)ethyl)amino)ethyl)benzoyl)piperidin-4-yl)methoxy)phenyl)-2-phenylacetate;
(S)-(1-benzylpiperidin-4-yl)methyl 2-hydroxy-2-(3-(3-(4-((((R)-2-hydroxy-2-(8-hydroxy-2-oxo-1,2-dihydroquinolin-5-yl)ethyl)amino)methyl)benzamido) propoxy)-phenyl)-2-phenylacetate;
(S)-(1-benzylpiperidin-4-yl)methyl 2-hydroxy-2-(3-((4-(4-((((R)-2-hydroxy-2-(8-hydroxy-2-oxo-1,2-dihydroquinolin-5-yl)ethyl)amino)methyl)-piperidine-1-carbonyl)benzyl)oxy)phenyl)-2-phenylacetate;
(R)-(1-benzylpiperidin-4-yl)methyl 2-hydroxy-2-(3-(2-(4-(2-(((R)-2-hydroxy-2-(8-hydroxy-2-oxo-1,2-dihydroquinolin-5-yl)ethyl)amino)ethyl)benzamido)ethoxyphenyl)-2-phenylacetate;
(S)-(1-benzylpiperidin-4-yl)methyl 2-hydroxy-2-(3-((3-(4-((((R)-2-hydroxy-2-(8-hydroxy-2-oxo-1,2-dihydroquinolin-5-yl)ethyl)amino)methyl)-piperidine-1-carbonyl)benzyl)oxy)phenyl)-2-phenylacetate;
(S)-(1-benzylpiperidin-4-yl)methyl 2-hydroxy-2-(3-(2-(4-((((R)-2-hydroxy-2-(8-hydroxy-2-oxo-1,2-dihydroquinolin-5-yl)ethyl)amino)methyl)piperidin-1-yl)-2-oxoethoxy)phenyl)-2-phenylacetate;
(S)-(1-benzylpiperidin-4-yl)methyl 2-hydroxy-2-(3-(3-(4-(2-(((R)-2-hydroxy-2-(8-hydroxy-2-oxo-1,2-dihydroquinolin-5-yl)ethyl)amino)ethyl)benzamido) propoxy)-phenyl)-2-phenylacetate;
(S)-(1-benzylpiperidin-4-yl)methyl 2-hydroxy-2-(3-(2-(4-(2-(((R)-2-hydroxy-2-(8-hydroxy-2-oxo-1,2-dihydroquinolin-5-yl)ethyl)amino)ethyl)benzamido) ethoxy)-phenyl)-2-phenylacetate;
(1-benzylpiperidin-4-yl)methyl 2-hydroxy-2-(3-(2-(4-((((R)-2-hydroxy-2-(8-hydroxy-2-oxo-1,2-dihydroquinolin-5-yl)ethyl)amino)methyl)benzamido)ethyl)phenyl)-2-phenylacetate;
(1-benzylpiperidin-4-yl)methyl 2-hydroxy-2-(3-(2-(4-(2-(((R)-2-hydroxy-2-(8-hydroxy-2-oxo-1,2-dihydroquinolin-5-yl)ethyl)amino)ethyl)benzamido)ethyl)phenyl)-2-phenylacetate;
1-benzylpiperidin-4-yl (S)-2-hydroxy-2-(3-(3-(4-((((R)-2-hydroxy-2-(8-hydroxy-2-oxo-1,2-dihydroquinolin-5-yl)ethyl)amino)methyl)benzamido)propoxy)phenyl)-2-phenylacetate;
((R)-1-benzylpyrrolidin-3-yl)methyl (S)-2-hydroxy-2-(3-(3-(4-((((R)-2-hydroxy-2-(8-hydroxy-2-oxo-1,2-dihydroquinolin-5-yl)ethyl)amino)methyl)benzamido)-propoxy)phenyl)-2-phenylacetate;
((S)-1-benzylpyrrolidin-3-yl)methyl (S)-2-hydroxy-2-(3-(3-(4-((((R)-2-hydroxy-2-(8-hydroxy-2-oxo-1,2-dihydroquinolin-5-yl)ethyl)amino)methyl)benzamido)-propoxy)phenyl)-2-phenylacetate;
(1-cyclobutylpiperidin-4-yl)methyl (S)-2-hydroxy-2-(3-(3-(4-((((R)-2-hydroxy-2-(8-hydroxy-2-oxo-1,2-dihydroquinolin-5-yl)ethyl)amino)methyl)benzamido)-propoxy)phenyl)-2-phenylacetate;
(1-methylpiperidin-4-yl)methyl (S)-2-hydroxy-2-(3-(3-(4-((((R)-2-hydroxy-2-(8-hydroxy-2-oxo-1,2-dihydroquinolin-5-yl)ethyl)amino)methyl)benzamido)-propoxy)phenyl)-2-phenylacetate;
(R)-1-benzylpyrrolidin-3-yl (S)-2-hydroxy-2-(3-(3-(4-((((R)-2-hydroxy-2-(8-hydroxy-2-oxo-1,2-dihydroquinolin-5-yl)ethyl)amino)methyl)benzamido)-propoxy) phenyl)-2-phenylacetate;
(S)-1-benzylpyrrolidin-3-yl (S)-2-hydroxy-2-(3-(3-(4-((((R)-2-hydroxy-2-(8-hydroxy-2-oxo-1,2-dihydroquinolin-5-yl)ethyl)amino)methyl)benzamido)-propoxy) phenyl)-2-phenylacetate;
1-benzylazetidin-3-yl (S)-2-hydroxy-2-(3-(3-(4-((((R)-2-hydroxy-2-(8-hydroxy-2-oxo-1,2-dihydroquinolin-5-yl)ethyl)amino)methyl)benzamido)propoxy)phenyl)-2-phenylacetate;
(S)-(1-benzylpiperidin-4-yl)methyl 2-hydroxy-2-(3-((1-(4-((((R)-2-hydroxy-2-(8-hydroxy-2-oxo-1,2-dihydroquinolin-5-yl)ethyl)amino)methyl)-benzoyl)azetidin-3-yl)methoxy)phenyl)-2-phenylacetate;
(S)-(1-benzylpiperidin-4-yl)methyl 2-hydroxy-2-(3-((1-(4-(2-(((R)-2-hydroxy-2-(8-hydroxy-2-oxo-1,2-dihydroquinolin-5-yl)ethyl)amino)ethyl)benzoyl)azetidin-3-yl)methoxy)phenyl)-2-phenylacetate;
(S)-(1-benzylpiperidin-4-yl)methyl 2-hydroxy-2-(3-((4-((3-(((R)-2-hydroxy-2-(8-hydroxy-2-oxo-1,2-dihydroquinolin-5-yl)ethyl)amino)propyl)carbamoyl)benzyl)-oxy)phenyl)-2-phenylacetate;
(R)-(1-benzylpiperidin-4-yl)methyl 2-hydroxy-2-(3-((4-((3-(((R)-2-hydroxy-2-(8-hydroxy-2-oxo-1,2-dihydroquinolin-5-yl)ethyl)amino)propyl)carbamoyl)benzyl)-oxy)phenyl)-2-phenylacetate;
(S)-(1-benzylpiperidin-4-yl)methyl 2-(3-((3-(benzyl(3-(((R)-2-hydroxy-2-(8-hydroxy-2-oxo-1,2-dihydroquinolin-5-yl)ethyl)amino)propyl)carbamoyl)benzyl) oxy)-phenyl)-2-hydroxy-2-phenylacetate;
(R)-quinuclidin-3-yl 2-hydroxy-2-(3-(4-((5-(((R)-2-hydroxy-2-(8-hydroxy-2-oxo-1,2-dihydroquinolin-5-yl)ethyl)amino)pentyl)oxy)benzamido)phenyl)-2-phenylacetate;
(1-benzylpiperidin-4-yl)methyl 2-hydroxy-2-(3-((4-(((R)-2-hydroxy-2-(8-hydroxy-2-oxo-1,2-dihydroquinolin-5-yl)ethyl)amino)butyl)carbamoyl)phenyl)-2-phenylacetate;
(R)-quinuclidin-3-yl 2-hydroxy-2-(3-((4-(((R)-2-hydroxy-2-(8-hydroxy-2-oxo-1,2-dihydroquinolin-5-yl)ethyl)amino)butyl)carbamoyl)phenyl)-2-phenylacetate;
(R)-1-methylpyrrolidin-3-yl 2-hydroxy-2-(3-((4-(((R)-2-hydroxy-2-(8-hydroxy-2-oxo-1,2-dihydroquinolin-5-yl)ethyl)amino)butyl)carbamoyl)phenyl)-2-phenylacetate;
(1-benzylpiperidin-4-yl)methyl 2-hydroxy-2-(3-((3-(4-((((R)-2-hydroxy-2-(8-hydroxy-2-oxo-1,2-dihydroquinolin-5-yl)ethyl)amino)methyl)benzamido)propyl)-carbamoyl)phenyl)-2-phenylacetate;
(1-benzylpiperidin-4-yl)methyl 2-hydroxy-2-(4-((5-(((R)-2-hydroxy-2-(8-hydroxy-2-oxo-1,2-dihydroquinolin-5-yl)ethyl)amino)pentyl)oxy)phenyl)-2-phenylacetate;
(R)-quinuclidin-3-yl 2-hydroxy-2-(4-((5-(((R)-2-hydroxy-2-(8-hydroxy-2-oxo-1,2-dihydroquinolin-5-yl)ethyl)amino)pentyl)oxy)phenyl)-2-phenylacetate;
(1-benzylpiperidin-4-yl)methyl 2-hydroxy-2-(4-((4-((4-((((R)-2-hydroxy-2-(8-hydroxy-2-oxo-1,2-dihydroquinolin-5-yl)ethyl)amino)methyl)benzamido)methyl)-benzyl)oxy)phenyl)-2-phenylacetate;
(1-benzylpiperidin-4-yl)methyl 2-hydroxy-2-(3-(((5-(((R)-2-hydroxy-2-(8-hydroxy-2-oxo-1,2-dihydroquinolin-5-yl)ethyl)amino)pentyl)oxy)carbonyl)amino)-phenyl)-2-phenylacetate;
(R)-quinuclidin-3-yl 2-hydroxy-2-(3-(5-(((R)-2-hydroxy-2-(8-hydroxy-2-oxo-1,2-dihydroquinolin-5-yl)ethyl)amino)pentanamido)phenyl)-2-phenylacetate;
(1-benzylpiperidin-4-yl)methyl 2-hydroxy-2-(3-(3-(3-(4-((((R)-2-hydroxy-2-(8-hydroxy-2-oxo-1,2-dihydroquinolin-5-yl)ethyl)amino)methyl)benzamido)propyl)-ureido)phenyl)-2-phenylacetate;

(S)-(1-benzylpiperidin-4-yl)methyl 2-hydroxy-2-(3-(3-(4-((((R)-2-hydroxy-2-(8-hydroxy-2-oxo-1,2-dihydroquinolin-5-yl)ethyl)amino)methyl)-3-methoxybenzamido)-propoxy)phenyl)-2-phenylacetate;

(S)-(1-benzylpiperidin-4-yl)methyl 2-hydroxy-2-(3-(3-(4-((((R)-2-hydroxy-2-(8-hydroxy-2-oxo-1,2-dihydroquinolin-5-yl)ethyl)amino)methyl)-2-methoxybenzamido)-propoxy)phenyl)-2-phenylacetate;

(S)-(1-benzylpiperidin-4-yl)methyl 2-hydroxy-2-(3-(3-(6-((((R)-2-hydroxy-2-(8-hydroxy-2-oxo-1,2-dihydroquinolin-5-yl)ethyl)amino)methyl)nicotinamido)-propoxy)phenyl)-2-phenylacetate;

(S)-(1-benzylpiperidin-4-yl)methyl 2-(3-(3-(3-ethoxy-4-((((R)-2-hydroxy-2-(8-hydroxy-2-oxo-1,2-dihydroquinolin-5-yl)ethyl)amino)methyl)benzamido)-propoxy)phenyl)-2-hydroxy-2-phenylacetate;

(S)-(1-benzylpiperidin-4-yl)methyl 2-hydroxy-2-(3-(3-(4-((((R)-2-hydroxy-2-(8-hydroxy-2-oxo-1,2-dihydroquinolin-5-yl)ethyl)amino)methyl)-3-(trifluoromethoxy)-benzamido)propoxy)phenyl)-2-phenylacetate;

(S)-(1-benzylpiperidin-4-yl)methyl 2-(3-(3-(2-fluoro-4-((((R)-2-hydroxy-2-(8-hydroxy-2-oxo-1,2-dihydroquinolin-5-yl)ethyl)amino)methyl)-3-methoxybenzamido)-propoxy)phenyl)-2-hydroxy-2-phenylacetate;

(S)-(1-benzylpiperidin-4-yl)methyl 2-hydroxy-2-(3-(3-(4-((((R)-2-hydroxy-2-(8-hydroxy-2-oxo-1,2-dihydroquinolin-5-yl)ethyl)amino)methyl)-3-isopropoxybenzamido)-propoxy)phenyl)-2-phenylacetate;

(S)-(1-benzylpiperidin-4-yl)methyl 2-(3-(3-(2-chloro-4-((((R)-2-hydroxy-2-(8-hydroxy-2-oxo-1,2-dihydroquinolin-5-yl)ethyl)amino)methyl)benzamido)propoxy)-phenyl)-2-hydroxy-2-phenylacetate;

(S)-(1-benzylpiperidin-4-yl)methyl 2-(3-(3-(2-fluoro-4-((((R)-2-hydroxy-2-(8-hydroxy-2-oxo-1,2-dihydroquinolin-5-yl)ethyl)amino)methyl)-5-methoxybenzamido)-propoxy)phenyl)-2-hydroxy-2-phenylacetate;

(S)-(1-benzylpiperidin-4-yl)methyl 2-(3-(3-(2-chloro-4-((((R)-2-hydroxy-2-(8-hydroxy-2-oxo-1,2-dihydroquinolin-5-yl)ethyl)amino)methyl)-5-methoxybenzamido)-propoxy)phenyl)-2-hydroxy-2-phenylacetate;

(S)-(1-benzylpiperidin-4-yl)methyl 2-hydroxy-2-(3-(3-(5-((((R)-2-hydroxy-2-(8-hydroxy-2-oxo-1,2-dihydroquinolin-5-yl)ethyl)amino)methyl)picolinamido)-propoxy)phenyl)-2-phenylacetate;

(S)-(1-benzylpiperidin-4-yl)methyl 2-(3-(3-(2,3-difluoro-4-((((R)-2-hydroxy-2-(8-hydroxy-2-oxo-1,2-dihydroquinolin-5-yl)ethyl)amino)methyl)benzamido)propoxy)-phenyl)-2-hydroxy-2-phenylacetate;

(S)-(1-benzylpiperidin-4-yl)methyl (S)-2-hydroxy-2-(3-(3-(4-((((R)-2-hydroxy-2-(8-hydroxy-2-oxo-1,2-dihydroquinolin-5-yl)ethyl)amino)methyl)-3-(trifluoromethyl)-benzamido)propoxy)phenyl)-2-phenylacetate;

(1-benzylpiperidin-4-yl)methyl (S)-2-hydroxy-2-(3-((4-(4-(2-(((R)-2-hydroxy-2-(4-hydroxy-6-oxo-5,6-dihydronaphthalen-1-yl)ethyl)amino)ethyl)piperidine-1-carbonyl)-benzyl)oxy)phenyl)-2-phenylacetate;

(1-benzylpiperidin-4-yl)methyl (S)-2-hydroxy-2-(3-(2-(4-(2-(((R)-2-hydroxy-2-(8-hydroxy-2-oxo-1,2-dihydroquinolin-5-yl)ethyl)amino)ethyl)piperidin-1-yl)-2-oxoethoxy)phenyl)-2-phenylacetate;

(S)-(1-benzylpiperidin-4-yl)methyl 2-hydroxy-2-(3-(2-((4-((((R)-2-hydroxy-2-(8-hydroxy-2-oxo-1,2-dihydroquinolin-5-yl)ethyl)amino)methyl)-3-methoxyphenyl)amino)-2-oxoethoxy)phenyl)-2-phenylacetate;

(1-benzylpiperidin-4-yl)methyl (S)-2-(3-(2-((2-fluoro-4-((((R)-2-hydroxy-2-(8-hydroxy-2-oxo-1,2-dihydroquinolin-5-yl)ethyl)amino)methyl)-5-methoxyphenyl)amino)-2-oxoethoxy)phenyl)-2-hydroxy-2-phenylacetate;

(1-benzylpiperidin-4-yl)methyl (S)-2-hydroxy-2-(3-((4-((4-(2-(((R)-2-hydroxy-2-(8-hydroxy-2-oxo-1,2-dihydroquinolin-5-yl)ethyl)amino)ethyl)benzamido)methyl)-benzyl)oxy)phenyl)-2-phenylacetate;

(1-benzylpiperidin-4-yl)methyl (S)-2-hydroxy-2-(3-((4-((4-((((R)-2-hydroxy-2-(8-hydroxy-2-oxo-1,2-dihydroquinolin-5-yl)ethyl)amino)methyl)benzamido)methyl)-benzyl)oxy)phenyl)-2-phenylacetate;

(1-benzylpiperidin-4-yl)methyl (S)-2-hydroxy-2-(3-((4-((((R)-2-hydroxy-2-(8-hydroxy-2-oxo-1,2-dihydroquinolin-5-yl)ethyl)amino)methyl)-2-methoxybenzamido)-methyl)benzyl)oxy)phenyl)-2-phenylacetate;

(1-benzylpiperidin-4-yl)methyl (S)-2-hydroxy-2-(3-((4-((((R)-2-hydroxy-2-(8-hydroxy-2-oxo-1,2-dihydroquinolin-5-yl)ethyl)amino)methyl)-3-methoxybenzamido)-methyl)benzyl)oxy)phenyl)-2-phenylacetate;

(1-benzylpiperidin-4-yl)methyl (S)-2-hydroxy-2-(3-(2-((2-(4-((((R)-2-hydroxy-2-(8-hydroxy-2-oxo-1,2-dihydroquinolin-5-yl)ethyl)amino)methyl)benzamido)ethyl)-amino)-2-oxoethoxy)phenyl)-2-phenylacetate;

(1-benzylpiperidin-4-yl)methyl (S)-2-hydroxy-2-(3-(2-(4-(4-((((R)-2-hydroxy-2-(8-hydroxy-2-oxo-1,2-dihydroquinolin-5-yl)ethyl)amino)methyl)benzoyl)piperazin-1-yl)-2-oxoethoxy)phenyl)-2-phenylacetate;

(1-benzylpiperidin-4-yl)methyl (S)-2-hydroxy-2-(3-(2-(4-(4-((((R)-2-hydroxy-2-(8-hydroxy-2-oxo-1,2-dihydroquinolin-5-yl)ethyl)amino)methyl)benzamido)piperidin-1-yl)-2-oxoethoxy)phenyl)-2-phenylacetate;

(1-benzylpiperidin-4-yl)methyl (S)-2-hydroxy-2-(3-(2-((2-(4-((((R)-2-hydroxy-2-(8-hydroxy-2-oxo-1,2-dihydroquinolin-5-yl)ethyl)amino)methyl)benzamido)ethyl)-(methyl)amino)-2-oxoethoxy)phenyl)-2-phenylacetate;

(1-benzylpiperidin-4-yl)methyl (S)-2-hydroxy-2-(3-(2-(4-((4-((((R)-2-hydroxy-2-(8-hydroxy-2-oxo-1,2-dihydroquinolin-5-yl)ethyl)amino)methyl)benzamido)-methyl)piperidin-1-yl)-2-oxoethoxy)phenyl)-2-phenylacetate;

(1-benzylpiperidin-4-yl)methyl (S)-2-hydroxy-2-(3-(2-(((1R,4S)-4-(4-((((R)-2-hydroxy-2-(8-hydroxy-2-oxo-1,2-dihydroquinolin-5-yl)ethyl)amino)methyl)benzamido)-cyclohexyl)amino)-2-oxoethoxy)phenyl)-2-phenylacetate;

(1-benzylpiperidin-4-yl)methyl (S)-2-hydroxy-2-(3-(2-(((1R,3S)-3-(4-((((R)-2-hydroxy-2-(8-hydroxy-2-oxo-1,2-dihydroquinolin-5-yl)ethyl)amino)methyl)benzamido)-cyclobutyl)amino)-2-oxoethoxy)phenyl)-2-phenylacetate;

(1-benzylpiperidin-4-yl)methyl (S)-2-hydroxy-2-(3-(2-(9-(4-((((R)-2-hydroxy-2-(8-hydroxy-2-oxo-1,2-dihydroquinolin-5-yl)ethyl)amino)methyl)benzoyl)-3,9-diazaspiro[5.5]undecan-3-yl)-2-oxoethoxy)phenyl)-2-phenylacetate;

(1-benzylpiperidin-4-yl)methyl (S)-2-hydroxy-2-(3-(2-((1-(4-((((R)-2-hydroxy-2-(8-hydroxy-2-oxo-1,2-dihydroquinolin-5-yl)ethyl)amino)methyl)benzoyl)piperidin-4-yl)amino)-2-oxoethoxy)phenyl)-2-phenylacetate;

(1-benzylpiperidin-4-yl)methyl (S)-2-hydroxy-2-(3-(2-((1-(4-((((R)-2-hydroxy-2-(8-hydroxy-2-oxo-1,2-dihydroquinolin-5-yl)ethyl)amino)methyl)benzoyl)azetidin-3-yl)amino)-2-oxoethoxy)phenyl)-2-phenylacetate;

(1-benzylpiperidin-4-yl)methyl (S)-2-hydroxy-2-(3-(2-(3-(4-((((R)-2-hydroxy-2-(8-hydroxy-2-oxo-1,2-dihydroquinolin-5-yl)ethyl)amino)methyl)benzamido)azetidin-1-yl)-2-oxoethoxy)phenyl)-2-phenylacetate;

(1-benzylpiperidin-4-yl)methyl (S)-2-hydroxy-2-(3-(2-(((R)-1-(4-((((R)-2-hydroxy-2-(8-hydroxy-2-oxo-1,2-dihydroquinolin-5-yl)ethyl)amino)methyl)benzoyl)-pyrrolidin-3-yl)amino)-2-oxoethoxy)phenyl)-2-phenylacetate;

(1-benzylpiperidin-4-yl)methyl (S)-2-hydroxy-2-(3-(2-(((S)-1-(4-((((R)-2-hydroxy-2-(8-hydroxy-2-oxo-1,2-dihydroquinolin-5-yl)ethyl)amino)methyl)benzoyl)-piperidin-3-yl)amino)-2-oxoethoxy)phenyl)-2-phenylacetate;

(1-benzylpiperidin-4-yl)methyl (S)-2-hydroxy-2-(3-(2-(((S)-1-(4-((((R)-2-hydroxy-2-(8-hydroxy-2-oxo-1,2-dihydroquinolin-5-yl)ethyl)amino)methyl)-benzoyl)pyrrolidin-3-yl)amino)-2-oxoethoxy)phenyl)-2-phenylacetate;

(1-benzylpiperidin-4-yl)methyl (S)-2-hydroxy-2-(3-(2-(((R)-1-(4-((((R)-2-hydroxy-2-(8-hydroxy-2-oxo-1,2-dihydroquinolin-5-yl)ethyl)amino)methyl)benzoyl)-piperidin-3-yl)amino)-2-oxoethoxy)phenyl)-2-phenylacetate;

(1-benzylpiperidin-4-yl)methyl (S)-2-hydroxy-2-(3-(2-((S)-3-(4-((((R)-2-hydroxy-2-(8-hydroxy-2-oxo-1,2-dihydroquinolin-5-yl)ethyl)amino)methyl)benzamido)piperidin-1-yl)-2-oxoethoxy)phenyl)-2-phenylacetate;

(1-benzylpiperidin-4-yl)methyl (S)-2-hydroxy-2-(3-(2-((S)-3-(4-((((R)-2-hydroxy-2-(8-hydroxy-2-oxo-1,2-dihydroquinolin-5-yl)ethyl)amino)methyl)benzamido)pyrrolidin-1-yl)-2-oxoethoxy)phenyl)-2-phenylacetate;

(1-benzylpiperidin-4-yl)methyl (S)-2-hydroxy-2-(3-(2-((3aR,6aR)-5-(4-((((R)-2-hydroxy-2-(8-hydroxy-2-oxo-1,2-dihydroquinolin-5-yl)ethyl)amino)methyl)benzoyl)-hexahydropyrrolo[3,4-b]pyrrol-1(2H)-yl)-2-oxoethoxy)phenyl)-2-phenylacetate;

(1-benzylpiperidin-4-yl)methyl (S)-2-hydroxy-2-(3-(2-((R)-3-(4-((((R)-2-hydroxy-2-(8-hydroxy-2-oxo-1,2-dihydroquinolin-5-yl)ethyl)amino)methyl)benzamido)-piperidin-1-yl)-2-oxoethoxy)phenyl)-2-phenylacetate;

(1-benzylpiperidin-4-yl)methyl (S)-2-hydroxy-2-(3-(2-((R)-3-(4-((((R)-2-hydroxy-2-(8-hydroxy-2-oxo-1,2-dihydroquinolin-5-yl)ethyl)amino)methyl)benzamido)-pyrrolidin-1-yl)-2-oxoethoxy)phenyl)-2-phenylacetate;

(1-benzylpiperidin-4-yl)methyl (S)-2-hydroxy-2-(3-(2-((3aS,6aS)-5-(4-((((R)-2-hydroxy-2-(8-hydroxy-2-oxo-1,2-dihydroquinolin-5-yl)ethyl)amino)methyl)benzoyl)-hexahydropyrrolo[3,4-b]pyrrol-1(2H)-yl)-2-oxoethoxy)phenyl)-2-phenylacetate;

(1-benzylpiperidin-4-yl)methyl (S)-2-hydroxy-2-(3-(2-((1-(4-((((R)-2-hydroxy-2-(8-hydroxy-2-oxo-1,2-dihydroquinolin-5-yl)ethyl)amino)methyl)-3-methoxybenzoyl)azetidin-3-yl)amino)-2-oxoethoxy)phenyl)-2-phenylacetate;

(1-benzylpiperidin-4-yl)methyl (S)-2-hydroxy-2-(3-(2-(9-(4-((((R)-2-hydroxy-2-(8-hydroxy-2-oxo-1,2-dihydroquinolin-5-yl)ethyl)amino)methyl)-3-methoxybenzoyl)-3,9-diazaspiro[5.5]undecan-3-yl)-2-oxoethoxy)phenyl)-2-phenylacetate;

(1-benzylpiperidin-4-yl)methyl (S)-2-hydroxy-2-(3-(2-(4-((4-((((R)-2-hydroxy-2-(8-hydroxy-2-oxo-1,2-dihydroquinolin-5-yl)ethyl)amino)methyl)-3-methoxybenzamido)methyl)piperidin-1-yl)-2-oxoethoxy)phenyl)-2-phenylacetate;

(1-benzylpiperidin-4-yl)methyl (S)-2-hydroxy-2-(3-(2-(9-(4-((((R)-2-hydroxy-2-(8-hydroxy-2-oxo-1,2-dihydroquinolin-5-yl)ethyl)amino)methyl)-2-methoxybenzoyl)-3,9-diazaspiro[5.5]undecan-3-yl)-2-oxoethoxy)phenyl)-2-phenylacetate;

(1-benzylpiperidin-4-yl)methyl (S)-2-hydroxy-2-(3-(2-((1-(4-((((R)-2-hydroxy-2-(8-hydroxy-2-oxo-1,2-dihydroquinolin-5-yl)ethyl)amino)methyl)-2-methoxybenzoyl)azetidin-3-yl)amino)-2-oxoethoxy)phenyl)-2-phenylacetate;

(1-benzylpiperidin-4-yl)methyl (S)-2-(3-(2-(ethyl(2-(4-(2-(((R)-2-hydroxy-2-(8-hydroxy-2-oxo-1,2-dihydroquinolin-5-yl)ethyl)amino)ethyl)benzamido)ethyl)amino)-2-oxoethoxy)phenyl)-2-hydroxy-2-phenylacetate;

(1-benzylpiperidin-4-yl)methyl (S)-2-hydroxy-2-(3-(2-((2-(4-(2-(((R)-2-hydroxy-2-(8-hydroxy-2-oxo-1,2-dihydroquinolin-5-yl)ethyl)amino)ethyl)benzamido)ethyl)-(methyl)amino)-2-oxoethoxy)phenyl)-2-phenylacetate;

(1-benzylpiperidin-4-yl)methyl (S)-2-hydroxy-2-(3-(2-((3-(4-(2-(((R)-2-hydroxy-2-(8-hydroxy-2-oxo-1,2-dihydroquinolin-5-yl)ethyl)amino)ethyl)benzamido)propyl)-amino)-2-oxoethoxy)phenyl)-2-phenylacetate;

(1-benzylpiperidin-4-yl)methyl (S)-2-hydroxy-2-(3-(2-(4-(4-(2-(((R)-2-hydroxy-2-(8-hydroxy-2-oxo-1,2-dihydroquinolin-5-yl)ethyl)amino)ethyl)benzoyl)piperazin-1-yl)-2-oxoethoxy)phenyl)-2-phenylacetate;

(1-benzylpiperidin-4-yl)methyl (S)-2-(3-(2-(benzyl(2-(4-(2-(((R)-2-hydroxy-2-(8-hydroxy-2-oxo-1,2-dihydroquinolin-5-yl)ethyl)amino)ethyl)benzamido)ethyl)amino)-2-oxoethoxy)phenyl)-2-hydroxy-2-phenylacetate;

(1-benzylpiperidin-4-yl)methyl (S)-2-hydroxy-2-(3-(2-(((1R,3S)-3-(4-(2-(((R)-2-hydroxy-2-(8-hydroxy-2-oxo-1,2-dihydroquinolin-5-yl)ethyl)amino)ethyl)benzamido)-cyclobutyl)amino)-2-oxoethoxy)phenyl)-2-phenylacetate;

(1-benzylpiperidin-4-yl)methyl (S)-2-hydroxy-2-(3-(2-(4-((4-(2-(((R)-2-hydroxy-2-(8-hydroxy-2-oxo-1,2-dihydroquinolin-5-yl)ethyl)amino)ethyl)benzamido)-methyl)piperidin-1-yl)-2-oxoethoxy)phenyl)-2-phenylacetate;

(1-benzylpiperidin-4-yl)methyl (S)-2-hydroxy-2-(3-(2-(((1R,4S)-4-(4-(2-(((R)-2-hydroxy-2-(8-hydroxy-2-oxo-1,2-dihydroquinolin-5-yl)ethyl)amino)ethyl)benzamido)-cyclohexyl)amino)-2-oxoethoxy)phenyl)-2-phenylacetate;

(1-benzylpiperidin-4-yl)methyl (S)-2-hydroxy-2-(3-(2-((1-(4-(2-(((R)-2-hydroxy-2-(8-hydroxy-2-oxo-1,2-dihydroquinolin-5-yl)ethyl)amino)ethyl)benzoyl)piperidin-4-yl)amino)-2-oxoethoxy)phenyl)-2-phenylacetate;

(1-benzylpiperidin-4-yl)methyl (S)-2-hydroxy-2-(3-(2-(4-(4-(2-(((R)-2-hydroxy-2-(8-hydroxy-2-oxo-1,2-dihydroquinolin-5-yl)ethyl)amino)ethyl)benzamido)piperidin-1-yl)-2-oxoethoxy)phenyl)-2-phenylacetate;

(1-benzylpiperidin-4-yl)methyl (S)-2-hydroxy-2-(3-(2-(6-(4-(2-(((R)-2-hydroxy-2-(8-hydroxy-2-oxo-1,2-dihydroquinolin-5-yl)ethyl)amino)ethyl)benzoyl)-2,6-diazaspiro[3.3]heptan-2-yl)-2-oxoethoxy)phenyl)-2-phenylacetate;

(1-benzylpiperidin-4-yl)methyl (S)-2-hydroxy-2-(3-(2-(7-(4-(2-(((R)-2-hydroxy-2-(8-hydroxy-2-oxo-1,2-dihydroquinolin-5-yl)ethyl)amino)ethyl)benzoyl)-2,7-diazaspiro[3.5]nonan-2-yl)-2-oxoethoxy)phenyl)-2-phenylacetate;

(1-benzylpiperidin-4-yl)methyl (S)-2-hydroxy-2-(3-(2-(9-(4-(2-(((R)-2-hydroxy-2-(8-hydroxy-2-oxo-1,2-dihydroquinolin-5-yl)ethyl)amino)ethyl)benzoyl)-3,9-diazaspiro[5.5]undecan-3-yl)-2-oxoethoxy)phenyl)-2-phenylacetate;

(1-benzylpiperidin-4-yl)methyl (S)-2-hydroxy-2-(3-(2-(2-(4-(2-(((R)-2-hydroxy-2-(8-hydroxy-2-oxo-1,2-dihydroquinolin-5-yl)ethyl)amino)ethyl)benzoyl)-2,7-diazaspiro[3.5]nonan-7-yl)-2-oxoethoxy)phenyl)-2-phenylacetate;

(1-benzylpiperidin-4-yl)methyl (S)-2-hydroxy-2-(3-(2-(((1-(4-(2-(((R)-2-hydroxy-2-(8-hydroxy-2-oxo-1,2-dihydroquinolin-5-yl)ethyl)amino)ethyl)benzoyl)piperidin-4-yl)methyl)amino)-2-oxoethoxy)phenyl)-2-phenyl acetate;

(1-benzylpiperidin-4-yl)methyl (S)-2-hydroxy-2-(3-(2-(6-(4-(2-(((R)-2-hydroxy-2-(8-hydroxy-2-oxo-1,2-dihydroquinolin-5-yl)ethyl)amino)ethyl)benzoyl)-2,6-diazaspiro[3.5]nonan-2-yl)-2-oxoethoxy)phenyl)-2-phenylacetate;

(1-benzylpiperidin-4-yl)methyl (S)-2-hydroxy-2-(3-(2-(9-(4-(2-(((R)-2-hydroxy-2-(8-hydroxy-2-oxo-1,2-dihydroquinolin-5-yl)ethyl)amino)ethyl)benzoyl)-2,9-diazaspiro[5.5]undecan-2-yl)-2-oxoethoxy)phenyl)-2-phenylacetate;

(1-benzylpiperidin-4-yl)methyl (S)-2-hydroxy-2-(3-(2-(9-(4-(2-(((R)-2-hydroxy-2-(8-hydroxy-2-oxo-1,2-dihydroquinolin-5-yl)ethyl)amino)ethyl)benzoyl)-1-oxa-4,9-diazaspiro[5.5]undecan-4-yl)-2-oxoethoxy)phenyl)-2-phenylacetate;

(1-benzylpiperidin-4-yl)methyl (S)-2-hydroxy-2-(3-(2-((1-(4-(2-(((R)-2-hydroxy-2-(8-hydroxy-2-oxo-1,2-dihydroquinolin-5-yl)ethyl)amino)ethyl)benzoyl)azetidin-3-yl)amino)-2-oxoethoxy)phenyl)-2-phenyl acetate;

(1-benzylpiperidin-4-yl)methyl (S)-2-hydroxy-2-(3-(2-(3-(4-(2-(((R)-2-hydroxy-2-(8-hydroxy-2-oxo-1,2-dihydroquinolin-5-yl)ethyl)amino)ethyl)benzamido)azetidin-1-yl)-2-oxoethoxy)phenyl)-2-phenylacetate;

(1-benzylpiperidin-4-yl)methyl (S)-2-hydroxy-2-(3-(2-((2-(4-(2-(((R)-2-hydroxy-2-(8-hydroxy-2-oxo-1,2-dihydroquinolin-5-yl)ethyl)amino)ethyl)benzamido)ethyl)-amino)-2-oxoethoxy)phenyl)-2-phenylacetate;

(1-benzylpiperidin-4-yl)methyl (S)-2-hydroxy-2-(3-(2-(((R)-1-(4-(2-(((R)-2-hydroxy-2-(8-hydroxy-2-oxo-1,2-dihydroquinolin-5-yl)ethyl)amino)ethyl)benzoyl)-pyrrolidin-3-yl)amino)-2-oxoethoxy)phenyl)-2-phenylacetate;

(1-benzylpiperidin-4-yl)methyl (S)-2-hydroxy-2-(3-(2-(((R)-1-(4-(2-(((R)-2-hydroxy-2-(8-hydroxy-2-oxo-1,2-dihydroquinolin-5-yl)ethyl)amino)ethyl)benzoyl)-piperidin-3-yl)amino)-2-oxoethoxy)phenyl)-2-phenylacetate;

(1-benzylpiperidin-4-yl)methyl (S)-2-hydroxy-2-(3-(2-(((S)-1-(4-(2-(((R)-2-hydroxy-2-(8-hydroxy-2-oxo-1,2-dihydroquinolin-5-yl)ethyl)amino)ethyl)benzoyl)-piperidin-3-yl)amino)-2-oxoethoxy)phenyl)-2-phenylacetate;

(1-benzylpiperidin-4-yl)methyl (S)-2-hydroxy-2-(3-(2-(((S)-1-(4-(2-(((R)-2-hydroxy-2-(8-hydroxy-2-oxo-1,2-dihydroquinolin-5-yl)ethyl)amino)ethyl)benzoyl)-pyrrolidin-3-yl)amino)-2-oxoethoxy)phenyl)-2-phenylacetate;

(1-benzylpiperidin-4-yl)methyl (S)-2-hydroxy-2-(3-(2-((S)-3-(4-(2-(((R)-2-hydroxy-2-(8-hydroxy-2-oxo-1,2-dihydroquinolin-5-yl)ethyl)amino)ethyl)benzamido)-piperidin-1-yl)-2-oxoethoxy)phenyl)-2-phenylacetate;

(1-benzylpiperidin-4-yl)methyl (S)-2-hydroxy-2-(3-(2-((S)-3-(4-(2-(((R)-2-hydroxy-2-(8-hydroxy-2-oxo-1,2-dihydroquinolin-5-yl)ethyl)amino)ethyl)benzamido)-pyrrolidin-1-yl)-2-oxoethoxy)phenyl)-2-phenylacetate;

(1-benzylpiperidin-4-yl)methyl (S)-2-hydroxy-2-(3-(2-((R)-3-(4-(2-(((R)-2-hydroxy-2-(8-hydroxy-2-oxo-1,2-dihydroquinolin-5-yl)ethyl)amino)ethyl)benzamido)-pyrrolidin-1-yl)-2-oxoethoxy)phenyl)-2-phenylacetate;

(1-benzylpiperidin-4-yl)methyl (S)-2-hydroxy-2-(3-(2-((3aR,6aR)-1-(4-(2-(((R)-2-hydroxy-2-(8-hydroxy-2-oxo-1,2-dihydroquinolin-5-yl)ethyl)amino)ethyl)benzoyl)-hexahydropyrrolo[3,4-b]pyrrol-5(1H)-yl)-2-oxoethoxy)phenyl)-2-phenylacetate;

(1-benzylpiperidin-4-yl)methyl (S)-2-hydroxy-2-(3-(2-((3aS,6aS)-1-(4-(2-(((R)-2-hydroxy-2-(8-hydroxy-2-oxo-1,2-dihydroquinolin-5-yl)ethyl)amino)ethyl)benzoyl)-hexahydropyrrolo[3,4-b]pyrrol-5(1H)-yl)-2-oxoethoxy)phenyl)-2-phenylacetate;

(1-benzylpiperidin-4-yl)methyl (S)-2-hydroxy-2-(3-(2-((R)-3-(4-(2-(((R)-2-hydroxy-2-(8-hydroxy-2-oxo-1,2-dihydroquinolin-5-yl)ethyl)amino)ethyl)benzamido)-piperidin-1-yl)-2-oxoethoxy)phenyl)-2-phenylacetate;

(1-benzylpiperidin-4-yl)methyl (S)-2-hydroxy-2-(3-((((1R,3S)-3-(4-(2-(((R)-2-hydroxy-2-(8-hydroxy-2-oxo-1,2-dihydroquinolin-5-yl)ethyl)amino)ethyl)benzamido)-cyclobutyl)carbamoyl)benzyl)oxy)phenyl)-2-phenylacetate;

(1-benzylpiperidin-4-yl)methyl (S)-2-hydroxy-2-(3-((4-(9-(4-(2-(((R)-2-hydroxy-2-(8-hydroxy-2-oxo-1,2-dihydroquinolin-5-yl)ethyl)amino)ethyl)benzoyl)-3,9-diazaspiro[5.5]undecane-3-carbonyl)benzyl)oxy)phenyl)-2-phenylacetate;

(1-benzylpiperidin-4-yl)methyl (S)-2-hydroxy-2-(3-((4-(6-(4-(2-(((R)-2-hydroxy-2-(8-hydroxy-2-oxo-1,2-dihydroquinolin-5-yl)ethyl)amino)ethyl)benzoyl)-2,6-diazaspiro[3.3]heptane-2-carbonyl)benzyl)oxy)phenyl)-2-phenylacetate;

(1-benzylpiperidin-4-yl)methyl (S)-2-hydroxy-2-(3-((4-(7-(4-(2-(((R)-2-hydroxy-2-(8-hydroxy-2-oxo-1,2-dihydroquinolin-5-yl)ethyl)amino)ethyl)benzoyl)-2,7-diazaspiro[3.5]nonane-2-carbonyl)benzyl)oxy)phenyl)-2-phenylacetate;

(1-benzylpiperidin-4-yl)methyl (S)-2-hydroxy-2-(3-((4-(4-(4-(2-(((R)-2-hydroxy-2-(8-hydroxy-2-oxo-1,2-dihydroquinolin-5-yl)ethyl)amino)ethyl)benzoyl)piperazine-1-carbonyl)benzyl)oxy)phenyl)-2-phenylacetate;

(1-benzylpiperidin-4-yl)methyl (S)-2-hydroxy-2-(3-((4-(2-(4-(2-(((R)-2-hydroxy-2-(8-hydroxy-2-oxo-1,2-dihydroquinolin-5-yl)ethyl)amino)ethyl)benzoyl)-2,7-diazaspiro[3.5]nonane-7-carbonyl)benzyl)oxy)phenyl)-2-phenylacetate;

(1-benzylpiperidin-4-yl)methyl (S)-2-hydroxy-2-(3-((4-(6-(4-(2-(((R)-2-hydroxy-2-(8-hydroxy-2-oxo-1,2-dihydroquinolin-5-yl)ethyl)amino)ethyl)benzoyl)-2,6-diazaspiro[3.5]nonane-2-carbonyl)benzyl)oxy)phenyl)-2-phenylacetate;

(1-benzylpiperidin-4-yl)methyl (S)-2-hydroxy-2-(3-((4-(9-(4-(2-(((R)-2-hydroxy-2-(8-hydroxy-2-oxo-1,2-dihydroquinolin-5-yl)ethyl)amino)ethyl)benzoyl)-1-oxa-4,9-diazaspiro[5.5]undecane-4-carbonyl)benzyl)oxy)phenyl)-2-phenylacetate;

(1-benzylpiperidin-4-yl)methyl (S)-2-hydroxy-2-(3-((4-(9-(4-(2-(((R)-2-hydroxy-2-(8-hydroxy-2-oxo-1,2-dihydroquinolin-5-yl)ethyl)amino)ethyl)benzoyl)-2,9-diazaspiro[5.5]undecane-2-carbonyl)benzyl)oxy)phenyl)-2-phenylacetate;

(1-benzylpiperidin-4-yl)methyl (S)-2-hydroxy-2-(3-((4-(((1R,3S)-3-(4-((((R)-2-hydroxy-2-(8-hydroxy-2-oxo-1,2-dihydroquinolin-5-yl)ethyl)amino)methyl)benzamido)-cyclobutyl)carbamoyl)benzyl)oxy)phenyl)-2-phenylacetate;

(1-benzylpiperidin-4-yl)methyl (S)-2-hydroxy-2-(3-((4-(((1R,3S)-3-(4-((((R)-2-hydroxy-2-(8-hydroxy-2-oxo-1,2-dihydroquinolin-5-yl)ethyl)amino)methyl)-3-methoxybenzamido)cyclobutyl)carbamoyl)benzyl)oxy)phenyl)-2-phenylacetate;

(1-benzylpiperidin-4-yl)methyl (S)-2-hydroxy-2-(3-((4-((2-(4-((((R)-2-hydroxy-2-(8-hydroxy-2-oxo-1,2-dihydroquinolin-5-yl)ethyl)amino)methyl)benzamido)ethyl)-carbamoyl)benzyl)oxy)phenyl)-2-phenylacetate;

(1-benzylpiperidin-4-yl)methyl (S)-2-hydroxy-2-(3-((4-((2-(4-((((R)-2-hydroxy-2-(8-hydroxy-2-oxo-1,2-dihydroquinolin-5-yl)ethyl)amino)methyl)-3-methoxybenzamido)-ethyl)carbamoyl)benzyl)oxy)phenyl)-2-phenylacetate;

(1-benzylpiperidin-4-yl)methyl (S)-2-hydroxy-2-(3-(2-(((1R,3S)-3-(3-hydroxy-4-((((R)-2-hydroxy-2-(8-hydroxy-2-oxo-1,2-dihydroquinolin-5-yl)ethyl)amino)methyl)-benzamido)cyclobutyl)amino)-2-oxoethoxy)phenyl)-2-phenylacetate;

(S)-(1-benzylpiperidin-4-yl)methyl 2-(3-(2-(((1R,3S)-3-(2-fluoro-4-((((R)-2-hydroxy-2-(8-hydroxy-2-oxo-1,2-dihydroquinolin-5-yl)ethyl)amino)methyl)benzamido)-cyclobutyl)amino)-2-oxoethoxy)phenyl)-2-hydroxy-2-phenylacetate;

(S)-(1-benzylpiperidin-4-yl)methyl 2-hydroxy-2-(3-(2-(((1R,3S)-3-(4-((((R)-2-hydroxy-2-(8-hydroxy-2-oxo-1,2-dihydroquinolin-5-yl)ethyl)amino)methyl)-3-methylbenzamido)cyclobutyl)amino)-2-oxoethoxy)phenyl)-2-phenylacetate;

(S)-(1-benzylpiperidin-4-yl)methyl 2-hydroxy-2-(3-(2-(((1R,3S)-3-(4-((((R)-2-hydroxy-2-(8-hydroxy-2-oxo-1,2-dihydroquinolin-5-yl)ethyl)amino)methyl)-2-methoxybenzamido)cyclobutyl)amino)-2-oxoethoxy)phenyl)-2-phenylacetate;

(S)-(1-benzylpiperidin-4-yl)methyl 2-hydroxy-2-(3-(2-(((1R,3S)-3-(4-((((R)-2-hydroxy-2-(8-hydroxy-2-oxo-1,2-dihydroquinolin-5-yl)ethyl)amino)methyl)-3-methoxybenzamido)cyclobutyl)amino)-2-oxoethoxy)phenyl)-2-phenylacetate;

(1-benzylpiperidin-4-yl)methyl (S)-2-(3-(2-(((1R,3S)-3-(3-fluoro-4-((((R)-2-hydroxy-2-(8-hydroxy-2-oxo-1,2-dihydroquinolin-5-yl)ethyl)amino)methyl)benzamido)-cyclobutyl)amino)-2-oxoethoxy)phenyl)-2-hydroxy-2-phenylacetate;

(1-benzylpiperidin-4-yl)methyl (S)-2-(3-(2-(((1R,3S)-3-(2-chloro-4-((((R)-2-hydroxy-2-(8-hydroxy-2-oxo-1,2-dihydroquinolin-5-yl)ethyl)amino)methyl)benzamido)-cyclobutyl)amino)-2-oxoethoxy)phenyl)-2-hydroxy-2-phenylacetate;

(1-benzylpiperidin-4-yl)methyl (S)-2-(3-(2-(((1R,3S)-3-(2,3-difluoro-4-((((R)-2-hydroxy-2-(8-hydroxy-2-oxo-1,2-dihydroquinolin-5-yl)ethyl)amino)methyl)benzamido)-cyclobutyl)amino)-2-oxoethoxy)phenyl)-2-hydroxy-2-phenylacetate;

(1-benzylpiperidin-4-yl)methyl (S)-2-(3-(2-(((1R,3S)-3-(3-chloro-4-((((R)-2-hydroxy-2-(8-hydroxy-2-oxo-1,2-dihydroquinolin-5-yl)ethyl)amino)methyl)benzamido)-cyclobutyl)amino)-2-oxoethoxy)phenyl)-2-hydroxy-2-phenylacetate;

(1-benzylpiperidin-4-yl)methyl (S)-2-(3-(2-(((1R,3S)-3-(2-bromo-4-((((R)-2-hydroxy-2-(8-hydroxy-2-oxo-1,2-dihydroquinolin-5-yl)ethyl)amino)methyl)benzamido)-cyclobutyl)amino)-2-oxoethoxy)phenyl)-2-hydroxy-2-phenylacetate;

(1-benzylpiperidin-4-yl)methyl (S)-2-(3-(2-(((1R,3S)-3-(2-chloro-4-((((R)-2-hydroxy-2-(8-hydroxy-2-oxo-1,2-dihydroquinolin-5-yl)ethyl)amino)methyl)-5-methoxybenzamido)cyclobutyl)amino)-2-oxoethoxy)phenyl)-2-hydroxy-2-phenylacetate;

(1-benzylpiperidin-4-yl)methyl (S)-2-hydroxy-2-(3-(2-(((1R,3S)-3-(4-((((R)-2-hydroxy-2-(8-hydroxy-2-oxo-1,2-dihydroquinolin-5-yl)ethyl)amino)methyl)-3-(trifluoromethyl)benzamido)cyclobutyl)amino)-2-oxoethoxy)phenyl)-2-phenylacetate;

(1-benzylpiperidin-4-yl)methyl (S)-2-(3-(2-(((1R,3S)-3-(2-fluoro-4-((((R)-2-hydroxy-2-(8-hydroxy-2-oxo-1,2-dihydroquinolin-5-yl)ethyl)amino)methyl)-3-methoxybenzamido)cyclobutyl)amino)-2-oxoethoxy)phenyl)-2-hydroxy-2-phenylacetate;

(1-benzylpiperidin-4-yl)methyl (S)-2-(3-(2-(((1R,3S)-3-(3-ethoxy-4-((((R)-2-hydroxy-2-(8-hydroxy-2-oxo-1,2-dihydroquinolin-5-yl)ethyl)amino)methyl)benzamido)-cyclobutyl)amino)-2-oxoethoxy)phenyl)-2-hydroxy-2-phenylacetate;

(1-benzylpiperidin-4-yl)methyl (S)-2-hydroxy-2-(3-(2-(((1R,3S)-3-(4-((((R)-2-hydroxy-2-(8-hydroxy-2-oxo-1,2-dihydroquinolin-5-yl)ethyl)amino)methyl)-3-(trifluoromethoxy)benzamido)cyclobutyl)amino)-2-oxoethoxy)phenyl)-2-phenylacetate;

(1-benzylpiperidin-4-yl)methyl (S)-2-(3-(2-(((1R,3S)-3-(2-fluoro-4-((((R)-2-hydroxy-2-(8-hydroxy-2-oxo-1,2-dihydroquinolin-5-yl)ethyl)amino)methyl)-5-methoxybenzamido)cyclobutyl)amino)-2-oxoethoxy)phenyl)-2-hydroxy-2-phenylacetate;

(1-benzylpiperidin-4-yl)methyl (S)-2-hydroxy-2-(3-(2-(((1R,3S)-3-(4-((((R)-2-hydroxy-2-(8-hydroxy-2-oxo-1,2-dihydroquinolin-5-yl)ethyl)amino)methyl)-3-isopropoxybenzamido)cyclobutyl)amino)-2-oxoethoxy)phenyl)-2-phenylacetate;

(1-benzylpiperidin-4-yl)methyl (S)-2-hydroxy-2-(3-(2-(((1R,3S)-3-(5-((((R)-2-hydroxy-2-(8-hydroxy-2-oxo-1,2-dihydroquinolin-5-yl)ethyl)amino)methyl)-picolinamido)cyclobutyl)amino)-2-oxoethoxy)phenyl)-2-phenylacetate;

(1-benzylpiperidin-4-yl)methyl (S)-2-hydroxy-2-(3-(2-(((1R,3S)-3-(6-((((R)-2-hydroxy-2-(8-hydroxy-2-oxo-1,2-dihydroquinolin-5-yl)ethyl)amino)methyl)-nicotinamido)cyclobutyl)amino)-2-oxoethoxy)phenyl)-2-phenylacetate;

(1-benzylpiperidin-4-yl)methyl (S)-2-hydroxy-2-(3-(2-(((1R,3S)-3-(2-(4-((((R)-2-hydroxy-2-(8-hydroxy-2-oxo-1,2-dihydroquinolin-5-yl)ethyl)amino)methyl)phenyl)-acetamido)cyclobutyl)amino)-2-oxoethoxy)phenyl)-2-phenylacetate;

(1-benzylpiperidin-4-yl)methyl (S)-2-hydroxy-2-(3-(2-(3-(4-((((R)-2-hydroxy-2-(8-hydroxy-2-oxo-1,2-dihydroquinolin-5-yl)ethyl)amino)methyl)piperidine-1-carbonyl)azetidin-1-yl)-2-oxoethoxy)phenyl)-2-phenylacetate;

(1-benzylpiperidin-4-yl)methyl (S)-2-hydroxy-2-(3-(2-(4-(4-((((R)-2-hydroxy-2-(8-hydroxy-2-oxo-1,2-dihydroquinolin-5-yl)ethyl)amino)methyl)piperidine-1-carbonyl)piperidin-1-yl)-2-oxoethoxy)phenyl)-2-phenylacetate;

(1-benzylpiperidin-4-yl)methyl (S)-2-hydroxy-2-(3-(2-(((1R,4S)-4-(4-((((R)-2-hydroxy-2-(8-hydroxy-2-oxo- 1,2-dihydroquinolin-5-yl)ethyl)amino)methyl)piperidine-1-carbonyl)cyclohexyl)amino)-2-oxoethoxy)phenyl)-2-phenylacetate;

(1-benzylpiperidin-4-yl)methyl (S)-2-hydroxy-2-(3-(2-((2-(4-((((R)-2-hydroxy-2-(8-hydroxy-2-oxo-1,2-dihydroquinolin-5-yl)ethyl)amino)methyl)piperidin-1-yl)-2-oxoethyl)amino)-2-oxoethoxy)phenyl)-2-phenylacetate;

(1-benzylpiperidin-4-yl)methyl (S)-2-hydroxy-2-(3-((1-(1-(4-(2-(((R)-2-hydroxy-2-(8-hydroxy-2-oxo-1,2-dihydroquinolin-5-yl)ethyl)amino)ethyl)benzoyl)piperidine-4-carbonyl)piperidin-4-yl)methoxy)phenyl)-2-phenylacetate;

(1-benzylpiperidin-4-yl)methyl (S)-2-hydroxy-2-(3-((1-((4-(2-(((R)-2-hydroxy-2-(8-hydroxy-2-oxo-1,2-dihydroquinolin-5-yl)ethyl)amino)ethyl)benzoyl)glycyl)piperidin-4-yl)methoxy)phenyl)-2-phenylacetate;

(1-benzylpiperidin-4-yl)methyl (S)-2-hydroxy-2-(3-((1-((4-((((R)-2-hydroxy-2-(8-hydroxy-2-oxo-1,2-dihydroquinolin-5-yl)ethyl)amino)methyl)-3-methoxybenzoyl)glycyl)piperidin-4-yl)methoxy)phenyl)-2-phenylacetate;

(1-benzylpiperidin-4-yl)methyl (S)-2-hydroxy-2-(3-((1-((4-((((R)-2-hydroxy-2-(8-hydroxy-2-oxo-1,2-dihydroquinolin-5-yl)ethyl)amino)methyl)benzoyl)glycyl)piperidin-4-yl)methoxy)phenyl)-2-phenylacetate;

(1-benzylpiperidin-4-yl)methyl (S)-2-hydroxy-2-(3-((1-((4-((((R)-2-hydroxy-2-(8-hydroxy-2-oxo-1,2-dihydroquinolin-5-yl)ethyl)amino)methyl)-2-methoxybenzoyl)glycyl)piperidin-4-yl)methoxy)phenyl)-2-phenylacetate;

(1-benzylpiperidin-4-yl)methyl (S)-2-hydroxy-2-(3-((1-(5-(4-((((R)-2-hydroxy-2-(8-hydroxy-2-oxo-1,2-dihydroquinolin-5-yl)ethyl)amino)methyl)piperidine-1-carbonyl)thiophene-2-carbonyl)piperidin-4-yl)methoxy)phenyl)-2-phenylacetate;

(1-benzylpiperidin-4-yl)methyl (S)-2-hydroxy-2-(3-((1-(((1R,4S)-4-(4-((((R)-2-hydroxy-2-(8-hydroxy-2-oxo-1,2-dihydroquinolin-5-yl)ethyl)amino)methyl)piperidine-1-carbonyl)cyclohexane-1-carbonyl)piperidin-4-yl)methoxy)phenyl)-2-phenylacetate;

1-benzylpiperidin-4-yl (S)-2-hydroxy-2-(3-((4-((3-(4-((((R)-2-hydroxy-2-(8-hydroxy-2-oxo-1,2-dihydroquinolin-5-yl)ethyl)amino)methyl)phenyl)ureido)-methyl)benzyl)oxy)phenyl)-2-phenylacetate;

1-benzylpiperidin-4-yl (S)-2-hydroxy-2-(3-((4-((3-(4-((((R)-2-hydroxy-2-(8-hydroxy-2-oxo-1,2-dihydroquinolin-5-yl)ethyl)amino)methyl)-3-methoxyphenyl)-ureido)methyl)benzyl)oxy)phenyl)-2-phenylacetate; and 1-benzylpiperidin-4-yl (S)-2-hydroxy-2-(3-((4-((3-(4-((((R)-2-hydroxy-2-(8-hydroxy-2-oxo-1,2-dihydroquinolin-5-yl)ethyl)amino)methyl)-2-methoxyphenyl)-ureido)methyl)benzyl)oxy)phenyl)-2-phenylacetate;

or a pharmaceutically acceptable salt of said compound.

11. A method according to claim 1, wherein said bronchoobstructive disease is asthma, chronic bronchitis, or chronic obstructive pulmonary disease (COPD).

12. A method according to claim 1, wherein said administering is by inhalation.

\* \* \* \* \*

UNITED STATES PATENT AND TRADEMARK OFFICE
CERTIFICATE OF CORRECTION

PATENT NO.         : 10,004,728 B2
APPLICATION NO.    : 15/404897
DATED              : June 26, 2018
INVENTOR(S)        : Fabio Rancati et al.

It is certified that error appears in the above-identified patent and that said Letters Patent is hereby corrected as shown below:

In the Claims

Column 334, Line 56:

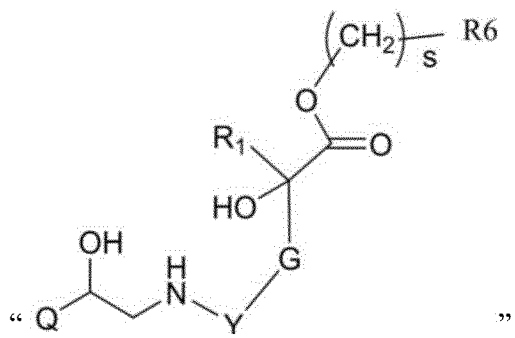

"                                                                "

Should read as:

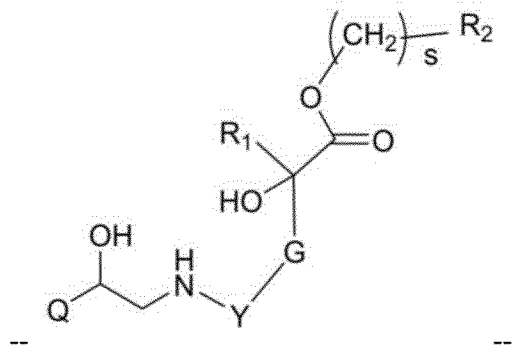

--                                                             --

Column 338, Lines 64-67:
"P is absent or is a divalent moiety selected from the group consisting of O, S, SO, $SO_2$, CO, $NR_6CH=CH$, $N(R_6)SO_2$, $N(R_6)COO$, $N(R_6)C(O)$, $SO_2N(R_6)$, $OC(O)N(R_6)$, and $C(O)N(R_6)$;"

Signed and Sealed this
Fourteenth Day of April, 2020

Andrei Iancu
*Director of the United States Patent and Trademark Office*

Should read as:
   --P is absent or is a divalent moiety selected from the group consisting of O, S, SO, $SO_2$, CO, $NR_6$ CH=CH, $N(R_6)SO_2$, $N(R_6)COO$, $N(R_6)C(O)$, $SO_2N(R_6)$, $OC(O)N(R_6)$, and $C(O)N(R_6)$;--

Column 343, Lines 40-67, Column 344, Lines 1-4:
   "(1-benzylpiperidin-4-yl)methyl 2-hydroxy-2-(3-(2-(4-(2-(((R)-2-hydroxy-2-(8-hydroxy-2-oxo-1,2-dihydroquinolin-5-yl)ethyl)amino)ethyl)benzamido)ethyl)phenyl)-2-phenylacetate;
   1-benzylpiperidin-4-yl (S)-2-hydroxy-2-(3-(3-(4-((((R)-2-hydroxy-2-(8-hydroxy-2-oxo-1,2-dihydroquinolin-5-yl)ethyl)amino)methyl)benzamido)propoxy)phenyl)-2-phenylacetate;
   ((R)-1-benzylpyrrolidin-3-yl)methyl (S)-2-hydroxy-2-(3-(3-(4-((((R)-2-hydroxy-2-(8-hydroxy-2-oxo-1,2-dihydroquinolin-5-yl)ethyl)amino)methyl)benzamido)-propoxy)phenyl)-2-phenylacetate;
   ((S)-1-benzylpyrrolidin-3-yl)methyl (S)-2-hydroxy-2-(3-(3-(4-((((R)-2-hydroxy-2-(8-hydroxy-2-oxo-1,2-dihydroquinolin-5-yl)ethyl)amino)methyl)benzamido)-propoxy)phenyl)-2-phenylacetate;
   (1-cyclobutylpiperidin-4-yl)methyl (S)-2-hydroxy-2-(3-(3-(4-((((R)-2-hydroxy-2-(8-hydroxy-2-oxo-1,2-dihydroquinolin-5-yl)ethyl)amino)methyl)benzamido)-propoxy)phenyl)-2-phenylacetate;
   (1-methylpiperidin-4-yl)methyl (S)-2-hydroxy-2-(3-(3-(4-((((R)-2-hydroxy-2-(8-hydroxy-2-oxo-1,2-dihydroquinolin-5-yl)ethyl)amino)methyl)benzamido)-propoxy)phenyl)-2-phenylacetate;
   (R)-1-benzylpyrrolidin-3-yl (S)-2-hydroxy-2-(3-(3-(4-((((R)-2-hydroxy-2-(8-hydroxy-2-oxo-1,2-dihydroquinolin-5-yl)ethyl)amino)methyl)benzamido)-propoxy)phenyl)-2-phenylacetate;
   (S)-1-benzylpyrrolidin-3-yl (S)-2-hydroxy-2-(3-(3-(4-((((R)-2-hydroxy-2-(8-hydroxy-2-oxo-1,2-dihydroquinolin-5-yl)ethyl)amino)methyl)benzamido)-propoxy)phenyl)-2-phenylacetate;
   1-benzylazetidin-3-yl (S)-2-hydroxy-2-(3-(3-(4-((((R)-2-hydroxy-2-(8-hydroxy-2-oxo-1,2-dihydroquinolin-5-yl)ethyl)amino)methyl)benzamido)propoxy)phenyl)-2-phenylacetate;"

Should read as:
   --"(1-benzylpiperidin-4-yl)methyl 2-hydroxy-2-(3-(2-(4-(2-(((R)-2-hydroxy-2-(8-hydroxy-2-oxo-1,2-dihydroquinolin-5-yl)ethyl)amino)ethyl)benzamido)ethyl)phenyl)-2-phenylacetate;
      (S)-(1-benzylpiperidin-4-yl)methyl 2-hydroxy-2-(3-((1-(4-((((R)-2-hydroxy-2-(8-hydroxy-2-oxo-1,2-dihydroquinolin-5-yl)ethyl)amino)methyl)-benzoyl)azetidin-3-yl)methoxy)phenyl)-2-phenylacetate;--

Column 349, Lines 10-15:
   "(1-benzylpiperidin-4-yl)methyl (S)-2-hydroxy-2-(3-(2-(((1-(4-(2-(((R)-2-hydroxy-2-(8-hydroxy-2-oxo-1,2-dihydroquinolin-5-yl)ethyl)amino)ethyl)benzoyl)piperidin-4-yl)methyl)amino)-2-oxoethoxy)phenyl)-2-phenyl acetate;"
Should read as:

--(1-benzylpiperidin-4-yl)methyl (S)-2-hydroxy-2-(3-(2-(((1-(4-(2-(((R)-2-hydroxy-2-(8-hydroxy-2-oxo-1,2-dihydroquinolin-5-yl)ethyl)amino)ethyl)benzoyl)piperidin-4-yl)methyl)amino)-2-oxoethoxy)phenyl)-2-phenylacetate;--

Column 349, Lines 31-35:
"(1-benzylpiperidin-4-yl)methyl (S)-2-hydroxy-2-(3-(2-((1-(4-(2-(((R)-2-hydroxy-2-(8-hydroxy-2-oxo-1,2-dihydroquinolin-5-yl)ethyl)amino)ethyl)benzoyl)azetidin-3-yl)amino)-2-oxoethoxy)phenyl)-2-phenyl acetate;"

Should read as:
--(1-benzylpiperidin-4-yl)methyl (S)-2-hydroxy-2-(3-(2-((1-(4-(2-(((R)-2-hydroxy-2-(8-hydroxy-2-oxo-1,2-dihydroquinolin-5-yl)ethyl)amino)ethyl)benzoyl)azetidin-3-yl)amino)-2-oxoethoxy)phenyl)-2-phenylacetate;--

Column 354, Line 10:
"(1-benzylpiperidin-4-yl)methyl (S)-2-hydroxy-2-(3-((1-((1R,4S)-4-(4-((((R)-2-hydroxy-2-(8-hydroxy-2-oxo-1,2-dihydroquinolin-5-yl)ethyl)amino)methyl)piperidine-1-carbonyl)cyclohexane-1-carbonyl)piperidin-4-yl)methoxy)phenyl)-2-phenylacetate;"

Should read as:
--(1-benzylpiperidin-4-yl)methyl (S)-2-hydroxy-2-(3-((1-((1R,4S)-4-(4-((((R)-2-hydroxy-2-(8-hydroxy-2-oxo-1,2-dihydroquinolin-5-yl)ethyl)amino)methyl)piperidine-1-carbonyl)cyclohexane-1-carbonyl)piperidin-4-yl)methoxy)phenyl)-2-phenylacetate;

1-benzylpiperidin-4-yl (S)-2-hydroxy-2-(3-(3-(4-((((R)-2-hydroxy-2-(8-hydroxy-2-oxo-1,2-dihydroquinolin-5-yl)ethyl)amino)methyl)benzamido)propoxy)phenyl)-2-phenylacetate;

((R)-1-benzylpyrrolidin-3-yl)methyl (S)-2-hydroxy-2-(3-(3-(4-((((R)-2-hydroxy-2-(8-hydroxy-2-oxo-1,2-dihydroquinolin-5-yl)ethyl)amino)methyl)benzamido)-propoxy)phenyl)-2-phenylacetate;

((S)-1-benzylpyrrolidin-3-yl)methyl (S)-2-hydroxy-2-(3-(3-(4-((((R)-2-hydroxy-2-(8-hydroxy-2-oxo-1,2-dihydroquinolin-5-yl)ethyl)amino)methyl)benzamido)-propoxy)phenyl)-2-phenylacetate;

(1-cyclobutylpiperidin-4-yl)methyl (S)-2-hydroxy-2-(3-(3-(4-((((R)-2-hydroxy-2-(8-hydroxy-2-oxo-1,2-dihydroquinolin-5-yl)ethyl)amino)methyl)benzamido)-propoxy)phenyl)-2-phenylacetate;

(1-methylpiperidin-4-yl)methyl (S)-2-hydroxy-2-(3-(3-(4-((((R)-2-hydroxy-2-(8-hydroxy-2-oxo-1,2-dihydroquinolin-5-yl)ethyl)amino)methyl)benzamido)-propoxy)phenyl)-2-phenylacetate;

(R)-1-benzylpyrrolidin-3-yl (S)-2-hydroxy-2-(3-(3-(4-((((R)-2-hydroxy-2-(8-hydroxy-2-oxo-1,2-dihydroquinolin-5-yl)ethyl)amino)methyl)benzamido)-propoxy)phenyl)-2-phenylacetate;

(S)-1-benzylpyrrolidin-3-yl (S)-2-hydroxy-2-(3-(3-(4-((((R)-2-hydroxy-2-(8-hydroxy-2-oxo-1,2-dihydroquinolin-5-yl)ethyl)amino)methyl)benzamido)-propoxy)phenyl)-2-phenylacetate;

1-benzylazetidin-3-yl (S)-2-hydroxy-2-(3-(3-(4-((((R)-2-hydroxy-2-(8-hydroxy-2- oxo-1,2-dihydroquinolin-5-yl)ethyl)amino)methyl)benzamido)propoxy)phenyl)-2-phenylacetate;--